United States Patent
Qiu et al.

(10) Patent No.: US 9,765,087 B2
(45) Date of Patent: Sep. 19, 2017

(54) BENZIMIDAZOLE DERIVATIVES

(71) Applicant: ENANTA PHARMACEUTICALS, INC., Watertown, MA (US)

(72) Inventors: Yao-Ling Qiu, Andover, MA (US); Ce Wang, Beijing (CN); Xiaowen Peng, Cambridge, MA (US); Hui Cao, Belmont, MA (US); Lu Ying, Shanghai (CN); Xuri Gao, Newton, MA (US); Bin Wang, Brighton, MA (US); Yat Sun Or, Watertown, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 14/245,001

(22) Filed: Apr. 4, 2014

(65) Prior Publication Data
US 2014/0341851 A1    Nov. 20, 2014

Related U.S. Application Data

(63) Continuation of application No. PCT/US2012/057834, filed on Sep. 28, 2012, and a
(Continued)

(51) Int. Cl.
| | |
|---|---|
| C07D 498/10 | (2006.01) |
| C07D 403/14 | (2006.01) |
| A61K 31/4184 | (2006.01) |
| C07D 401/14 | (2006.01) |
| A61K 31/444 | (2006.01) |
| C07D 405/14 | (2006.01) |
| A61K 31/4545 | (2006.01) |
| A61K 31/5377 | (2006.01) |
| A61K 31/496 | (2006.01) |
| A61K 31/675 | (2006.01) |
| C07D 487/08 | (2006.01) |
| A61K 31/506 | (2006.01) |
| C07D 409/14 | (2006.01) |
| C07D 413/14 | (2006.01) |

(Continued)

(52) U.S. Cl.
CPC ............ *C07D 498/10* (2013.01); *A61K 31/13* (2013.01); *A61K 31/4184* (2013.01); *A61K 31/422* (2013.01); *A61K 31/427* (2013.01); *A61K 31/444* (2013.01); *A61K 31/4545* (2013.01); *A61K 31/496* (2013.01); *A61K 31/506* (2013.01); *A61K 31/517* (2013.01); *A61K 31/5377* (2013.01); *A61K 31/675* (2013.01); *A61K 31/7056* (2013.01); *A61K 38/19* (2013.01); *A61K 38/21* (2013.01); *A61K 45/06* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 487/08* (2013.01); *C07D 491/107* (2013.01); *C07F 9/65583* (2013.01)

(58) Field of Classification Search
CPC .................................................. C07D 403/10
See application file for complete search history.

(56) References Cited

U.S. PATENT DOCUMENTS

| | | |
|---|---|---|
| 5,935,982 A | 8/1999 | Dykstra et al. |
| 7,141,574 B2 | 11/2006 | Beaulieu et al. |

(Continued)

FOREIGN PATENT DOCUMENTS

| | | |
|---|---|---|
| WO | 2006133326 A1 | 12/2006 |
| WO | 2007128086 A2 | 11/2007 |

(Continued)

OTHER PUBLICATIONS

Kondrashov, et al., "Reactions of N-(Polychloroethylidene)arene- and-trifluoromethanesulfonamides with Indoles," Russian Journal of Organic Chemistry, 44(1):86-94, 2008.
(Continued)

*Primary Examiner* — Rebecca Anderson
*Assistant Examiner* — Karen Cheng
(74) *Attorney, Agent, or Firm* — Edgar W. Harlan; Carolyn S. Elmore, Esq.; Elmore Patent Law Group, P.C.

(57) ABSTRACT

The present invention discloses compounds of Formula (I), or pharmaceutically acceptable salts, esters, or prodrugs thereof:

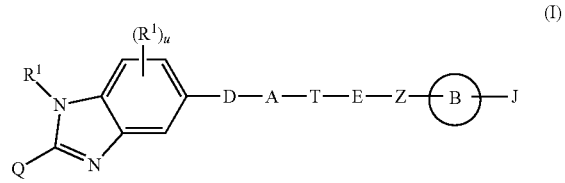

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

18 Claims, No Drawings

Related U.S. Application Data continuation-in-part of application No. 13/252,924, filed on Oct. 4, 2011, now Pat. No. 8,673,954, and a continuation-in-part of application No. 12/714,583, filed on Mar. 1, 2010, now Pat. No. 8,101,643.

(60) Provisional application No. 61/156,131, filed on Feb. 27, 2009.

(51) Int. Cl.
| | |
|---|---|
| *A61K 31/422* | (2006.01) |
| *C07D 491/107* | (2006.01) |
| *A61K 31/517* | (2006.01) |
| *C07D 417/14* | (2006.01) |
| *A61K 45/06* | (2006.01) |
| *A61K 38/19* | (2006.01) |
| *A61K 38/21* | (2006.01) |
| *A61K 31/427* | (2006.01) |
| *A61K 31/7056* | (2006.01) |
| *C07F 9/6558* | (2006.01) |
| *A61K 31/13* | (2006.01) |

(56) References Cited

U.S. PATENT DOCUMENTS

| | | |
|---|---|---|
| 8,188,132 B2 | 5/2012 | Or et al. |
| 8,242,156 B2 | 8/2012 | Qiu et al. |
| 8,314,135 B2 | 11/2012 | Qiu et al. |
| 8,420,686 B2 | 4/2013 | Or et al. |
| 8,426,458 B2 | 4/2013 | Or et al. |
| 8,507,522 B2 | 8/2013 | Or et al. |
| 8,673,954 B2 | 3/2014 | Qiu et al. |
| 8,921,573 B2 * | 12/2014 | Tang et al. ............ 548/300.7 |
| 2005/0222198 A1 | 10/2005 | Bondy et al. |
| 2006/0003942 A1 | 1/2006 | Tung et al. |
| 2006/0058317 A1 | 3/2006 | Gravestock et al. |
| 2006/0178399 A1 | 8/2006 | Nishizawa et al. |
| 2007/0197558 A1 | 8/2007 | Betebenner et al. |
| 2007/0244148 A1 | 10/2007 | Bondy et al. |
| 2007/0299068 A1 | 12/2007 | Karp et al. |
| 2008/0044379 A1 | 2/2008 | Bachand et al. |
| 2008/0194803 A1 | 8/2008 | Sinclair et al. |
| 2008/0299075 A1 | 12/2008 | Bachand et al. |
| 2009/0004140 A1 | 1/2009 | Qiu et al. |
| 2009/0020478 A1 | 1/2009 | Erwe et al. |
| 2009/0047247 A1 | 2/2009 | Qiu et al. |
| 2009/0202483 A1 | 8/2009 | Bachard et al. |
| 2009/0317360 A1 | 12/2009 | Rai et al. |
| 2010/0041591 A1 * | 2/2010 | Niu et al. ............ 514/10 |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0260708 A1 | 10/2010 | Belema et al. |
| 2010/0260715 A1 | 10/2010 | Or et al. |
| 2010/0305117 A1 | 12/2010 | Herdewijn et al. |
| 2010/0310512 A1 | 12/2010 | Guo et al. |
| 2010/0316607 A1 | 12/2010 | Or et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0142798 A1 | 6/2011 | Qiu et al. |
| 2011/0189129 A1 | 8/2011 | Qiu et al. |
| 2011/0195044 A1 | 8/2011 | Romine |
| 2011/0217261 A1 | 9/2011 | Or et al. |
| 2011/0250172 A1 | 10/2011 | Qiu et al. |
| 2011/0300104 A1 | 12/2011 | Qiu et al. |
| 2012/0039848 A1 | 2/2012 | Qiu et al. |

FOREIGN PATENT DOCUMENTS

| | | |
|---|---|---|
| WO | 2008021927 A2 | 2/2008 |
| WO | 2008021928 A2 | 2/2008 |
| WO | 2008021936 A2 | 2/2008 |
| WO | 2008144380 A1 | 11/2008 |
| WO | 2009020825 A1 | 2/2009 |
| WO | 2009020828 A1 | 2/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2010014744 A1 | 2/2010 |
| WO | 2010017401 A1 | 2/2010 |
| WO | 2010039793 A1 | 4/2010 |
| WO | 2010065668 A1 | 6/2010 |
| WO | 2010065674 A1 | 6/2010 |
| WO | 2010065681 A1 | 6/2010 |
| WO | 2010065687 A1 | 6/2010 |
| WO | 2010096302 A1 | 8/2010 |
| WO | 2010096777 A1 | 8/2010 |
| WO | 2010111483 A1 | 9/2010 |
| WO | 2010111534 A1 | 9/2010 |
| WO | 2010111673 A1 | 9/2010 |
| WO | 2010117635 A1 | 10/2010 |
| WO | 2010117704 A1 | 10/2010 |
| WO | 2010117977 A1 | 10/2010 |
| WO | 2010120621 A1 | 10/2010 |
| WO | 2010120935 A1 | 10/2010 |
| WO | 2010122162 A1 | 10/2010 |
| WO | 2010132538 A1 | 11/2010 |
| WO | 2010132810 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2011004276 A1 | 1/2011 |
| WO | 2011009084 A2 | 1/2011 |
| WO | 2011015657 A1 | 2/2011 |
| WO | 2011015658 A1 | 2/2011 |
| WO | 2011026920 A1 | 3/2011 |
| WO | 2011028596 A1 | 3/2011 |
| WO | 2011031904 A1 | 3/2011 |
| WO | 2011031934 A1 | 3/2011 |
| WO | 2011150243 A1 | 12/2011 |
| WO | 2012018325 A1 | 2/2013 |

OTHER PUBLICATIONS

Bressanelli, et al., "Crystal Structure of the RNA-dependent RNA Polymerase of Hepatitis C Virus," PNAS, 96 (23):13034-13039, 1999.

Tellinghuisen, et al., "Structure of the zinc-binding domain of an essential component of the hepatitis C virus replicase," Nature letters, 435:374-479 & 374, abstract (2005).

"Interferon", http://en.wiktionary.org/wiki/interferon, accessed Apr. 6, 2011.

"Inhibitor", http://www.biology-online.org/dictionary/Inhibitor, accessed Apr. 6, 2011.

Porter, "Resolution of Chiral Drugs," Pure & Appl. Chem., 63(8):1119-1122, 1991.

International Search Report for PCT/US2010/24447, dated Apr. 12, 2010.

International Search Report for PCT/US12/57834, dated Nov. 5, 2012.

* cited by examiner

BENZIMIDAZOLE DERIVATIVES

RELATED APPLICATIONS

This is a continuation of International Application No. PCT/US2012/057834, which designated the United States and was filed on Sep. 28, 2012, published in English, which is a continuation-in-part of U.S. application Ser. No. 13/252,924 filed Oct. 4, 2011, now U.S. Pat. No. 8,673,954, issued on Mar. 18, 2012, which is a continuation-in-part of U.S. application Ser. No. 12/714,583, filed Mar. 1, 2010, now U.S. Pat. No. 8,101,643, issued on Jan. 24, 2012, which claims the benefit of U.S. Provisional Application No. 61/156,131 filed Feb. 27, 2009. The entire teachings of the above applications are incorporated herein by reference.

TECHNICAL FIELD

The present invention relates to novel antiviral agents. More specifically, the present invention relates to compounds which can inhibit the function of the NS5A protein encoded by Hepatitis C virus (HCV), compositions comprising such compounds, methods for inhibiting HCV viral replication, methods for treating or preventing HCV infection, and processes for making the compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. Recently, with the introduction of pegylated interferon (Peg-IFN), both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several nonstructural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyper-phosphorylated (58 kDa) forms. While its function has not fully been elucidated, NS5A is believed to be important in viral replication. The NS5B protein (591 amino acids, 65 kDa) of HCV (Behrens, S. E. et al (1996) *EMBO J.* 151 2-22) encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) *Journal of Virology,* 74(4): 2046-2051). Thus, inhibition of NS5B RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215744-749; Tanaka, T. et al (1996) J. Virology 70:3307-3312; Yamada, N. et al (1996) Virology 223:255-261). The 3'NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1; and in Rice, C. M. Nature 2005, 435, 374.

Based on the foregoing, there exists a significant need to identify compounds with the ability to inhibit HCV. A general strategy for the development of antiviral agents is to inactivate virally encoded proteins, including NS5A, that are essential for the replication of the virus. The relevant patent disclosures describing the synthesis of HCV NS5A inhibitors are: US 2009/0202478; US 2009/0202483; WO 2009/020828; WO 2009/020825; WO 2009/102318; WO 2009/102325; WO 2009/102694; WO 2008/144380; WO 2008/021927; WO 2008/021928; WO 2008/021936; WO 2006/133326; WO 2004/014852; WO 2008/070447; WO 2009/034390; WO 2006/079833; WO 2007/031791; WO 2007/070556; WO 2007/070600; WO 2008/064218; WO 2008/154601; WO 2007/082554; and WO 2008/048589; the contents of each of which are expressly incorporated by reference herein.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal aspect, the present invention provides a compound of Formula (I)

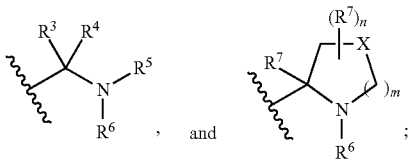

(I)

or a pharmaceutically acceptable salt thereof, wherein:

D and Z are each independently absent or optionally substituted linear aliphatic group containing zero to eight carbons;

A and E are each independently absent or a cyclic group independently selected from aryl, heteroaryl, heterocyclic, $C_3$-$C_8$ cycloalkyl, and $C_3$-$C_8$ cycloalkenyl, each optionally substituted;

T is absent or an optionally substituted aliphatic group;

Wherein one to four of A, D, E, T and Z is absent;

Ring B is a five-membered heteroaryl wherein said heteroaryl is optionally substituted; preferably, a five-membered heteroaryl containing one or more nitrogen; more preferably, imidazolyl that is C-attached to group J and one of groups Z, E, T, A and D;

$R^1$ at each occurrence is independently selected from the group consisting of hydrogen, halogen, cyano, optionally substituted $C_1$-$C_4$ alkyl, —O—$R^{11}$, —N$R^a R^b$, —C(O)$R^{11}$, —CO$_2 R^{11}$, and —C(O)N$R^a R^b$; preferably hydrogen, halogen and optionally substituted $C_1$-$C_4$ alkyl;

$R^{11}$ at each occurrence is independently hydrogen or optionally substituted $C_1$-$C_8$ alkyl;

$R^a$ and $R^b$ at each occurrence are each independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic or optionally substituted heteroaryl group;

u is 1, 2, or 3;

Q and J are each independently selected from:

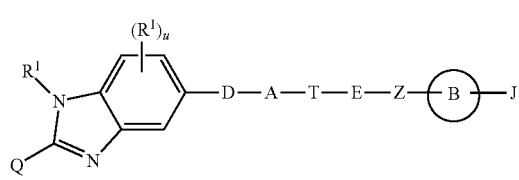

$R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; preferably hydrogen or optionally substituted $C_1$-$C_4$ alkyl; or alternatively, $R^3$ and $R^4$ can be taken together with the carbon atom to which they are attached to form optionally substituted $C_3$-$C_8$ cycloalkyl or optionally substituted heterocyclic;

$R^5$ at each occurrence is independently hydrogen, optionally substituted $C_1$-$C_8$ alkyl, or optionally substituted $C_3$-$C_8$ cycloalkyl; preferably hydrogen or optionally substituted $C_1$-$C_4$ alkyl;

$R^6$ at each occurrence is independently selected from the group consisting of —C(O)—$R^{12}$, —C(O)—C(O)—$R^{12}$, —S(O)$_2$—$R^{12}$, and —C(S)—$R^{12}$, preferably —C(O)—$R^{12}$, more preferably an optionally substituted amino acid acyl;

$R^{12}$ at each occurrence is independently selected from the group consisting of —O—$R^{11}$, —N$R^a R^b$, —$R^{13}$, and —N$R^c R^d$, preferably optionally substituted $C_1$-$C_8$ alkyl and —O—$R^{11}$;

$R^{13}$ at each occurrence is independently selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably optionally substituted $C_1$-$C_8$ alkyl; more preferably $C_1$-$C_8$ alkyl optionally substituted with amino, hydroxy, optionally substituted phenyl, protected amino, or O($C_1$-$C_4$ alkyl); and $R^c$ and $R^d$ at each occurrence are each independently selected from the group consisting of hydrogen, —$R^{13}$, —C(O)—$R^{13}$, —C(O)—O$R^{13}$, —S(O)$_2$—$R^{13}$, —C(O)N($R^{13}$)$_2$, and —S(O)$_2$N($R^{13}$)$_2$;

m is 0, 1, or 2, preferably 1;

n is 1, 2, 3, or 4, preferably 1 or 2;

X at each occurrence is independently selected from O, S, S(O), SO$_2$, and C(R$^7$)$_2$, preferably CH$_2$ or CHR$^7$; provided that when m is 0, X is C(R$^7$)$_2$; and R$^7$ at each occurrence is independently selected from the group consisting of hydrogen, halogen, cyano, —O—R$^{11}$, —NR$^a$R$^b$, optionally substituted aryl, optionally substituted heteroaryl, optionally substituted —C$_1$-C$_4$ alkyl; and optionally substituted C$_3$-C$_8$-cycloalkyl, preferably hydrogen, methyl, cyclopropyl or halogen; or two vicinal R$^7$ groups are taken together with the two adjacent atoms to which they are attached to form a fused, optionally substituted C$_3$-C$_8$ cycloalkyl or optionally substituted heterocyclic ring; preferably a fused, optionally substituted cyclopropyl; or alternatively two geminal R$^7$ groups are taken together with the carbon atom to which they are attached to form a spiro, optionally substituted C$_3$-C$_8$ cycloalkyl or optionally substituted heterocyclic ring; preferably a spiro, optionally substituted cyclopropyl.

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with a therapeutically effective amount of a compound or a combination of compounds of the present invention, or a pharmaceutically acceptable salt thereof. Particularly, this invention is directed to methods of inhibiting the replication of HCV.

In still another aspect, the present invention provides a method of treating or preventing infection caused by an RNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HCV.

Yet another aspect of the present invention provides the use of a compound or combination of compounds of the present invention, or a therapeutically acceptable salt thereof, as defined hereinafter, in the preparation of a medicament for the treatment or prevention of infection caused by RNA-containing virus, specifically HCV.

DETAILED DESCRIPTION OF THE INVENTION

The present invention relates to compounds of Formula (I) as illustrated above, or a pharmaceutically acceptable salt thereof.

The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. application Ser. No. 12/702,673 filed Feb. 9, 2010 entitled "Linked Dibenzimidazole Antivirals"; U.S. application Ser. No. 12/702,692 filed Feb. 9, 2010 entitled "Linked Dibenzimidazole Derivatives"; U.S. application Ser. No. 12/702,802 filed Feb. 9, 2010 entitled "Linked Dibenzimidazole Derivatives"; U.S. application Ser. No. 12/707,190 filed Feb. 17, 2010 entitled "Linked Diimidazole Antivirals"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; and U.S. Provisional Application Ser. No. 61/158,071 filed Mar. 6, 2009 entitled "Hepatitis C Virus Inhibitors"; the contents of each of which are expressly incorporated by reference herein.

In one embodiment, the present invention relates to compounds of Formula (Ia), or a pharmaceutically acceptable salt thereof:

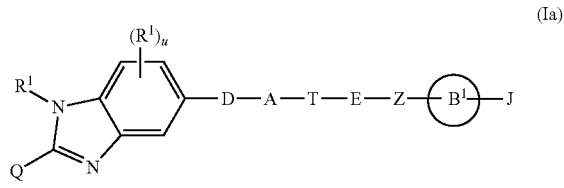

(Ia)

wherein A, D, E, T, Z, Q, J, u, and R$^1$ are as previously defined and Ring B$^1$ is a five-membered heteroaryl that is C-attached to J and to one Z, E, T, A and D.

In another embodiment, the present invention relates to compounds of Formula (Ib), or a pharmaceutically acceptable salt thereof:

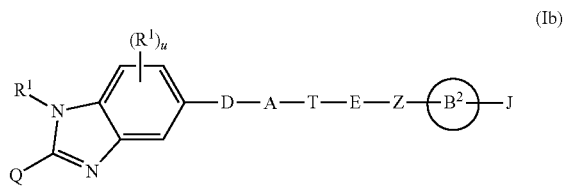

(Ib)

wherein A, D, E, T, Z, Q, J, u, and R$^1$ are as previously defined and Ring B$^2$ is selected from imidazolyl, pyrazolyl, triazolyl, oxadiazolyl, thiazolyl, and isoxazolyl; and B$^2$ is C-attached to J and to one Z, E, T, A and D.

In yet another embodiment, the present invention relates to compounds of Formulae (Ic-1~Ic-4), or a pharmaceutically acceptable salt thereof:

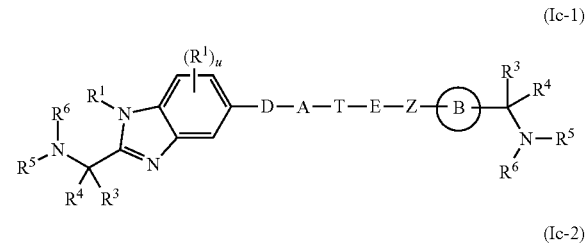

(Ic-1)

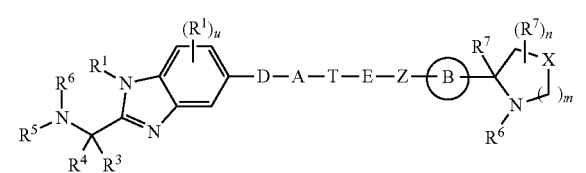

(Ic-2)

-continued

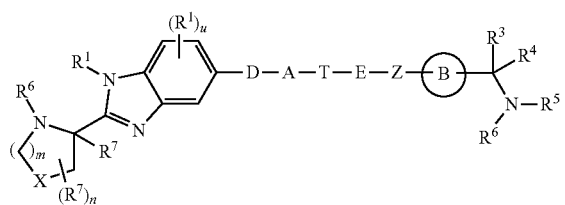
(Ic-3)

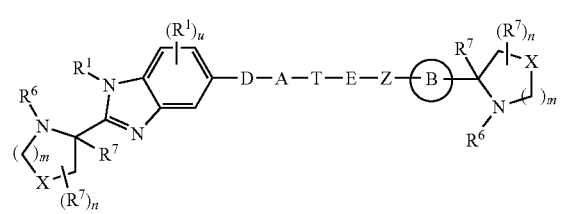
(Ic-4)

wherein A, D, E, T, Z, Ring B, X, u, m, n, $R^1$, $R^3$, $R^4$, $R^5$, $R^6$ and $R^7$ are as previously defined.

In still another embodiment, the present invention relates to compounds of Formulae (Id-1~Id-4), or a pharmaceutically acceptable salt thereof:

(Id-1)

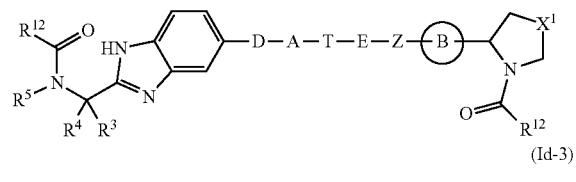
(Id-2)

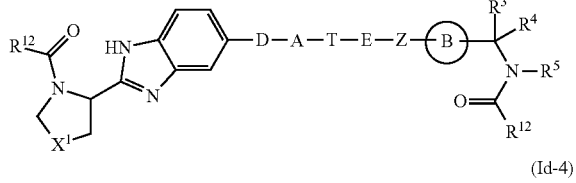
(Id-3)

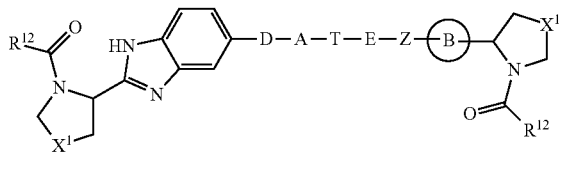
(Id-4)

wherein A, D, E, T, Z, Ring B, $R^3$, $R^4$, $R^5$, and $R^{12}$ are as previously defined and $X^1$ is independently $CH_2$, CHF, CH(OH), or $CF_2$.

In still another embodiment of the present invention, the absolute stereochemistry of the pyrrolidine and 2-benzimidazolylmethylamine or five-membered heteroarylmethylamine moiety is represented by Formulae (Ie-1~Ie-4):

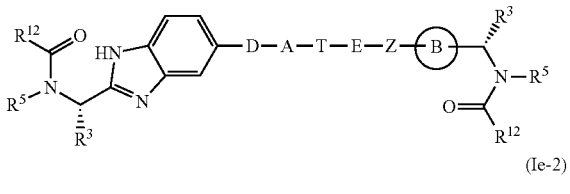
(Ie-1)

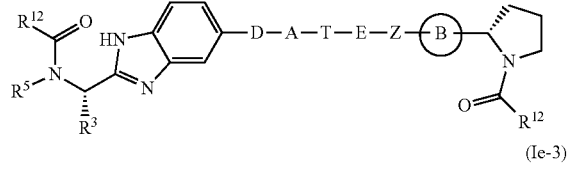
(Ie-2)

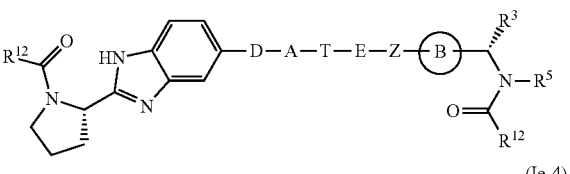
(Ie-3)

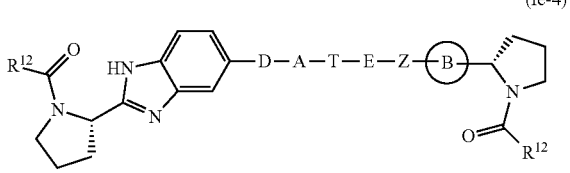
(Ie-4)

wherein A, D, E, T, Z, Ring B, $R^3$, $R^5$, and $R^{12}$ are as previously defined.

In still another embodiment, the present invention relates to compounds of Formula (If), or a pharmaceutically acceptable salt thereof:

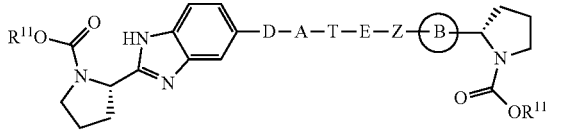
(If)

wherein A, D, E, T, Z, Ring B, and $R^{11}$ are as previously defined.

In still another embodiment, the present invention relates to compounds of Formula (Ig), or a pharmaceutically acceptable salt thereof:

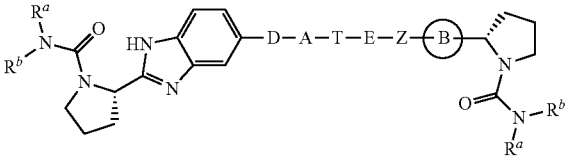
(Ig)

wherein A, D, E, T, Z, Ring B, $R^a$ and $R^b$ are as previously defined.

In still another embodiment, the present invention relates to compounds of Formula (Ih), or a pharmaceutically acceptable salt thereof:

(Ih)

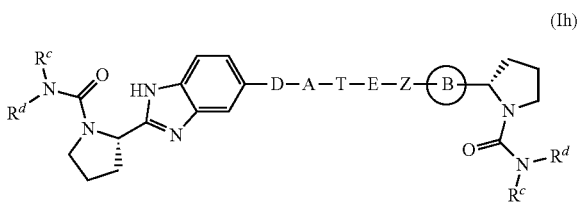

wherein A, D, E, T, Z, Ring B, $R^c$ and $R^d$ are as previously defined.

In still another embodiment, the present invention relates to compounds of Formula (Ii), or a pharmaceutically acceptable salt thereof:

(Ii)

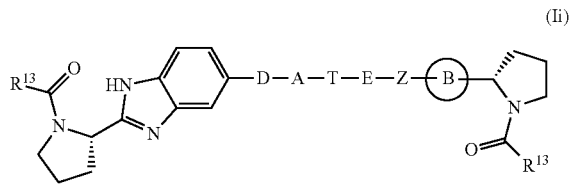

wherein A, D, E, T, Z, Ring B, and $R^{13}$ are as previously defined.

In still another embodiment, the present invention relates to compounds of Formula (Ij), or a pharmaceutically acceptable salt thereof:

(Ij)

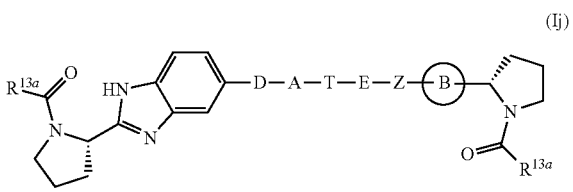

wherein A, D, E, T, Z, Ring B are as previously defined and $R^{13a}$ at each occurrence is independently an optionally substituted $C_1$-$C_8$ alkyl; preferably $C_1$-$C_8$ alkyl optionally substituted with amino, hydroxy, phenyl, protected amino, or $O(C_1$-$C_4$ alkyl); or a pharmaceutically acceptable salt thereof.

In still another embodiment, the present invention relates to compounds of Formula (IIa), or a pharmaceutically acceptable salt thereof:

(IIa)

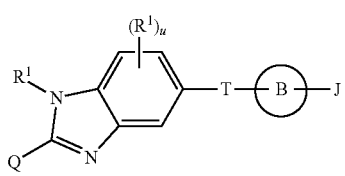

wherein Q, J, Ring B, u, and $R^1$ are as previously defined and T is present and as previously defined.

In still another embodiment, the present invention relates to compounds of Formula (IIb), or a pharmaceutically acceptable salt thereof:

(IIb)

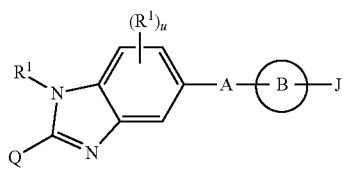

wherein Q, J, Ring B, u, and $R^1$ are as previously defined and A is present and as previously defined.

In still another embodiment, the present invention relates to compounds of Formula (IIc), or a pharmaceutically acceptable salt thereof:

(IIc)

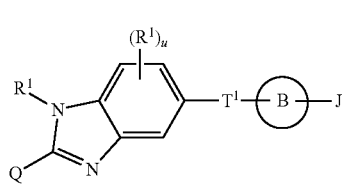

wherein Q, J, Ring B, u, and $R^1$ are as previously defined and $T^1$ is a linear aliphatic group, optionally containing one or more of an olefinic double bond and an alkynic triple bond and further, optionally comprising one or more groups selected from the group consisting of O, $N(R^{11})$, C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ and $C(O)N(R^{11})S(O)_2N(R^{11})$.

In still another embodiment, the present invention relates to compounds of Formula (IId), or a pharmaceutically acceptable salt thereof:

(IId)

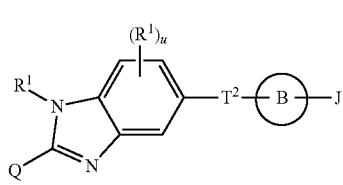

wherein Q, J, Ring B, u, and $R^1$ are as previously defined and $T^2$ is an aliphatic group comprising a $C_3$-$C_8$ cycloalkyl or $C_3$-$C_8$ cycloalkenyl and optionally contains one or more of an olefinic double bond and an alkynic triple bond and further, optionally comprises one or more groups selected from the group consisting of O, $N(R^{11})$, C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ and $C(O)N(R^{11})S(O)_2N(R^{11})$.

In still another embodiment, the present invention relates to compounds of Formulae (IIIa-1 and IIIa-2), or a pharmaceutically acceptable salt thereof:

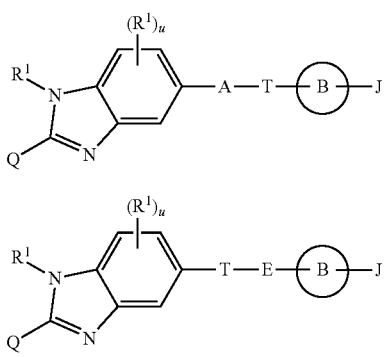

wherein Q, J, Ring B, u, and $R^1$ are as previously defined; in Formula (IIIa-1), A and T are each present and as previously defined; and in Formula (IIIa-2), T and E are each present and as previously defined.

In still another embodiment, the present invention relates to compounds of Formula (IIIa-3), or a pharmaceutically acceptable salt thereof:

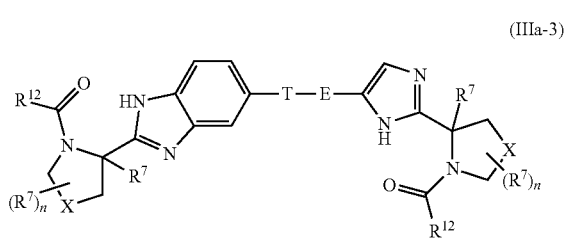

wherein n is 1 or 2; T is absent or optionally substituted $C_2$-$C_4$ alkenyl or optionally substituted $C_2$-$C_4$ alkynyl; E is phenyl, monocyclic heteroaryl, bicyclic aryl, or bicyclic heteroaryl, each optionally substituted; X at each occurrence is independently $CH_2$, CHF, CH(OH), CHMe, $CF_2$, or $C(R^7)_2$; wherein $R^7$ at each occurrence is independently hydrogen or methyl; alternatively, the two geminal $R^7$ groups are taken together with the carbon to which they are attached to form a spiro, optionally substituted $C_3$-$C_8$ cycloalkyl; or yet alternatively, two vicinal $R^7$ groups are taken together with the two adjacent atoms to which they are attached to form a fused, optionally substituted $C_3$-$C_8$ cycloalkyl; and $R^{12}$ at each occurrence is independently optionally substituted $C_1$-$C_8$ alkyl. In certain aspects, the invention is a compound of Formula (IIIa-3), wherein $R^{12}$ at each occurrence is independently $C_1$-$C_8$ alkyl substituted with —$NHCO_2$($C_1$-$C_4$ alkyl) or O($C_1$-$C_4$ alkyl).

In still another embodiment, the present invention relates to compounds of Formula (IIIa-3), or a pharmaceutically acceptable salt thereof; wherein two geminal $R^7$ groups are taken together with the carbon to which they are attached to form a spiro cyclopropyl; and $R^{12}$ at each occurrence is independently $C_1$-$C_8$ alkyl optionally substituted with amino, hydroxy, protected amino, or O($C_1$-$C_4$ alkyl).

In still another embodiment, the present invention relates to compounds of Formula (IIIa-3), or a pharmaceutically acceptable salt thereof; wherein two vicinal $R^7$ groups are taken together with the two adjacent atoms to which they are attached to form a fused cyclopropyl; and $R^{12}$ at each occurrence is independently $C_1$-$C_8$ alkyl optionally substituted with amino, hydroxy, protected amino, or O($C_1$-$C_4$ alkyl).

In still another embodiment, the present invention relates to compounds of Formula (III-a), (III-b), (III-c) or (III-d), or a pharmaceutically acceptable salt thereof:

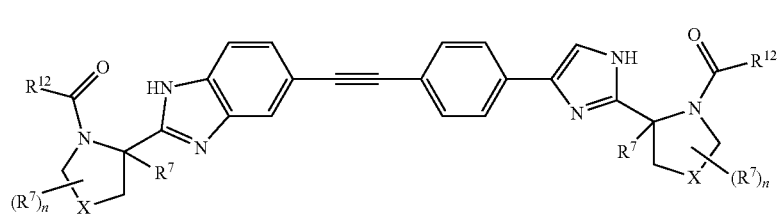

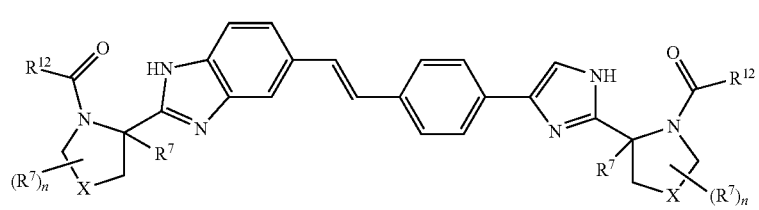

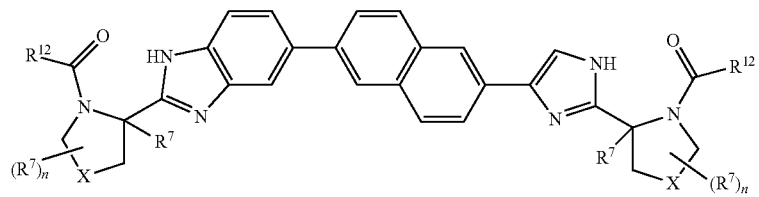

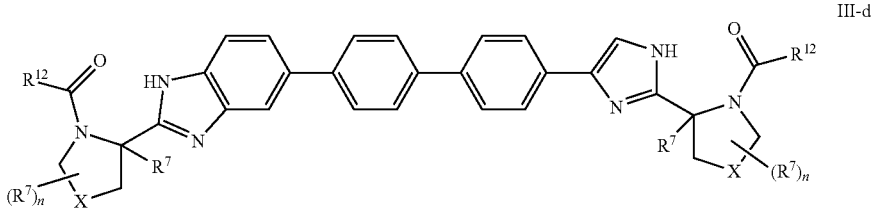

(III-d)

wherein n is 1 or 2; X at each occurrence is each independently $CH_2$, CHF, CH(OH), CHMe, $CF_2$, or $C(R^7)_2$; wherein $R^7$ at each occurrence is independently hydrogen or methyl; alternatively, two geminal $R^7$ groups are taken together with the carbon to which they are attached to form a spiro cyclopropyl; or yet alternatively, two vicinal $R^7$ groups can be taken together with the two adjacent atoms to which they are attached to form a fused cyclopropyl; and $R^{12}$ at each occurrence is independently $C_1$-$C_8$ alkyl optionally substituted with amino, hydroxy, protected amino, or $O(C_1$-$C_4$ alkyl).

In still another embodiment, the present invention relates to compounds of Formula (III-a), (III-b), (III-c) or (III-d); wherein $R^{12}$ at each occurrence is independently $C_1$-$C_8$ alkyl substituted with —$NHCO_2(C_1$-$C_4$ alkyl) or $O(C_1$-$C_4$ alkyl); or a pharmaceutically acceptable salt thereof.

In still another embodiment, the present invention relates to compounds of Formula (IIIb), or a pharmaceutically acceptable salt thereof:

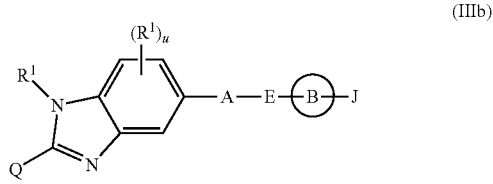

(IIIb)

wherein Q, J, Ring B, u, and $R^1$ are as previously defined; A and E are each present and as previously defined.

In still another embodiment, the present invention relates to compounds of Formulae (IVa-1 and IVa-2), or a pharmaceutically acceptable salt thereof:

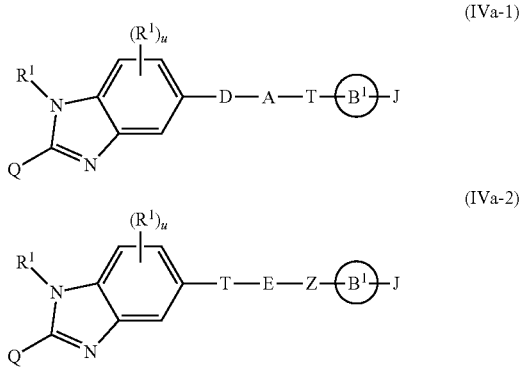

(IVa-1)

(IVa-2)

wherein Ring $B^1$, Q, J, u, and $R^1$ are as previously defined; in Formula (IVa-1), A, D, and T are each present and as previously defined; and in Formula (IVa-2), E, T, and Z are each present and as previously defined.

In still another embodiment, the present invention relates to compounds of Formula (IVb), or a pharmaceutically acceptable salt thereof:

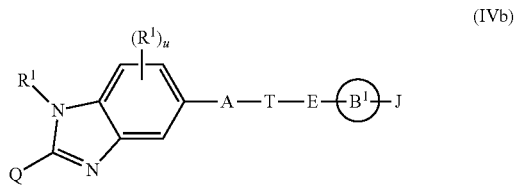

(IVb)

wherein Ring $B^1$, Q, J, u, and $R^1$ are as previously defined; A, E, and T are each present and as previously defined.

In still another embodiment, the present invention relates to compounds of Formulae (Va-1 and Va-2), or a pharmaceutically acceptable salt thereof:

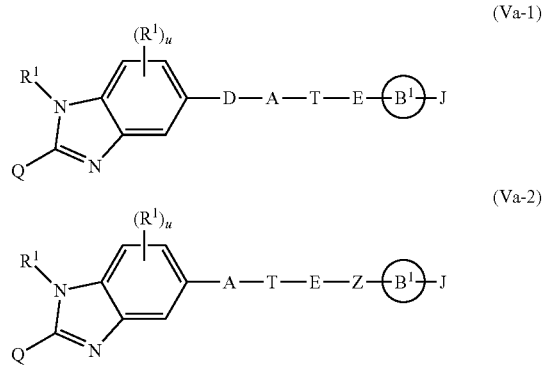

(Va-1)

(Va-2)

wherein Ring $B^1$, Q, J, u, and $R^1$ are as previously defined; in Formula (Va-1), D, A, T and E are each present and as previously defined; in Formula (Va-2), A, E, T, and Z are each present and as previously defined.

In still another embodiment, the present invention relates to compounds of Formula (I), or a pharmaceutically acceptable salt thereof; wherein at each occurrence is independently illustrated by one of the following groups:

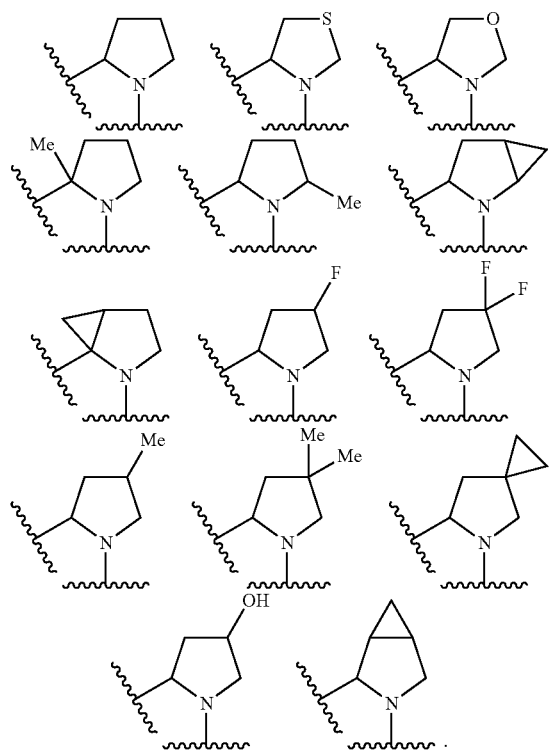
In still another embodiment, the present invention relates to compounds of Formula (I), or a pharmaceutically acceptable salt thereof; wherein
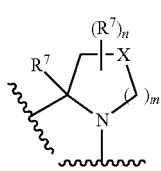
at each occurrence is independently illustrated by one of the following groups:
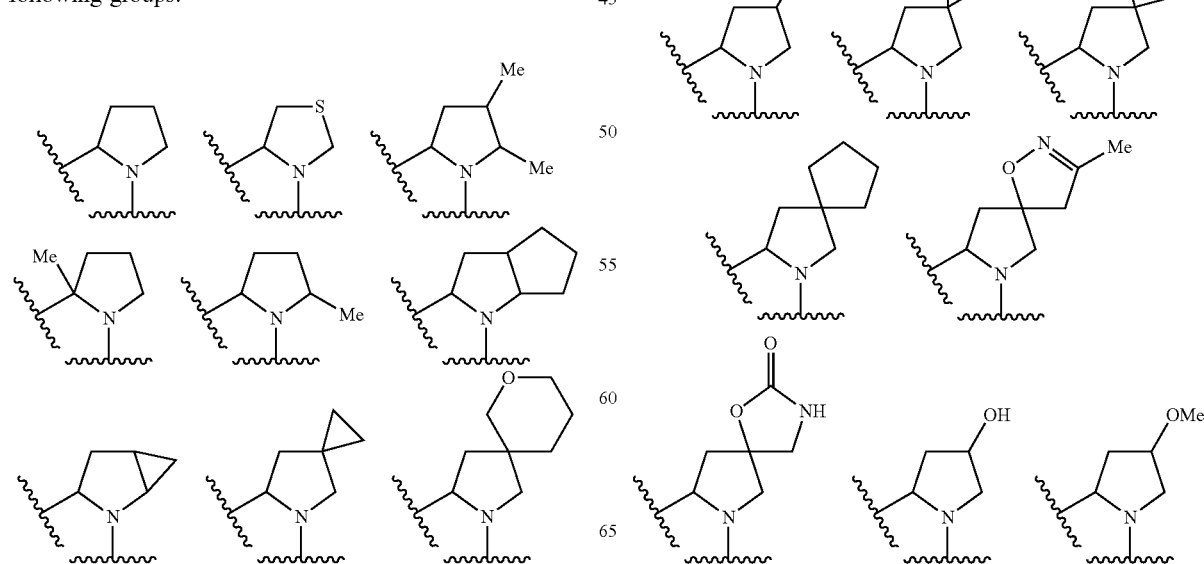
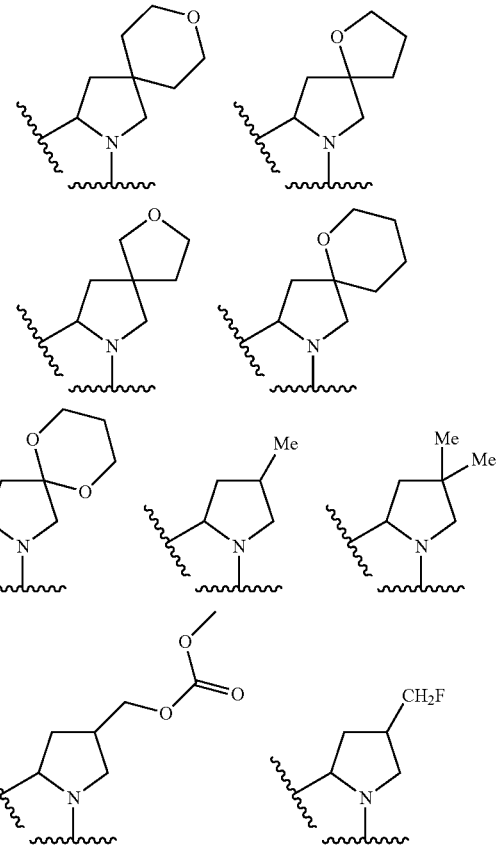

17
-continued
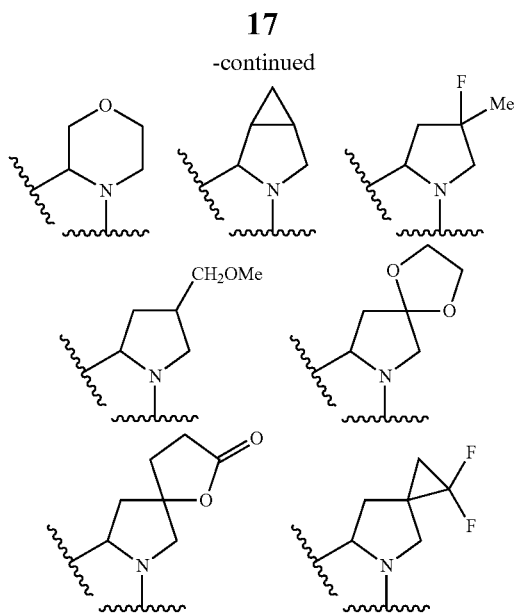
18
-continued
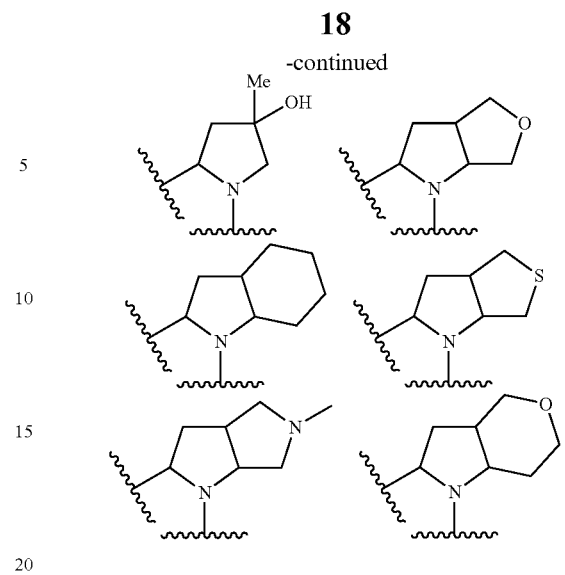
Representative compounds of the present invention are those selected from compounds 1-1, 2-1, and 2-2 (shown below), and compounds 1-695 compiled in Tables 1-9:
compound 1-1
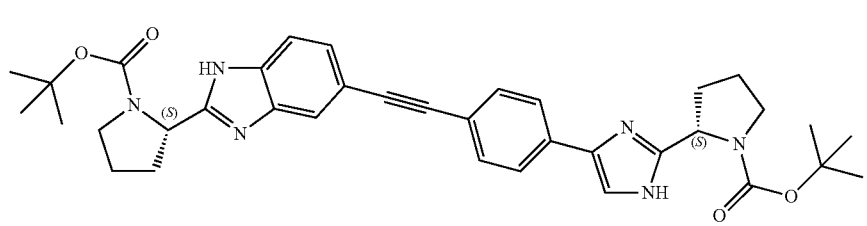
compound 2-1
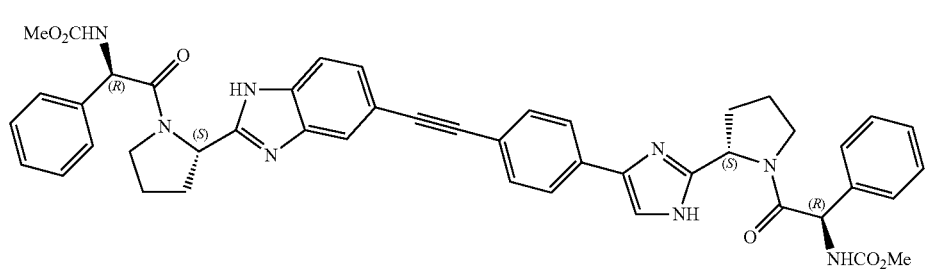
compound 2-2
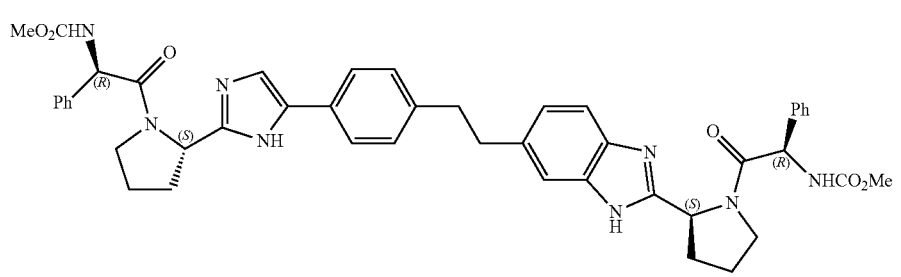

TABLE 1

Compounds 1-219.

| Entry | R group |
|---|---|
| 1 | tert-butyl ester (OC(CH3)3) |
| 2 | N-(methoxycarbonyl)phenylglycinyl |
| 3 | N,N-dimethylamino phenylglycinyl |
| 4 | (S)-2-hydroxypropanoyl (lactyl) |
| 5 | (S)-2-hydroxybutanoyl |
| 6 | propanoyl |
| 7 | methoxyacetyl |
| 8 | N,N-dimethylcarbamoyl |
| 9 | methoxycarbonyl |

TABLE 1-continued

Compounds 1-219.

| Entry | R group |
|---|---|
| 10 | 2,5-dioxohexanoyl (CH₃C(O)CH₂CH₂C(O)–) |
| 11 | (S)-2-hydroxy-3-methylbutanoyl ((CH₃)₂CHCH(OH)C(O)–) |
| 12 | 2-(dimethylamino)-2-oxoacetyl ((CH₃)₂NC(O)C(O)–) |
| 13 | cyclopropanecarbonyl |
| 14 | 1-(trifluoromethyl)cyclopropanecarbonyl |
| 15 | 1-hydroxycyclopropanecarbonyl |
| 16 | benzoyl (PhC(O)–) |
| 17 | phenylacetyl (PhCH₂C(O)–) |

TABLE 1-continued

Compounds 1-219.

| Entry | R group (R-C(=O)-) |
|---|---|
| 18 | cyclopropylmethyl ketone |
| 19 | 2-phenyl-2-hydroxypropanoyl (with methyl, OH) |
| 20 | α-methoxybenzyl carbonyl (Ph, OMe) |
| 21 | α-hydroxybenzyl carbonyl (Ph, OH) |
| 22 | pyridin-3-ylmethyl carbonyl |
| 23 | pyridin-4-ylmethyl carbonyl |
| 24 | 3-phenyl-2-hydroxypropanoyl (Ph, OH) |
| 25 | tetrahydrofuran-2-yl carbonyl |

TABLE 1-continued
Compounds 1-219.
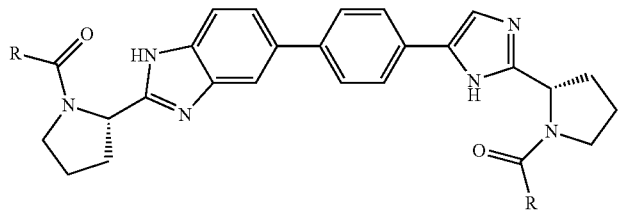
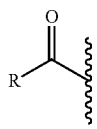
| Entry | |
|---|---|
| 26 | 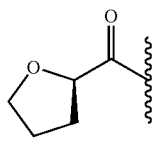 [SMILES: *C(=O)[C@H]1CCCO1] |
| 27 | 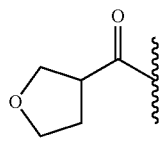 [SMILES: *C(=O)C1CCOC1] |
| 28 | 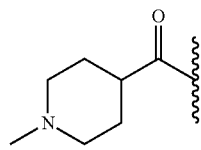 [SMILES: *C(=O)C1CCN(C)CC1] |
| 29 | 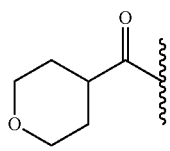 [SMILES: *C(=O)C1CCOCC1] |
| 30 | 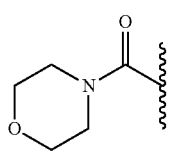 [SMILES: *C(=O)N1CCOCC1] |
| 31 | 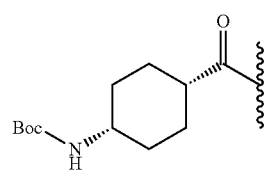 [SMILES: *C(=O)[C@H]1CC[C@@H](NC(=O)OC(C)(C)C)CC1] |
| 32 | 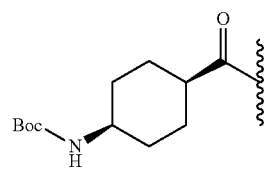 [SMILES: *C(=O)[C@H]1CC[C@@H](NC(=O)OC(C)(C)C)CC1] |

TABLE 1-continued
Compounds 1-219.
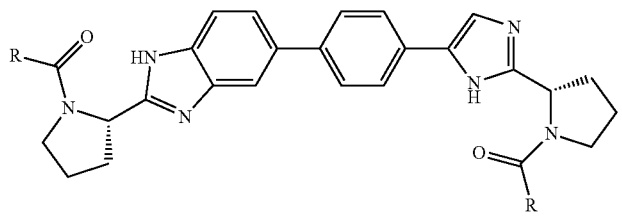
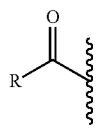
| Entry | |
|---|---|
| 33 |  |
| 34 |  |
| 35 | 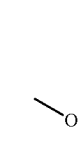 |
| 36 |  |
| 37 |  |
| 38 |  |

TABLE 1-continued
Compounds 1-219.
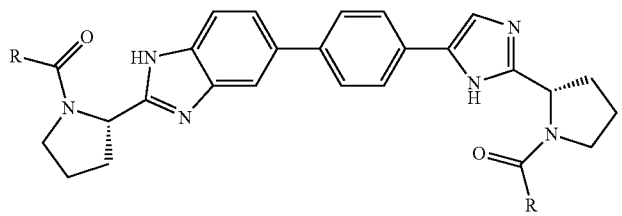
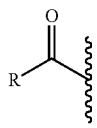
| Entry | |
|---|---|
| 39 | 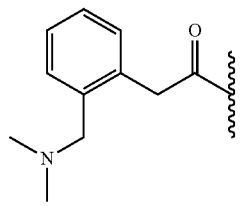 [SMILES: *C(=O)Cc1ccccc1CN(C)C] |
| 40 | 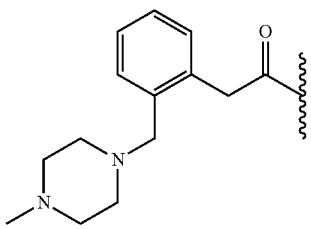 [SMILES: *C(=O)Cc1ccccc1CN1CCN(C)CC1] |
| 41 | 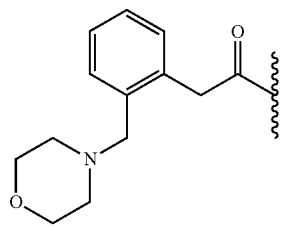 [SMILES: *C(=O)Cc1ccccc1CN1CCOCC1] |
| 42 | 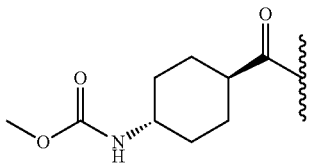 [SMILES: *C(=O)[C@H]1CC[C@H](NC(=O)OC)CC1] |
| 43 | 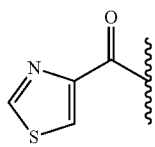 |
| 44 | 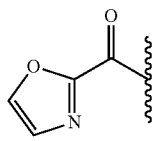 |

TABLE 1-continued
Compounds 1-219.
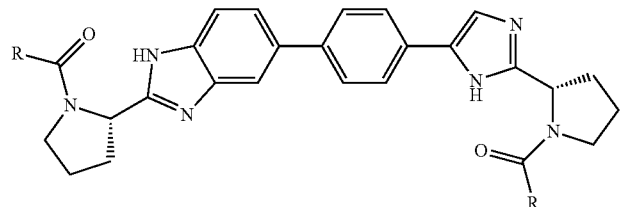
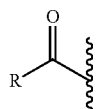
| Entry | |
|---|---|
| 45 | 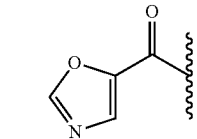 [SMILES: *C(=O)c1cnco1] |
| 46 | 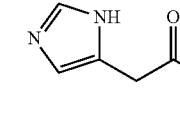 |
| 47 | 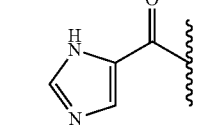 |
| 48 | 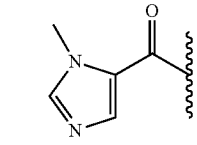 [SMILES: *C(=O)c1cncn1C] |
| 49 | 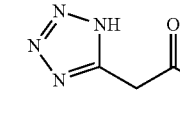 |
| 50 | 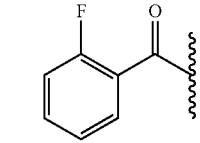 [SMILES: *C(=O)c1ccccc1F] |
| 51 | 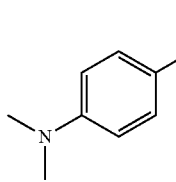 |

TABLE 1-continued
Compounds 1-219.
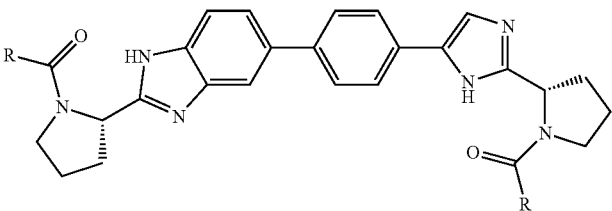
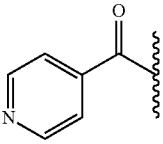 [SMILES: *C(=O)c1ccncc1]
| Entry | |
|---|---|
| 52 | 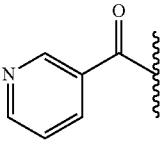 [SMILES: *C(=O)c1cccnc1] |
| 53 | 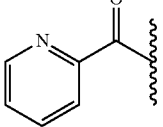 |
| 54 | 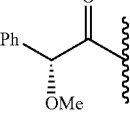 |
| 55 | 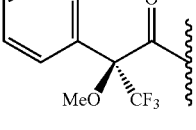 |
| 56 | 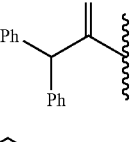 |
| 57 | 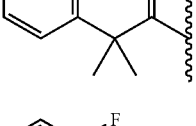 |
| 58 | |
| 59 | 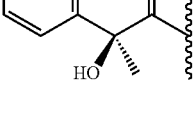 |

TABLE 1-continued

Compounds 1-219.

| Entry | R-C(O)- group |
|---|---|
| 60 | 1-phenylcyclopropanecarbonyl |
| 61 | (S)-2-(methoxycarbonylamino)propanoyl |
| 62 | (R)-2-(methoxycarbonylamino)propanoyl |
| 63 | (S)-2-(ethoxycarbonylamino)propanoyl |
| 64 | (S)-2-((tetrahydro-2H-pyran-4-yloxy)carbonylamino)propanoyl |
| 65 | (R)-2-((tetrahydro-2H-pyran-4-yloxy)carbonylamino)propanoyl |
| 66 | (S)-2-(methoxycarbonylamino)-3-methoxypropanoyl |

TABLE 1-continued

Compounds 1-219.

[Structure: bis-benzimidazole/imidazole-phenylene core with two acyl-pyrrolidine substituents bearing R-C(=O)- groups]

R-C(=O)- group:

| Entry | R-C(=O)- |
|---|---|
| 67 | methyl carbamate-NH-CH(Et)-C(=O)- |
| 68 | methyl carbamate-NH-CH(Et)-C(=O)- |
| 69 | methyl carbamate-NH-CH(CH2CH2OMe)-C(=O)- |
| 70 | methyl carbamate-NH-CH(CH(OH)CH3)-C(=O)- |
| 71 | methyl carbamate-NH-CH(CH(OH)CH3)-C(=O)- |
| 72 | methyl carbamate-NH-CH(CH(OMe)CH3)-C(=O)- |
| 73 | methyl carbamate-NH-CH(CH2CH=CH2)-C(=O)- |

TABLE 1-continued

Compounds 1-219.

| Entry | R group |
|---|---|
| 74 | methyl ((S)-1-oxopentyl)carbamate with NHC(O)OMe (norvaline-type, MeO-C(O)-NH-CH(CH2CH2CH3)-C(O)-) |
| 75 | (S)-4-(dimethylamino)-2-((tert-butoxycarbonyl)amino)butanoyl |
| 76 | methyl (2-methyl-1-oxopropan-2-yl)carbamate (α,α-dimethyl, MeO-C(O)-NH-C(CH3)2-C(O)-) |
| 77 | methyl ((S)-1-cyclopropyl-2-oxoethyl)carbamate |
| 78 | methyl ((R)-1-cyclopropyl-2-oxoethyl)carbamate |
| 79 | methyl ((S)-3-hydroxy-3-methyl-1-oxobutan-2-yl)carbamate |
| 80 | methyl ((S)-4-(benzyloxy)-1,4-dioxobutan-2-yl)carbamate (CO2Bn side chain) |

TABLE 1-continued
Compounds 1-219.
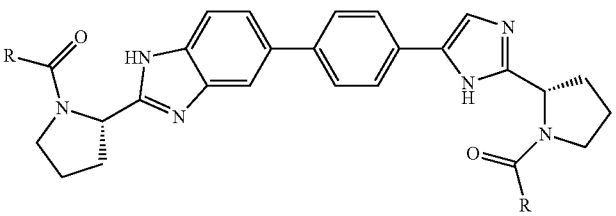
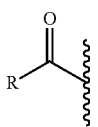
| Entry | |
|---|---|
| 81 | 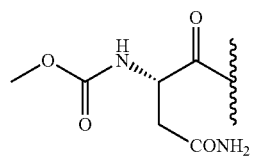 |
| 82 | 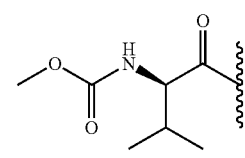 [SMILES: *C(=O)[C@H](NC(=O)OC)C(C)C] |
| 83 | 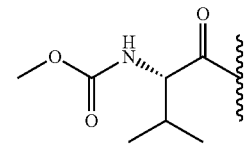 [SMILES: *C(=O)[C@@H](NC(=O)OC)C(C)C] |
| 84 | 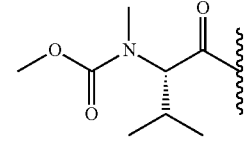 [SMILES: *C(=O)[C@H](C(C)C)N(C)C(=O)OC] |
| 85 | 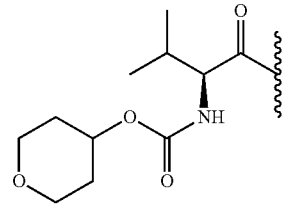 [SMILES: *C(=O)[C@@H](NC(=O)OC1CCOCC1)C(C)C] |
| 86 | 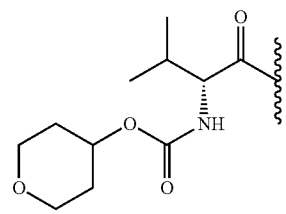 [SMILES: *C(=O)[C@H](NC(=O)OC1CCOCC1)C(C)C] |

TABLE 1-continued
Compounds 1-219.
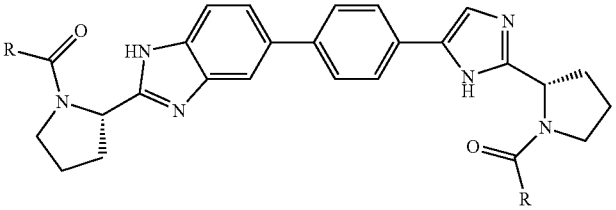
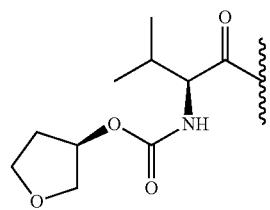 [SMILES: *C(=O)[C@@H](NC(=O)O[C@@H]1CCOC1)C(C)C]
| Entry | |
|---|---|
| 87 | 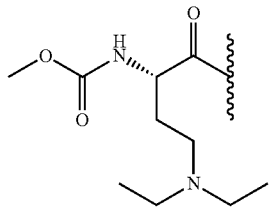 [SMILES: *C(=O)[C@H](CCN(CC)CC)NC(=O)OC] |
| 88 | 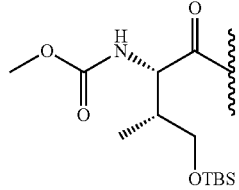 [SMILES: *C(=O)[C@@H](NC(=O)OC)[C@@H](C)CO[Si](C)(C)C(C)(C)C] |
| 89 | 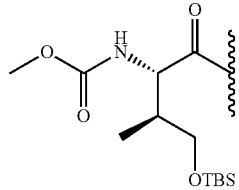 [SMILES: *C(=O)[C@@H](NC(=O)OC)[C@H](C)CO[Si](C)(C)C(C)(C)C] |
| 90 | 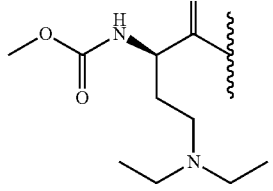 |
| 91 | |

TABLE 1-continued
Compounds 1-219.
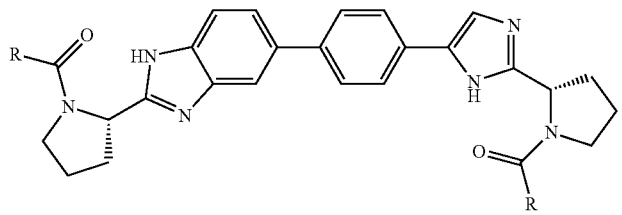
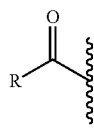
| Entry | |
|---|---|
| 92 | 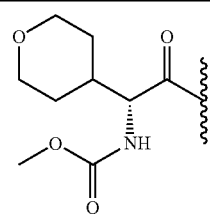 |
| 93 | 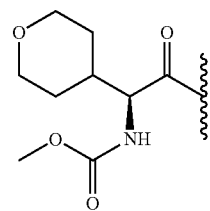 [SMILES: *C(=O)[C@@H](NC(=O)OC)C1CCOCC1] |
| 94 | 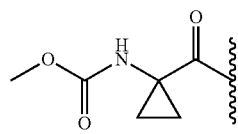 [SMILES: *C(=O)C1(NC(=O)OC)CC1] |
| 95 | 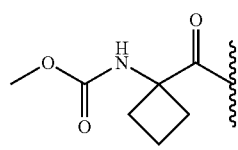 [SMILES: *C(=O)C1(NC(=O)OC)CCC1] |
| 96 | 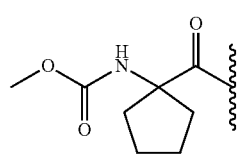 [SMILES: *C(=O)C1(NC(=O)OC)CCCC1] |
| 97 | 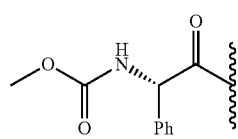 [SMILES: *C(=O)[C@@H](NC(=O)OC)c1ccccc1] |
| 98 | 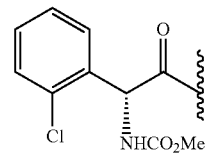 |

TABLE 1-continued

Compounds 1-219.

| Entry | R–C(O)– group |
|---|---|
| 99 | (S)-2-acetamido-2-phenylacetyl |
| 100 | (S)-2-(3-methylureido)-2-phenylacetyl |
| 101 | (S)-2-(3,3-dimethylureido)-2-phenylacetyl |
| 102 | (S)-2-(3-ethylureido)-2-phenylacetyl |
| 103 | (S)-2-(3-cyclopentylureido)-2-phenylacetyl |
| 104 | (S)-1-(methoxycarbonyl)azetidine-2-carbonyl |

TABLE 1-continued
Compounds 1-219.
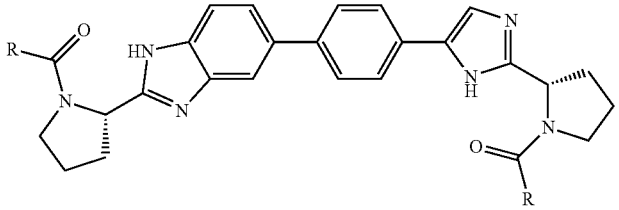
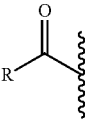
| Entry | |
|---|---|
| 105 | 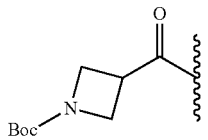 |
| 106 | 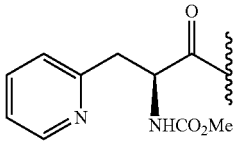 |
| 107 | 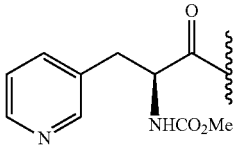 |
| 108 | 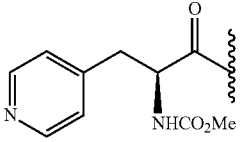 |
| 109 | 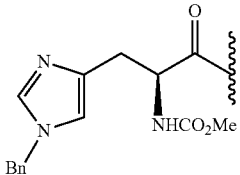 |
| 110 | 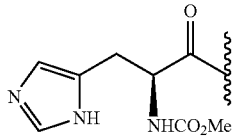 |
| 111 | 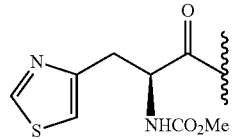 |

TABLE 1-continued
Compounds 1-219.
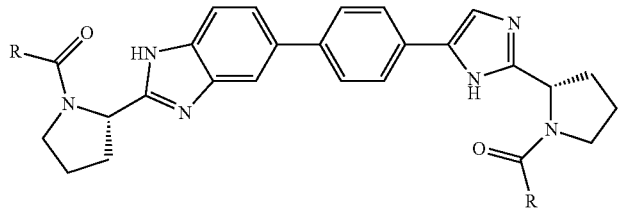
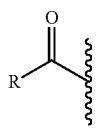
| Entry | |
|---|---|
| 112 | 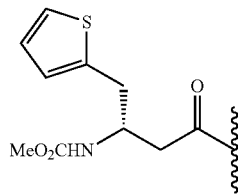 |
| 113 | 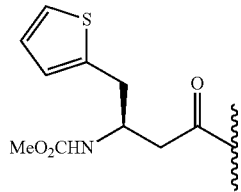 |
| 114 | 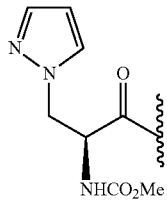 |
| 115 | 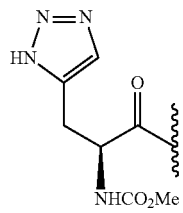 |
| 116 | 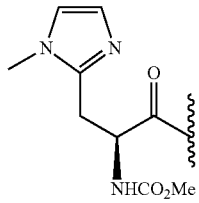 |

TABLE 1-continued
Compounds 1-219.
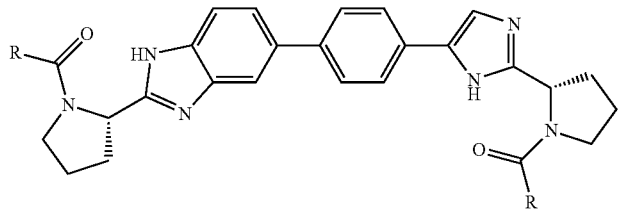
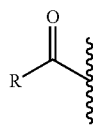
Entry
117
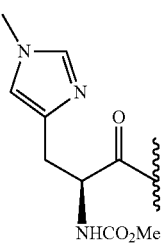
118
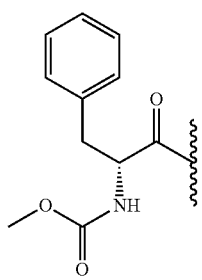 [SMILES: *C(=O)[C@@H](Cc1ccccc1)NC(=O)OC]
119
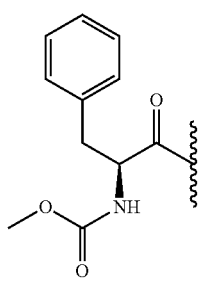 [SMILES: *C(=O)[C@H](Cc1ccccc1)NC(=O)OC]
120
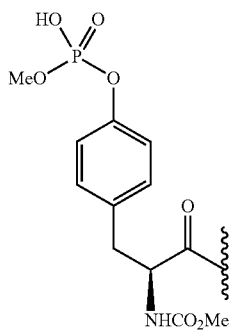

TABLE 1-continued
Compounds 1-219.
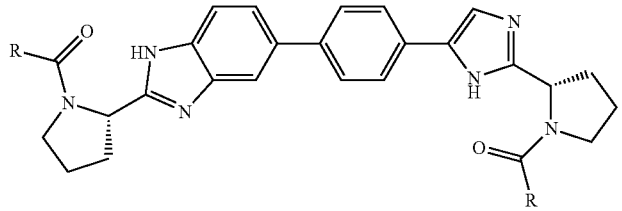
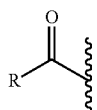
| Entry | |
|---|---|
| 121 | 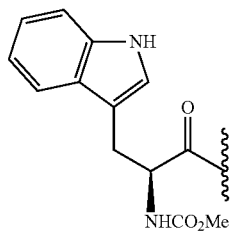 |
| 122 | 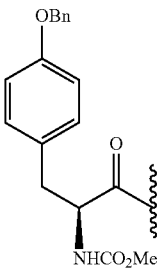 |
| 123 | 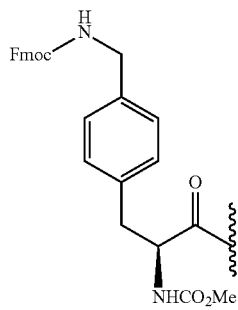 |
| 124 | 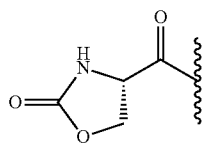 [SMILES: *C(=O)[C@@H]1COC(=O)N1] |
| 125 | 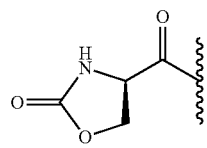 [SMILES: *C(=O)[C@H]1COC(=O)N1] |

TABLE 1-continued

Compounds 1-219.

[Structure: core compound with R-C(=O)- groups on both pyrrolidine nitrogens, connected via benzimidazole-phenyl-imidazole system]

R-C(=O)-~ (substituent definition)

| Entry | |
|---|---|
| 126 | [oxazolidinone-2-one with methyl substituent, connected via C(=O)] |
| 127 | [methyl carbamate on cyclopentane, cis, with C(=O) linker] |
| 128 | [methyl carbamate on cyclopentane, trans, with C(=O) linker] |
| 129 | [methyl carbamate on cyclohexane with C(=O) linker] |
| 130 | [methyl carbamate on 1,3-cyclopentane with C(=O) linker] |
| 131 | [methyl carbamate on 1,3-cyclopentane, different stereochemistry, with C(=O) linker] |

TABLE 1-continued
Compounds 1-219.
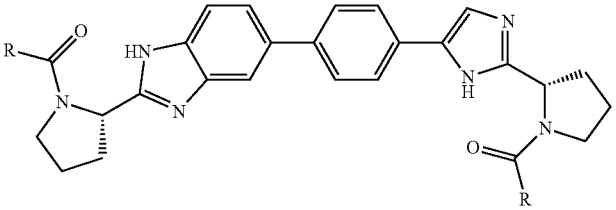
| Entry | R-C(O)- |
|---|---|
| 132 | 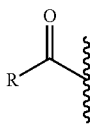 |
| 133 | 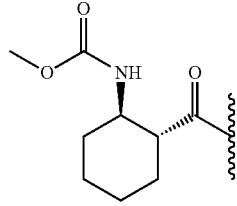 [SMILES: *C(=O)[C@@H]1CCCC[C@H]1NC(=O)OC] |
| 134 | 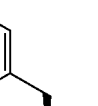 |
| 135 | 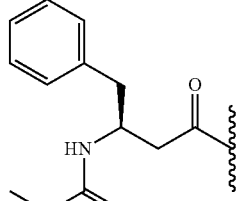 |
| 136 | 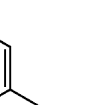 |

TABLE 1-continued
Compounds 1-219.
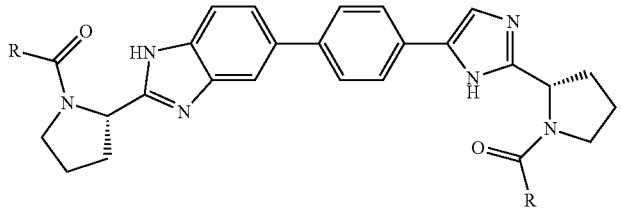
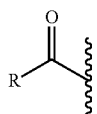
| Entry | |
|---|---|
| 137 | 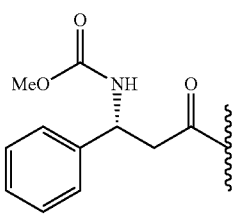 [SMILES: *C(=O)C[C@@H](NC(=O)OC)c1ccccc1] |
| 138 | 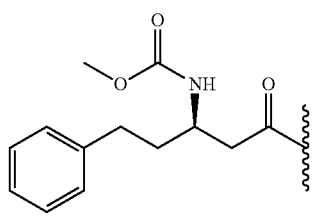 [SMILES: *C(=O)C[C@@H](CCc1ccccc1)NC(=O)OC] |
| 139 | 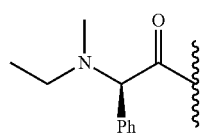 [SMILES: *C(=O)[C@@H](c1ccccc1)N(C)CC] |
| 140 | 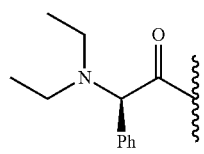 [SMILES: *C(=O)[C@@H](c1ccccc1)N(CC)CC] |
| 141 | 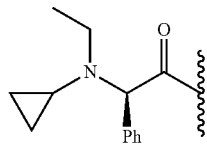 [SMILES: *C(=O)[C@@H](c1ccccc1)N(CC)C1CC1] |
| 142 | 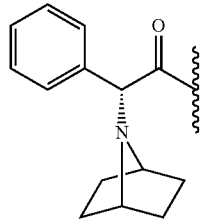 [SMILES: *C(=O)[C@@H](c1ccccc1)N1C2CCC1CC2] |

TABLE 1-continued
Compounds 1-219.
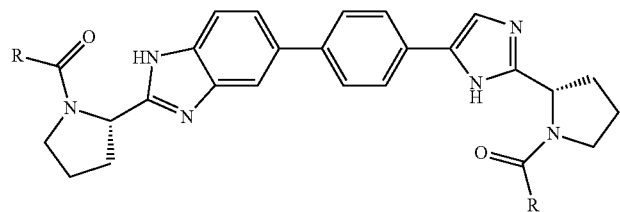
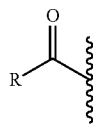
| Entry | |
|---|---|
| 143 | 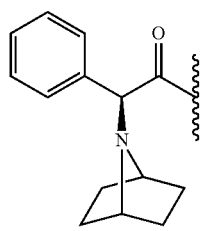 [SMILES: *C(=O)[C@H](c1ccccc1)N1C2CCC1CC2] |
| 144 | 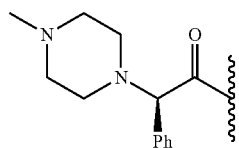 [SMILES: *C(=O)[C@@H](c1ccccc1)N1CCN(C)CC1] |
| 145 | 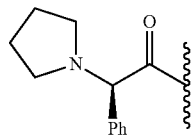 [SMILES: *C(=O)[C@@H](c1ccccc1)N1CCCC1] |
| 146 | 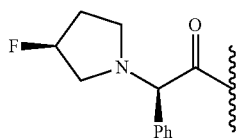 [SMILES: *C(=O)[C@@H](c1ccccc1)N1CC[C@H](F)C1] |
| 147 | 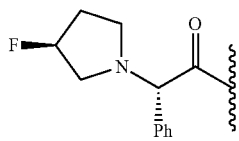 [SMILES: *C(=O)[C@H](c1ccccc1)N1CC[C@H](F)C1] |
| 148 | 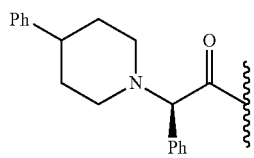 [SMILES: *C(=O)[C@@H](c1ccccc1)N1CCC(c2ccccc2)CC1] |
| 149 | 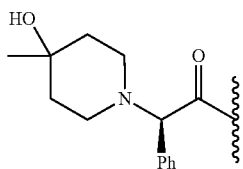 [SMILES: *C(=O)[C@@H](c1ccccc1)N1CCC(C)(O)CC1] |

TABLE 1-continued
Compounds 1-219.
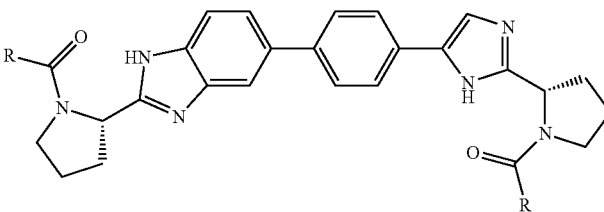
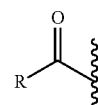
| Entry | |
|---|---|
| 150 | 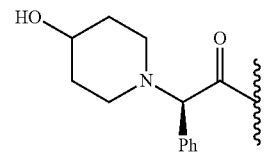 |
| 151 | 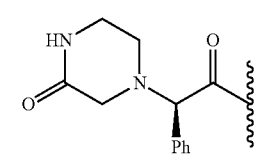 [SMILES: *C(=O)[C@@H](c1ccccc1)N1CCNC(=O)C1] |
| 152 | 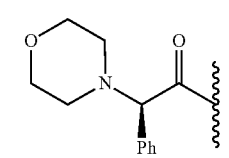 [SMILES: *C(=O)[C@@H](c1ccccc1)N1CCOCC1] |
| 153 | 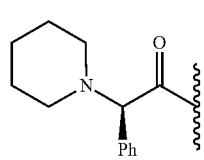 [SMILES: *C(=O)[C@@H](c1ccccc1)N1CCCCC1] |
| 154 | 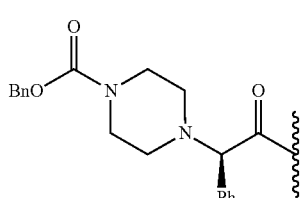 |
| 155 | 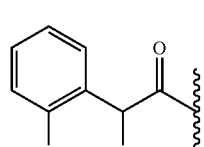 |
| 156 | 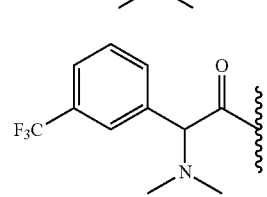 |

TABLE 1-continued
Compounds 1-219.
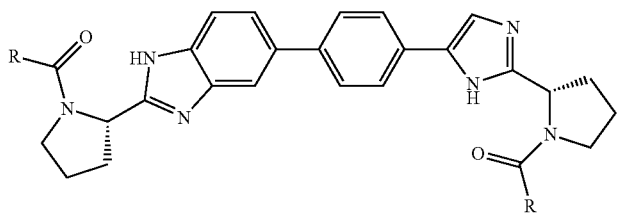
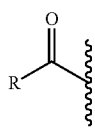
| Entry | |
|---|---|
| 157 | 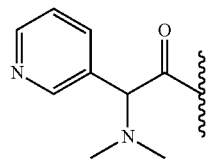 [SMILES: *C(=O)C(c1cccnc1)N(C)C] |
| 158 |  |
| 159 | 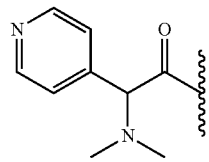 [SMILES: *C(=O)C(c1ccncc1)N(C)C] |
| 160 | 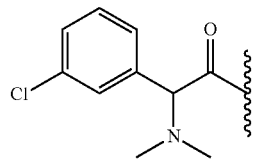 [SMILES: *C(=O)C(c1cccc(Cl)c1)N(C)C] |
| 161 | 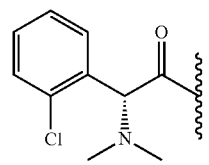 [SMILES: *C(=O)[C@@H](c1ccccc1Cl)N(C)C] |
| 162 | 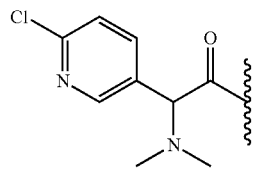 [SMILES: *C(=O)C(c1ccc(Cl)nc1)N(C)C] |
| 163 | 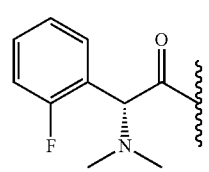 [SMILES: *C(=O)[C@@H](c1ccccc1F)N(C)C] |

TABLE 1-continued
Compounds 1-219.
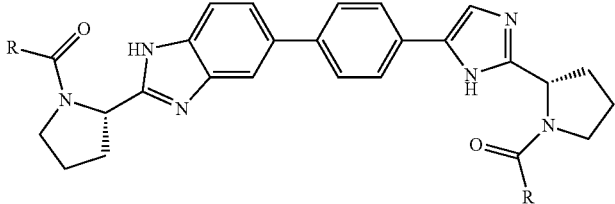
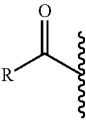
| Entry | |
|---|---|
| 164 | 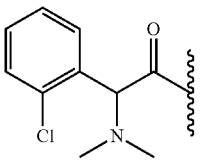 |
| 165 | 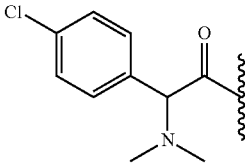 [SMILES: *C(=O)C(c1ccc(Cl)cc1)N(C)C] |
| 166 | 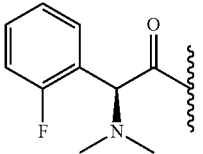 [SMILES: *C(=O)[C@H](c1ccccc1F)N(C)C] |
| 167 | 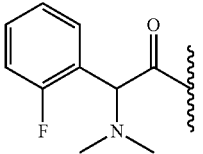 [SMILES: *C(=O)C(c1ccccc1F)N(C)C] |
| 168 | 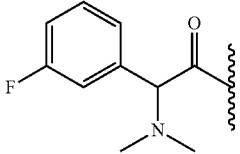 |
| 169 | 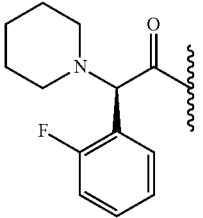 [SMILES: *C(=O)[C@@H](c1ccccc1F)N1CCCCC1] |

TABLE 1-continued
Compounds 1-219.
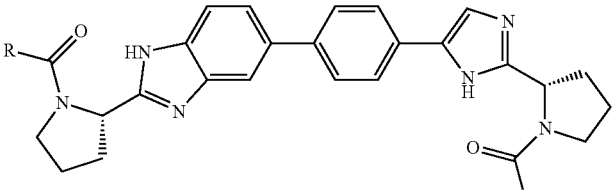
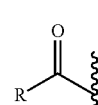
| Entry | |
|---|---|
| 170 | 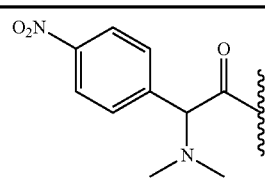 |
| 171 | 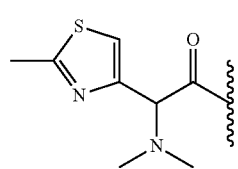 [SMILES: *C(=O)C(c1csc(C)n1)N(C)C] |
| 172 | 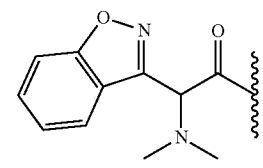 |
| 173 | 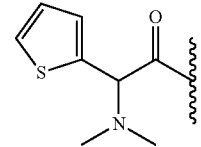 [SMILES: *C(=O)C(c1cccs1)N(C)C] |
| 174 | 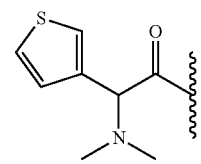 [SMILES: *C(=O)C(c1ccsc1)N(C)C] |
| 175 | 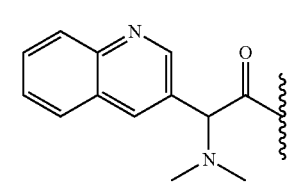 [SMILES: *C(=O)C(c1cnc2ccccc2c1)N(C)C] |
| 176 | 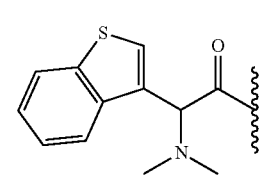 [SMILES: *C(=O)C(c1csc2ccccc12)N(C)C] |

TABLE 1-continued
Compounds 1-219.
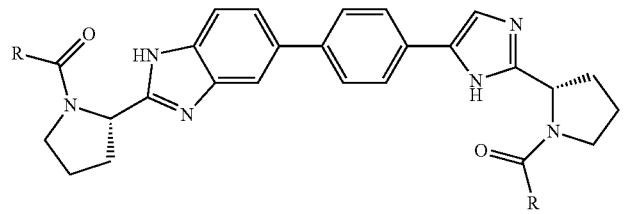
| Entry | 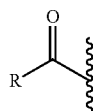 |
|---|---|
| 177 | 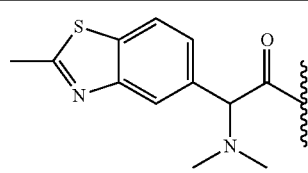 |
| 178 | 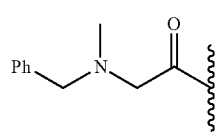 [SMILES: *C(=O)CN(C)Cc1ccccc1] |
| 179 | 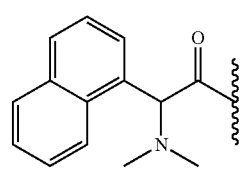 [SMILES: *C(=O)C(c1cccc2ccccc12)N(C)C] |
| 180 | 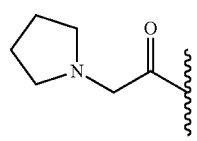 [SMILES: *C(=O)CN1CCCC1] |
| 181 | 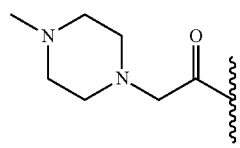 [SMILES: *C(=O)CN1CCN(C)CC1] |
| 182 | 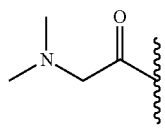 |
| 183 | 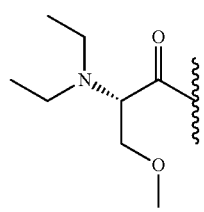 [SMILES: *C(=O)[C@H](COC)N(CC)CC] |

TABLE 1-continued
Compounds 1-219.
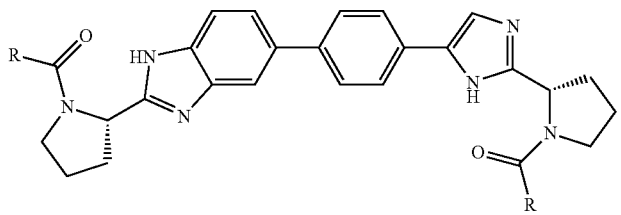
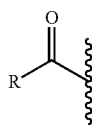
| Entry | |
|---|---|
| 184 | 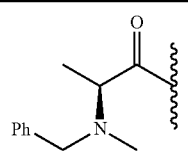 |
| 185 | 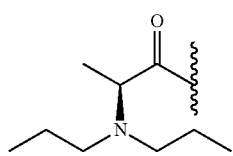 [SMILES: *C(=O)[C@H](C)N(CCC)CCC] |
| 186 | 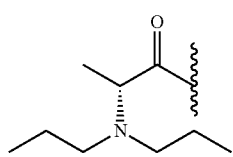 [SMILES: *C(=O)[C@@H](C)N(CCC)CCC] |
| 187 | 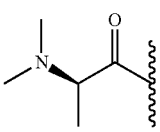 [SMILES: *C(=O)[C@@H](C)N(C)C] |
| 188 | 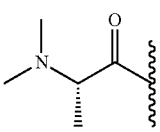 [SMILES: *C(=O)[C@H](C)N(C)C] |
| 189 | 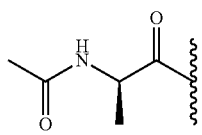 [SMILES: *C(=O)[C@@H](C)NC(C)=O] |
| 190 | 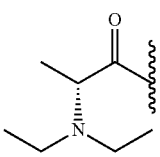 |
| 191 | 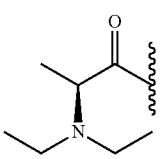 [SMILES: *C(=O)[C@H](C)N(CC)CC] |

TABLE 1-continued
Compounds 1-219.
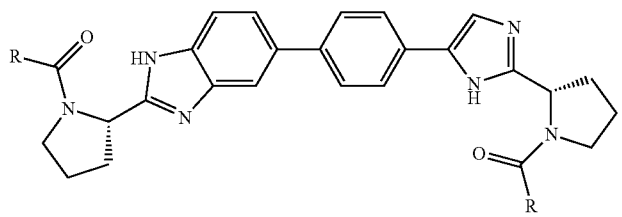
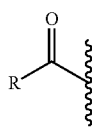
| Entry | |
|---|---|
| 192 | 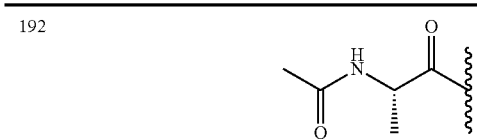 |
| 193 | 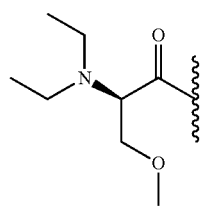 [SMILES: *C(=O)[C@@H](COC)N(CC)CC] |
| 194 | 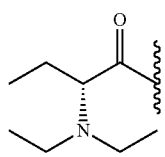 [SMILES: *C(=O)[C@@H](CC)N(CC)CC] |
| 195 | 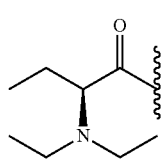 |
| 196 | 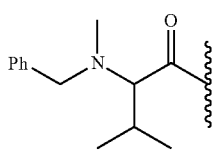 [SMILES: *C(=O)C(C(C)C)N(C)Cc1ccccc1] |
| 197 | 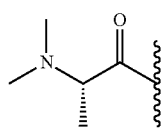 |
| 198 | 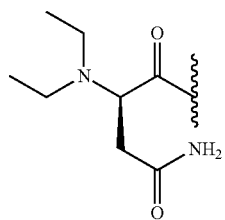 [SMILES: *C(=O)[C@@H](CC(N)=O)N(CC)CC] |

TABLE 1-continued

Compounds 1-219.

| Entry | |
|---|---|
| 199 | (isopropyl, N(Et)₂ substituted acyl group) |
| 200 | (4,5-dihydro-1H-imidazol-2-ylamino, isopropyl acyl group) |
| 201 | (4,5-dihydro-1H-imidazol-2-ylamino, isopropyl acyl group) |
| 202 | (1-methyl-4,5-dihydro-1H-imidazol-2-ylamino, isopropyl acyl group) |
| 203 | (5-amino-1-methyl-1H-1,2,4-triazol-3-ylamino, isopropyl acyl group) |
| 204 | (4,5-dihydrothiazol-2-ylamino, isopropyl acyl group) |
| 205 | (5-amino-1H-1,2,4-triazol-3-ylamino, isopropyl acyl group) |

TABLE 1-continued
Compounds 1-219.
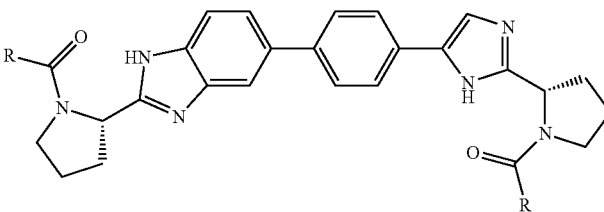
| Entry | |
|---|---|
| 206 | 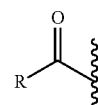 |
| 207 | 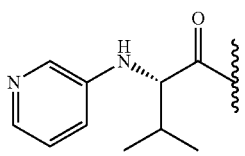 [SMILES: *C(=O)[C@@H](Nc1cccnc1)C(C)C] |
| 208 | 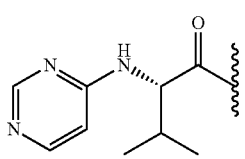 [SMILES: *C(=O)[C@@H](Nc1ccncn1)C(C)C] |
| 209 | 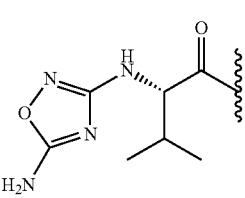 |
| 210 | 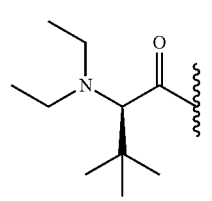 [SMILES: *C(=O)[C@H](N(CC)CC)C(C)(C)C] |
| 211 | 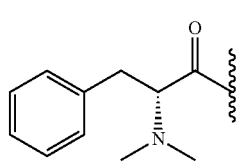 [SMILES: *C(=O)[C@@H](Cc1ccccc1)N(C)C] |
| 212 | 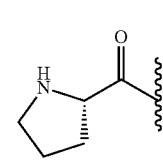 [SMILES: *C(=O)[C@@H]1CCCN1] |

TABLE 1-continued

Compounds 1-219.

| Entry | R-C(O)- group |
|---|---|
| 213 | pyrimidin-5-ylamino-valine acyl |
| 214 | 4,4-difluoropyrrolidine-2-carbonyl |
| 215 | 4-fluoropyrrolidine-2-carbonyl |
| 216 | 3,4-methano-pyrrolidine-2-carbonyl (bicyclic) |
| 217 | 1-methylpyrrolidine-2-carbonyl |
| 218 | 1-methyl-4-fluoropyrrolidine-2-carbonyl |
| 219 | 4-fluoropyrrolidine-2-carbonyl |

TABLE 2
Compounds 220-229.
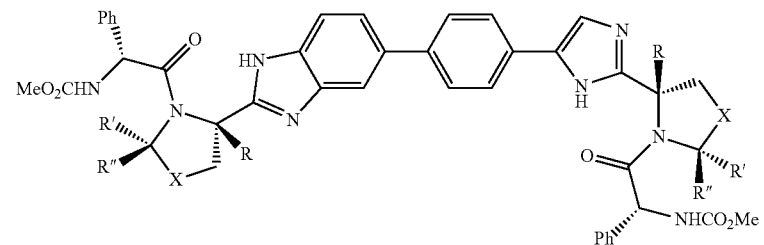
| Entry | R | R' | R" | X |
|---|---|---|---|---|
| 220 | Me | H | H | CH$_2$ |
| 221 | H | H | H | CF$_2$ |
| 222 | Me | H | H | S |
| 223 | H | H | H | ⸺CHF⸺(Me) |
| 224 | Me | H | H | O |
| 225 | H | H | H | ⸺CFH⸺(Me) |
| 226 | H | Ph | H | CH$_2$ |
| 227 | H | H | H | ⸺CH(OH)⸺(Me) |
| 228 | H | H | Ph | CH$_2$ |
| 229 | H | H | H | ⸺C(OH)(H)⸺(Me) |
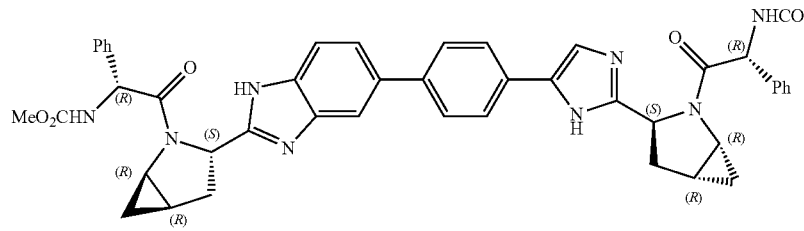
Compound 230

Compound 231
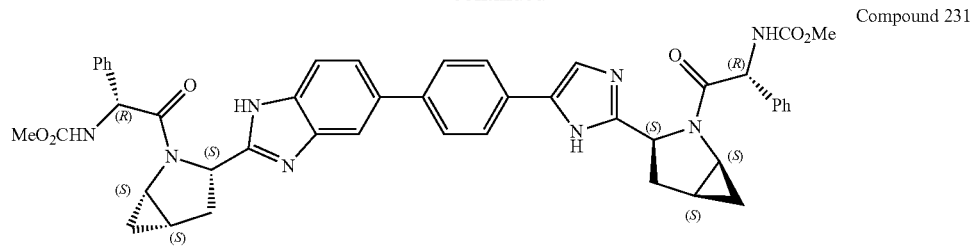
Compound 232
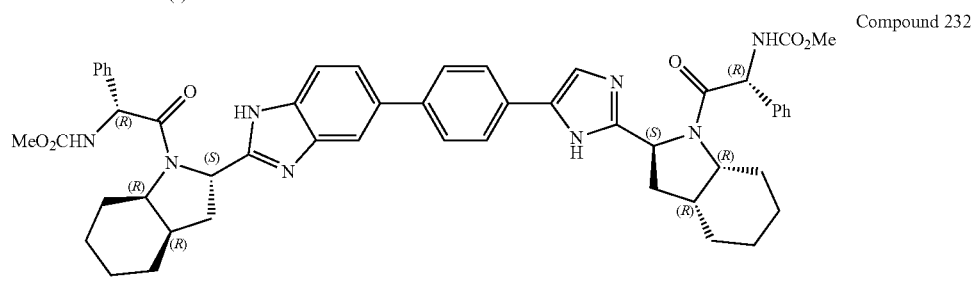
Compound 233
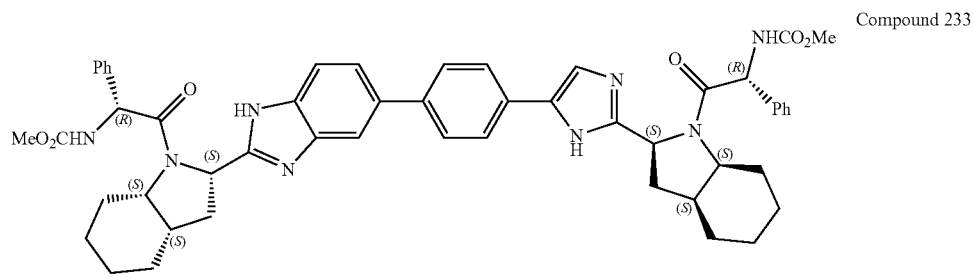
TABLE 3
Compounds 234-243.
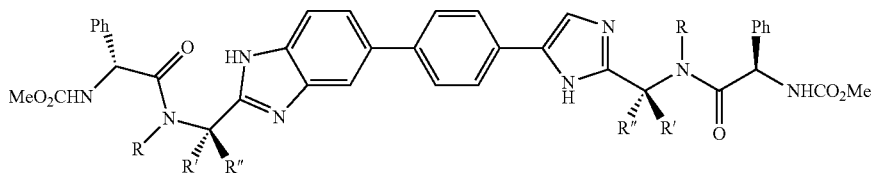
| Entry | R | R" | R" |
|---|---|---|---|
| 234 | Me | Me | H |
| 235 | H | Me | H |
| 236 | Me | H | Me |
| 237 | cyclopropyl | Me | H |
| 238 | Me | Me | Me |
| 239 | Me | cyclopropyl | H |
| 240 | Me | Allyl | H |
| 241 | Et | Me | H |
| 242 | Me | CHMe$_2$ | H |
| 243 | Me | Et | H. |

TABLE 4
Compounds 244-263.
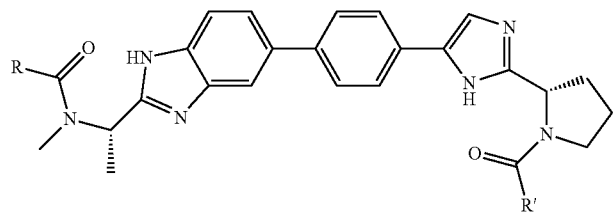
| Entry | R | R' |
|---|---|---|
| 244 | MeO₂CHN-CH(Ph)- | MeO₂CHN-CH(Ph)- |
| 245 | Me₂N-CH(Ph)- | Me₂N-CH(Ph)- |
| 246 | Me₂N-CH(Ph)- | MeO₂CHN-CH(Ph)- |
| 247 | MeO₂CHN-CH(Ph)- | Me₂N-CH(Ph)- |
| 248 | MeO₂CHN-CH(iPr)- | MeO₂CHN-CH(Ph)- |
| 249 | MeO₂CHN-CH(Ph)- | MeO₂CHN-CH(iPr)- |
| 250 | (tetrahydrofuran-2-yl)C(O)NH-CH(Ph)- | piperidin-1-yl-CH(Ph)- |
| 251 | MeO₂CHN-CH(Ph)- | MeO₂C-NH-CH₂- |
| 252 | (pyridin-3-yl)CH₂- | (tetrahydrofuran-2-yl)C(O)NH-CH(Ph)- |

US 9,765,087 B2
TABLE 4-continued
Compounds 244-263.
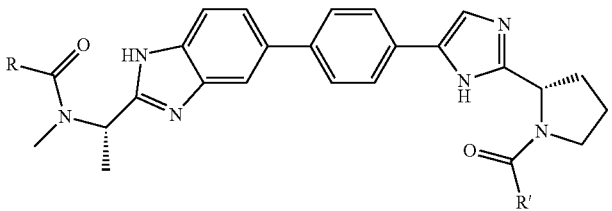
| Entry | R | R' |
|---|---|---|
| 253 | 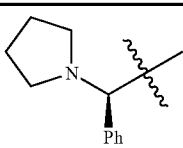 | 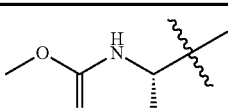 |
| 254 | 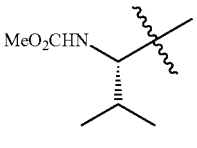 | 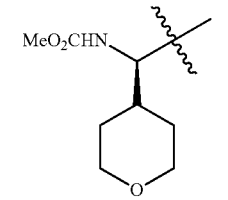 |
| 255 | 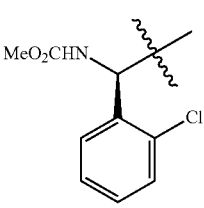 | 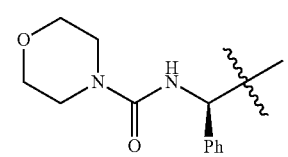 [SMILES: *[C@H](NC(=O)N1CCOCC1)c1ccccc1] |
| 256 | 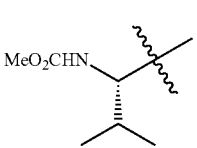 | 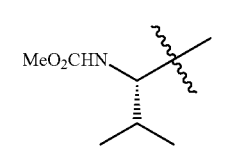 |
| 257 | 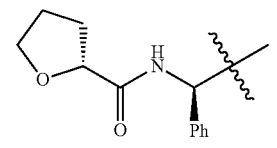 [SMILES: *[C@H](NC(=O)[C@H]1CCCO1)c1ccccc1] | 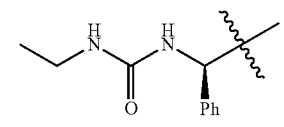 [SMILES: *[C@H](NC(=O)NCC)c1ccccc1] |
| 258 | 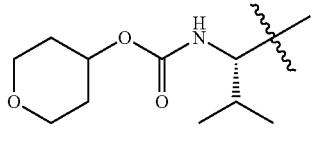 [SMILES: *[C@@H](NC(=O)OC1CCOCC1)C(C)C] | 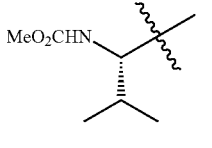 |
| 259 | 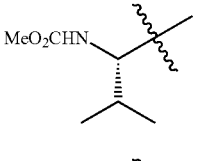 | 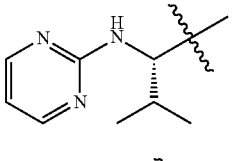 |
| 260 | 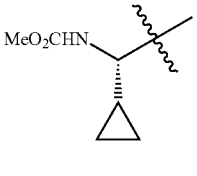 | 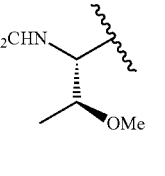 |

TABLE 4-continued

Compounds 244-263.

| Entry | R | R' |
|---|---|---|
| 261 | MeO₂CHN—CH(iPr)— (α-Me) | MeO₂CHN—CH(CH₂-pyrazol-1-yl)— |
| 262 | MeO₂CHN—CH(iPr)— (α-Me) | MeO₂CHN—cyclopentyl— |
| 263 | MeO₂CHN—CH(CH(Me)OMe)— (α-Me) | 3-pyridyl-NH—CH(iPr)— |

TABLE 5

Compounds 264-273.

| Entry | R | R' | R'' | R''' |
|---|---|---|---|---|
| 264 | F | H | H | H |
| 265 | F | F | H | H |
| 266 | Me | H | H | H |
| 267 | Me | Me | H | H |
| 268 | H | H | Me | Me |
| 269 | H | H | Et | Et |
| 270 | CF₃ | H | H | H |
| 271 | CF₃ | H | CF₃ | H |
| 272 | Cl | H | H | H |
| 273 | Cl | H | Cl | H. |

TABLE 6
Compounds 274-299.
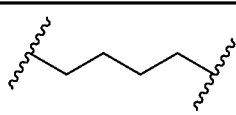
| Entry | R | R' | R" | R''' |
|---|---|---|---|---|
| 274 | Me | H | H | H |
| 275 | H | CO$_2$H | H | H |
| 276 | H | F | H | H |
| 277 | H | H | CO$_2$H | H |
| 278 | H | H | F | H |
| 279 | H | H | H | CO$_2$H |
| 280 | H | H | H | F |
| 281 | H | CO$_2$Me | H | H |
| 282 | H | Cl | H | H |
| 283 | H | H | CO$_2$Me | H |
| 284 | H | H | Cl | H |
| 285 | H | H | H | CO$_2$Me |
| 286 | H | H | H | Cl |
| 287 | H | CONH$_2$ | H | H |
| 288 | H | Me | H | H |
| 289 | H | H | CONH$_2$ | H |
| 290 | H | H | Me | H |
| 291 | H | H | H | CONH$_2$ |
| 292 | H | H | H | Me |
| 293 | H | OMe | H | H |
| 294 | H | CF$_3$ | H | H |
| 295 | H | H | OMe | H |
| 296 | H | H | CF$_3$ | H |
| 297 | H | H | H | OMe |
| 298 | H | H | H | CF$_3$ |
| 299 | CO$_2$Me | H | H | H. |
TABLE 7
Compounds 300-434.
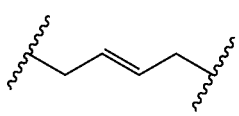
| Entry | A$^a$ |
|---|---|
| 300 | ![chain] |
| 301 | ![chain] |

TABLE 7-continued
Compounds 300-434.
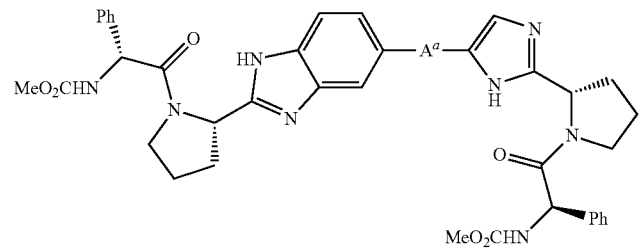
| Entry | $A^a$ |
|---|---|
| 302 | |
| 303 | |
| 304 | |
| 305 | |
| 306 | |
| 307 | |
| 308 | |
| 309 | |

TABLE 7-continued
Compounds 300-434.
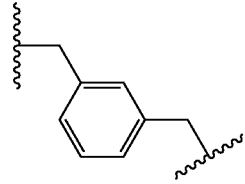 [SMILES: *Cc1cccc(C*)c1]
| Entry | $A^a$ |
|---|---|
| 310 | 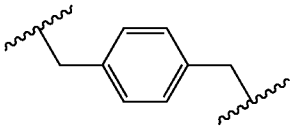 [SMILES: *Cc1ccc(C*)cc1] |
| 311 | 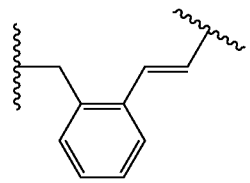 [SMILES: */C=C/c1ccccc1C*] |
| 312 | 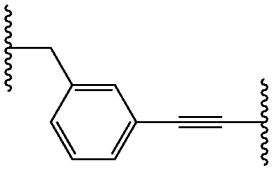 |
| 313 | 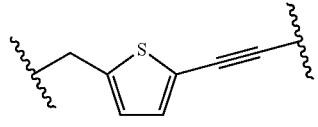 [SMILES: *C#Cc1ccc(C*)s1] |
| 314 | 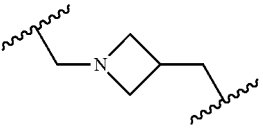 [SMILES: *CC1CN(C*)C1] |
| 315 | 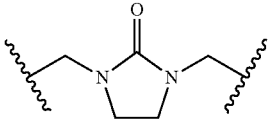 [SMILES: *CN1CCN(C*)C1=O] |
| 316 | 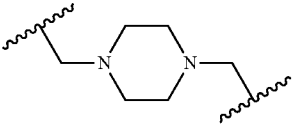 [SMILES: *CN1CCN(C*)CC1] |
| 317 | |

TABLE 7-continued

Compounds 300-434.

| Entry | $A^a$ |
|---|---|
| 318 | -CH₂-O-C(=O)-O-CH₂- |
| 319 | -CH₂-O-C(=O)-NH-CH₂- |
| 320 | -CH₂-NH-C(=O)-NH-CH₂- |
| 321 | -CH₂-C(=O)-O-CH₂- |
| 322 | -CH₂-C(=O)-NH-CH₂- |
| 323 | -CH₂-S(=O)₂-NH-CH₂- |
| 324 | -CH₂-O-CH₂- |
| 325 | -CH₂-N(CH₃)-CH₂- |
| 326 | -CH₂CH₂-O-CH₂CH₂- |
| 327 | -CH₂-O-CH₂-CH=CH- |
| 328 | -CH₂-O-CH₂-C≡C- |

TABLE 7-continued

Compounds 300-434.

| Entry | A$^a$ |
|---|---|
| 329 | -CH₂CH₂-N(CH₃)-CH₂CH₂- |
| 330 | -CH₂-O-CH₂CH₂-O-CH₂- |
| 331 | -CH₂-O-CH₂-CH=CH-CH₂-O-CH₂- |
| 332 | -CH₂-O-CH₂-C≡C-CH₂-O-CH₂- |
| 333 | carbamate linker (-O-C(=O)-NH-) |
| 334 | sulfamide linker (-NH-S(=O)₂-NH-) |
| 335 | acylsulfamide linker (-C(=O)-NH-S(=O)₂-NH-) |
| 336 | azetidine-pyridine linker |
| 337 | piperazine-pyrimidine linker |

TABLE 7-continued

Compounds 300-434.

| Entry | A$^a$ |
|---|---|
| 338 | (pyrazole-pyridine) |
| 339 | (biphenyl) |
| 340 | (thiophene-phenyl) |
| 341 | (oxazole-indole) |
| 342 | (isoindoline with acyl) |
| 343 | (pyrazole carboxylate ester) |
| 344 | (piperidine with acyl) |
| 345 | (azetidine-O-C(O)-NH) |
| 346 | (acylamino-thiazole) |

TABLE 7-continued

Compounds 300-434.

| Entry | $A^a$ |
|---|---|
| 347 | azetidine-N, 3-O-C(=O)-NH- |
| 348 | -CH2-(cyclohexane-1,4-diyl)-O- |
| 349 | piperidine-N,4-O- |
| 350 | -O-(phenylene-1,4)- |
| 351 | imidazolidin-2-one-1,3-diyl-CH2- |
| 352 | oxazol-2(3H)-one-3,5-diyl-CH2- |
| 353 | isoxazole-3,5-diyl-CH2- |
| 354 | azetidine-N,3-diyl-CH2- |
| 355 | -CH2-(phenylene-1,4)- |
| 356 | -CH2-piperazine-1,4-diyl- |

TABLE 7-continued
Compounds 300-434.
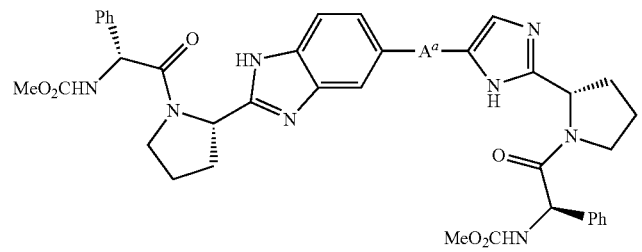
| Entry | $A^a$ |
|---|---|
| 357 | |
| 358 | |
| 359 | |
| 360 | |
| 361 | |
| 362 | |
| 363 | |

TABLE 7-continued

Compounds 300-434.

| Entry | $A^a$ |
|---|---|
| 364 | (E)-CH=CH-C(O)-NH- |
| 365 | -CH2-NH-C(O)-NH- |
| 366 | -NH-S(O)2-NH-CH2- |
| 367 | -C(O)-NH-S(O)2-CH2- |
| 368 | -C≡C-CH2-O-C(O)-NH- |
| 369 | -O-CH2-CH=CH-C(CH3)- |
| 370 | -O-CH2-C≡C- |
| 371 | -O-CH2-CH=CH-CH2- |

TABLE 7-continued
Compounds 300-434.
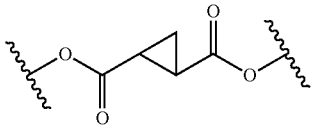 [SMILES: *OC(=O)C1CC1C(=O)O*]
| Entry | $A^a$ |
|---|---|
| 372 | 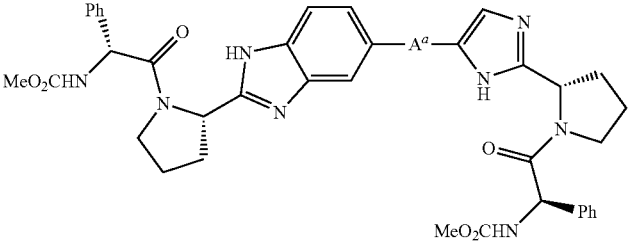 |
| 373 | 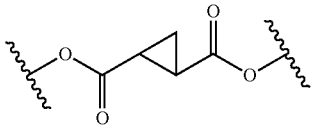 [SMILES: *OC(=O)C1CC1C(=O)O*] |
| 374 | 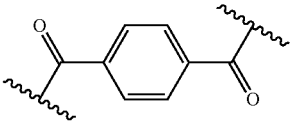 [SMILES: *C(=O)c1ccc(C(*)=O)cc1] |
| 375 | 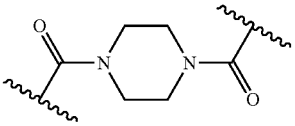 [SMILES: *C(=O)N1CCN(C(*)=O)CC1] |
| 376 | 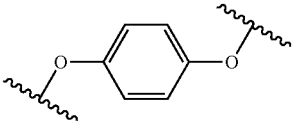 [SMILES: *Oc1ccc(O*)cc1] |
| 377 | 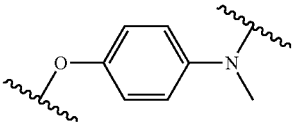 [SMILES: *Oc1ccc(N(*)C)cc1] |
| 378 | 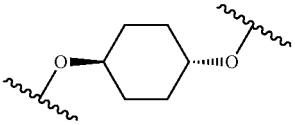 [SMILES: *O[C@H]1CC[C@H](O*)CC1] |
| 379 | 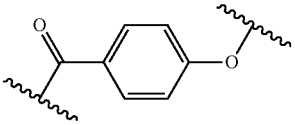 [SMILES: *Oc1ccc(C(*)=O)cc1] |
| 380 | 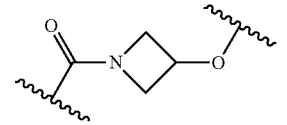 [SMILES: *OC1CN(C(*)=O)C1] |

TABLE 7-continued
Compounds 300-434.
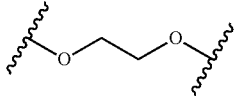 [SMILES: *OCCO*]
| Entry | $A^a$ |
|---|---|
| 381 | 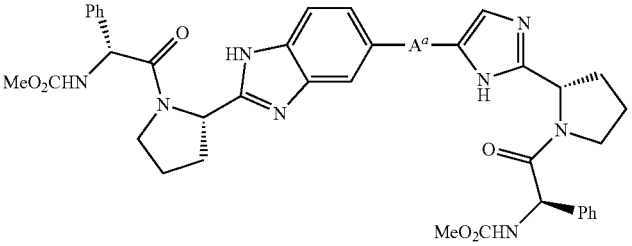 |
| 382 |  |
| 383 | 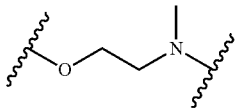 [SMILES: *OCCN(*)C] |
| 384 | 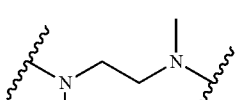 |
| 385 | 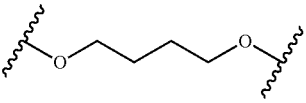 [SMILES: *OCCCCO*] |
| 386 | 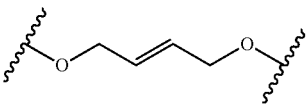 [SMILES: *OC/C=C/CO*] |
| 387 | 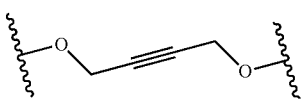 [SMILES: *OCC#CCO*] |
| 388 | 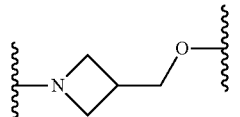 |
| 389 | 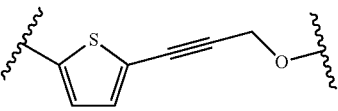 [SMILES: *OCC#Cc1ccc(*)s1] |

TABLE 7-continued
Compounds 300-434.
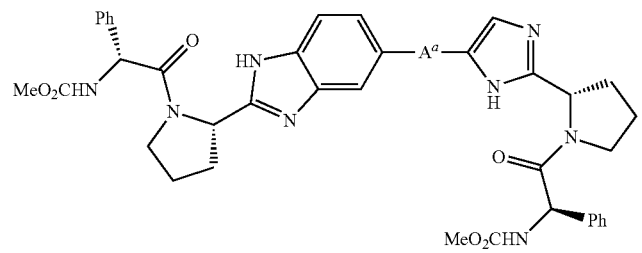
| Entry | $A^a$ |
|---|---|
| 390 | 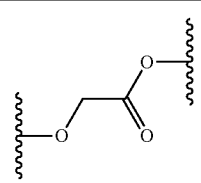 |
| 391 | 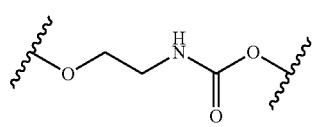 [SMILES: *OCCNC(=O)O*] |
| 392 | 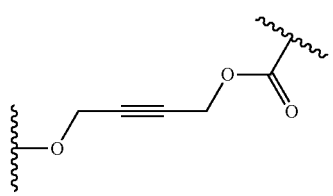 [SMILES: *OCC#CCOC(*)=O] |
| 393 | 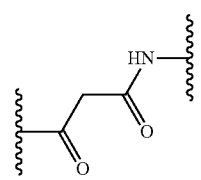 [SMILES: *NC(=O)CC(*)=O] |
| 394 | 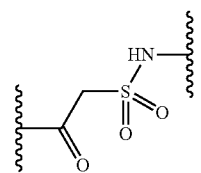 [SMILES: *NS(=O)(=O)CC(*)=O] |
| 395 | 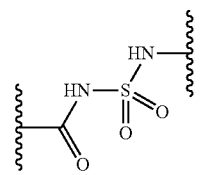 [SMILES: *NS(=O)(=O)NC(*)=O] |
| 396 | 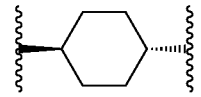 |

TABLE 7-continued
Compounds 300-434.
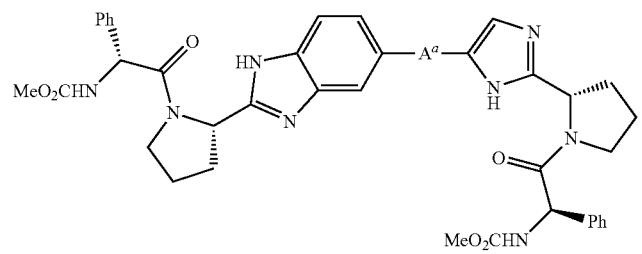
| Entry | $A^a$ |
|---|---|
| 397 | |
| 398 | |
| 399 | |
| 400 | |
| 401 | |
| 402 | |
| 403 | |

TABLE 7-continued
Compounds 300-434.
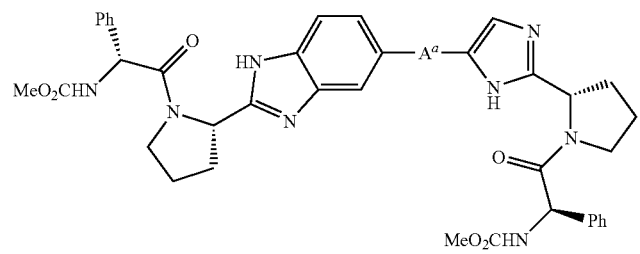
| Entry | $A^a$ |
|---|---|
| 404 | |
| 405 | |
| 406 | |
| 407 | |
| 408 | |
| 409 | |
| 410 | |

TABLE 7-continued
Compounds 300-434.
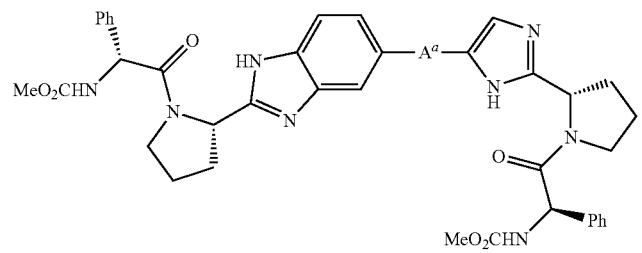
| Entry | $A^a$ |
|---|---|
| 411 | |
| 412 | |
| 413 | |
| 414 | |
| 415 | |
| 416 | |

TABLE 7-continued
Compounds 300-434.
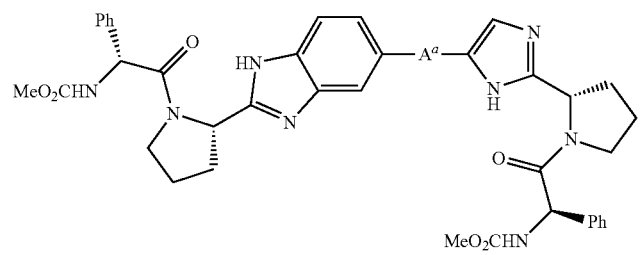
| Entry | A<sup>a</sup> |
|---|---|
| 417 | 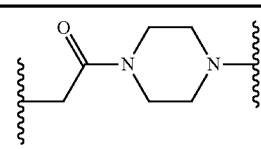 |
| 418 | 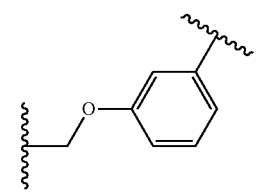 [SMILES: *COc1cccc(*)c1] |
| 419 | 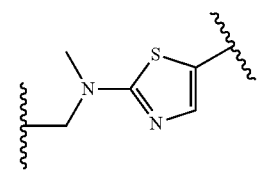 [SMILES: *CN(C)c1ncc(*)s1] |
| 420 | 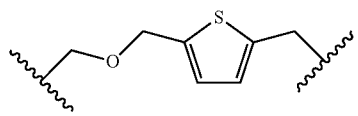 [SMILES: *COCc1ccc(C*)s1] |
| 421 | 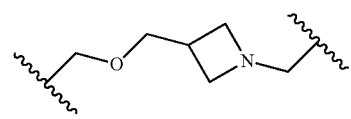 [SMILES: *COCC1CN(C*)C1] |
| 422 | 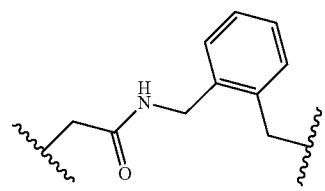 [SMILES: *CC(=O)NCc1ccccc1C*] |
| 423 | 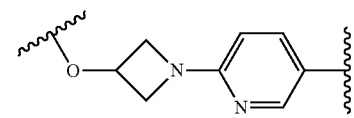 [SMILES: *OC1CN(c2ccc(*)cn2)C1] |
| 424 | 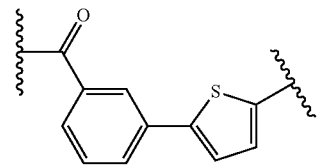 [SMILES: *C(=O)c1cccc(-c2ccc(*)s2)c1] |

TABLE 7-continued
Compounds 300-434.
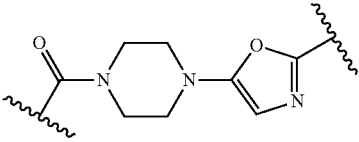 [SMILES: *C(=O)N1CCN(c2cnc(*)o2)CC1]
| Entry | A$^a$ |
|---|---|
| 425 | 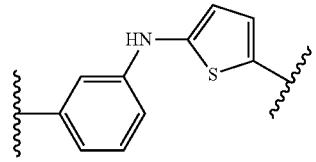 |
| 426 | 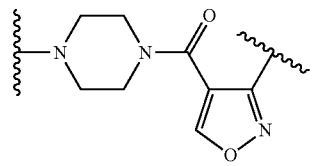 [SMILES: *c1nocc1C(=O)N1CCN(*)CC1] |
| 427 | 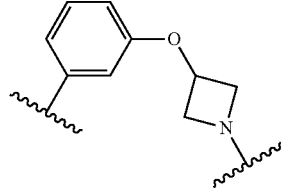 [SMILES: *c1cccc(OC2CN(*)C2)c1] |
| 428 | 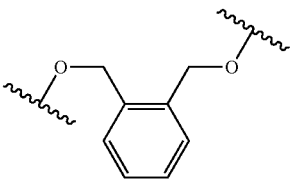 [SMILES: *OCc1ccccc1CO*] |
| 429 | 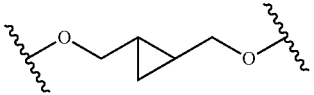 |
| 430 | 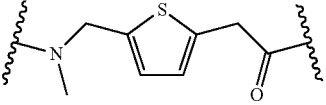 [SMILES: *C(=O)Cc1ccc(CN(*)C)s1] |
| 431 | 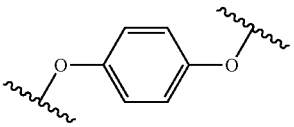 [SMILES: *Oc1ccc(O*)cc1] |
| 432 | |

TABLE 7-continued

Compounds 300-434.

| Entry | $A^a$ |
|---|---|
| 433 | (CH₂-O-azetidine-N-CH₂ linker) |
| 434 | (CH₂-C(O)NH-phenyl-CH₂ linker, ortho-substituted) |

TABLE 8

Compounds 435-440.

| Entry | $B^b$ |
|---|---|
| 435 | 1H-pyrazole-3,5-diyl |
| 436 | 4H-1,2,4-triazole-3,5-diyl |
| 437 | 1,3,4-oxadiazole-2,5-diyl |
| 438 | 1,3-oxazole-2,5-diyl |

TABLE 8-continued
Compounds 435-440.
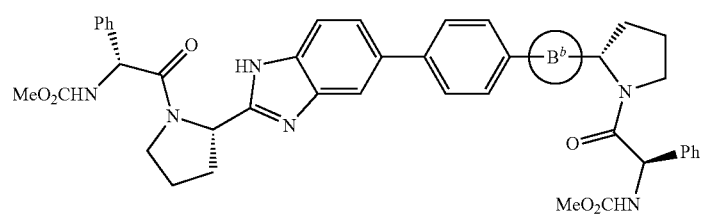
| Entry | $B^b$ |
|---|---|
| 439 | 1,3-oxazole-2,5-diyl |
| 440 | 1,3-thiazole-2,5-diyl |
TABLE 9
Compounds 441-545

TABLE 9-continued
Compounds 441-545
445
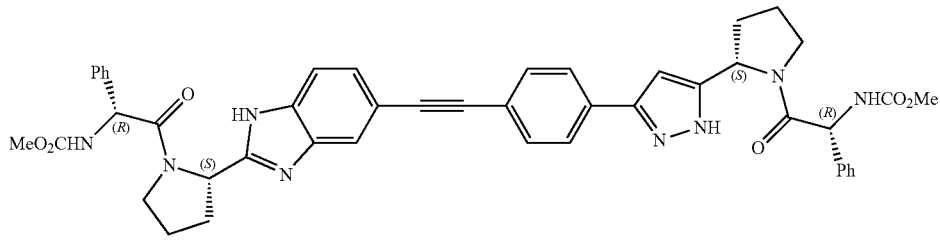
446
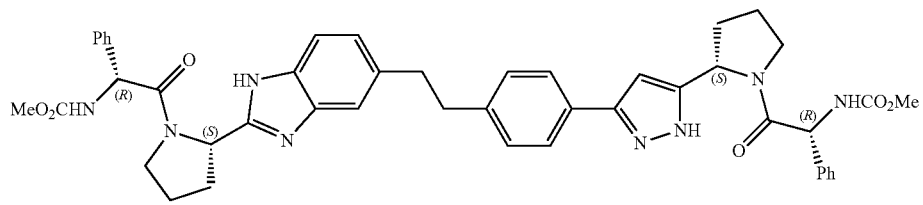
447
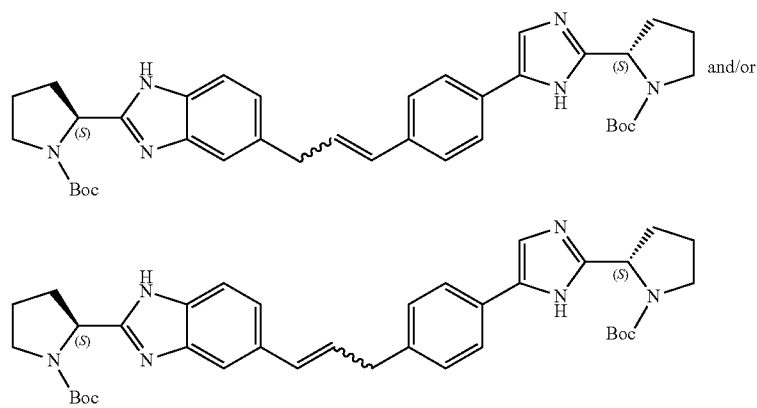
448
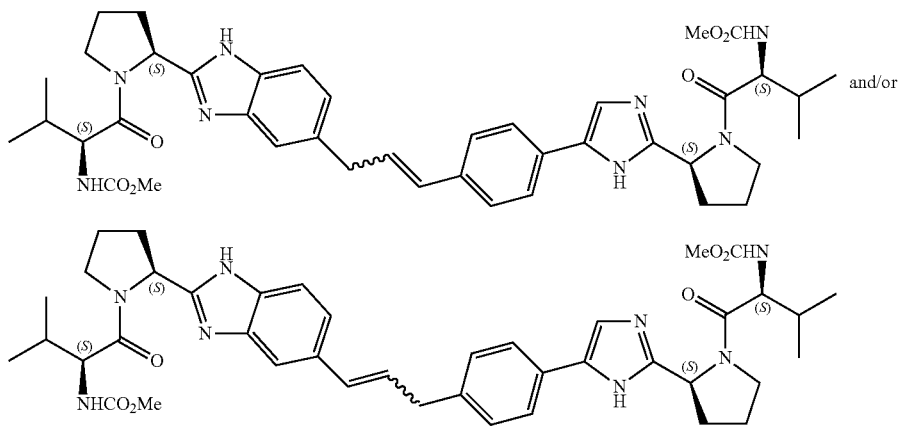
449
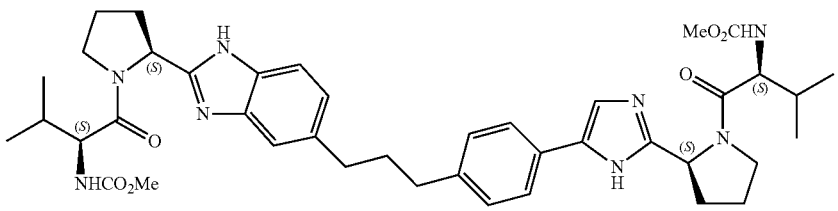

TABLE 9-continued
Compounds 441-545
450 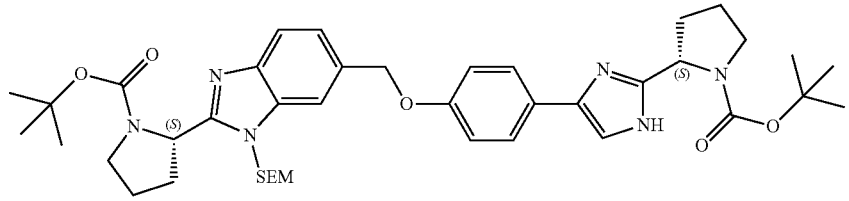
451 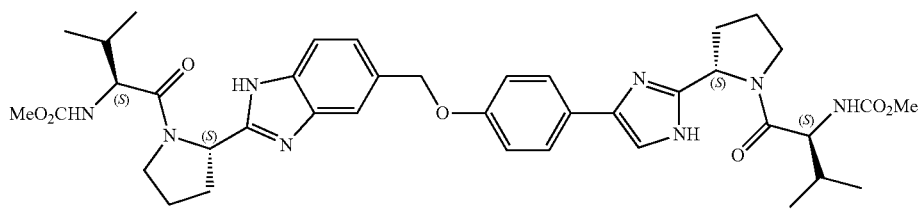
452 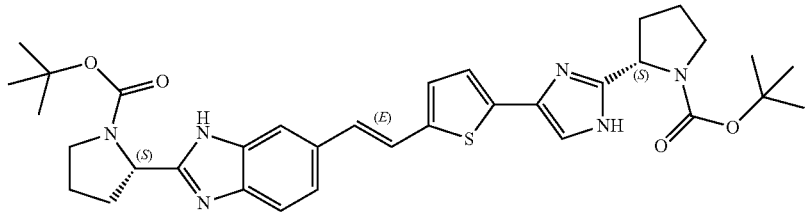
453 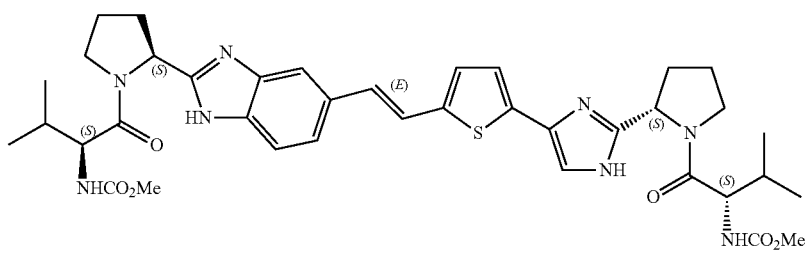
454 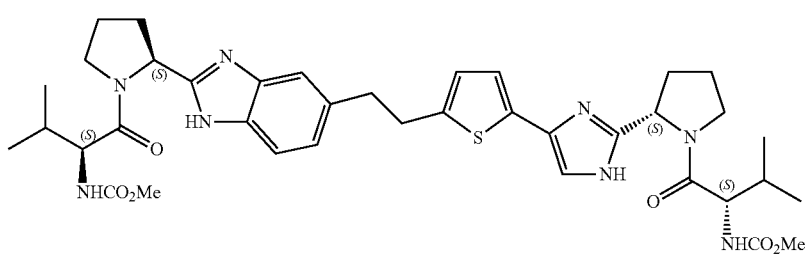
455 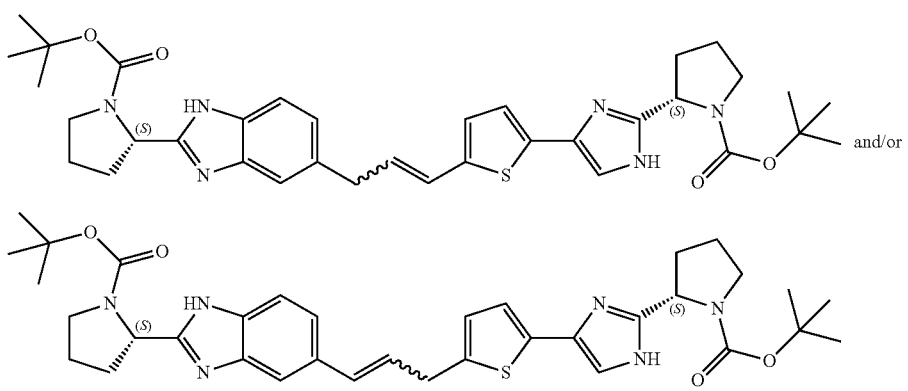
US 9,765,087 B2
137 138
TABLE 9-continued
Compounds 441-545
456 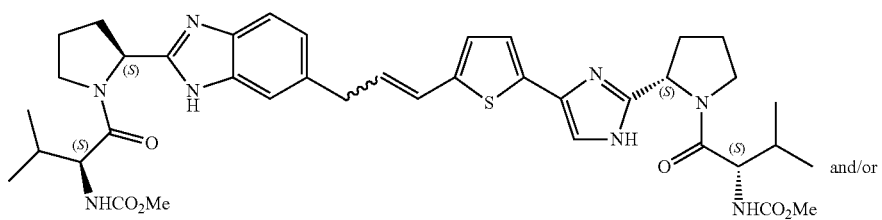 and/or
457 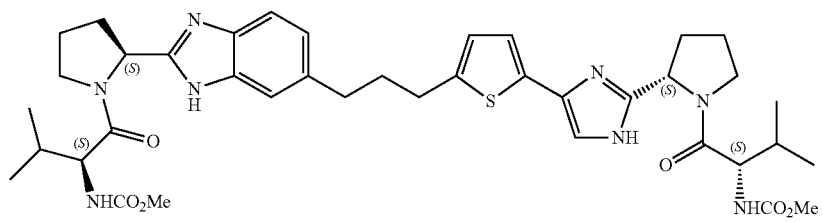
458 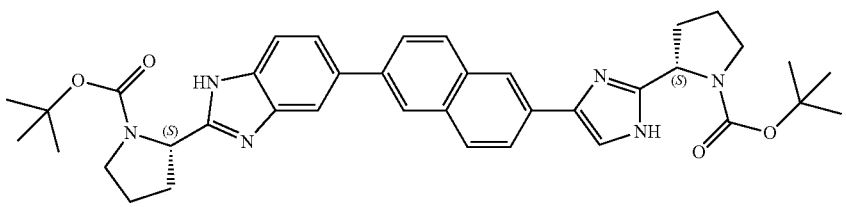
459 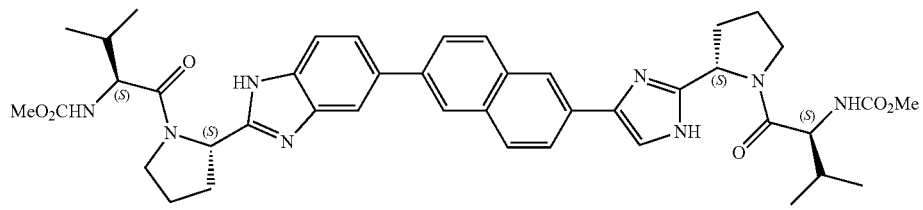
460 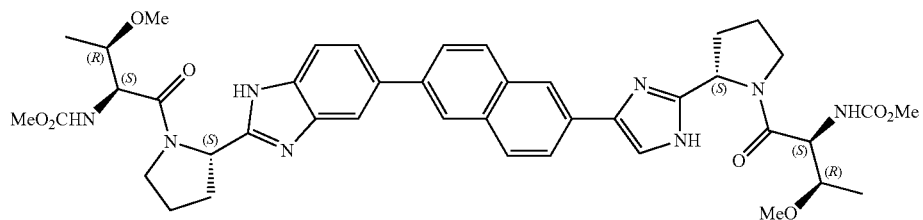
461 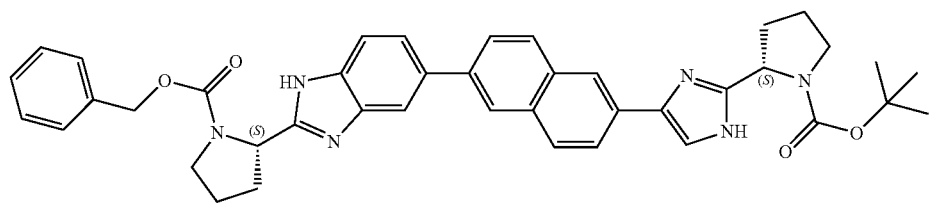

TABLE 9-continued
Compounds 441-545
462
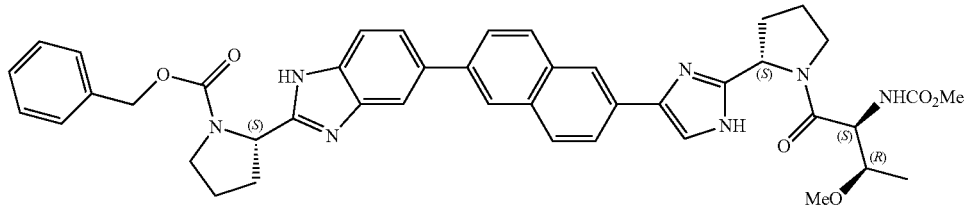
463
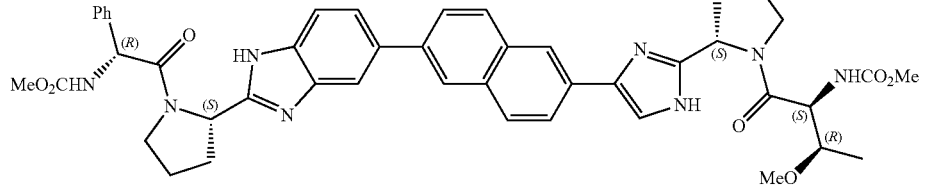
464
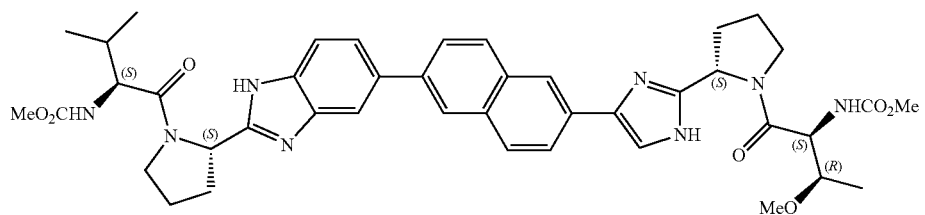
465
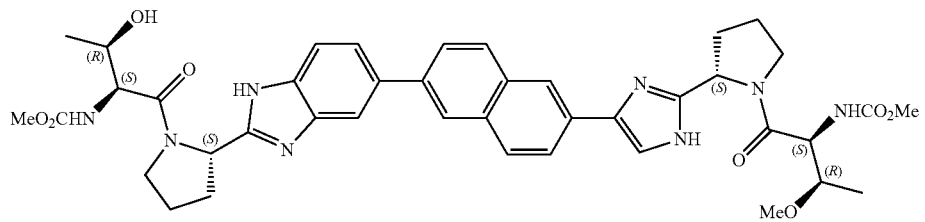
466
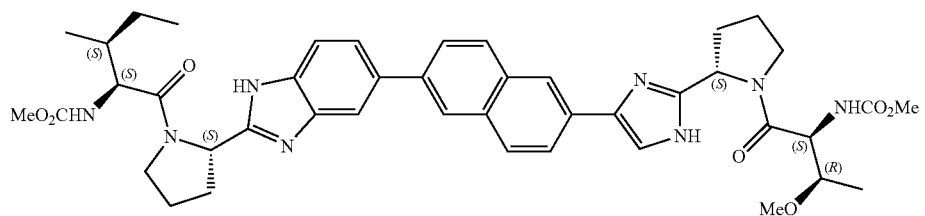
467
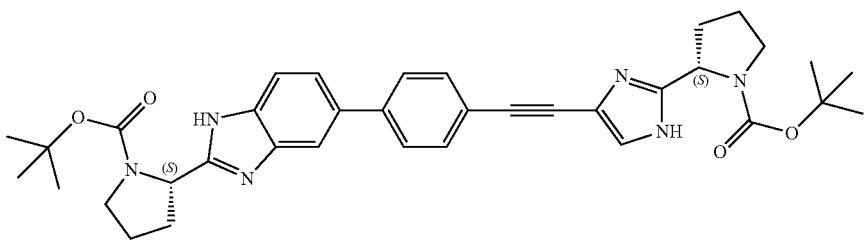
468
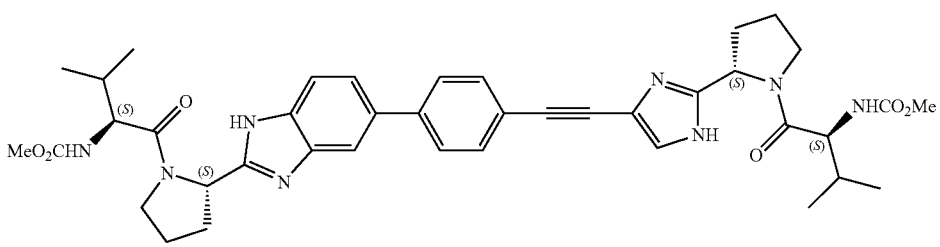

TABLE 9-continued
Compounds 441-545
469 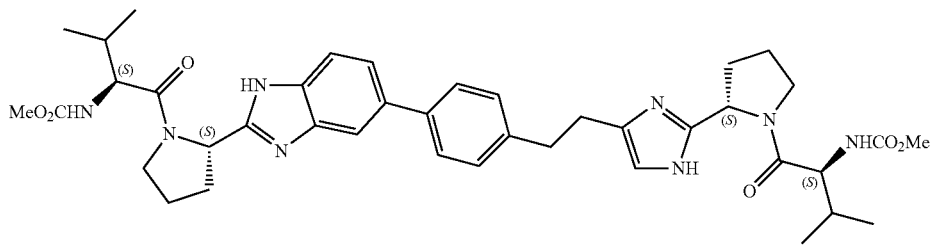
470 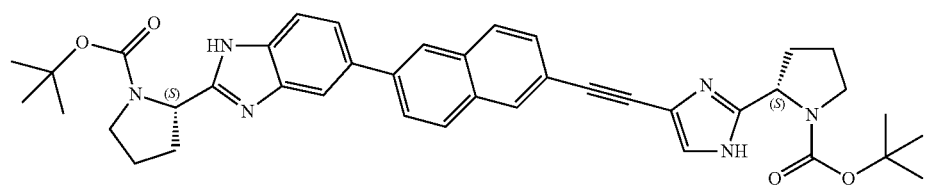
471 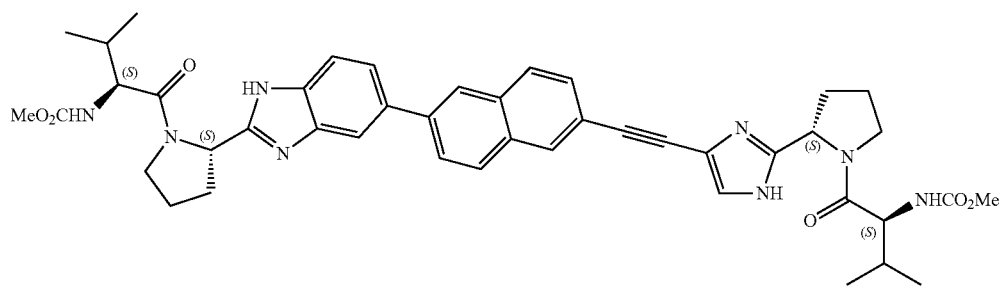
472 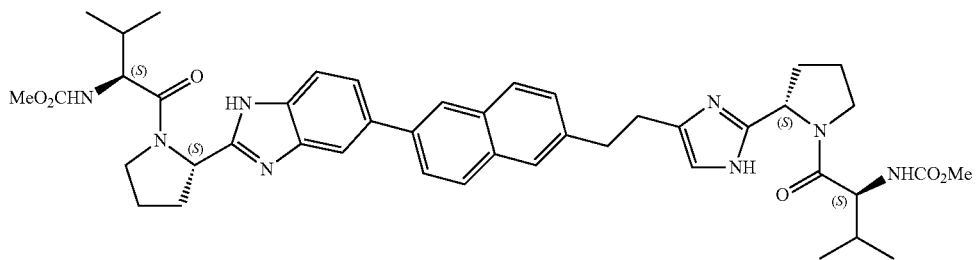
473 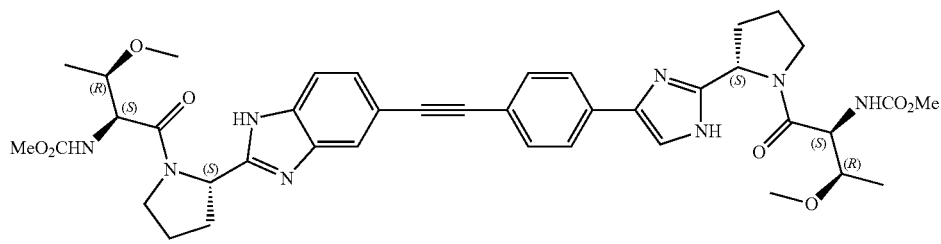
474 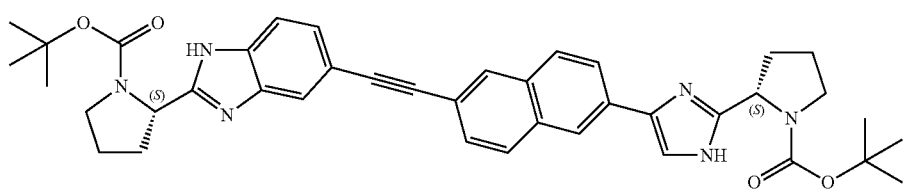

TABLE 9-continued
Compounds 441-545
475 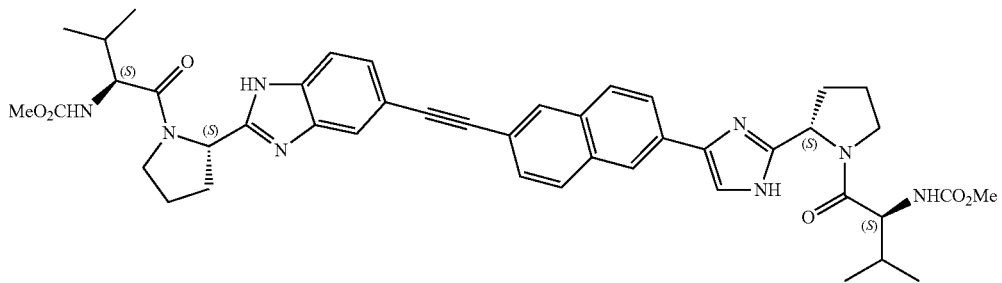
476 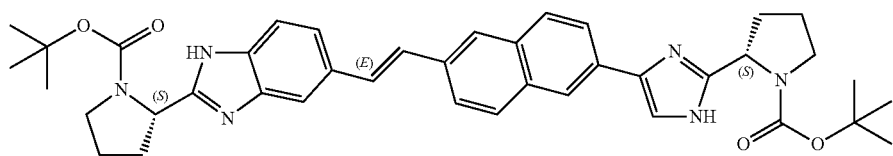
477 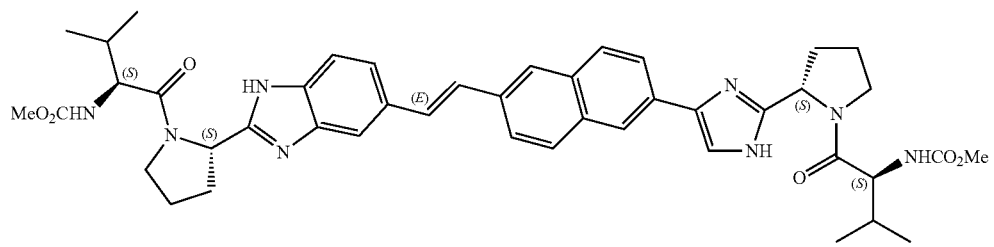
478 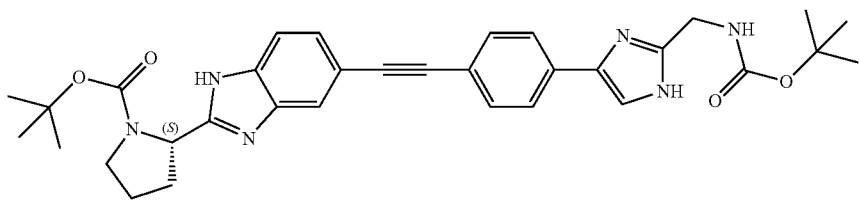
479 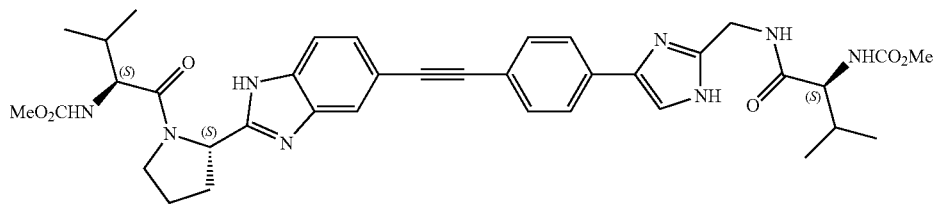
480 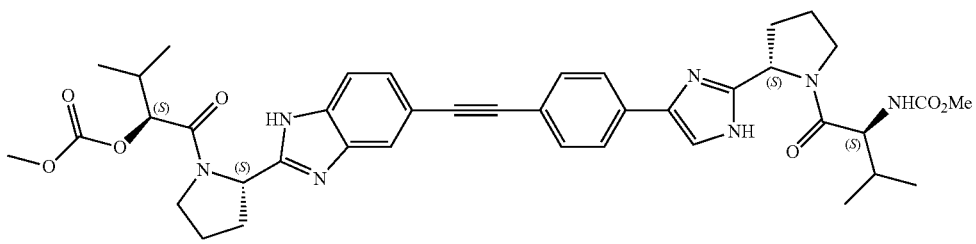

TABLE 9-continued
Compounds 441-545
481 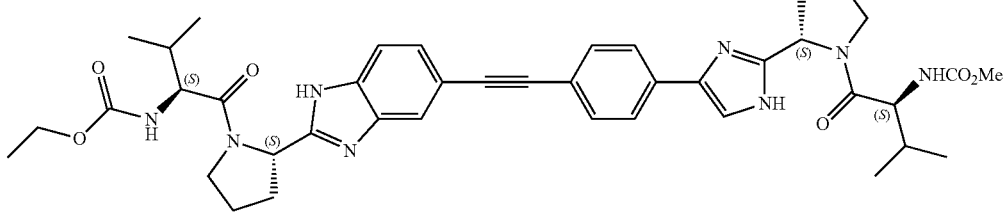
482 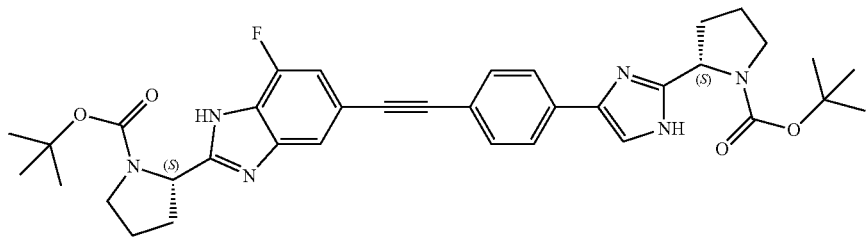
483 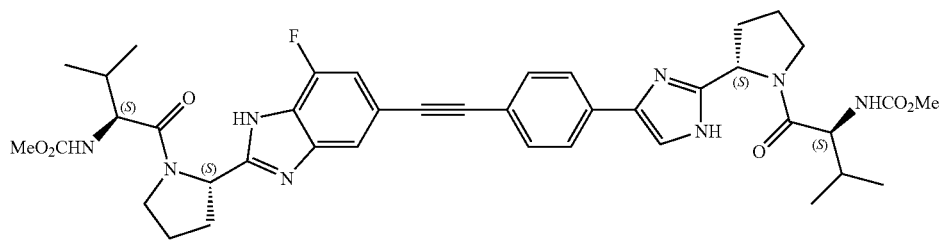
484 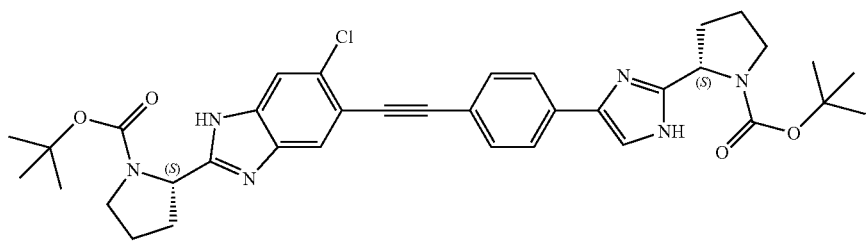
485 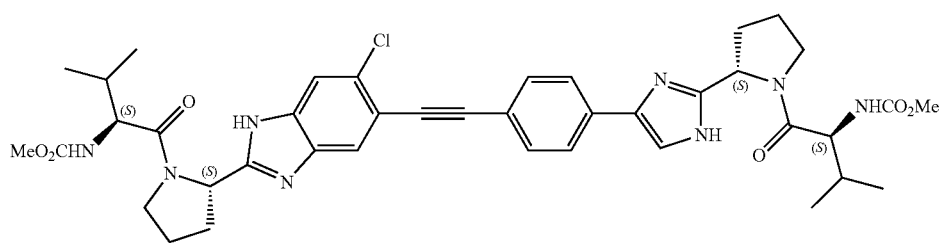
486 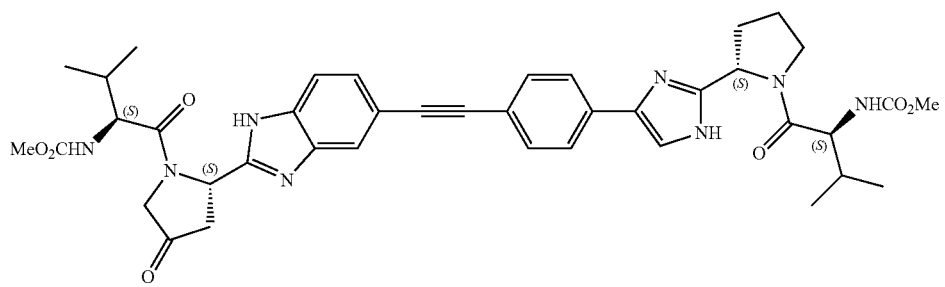

TABLE 9-continued
Compounds 441-545
487
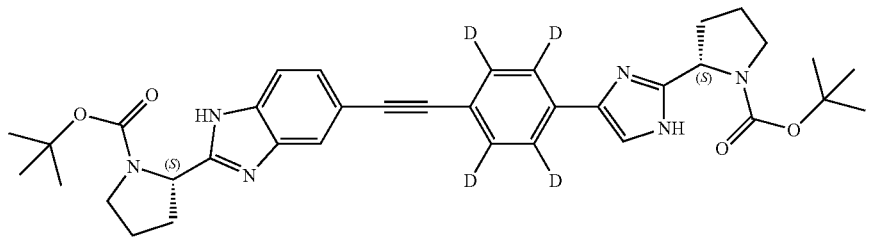
each D is deuterium
488
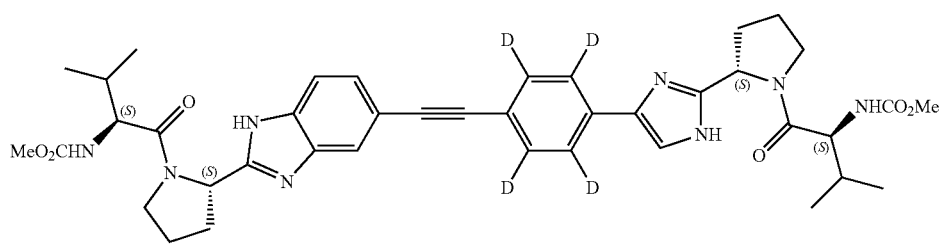
each D is deuterium
489
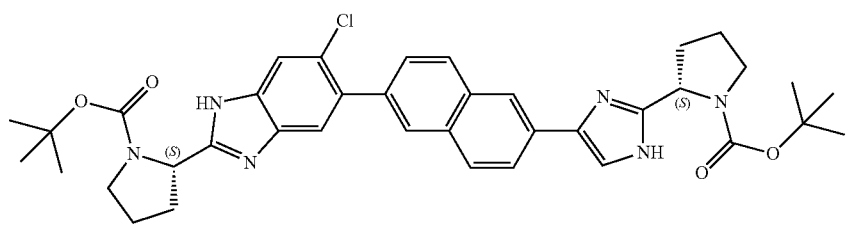
490
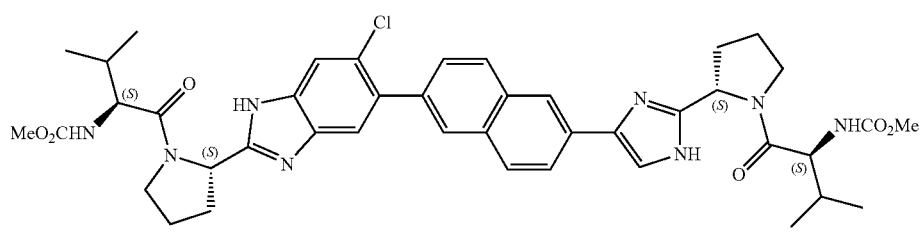
491
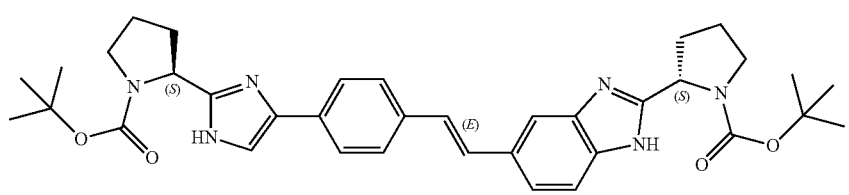
492
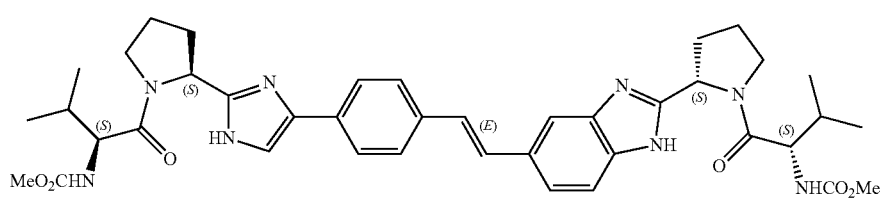

TABLE 9-continued
Compounds 441-545
493 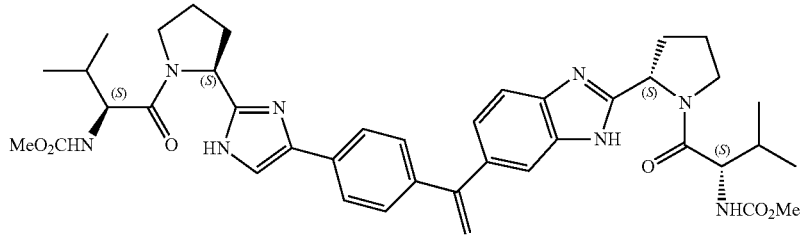
494 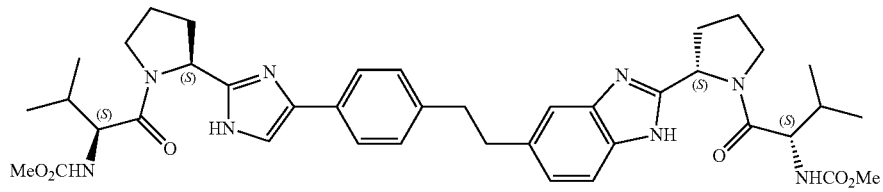
495 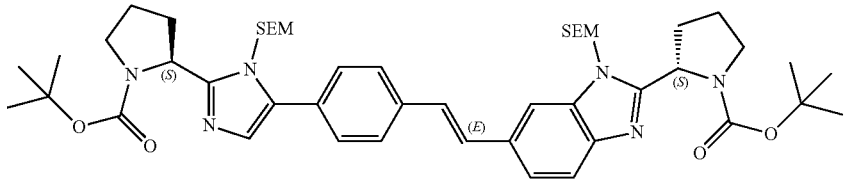
496 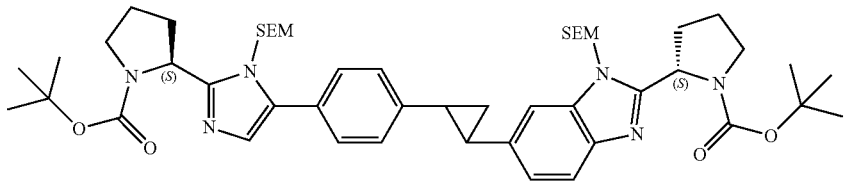
497-a 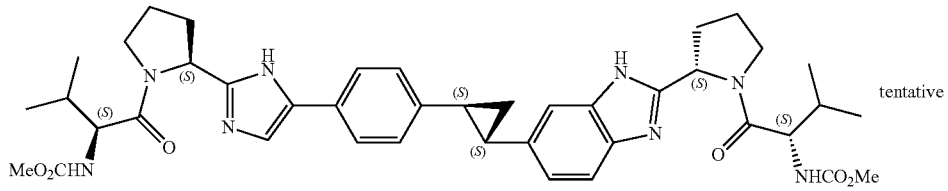 tentative
497-b 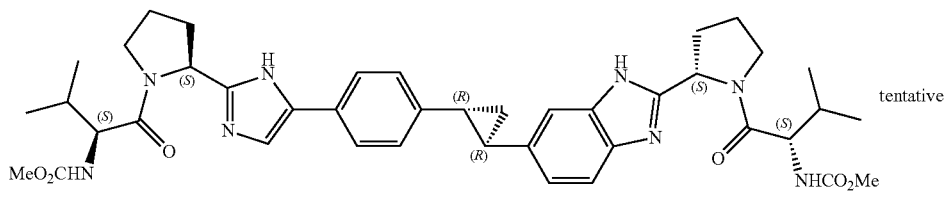 tentative
498 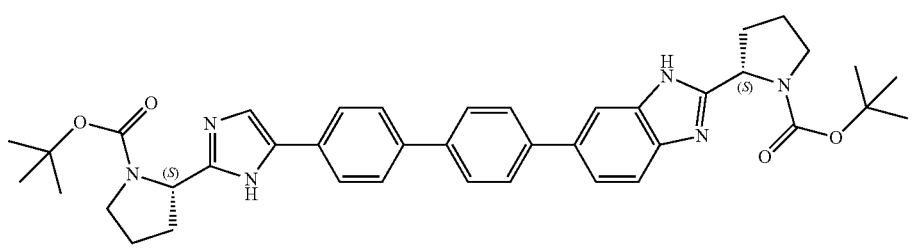

TABLE 9-continued
Compounds 441-545
499
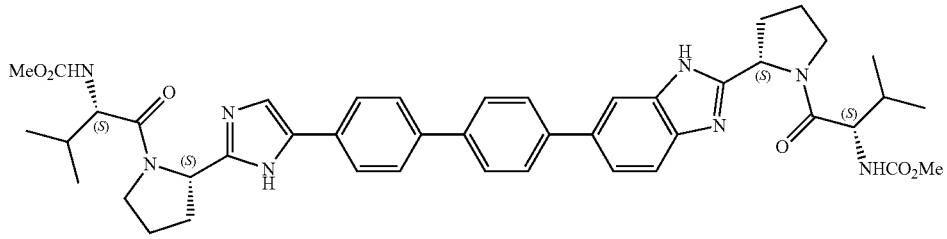
500
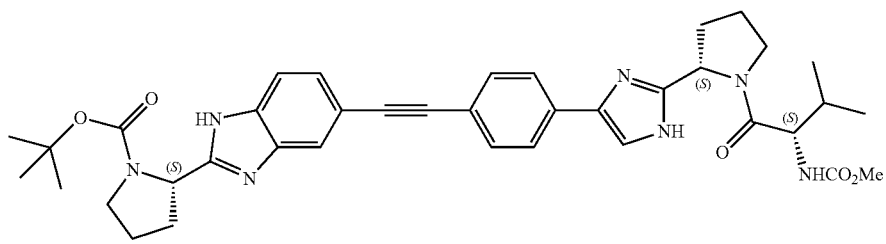
501
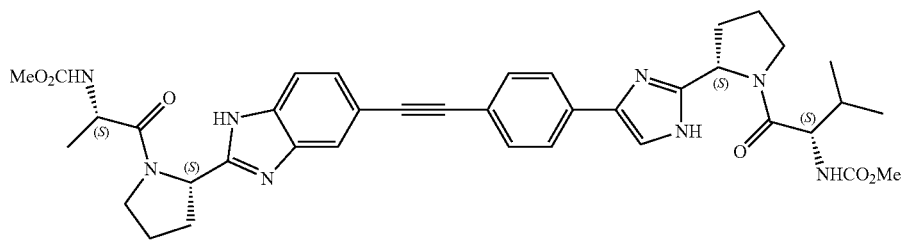
502
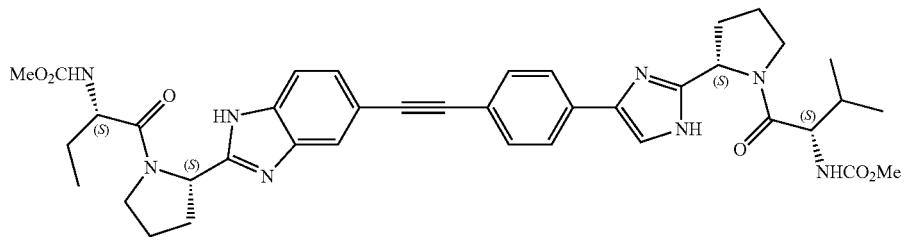
503
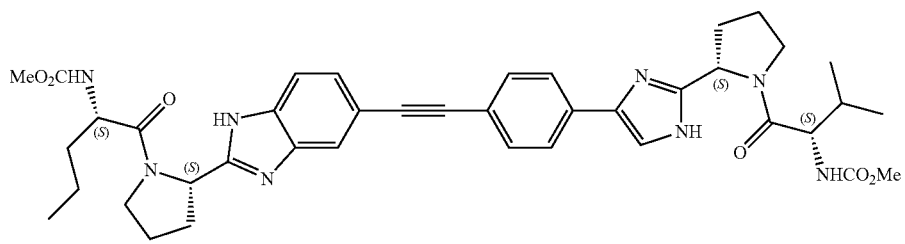
504
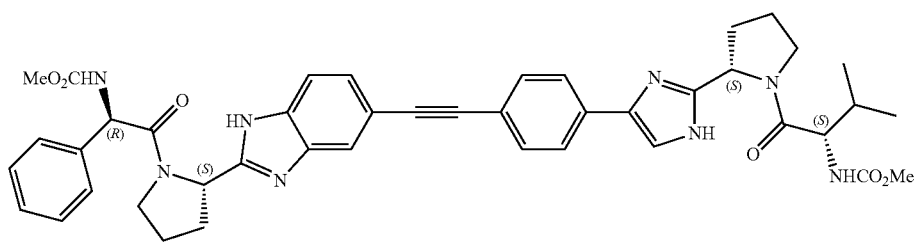

TABLE 9-continued
Compounds 441-545
505 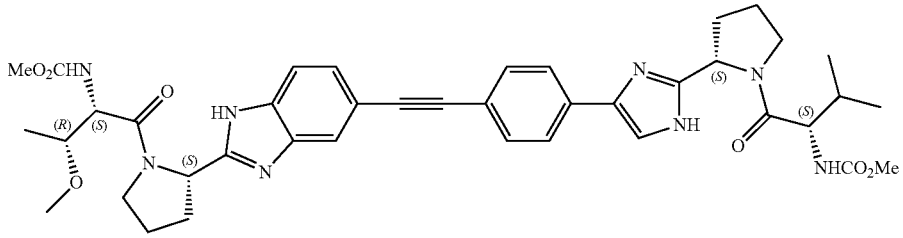
506 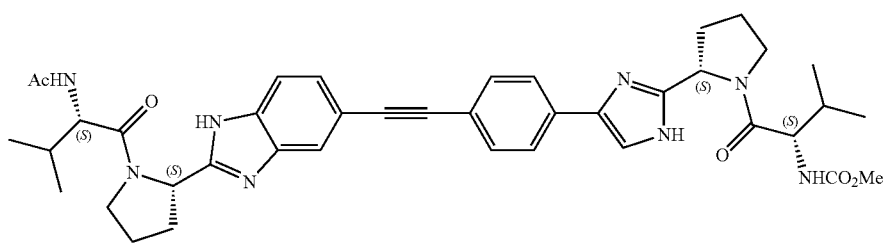
507 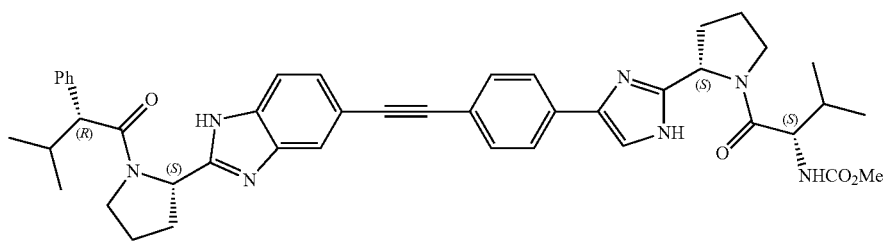
508 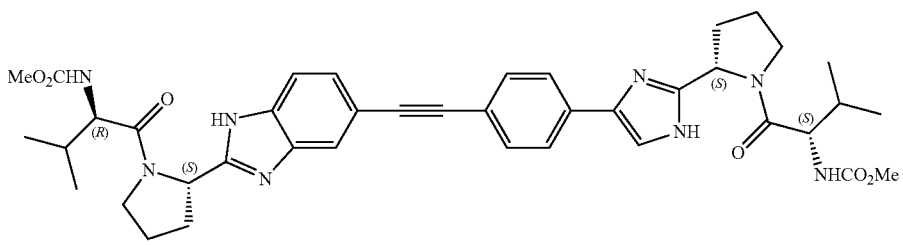
509 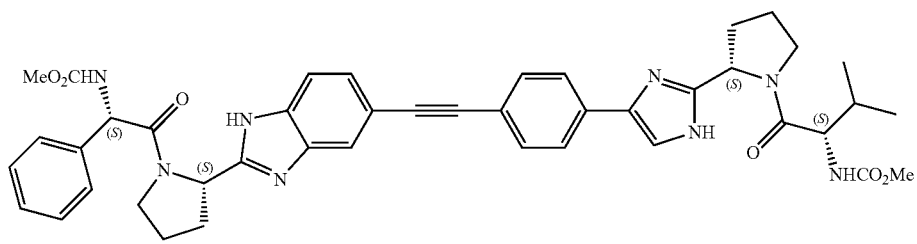
510 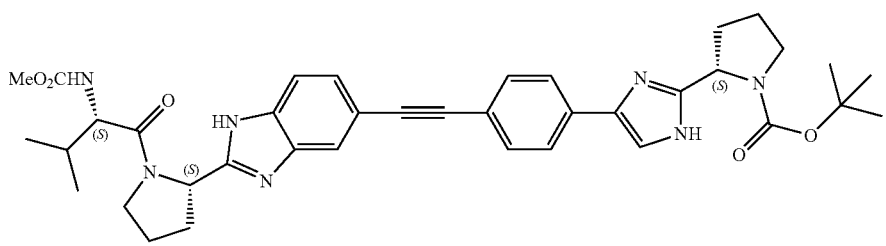

TABLE 9-continued
Compounds 441-545
511
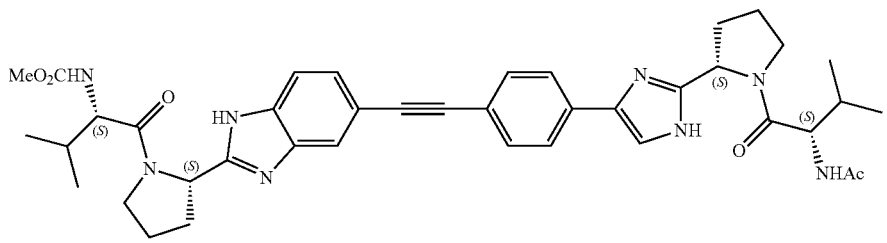
512
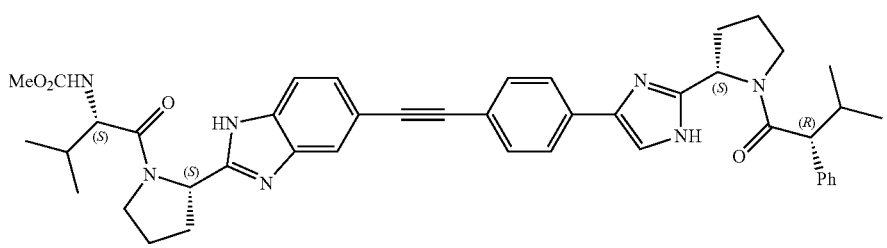
513
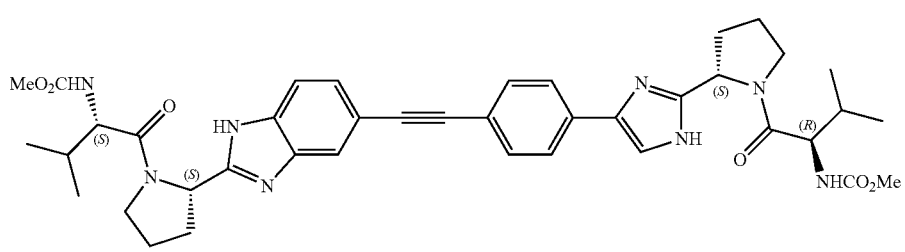
514
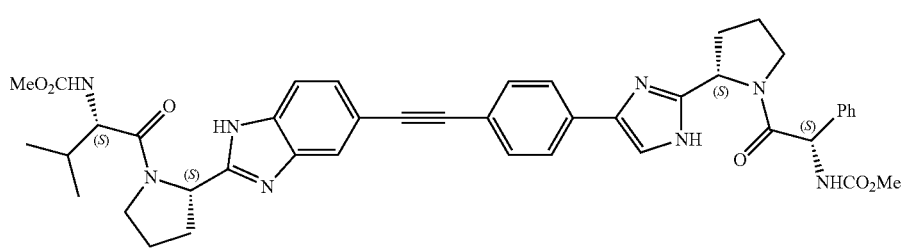
515
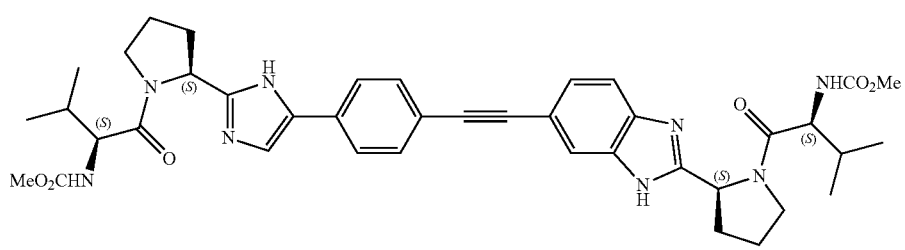
516
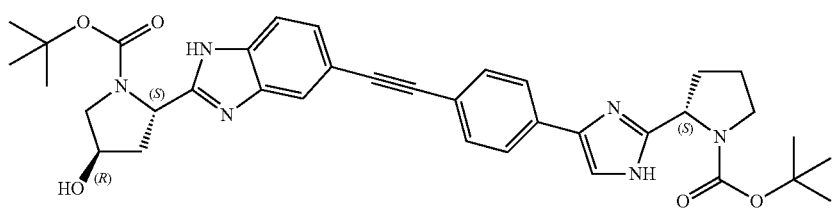

TABLE 9-continued
Compounds 441-545
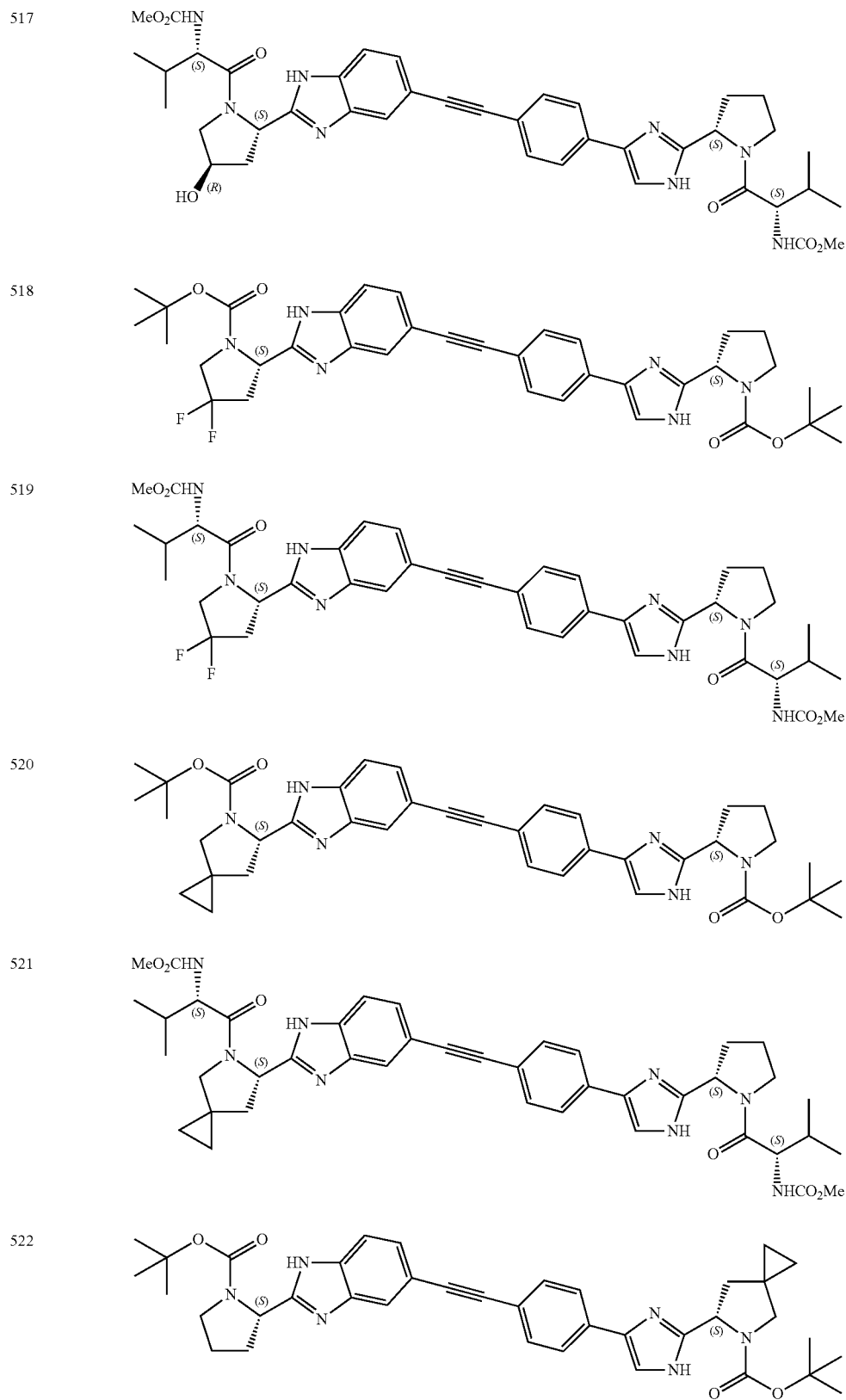

TABLE 9-continued
Compounds 441-545
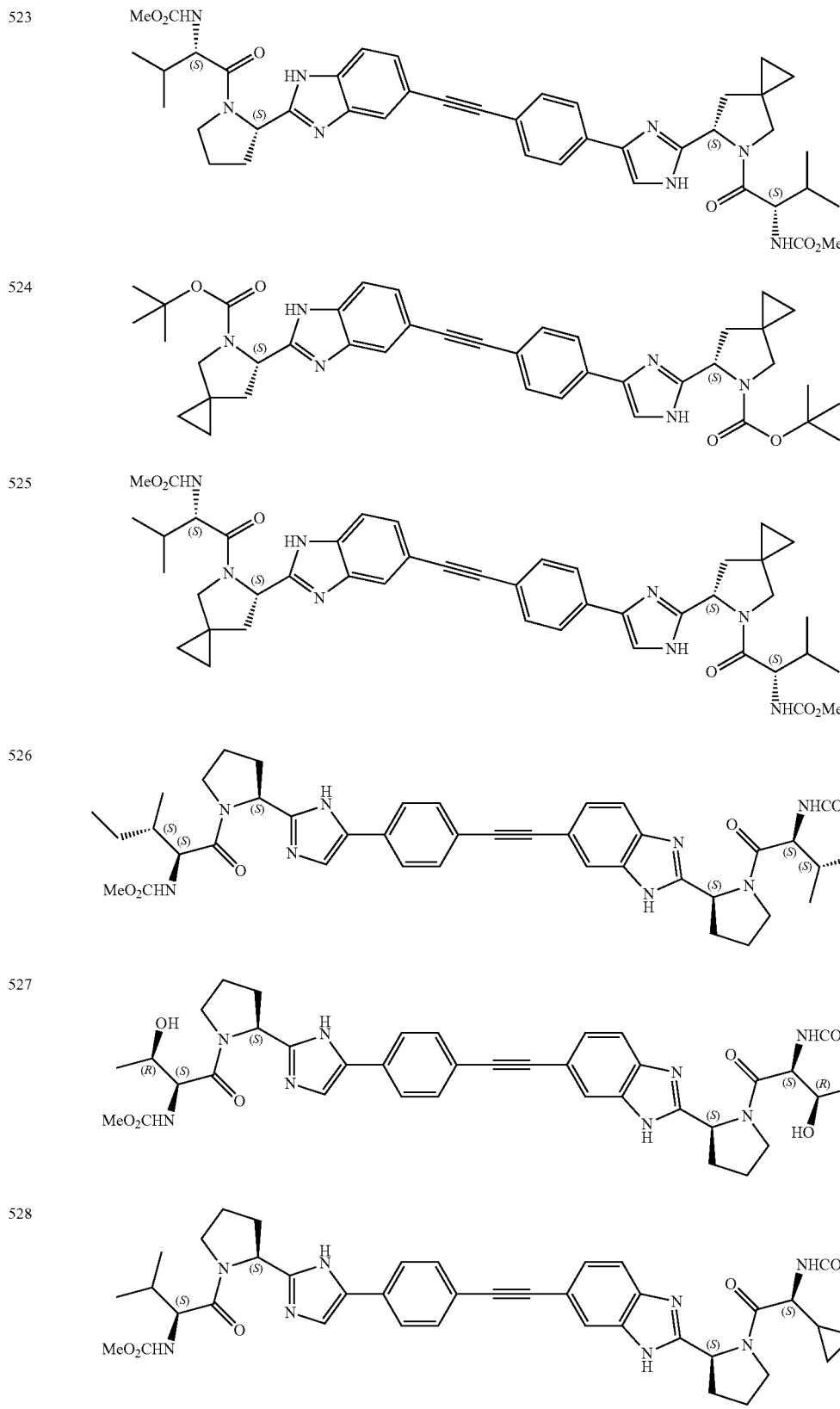

TABLE 9-continued
Compounds 441-545
529 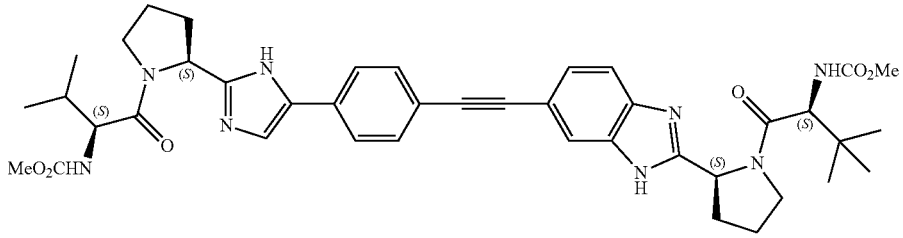
530 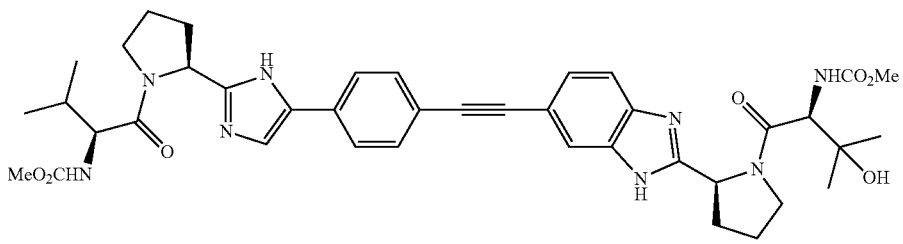
531 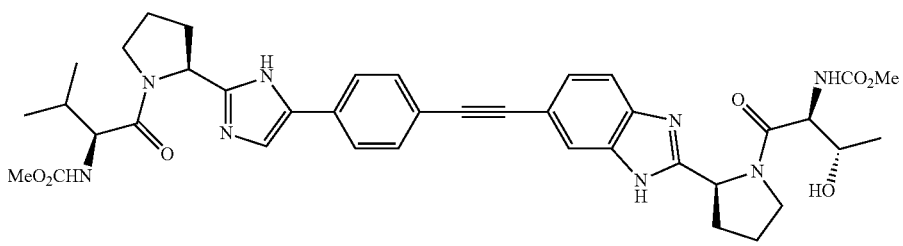
532 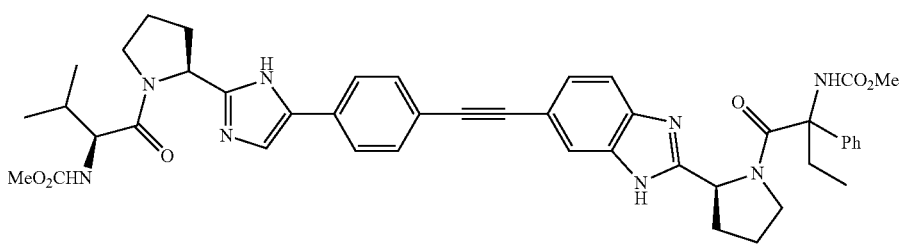
533 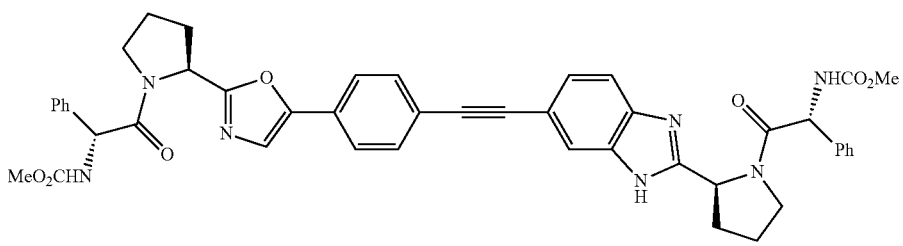
534 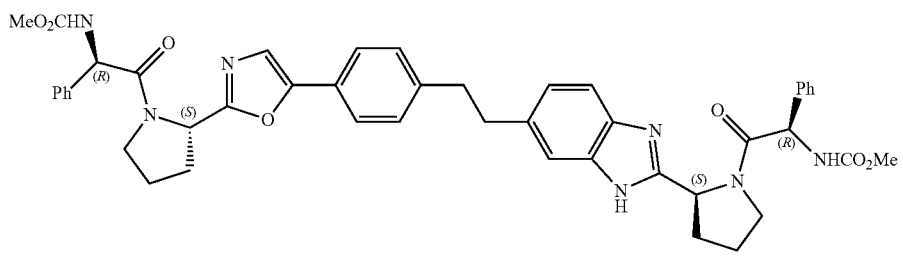

TABLE 9-continued
Compounds 441-545
535 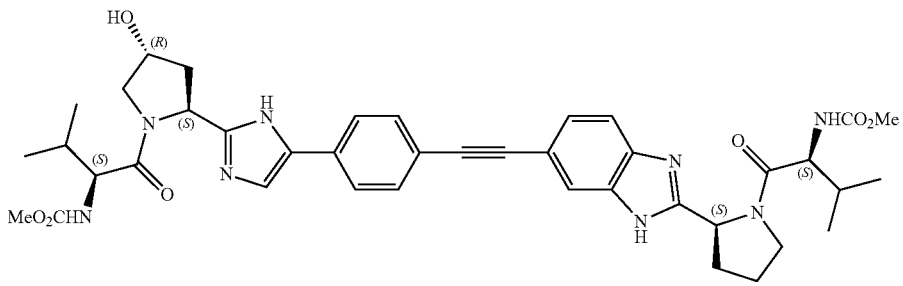
536 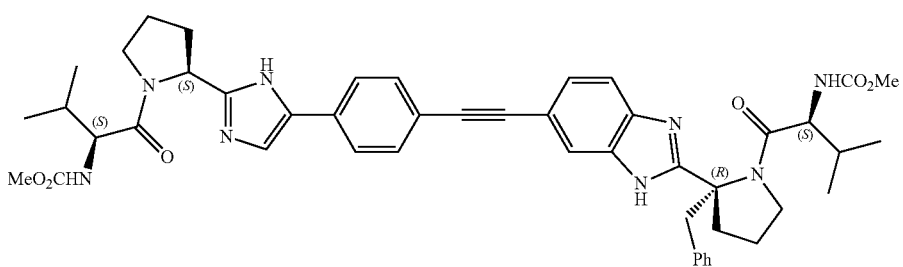
537 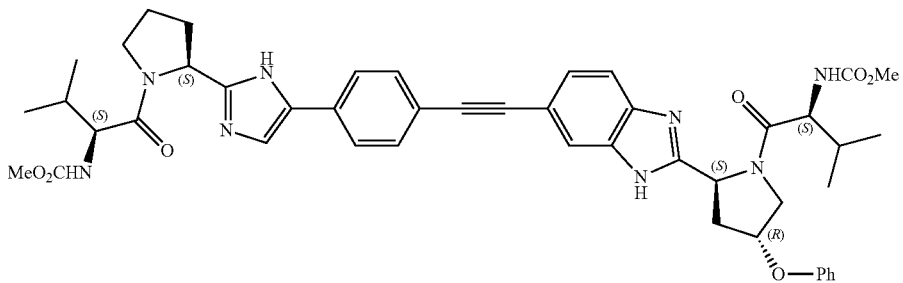
538 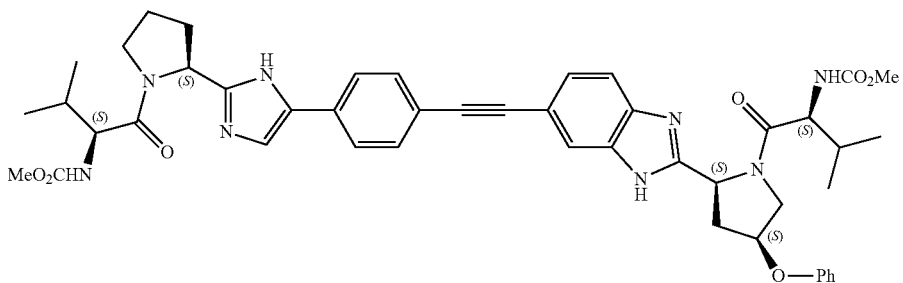
539 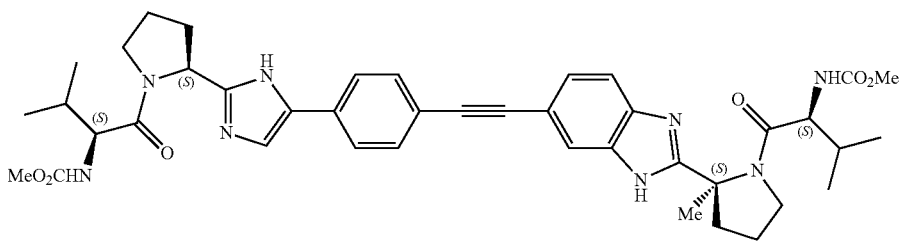

TABLE 9-continued
Compounds 441-545
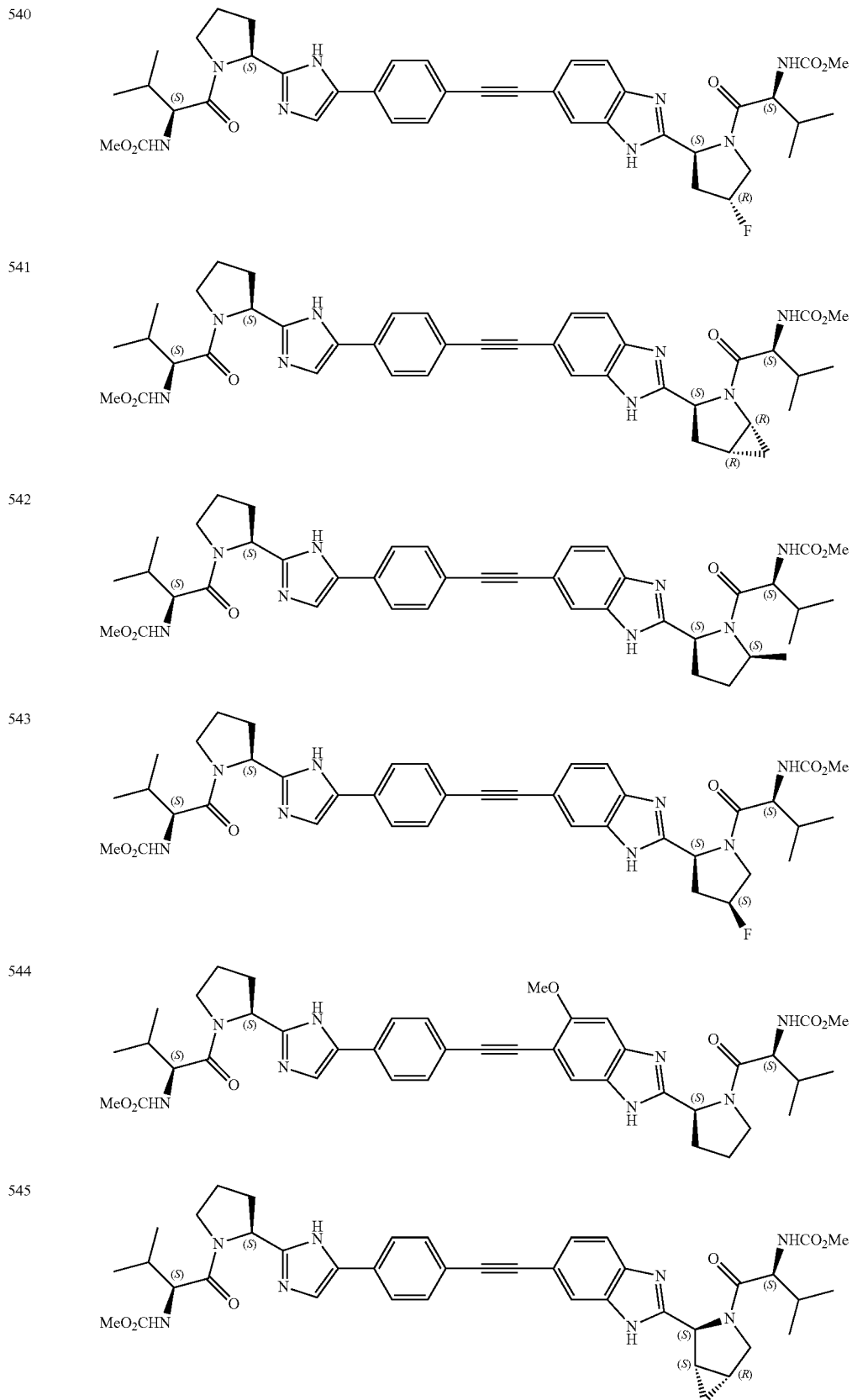

TABLE 9-continued
Compounds 441-545
546
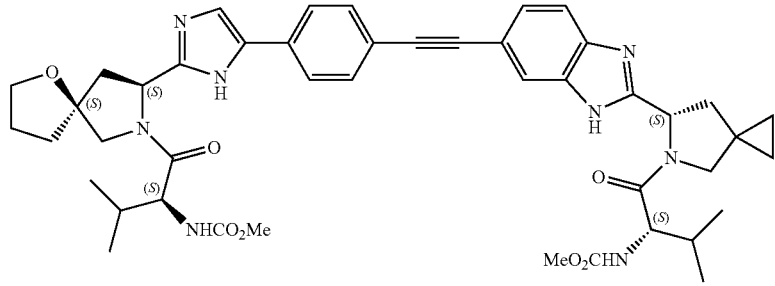
547
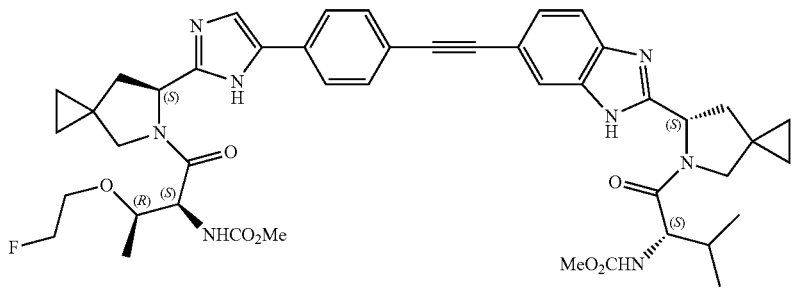
548
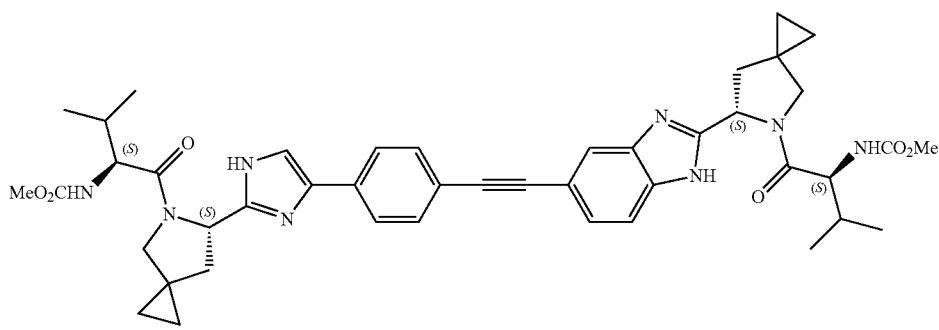
549
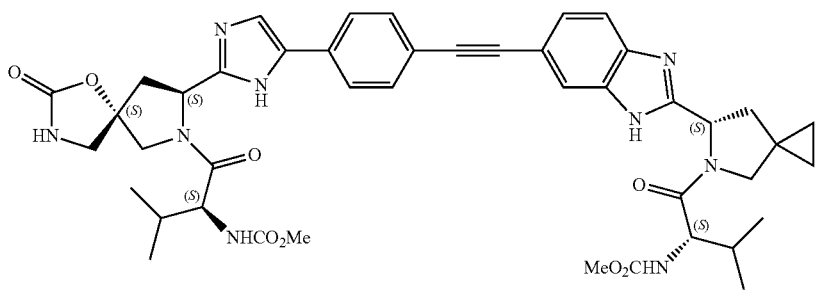
550
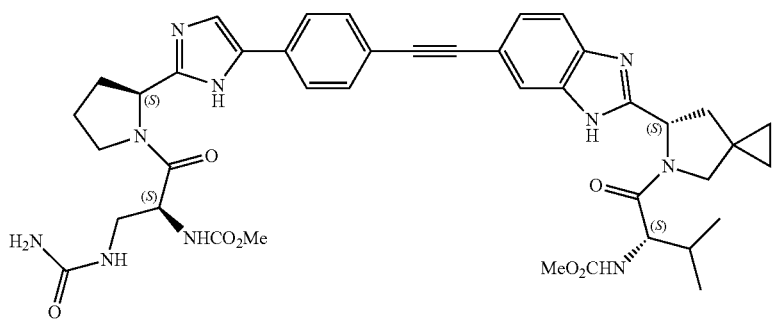

TABLE 9-continued
Compounds 441-545
551 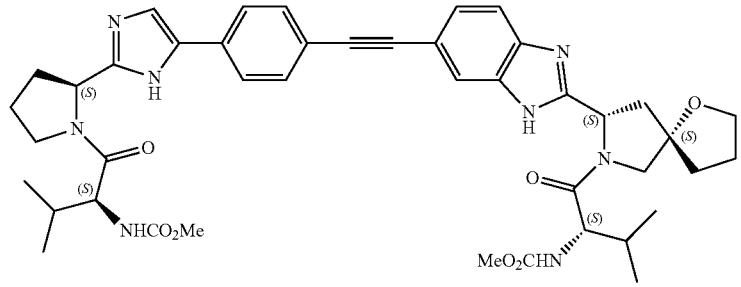
552 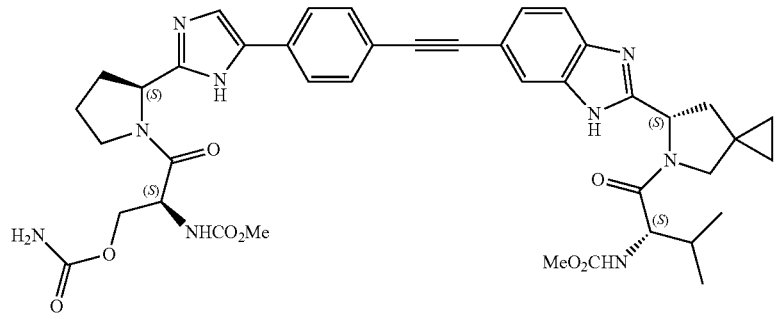
553 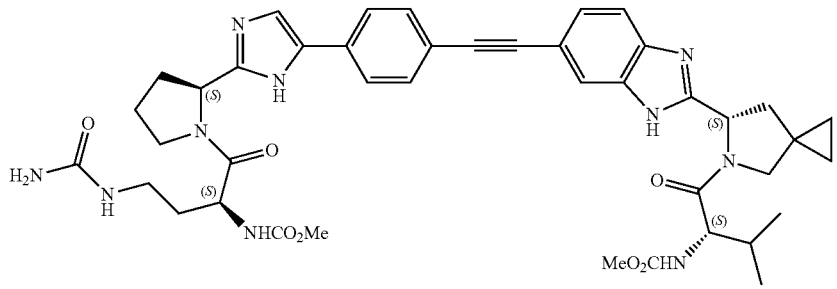
554 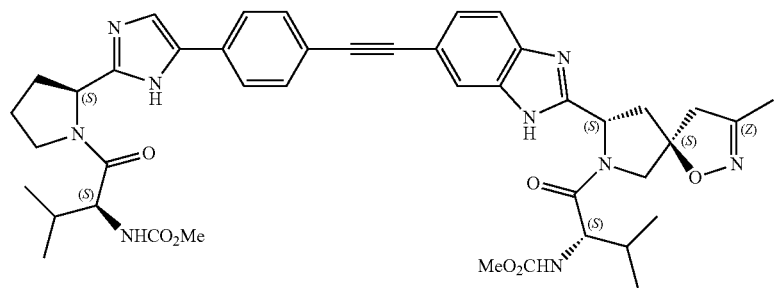
555 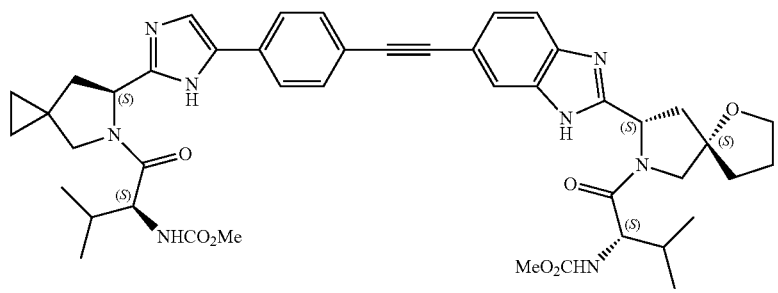

TABLE 9-continued
Compounds 441-545
556
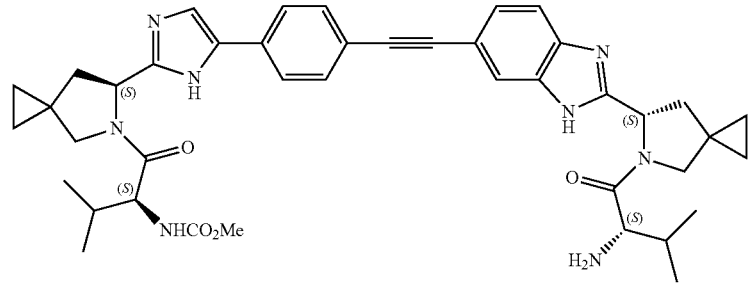
557
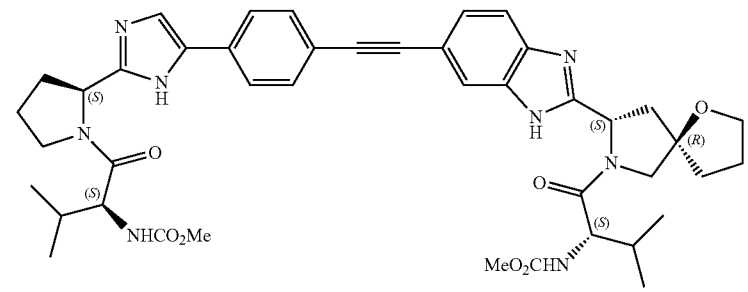
558
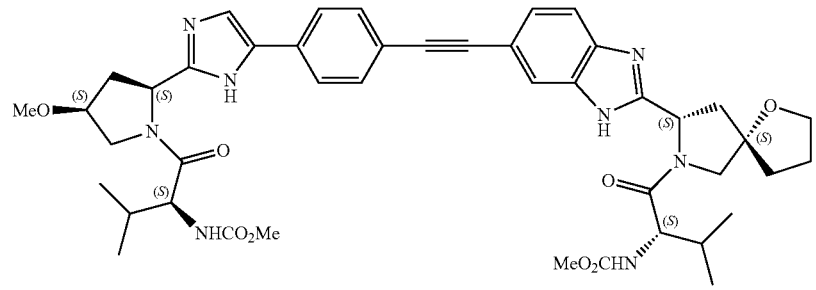
559
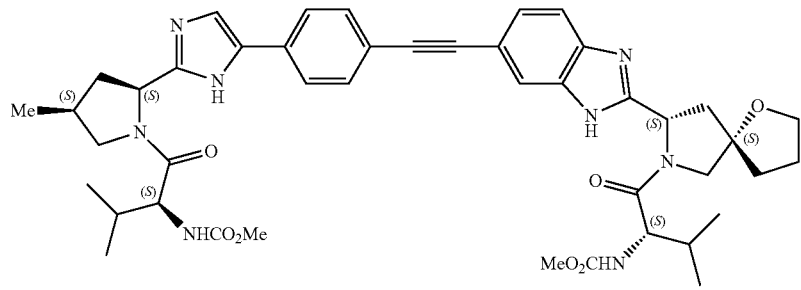
560
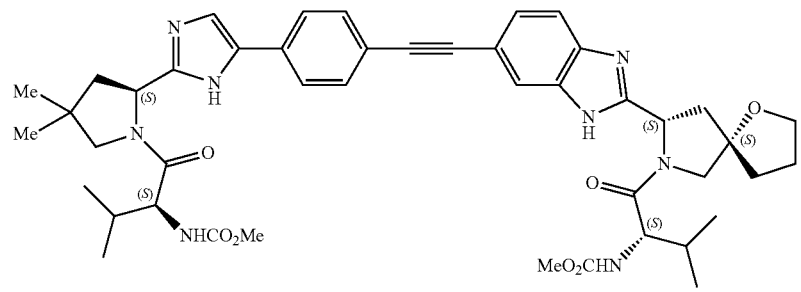

TABLE 9-continued
Compounds 441-545
561 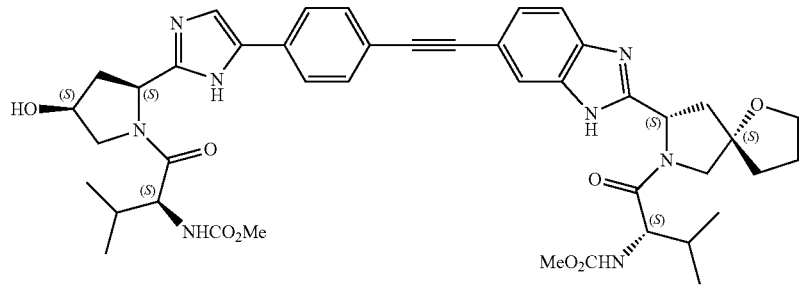
562 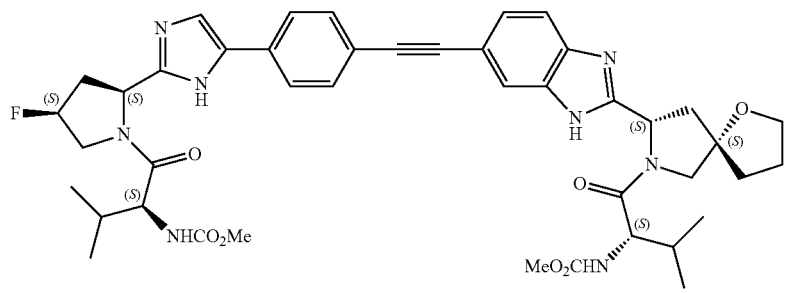
563 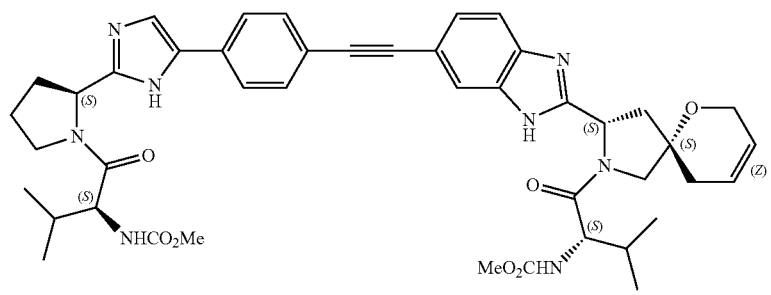
564 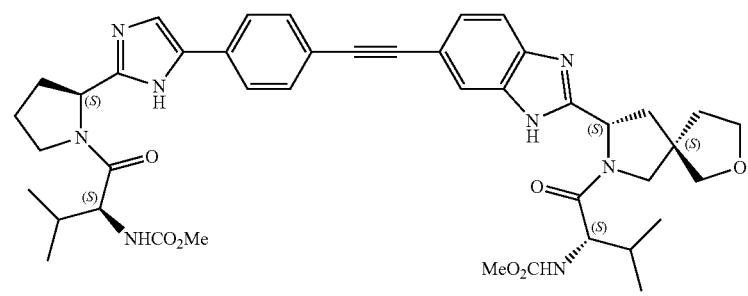
565 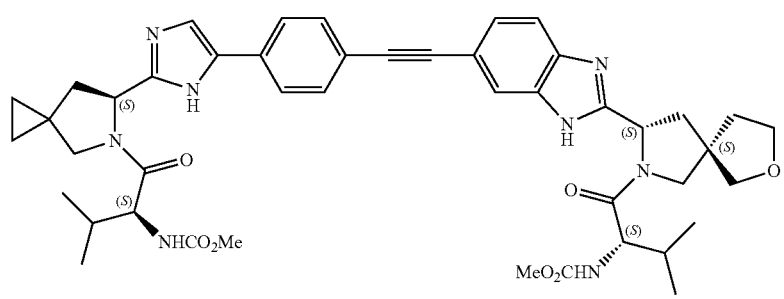

TABLE 9-continued
Compounds 441-545
566 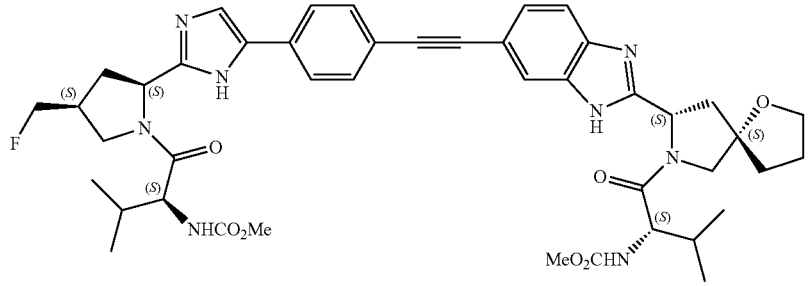
567 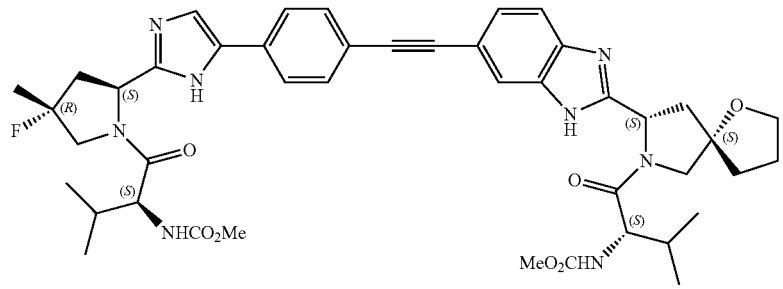
568 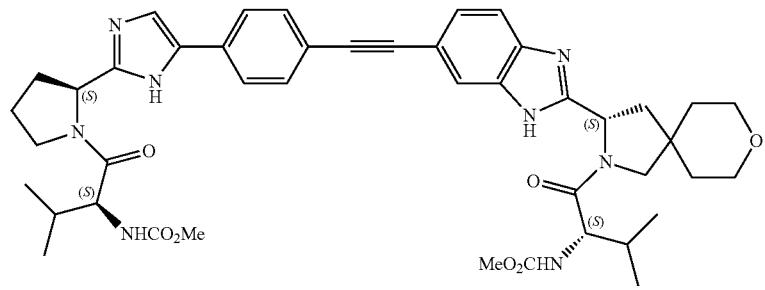
569 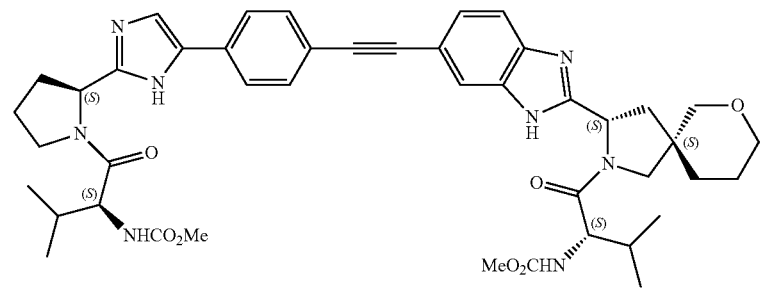
570 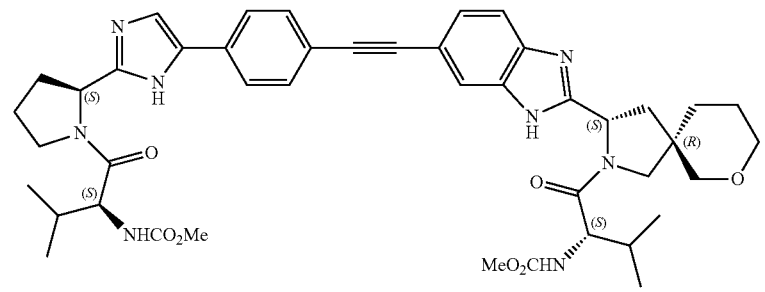

TABLE 9-continued
Compounds 441-545
571 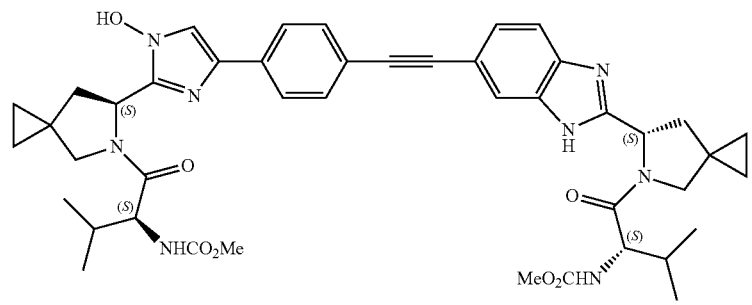
572 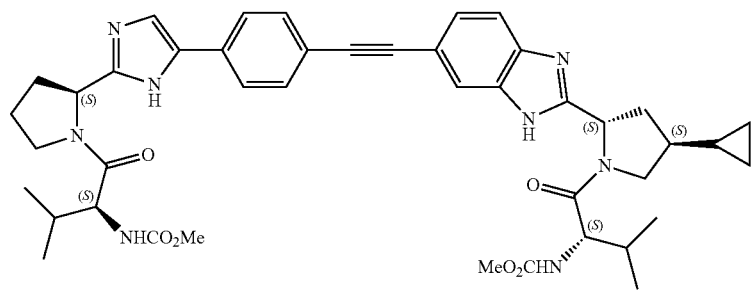
573 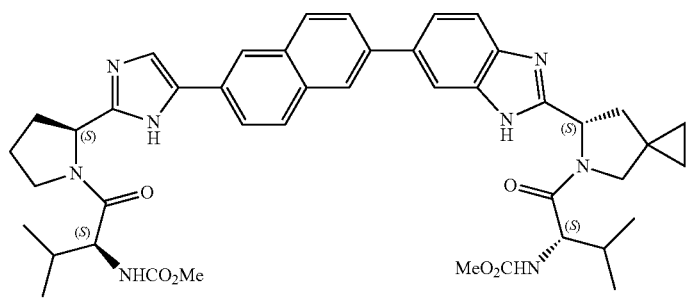
574 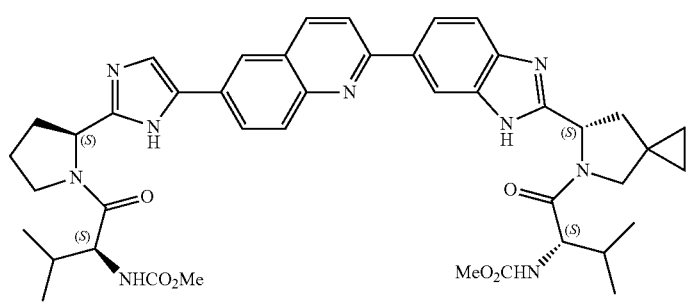
575 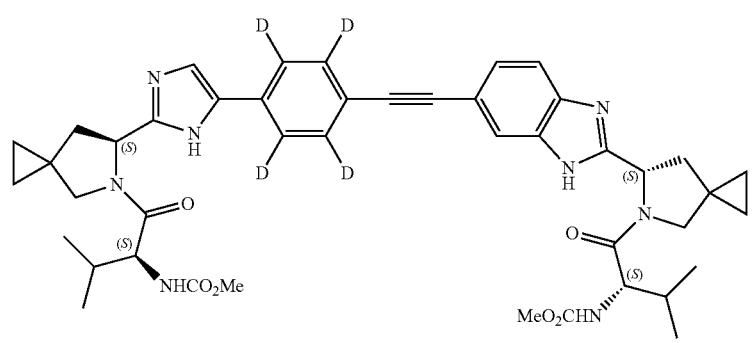

TABLE 9-continued
Compounds 441-545
576 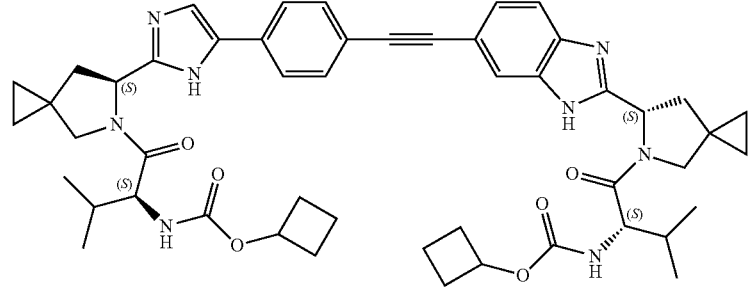
577 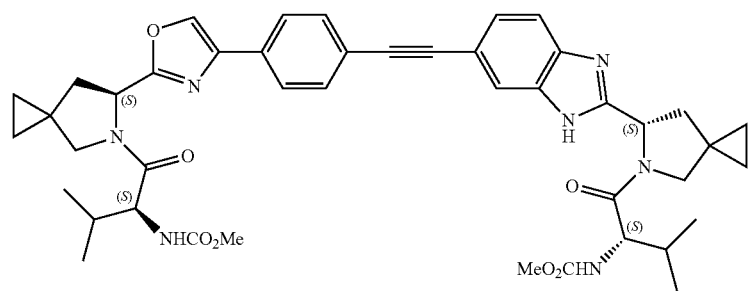
578 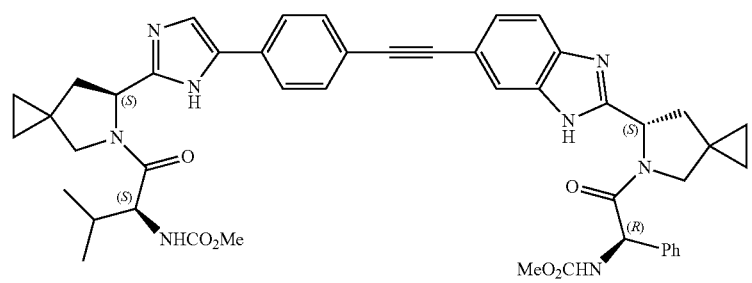
579 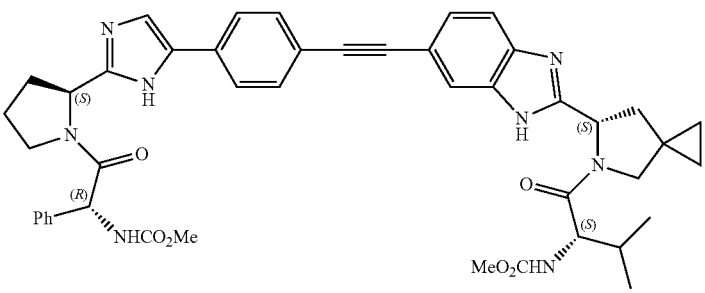
580 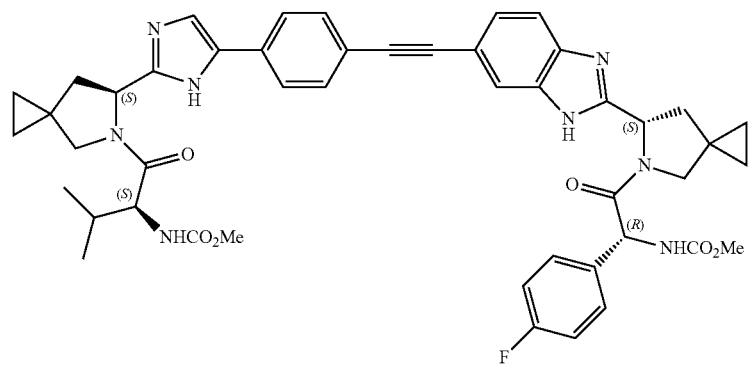

TABLE 9-continued
Compounds 441-545
581 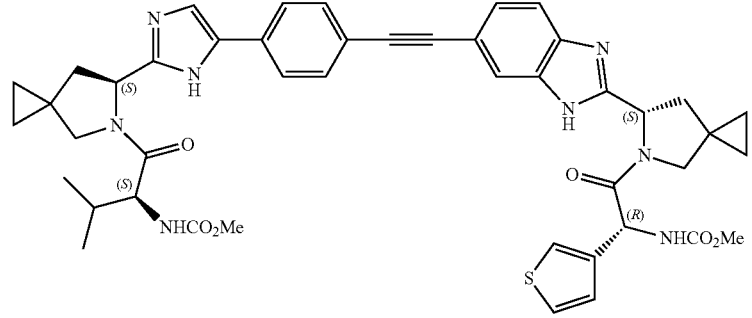
582 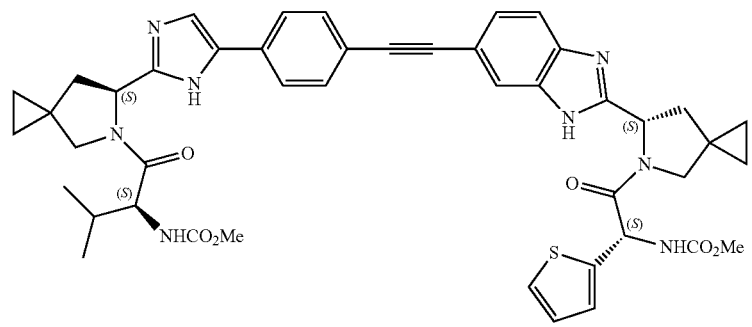
583 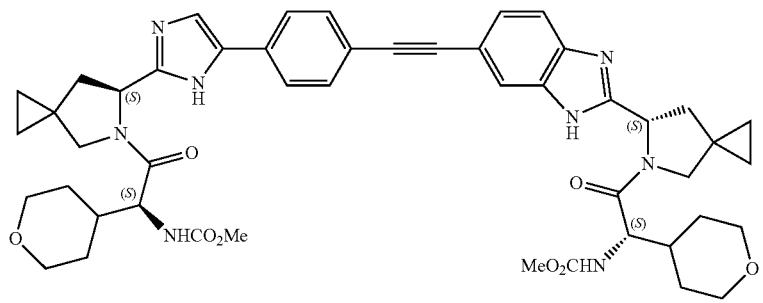
584 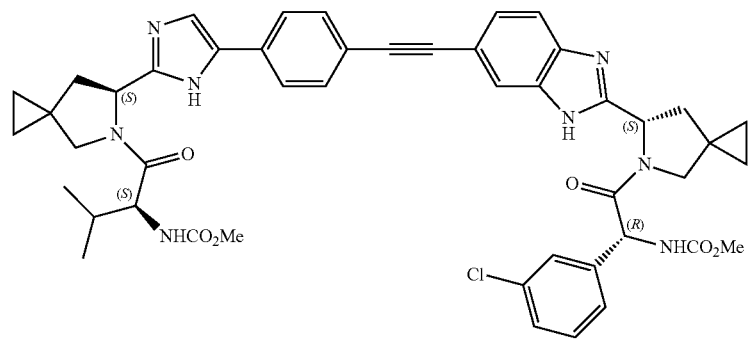

TABLE 9-continued
Compounds 441-545
585 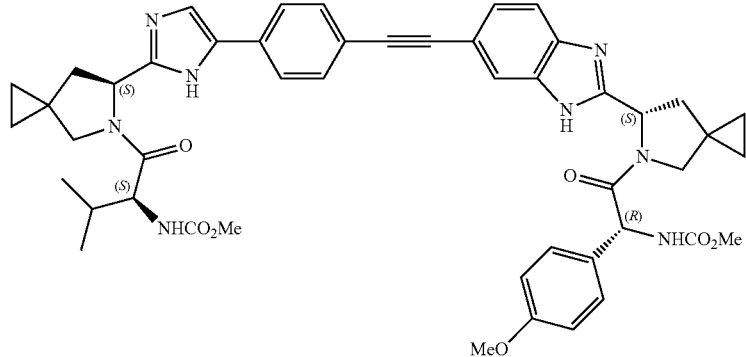
586 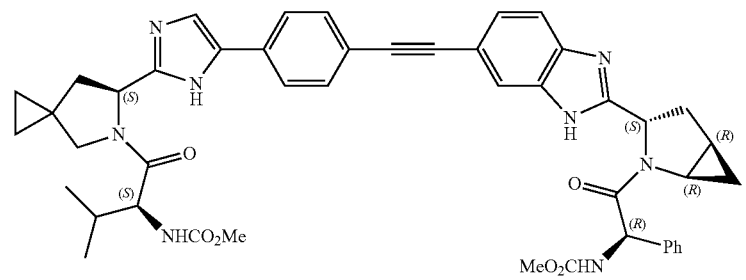
587 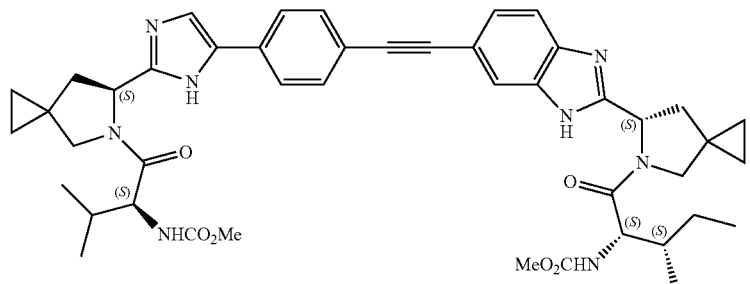
588 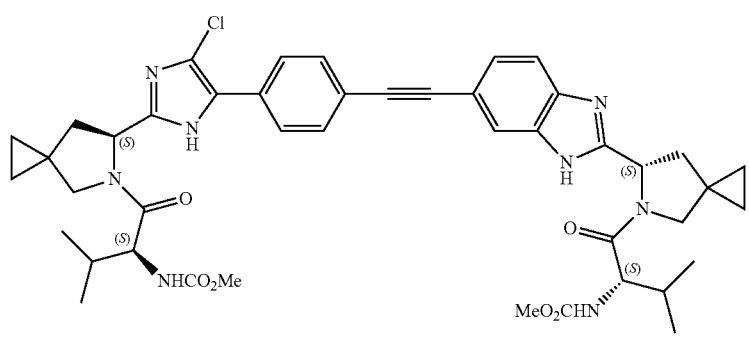
589 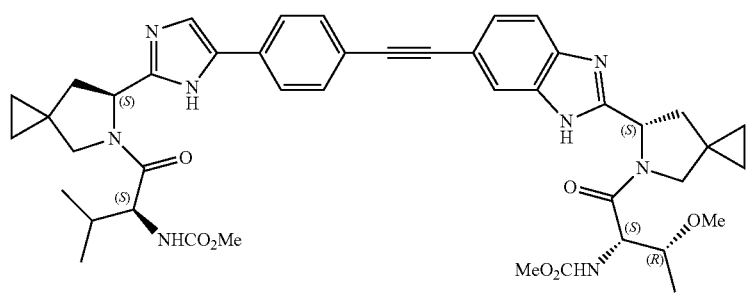

TABLE 9-continued
Compounds 441-545
590 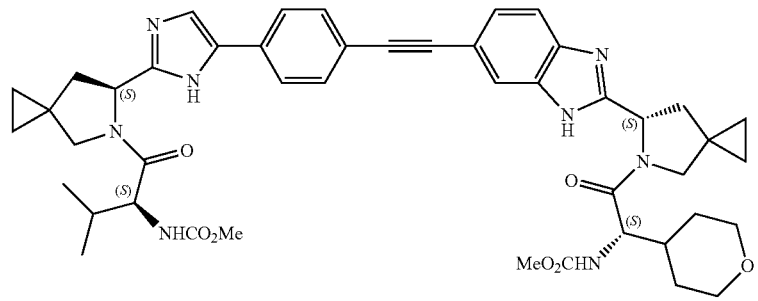
591 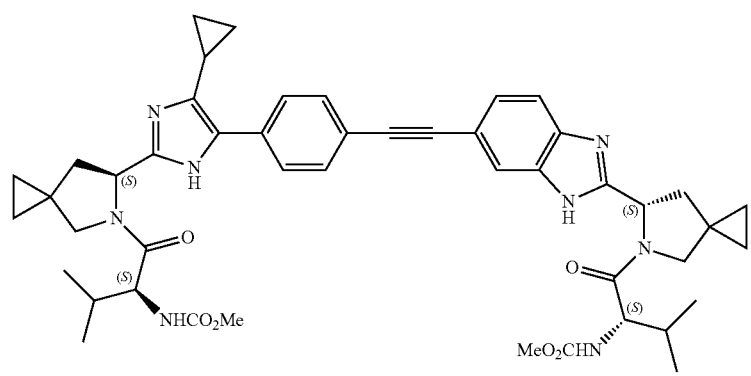
592 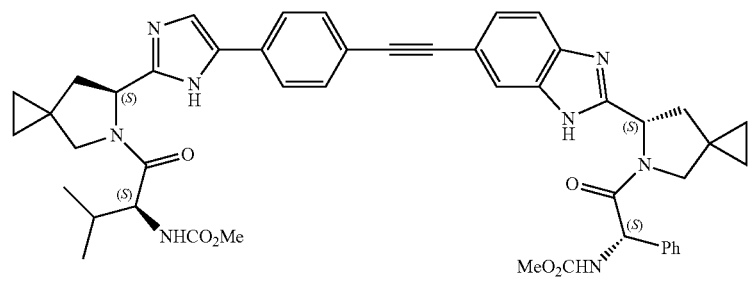
593 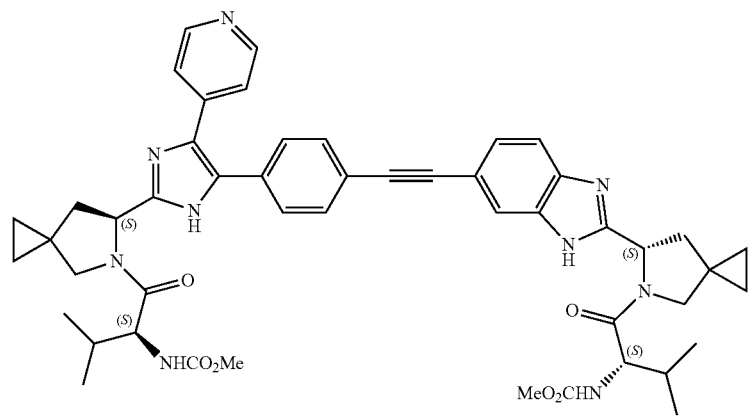

TABLE 9-continued
Compounds 441-545
594
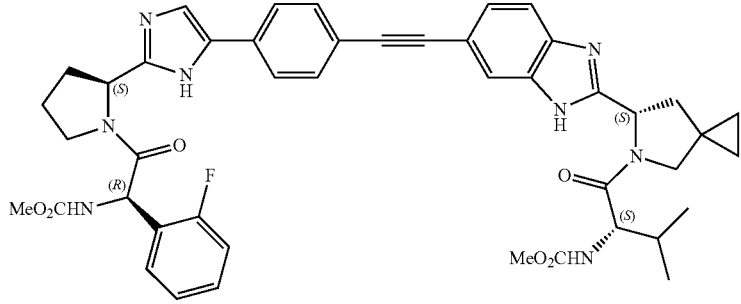
595
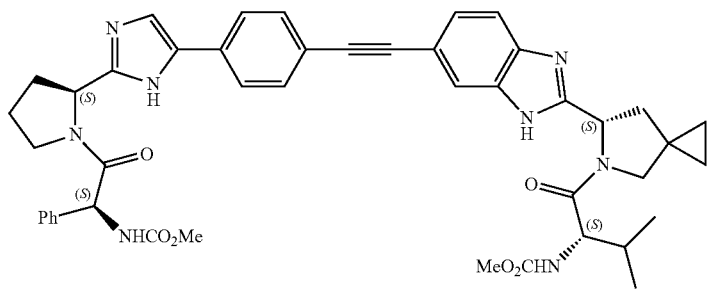
596
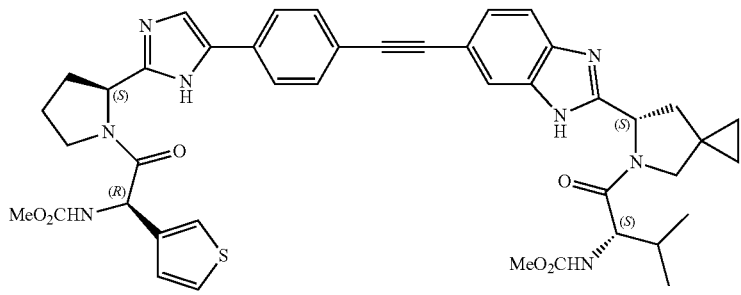
597
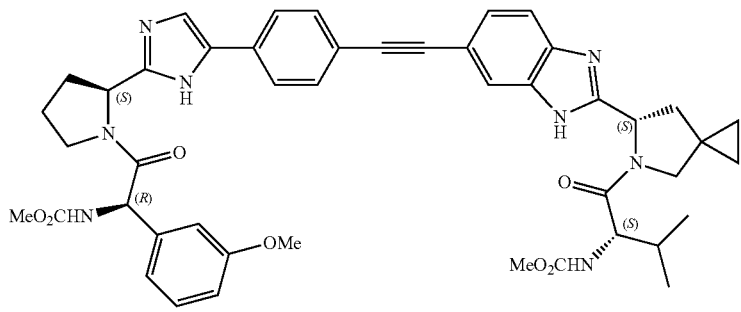
598
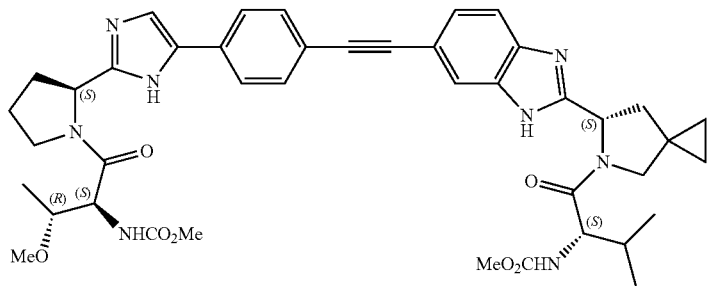

TABLE 9-continued
Compounds 441-545
599
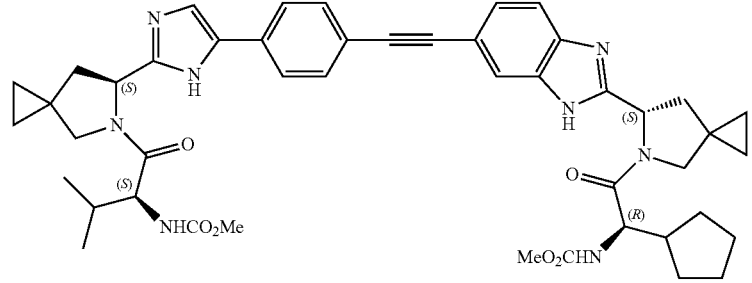
600
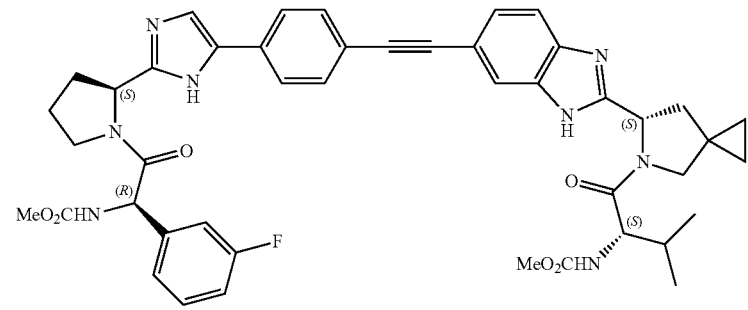
601
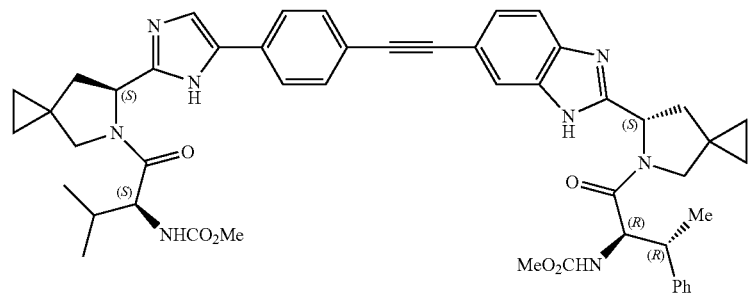
602
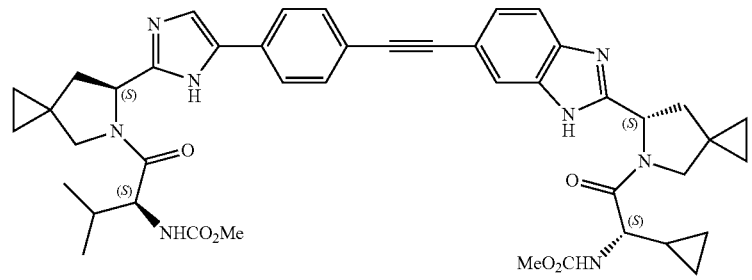
603
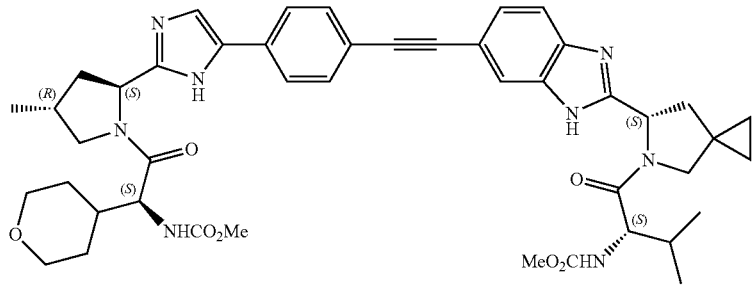

TABLE 9-continued
Compounds 441-545
604
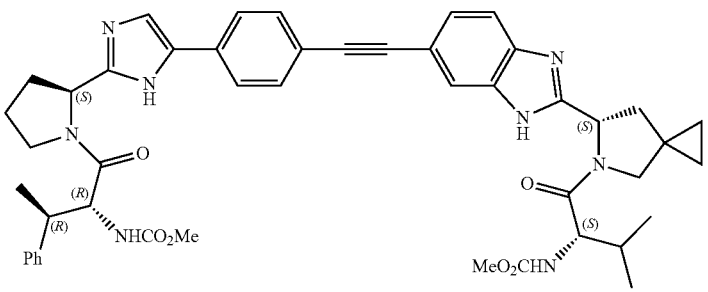
605
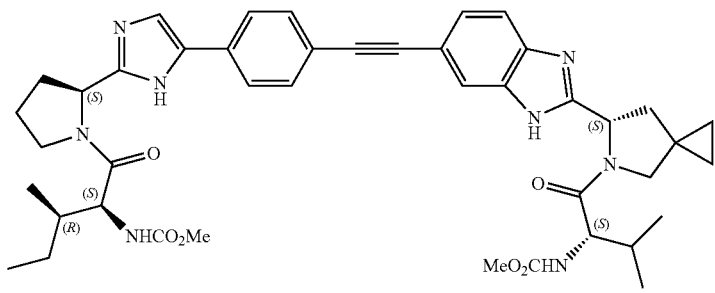
606
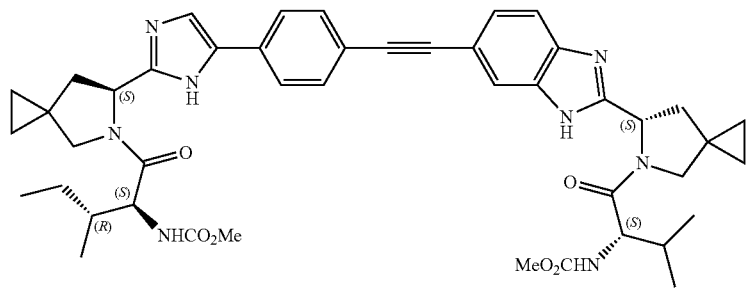
607
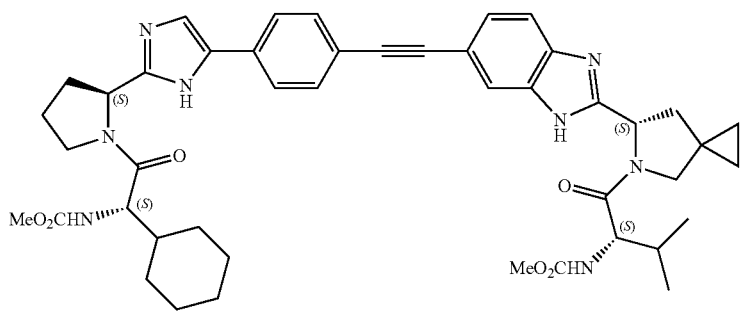
608
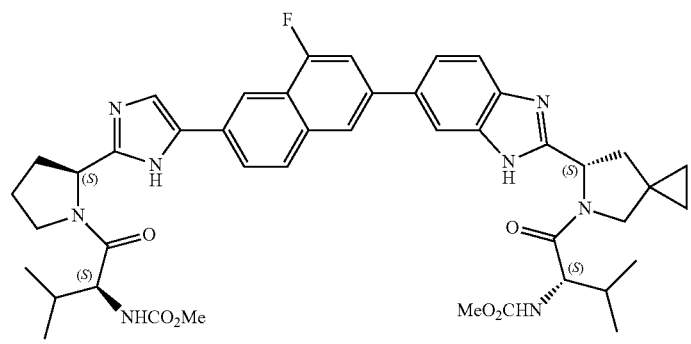

US 9,765,087 B2
193                                                        194
TABLE 9-continued
Compounds 441-545
609 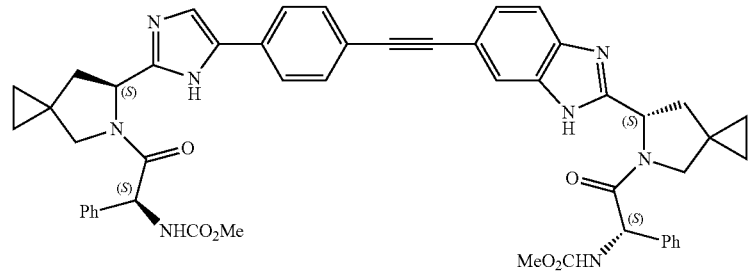
610 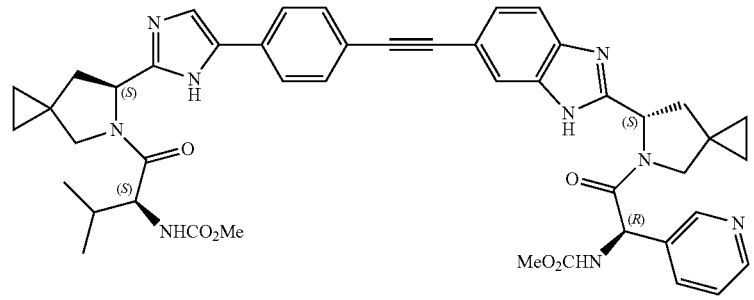
611 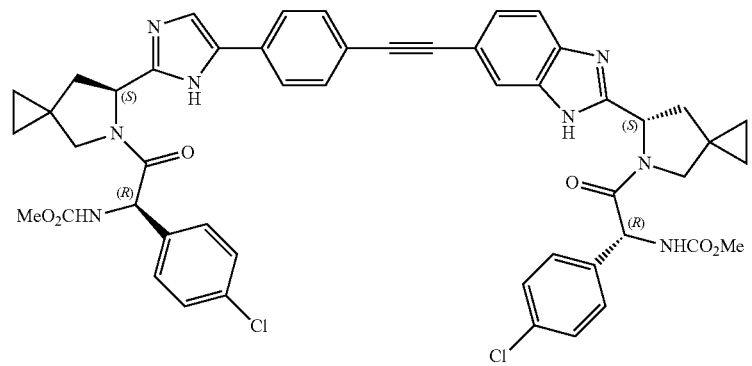
612 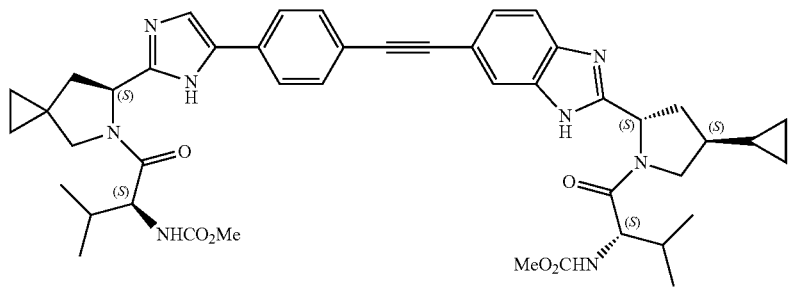
613 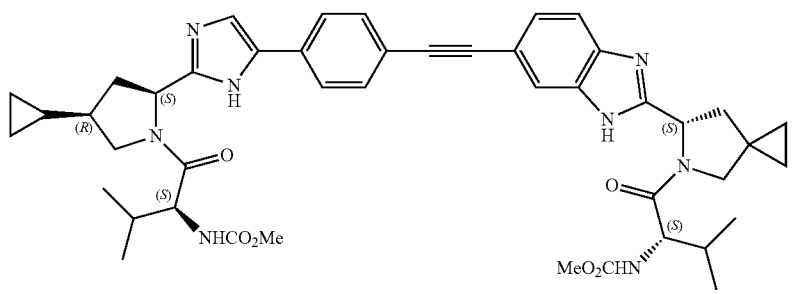

TABLE 9-continued
Compounds 441-545
614
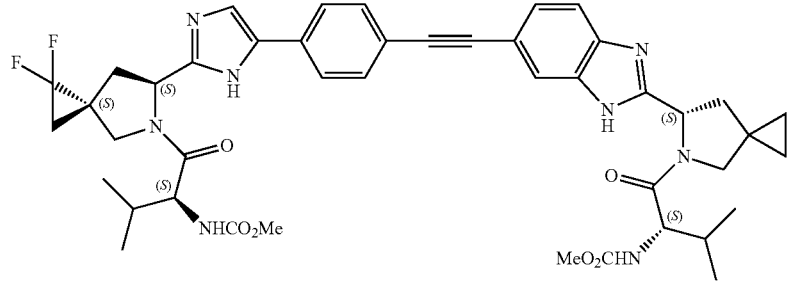
615
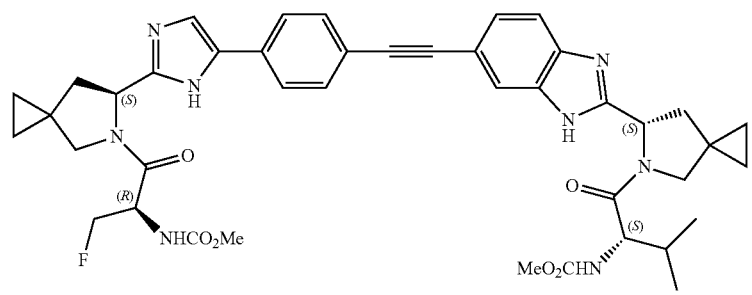
616
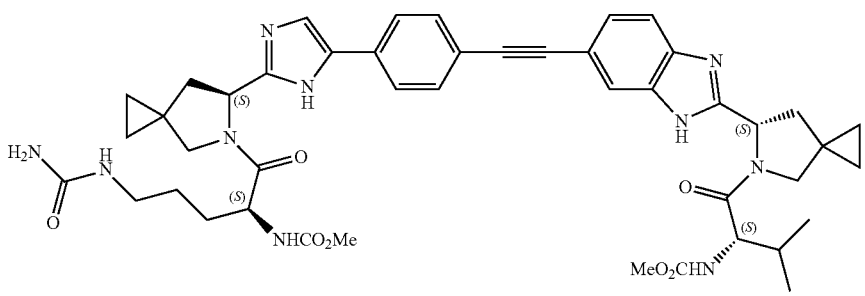
617
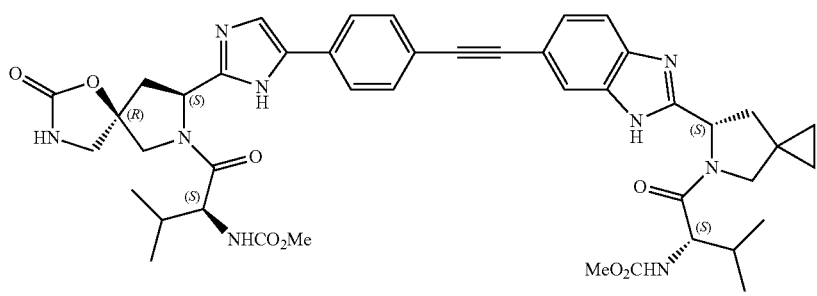
618
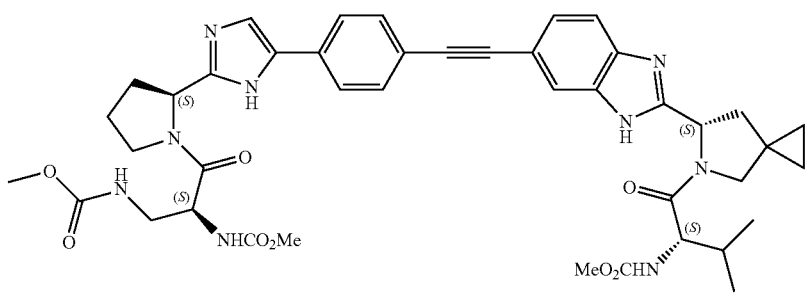

TABLE 9-continued
Compounds 441-545
619
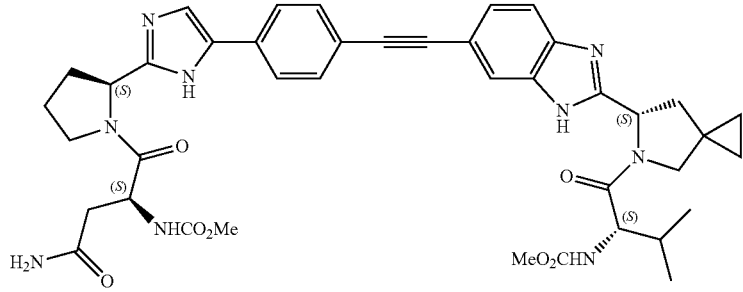
620
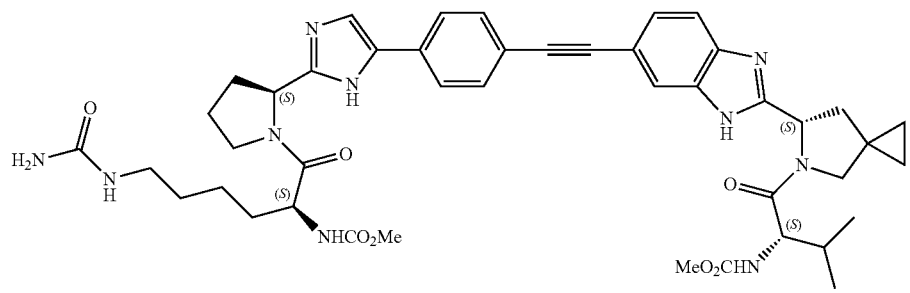
621
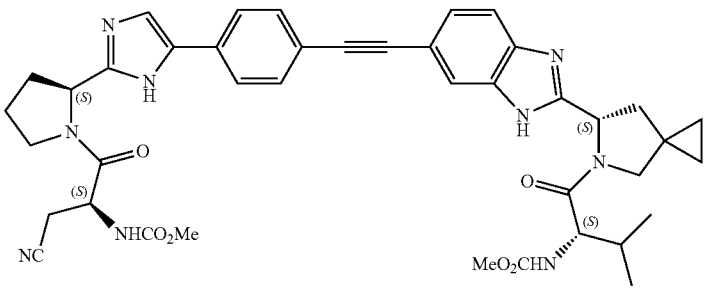
622
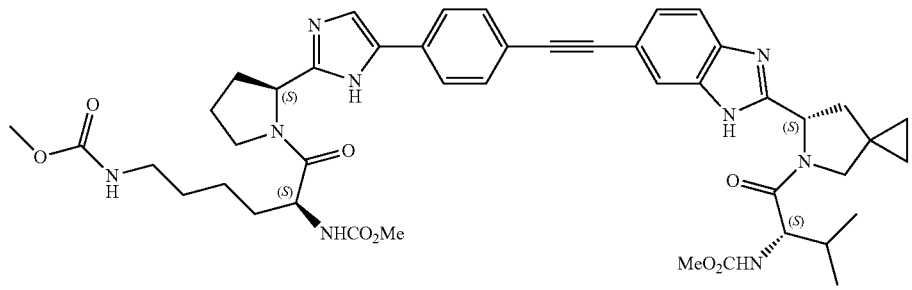
623
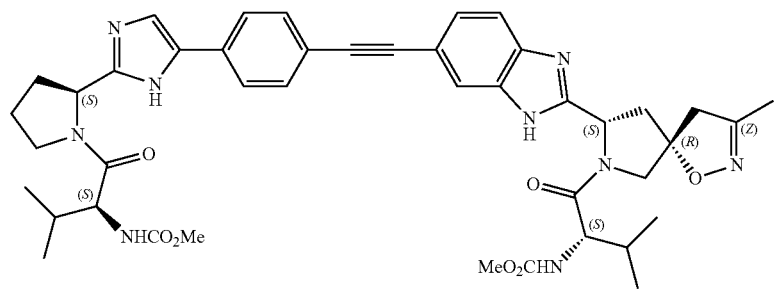

TABLE 9-continued
Compounds 441-545
624
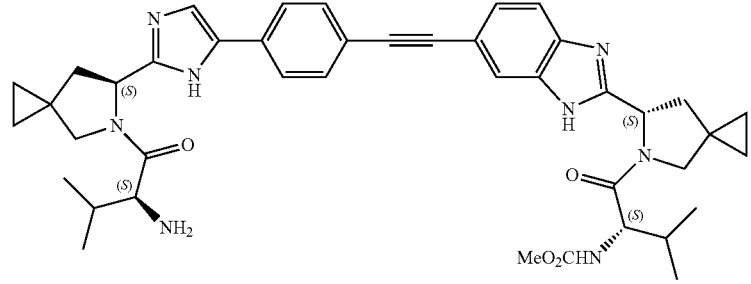
625
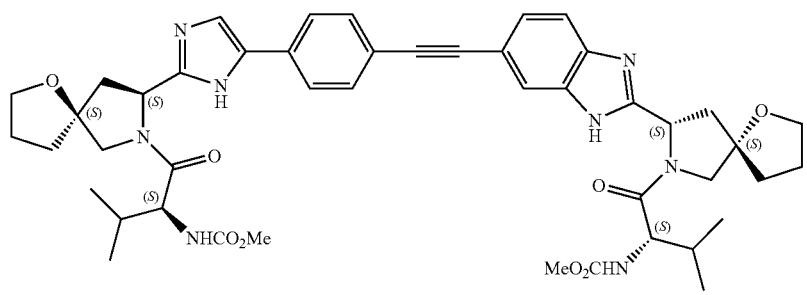
626
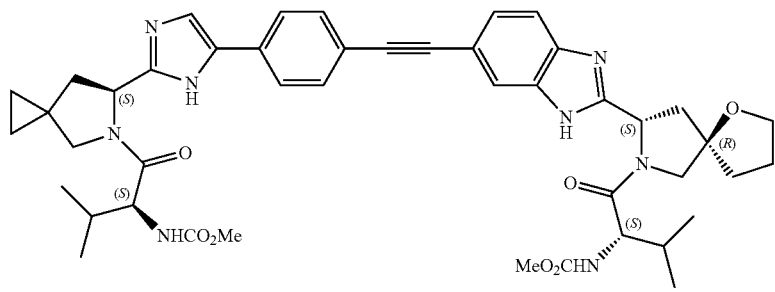
627
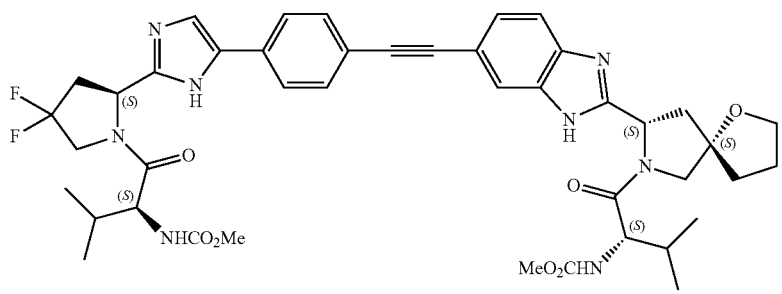
628
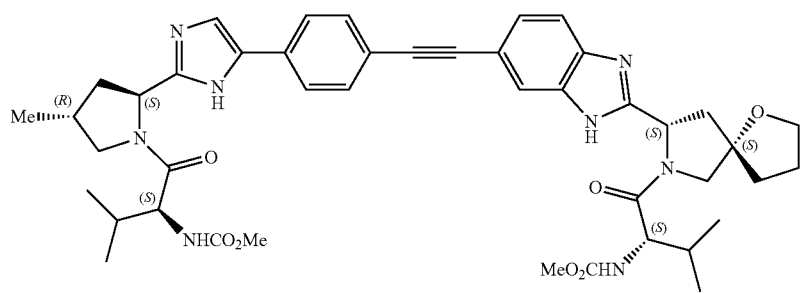

TABLE 9-continued
Compounds 441-545
629 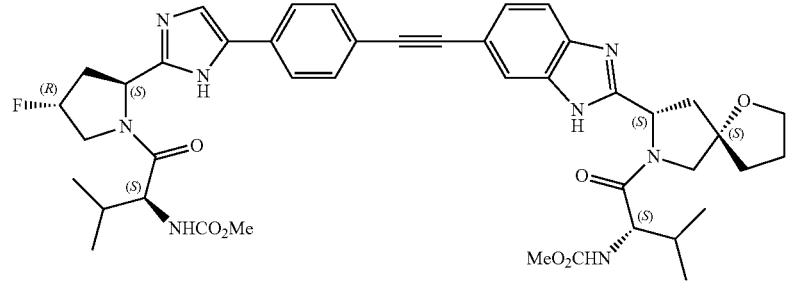
630 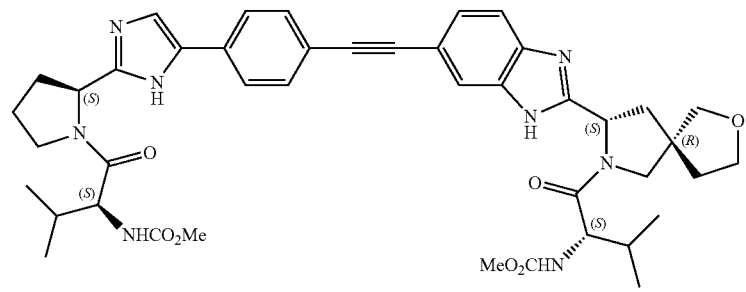
631 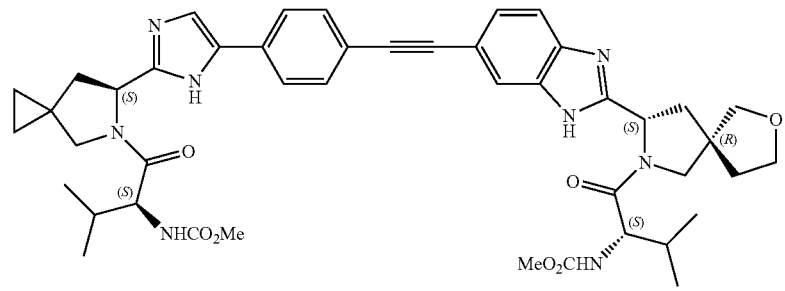
632 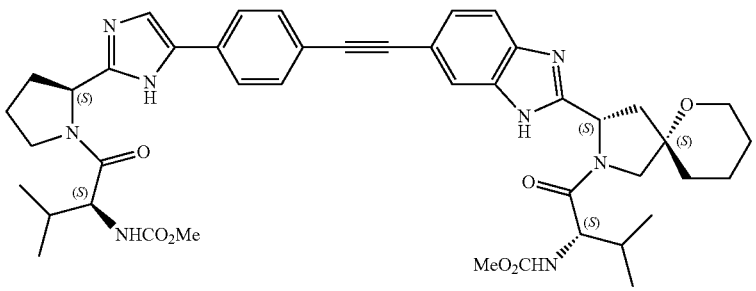
633 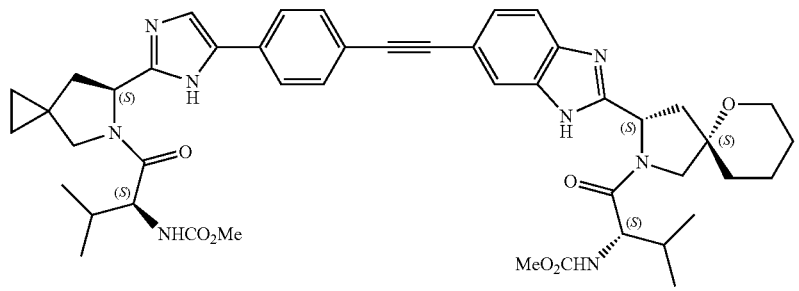

TABLE 9-continued
Compounds 441-545
634 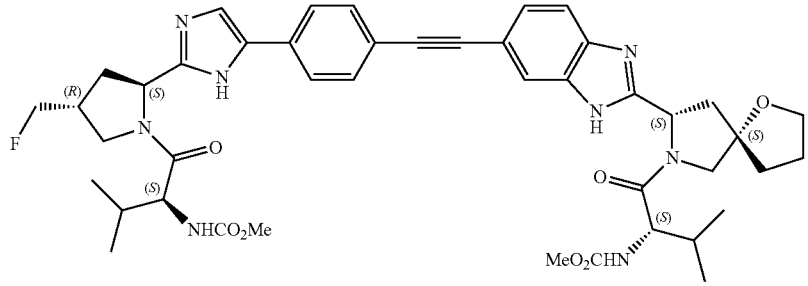
635 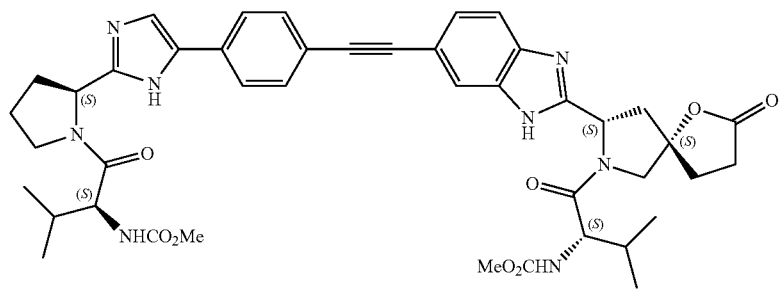
636 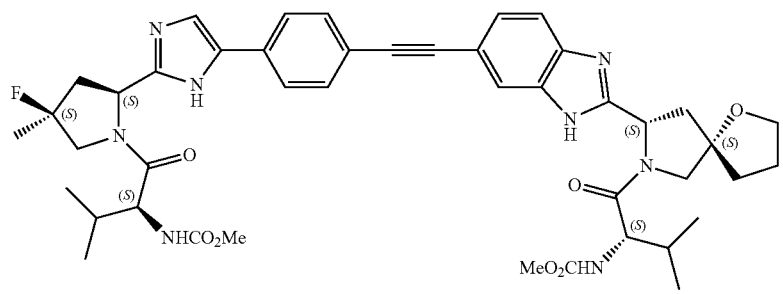
637 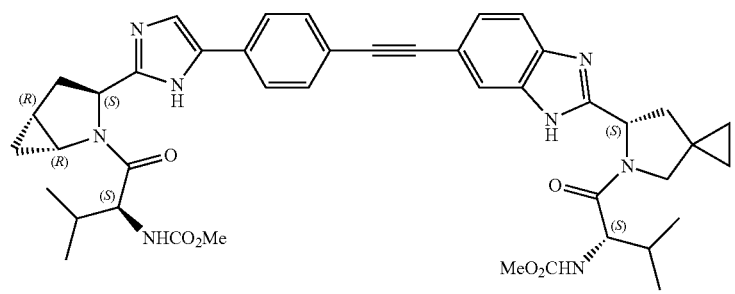
638 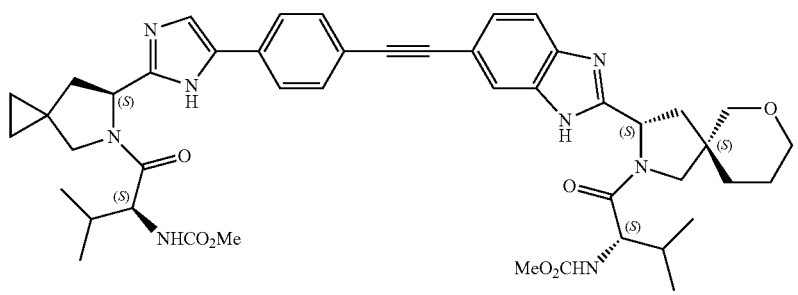

TABLE 9-continued
Compounds 441-545
639 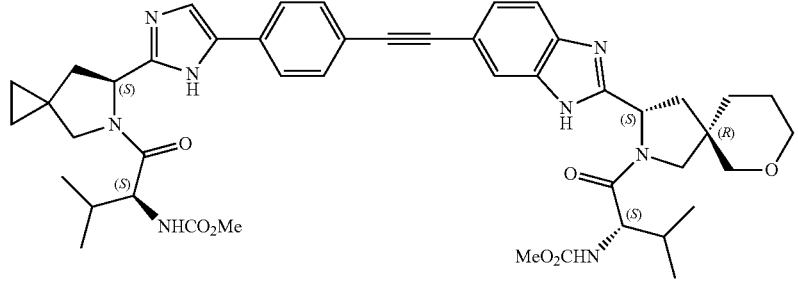
640 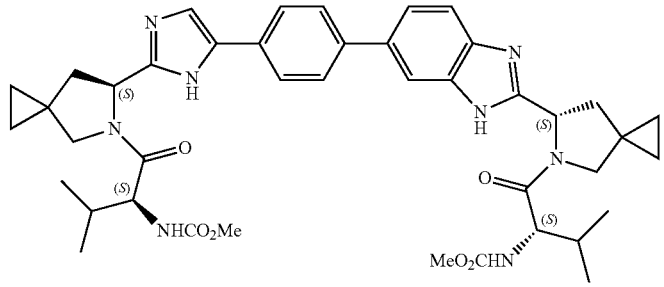
641 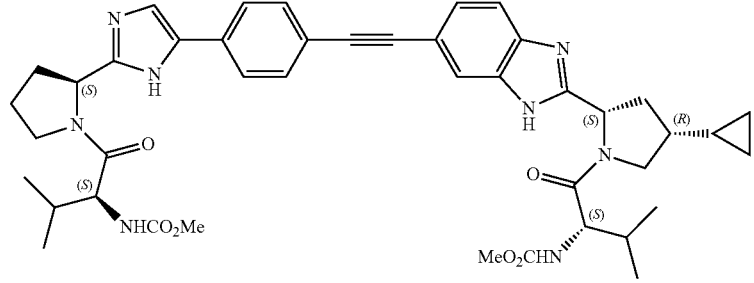
642 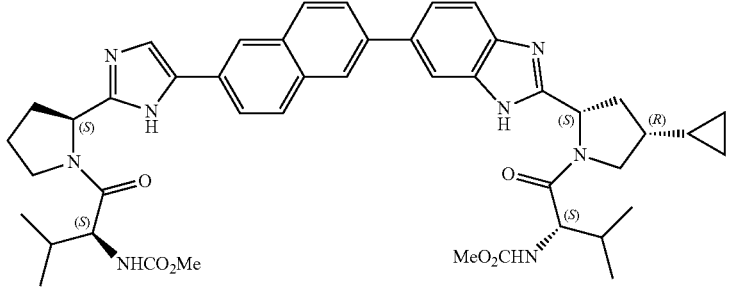
643 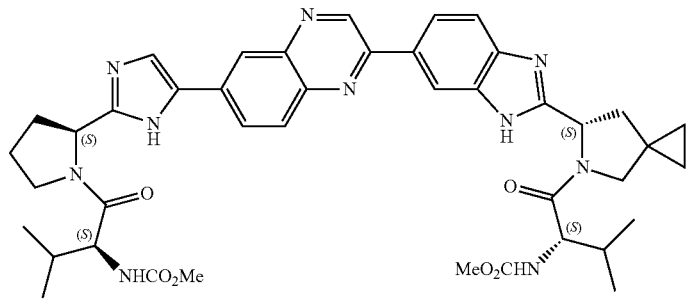

TABLE 9-continued
Compounds 441-545
644
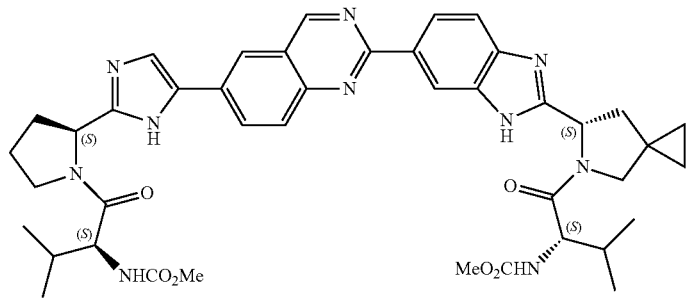
645
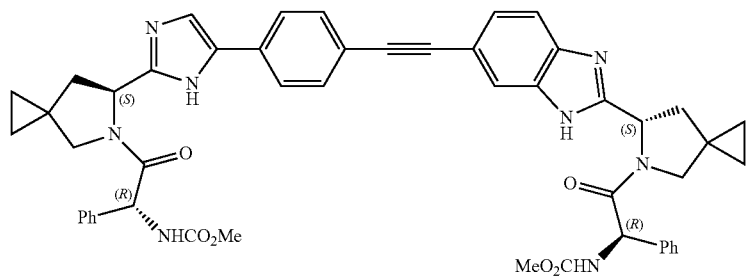
646
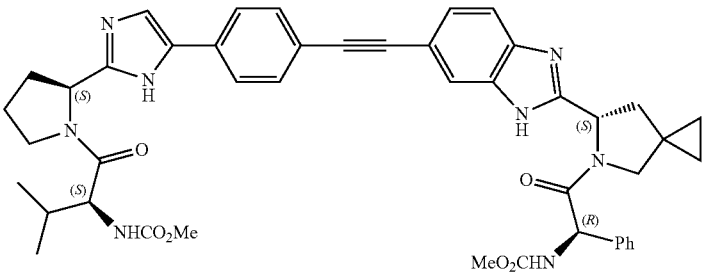
647
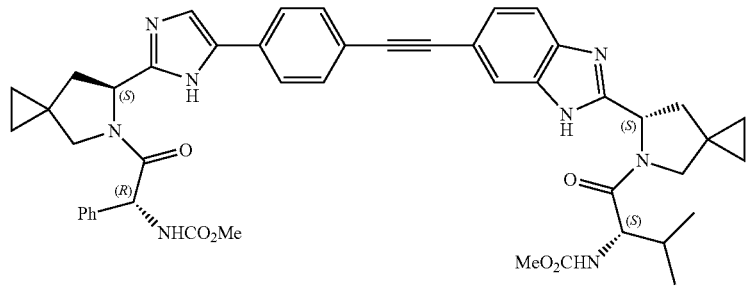
648
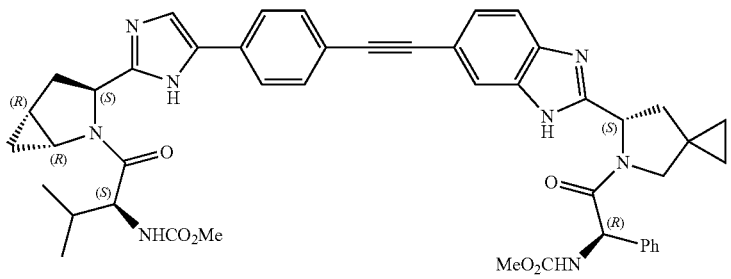

TABLE 9-continued
Compounds 441-545
649 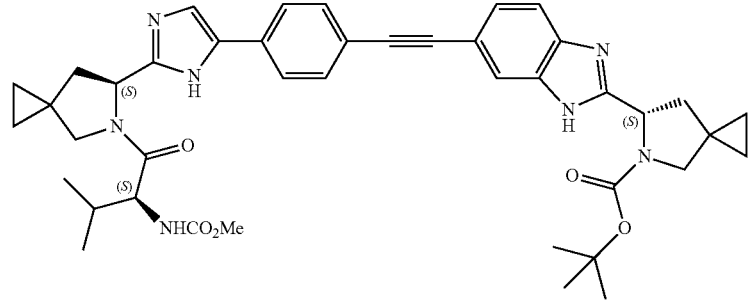
650 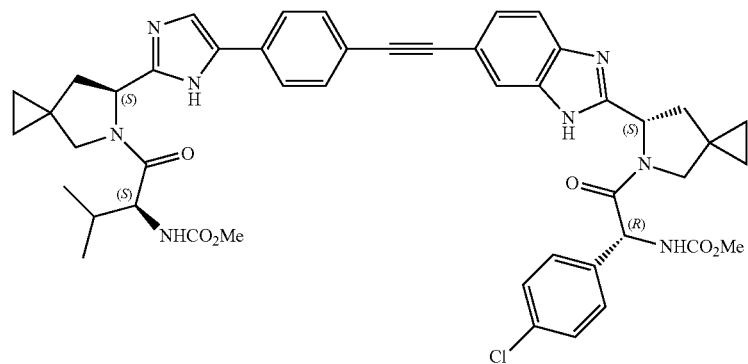
651 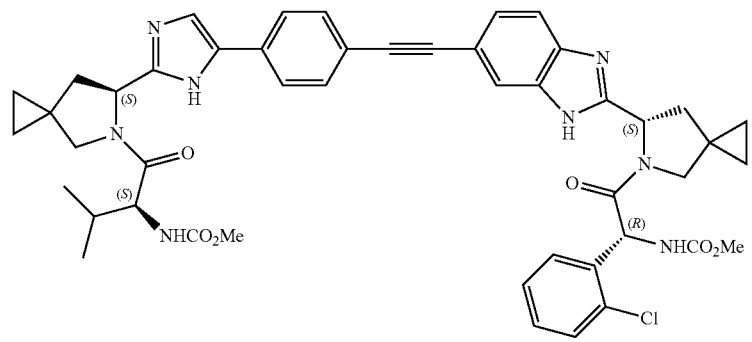
652 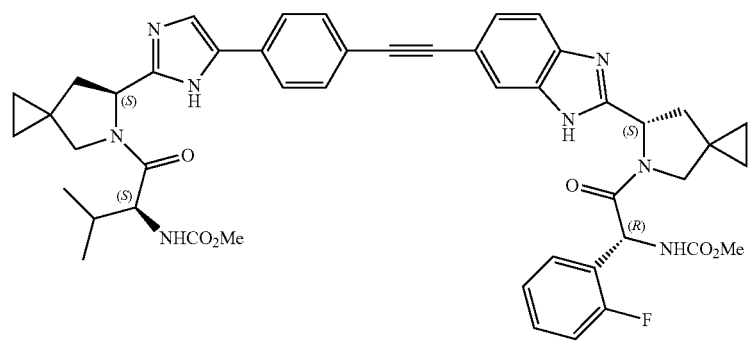

TABLE 9-continued
Compounds 441-545
653 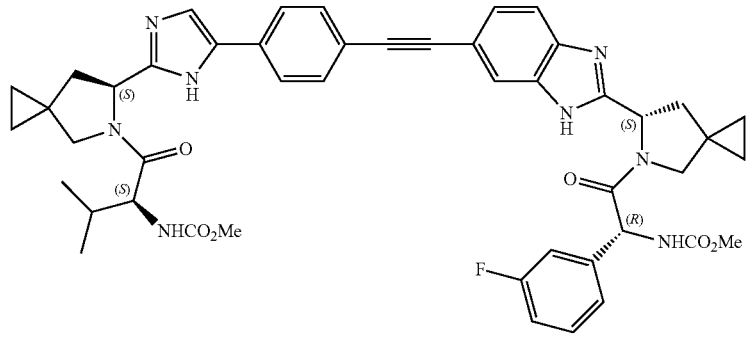
654 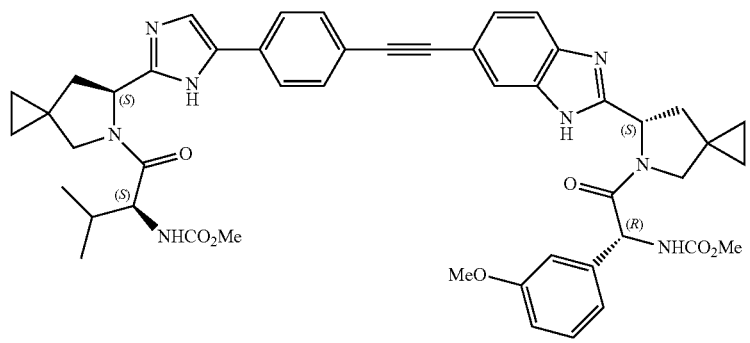
655 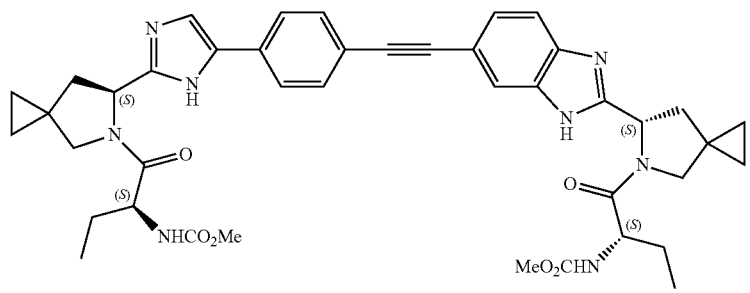
656 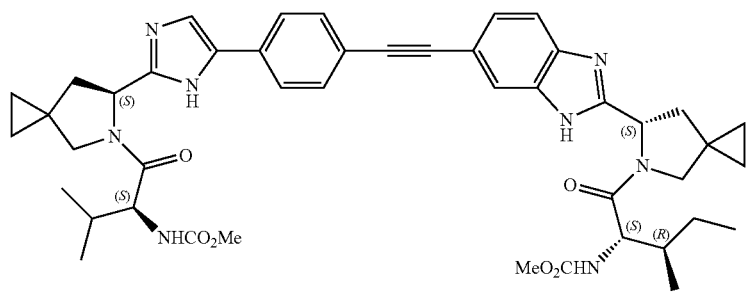
657 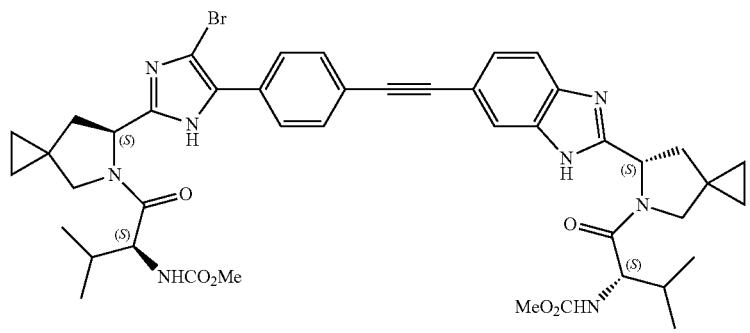

TABLE 9-continued
Compounds 441-545
658
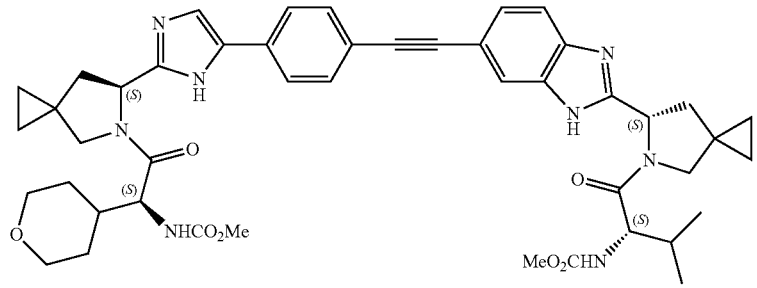
659
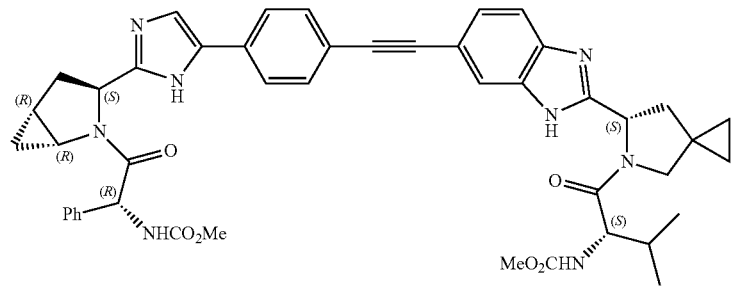
660
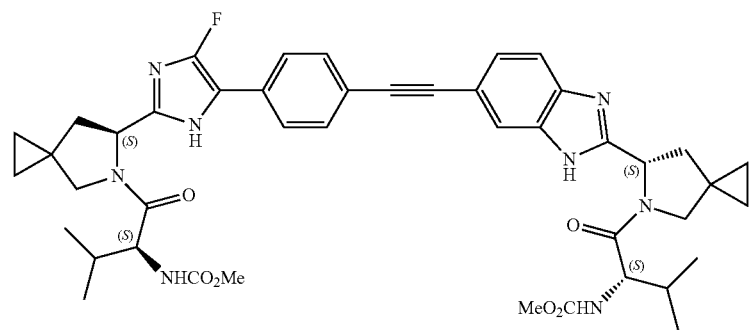
661
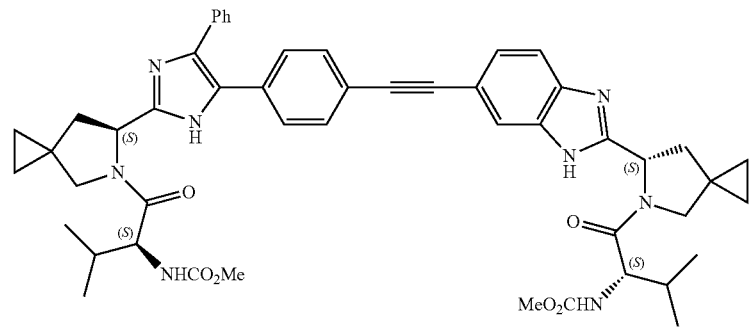

TABLE 9-continued
Compounds 441-545
662
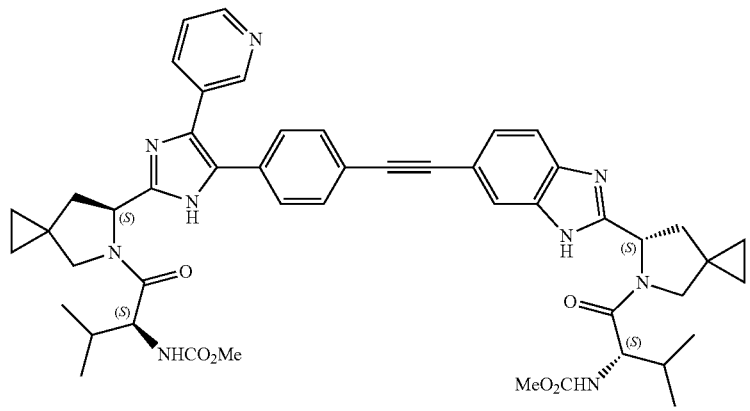
663
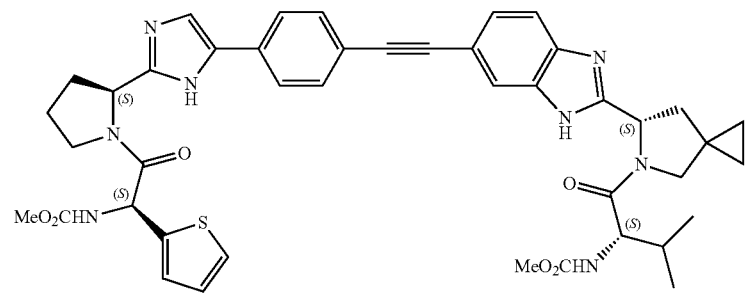
664
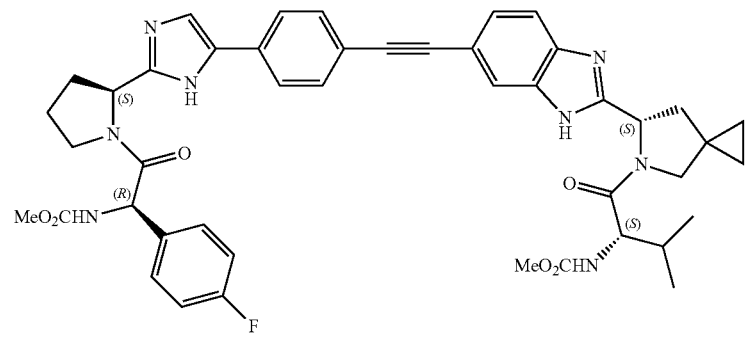
665
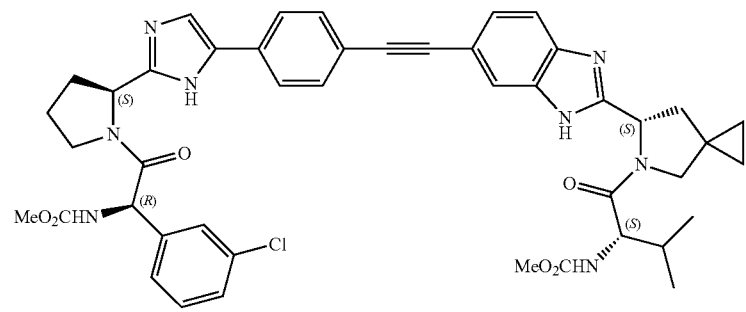

TABLE 9-continued
Compounds 441-545
666 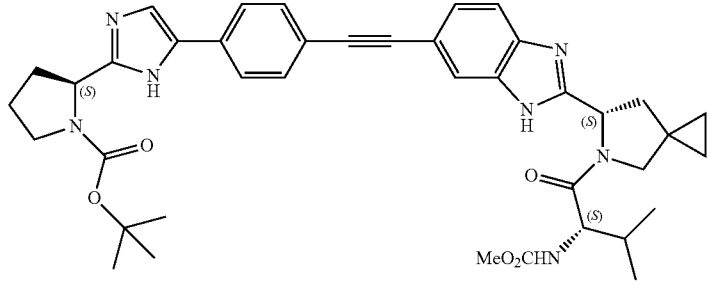
667 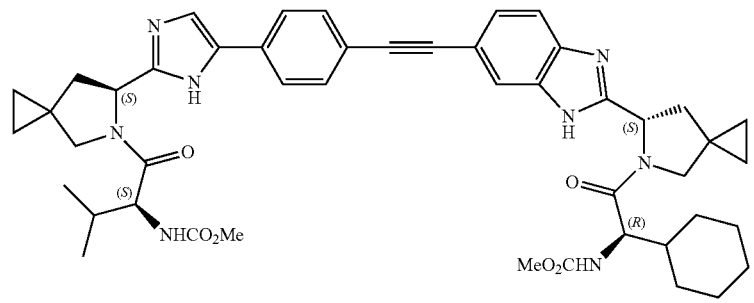
668 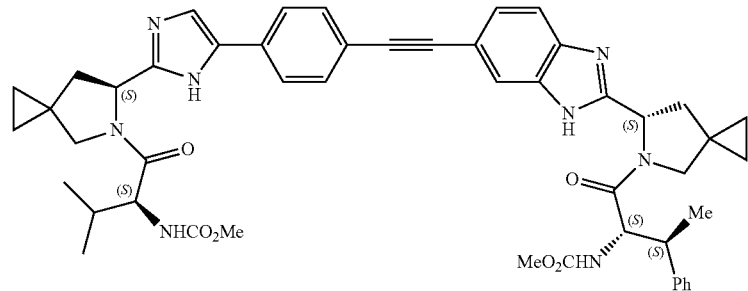
669 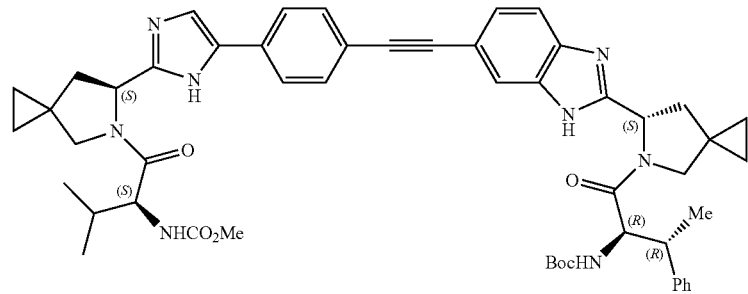
670 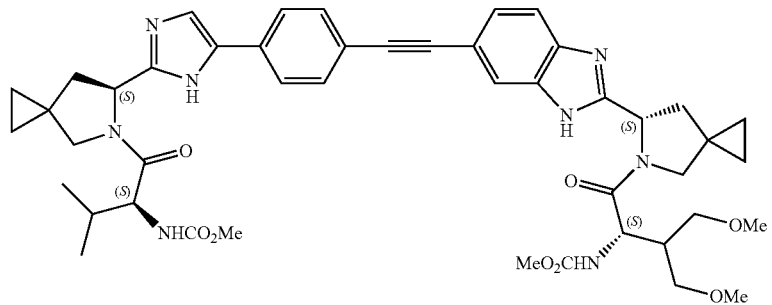

TABLE 9-continued
Compounds 441-545
671 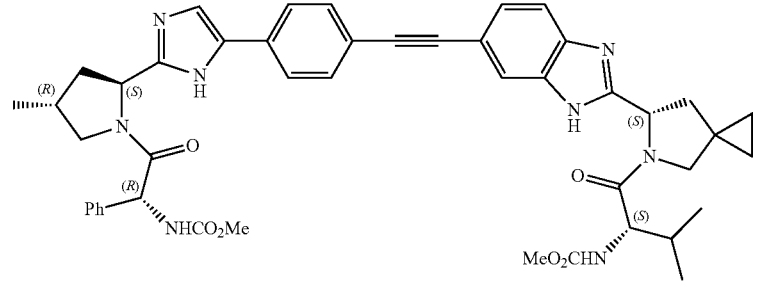
672 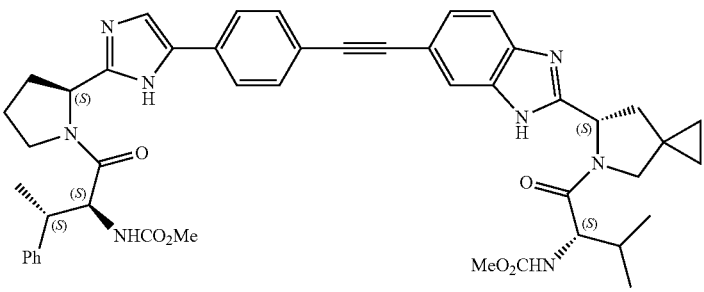
673 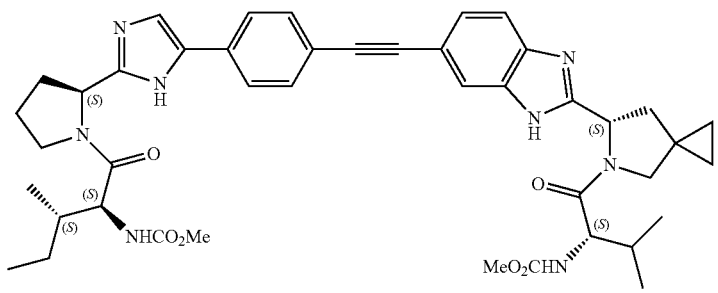
674 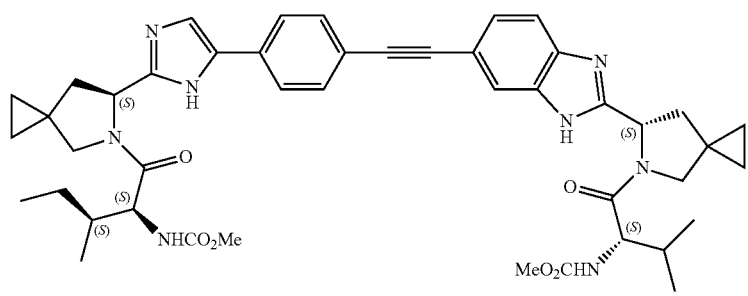
675 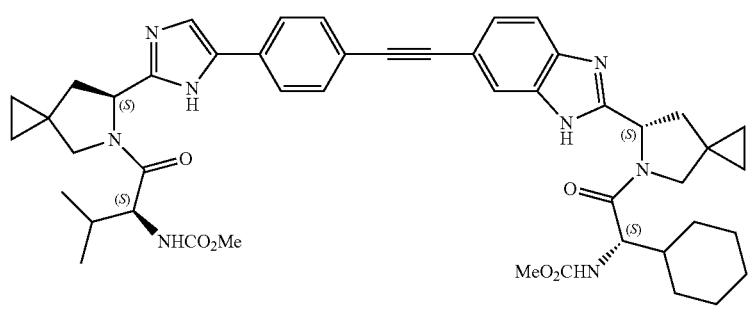

TABLE 9-continued
Compounds 441-545
676 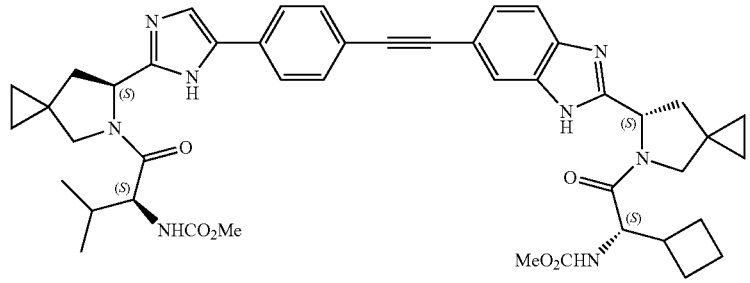
677 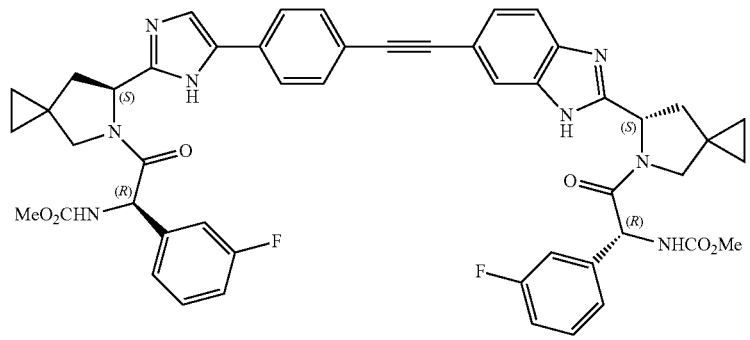
678 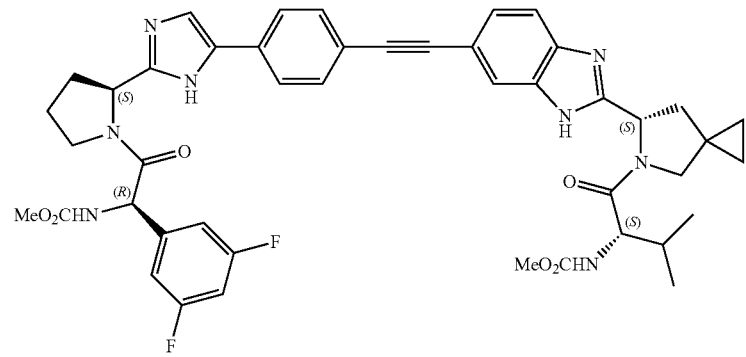
679 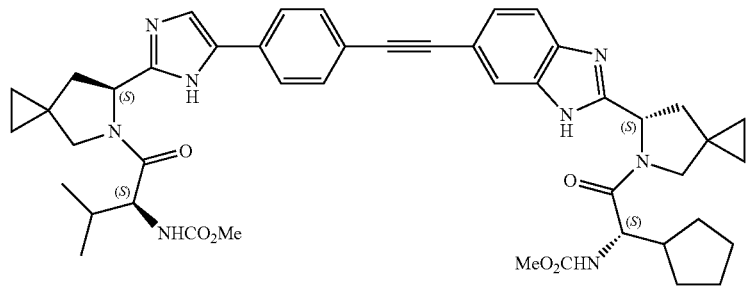
680 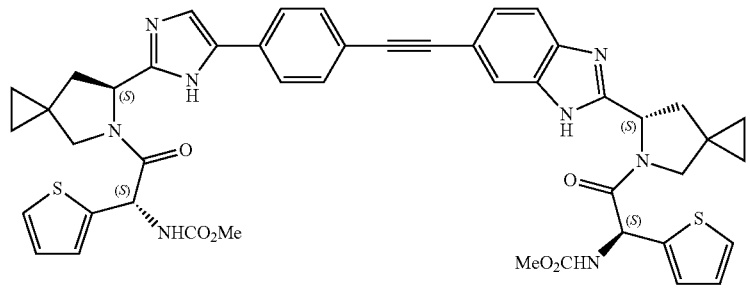

TABLE 9-continued
Compounds 441-545
681 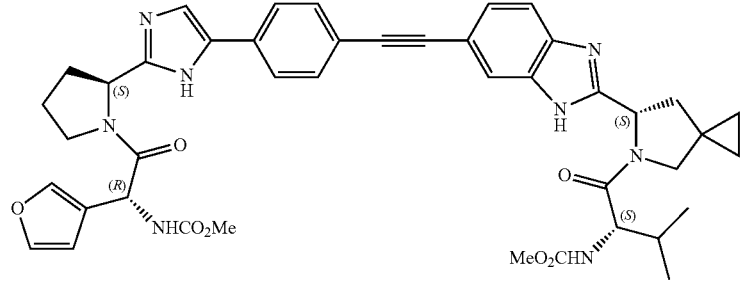
682 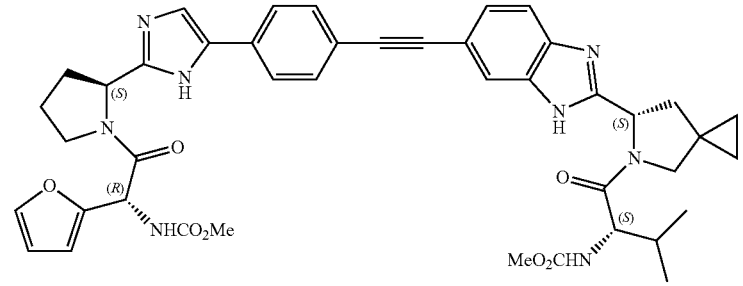
683 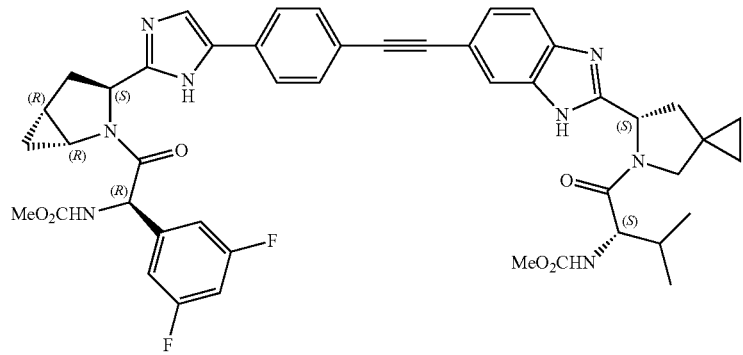
684 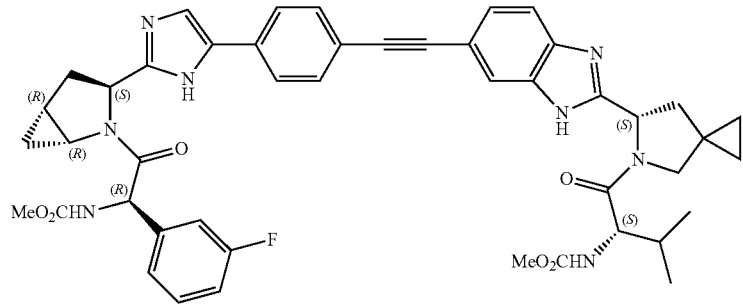
685 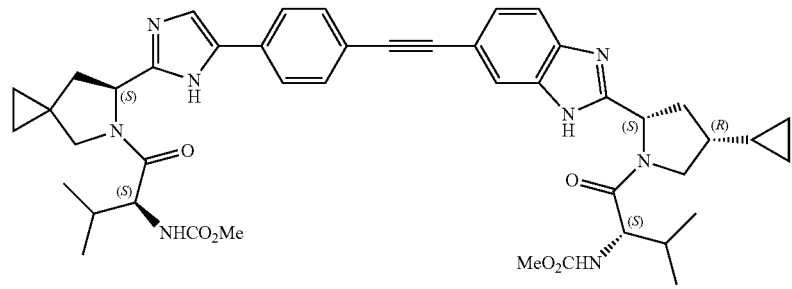

US 9,765,087 B2
TABLE 9-continued
Compounds 441-545
686 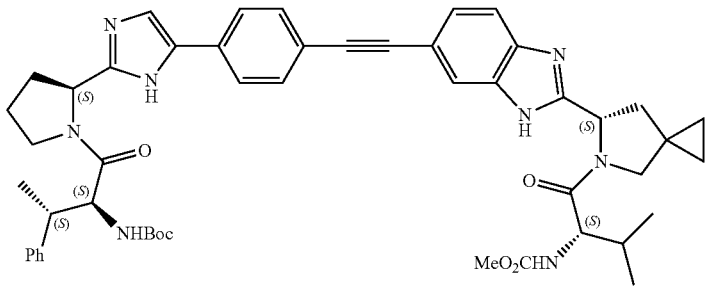
687 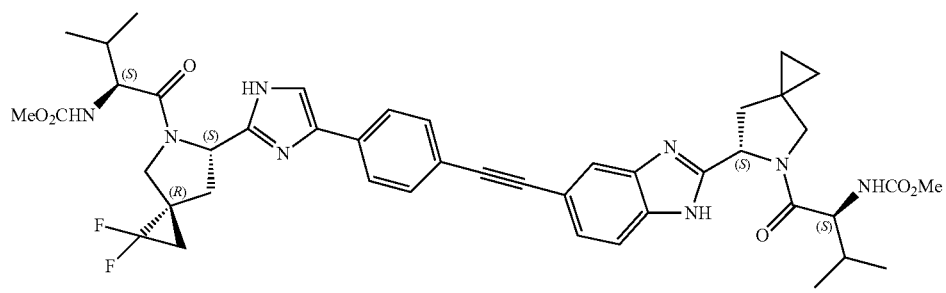
688 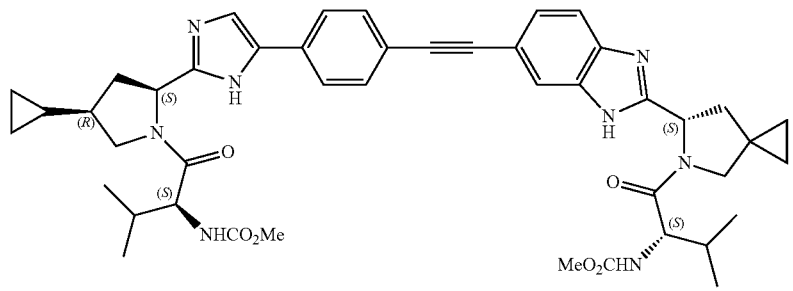
689 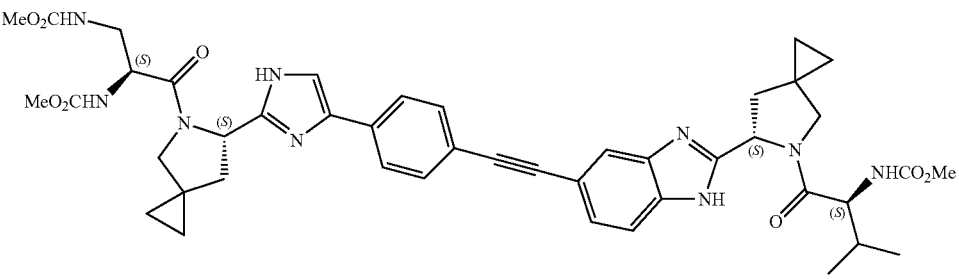
690 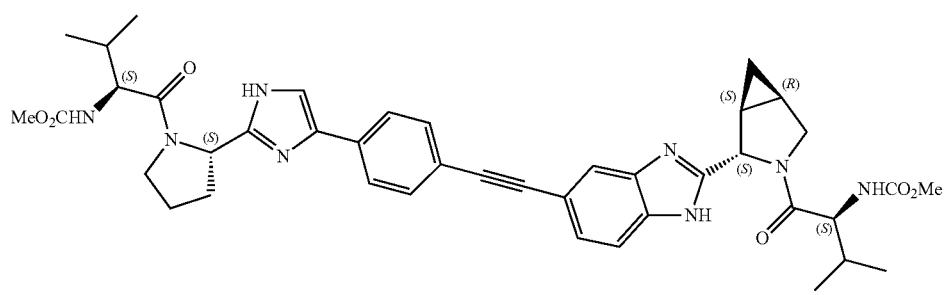

TABLE 9-continued
Compounds 441-545
691 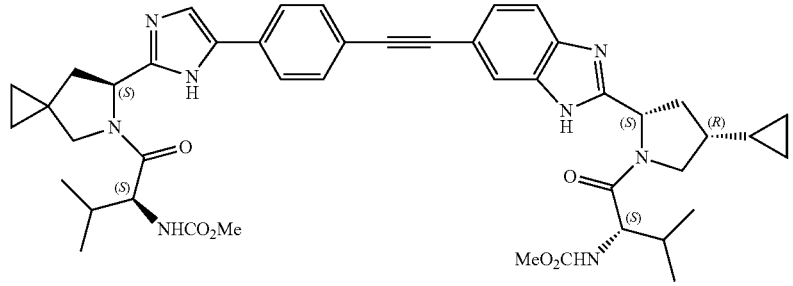
692 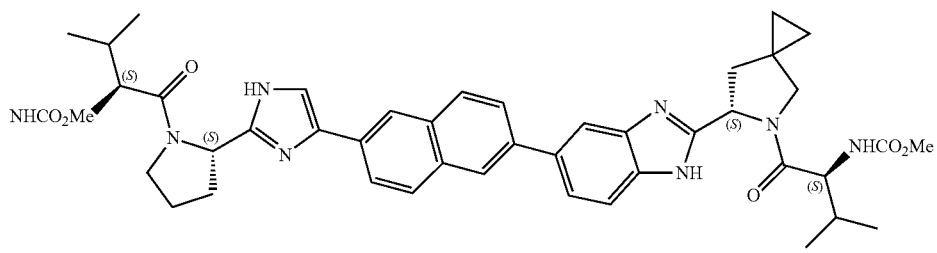
693 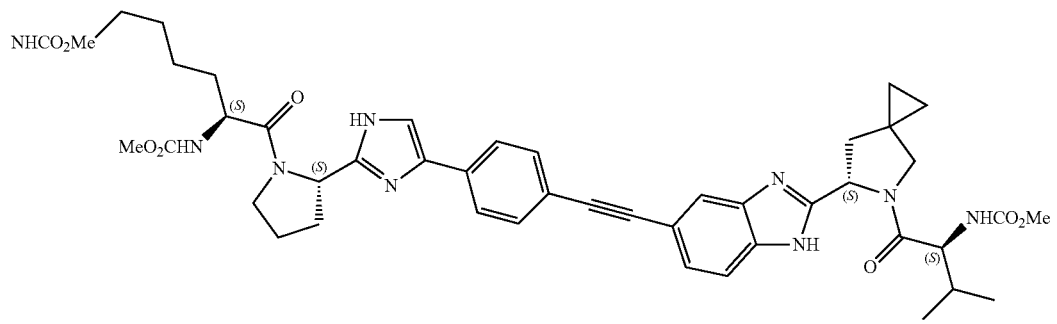
694 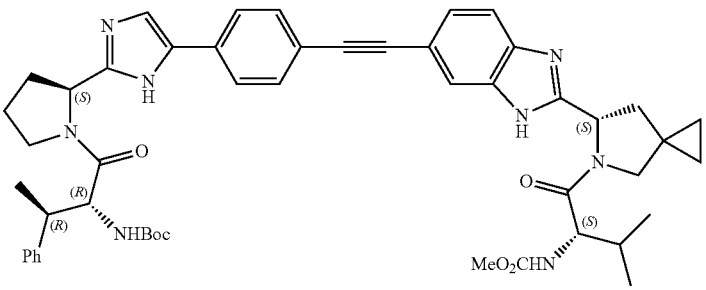
695 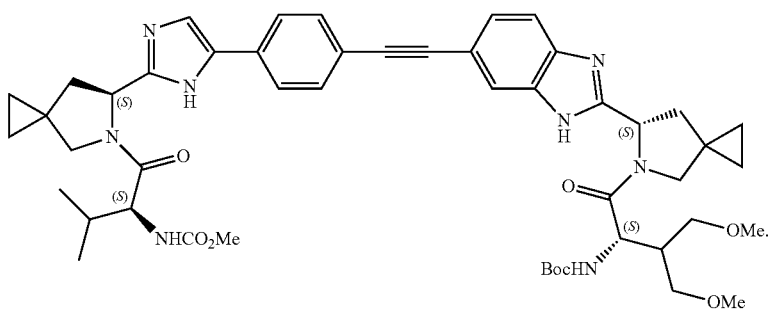

It will be appreciated that the description of the present invention herein should be construed in congruity with the laws and principals of chemical bonding. In some instances it may be necessary to remove a hydrogen atom in order to accommodate a substitutent at any given location.

It is intended that the definition of any substituent or variable (e.g., $R^1$, $R^2$, X, u, m, etc.) at a particular location in a molecule be independent of its definitions elsewhere in that molecule. For example, when u is 2, each of the two $R^1$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound or a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleo-tides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. A non-limiting example of the RNA-containing virus is hepatitis C virus (HCV).

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenfovir, or any combination thereof. A non-limiting example of the RNA-containing virus is hepatitis C virus (HCV).

Another further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of the RNA-containing virus is hepatitis C virus (HCV).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated herein is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and one or more additional antiviral agents, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant. Preferably said additional antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, or as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including, but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents that can be administered in combination with a compound of the present invention include a cytochrome P450 monooxygenase inhibitor (also referred to herein as a CYP inhibitor), which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount sufficient to improve one or more pharmacokinetic (PK) feautures including, but not limited to, plasma concentration, bioavailiablity, area under the plasma concentration time curve (AUC), elimination half-life, and systemic clearance, of a compound of the invention when one or more of its PK feautures of said compound is improved in comparison to that in the absence of the CYP inhibitor.

In one embodiment, the invention provides methods for improving the pharmacokinetics of compounds of the invention. The advantages of improving the pharmacokinetics of drugs are recognized in the art (see, for example, US Patent Publication No.'s. 2004/0091527; US 2004/0152625; and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, ditiazem, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect of the invention, is a pack comprising at least a compound of the invention and a CYP inhibitor and an information insert containing directions on the use of the combination of the invention. In an alternative embodiment of this invention, the pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e.g. a composition of a compound of the invention and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_5$-$C_7$-cycloalkyl," as used herein, refers to a monocyclic or polycyclic saturated carbocyclic ring compound, and the carbon atoms may be optionally oxo-substituted. Examples of $C_3$-$C_8$-cycloalkyl include, but not limited to, cyclopropyl, cyclobutyl, cyclopentyl, cyclohexyl, cyclopentyl and cyclooctyl; and examples of $C_5$-$C_7$-cycloalkyl include, but not limited to, cyclopentyl, cyclohexyl, bicyclo[2.2.1]heptyl, and the like.

The term "$C_3$-$C_8$ cycloalkenyl", or "$C_5$-$C_7$ cycloalkenyl" as used herein, refers to monocyclic or polycyclic carbocyclic ring compound having at least one carbon-carbon double bond, and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

The term "arylalkyl", as used herein, refers to an aryl-substituted alkyl group. More preferred arylalkyl groups are aryl-$C_1$-$C_6$-alkyl groups.

The term "heteroarylalkyl", as used herein, refers to a heteroaryl-substituted alkyl group. More preferred heteroarylalkyl groups are heteroaryl-$C_1$-$C_6$-alkyl groups.

It is understood that any alkyl, alkenyl, alkynyl, cycloalkyl and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2$NH, $S(O)_2NH_2$, $NHC(O)NH_2$, NHC(O)C(O)NH, $NHS(O)_2$NH, $NHS(O)_2NH_2$, $C(O)NHS(O)_2$, $C(O)NHS(O)_2$NH or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched or cyclic and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can, for example, be selected from one or more of the specified functional groups or a combination thereof, or a group wherein one or more carbons of a non-aromatic hydrocarbon (optionally substituted) is replaced by a specified functional group. In some examples, the aliphatic group can be represented by the formula M-Y-M', where M and M' are each independently absent or an alkyl, alkenyl or alkynyl, each optionally substituted, and Y is a functional group. In some examples, Y is selected from the group consisting of C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ or $C(O)N(R^{11})S(O)_2N(R^{11})$; wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated, (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent group when used as a linkage to connect two groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$— aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$— heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH— heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenylmethoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed.). "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" include, but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

A compound of the present invention can also be administered in combination or alternation with antiviral agent. Examplary antiviral agents include ribavarin, interferon, interleukin or a stabilized prodrug of any of them. More broadly described, the compound can be administered in combination or alternation with any of the anti-HCV drugs listed in Table 10 below.

TABLE 10

Table of anti-Hepatitis C Compounds in Current Clinical Development

| Drug name | Drug category | Pharmaceutical Company |
| --- | --- | --- |
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |

TABLE 10-continued

Table of anti-Hepatitis C Compounds in Current Clinical Development

| Drug name | Drug category | Pharmaceutical Company |
|---|---|---|
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HEPX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |
| Narlaprevir (SCH 900518) | Protease inhibitor | Schering/Merck |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| R1626 | Polymerase Inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| VCH-759 | Polymerase Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-ANTIMIR ™-122) | microRNA | Santaris Pharma |
| Debio 025 | Cyclophilin inhibitor | Debiopharm |
| SCY-635 | Cyclophilin inhibitor | Scynexis |

Unless otherwise defined, all technical and scientific terms used herein are accorded the meaning commonly known to one of ordinary skill in the art. All publications, patents, published patent applications, and other references mentioned herein are hereby incorporated by reference in their entirety.

ABBREVIATIONS

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc₂O for di-tert-butyl-dicarbonate; Boc for t-butoxycarbonyl; Bpoc for 1-methyl-1-(4-biphenylyl)ethyl carbonyl; BtOH for 1-hydroxybenzotriazole; Bz for benzoyl; Bn for benzyl; BocNHOH for tert-butyl N-hydroxycarbamate; t-BuOK for potassium tert-butoxide; Bu₃SnH for tributyltin hydride; BOP for (benzotriazol-1-yloxy)tris(dimethylamino)phos-phonium Hexafluorophosphate; Brine for sodium chloride solution in water; Cbz for carbobenzyloxy; CDI for carbonyldiimidazole; CH₂Cl₂ for dichloromethane; CH₃ for methyl; CH₃CN for acetonitrile; Cs₂CO₃ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIBAL-H for diisobutylaluminium hydride; DIPEA or (i-Pr)₂EtN for N,N-diisopropylethyl amine; Dess-Martin periodinane for 1,1,1-tris(acetyloxy)-1,1-dihydro-1,2-benziodoxol-3-(1H)-one; DMAP for 4-dimethylaminopyridine; DME for 1,2-dimethoxy-ethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylaminopropyl)-N'-ethylcarbodiimide; EDC HCl for N-(3-dimethylamino-propyl)-N'-ethylcarbodiimide hydrochloride; EtOAc for ethyl acetate; EtOH for ethanol; Et$_2$O for diethyl ether; Fmoc for 9-fluorenylmethoxycarbonyl; Grubbs-1 catalyst for benzylidene-bis(tricyclohexylphosphine)dichlororuthenium; HATU for O-(7-azabenzotriazol-1-yl)-N,N,N',N'-tetramethyluronium hexafluorophosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; NaBH$_4$ for sodium borohydride; NaBH$_3$CN for sodium cyanoborohydride; NaN(TMS)$_2$ for sodium bis(trimethylsilyl)amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMMO for N-methylmorpholine N-oxide; NaIO$_4$ for sodium periodate; Ni for nickel; OH for hydroxyl; OsO$_4$ for osmium tetroxide; Pd for palladium; Ph for phenyl; PMB for p-methoxybenzyl; POPd for dihydrogen dichlorobis(di-tert-butylphosphinito-KP)palladate(II); Pd$_2$(dba)$_3$ for tris(dibenzylidene-acetone)dipalladium (0); Pd(PPh$_3$)$_4$ for tetrakis(triphenylphosphine)palladium (0); PdCl$_2$(PPh$_3$)$_2$ for trans-dichlorobis(triphenyl-phosphine)palladium (II); Pt for platinum; Rh for rhodium; rt for romm temperature; Ru for ruthenium; SEM for (trimethylsilyl)ethoxymethyl; TBAF for tetrabutylammonium fluoride; TBS for tert-butyl dimethylsilyl; TEA or Et$_3$N for triethylamine; Teoc for 2-trimethylsilyl-ethoxy-carbonyl; TFA for trifluoroacetic acid; THF for tetrahydrofuran; TMEDA for N,N,N',N'-tetramethylethylenediamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolylsulfonic acid; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of benzimidazole and imidazole related intermediates. A retrosynthesis of those title compounds include direct formation of a suitably linked benzimidazole and imidazole core structure followed by attachment of a suitable R$^6$ group, plus some functional group manipulations in between and/or after.

A general synthesis and further elaboration of some benzimidazole related intermediates are summarized in Scheme 1.

The synthesis starts from the construction of an optionally substituted benzimidazole 1-2, which may be obtained by condensation of an amino acid or its derivative 1-1.1 or 1-1.2 and an o-phenylenediamine 1-1 under the conditions to those skilled in the art. The benzimidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDC HCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat.

Optionally, the NH group in the newly formed benzimidazole ring of 1-2 may be protected with an amino protecting group, such as SEM (i.e. SEM-Cl, NaH), Boc, Cbz, Teoc, Troc, or the like. The protected benzimidazole 1-2 may be subjected to lithium-halogen exchange with various (n-, s-, or t-) butyl lithium and the resulting lithiate can be trapped with a nucleophile, i.e. a halide such as various allyl halide to give the allylated 1-6 as a key intermediate. Alternatively, 1-6 may be obtained from the Stille reaction conditions to those skilled in the art (see reviews: A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European J.* 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), using an allylstanne such as allyltributylstanne as the allyl donor. Analogously a key vinyl intermediates 1-3 may be prepared by Stille reaction from bromide 1-2 with tributylvinylstanne. Also, Sonogashira coupling between bromide 1-2 and propargyl alcohol or trimethylsilylacetylene can generate propargyl alcohol 1-4 or alkyne 1-5 after removal of TMS. Further bromination of intermediate 1-4 may form the propargyl bromide 1-9. In addition, benzimidazole bromide 1-2 may be converted to methyl ketone 1-7 by coupling with tributyl(1-ethoxyvinyl)tin under Stille coupling conditions followed by acidic hydrolysis.

Scheme 1
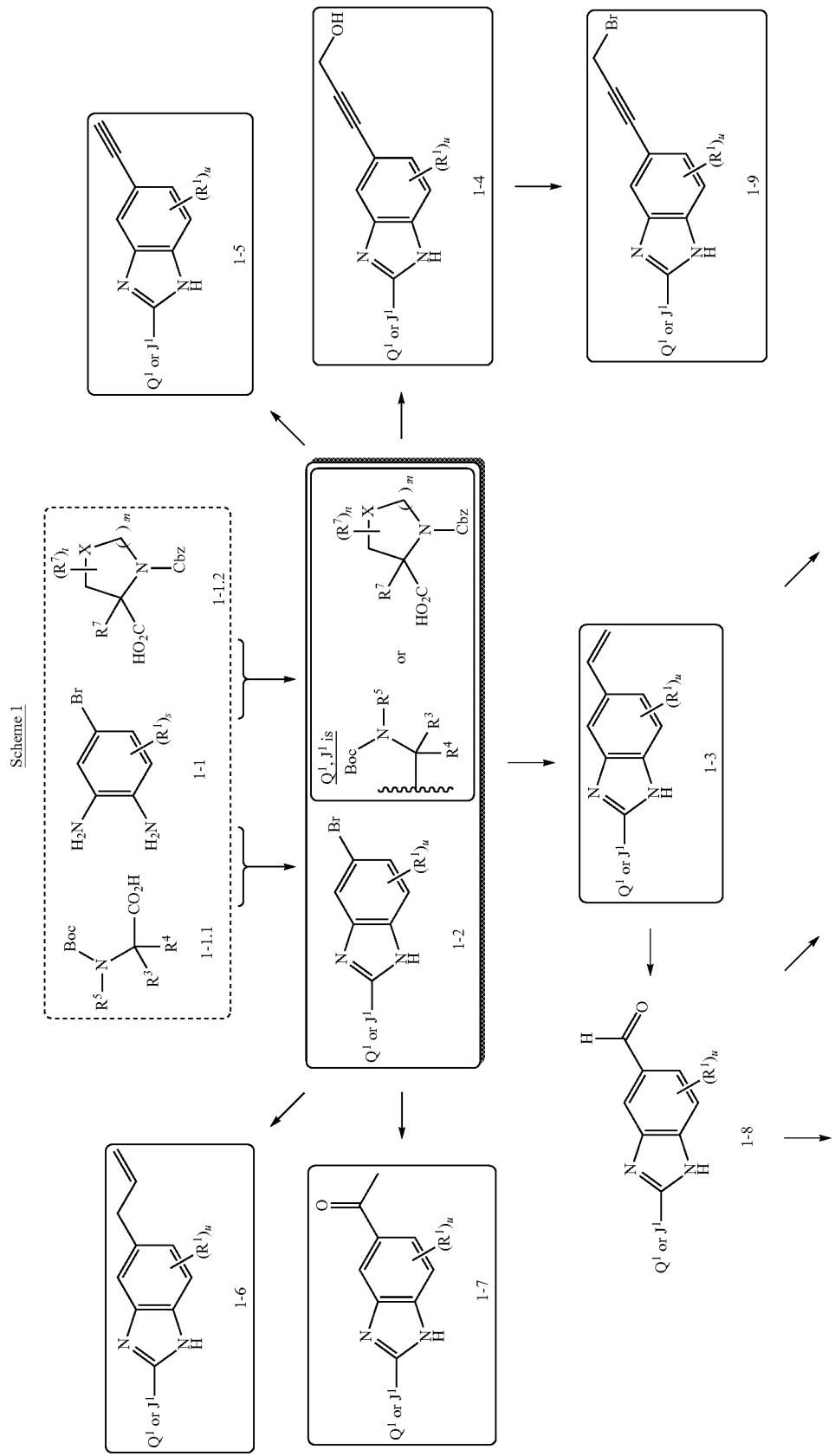

-continued
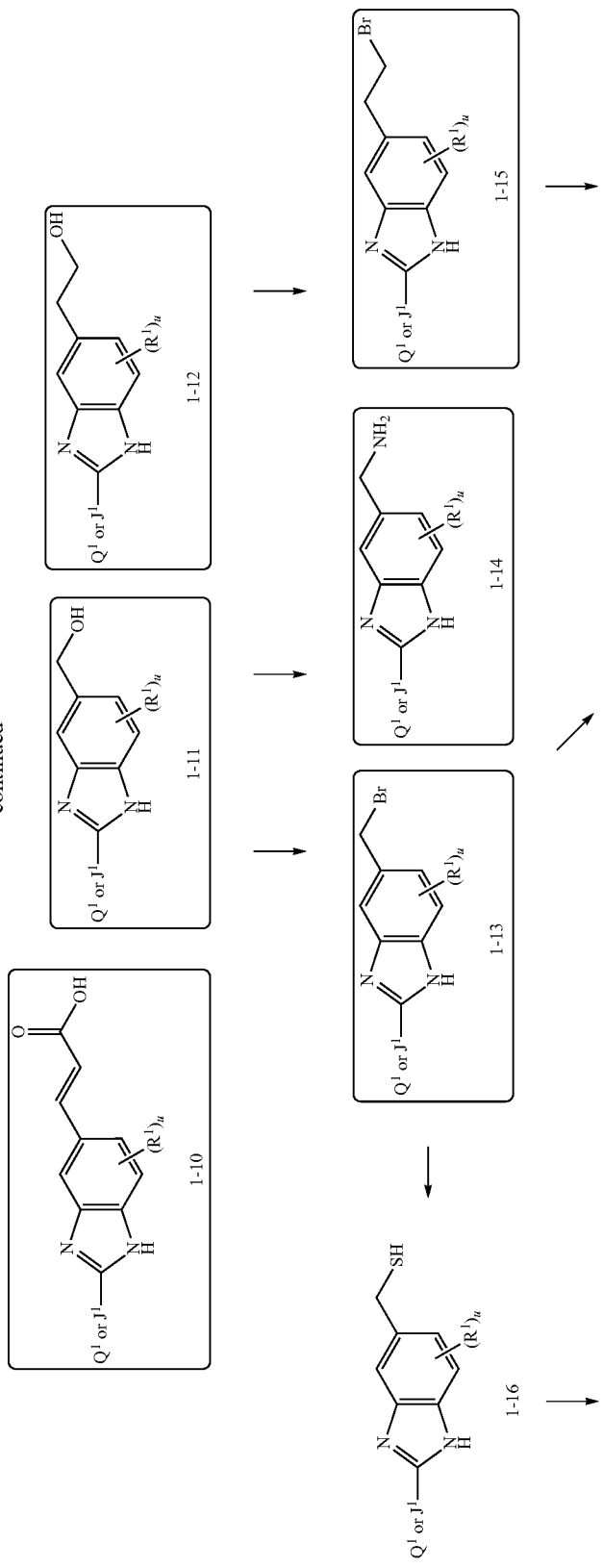

-continued
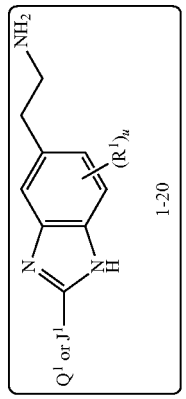
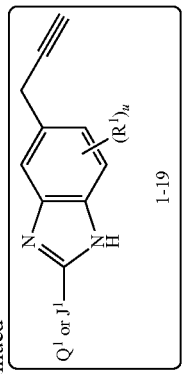
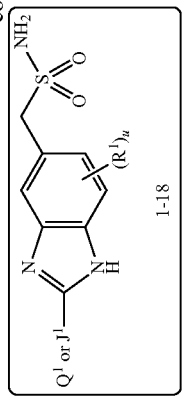
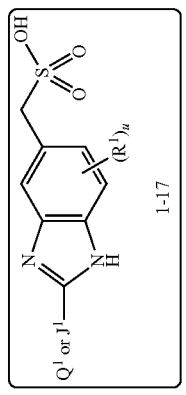
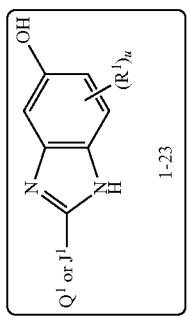
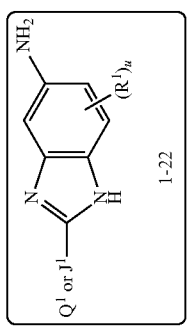
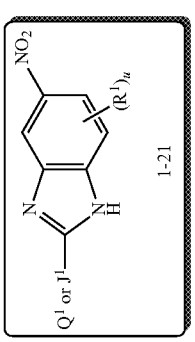
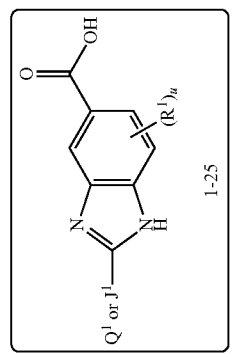
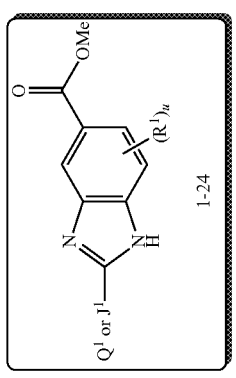

Further elaboration of the benzimidazole intermediates starts from the vinyl intermediate 1-3, which may be transformed to aldehyde 1-8 through ozonolysis cleavage or to alcohol 1-12 by hydroboration-oxidation sequence. Alcohol 1-12 may be converted to bromide 1-15 by the well-known bromination procedure, which can be further functionalized to amine 1-20 through azide substitution followed by reduction. Aldehyde 1-8 can then either be reduced to alcohol 1-11, or be converted to α,β-unsatuated acid 1-10 through Horner-Wadsworth-Emmons aldehyde homologation reaction followed by saponification. Alcohol 1-11 may be similarly converted to the corresponding amine intermediate 1-14 and bromide intermediate 1-13 as described previously. Bromide 1-13 can be homologated to alkyne intermediate 1-19 with a metal acetylide. In addition, bromide 1-13 may be also tranformed to thiol 1-16 through nucleophilic substitution, which can be further oxidized to sulfonic acid 1-17. Sulfonamide 1-18 may then be derived from 1-17 through the sulfonyl chloride activation process.

The compounds of the present invention may also be derived from nitrobenzimidazole 1-21, which can be prepared from the corresponding 4-nitro-1,2-diaminobenzene using the similar procedures described above. Intermediate 1-21 can be converted to amine 1-22 through $NO_2$-reduction (i.e. $H_2$, catalytical Pd). Diazotization of amine 1-22 with a nitrite such as sodium nitrite, isobutyl nitrite, or the like, in an aqueous acid such as acetic acid, hydrochloric aicd, sulfuric acid, or the like, optionally in the presence of a copper or copper salt, may afford hydroxy 1-23.

Analogously, benzimidazolecarboxylate 1-24, which can be prepared from the corresponding 4-methyl-1,2-diaminobenzoate using the procedures described above, may be hydrolyzed to the corresponding carboxylic acid 1-25.

It should be noted that optionally the NH group of all the benzimidazole related intermediates listed above may be protected with an amino protecting group, such as SEM (i.e. SEM-Cl, NaH), Boc, Cbz, Teoc, Troc, or the like.

Scheme 2

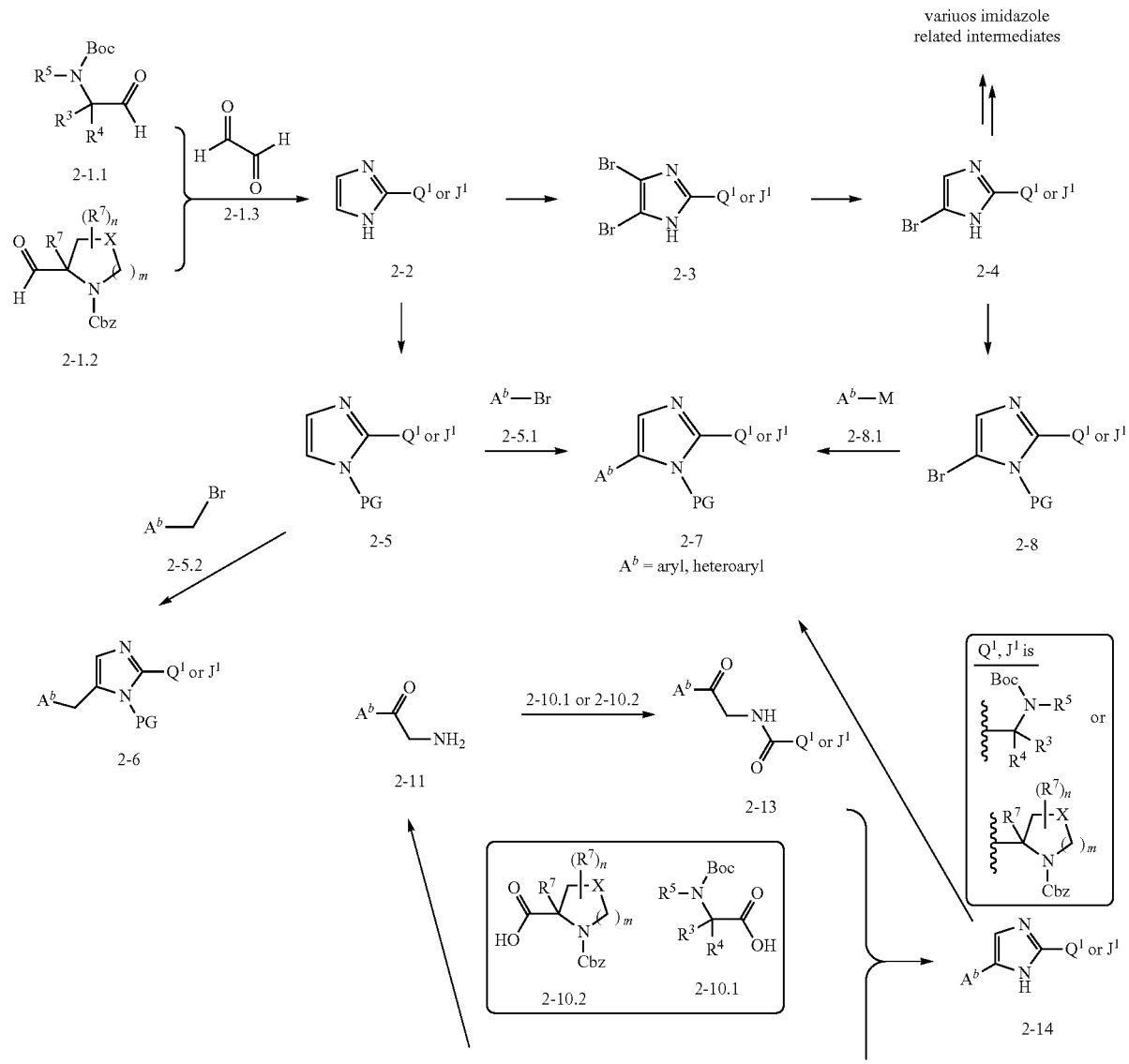

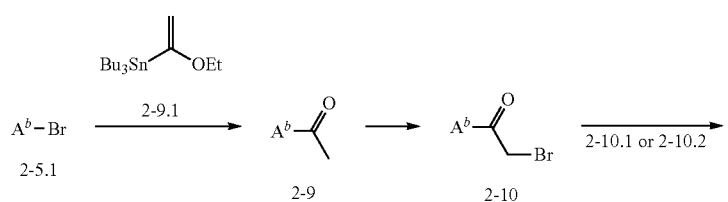
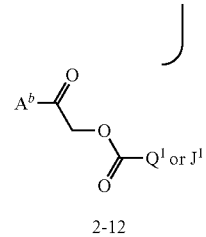

A typical synthesis of imidazole related intermediates are analogous to that of the benzimidazole intermediates. As shown in Scheme 2, bromo-imidazole 2-4 can be synthesized in a three-step sequence: 1) condensation between amino acid derived aldehyde 2-1.1 or 2-1.2 and glyoxal 2-1.3 in the presence of methanolic ammonia to generate imidazole 2-2; 2) bromination of 2-2 with excess amount of bromination reagent such as 2,4,4,6-tetrabromo-2,5-cyclohexadienone, NBS, etc. to afford dibromide 2-3; and 3) selective reduction of the dibromide 2-3 by heating in aq. $Na_2SO_3$ or aq. $NaHSO_3$. 2-4 then may be served as a universal intermediate further elaborable to many other imidazole derivatives using the chemistry discussed in Scheme 1, some of which are listed in the table below.

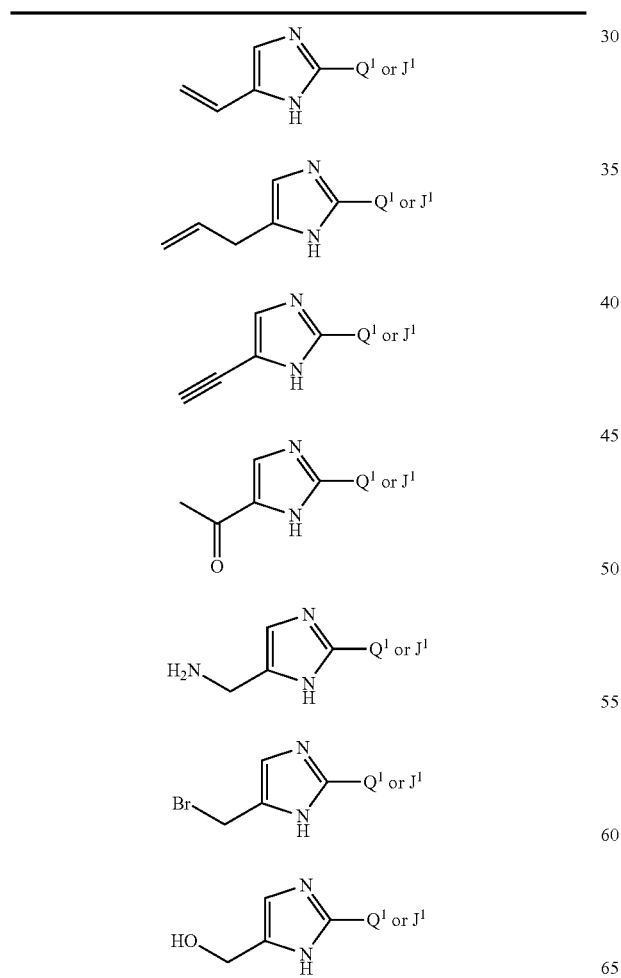

-continued

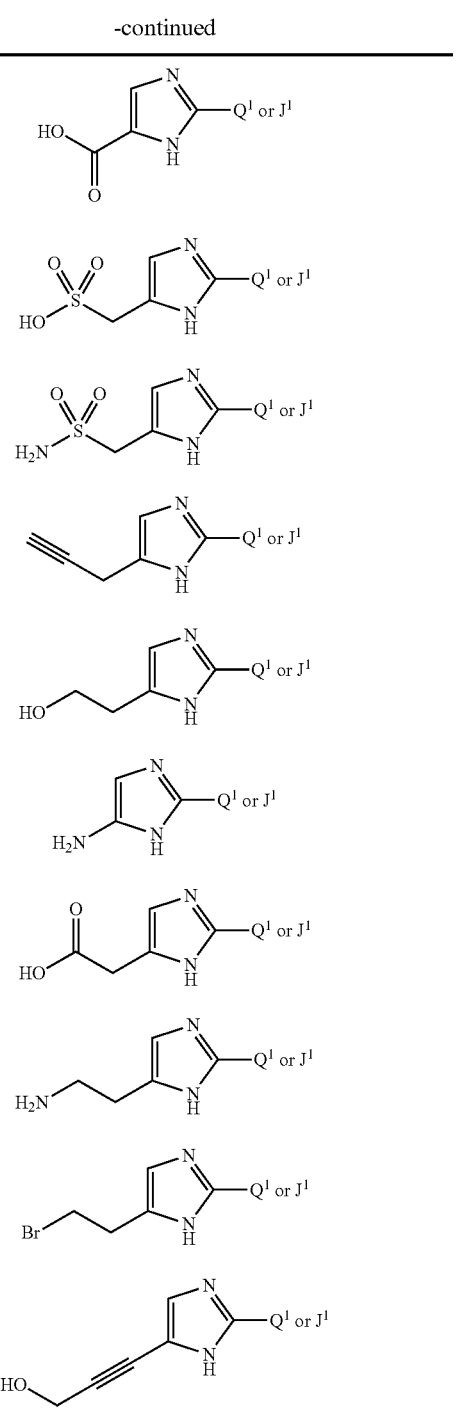

-continued

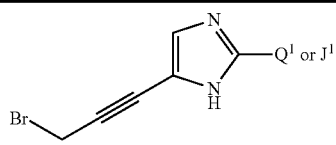

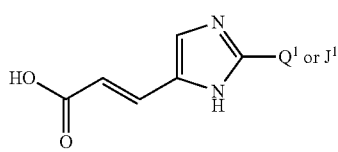

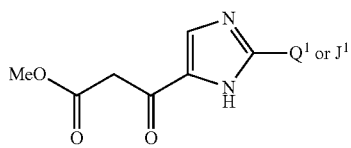

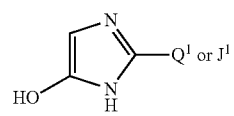

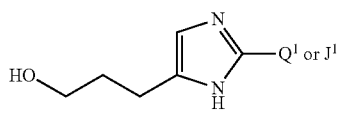

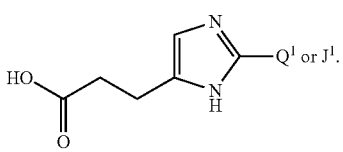

Optionally, the NH group of imidazole related intermediates listed above may be protected with an amino protecting group (shown in Scheme 2 as PG), such as SEM (i.e. SEM-Cl, NaH), Boc, Cbz, Teoc, Troc, or the like. The protected imidazole 2-5 may be deprotonated with a strong base such as LDA, BuLi, etc to generate a carbon anion, which may either undergo a nucleophilic substitution with an activated halide such as 2-5.2 to afford aryl or heteroaryl substituted imidazole 2-6 or couple with an aryl or heteroaryl halide 2-5.1 in the presence appropriate transition metal salt to generate bicyclic heteroaryl 2-7. Similarly, the protected bromo imidazole 2-8 may be subjected to lithium-halogen exchange with various (n-, s-, or t-) butyl lithium, the resulting lithiate may undergo similar reactions to afford 2-6 and 2-7. Also, when 2-8 is treated with metalated aryl or heteroaryl 2-8.1, in which M at each occurrence is independently a boron, tin, silicon, zinc, zirconium, or copper species, under Suzuki or Stille conditions to those skilled in the art (see reviews: A. Suzuki, *Pure Applied Chem.* 1991, 63, 419; A. Suzuki, *Handbook of Organopalladium Chemistry for Organic Synthesis* 2002, 1, 249; A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European J.* 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), to provide coupling product 2-7. In addition to these direct coupling strategy, aryl or heteroaryl bromide 2-5.1 may be converted to methyl ketone 2-9 under Stille coupling conditions with tributyl(1-ethoxyvinyl)tin 2-9.1. 2-9 may be brominated under conditions to those skilled in the art to afford bromide 2-10, which may be either converted to the corresponding amine 2-11, or coupled with protected amino acid 2-10.1 or 2-10.2 in the presence of a base such as $Et_3N$ and DIPEA to afford keto-ester 2-12. Similarly, amine 2-11 may be converted to the corresponding keto-amide 2-13 via condensation with appropriate amino acid under standard amide formation conditions. 2-12 and 2-13 may be transformed to key intermediate 2-14 via heating with $(NH_4)Oac$ under thermal or microwave conditions.

With a variety of suitably substituted benzimidazoles and imidazoles in hand, such as those listed in Scheme 1, Scheme 2 and the table above, the compounds of the present invention may be prepared through various coupling strategy or a combination of strategies to connect two fragments, optionally with a suitable cyclic or acyclic linker or formation of a cyclic or acyclic linker. The said strategy includes, but not limited to, Stille coupling, Suzuki coupling, Sonogashira coupling, Heck coupling, Buchwald amidation, Buchwald amination, amide coupling, ester bond formation, William etherification, Buchwald etherification, alkylation, pericyclic reaction with different variations, or the like.

An example of the strategies that may be used to prepare the compounds of the present invention is shown in Scheme 3, wherein $R^2$ is independently $R^1$. Both bromides 3-1 and 3-2 can be prepared using the procedures described in Scheme 1 and Scheme 2. Bromide 3-2 can be converted to the corresponding metalated aryl 3-3 under Suzuki or Stille conditions, which may be further coupled with benzimidazole bromide 2-1 under similar conditions to generate a structural core 3-4.

Scheme 3

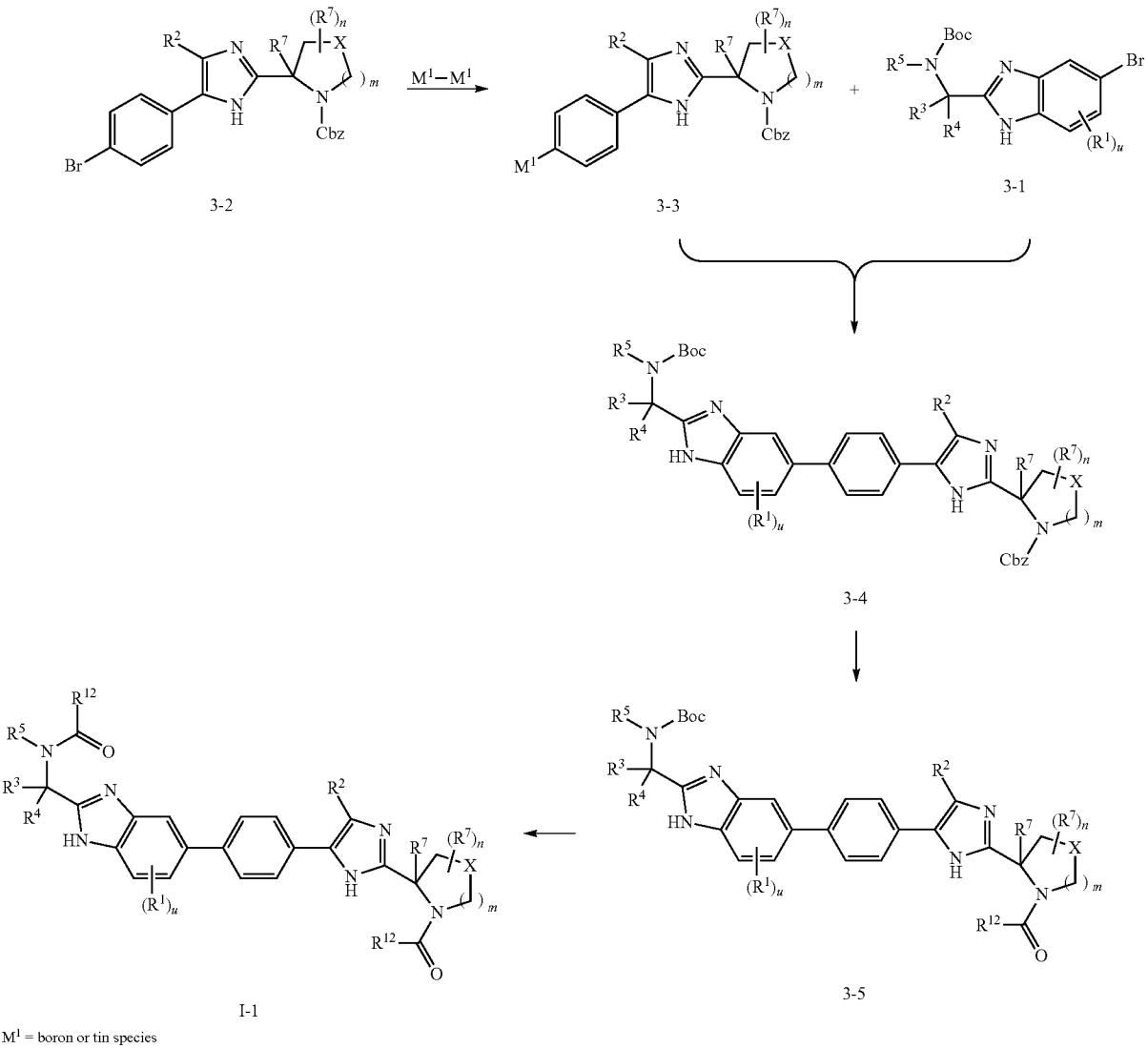

$M^1$ = boron or tin species

Compound 3-4 may then serve as a common intermediate for further derivatizations to 3-5 in two steps: 1) mono-deprotection of the linear or cyclic amine moiety may be accomplished, for example, treatment to hydrogenolytic conditions under Pd catalyst in the presence of a base such as potassium carbonate to remove the Cbz protection group; and 2) the released amine functionality may be acylated with an carboxylic acid under standard acylation conditions, for example a coupling reagent such as HATU in combination with an organic base such as DIPEA can be used in this regard; alternatively, the released amine may be reacted with an isocyanate, carbamoyl chloride or chloroformate to provide an urea or carbamate. Various carboxylic acids including amino acids in racemic or optical form are commercially available, and/or can be synthesized in racemic or optical form, see references cited in reviews by D. Seebach, et al, *Synthesis* 2009, 1; C. Cativiela and M. D. Diaz-de-Villegas, *Tetrahedron: Asymmetry* 2007, 18, 569; 2000, 11, 645; and 1998, 9, 3517; and experimental examples compiled in patent application WO 2008/021927A2 by C. Bachand, et al, from BMS, which is incorporated herein by reference. 3-5 may be further deprotected under hydrolytic conditions in the presence of an acid such as TFA or hydrogen chloride to remove the Boc protection group and the released amine functionality can be further derivatized to the title compounds I-1 using the conditions described above.

Other examples of some of the linkers that can be used to construct the title compounds of the present invention are compiled in the table below, in which PG and PG' at each occurrence are each independently amino or alcohol protecting group, such as Boc, Cbz, Troc, Teoc, PMB, TMS etc. These linkers are either commercially available or may be synthesized in several steps through strategies which are known to those skilled in the art.

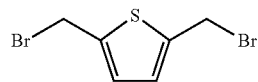

265
-continued
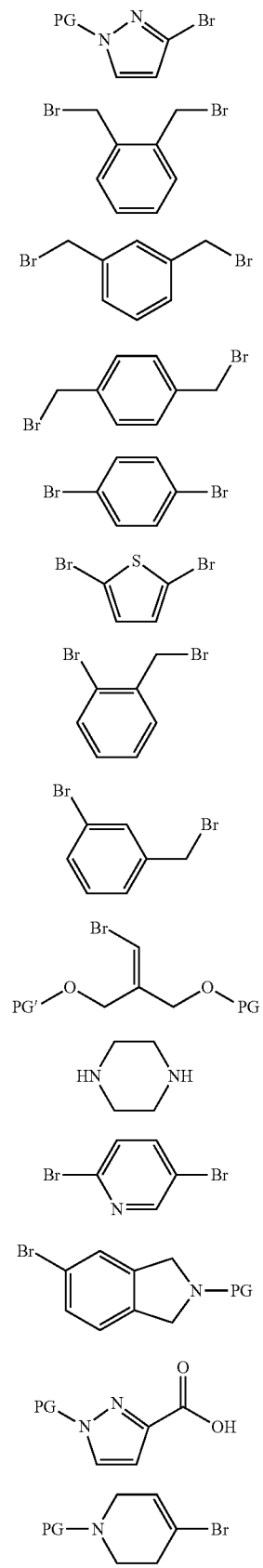
266
-continued
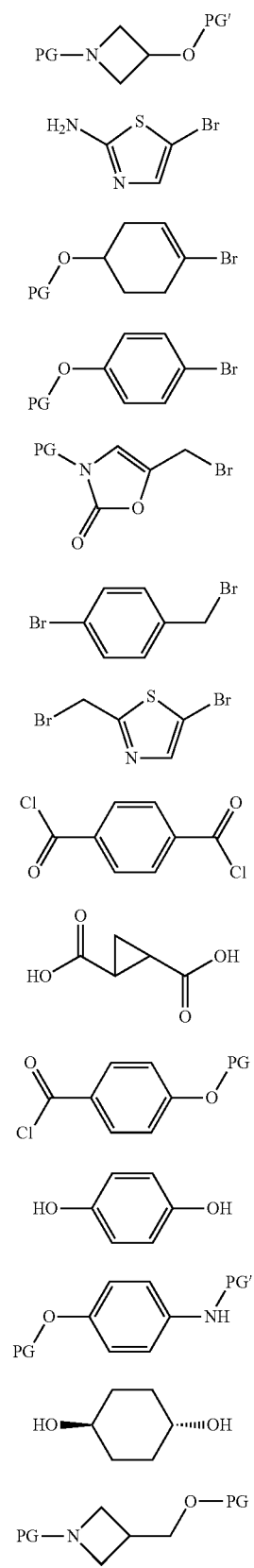

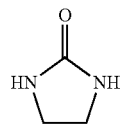
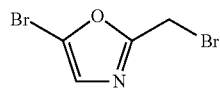
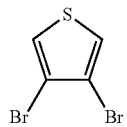
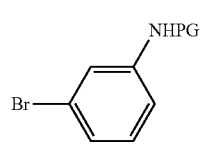
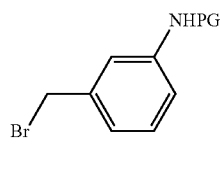
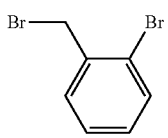
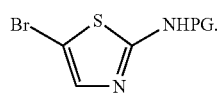

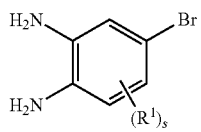

2-10.1b

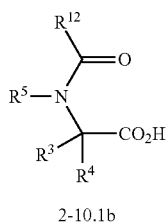

4-1

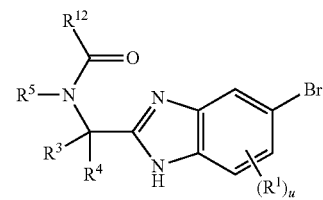

2-10.2a
PG is carboxylic acid protecting group
$R^2$ is independently R1

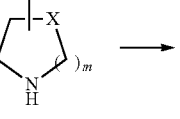

2-10.2b

Alternatively, as shown in Scheme 4, the compounds of the present invention (for example I-1) may also be derived from bromobenzimidazoles 4-1 and imidazole 4-2 using the procedures described previously. The intermediates 4-1 and 4-2 have the desired acyl groups already installed as seen in amino acid derivatives 2-10.1b and 2-10.2b, which can be prepared from protected amino acids 2-10.1a and 2-10.2a through the sequences shown in Scheme 1 and 2.

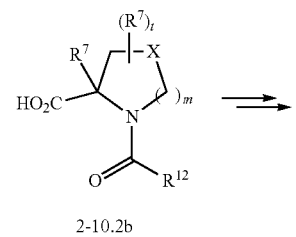

4-2

Scheme 4

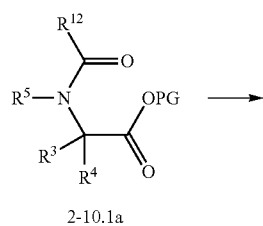

2-10.1a

-continued

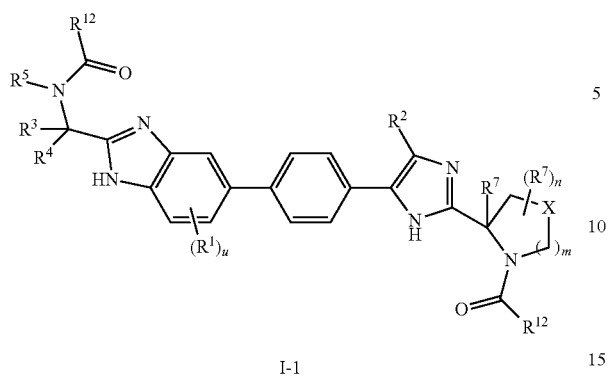

I-1

The compounds of the present invention containing benzimidazole linked with other five-membered heteroaryl other than imidazole may be prepared using similar procedures described above in Schemes 1-4. For example, some intermediates containing a desired, suitably substituted five-membered heteroaryl have been published in US 2008/0311075A1 by C. Bachand, et al from BMS, which is incorporated by reference. Theses intermediates are compiled in the following table.

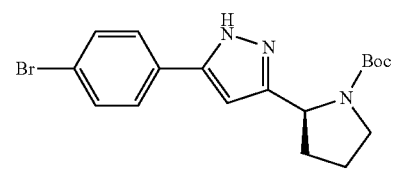 [SMILES: CC(C)(C)OC(=O)N1CCC[C@H]1c1cc(-c2ccc(Br)cc2)[nH]n1]

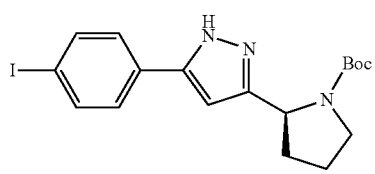 [SMILES: CC(C)(C)OC(=O)N1CCC[C@H]1c1cc(-c2ccc(I)cc2)[nH]n1]

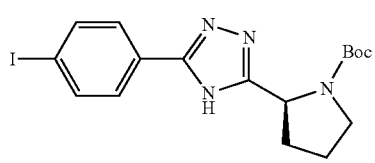 [SMILES: CC(C)(C)OC(=O)N1CCC[C@H]1c1nnc(-c2ccc(I)cc2)[nH]1]

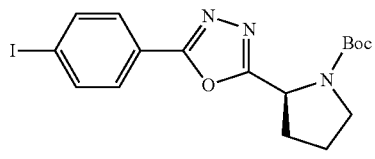

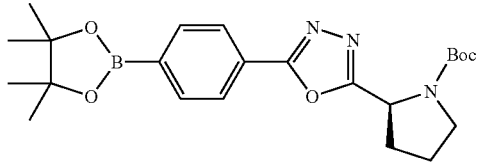 [SMILES: CC(C)(C)OC(=O)N1CCC[C@H]1c1nnc(-c2ccc(B3OC(C)(C)C(C)(C)O3)cc2)o1]

-continued

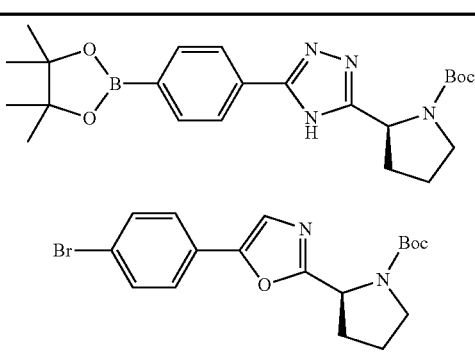

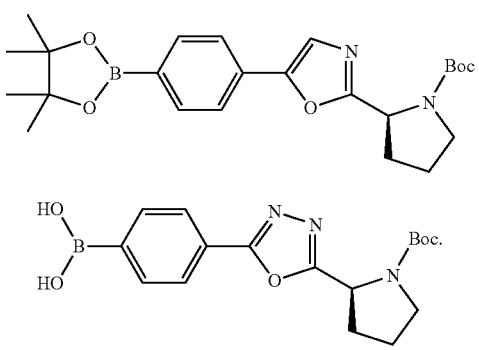

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

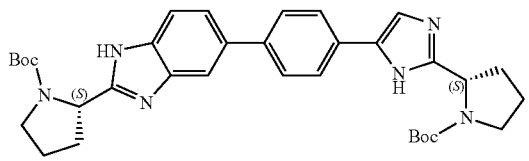

Step 1a.

A mixture of N-Boc-L-proline (5.754 g, 26.7 mmol) and TEA (3.73 mL, 26.7 mmol) in THF (60 mL) at −20° C. was treated with ethyl chloroformate (2.55 mL, 26.7 mmol) for 30 minutes before a slow addition of 4-bromo-1,2-diaminobenzene (5.00 g, 26.7 mmol) in THF (20 mL). It was then kept at −20° C. for 1 hour and then slowly warmed up to rt and stirred at rt overnight. The volatiles were evaporated and the residue was partitioned (EtOAc-water). The organics were washed with brine, dried ($Na_2SO_4$), filtered and evaporated to give the crude desired compound as a dark brown foam (10.7 g). ESIMS m/z=384.18, 386.18 $[M+H]^+$.

Step 1b.

A solution of the crude compound from step 1a (10.7 g, 26.7 mmol at most) in glacial acetic acid (100 mL) was heated at 50° C. for 2 hours. The volatiles were evaporated off and the residue was partitioned (EtOAc-aqueous $NaHCO_3$). The organics were washed with brine, dried ($Na_2SO_4$), filtered and evaporated. The residue was purified by chromatography (silica, hexanes-ethyl acetate) to give the desired compound as a brown foam (5.78 g, 59%). ESIMS m/z=366.17, 368.17 $[M+H]^+$. $^1H$ NMR ($CDCl_3$) 10.96, 10.93 (2 s, 1H), 7.81, 7.30 (2s, 1H), 7.53, 7.17 (2d, J=8.5 Hz, 1H), 7.23, 7.03 (2d, J=8.5 Hz, 1H), 5.09, 5.07 (2s, 1H), 3.42-3.49 (m, 2H), 2.75-2.85 (m, 1H), 2.13-2.23 (m, 2H), 1.97-2.00 (m, 1H), 1.48 (s, 9H).

Step 1c.

A mixture of 2,4'-dibromoacetophenone (5.00 g, 18.0 mmol), N-Boc-L-proline (3.87 g, 18.0 mmol) and in $CH_3CN$ (60 mL) was treated with TEA (5.40 mL, 37.8 mmol) at room temperature until the disappearence of the starting material. The volatiles were evaporated and the residue was partitioned (EtOAc-water). The organics were washed with brine, dried ($Na_2SO_4$), filtered and evaporated. The residue was purified by chromatography (silica, hexanes-ethyl acetate) to give the desired compound as a light yellow foam (6.73 g, 91%). $^1H$ NMR ($CDCl_3$) 7.76 (t, J=8.0 Hz, 2H), 7.63 (dd, J=5.0, 8.5 Hz, 2H), 5.51, 5.16 (2d, J=16.0 Hz, 1H), 5.32, 5.28 (2d, J=16.5 Hz, 1H), 4.48, 4.40 (dd, J=5.0, 8.5 Hz, 1H), 3.56 (m, 1H), 3.43 (m, 1H), 2.30 (m, 2H), 2.06 (m, 1H), 1.92 (m, 1H), 1.46, 1.43 (2s, 9H).

Step 1d.

A solution of the compound from step 1c (6.73 g, 16.3 mmol) in toluene (100 mL) was treated with ammonium acetate (25.1 g, 0.327 mol) at 100° C. for 14 hours. The volatiles were evaporated and the residue was partitioned (EtOAc-aqueous $NaHCO_3$). The organics were washed with brine, dried ($Na_2SO_4$), filtered and evaporated. The residue was purified by chromatography (silica, hexanes-ethyl acetate) to give the desired compound as a yellow foam (6.10 g, 95%). ESIMS m/z=392.24, 394.24 $[M+H]^+$. $^1H$ NMR ($CDCl_3$) 7.57 (bs, 1H), 7.48 (m, 3H), 7.23 (s, 1H), 4.97 (m, 1H), 3.42 (m, 2H), 2.99 (m, 1H), 2.16 (m, 2H), 1.97 (m, 1H), 1.46 (s, 9H).

Step 1e.

A mixture of the compound from step 1d (1.00 g, 2.55 mmol), bis(pinacolato)diboron (1.35 g, 5.33 mmol), $Pd(PPh_3)_4$ (0.147 g, 0.128 mmol) and potassium acetate (0.640 g, 6.53 mmol) in 1,4-dioxane (20 mL) was degassed and heated at 80° C. under $N_2$ for 14 hours. The volatiles were evaporated and the residue was partitioned (EtOAc-water). The organics were washed with brine, dried ($Na_2SO_4$), filtered and evaporated. The residue was purified by chromatography (silica, hexanes-ethyl acetate) to give the desired compound as a light yellow solid (0.978 g, 87%). ESIMS m/z=440.39 $[M+H]^+$. $^1H$ NMR ($CDCl_3$) 11.03, 10.55 (2s, 1H), 7.79 (m, 3H), 7.45 (m, 1H), 7.26 (m, 1H), 4.97 (m, 1H), 3.41 (m, 2H), 3.06, 2.91 (2m, 1H), 2.17 (m, 2H), 1.97 (m, 1H), 1.49 (s, 9H), 1.35 (s, 12H).

Step 1f.

A mixture of compound from step 1b (0.188 g, 0.512 mmol), the compound from step 1e (0.150 g, 0.342 mmol) $Pd(PPh_3)_4$, (39.4 mg, 34.1 μmol) and $NaHCO_3$ (0.115 g, 1.37 mmol) in DME (6 mL) and $H_2O$ (2 mL) was degassed and heated at 80° C. under $N_2$ for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a white needle crystal (0.106 g, 52%). ESIMS m/z=599.59 $[M+H]^+$.

Example 2

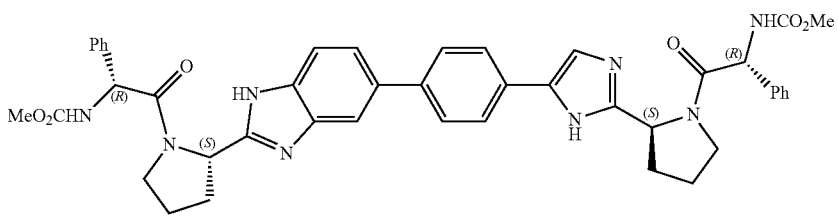

Step 2a.

A solution of the compound of example 1 (20.0 mg, 33.4 μmol) in 1,4-dioxane (1 mL) was treated with HCl in 1,4-dioxane (4 M, 4 mL) at rt for 30 minutes. The volatiles were evaporated off to give the crude desired compound as a yellow solid which was directly used in the next step. ESIMS m/z=399.35 $[M+H]^+$.

Step 2b.

A mixture of the crude compound from step 2a (33.4 μmol at most) and (R)-(methoxycarbonyl)amino phenyl acetic acid (prepared according to WO 2008/021927, 20.9 mg, 0.100 mmol) in DMF (3 mL) was treated with HATU (31.7 mg, 83.5 μmol) in the presence of DIPEA (83.0 μL, 0.668 mmol) for 2 hours at rt and the volatiles were evaporated off

Example 1-1

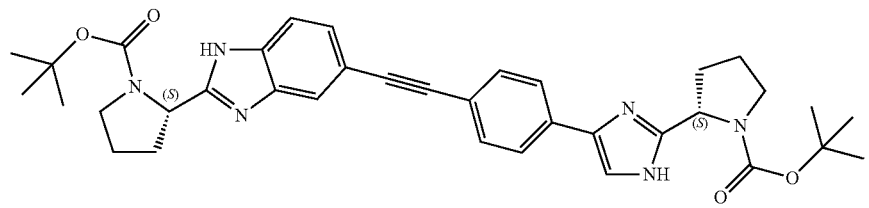

Step 1-1a.

A mixture of the compound from step 1d (0.559 g, 1.425 mmol), trimethylsilyl-acetylene (0.60 ml, 4.275 mmol), CuI (28.5 mg, 0.150 mmol) and $Pd(PPh_3)_2Cl_2$ (80.0 mg, 0.114 mmol) in $Et_3N$ (15 mL) was heated at 80° C. under $N_2$ for 6 hours before being evaporated. The residue was purified by chromatography (silica, hexanes-ethyl acetate with 1% $Et_3N$ in ethyl acetate) to give the desired compound as a yellow foam (0.484 g, 83%). ESIMS m/z=410.24 $[M+H]^+$.

Step 1-1b.

A suspension of the compound from step 1-1a (0.484 g, 1.182 mmol) and $K_2CO_3$ (0.408 g, 2.954 mmol) in methanol (12 ml) was stirred at rt for 3 hour. The volatiles were evaporated off. The residue was purified by chromatography (silica, dichloromethane-ethyl acetate) to give the desired compound as a yellow foam (0.370 g, 93%). ESIMS m/z=338.24 $[M+H]^+$.

Step 1-1c.

A mixture of the compound from step 1-1b (80.0 mg, 0.2371 mmol), the compound from step 1b (86.8 mg, 0.2371 mmol), CuI (2.2 mg, 0.01185 mmol) and $Pd(PPh_3)_2Cl_2$ (16.6 mg, 0.02371 mmol) in $Et_3N$ (0.3 mL) and $CH_3CN$ (2 mL) was heated at 85° C. under $H_2/N_2$ mixed gas for 2 hours before being evaporated. The residue was purified by chromatography (silica, hexanes-ethyl acetate with 1% $Et_3N$ in ethyl acetate) to give the title compound as a yellow solid (48.3 mg, 33%). ESIMS m/z=623.32 $[M+H]^+$.

to provide a brown sirup. It was purified by chromatography (silica, $CH_2Cl_2$-MeOH) to give the title compound as a yellow solid (23.8 mg, 2 steps 91%). ESIMS m/z=781.67 $[M+H]^+$.

Step 2-1a.

A solution of the compound of example 1-1 (48.3 mg, 0.0776 mmol) in 1,4-dioxane (1.5 mL) was treated with HCl in 1,4-dioxane (4 M, 6 mL) at rt for 30 minutes. The volatiles were evaporated off to give the crude desired compound as a yellow solid which was used directly in the next step.

Step 2-1b.

A mixture of the crude compound from step 2-1a (0.127 mmol at most) and (R)-(methoxycarbonyl)amino phenyl acetic acid (prepared according to WO 2008/021927, 40.6 mg, 0.194 mmol) in DMF (1.5 mL) was treated with HATU (67.8 mg, 0.178 mmol) in the presence of DIPEA (0.27 mL, 1.551 mmol) for 2 hours at rt and the volatiles were evaporated off to provide a brown syrup. It was purified by chromatography (silica, $CH_2Cl_2$-MeOH) to give the title compound as a yellow solid (36.2 mg, 2 steps 58%). ESIMS m/z=805.29 $[M+H]^+$.

Example 2-1

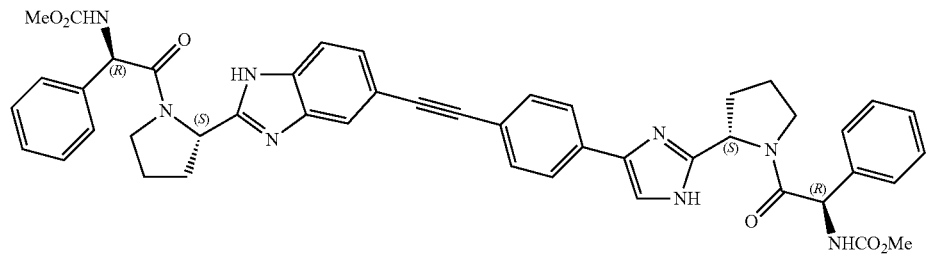

Example 2-2

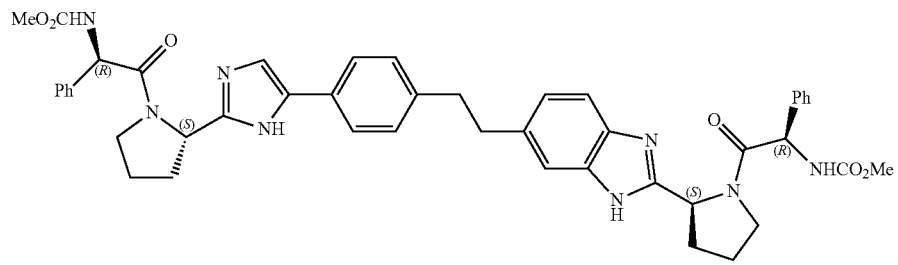

A solution of the compound of example 2-1 (23.0 mg, 0.0286 mmol) in ethanol (2 mL) was treated with Pd(OH)$_2$ (20 wt % on carbon, 23 mg) at rt with a hydrogen balloon for 7 hourr. The mixture was filtered through a short pad of Celite. The volatiles were evaporated off. The residue was purified by chromatography (silica, CH$_2$Cl$_2$-MeOH) to give the title compound as a white solid (16.0 mg, 70%). ESIMS m/z=809.40 [M+H]$^+$.

The compounds of examples 3-356 and 358-440 may be prepared using procedures similar to those described in examples 1, 2, 1-1, 2-1, 2-2, 357 (described below), and 441-545 (described below), and/or as described in the Synthetic Methods.

TABLE 1a-continued

Examples 3-219.

| Entry | R group |
|---|---|
| 13 | cyclopropyl-C(=O)- |
| 14 | 1-(trifluoromethyl)cyclopropyl-C(=O)- |
| 15 | 1-hydroxycyclopropyl-C(=O)- |
| 16 | Ph-C(=O)- |
| 17 | Ph-CH$_2$-C(=O)- |
| 18 | cyclopropyl-CH$_2$-C(=O)- |
| 19 | Ph-C(CH$_3$)(OH)-C(=O)- |
| 20 | Ph-CH(OMe)-C(=O)- |
| 21 | Ph-CH(OH)-C(=O)- |
| 22 | (pyridin-3-yl)-CH$_2$-C(=O)- |
| 23 | (pyridin-4-yl)-CH$_2$-C(=O)- |
| 24 | Ph-CH$_2$-CH(OH)-C(=O)- |
| 25 | (tetrahydrofuran-2-yl)-C(=O)- |
| 26 | (tetrahydrofuran-2-yl)-C(=O)- |
| 27 | (tetrahydrofuran-3-yl)-C(=O)- |
| 28 | (1-methylpiperidin-4-yl)-C(=O)- |
| 29 | (tetrahydropyran-4-yl)-C(=O)- |

TABLE 1a-continued

Examples 3-219.

| Entry | R group |
|---|---|
| 30 | morpholine-N-C(=O)- |
| 31 | trans-4-(Boc-amino)cyclohexyl-C(=O)- |
| 32 | cis-4-(Boc-amino)cyclohexyl-C(=O)- |
| 33 | 1-Boc-piperidin-4-yl-C(=O)- |
| 34 | 4-(diethylamino)cyclohexyl-C(=O)- |
| 35 | 4-(methoxycarbonylamino)cyclohexyl-C(=O)- |
| 36 | 4-methylpiperazin-1-yl-C(=O)- |
| 37 | 2-(piperidin-1-ylmethyl)phenyl-CH₂-C(=O)- |
| 38 | 2-(pyrrolidin-1-ylmethyl)phenyl-CH₂-C(=O)- |
| 39 | 2-((dimethylamino)methyl)phenyl-CH₂-C(=O)- |
| 40 | 2-((4-methylpiperazin-1-yl)methyl)phenyl-CH₂-C(=O)- |
| 41 | 2-(morpholinomethyl)phenyl-CH₂-C(=O)- |

TABLE 1a-continued

Examples 3-219.

| Entry | |
|---|---|
| 42 | methyl (4-(carbonyl)cyclohexyl)carbamate |
| 43 | thiazol-4-yl carbonyl |
| 44 | oxazol-2-yl carbonyl |
| 45 | oxazol-5-yl carbonyl |
| 46 | 2-(1H-imidazol-5-yl)acetyl |
| 47 | 1H-imidazol-5-yl carbonyl |
| 48 | 1-methyl-1H-imidazol-5-yl carbonyl |
| 49 | 2-(1H-tetrazol-5-yl)acetyl |
| 50 | 2-fluorophenyl carbonyl |
| 51 | 4-(dimethylamino)phenyl carbonyl |
| 52 | pyridin-4-yl carbonyl |
| 53 | pyridin-3-yl carbonyl |
| 54 | pyridin-2-yl carbonyl |
| 55 | (S)-2-methoxy-2-phenylacetyl |
| 56 | 3,3,3-trifluoro-2-methoxy-2-phenylpropanoyl |
| 57 | 2,2-diphenylacetyl |

TABLE 1a-continued

Examples 3-219.

[Structure 283: R-C(=O)-N-pyrrolidine-benzimidazole-phenyl-imidazole-pyrrolidine-N-C(=O)-R]

[Structure 284: R-C(=O)-N-pyrrolidine-benzimidazole-phenyl-imidazole-pyrrolidine-N-C(=O)-R]

R group: R-C(=O)-

| Entry | R group |
|---|---|
| 58 | phenyl-C(CH₃)₂-C(=O)- |
| 59 | (2-fluorophenyl)-C(OH)(CH₃)-C(=O)- |
| 60 | Ph-cyclopropyl-C(=O)- |
| 61 | MeO-C(=O)-NH-CH(CH₃)-C(=O)- |
| 62 | MeO-C(=O)-NH-CH(CH₃)-C(=O)- |
| 63 | EtO-C(=O)-NH-CH(CH₃)-C(=O)- |
| 64 | (tetrahydropyran-4-yl)-O-C(=O)-NH-CH(CH₃)-C(=O)- |
| 65 | (tetrahydropyran-4-yl)-O-C(=O)-NH-CH(CH₃)-C(=O)- |
| 66 | MeO-C(=O)-NH-CH(CH₂OMe)-C(=O)- |
| 67 | MeO-C(=O)-NH-CH(Et)-C(=O)- |
| 68 | MeO-C(=O)-NH-CH(Et)-C(=O)- |
| 69 | MeO-C(=O)-NH-CH(CH₂CH₂OMe)-C(=O)- |
| 70 | MeO-C(=O)-NH-CH(CH(OH)CH₃)-C(=O)- |
| 71 | MeO-C(=O)-NH-CH(CH(OH)CH₃)-C(=O)- |

TABLE 1a-continued

Examples 3-219.

| Entry | R-C(O)- group |
|-------|---------------|
| 72 | methyl carbamate-NH-CH(CH(OH)CH₃)-C(O)- (threonine-like, Moc-Thr) |
| 73 | methyl carbamate-NH-CH(CH₂CH=CH₂)-C(O)- (Moc-allylglycine) |
| 74 | methyl carbamate-NH-CH(CH₂CH₂CH₂CH₃)-C(O)- (Moc-norleucine) |
| 75 | Boc-NH-CH(CH₂CH₂N(CH₃)₂)-C(O)- |
| 76 | methyl carbamate-NH-C(CH₃)₂-C(O)- (Moc-Aib) |
| 77 | Moc-NH-CH(cyclopropyl)-C(O)- |
| 78 | Moc-NH-CH(cyclopropyl)-C(O)- (stereoisomer) |
| 79 | Moc-NH-C(CH₃)₂(OH... ) — Moc-NH-CH(C(CH₃)₂OH)-C(O)- |
| 80 | Moc-NH-CH(CH₂CO₂Bn)-C(O)- |
| 81 | Moc-NH-CH(CH₂CONH₂)-C(O)- (Moc-Asn) |
| 82 | Moc-Val |
| 83 | Moc-Val (stereoisomer) |
| 84 | Moc(N-Me)-Val |
| 85 | tetrahydropyran-4-yl-O-C(O)-NH-CH(iPr)-C(O)- |

TABLE 1a-continued

Examples 3-219.

| Entry | R group |
|---|---|
| 86 | valine with tetrahydropyran-4-yl carbamate |
| 87 | valine with tetrahydrofuran-3-yl carbamate |
| 88 | methyl carbamate amino acid with CH2CH2N(Et)2 side chain |
| 89 | methyl carbamate amino acid with CH(Me)CH2OTBS side chain |
| 90 | methyl carbamate amino acid with CH(Me)CH2OTBS side chain (other diastereomer) |
| 91 | methyl carbamate amino acid with CH2CH2N(Et)2 side chain |
| 92 | methyl carbamate amino acid with tetrahydropyran-4-yl side chain |
| 93 | methyl carbamate amino acid with tetrahydropyran-4-yl side chain (other stereochem) |
| 94 | 1-(methoxycarbonylamino)cyclopropanecarbonyl |
| 95 | 1-(methoxycarbonylamino)cyclobutanecarbonyl |
| 96 | 1-(methoxycarbonylamino)cyclopentanecarbonyl |
| 97 | methyl carbamate phenylglycine |
| 98 | 2-chlorophenyl glycine methyl carbamate |

TABLE 1a-continued

Examples 3-219.

Entry 99–111: R-group structures for the bis-benzimidazole/imidazole core scaffold shown above.

TABLE 1a-continued

Examples 3-219.

TABLE 1a-continued

Examples 3-219.

TABLE 1a-continued

Examples 3-219.

| Entry | (structure) |
|---|---|
| 134 | (S)-methyl (1-phenyl-4-oxobutan-2-yl)carbamate |
| 135 | (S)-methyl (1-(2-fluorophenyl)-4-oxobutan-2-yl)carbamate |
| 136 | (S)-methyl (1-phenyl-3-oxopropyl)carbamate |
| 137 | (R)-methyl (1-phenyl-3-oxopropyl)carbamate |
| 138 | methyl (1-oxo-5-phenylpentan-3-yl)carbamate |
| 139 | (S)-2-(ethyl(methyl)amino)-2-phenylacetyl |
| 140 | (S)-2-(diethylamino)-2-phenylacetyl |
| 141 | (S)-2-(cyclopropyl(ethyl)amino)-2-phenylacetyl |
| 142 | (R)-2-(7-azabicyclo[2.2.1]heptan-7-yl)-2-phenylacetyl |
| 143 | (S)-2-(7-azabicyclo[2.2.1]heptan-7-yl)-2-phenylacetyl |
| 144 | (S)-2-(4-methylpiperazin-1-yl)-2-phenylacetyl |
| 145 | (S)-2-(pyrrolidin-1-yl)-2-phenylacetyl |
| 146 | (S)-2-((S)-3-fluoropyrrolidin-1-yl)-2-phenylacetyl |

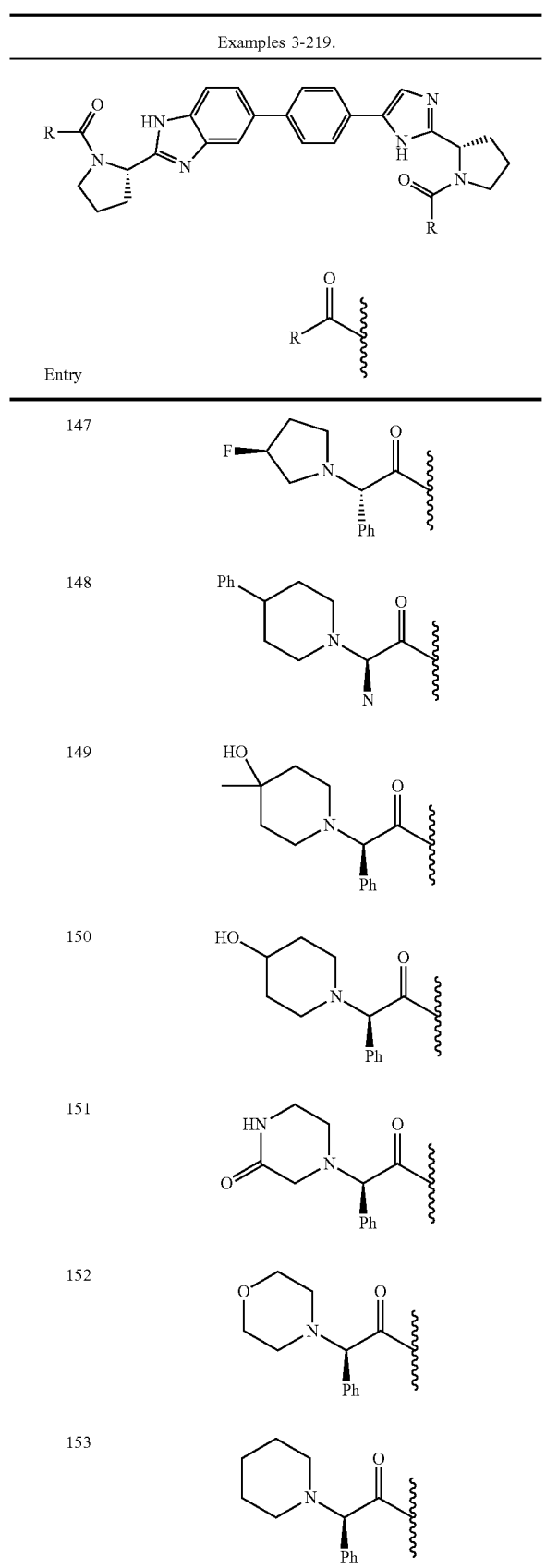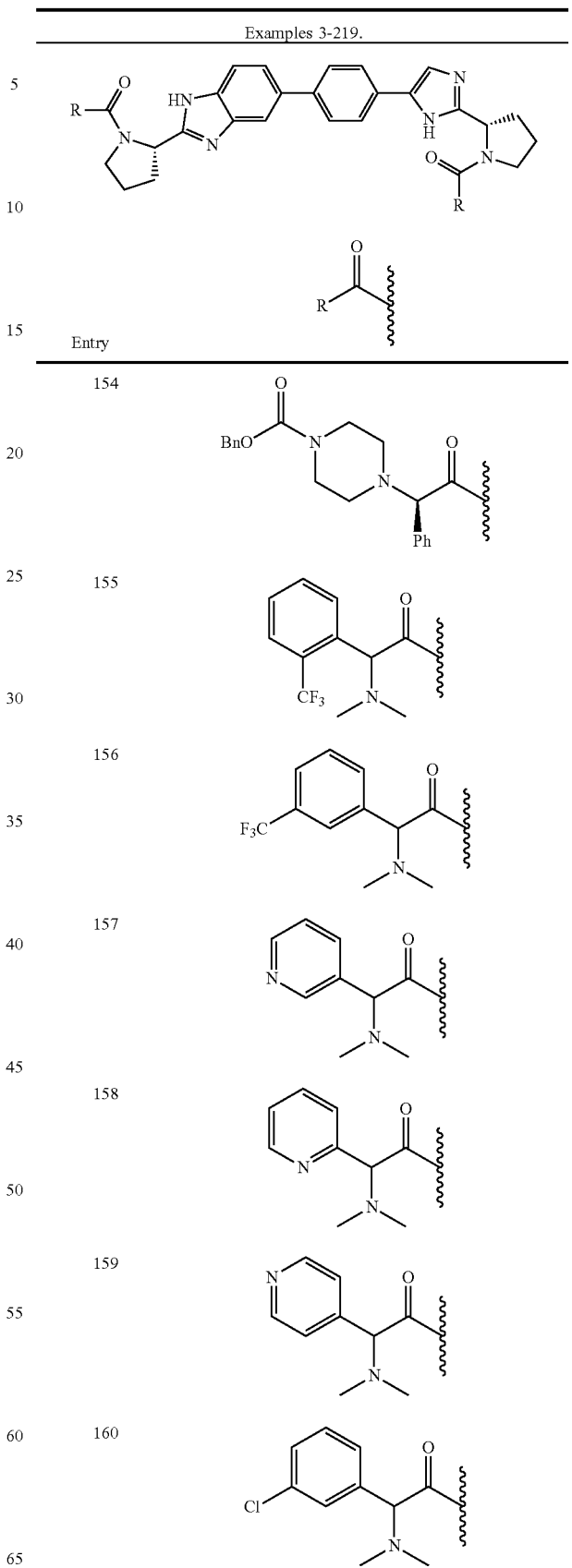

TABLE 1a-continued

Examples 3-219.

TABLE 1a-continued

Examples 3-219.

(Structural formula with R groups, benzimidazole, phenyl, imidazole, and pyrrolidine units)

| Entry | R-C(=O)- group |
|---|---|
| 175 | quinolin-3-yl, CH(N(CH₃)₂)-C(=O)- |
| 176 | benzothiophen-3-yl, CH(N(CH₃)₂)-C(=O)- |
| 177 | 2-methylbenzothiazol-5-yl, CH(N(CH₃)₂)-C(=O)- |
| 178 | PhCH₂-N(CH₃)-CH₂-C(=O)- |
| 179 | naphthalen-1-yl, CH(N(CH₃)₂)-C(=O)- |
| 180 | pyrrolidin-1-yl-CH₂-C(=O)- |
| 181 | 4-methylpiperazin-1-yl-CH₂-C(=O)- |
| 182 | (CH₃)₂N-CH₂-C(=O)- |
| 183 | (Et)₂N-CH(CH₂OCH₃)-C(=O)- |
| 184 | PhCH₂-N(CH₃)-CH(CH₃)-C(=O)- |
| 185 | (nPr)₂N-CH(CH₃)-C(=O)- |
| 186 | (nPr)₂N-CH(CH₃)-C(=O)- |
| 187 | (CH₃)₂N-CH(CH₃)-C(=O)- |
| 188 | (CH₃)₂N-CH(CH₃)-C(=O)- |
| 189 | CH₃C(=O)NH-CH(CH₃)-C(=O)- |
| 190 | (Et)₂N-CH(CH₃)-C(=O)- |

TABLE 1a-continued
Examples 3-219.
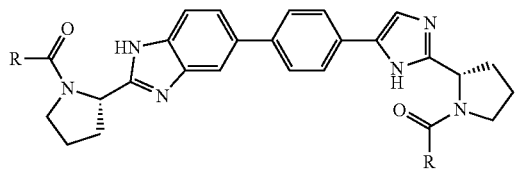
| Entry | |
|---|---|
| 191 | 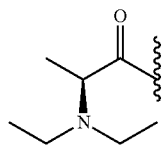 [SMILES: *C(=O)[C@H](C)N(CC)CC] |
| 192 | 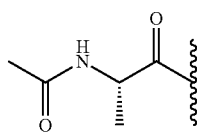 [SMILES: *C(=O)[C@H](C)NC(C)=O] |
| 193 | 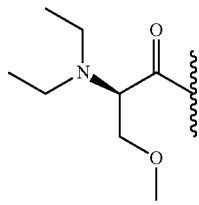 [SMILES: *C(=O)[C@@H](COC)N(CC)CC] |
| 194 | 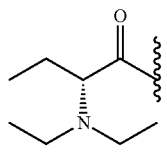 [SMILES: *C(=O)[C@@H](CC)N(CC)CC] |
| 195 | 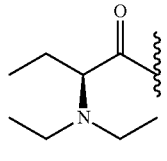 [SMILES: *C(=O)[C@H](CC)N(CC)CC] |
| 196 | 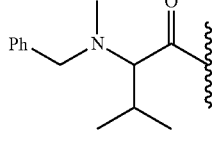 |
| 197 | 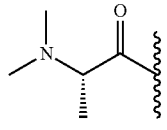 |
TABLE 1a-continued
Examples 3-219.
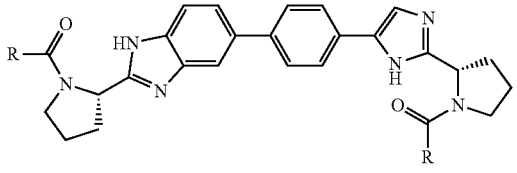
| Entry | |
|---|---|
| 198 | 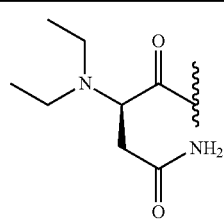 |
| 199 | 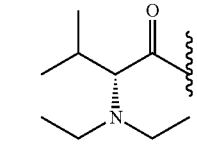 [SMILES: *C(=O)[C@@H](C(C)C)N(CC)CC] |
| 200 | 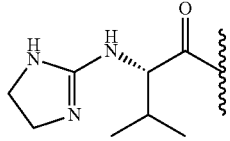 [SMILES: *C(=O)[C@@H](NC1=NCCN1)C(C)C] |
| 201 | 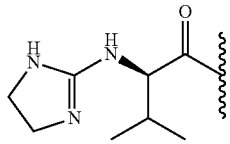 [SMILES: *C(=O)[C@H](NC1=NCCN1)C(C)C] |
| 202 | 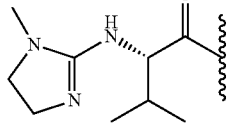 |
| 203 | 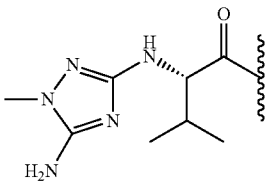 [SMILES: *C(=O)[C@@H](Nc1nc(N)n(C)n1)C(C)C] |
| 204 | |

TABLE 1a-continued

Examples 3-219.

(Structures at top of both columns showing bis-benzimidazole/imidazole core with pyrrolidine-R groups)

| Entry | R-C(O)- group |
|---|---|
| 205 | 3-amino-1H-1,2,4-triazol-5-ylamino-valine acyl |
| 206 | pyridin-3-ylamino-valine acyl |
| 207 | pyrimidin-4-ylamino-valine acyl |
| 208 | 5-amino-1,2,4-oxadiazol-3-ylamino-valine acyl |
| 209 | N,N-diethylamino-tert-leucine acyl |
| 210 | N,N-dimethylamino-phenylalanine acyl |
| 211 | prolyl |
| 212 | 5-oxo-prolyl (pyroglutamyl) |
| 213 | pyrimidin-5-ylamino-valine acyl |
| 214 | 4,4-difluoro-prolyl |
| 215 | 4-fluoro-prolyl |
| 216 | 3,4-methano-prolyl (azabicyclo[3.1.0]) |
| 217 | N-methyl-prolyl |
| 218 | N-methyl-4-fluoro-prolyl |

TABLE 1a-continued

Examples 3-219.

| Entry | R-C(=O)- group |
|---|---|
| 5 | (bis-pyrrolidine bis-benzimidazole/imidazole-phenyl core with R-C(=O)- on each pyrrolidine N) |
| 10 | R-C(=O)- (acyl) |
| 15 | (generic acyl: R-C(=O)-) |
| 20 | 4-fluoropyrrolidine-2-carbonyl |

TABLE 2

Examples 220-229.

| Entry | R | R' | R" | X |
|---|---|---|---|---|
| 220 | Me | H | H | $CH_2$ |
| 221 | H | H | H | $CF_2$ |
| 222 | Me | H | H | S |
| 223 | H | H | H | CHF (H up, F down) |
| 224 | Me | H | H | O |
| 225 | H | H | H | CHF (F up, H down) |
| 226 | H | Ph | H | $CH_2$ |
| 227 | H | H | H | CHOH (H up, OH down) |

TABLE 2-continued
Examples 220-229.
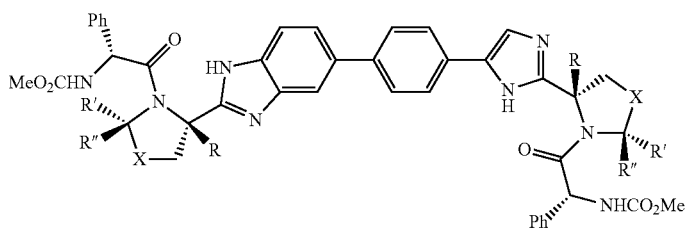
| Entry | R | R' | R" | X |
|---|---|---|---|---|
| 228 | H | H | Ph | CH₂ |
| 229 | H | H | H | ![OH,H structure] |
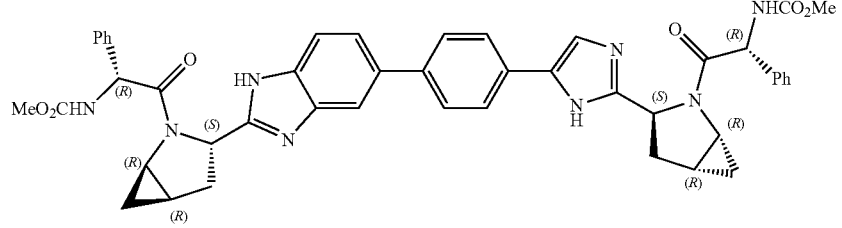
Example 230
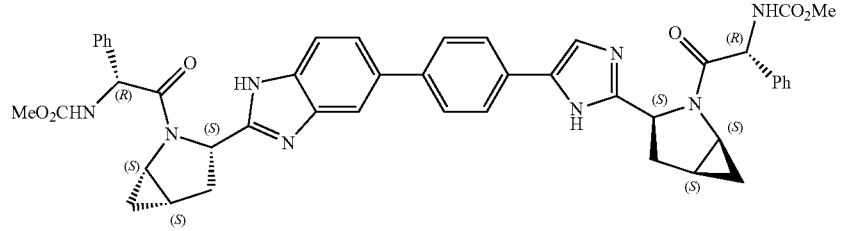
Example 231
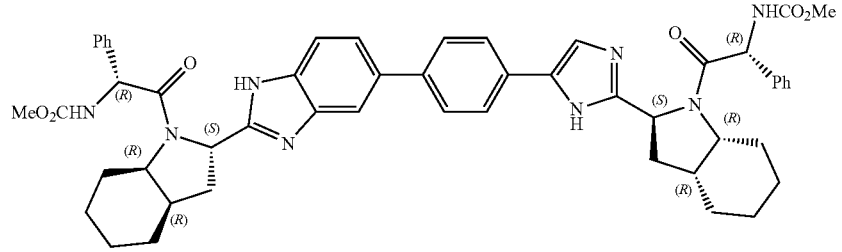
Example 232
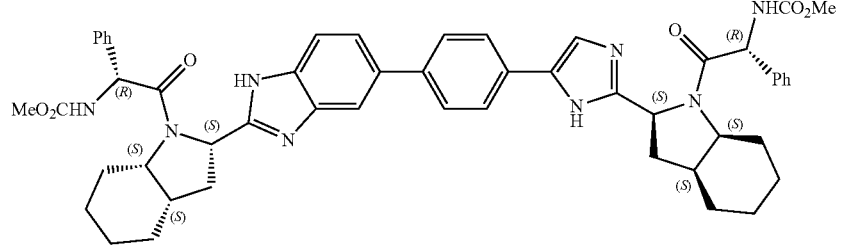
Example 233

TABLE 3
Examples 234-243.
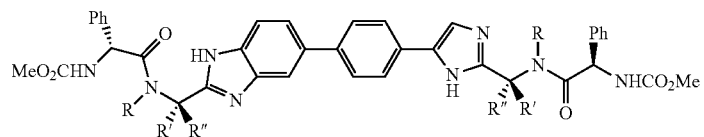
| Entry | R | R' | R" |
|---|---|---|---|
| 234 | Me | Me | H |
| 235 | H | Me | H |
| 236 | Me | H | Me |
| 237 | cyclopropyl | Me | H |
| 238 | Me | Me | Me |
| 239 | Me | cyclopropyl | H |
| 240 | Me | Allyl | H |
| 241 | Et | Me | H |
| 242 | Me | CHMe₂ | H |
| 243 | Me | Et | H. |
TABLE 4
Examples 244-263.
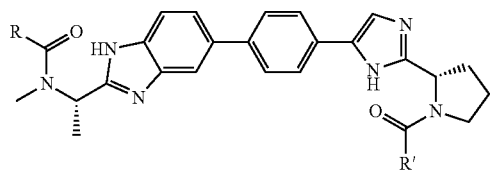
TABLE 4-continued
Examples 244-263.
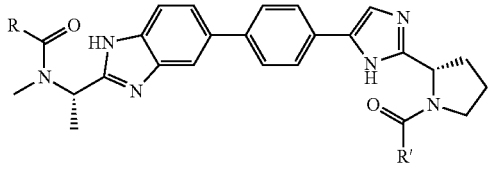

TABLE 4-continued

Examples 244-263.

| Entry | R | R' |
|---|---|---|
| 254 | MeO₂CHN-CH(iPr)- | MeO₂CHN-CH(tetrahydropyran-4-yl)- |
| 255 | MeO₂CHN-CH(2-chlorophenyl)- | morpholine-N-C(O)NH-CH(Ph)- |
| 256 | MeO₂CHN-CH(iPr)- | MeO₂CHN-CH(iPr)- |
| 257 | tetrahydrofuran-2-yl-C(O)NH-CH(Ph)- | EtNH-C(O)NH-CH(Ph)- |
| 258 | tetrahydropyran-4-yl-O-C(O)NH-CH(iPr)- | MeO₂CHN-CH(iPr)- |
| 259 | MeO₂CHN-CH(iPr)- | pyrimidin-2-yl-NH-CH(iPr)- |
| 260 | MeO₂CHN-CH(cyclopropyl)- | MeO₂CHN-CH(CH(OMe)Me)- |
| 261 | MeO₂CHN-CH(iPr)- | MeO₂CHN-CH(CH₂-pyrazol-1-yl)- |
| 262 | MeO₂CHN-CH(iPr)- | MeO₂CHN-cyclopentyl- |
| 263 | MeO₂CHN-CH(CH(OMe)Me)- | pyridin-3-yl-NH-CH(iPr)- |

TABLE 5

Examples 264-273.

| Entry | R | R' | R'' | R''' |
|---|---|---|---|---|
| 264 | F | H | H | H |
| 265 | F | F | H | H |
| 266 | Me | H | H | H |
| 267 | Me | Me | H | H |
| 268 | H | H | Me | Me |
| 269 | H | H | Et | Et |
| 270 | CF₃ | H | H | H |
| 271 | CF₃ | H | CF₃ | H |
| 272 | Cl | H | H | H |
| 273 | Cl | H | Cl | H. |

TABLE 6

Examples 274-299.

| Entry | R | R' | R'' | R''' |
|---|---|---|---|---|
| 274 | Me | H | H | H |
| 275 | H | CO₂H | H | H |
| 276 | H | F | H | H |

TABLE 6-continued

Examples 274-299.

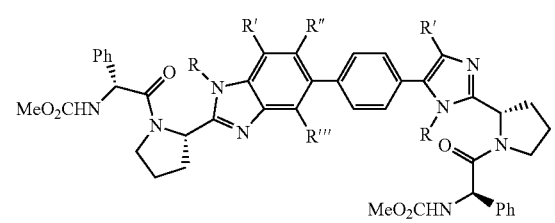

| Entry | R | R' | R" | R''' |
|---|---|---|---|---|
| 277 | H | H | CO$_2$H | H |
| 278 | H | H | F | H |
| 279 | H | H | H | CO$_2$H |
| 280 | H | H | H | F |
| 281 | H | CO$_2$Me | H | H |
| 282 | H | Cl | H | H |
| 283 | H | H | CO$_2$Me | H |
| 284 | H | H | Cl | H |
| 285 | H | H | H | CO$_2$Me |
| 286 | H | H | H | Cl |
| 287 | H | CONH$_2$ | H | H |
| 288 | H | Me | H | H |
| 289 | H | H | CONH$_2$ | H |
| 290 | H | H | Me | H |
| 291 | H | H | H | CONH$_2$ |
| 292 | H | H | H | Me |
| 293 | H | OMe | H | H |
| 294 | H | CF$_3$ | H | H |
| 295 | H | H | OMe | H |
| 296 | H | H | CF$_3$ | H |
| 297 | H | H | H | OMe |
| 298 | H | H | H | CF$_3$ |
| 299 | CO$_2$Me | H | H | H. |

TABLE 7

Examples 300-434.

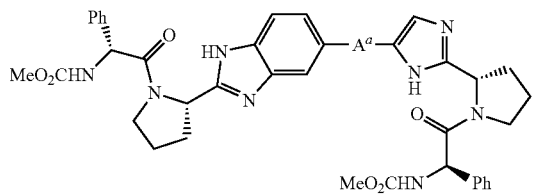

| Entry | A$^a$ |
|---|---|
| 300 | ![chain] |
| 301 | ![chain with double bond] |
| 302 | ![chain with triple bond] |

TABLE 7-continued

Examples 300-434.

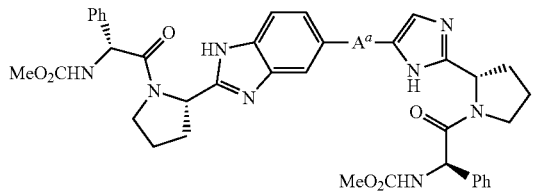

| Entry | A$^a$ |
|---|---|
| 303 | ![cyclopropyl] |
| 304 | ![cyclobutyl] |
| 305 | ![cyclopentenyl] |
| 306 | ![thiophene] |
| 307 | ![isoxazole] |
| 308 | ![pyrazole] |
| 309 | ![1,2-phenyl] |
| 310 | ![1,3-phenyl] |
| 311 | ![1,4-phenyl] |

TABLE 7-continued

Examples 300-434.

| Entry | A$^a$ |
|---|---|
| 312 | (2-vinylbenzyl linker) |
| 313 | (3-(ethynyl)benzyl linker) |
| 314 | (2,5-thiophene with ethynyl linker) |
| 315 | (azetidine linker) |
| 316 | (imidazolidin-2-one linker) |
| 317 | (piperazine linker) |
| 318 | (-CH$_2$OC(O)OCH$_2$-) |
| 319 | (-CH$_2$OC(O)NHCH$_2$-) |
| 320 | (-CH$_2$NHC(O)NHCH$_2$-) |
| 321 | (-CH$_2$C(O)OCH$_2$-) |
| 322 | (-CH$_2$C(O)NHCH$_2$-) |
| 323 | (-CH$_2$S(O)$_2$NHCH$_2$-) |
| 324 | (-CH$_2$OCH$_2$-) |
| 325 | (-CH$_2$N(CH$_3$)CH$_2$-) |
| 326 | (-CH$_2$CH$_2$OCH$_2$CH$_2$-) |
| 327 | (-CH$_2$OCH$_2$CH=CHCH$_2$-) |
| 328 | (-CH$_2$OCH$_2$C≡C-) |
| 329 | (-CH$_2$CH$_2$N(CH$_3$)CH$_2$CH$_2$-) |
| 330 | (-CH$_2$OCH$_2$CH$_2$OCH$_2$-) |

TABLE 7-continued
Examples 300-434.
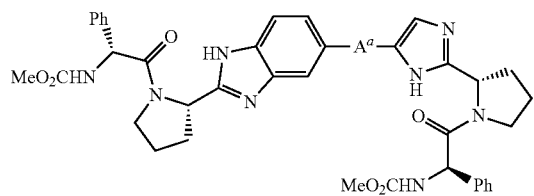
| Entry | A$^a$ |
|---|---|
| 331 | 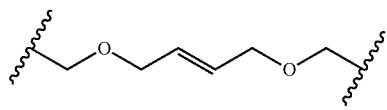 [SMILES: *COC/C=C/COC*] |
| 332 |  |
| 333 | 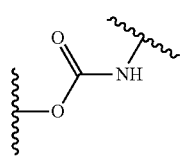 [SMILES: *NC(=O)O*] |
| 334 | 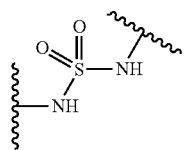 |
| 335 | 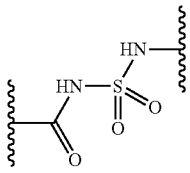 [SMILES: *NS(=O)(=O)NC(*)=O] |
| 336 | 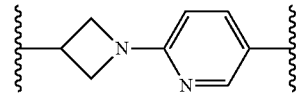 [SMILES: *c1ccc(N2CC(*)C2)nc1] |
| 337 | 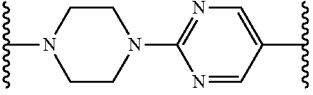 |
| 338 | 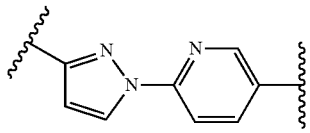 [SMILES: *c1ccc(-n2ccc(*)n2)nc1] |
| 339 | 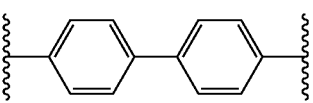 |
| 340 | 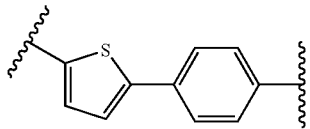 [SMILES: *c1ccc(-c2ccc(*)s2)cc1] |
TABLE 7-continued
Examples 300-434.
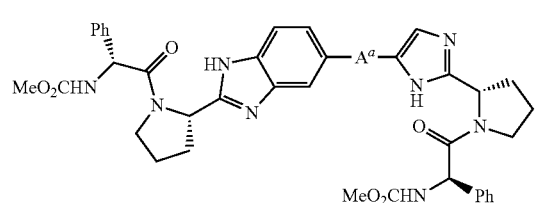
| Entry | A$^a$ |
|---|---|
| 341 | 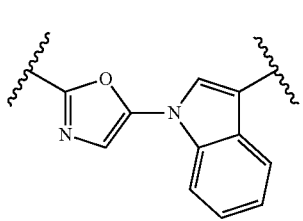 [SMILES: *c1ncc(-n2cc(*)c3ccccc32)o1] |
| 342 | 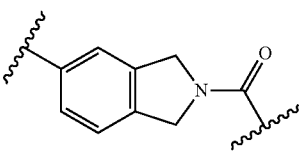 [SMILES: *C(=O)N1Cc2ccc(*)cc2C1] |
| 343 | 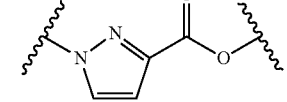 |
| 344 | 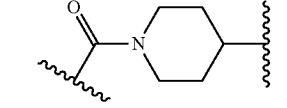 [SMILES: *C(=O)N1CCC(*)CC1] |
| 345 | 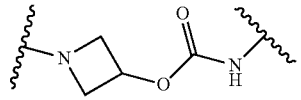 [SMILES: *NC(=O)OC1CN(*)C1] |
| 346 | 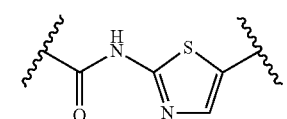 |
| 347 | 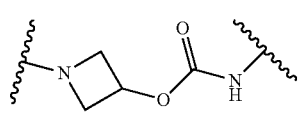 [SMILES: *NC(=O)OC1CN(*)C1] |
| 348 | 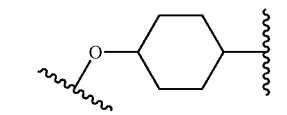 |
| 349 | 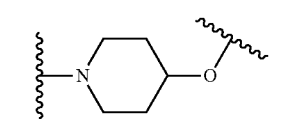 [SMILES: *OC1CCN(*)CC1] |

TABLE 7-continued
Examples 300-434.
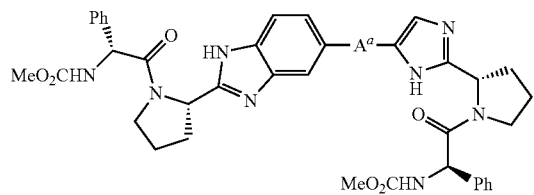
| Entry | $A^a$ |
|---|---|
| 350 | 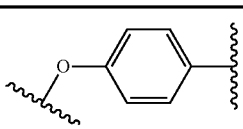 |
| 351 | 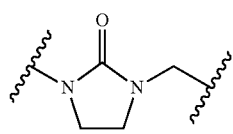 [SMILES: *CN1CCN(*)C1=O] |
| 352 | 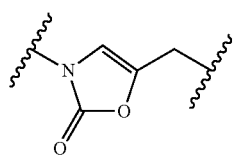 [SMILES: *Cc1cn(*)c(=O)o1] |
| 353 | 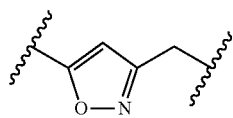 [SMILES: *Cc1cc(*)on1] |
| 354 | 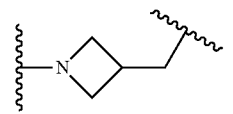 [SMILES: *CC1CN(*)C1] |
| 355 | 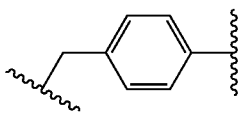 |
| 356 | 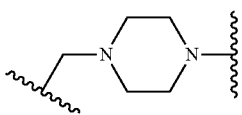 [SMILES: *CN1CCN(*)CC1] |
| 357 | 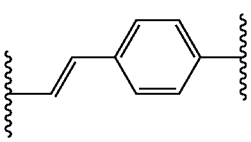 [SMILES: */C=C/c1ccc(*)cc1] |
| 358 | 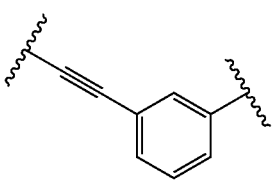 [SMILES: *C#Cc1cccc(*)c1] |
TABLE 7-continued
Examples 300-434.
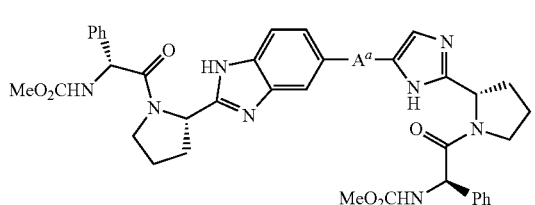
| Entry | $A^a$ |
|---|---|
| 359 | 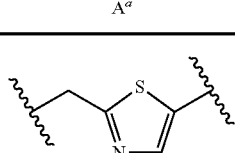 |
| 360 | 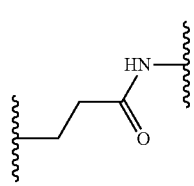 |
| 361 | 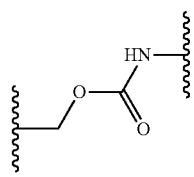 [SMILES: *COC(=O)N*] |
| 362 | 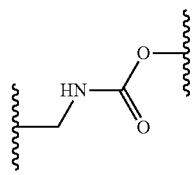 [SMILES: *CNC(=O)O*] |
| 363 | 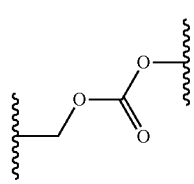 [SMILES: *COC(=O)O*] |
| 364 | 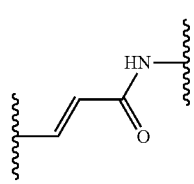 [SMILES: */C=C/C(=O)N*] |
| 365 | 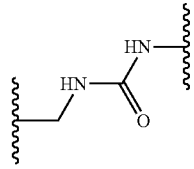 [SMILES: *CNC(=O)N*] |

TABLE 7-continued
Examples 300-434.
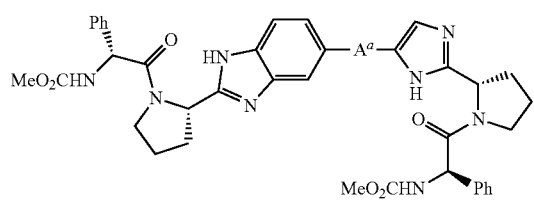
| Entry | A<sup>a</sup> |
|---|---|
| 366 | 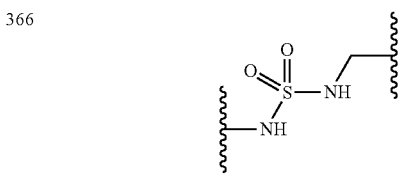 |
| 367 | 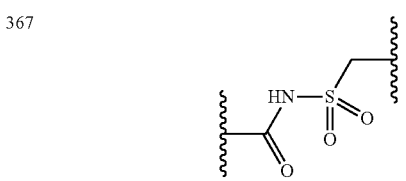 |
| 368 | 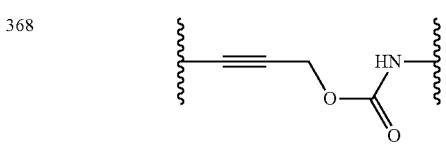 |
| 369 | 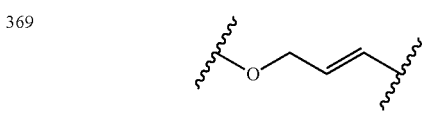 |
| 370 | 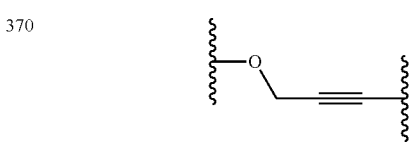 |
| 371 | 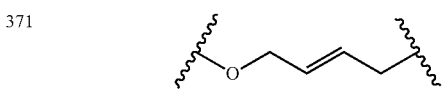 |
| 372 | 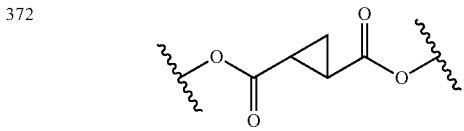 |
| 373 | 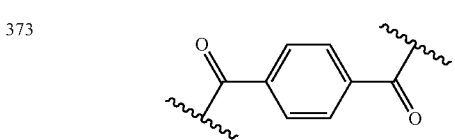 |
| 374 | 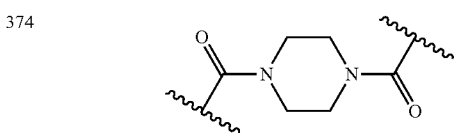 |
TABLE 7-continued
Examples 300-434.
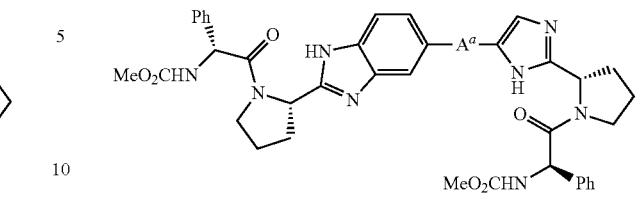
| Entry | A<sup>a</sup> |
|---|---|
| 375 | 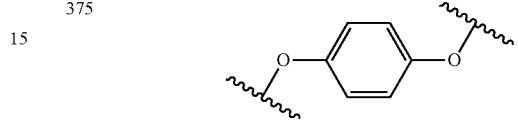 |
| 376 | 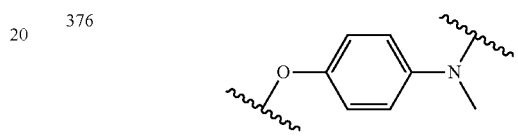 |
| 377 | 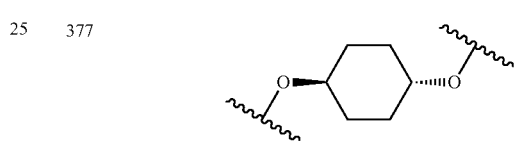 |
| 378 | 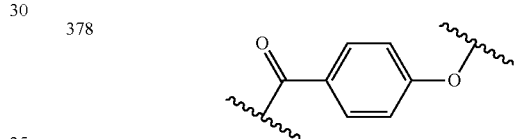 |
| 379 | 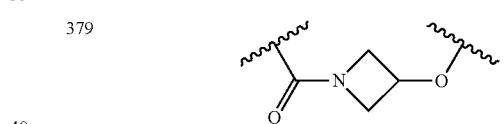 |
| 380 | 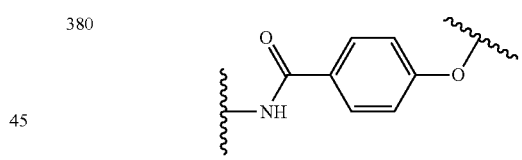 |
| 381 | 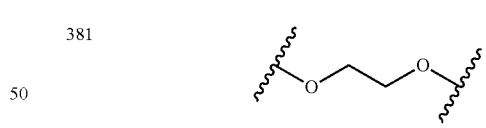 |
| 382 | 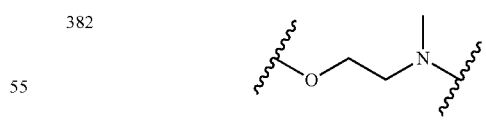 |
| 383 | 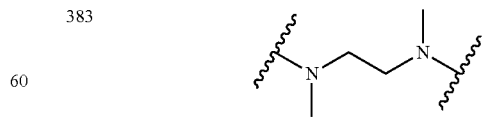 |
| 384 | 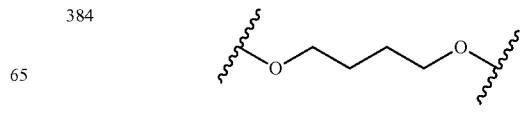 |

TABLE 7-continued

Examples 300-434.

| Entry | $A^a$ |
|---|---|
| 385 | (but-2-ene-1,4-diyl bis-ether) |
| 386 | (but-2-yne-1,4-diyl bis-ether) |
| 387 | (azetidin-1-yl, 3-methyleneoxy) |
| 388 | (thiophene-2,5-diyl with ethynyl-methyleneoxy) |
| 389 | (1,3-phenylene with methyleneoxy) |
| 390 | (oxy-methylene-C(O)O) |
| 391 | (O-CH2CH2-NH-C(O)-O) |
| 392 | (O-CH2-C≡C-CH2-O-C(O)) |

TABLE 7-continued

Examples 300-434.

| Entry | $A^a$ |
|---|---|
| 393 | (C(O)-CH2-C(O)-NH) |
| 394 | (C(O)-CH2-S(O)2-NH) |
| 395 | (C(O)-NH-S(O)2-NH-C(CH3)2) |
| 396 | (trans-1,4-cyclohexylene) |
| 397 | (2,5-dioxopiperazine-1,4-diyl) |
| 398 | (isoindole-2,5-diyl) |
| 399 | (1,2-phenylene-bis(methylene)-1,2-phenylene) |

TABLE 7-continued

Examples 300-434.

| Entry | A$^a$ |
|---|---|
| 400 | (bicyclic: benzene fused with cyclobutane via two CH$_2$ linkers) |
| 401 | (thiophene-CH$_2$-cyclopropane-CH$_2$-) |
| 402 | (azetidine-N, CH$_2$-O-C(=O)-CH$_2$-) |
| 403 | (oxazole-CH$_2$-C(=O)-NH-CH$_2$-) |
| 404 | (cyclopropane-CH$_2$-C(=O)-NH-CH$_2$-) |
| 405 | (azetidine-N, CH$_2$-O-CH$_2$-) |
| 406 | (thiophene-CH$_2$-N(Me)-CH$_2$-) |
| 407 | (phenyl-CH$_2$-O-CH$_2$-) |
| 408 | (phenyl-thiophene-CH$_2$-) |
| 409 | (cyclobutane-oxazole-CH$_2$-) |
| 410 | (pyridine-azetidine-N-CH$_2$-) |
| 411 | (phenyl-CH$_2$-azetidine-N-) |
| 412 | (pyridine-CH$_2$-cyclopropane-) |
| 413 | (oxazole-CH$_2$-azetidine-N-) |

TABLE 7-continued
Examples 300-434.
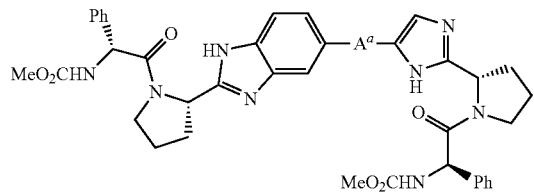
| Entry | A<sup>a</sup> |
|---|---|
| 414 | 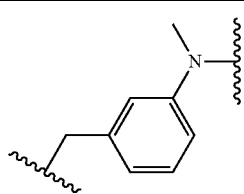 |
| 415 | 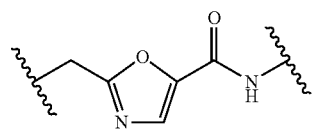 [SMILES: *Cc1ncc(C(=O)N*)o1] |
| 416 | 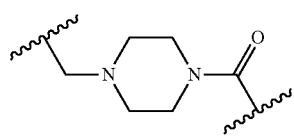 [SMILES: *CN1CCN(C(*)=O)CC1] |
| 417 | 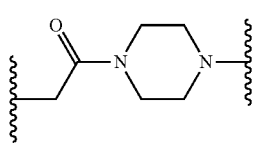 [SMILES: *CC(=O)N1CCN(*)CC1] |
| 418 | 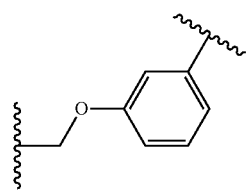 [SMILES: *COc1cccc(*)c1] |
| 419 | 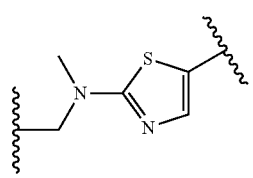 [SMILES: *CN(C)c1ncc(*)s1] |
| 420 | 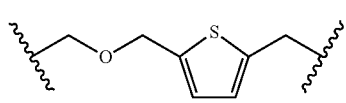 [SMILES: *COCc1ccc(C*)s1] |
| 421 | 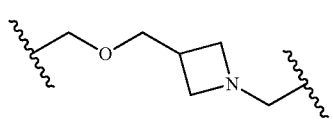 [SMILES: *COCC1CN(C*)C1] |
TABLE 7-continued
Examples 300-434.
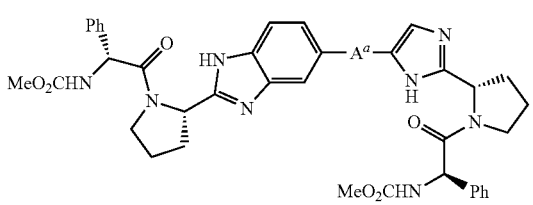
| Entry | A<sup>a</sup> |
|---|---|
| 422 | 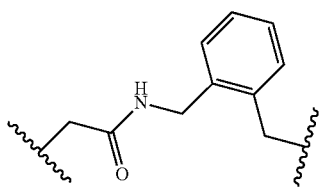 [SMILES: *CC(=O)NCc1ccccc1C*] |
| 423 | 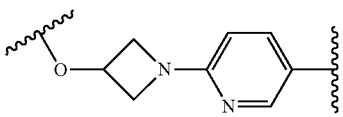 [SMILES: *OC1CN(c2ccc(*)cn2)C1] |
| 424 | 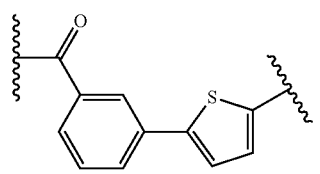 |
| 425 | 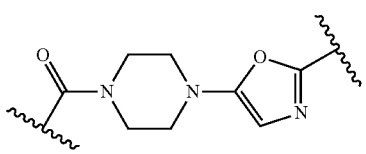 [SMILES: *C(=O)N1CCN(c2cnc(*)o2)CC1] |
| 426 | 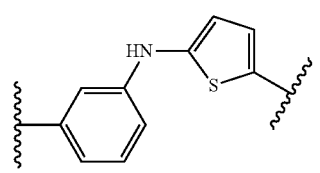 [SMILES: *c1cccc(Nc2ccc(*)s2)c1] |
| 427 | 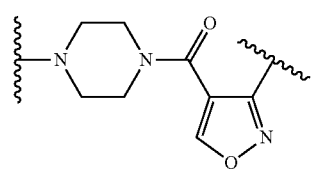 [SMILES: *c1nocc1C(=O)N1CCN(*)CC1] |
| 428 | 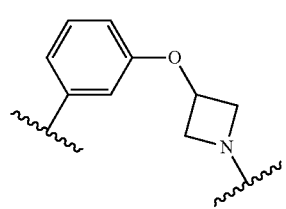 [SMILES: *c1cccc(OC2CN(*)C2)c1] |

TABLE 7-continued
Examples 300-434.
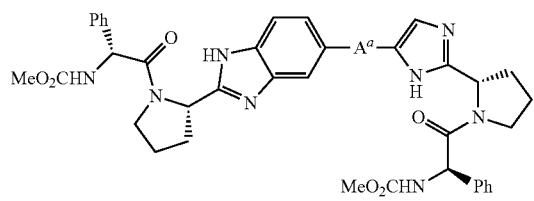
| Entry | $A^a$ |
|---|---|
| 429 | 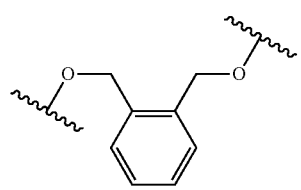 [SMILES: *OCc1ccccc1CO*] |
| 430 | 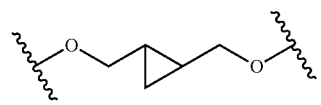 [SMILES: *OCC1CC1CO*] |
| 431 | 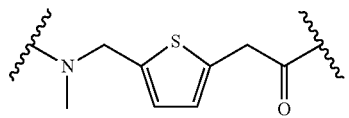 [SMILES: *C(=O)Cc1ccc(CN(*)C)s1] |
| 432 | 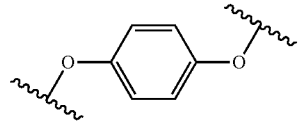 [SMILES: *Oc1ccc(O*)cc1] |
| 433 | 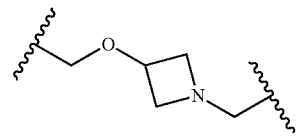 [SMILES: *COC1CN(C*)C1] |
| 434 | 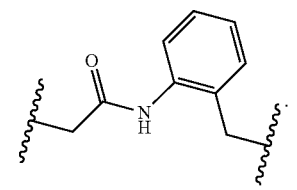 [SMILES: *CC(=O)Nc1ccccc1C*] |
TABLE 8
Examples 435-440.
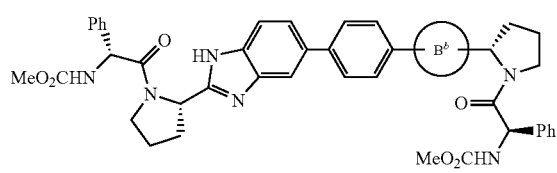
| Entry | $B^b$ |
|---|---|
| 435 | 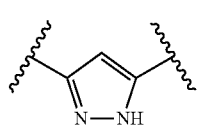 [SMILES: *c1cc(*)[nH]n1] |
| 436 | 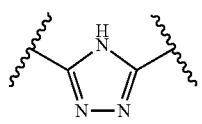 [SMILES: *c1nnc(*)[nH]1] |
| 437 | 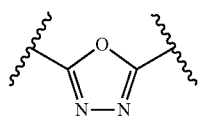 [SMILES: *c1nnc(*)o1] |
| 438 | 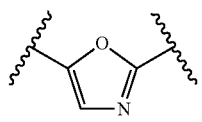 [SMILES: *c1cnc(*)o1] |
| 439 | 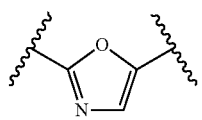 [SMILES: *c1cnc(*)o1] |
| 440 | 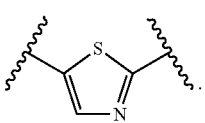 [SMILES: *c1cnc(*)s1] |

Example 357

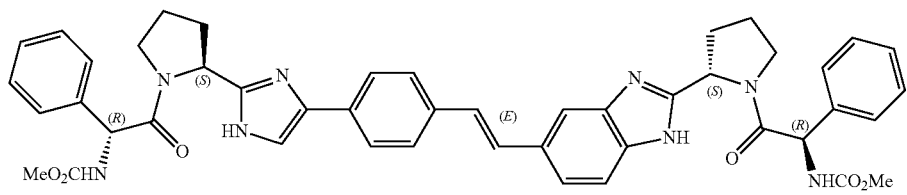

Step 357a.
A solution of the compound of example 491 (0.122 g, 0.196 mmol) in 1,4-dioxane (2 mL) was treated with HCl in 1,4-dioxane (4 M, 8 mL) at rt for 1 hour. The volatiles were evaporated off to give the crude desired compound as a yellow solid which was used directly in the next step.

Step 357b.
A mixture of the crude compound from step 357a (0.196 mmol at most) and (R)-(methoxycarbonyl)amino phenyl acetic acid (prepared according to WO 2008/021927, 0.102 g, 0.490 mmol) in DMF (3 mL) was treated with HATU (0.171 g, 0.451 mmol) in the presence of DIPEA (0.68 mL, 3.920 mmol) for 2 hours at rt and the volatiles were evaporated off to provide a brown syrup. It was patitioned (EtOAc—H$_2$O). The organic layer was washed with brine, dried (Na$_2$SO$_4$), filtered and concentrated. The crude was purified by flash column chromatography (silica, CH$_2$Cl$_2$-MeOH) to give the title compound as a yellow solid (0.144 g, 91% over 2 steps). ESIMS m/z=806.96 [M+H]$^+$.

Example 441

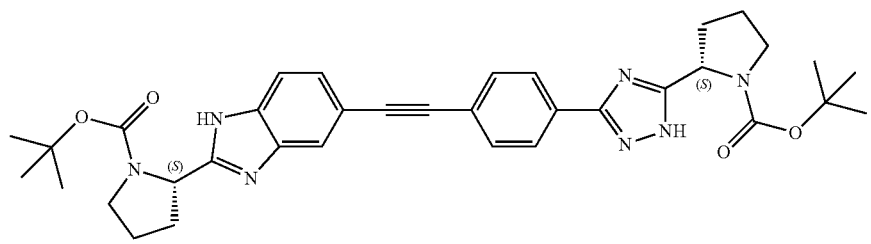

A mixture of (S)-tert-butyl 2-(3-(4-iodophenyl)-1H-1,2,4-triazol-5-yl)pyrrolidine-1-carboxylate (prepared according to US 2008/0311075, 84.9 mg, 0.193 mmol), the compound from step 515d (66.0 mg, 0.212 mmol), CuI (1.1 mg, 5.7 µmol) and Pd(PPh$_3$)$_2$Cl$_2$ (6.7 mg, 9.6 mmol) in CH$_3$CN (5 mL) and triethylamine (5 mL) was degassed and heated to 50° C. under N$_2$ for 3 hours. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the title compound as a light yellow oil (94.0 mg, 78%). ESIMS m/z=624.34 [M+H]$^+$.

Example 442

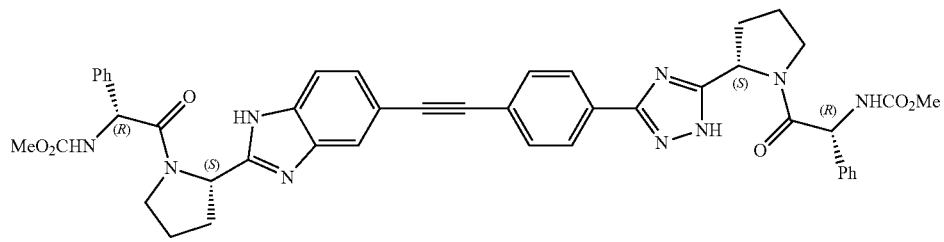

Step 442a.
A solution of the compound of Example 441 (90.0 mg, 0.144 mmol) in 1,4-dioxane (1 mL) was treated with HCl in 1,4-dioxane (4 M, 4 mL) at rt for 30 minutes. The volatiles were evaporated off to give the crude desired compound as a yellow solid which was directly used in the next step. ESIMS m/z=424.11 [M+H]$^+$.

Step 442b.
A mixture of the crude compound from step 442a (0.144 mmol at most) and (R)-(methoxycarbonyl)amino phenyl acetic acid (prepared according to WO 2008/021927, 75.4 mg, 0.361 mmol) in DMF (3 mL) was treated with HATU (0.126 g, 0.332 mmol) in the presence of DIPEA (0.36 mL, 2.89 mmol) for 2 hours at rt and the volatiles were evaporated off to provide a brown sirup. It was purified by flash column chromatography (silica, CH$_2$Cl$_2$-MeOH) to give the title compound as a very light yellow solid (98.1 mg, 2 steps 80%). ESIMS m/z=806.16 [M+H]$^+$.

Example 443

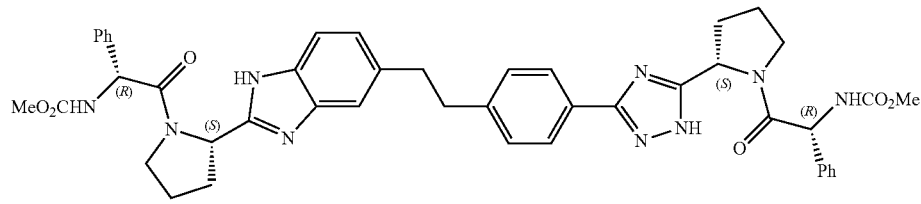

A mixture of the title compound of example 442 (51.6 mg, 63.3 µmol) and Pd(OH)$_2$ on carbon (20%, 50.0 mg) in ethanol (3 mL) was treated with H$_2$ balloon overnight. The mixture was filtered through celite and the filtrate was concentrated. The residue was purified by flash column chromatography (silica, CH$_2$Cl$_2$-MeOH) to give the title compound as a white solid (42.5 mg, 82%). ESIMS m/z=810.23 [M+H]$^+$.

Example 444

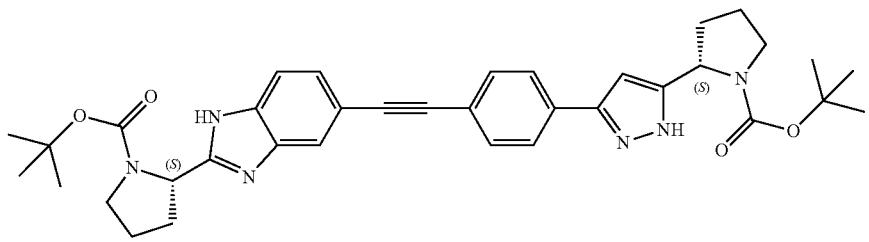

A mixture of (S)-tert-butyl 2-(3-(4-iodophenyl)-1H-pyrazol-5-yl)pyrrolidine-1-carboxylate (prepared according to US 2008/0311075, 85.0 mg, 0.213 mmol), the compound from step 515d (66.2 mg, 0.213 mmol), CuI (1.1 mg, 5.8 µmol) and Pd(PPh$_3$)$_2$Cl$_2$ (6.7 mg, 9.6 mmol) in CH$_3$CN (5 mL) and triethylamine (5 mL) was degassed and heated at 60° C. under N$_2$ overnight. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the title compound as a light yellow oil (91.1 mg, 76%). ESIMS m/z=623.20 [M+H]$^+$.

Example 445

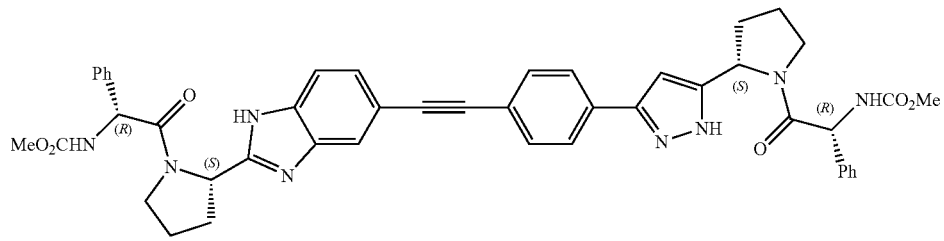

The title compound was synthesized from the compound of Example 444 using procedures similar to that described in Example 442. ESIMS m/z=805.36 [M+H]$^+$.

Example 446

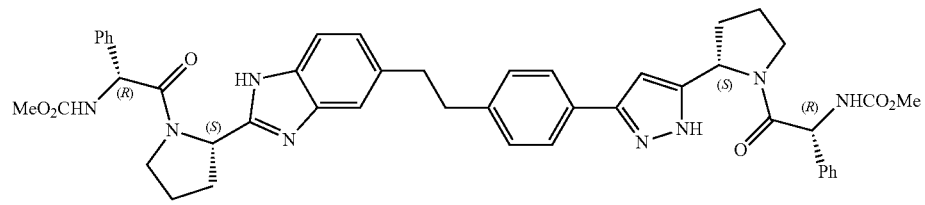

The title compound was synthesized from the compound of Example 445 using procedures similar to that described in Example 443. ESIMS m/z=809.42 [M+H]⁺.

Example 447

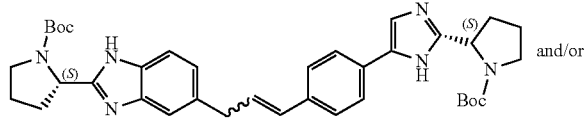

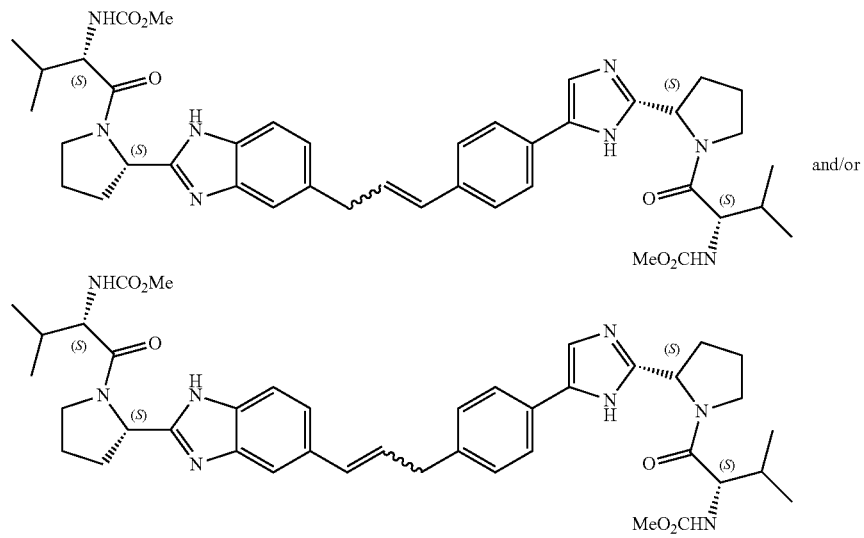

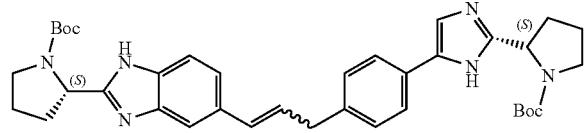

Step 447a.

A mixture of the compound of step 1b (0.250 g, 0.683 mmol), allyltributyl-stannane (0.26 mL, 0.820 mmol) and Pd(PPh₃)₄ (39.4 mg, 34.1 μmol) in toluene (6 mL) was degassed and heated at 110° C. under N₂ overnight. The volatiles were evaporated and the residue was partitioned (EtOAc-saturated aqueous NaHCO₃). The organics were washed with brine, dried (Na₂SO₄), filtered and evaporated. The residue was purified by flash column chromatography (silica, hexanes-ethyl acetate) to give the desired compound as a colorless oil (0.127 g, 60%). ESIMS m/z=328.23 [M+H]⁺.

Step 447b.

A mixture of the compound of step 1d (0.180 g, 0.459 mmol), the compound of step 447a (0.150 g, 0.459 mmol), triethylamine (0.64 mL, 4.59 mmol), tri-o-tolylphosphine (18.0 mg, 57.3 μmol) and Pd(OAc)₂ (5.1 mg, 22.9 μmol) in CH₃CN (8 mL) was degassed and heated to 90° C. under N₂ overnight. The volatiles were evaporated and the residue was partitioned (EtOAc-saturated aqueous NaHCO₃). The organics were washed with brine, dried (Na₂SO₄), filtered and evaporated. The residue was purified by flash column chromatography (silica, hexanes-ethyl acetate) to give the title compounds as a light yellow solid (0.165 g, 70%). The regio- and stereochemistry of the olefinic double bond was not determined. ESIMS m/z=639.36 [M+H]⁺.

Example 448

Step 448a.

A solution of the compound of Example 447 (0.104 g, 0.163 mmol) in 1,4-dioxane (1 mL) was treated with HCl in 1,4-dioxane (4 M, 4 mL) at rt for 30 minutes. The volatiles were evaporated off to give the crude desired compound as a yellow solid which was directly used in the next step. ESIMS m/z=439.24 [M+H]⁺.

Step 448b.

A mixture of the crude compound of step 448a (0.163 mmol at most) and (S)-2-(methoxycarbonylamino)-3-methylbutanoic acid (prepared according to WO 2008/021927, 71.3 mg, 0.408 mmol) in DMF (3 mL) was treated with HATU (0.142 g, 0.375 mmol) in the presence of DIPEA (0.41 mL, 3.26 mmol) for 2 hours at rt and the volatiles were evaporated off to provide a brown sirup. It was purified by flash column chromatography (silica, CH₂Cl₂-MeOH) to give the title compounds as a white solid (89.5 mg, 2 steps 73%). The regio- and stereochemistry of the olefinic double bond was not determined. ESIMS m/z=753.39 [M+H]⁺.

Example 449

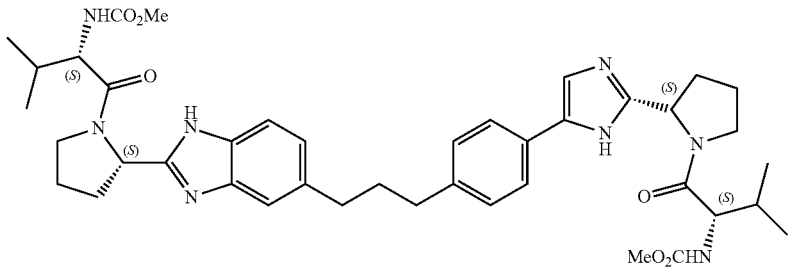

The title compound was synthesized from the compound of Example 448 using procedures similar to that described in Example 443. ESIMS m/z=755.47 [M+H]+.

Example 450

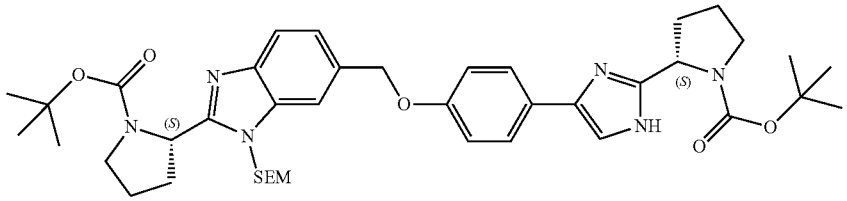

Step 450a.
The compound of step 1e (0.200 g, 0.455 mmol) in THF (5 mL) was treated with a mixture of 30% aqueous $H_2O_2$ (0.5 mL) and 1N aqueous NaOH (1 mL) for 30 minutes. The volatiles were removed and the residue was partitioned (EtOAc-water). The organics were washed with brine, dried ($Na_2SO_4$), filtered and evaporated. The residue was purified by flash column chromatography (silica, hexanes-ethyl acetate) to give the desired compound as a light yellow oil (0.144 g, 96%). ESIMS m/z=330.15 [M+H]+.

Step 450b.
The mixture of (S)-1-(tert-butoxycarbonyl)pyrrolidine-2-carboxylic acid (5 g, 23.2 mmol) in acetonitrile (40 mL) was added 1,1'-carbonyldiimidazole (3.95 g, 24.5 mmol). The resulting mixture was stirred at room temperature for 20 min before being added methyl 3,4-diaminobenzoate (3.86 g, 23.2 mmol). The solution was stirred at room temperature for another 3 hours before being partitioned between water and EtOAc. The organic phase was separated, dried ($Na_2SO_4$) and concentrated to afford a brown slurry, which was purified by flash column chromatography (silica, hexane-EtOAc) to give the desired product as a light yellow oil (8.14 g, 98%). ESIMS m/z=364.17 [M+H]+.

Step 450c.
The solution of compound from step 450b in acetic acid (150 mL) was stirred at 60° C. for three days before all volatiles were removed. The resulting residue was partitioned between aqueous $NaHCO_3$ and EtOAc. The organic phase was separated, dried ($Na_2SO_4$) and concentrated to afford a brown oil, which was purified by flash column chromatography (silica, hexane-EtOAc) to give the desired product as a light yellow solid (2.02 g, 28%). ESIMS m/z=346.15 [M+H]+.

Step 450d.
The solution of compound from step 450c (2.02 g, 5.8 mmol) in DMF (50 mL) was added sodium hydride (55% in mineral oil, 269 mg, 6.4 mmol). The reaction was stirred at room temperature for 1.5 hours before being added 2-(Trimethylsilyl)ethoxymethyl chloride (1.02 mL, 5.8 mmol). The mixture was stirred at room temperature for another 3 hours before being partitioned between water and EtOAc. The organic phase was separated, dried ($Na_2SO_4$) and concentrated to afford a brown oil, which was purified by flash column chromatography (silica, hexane-EtOAc) to give the desired product as a light yellow solid (2.6 g, 94%). ESIMS m/z=475.97 [M+H]+.

Step 450e.
The solution of compound from step 450d (2.6 g, 5.47 mmol) in THF (50 mL) and water (25 mL) was added lithium hydroxide monohydrate (690 mg, 16.4 mmol). The resulting mixture was stirred at room temperature for 3 hours before being partitioned between water, AcOH (10 mL) and EtOAc. The organic phase was separated, dried ($Na_2SO_4$) and concentrated to afford a brown oil, which was directly used for the next step without further purification (2.6 g, crude, 100%). ESIMS m/z=462.02 [M+H]+.

Step 450f.
The solution of compound from step 450e (2.0 g, 4.3 mmol) in THF (45 mL) was added triethylamine (1.85 mL, 12.9 mmol) and ethyl chloroformate (1.05 mL, 10.8 mmol) at 0° C. The resulting mixture stirred at 0° C. for 20 minutes before all volatiles were removed by rotavap. The residue was dissolved in THF (70 mL) before being added sodium borohydride (1 g, 26.4 mmol). The mixture was stirred at 0° C. for another 2 hours before being partitioned between water and EtOAc. The organic phase was separated, dried ($Na_2SO_4$) and concentrated to afford a brown oil, which was purified by flash column chromatography (silica, EtOAc-methanol) to give the desired product as a light yellow solid (1.57 g, 81%). ESIMS m/z=448.13 [M+H]+.

Step 450 g. The compound from step 450a (70.0 mg, 0.213 mmol) in THF (5 mL) was treated with the compound from step 450f (95.1 mg, 0.213 mmol), $PPh_3$ (83.6 mg, 0.319 mmol) and DEAD (50.2 µL, 0.319 mmol) overnight before being evaporated to dryness. The residue was partitioned (EtOAc-water) and the organics were washed with brine, dried (Na$_2$SO$_4$), filtered and evaporated. The residue was purified by flash column chromatography (silica, hexanes-ethyl acetate) to give the title compound as a colorless oil (22.6 mg, 14%). The regiochemistry of the SEM group was not determined. ESIMS m/z=759.39 [M+H]$^+$.

Example 451

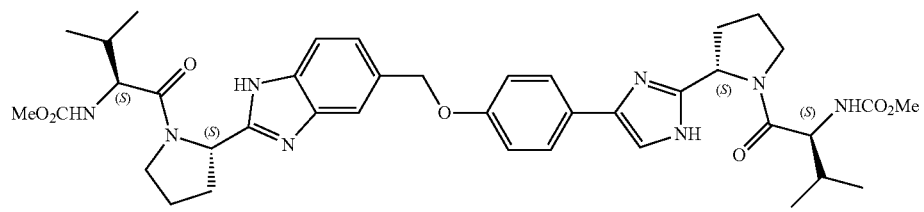

The title compound was synthesized from the compound of Example 450 using procedures similar to that described in steps 497a and 448b. ESIMS m/z=743.32 [M+H]$^+$.

Example 452

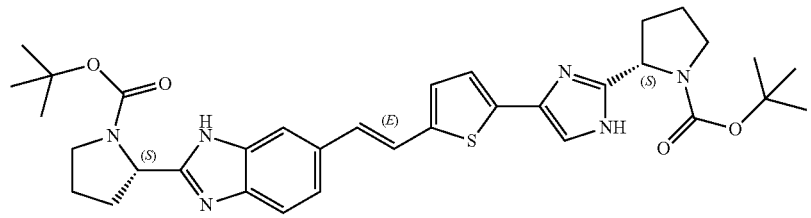

Step 452a.

A mixture of 2-bromo-1-(5-bromothiophen-2-yl)ethanone (1.00 g, 3.52 mmol) and N-Boc-L-proline (0.758 g, 3.52 mmol) in CH$_3$CN (12 mL) was added TEA (1.06 mL, 7.40 mmol) slowly. The mixture was stirred at rt until the disappearence of the starting material. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the desired compound as a yellow sticky oil (1.47 g, 100%). $^1$H NMR (CDCl$_3$) 7.49 (t, J=4.0 Hz, 1H), 7.13 (dd, J=4.5, 6.0 Hz, 1H), 5.36, 5.04 (2d, J=16.0 Hz, 1H), 5.22, 5.15 (2d, J=16.5 Hz, 1H), 4.45, 4.38 (dd, J=5.5, 7.5 Hz, 1H), 3.56 (m, 1H), 3.41 (m, 1H), 2.25 (m, 2H), 2.05 (m, 1H), 1.90 (m, 1H), 1.46, 1.42 (2s, 9H).

Step 452b.

A solution of the compound of step 452a (1.47 g, 3.52 mmol) in toluene (22 mL) was added ammonium acetate (5.42 g, 70.3 mmol) and the resultant mixture was heated at 100° C. for 16 hours. The volatiles were evaporated and the residue was partitioned (EtOAc-aq. NaHCO$_3$). The organics were washed with brine, dried (Na$_2$SO$_4$), filtered and evaporated. The residue was purified by flash column chromatography (silica, hexanes-ethyl acetate) to give the desired compound as a brown yellow foam (0.586 g, 42%) with a recovery of the compound from step 452a (0.616 g, 42%). ESIMS m/z=398.16, 400.16 [M+H]$^+$. $^1$H NMR (CDCl$_3$) 10.55 (bs, 1H), 7.07 (s, 1H), 6.94 (m, 2H), 4.92 (m, 1H), 3.40 (m, 2H), 2.96 (m, 1H), 2.12 (m, 2H), 1.92 (m, 1H), 1.49 (s, 9H).

Step 452c.

A mixture of the compound of step 452b (0.150 g, 0.377 mmol), the compound from step 491a (0.118 g, 0.377 mmol), triethylamine (0.52 mL, 3.77 mmol), tri-o-tolylphosphine (14.8 mg, 47.1 µmol) and Pd(OAc)$_2$ (4.2 mg, 18.8 µmol) in CH$_3$CN (6 mL) was degassed and heated to 110° C. in sealed tube for 36 hours. The volatiles were evaporated and the residue was partitioned (EtOAc-saturated aqueous NaHCO$_3$). The organics were washed with brine, dried (Na$_2$SO$_4$), filtered and evaporated. The residue was purified by flash column chromatography (silica, hexanes-ethyl acetate) to give the title compound as a yellow oil (64.1 mg, 27%). ESIMS m/z=631.26 [M+H]$^+$.

Example 453

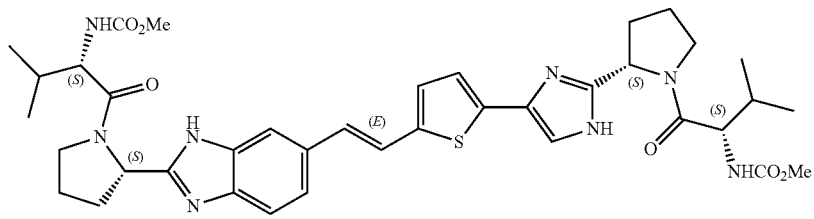

The title compound was synthesized from the compound from Example 452 using procedures similar to that described in Example 448. ESIMS m/z=745.43 [M+H]⁺.

Example 454

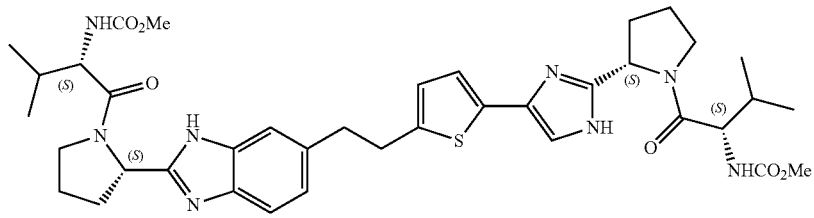

The title compound was synthesized from the compound from Example 453 using procedures similar to that described in Example 443. ESIMS m/z=747.40 [M+H]⁺.

Example 455

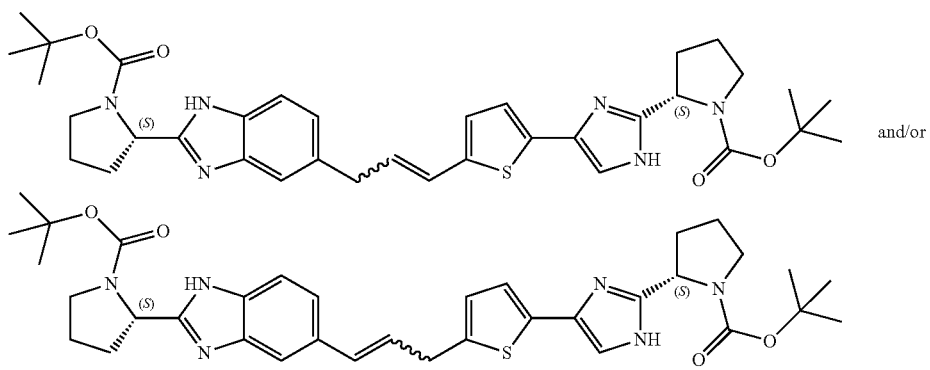

and/or

A mixture of the compound from step 452b (0.150 g, 0.377 mmol), the compound from step 447a (0.123 g, 0.377 mmol), triethylamine (0.52 mL, 3.77 mmol), tri-o-tolylphosphine (14.8 mg, 47.1 μmol) and Pd(OAc)₂ (4.2 mg, 18.8 μmol) in CH₃CN (6 mL) was degassed and heated to 110° C. in sealed tube for 36 hours. The volatiles were evaporated and the residue was partitioned (EtOAc-saturated aqueous NaHCO₃). The organics were washed with brine, dried (Na₂SO₄), filtered and evaporated. The residue was purified by flash column chromatography (silica, hexanes-ethyl acetate) to give the title compounds as a yellow oil (52.7 mg, 22%). The regio- and stereochemistry of the olefinic double bond was not determined. ESIMS m/z=645.27 [M+H]⁺.

Example 456

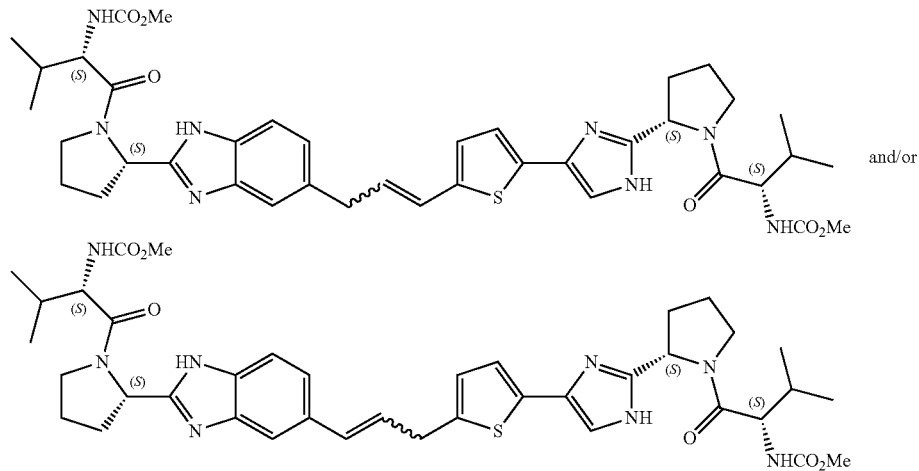

The title compound was synthesized from the compound from Example 455 using procedures similar to that described in Example 448. The regio- and stereochemistry of the olefinic double bond was not determined. ESIMS m/z=759.51 [M+H]⁺.

Example 457

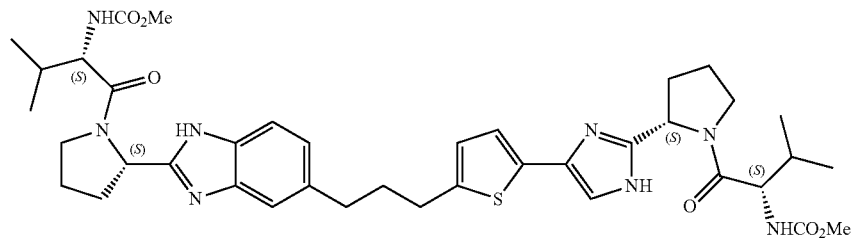

The title compound was synthesized from the compound from Example 456 using procedures similar to that described in Example 443. ESIMS m/z=761.41 [M+H]⁺.

Example 458

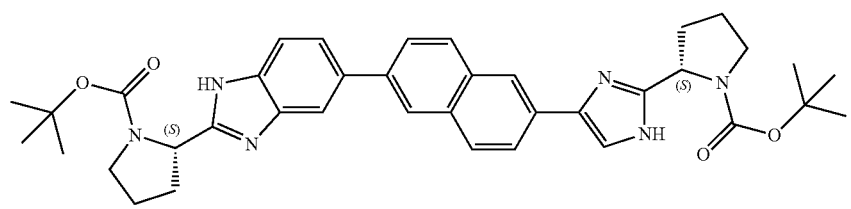

Step 458a.

6-bromo-N-methoxy-N-methyl-2-naphthamide (prepared according to *J. Med. Chem.*, 2006, 49, 4721-4736, 3.57 g, 12.1 mmol) in THF (60 mL) was treated with methyl magnesium bromide (3M in Et₂O, 8.09 mL, 24.3 mmol) slowly at 0° C. for 1 hour. The solution was warmed up to rt for 2 hours before being quenched with aqueous NH₄Cl. The volatiles were removed and the residue was partitioned (EtOAc-water). The organics were washed with brine, dried (Na₂SO₄), filtered and evaporated to give the crude desired compound as a white solid (2.89 g, 96%).

Step 458b.

The compound from step 458a (2.89 g, 11.6 mmol) in acetic acid (60 mL) was treated with bromine (0.59 mL, 11.6 mmol) dropwise for 1 hour. The volatiles were evaporated and the residue was partitioned (EtOAc-saturated aqueous NaHCO₃). The organics were washed with brine, dried (Na₂SO₄), filtered and evaporated to give the crude desired compound as a light yellow solid (3.898 g).

Step 458c.

A mixture of the compound from step 458b (at most 11.6 mmol) and N-Boc-L-proline (3.75 g, 17.4 mmol) in CH$_3$CN (60 mL) was added DIPEA (2.89 mL, 23.2 mmol) slowly. The mixture was stirred at rt until the disappearence of the starting material. The volatiles were evaporated and the residue was partitioned (EtOAc-water). The organics were washed with brine, dried (Na$_2$SO$_4$), filtered and evaporated to give the crude desired compound as a yellow-white foam (4.762 g). ESIMS m/z=462.03, 464.02 [M+H]$^+$.

Step 458d.

A solution of the compound from step 458c (at most 11.6 mmol) in toluene (60 mL) was added ammonium acetate (13.4 g, 0.174 mol) and the resultant mixture was heated up at 100° C. for 14 hours. The volatiles were evaporated and the residue was partitioned (EtOAc-aq. NaHCO$_3$). The organics were washed with brine, dried (Na$_2$SO$_4$), filtered and evaporated. The residue was purified by flash column chromatography (silica, hexanes-ethyl acetate) to give the desired compound as a yellow brown powder (3.14 g, 4 steps, 61%). ESIMS m/z=442.02, 444.02 [M+H]$^+$.

Step 458e.

A mixture of the compound from step 1b (1 g, 2.73 mmol), bis-(pinacolato)-diboron (763 mg, 3.0 mmol), potassium acetate (402 mg, 4.0 mmol) in 1,4-dioxane (9.1 mL) was added tetrakis(triphenylphosphine)palladium(0) (158 mg, 0.14 mmol). The resulting solution was degased and then heated at 80° C. under N$_2$ overnight before being evaporated. The residue was purified by chromatography (silica, hexanes-ethyl acetate with 1% Et$_3$N in ethyl acetate) to give the desired compound as a yellow solid (680 mg, 60%). ESIMS m/z=414.24 [M+H]$^+$.

Step 458f.

A mixture of the compound from step 458d (0.100 g, 0.226 mmol), the compound from step 458e (93.4 mg, 0.226 mmol), Pd(PPh$_3$)$_4$, (13.1 mg, 11.3 μmol) and NaHCO$_3$ (76.0 mg, 0.905 mmol) in DME (6 mL) and H$_2$O (2 mL) was degassed and heated at 85° C. under N$_2$ for 14 hours. The volatiles were evaporated and the residue was partitioned (EtOAc—H$_2$O). The organics were washed with brine, dried (Na$_2$SO$_4$), filtered and evaporated. The residue was purified by chromatography (silica, hexanes-ethyl acetate) to give the title compound as a light yellow solid (92.0 mg, 59%). ESIMS m/z=649.54 [M+H]$^+$.

Example 459

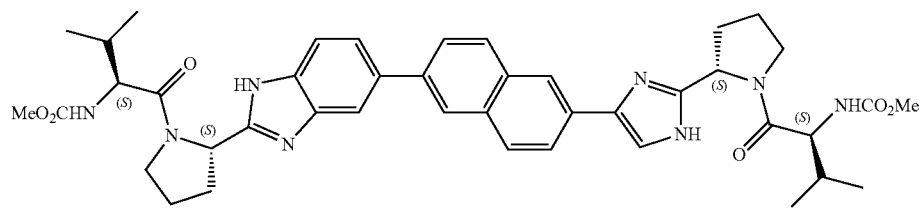

The title compound was synthesized from the compound from Example 458 using procedures similar to that described in Example 448. ESIMS m/z=763.21 [M+H]$^+$.

Example 460

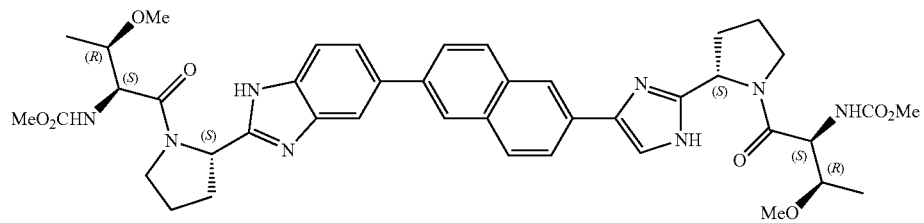

Step 460a.

A solution of the compound of example 458 (92.0 mg, 0.142 mmol) in 1,4-dioxane (1 mL) was treated with HCl in 1,4-dioxane (4 M, 4 mL) rt for 30 minutes. The volatiles were evaporated off to give the crude desired compound as a yellow solid which was directly used in the next step. ESIMS m/z=449.39 [M+H]$^+$.

Step 460b.

A mixture of the crude compound from step 460a (0.142 mmol at most) and (2S,3R)-3-methoxy-2-(methoxycarbonylamino)butanoic acid (prepared according to WO 2008/021927, 56.9 mg, 0.298 mmol) in DMF (3 mL) was treated with HATU (0.108 g, 0.284 mmol) in the presence of DIPEA (0.35 mL, 2.84 mmol) for 2 hours at rt and the volatiles were evaporated off to provide a brown sirup. It was purified by flash column chromatography (silica, CH$_2$Cl$_2$-MeOH) to give the title compound as a yellow solid (60.3 mg, 2 steps 54%). ESIMS m/z=795.68 [M+H]$^+$.

Example 461

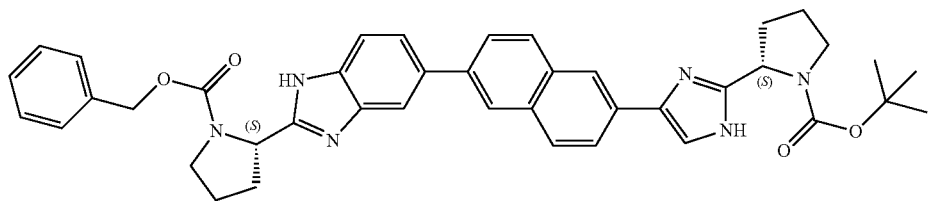

Step 461a.
The desired compound was prepared from 4-bromo-1,2-diaminobenzene and N-Cbz-L-proline using procedures similar to that described in steps 1a and 1b. ESIMS m/z=400.11, 402.11 [M+H]+.

Step 461b.
A mixture of the compound from step 461a (1.00 g, 2.50 mmol), bis(pinacolato)-diboron (1.27 g, 5.00 mmol) and potassium acetate (0.613 g, 6.25 mmol) in 1,4-dioxane (25 mL) was added Pd(PPh$_3$)$_4$ (0.144 g, 0.125 mmol). The resultant mixture were degassed and heated up at 85° C. under N$_2$ for 14 hours. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the desired compound as a light yellow solid (0.801 g, 72%). ESIMS m/z=448.18 [M+H]+.

Step 461c.
A mixture of the compound from step 458d (0.790 g, 1.79 mmol), the compound from step 461b (0.800 g, 1.79 mmol), Pd(PPh$_3$)$_4$, (0.103 g, 89.4 μmol) and NaHCO$_3$ (0.601 g, 7.16 mmol) in DME (24 mL) and H$_2$O (8 mL) was degassed and heated at 85° C. under N$_2$ for 14 hours. The volatiles were evaporated and the residue was partitioned (EtOAc—H$_2$O). The organics were washed with brine, dried (Na$_2$SO$_4$), filtered and evaporated. The residue was purified by chromatography (silica, hexanes-ethyl acetate) to give the title compound as a light yellow solid (0.854 g, 70%). ESIMS m/z=683.14 [M+H]+.

Example 462

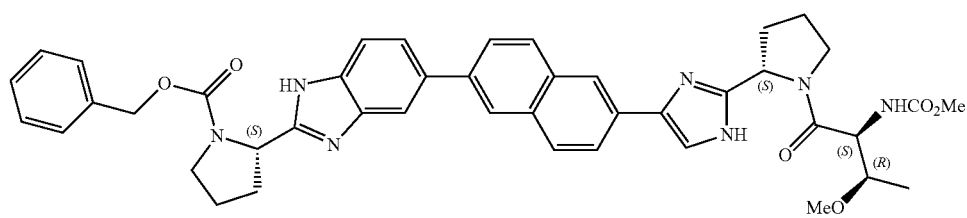

The title compound was synthesized from the compound of Example 461 using procedures similar to that described in Example 460. ESIMS m/z=756.26 [M+H]⁺.

Example 463

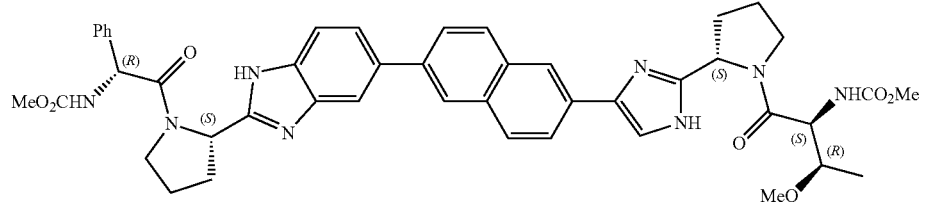

Step 463a.

A mixture of the compound from example 462 (0.314 g, 0.416 mmol) and Pd(OH)₂ (20 wt % on carbon, 150 mg) in methanol (6 mL) was adjusted pH to 3 with aqueous 6N HCl and then treated with hydrogen (60 psi) for 24 hours. The mixture was filtered through Celite and the filtrate was concentrated to give the crude desired compound as a light yellow solid (0.401 g). ESIMS m/z=622.13 [M+H]⁺.

Step 463b.

The title compound was synthesized from the compound from step 463a using procedures similar to that described in Example 442. ESIMS m/z=813.32 [M+H]⁺.

Example 464

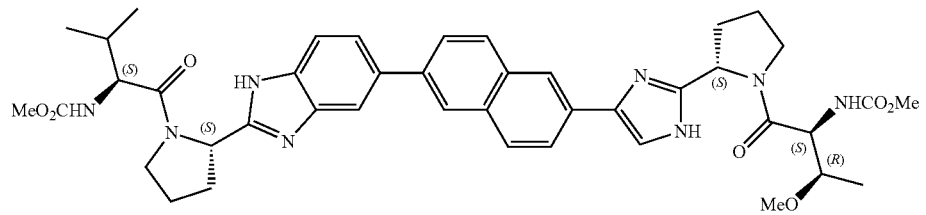

The title compound was synthesized from the compound of step 463a using procedures similar to that described in Example 448. ESIMS m/z=779.33 [M+H]⁺.

Example 465

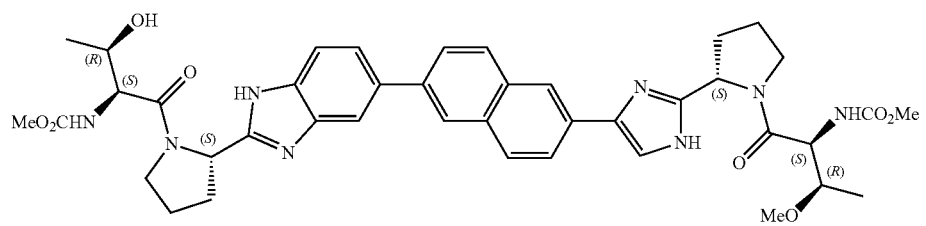

A mixture of the crude compound from step 463a (0.104 mmol at most) and (2S,3R)-3-hydroxy-2-(methoxycarbonylamino)butanoic acid (prepared according to WO 2008/021927, 20.2 mg, 0.114 mmol) in DMF (3 mL) was treated with HATU (35.5 mg, 93.5 mmol) in the presence of DIPEA (0.13 mL, 1.04 mmol) for 2 hours at rt and the volatiles were evaporated off to provide a brown sirup. It was purified by flash column chromatography (silica, CH₂Cl₂-MeOH) to give the title compound as a yellow white solid (12.8 mg, 2 steps 16%). ESIMS m/z=781.30 [M+H]⁺.

Example 466

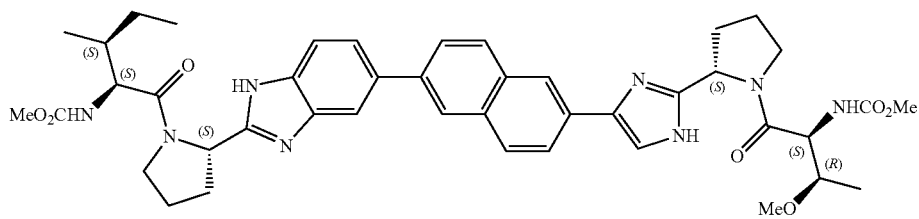

A mixture of the crude compound from step 463a (0.104 mmol at most) and (2S,3S)-2-(methoxycarbonylamino)-3-methylpentanoic acid (prepared according to WO 2008/021927, 21.6 mg, 0.114 mmol) in DMF (3 mL) was treated with HATU (35.5 mg, 93.5 µmol) in the presence of DIPEA (0.13 mL, 1.04 mmol) for 2 hours at rt and the volatiles were evaporated off to provide a brown sirup. It was purified by flash column chromatography (silica, $CH_2Cl_2$-MeOH) to give the title compound as a light yellow solid (15.6 mg, 2 steps 19%). ESIMS m/z=793.33 $[M+H]^+$.

Example 467

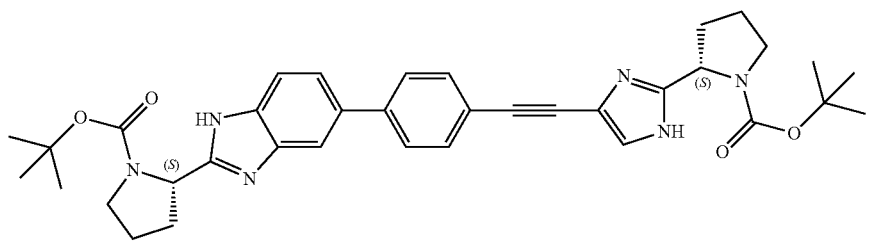

Step 467a.

(S)-tert-butyl 2-(5-bromo-1H-imidazol-2-yl)pyrrolidine-1-carboxylate (prepared according to WO 2008/021927, 0.500 g, 1.58 mmol) in $CH_2Cl_2$ (16 mL) was treated with triethyl amine (0.66 mL, 4.75 mmol), di-tert-butyl dicarbonate (0.518 g, 0.237 mmol) and DMAP (38.7 mg, 0.316 mmol) for 1 hours before being evaporated to dryness. The residue was purified by flash column chromatography (silica, hexanes-ethyl acetate) to give the desired compound as a white solid (0.650 g, 98%). ESIMS m/z=416.11, 418.11 $[M+H]^+$.

Step 467b.

A mixture of the compound from step 467a (0.650 g, 1.56 mmol), ethynyltrimethylsilane (2.16 mL, 15.6 mmol), CuI (8.9 mg, 46.8 µmol) and $Pd(PPh_3)_4$ (90.3 mg, 78.1 mmol) in $CH_3CN$ (5 mL) and triethylamine (10 mL) was degassed and heated at 80° C. under $N_2$ overnight. The volatiles were evaporated and the residue was partitioned (EtOAc-water). The organics were washed with brine, dried ($Na_2SO_4$), filtered and evaporated. The residue was purified by flash column chromatography (silica, hexanes-ethyl acetate) to give the desired compound as a light yellow oil (0.560 g, 83%). ESIMS m/z=434.22 $[M+H]^+$.

Step 467c.

The compound from step 467b (0.560 g, 1.29 mmol) in MeOH (30 mL) was treated with potassium carbonate (0.535 g, 3.88 mmol) for 30 minutes before being evaporated to dryness. The residue was partitioned (EtOAc-water), and the organics were washed with brine, dried ($Na_2SO_4$), filtered and evaporated. The residue was purified by flash column chromatography (silica, hexanes-ethyl acetate) to give the desired compound as a light yellow solid (0.312 g, 92%). ESIMS m/z=262.15 $[M+H]^+$.

Step 467d.

A mixture of the compound from step 467c (0.103 g, 0.395 mmol), 1,4-diiodo-benzene (62.0 mg, 0.188 mmol), CuI (2.1 mg, 11.2 µmol) and $Pd(PPh_3)_4$ (21.6 mg, 18.7 mmol) in $CH_3CN$ (1 mL) and triethylamine (4 mL) was degassed and heated to 60° C. under $N_2$ for 4 hours. The volatiles were evaporated and the residue was partitioned (EtOAc-water). The organics were washed with brine, dried ($Na_2SO_4$), filtered and evaporated. The residue was purified by flash column chromatography (silica, hexanes-ethyl acetate) to give the desired compound as a very light yellow solid (20.0 mg, 23%). ESIMS m/z=464.06 $[M+H]^+$.

Step 467e.

A mixture of the compound from step 467d (20.0 mg, 43.1 µmol), the compound from step 458e (17.8 mg, 43.1 µmol), $Pd(PPh_3)_4$, (9.9 mg, 8.6 µmol) and $NaHCO_3$ (14.5 mg, 0.172 mmol) in DME (3 mL) and $H_2O$ (1 mL) was degassed and heated at 90° C. under $N_2$ for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (26.1 mg, 86%). ESIMS m/z=623.28 $[M+H]^+$.

Example 468

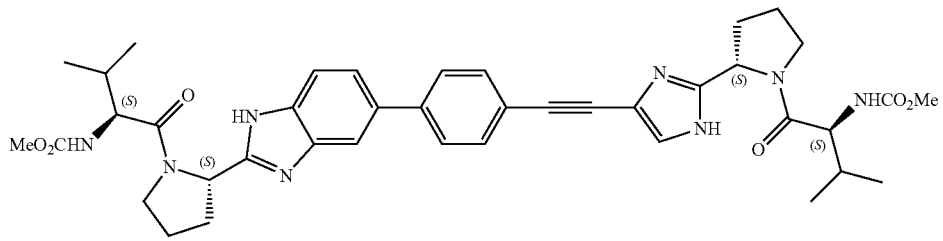

The title compound was synthesized from the compound of Example 467 using procedures similar to that described in Example 448. ESIMS m/z=737.26 [M+H]+.

Example 469

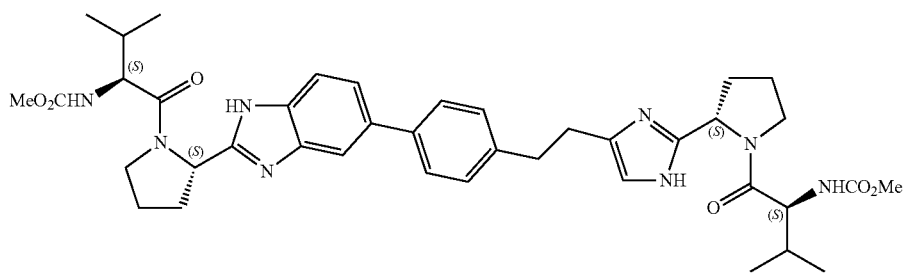

The title compound was synthesized from the compound of Example 468 using procedures similar to that described in Example 443. ESIMS m/z=741.23 [M+H]+.

Example 470

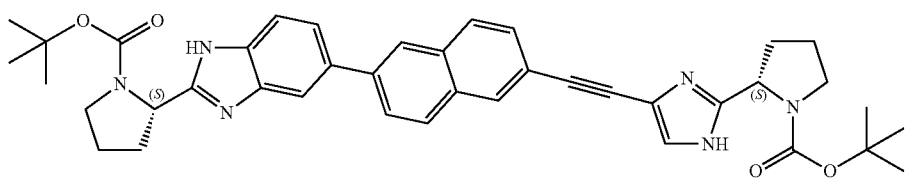

Step 470a.

A mixture of the compound of step 467c (0.150 g, 0.575 mmol), 2,6-dibromonaphthalene (98.6 mg, 0.345 mmol), CuI (3.3 mg, 17.2 µmol) and Pd(PPh$_3$)$_4$ (33.2 mg, 28.7 µmol) in CH$_3$CN (1 mL) and triethylamine (4 mL) was degassed and heated to 90° C. under N$_2$ overnight. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the desired compound as a very light yellow oil (67.6 mg, 25%). ESIMS m/z=466.00, 467.99 [M+H]+.

Step 470b.

A mixture of the compound from step 470a (67.6 mg, 0.145 mmol), the compound from step 458e (59.9 mg, 0.145 mmol), Pd(PPh$_3$)$_4$, (16.8 mg, 14.5 µmol) and NaHCO$_3$ (48.7 mg, 0.580 mmol) in DME (6 mL) and H$_2$O (2 mL) was degassed and heated at 90° C. under N$_2$ for 14 hours. The volatiles were evaporated and the residue was partitioned (EtOAc—H$_2$O). The organics were washed with brine, dried (Na$_2$SO$_4$), filtered and evaporated. The residue was purified by chromatography (silica, hexanes-ethyl acetate) to give the title compound as a light yellow solid (78.8 mg, 81%). ESIMS m/z=673.14 [M+H]+.

Example 471

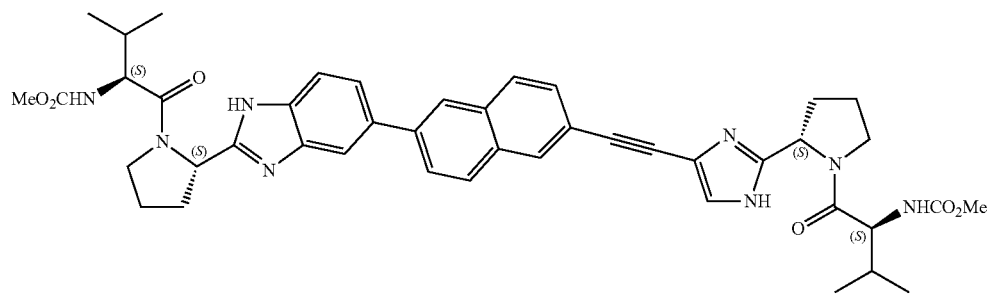

The title compound was synthesized from the compound of Example 470 using procedures similar to that described in Example 448. ESIMS m/z=787.26 [M+H]+.

Example 472

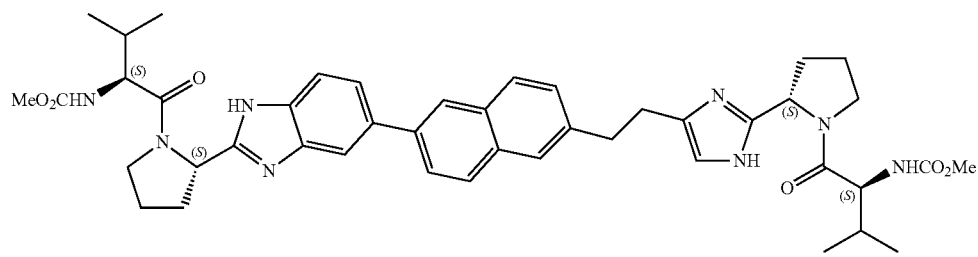

The title compound was synthesized from the compound of Example 471 using procedures similar to that described in Example 443. ESIMS m/z=791.23 [M+H]+.

Example 473

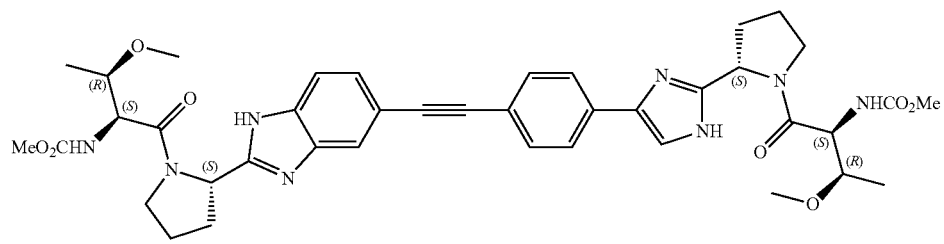

The title compound was synthesized from the compound of Example 1-1 using procedures similar to that described in Example 460. ESIMS m/z=769.37 [M+H]+.

Example 474

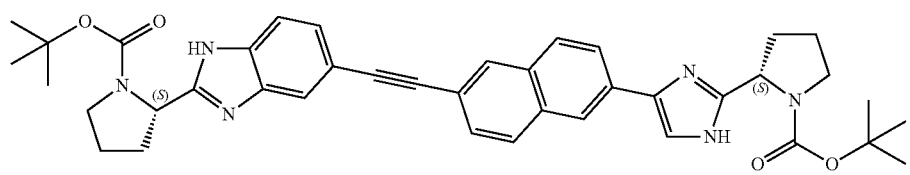

Step 474a.

A mixture of the compound from step 515d (0.200 g, 0.643 mmol), 2,6-dibromonaphthalene (0.368 g, 1.29 mmol), CuI (3.6 mg, 19.2 μmol) and Pd(PPh₃)₄ (37.1 mg, 32.1 μmol) in CH₃CN (6 mL) and triethylamine (6 mL) was degassed and heated at 90° C. under N₂ overnight. The volatiles were evaporated and the residue was partitioned (EtOAc-water). The organics were washed with brine, dried (Na₂SO₄), filtered and evaporated. The residue was purified by flash column chromatography (silica, hexanes-ethyl acetate) to give the desired compound as a light yellow oil (214 mg, 65%). ESIMS m/z=516.08, 518.08 [M+H]⁺.

Step 474b.

A mixture of the compound from step 474a (0.214 g, 0.415 mmol), bis-(pinacolato)diboron (0.211 g, 0.829 mmol) and potassium acetate (0.102 g, 1.04 mmol) in 1,4-dioxane (8 mL) was added Pd(PPh₃)₄ (23.9 mg, 20.7 μmol). The resultant mixture were degassed and heated up at 85° C. under N₂ for 14 hours. The volatiles were evaporated and the residue was partitioned (EtOAc-water). The organics were washed with brine, dried (Na₂SO₄), filtered and evaporated. The residue was purified by flash column chromatography (silica, hexanes-ethyl acetate) to give the desired compound as a light yellow oil (0.163 g, 60% purity). ESIMS m/z=564.17 [M+H]⁺.

Step 474c.

A mixture of the compound from step 474b (0.163 g, 0.290 mmol), (S)-tert-butyl 2-(5-bromo-1H-imidazol-2-yl)pyrrolidine-1-carboxylate (prepared according to WO 2008/021927, 0.137 g, 0.434 mmol), Pd(PPh₃)₄, (33.4 mg, 28.9 μmol) and NaHCO₃ (97.2 mg, 1.16 mmol) in DME (6 mL) and H₂O (2 mL) was degassed and heated at 90° C. under N₂ for 14 hours. The volatiles were evaporated and the residue was partitioned (EtOAc—H₂O). The organics were washed with brine, dried (Na₂SO₄), filtered and evaporated. The residue was purified by chromatography (silica, hexanes-ethyl acetate) to give the title compound as a light yellow solid (0.122 g, 60% purity). ESIMS m/z=673.29 [M+H]⁺.

Example 475

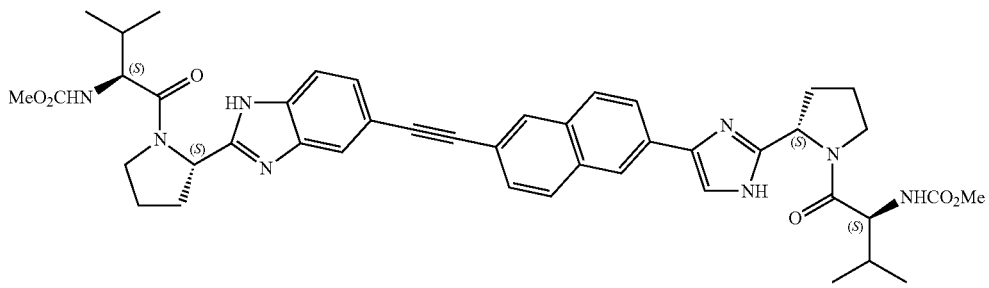

The title compound was synthesized from the compound from Example 474 using procedures similar to that described in Example 448 after HPLC purification. ESIMS m/z=787.20 [M+H]⁺.

Example 476

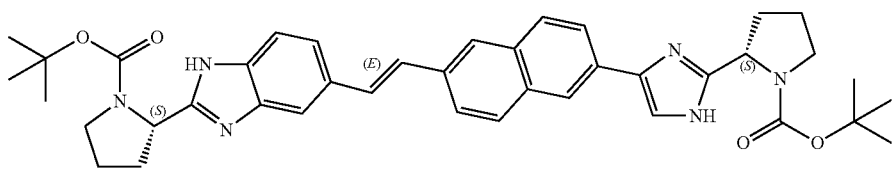

The title compound was obtained as an impurity in the compound of example 474. ESIMS m/z=675.30 [M+H]⁺.

Example 477

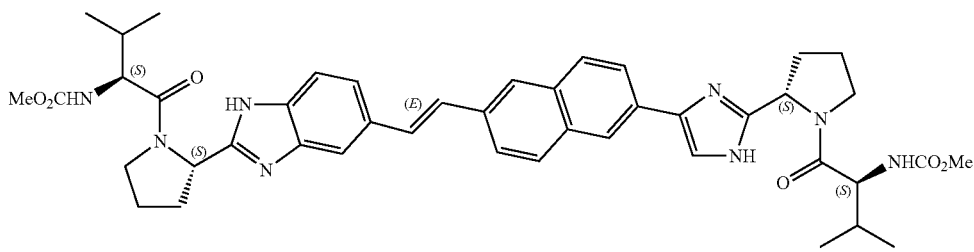

The title compound was synthesized and purified as a minor product in example 475. ESIMS m/z=789.21 [M+H]+.

Example 478

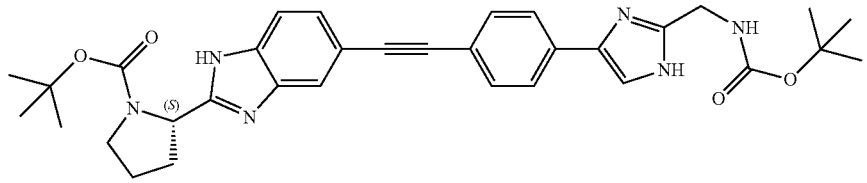

Step 478a.

A mixture of 2,4'-dibromoacetophenone (1.59 g, 5.71 mmol) and N-Boc-glycine (1.00 g, 5.71 mmol) in CH₃CN (20 mL) was added DIPEA (1.42 mL, 11.4 mmol) slowly. The mixture was stirred at rt until the disappearence of the starting material. The volatiles were evaporated and the residue was partitioned (EtOAc-water). The organics were washed with brine, dried (Na₂SO₄), filtered and evaporated. The residue was purified by flash column chromatography (silica, hexanes-ethyl acetate) to give the desired compound as a light yellow solid (2.02 g, 95%). ESIMS m/z=394.15, 396.15 [M+Na]+.

Step 478b.

A solution of the compound from step 478a (2.02 g, 5.43 mmol) in toluene (30 mL) was added ammonium acetate (8.35 g, 0.108 mol) and the resultant mixture was heated up at 100° C. for 20 hours. The volatiles were evaporated and the residue was partitioned (EtOAc-aq. NaHCO₃). The organics were washed with brine, dried (Na₂SO₄), filtered and evaporated. The residue was purified by flash column chromatography (silica, hexanes-ethyl acetate) to the desired compound as a yellow brown solid (1.62 g, 85%). ESIMS m/z=352.14, 354.14 [M+H]+.

Step 478c.

A mixture of the compound from step 478b (80.0 mg, 0.227 mmol), the compound from step 515d (77.8 mg, 0.250 mmol), CuI (1.3 mg, 6.8 µmol) and Pd(PPh₃)₄ (26.2 mg, 22.7 µmol) in triethylamine (6 mL) was degassed and heated at 85° C. under N₂ overnight. The volatiles were evaporated and the residue was partitioned (EtOAc-water). The organics were washed with brine, dried (Na₂SO₄), filtered and evaporated. The residue was purified by flash column chromatography (silica, hexanes-ethyl acetate) to give the title compound as a light yellow solid (50.9 mg, 39%). ESIMS m/z=583.37 [M+H]+.

Example 479

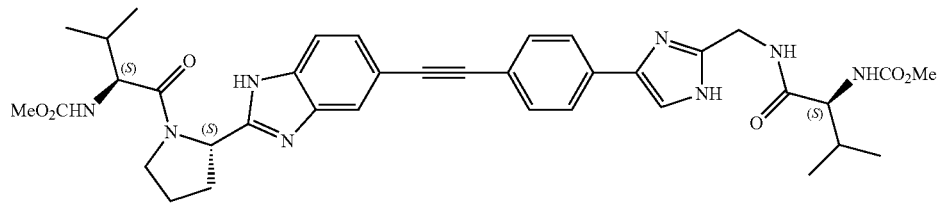

The title compound was synthesized from the compound of Example 478 using procedures similar to that described in Example 448. ESIMS m/z=697.64 [M+H]+.

Example 480

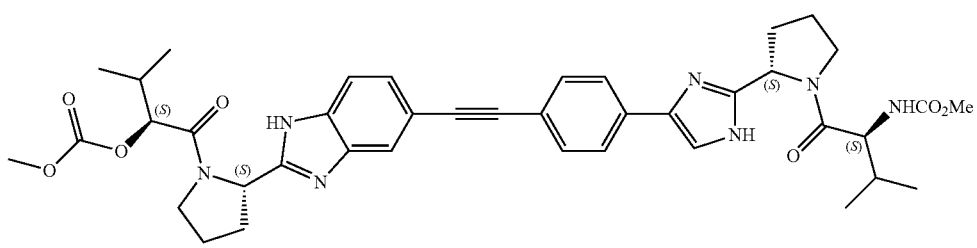

Step 480a.

A solution of the compound of example 500 (10.0 mg, 14.7 µmol) in 1,4-dioxane (1 mL) was treated with HCl in 1,4-dioxane (4 M, 4 mL) rt for 30 min. The volatiles were evaporated off to give the crude desired compound as a yellow solid which was directly used in the next step. ESIMS m/z=580.55 [M+H]+.

Step 480b.

A mixture of the crude compound from step 480a (14.7 µmol at most) and (S)-2-(methoxycarbonyloxy)-3-methylbutanoic acid (prepared according to Chemical & Pharmaceutical Bulletin, 1985, 33, 3922-3928, 2.8 mg, 16.1 µmol) in DMF (3 mL) was treated with HATU (5.6 mg, 14.7 µmol) in the presence of DIPEA (37.0 µL, 0.294 mmol) for 2 hours at rt and the volatiles were evaporated off to provide a brown sirup. It was purified by flash column chromatography (silica, CH2Cl2-MeOH) to give the title compound as a yellow solid (8.3 mg, 2 steps 76%). ESIMS m/z=738.64 [M+H]+.

Example 481

Step 482a.

A mixture of N-Boc-L-proline (0.210 g, 0.976 mmol) and TEA (0.14 mL, 0.976 mmol) in THF (10 mL) at −20° C. was treated with iso-butyl chloroformate (0.13 mL, 0.976 mmol) for 30 minutes before a slow addition of 5-bromo-3-fluorobenzene-1,2-diamine (0.200 g, 0.976 mmol) in THF (2 mL). It was then kept at −20° C. for 1 hour and then slowly warmed up to rt and stirred at rt overnight. The volatiles were evaporated and the residue was partitioned (EtOAc-water). The organics were washed with brine, dried (Na2SO4), filtered and evaporated to give the crude desired compound as a brown foam (0.436 g). ESIMS m/z=402.23, 404.23 [M+H]+.

Step 482b.

A solution of the crude compound from step 482a (0.976 mmol at most) in glacial acetic acid (10 mL) was heated at 65° C. for 24 hours. The volatiles were evaporated off and the residue was partitioned (EtOAc-saturated aqueous NaHCO3). The organics were washed with brine, dried (Na2SO4), filtered and evaporated. The residue was purified by flash column chromatography (silica, hexanes-ethyl acetate) to give the desired compound as a light yellow oil (0.327 g, 2 steps 87%). ESIMS m/z=384.16, 386.16 [M+H]+.

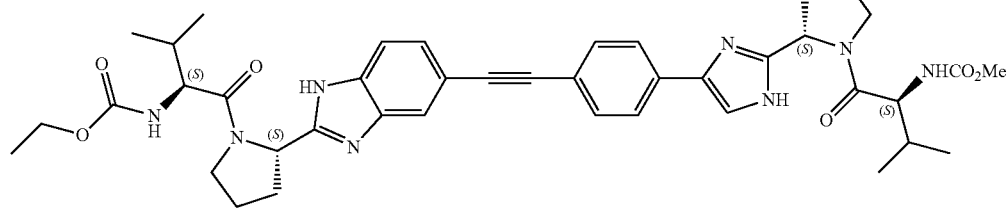

A mixture of the crude compound from step 480a (14.7 µmol at most) and (S)-2-(ethoxy-carbonylamino)-3-methylbutanoic acid (prepared according to WO 2008/021927, 3.0 mg, 16.1 µmol) in DMF (3 mL) was treated with HATU (5.6 mg, 14.7 µmol) in the presence of DIPEA (37.0 µL, 0.294 mmol) for 2 hours at rt and the volatiles were evaporated off to provide a brown sirup. It was purified by flash column chromatography (silica, CH2Cl2-MeOH) to give the title compound as a very yellow solid (10.2 mg, 2 steps 91%). ESIMS m/z=751.67 [M+H]+.

Example 482

Step 482c.

A mixture of the compound from step 482b (60.0 mg, 0.156 mmol), the compound from step 1-1b (58.0 mg, 0.172 mmol), CuI (0.9 mg, 4.6 µmol) and Pd(PPh3)4 (9.0 mg, 7.8 µmol) in triethylamine (4 mL) and CH3CN (4 mL) was degassed and heated to 90° C. under N2 overnight. The volatiles were evaporated and the residue was partitioned (EtOAc-water). The organics were washed with brine, dried (Na2SO4), filtered and evaporated. The residue was purified by flash column chromatography (silica, hexanes-ethyl acetate) to give the title compound as a light yellow solid (54.2 mg, 54%). ESIMS m/z=641.22 [M+H]+.

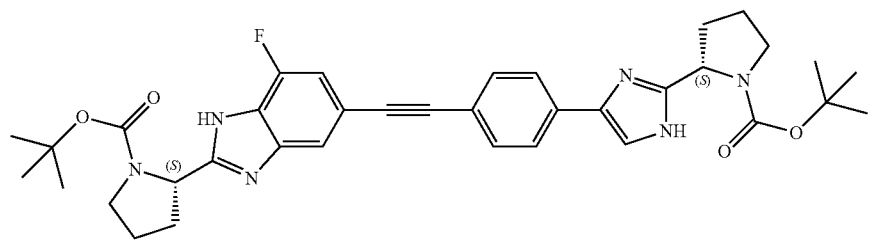

Example 483

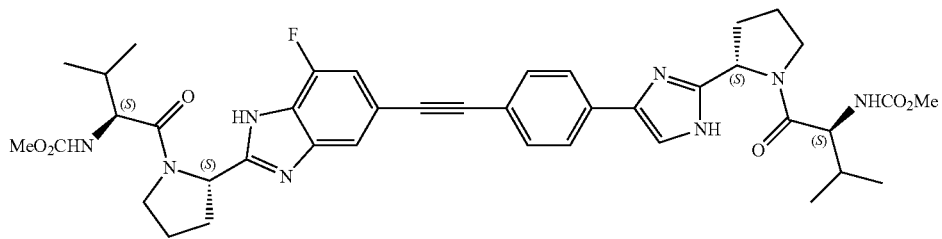

The title compound was synthesized from the compound of Example 482 using procedures similar to that described in Example 448. ESIMS m/z=755.55 [M+H]$^+$.

Example 484

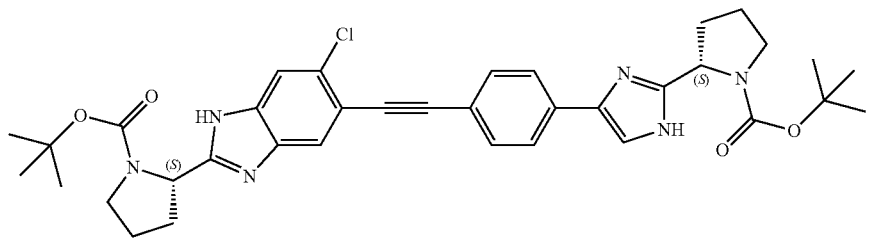

Step 484a.

A mixture of 4-bromo-5-chlorobenzene-1,2-diamine (0.3 g, 1.19 mmol) and tin(II) chloride dihydrate (1.08 g, 4.77 mmol) in DMF (10 mL) was heated at 80° C. for 2 hours. The reaction was cooled and then neutralized by the addition of aqueous 2N NaOH. The resultant mixture were partitioned (EtOAc-water) and the organics were washed with brine, dried (Na$_2$SO$_4$), filtered and evaporated. The residue was purified by flash column chromatography (silica, hexanes-ethyl acetate) to give the desired compound as a light yellow brown solid (0.256 g, 96%).

Step 484b.

The compound from step 484a (0.250 g, 1.13 mmol) in DMF (10 mL) was treated with N-Boc-L-proline (0.243 g, 1.13 mmol), EDC.HCl (0.281 g, 1.47 mmol) and DMAP (27.6 mg, 0.226 mmol) for 12 hours before being partitioned (EtOAc-water). The organics were washed with aqueous 1N HCl, brine, dried (Na$_2$SO$_4$), filtered and evaporated to give the crude desired compound as a light red brown foam (0.401 g). ESIMS m/z=418.20, 420.20 [M+H]$^+$.

Step 484c.

A solution of the crude compound from step 484b (1.13 mmol at most) in glacial acetic acid (10 mL) was heated at 50° C. for 2 hours. The volatiles were evaporated off and the residue was partitioned (EtOAc-saturated aqueous NaHCO$_3$). The organics were washed with brine, dried (Na$_2$SO$_4$), filtered and evaporated. The residue was purified by flash column chromatography (silica, hexanes-ethyl acetate) to give the desired compound as a yellow brown solid (0.326 g, 2 steps 85%). ESIMS m/z=400.21, 402.21 [M+H]$^+$.

Step 484d.

A mixture of the compound from step 484c (55.0 mg, 0.140 mmol), the compound from step 1-1b (56.5 mg, 0.168 mmol), CuI (0.8 mg, 4.1 μmol) and Pd(PPh$_3$)$_4$ (8.0 mg, 6.9 μmol) in triethylamine (3 mL) and CH$_3$CN (3 mL) was degassed and heated to 95° C. under N$_2$ overnight. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the title compound as a light yellow solid (49.7 mg, 55%). ESIMS m/z=657.40 [M+H]$^+$.

Example 485

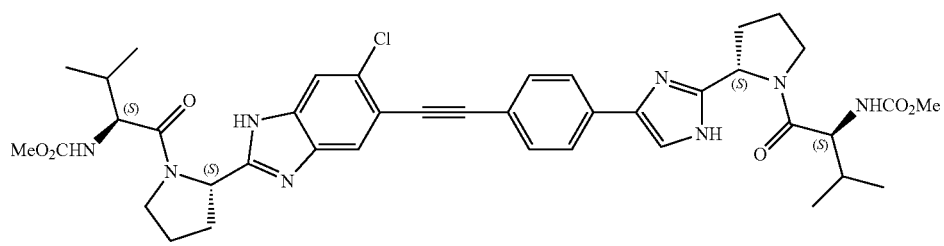

The title compound was synthesized from the compound of Example 484 using procedures similar to that described in Example 448. ESIMS m/z=771.63 [M+H]⁺.

Example 486

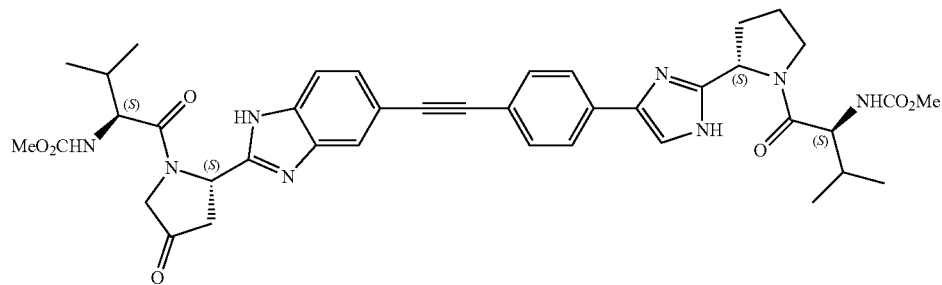

A solution the compound of example 517 (38.6 mg, 51.3 μmol) in $CH_2Cl_2$ (3 mL) was treated with camphorsulfonic acid (23.8 mg, 0.103 mmol) and Dess-Martin periodinane (0.131 mg, 0.308 mmol) for 5 hours before being quenched with satuated aqueous $NsS_2O_3$ and $NaHCO_3$. The mixture was partitioned (EtOAc-water) and the organics were washed with brine, dried ($Na_2SO_4$), filtered and evaporated. The residue was purified by flash column chromatography (silica, MeOH—$CH_2Cl_2$) to give the title compound as a yellow brown solid (33.2 mg, 86%). ESIMS m/z=751.54 [M+H]⁺.

Example 487

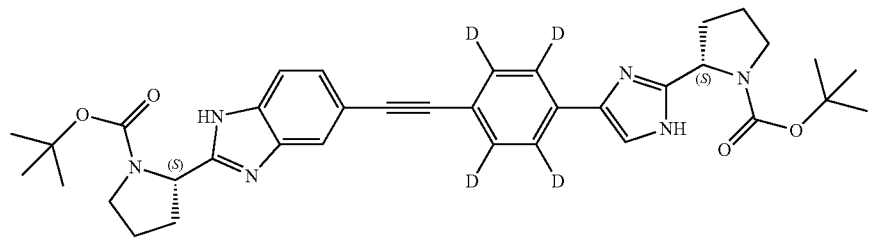

each D is deuterium

Step 487a.

A solution of 4'-bromoacetophenone-d₇ (0.500 g, 2.43 mmol) in AcOH (10 mL) was treated with bromine (0.12 mL, 2.43 mmol) for 24 hours before being evaporated to dryness. The residue was partitioned (EtOAc-aqueous satuated $NaHCO_3$) and the organics were washed with brine, dried ($Na_2SO_4$), filtered and evaporated to give the desired compound as a white crystal (0.672 g, 98%).

Step 487b.

A mixture of the compound from step 487a (0.670 g, 2.38 mmol) and N-Boc-L-proline (0.511 g, 2.38 mmol) in $CH_3CN$ (20 mL) was added DIPEA (0.59 mL, 4.75 mmol) slowly. The mixture was stirred at rt until the disappearence of the starting material. The volatiles were evaporated and the residue was partitioned (EtOAc-water). The organics were washed with brine, dried ($Na_2SO_4$), filtered and evaporated to give the crude desired compound as a yellow brown oil (1.06 g). ESIMS m/z=416.32, 418.32 [M+H]⁺.

Step 487c.

A solution of the compound from step 487b (at most 2.38 mmol) in toluene (24 mL) was added ammonium acetate (3.66 g, 47.5 mmol) and the resultant mixture was heated up at 100° C. for 14 hours. The volatiles were evaporated and the residue was partitioned (EtOAc-aq. $NaHCO_3$). The organics were washed with brine, dried ($Na_2SO_4$), filtered and evaporated. The residue was purified by flash column chromatography (silica, hexanes-ethyl acetate) to give the desired compound as a yellow brown powder (0.749 g, 2 steps, 78%). ESIMS m/z=396.20, 398.20 [M+H]⁺.

Step 487d.

A mixture of the compound from step 487c (200 mg, 0.505 mmol), the compound from step 515d (0.188 g, 0.606 mmol), CuI (2.9 mg, 15.1 μmol) and Pd(PPh₃)₄ (29.1 mg, 25.2 mmol) in triethylamine (5 mL) and $CH_3CN$ (5 mL) was degassed and heated at 95° C. under $N_2$ overnight. The volatiles were evaporated and the residue was partitioned (EtOAc-water). The organics were washed with brine, dried ($Na_2SO_4$), filtered and evaporated. The residue was purified by flash column chromatography (silica, hexanes-ethyl acetate) to give the title compound as a light yellow solid (0.151 g, 48%). ESIMS m/z=627.58 [M+H]⁺.

Example 488

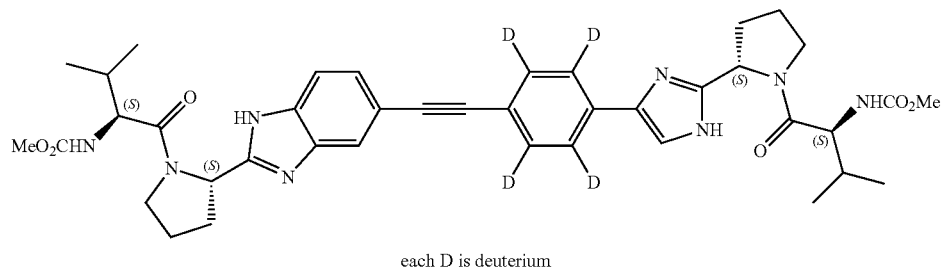

each D is deuterium

The title compound was synthesized from the compound from Example 487 using procedures similar to that described in Example 448. ESIMS m/z=741.70 [M+H]$^+$.

Example 489

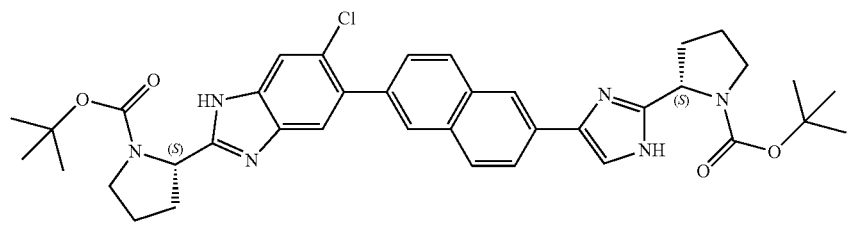

Step 489a.

A mixture of the compound from step 458d (0.200 g, 0.452 mmol), bis(pinacolato)diboron (0.144 g, 0.565 mmol), PdCl$_2$(dppf)$_2$ (36.9 mg, 0.0452 mmol) and potassium acetate (88.7 mg, 0.904 mmol) in DMSO (5 mL) was degassed and heated at 80° C. under N$_2$ for 17 hours. The reaction mixture was allowed to cool down and partitioned (EtOAc-water). The organic layer was washed with brine, dried (Na$_2$SO$_4$), filtered and evaporated. The residue was purified by chromatography (silica, hexanes-ethyl acetate) to give the desired compound as a yellow solid (0.188 g, 85%). ESIMS m/z=490.12 [M+H]$^+$.

Step 489b.

A mixture of the compound from step 484c (50.0 mg, 0.125 mmol), the compound from step 489a (73.2 mg, 0.150 mmol), Pd(PPh$_3$)$_4$, (7.2 mg, 6.2 µmol) and NaHCO$_3$ (41.9 mg, 0.499 mmol) in DME (6 mL) and H$_2$O (2 mL) was degassed and heated at 95° C. under N$_2$ for 14 hours. The volatiles were evaporated and the residue was partitioned (EtOAc—H$_2$O). The organics were washed with brine, dried (Na$_2$SO$_4$), filtered and evaporated. The residue was purified by chromatography (silica, hexanes-ethyl acetate) to give the title compound as a white solid (21.3 mg, 25%). ESIMS m/z=683.52 [M+H]$^+$.

Example 490

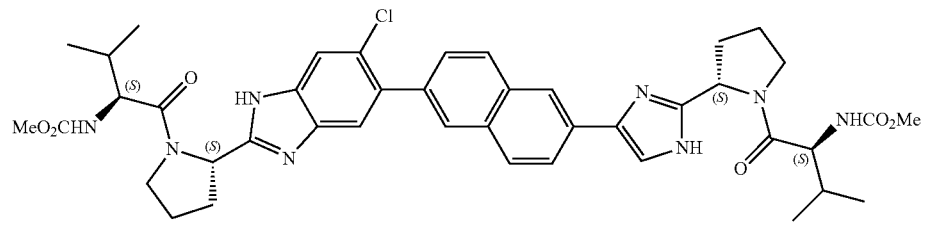

The title compound was synthesized from the compound from Example 489 using procedures similar to that described in Example 448. ESIMS m/z=797.62 [M+H]$^+$.

Example 491

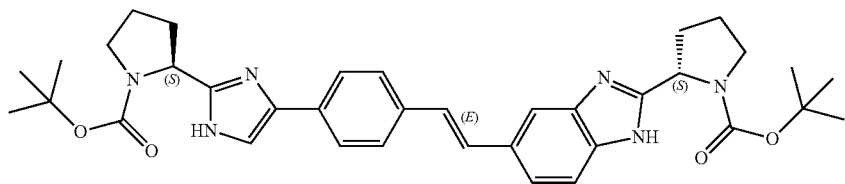

Step 491a.

A mixture of the compound of step 1b (1.600 g, 4.369 mmol), tributyl(vinyl)tin (1.53 ml, 5.242 mmol) and Pd(PPh$_3$)$_4$ (5 mol %, 0.250 g, 0.218 mmol) in toluene (20 mL) was degassed and then refluxed under N$_2$ for 18 h before being allowed to cool to rt. The mixture was directly purified by flash column chromatography (silica, hexanes-ethyl acetate with 1% Et$_3$N in ethyl acetate) to give the desired compound as a pink foam (0.912 g, 67%). ESIMS m/z=314.18 [M+H]$^+$.

Step 491b.

A mixture of the compound from step 491a (1.251 g, 3.191 mmol), the compound of step 1d (1.000 g, 3.191 mmol), Pd(OAc)$_2$ (5 mol %, 35.8 mg, 0.160 mmol) and P(o-tolyl)$_3$ (0.121 g, 0.399 mmol) in Et$_3$N (4.45 mL) and CH$_3$CN (30 mL) was degassed and refluxed under N$_2$ gas for 20 hours before being evaporated. The residue was taken up in dichloromethane and filtered through a short pad of Celite. The filtrate was purified by chromatography (silica, hexanes-ethyl acetate with 1% Et$_3$N in ethyl acetate) to give the title compound as a yellow solid (1.471 g, 74%). ESIMS m/z=625.05 [M+H]$^+$.

Example 492

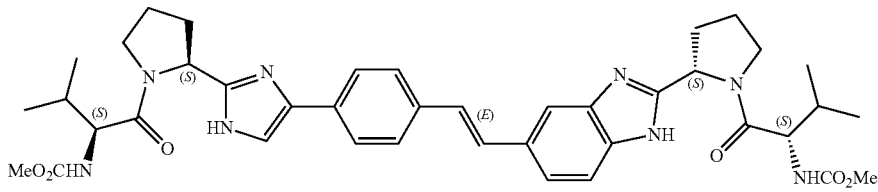

The title compound was prepared from the compound of example 491 using procedures similar to that described in example 448. ESIMS m/z=739.15 [M+H]$^+$.

Example 493

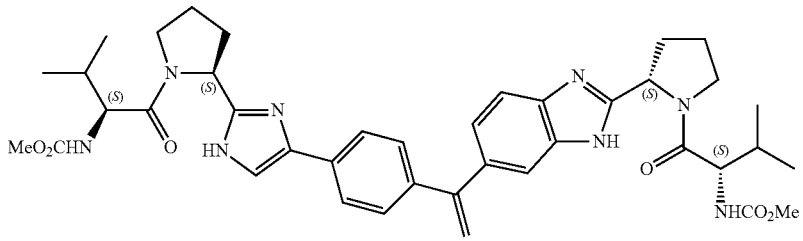

The title compound was obtained as a minor product (~2%) in example 492. ESIMS m/z=739.03 [M+H]$^+$.

Example 494

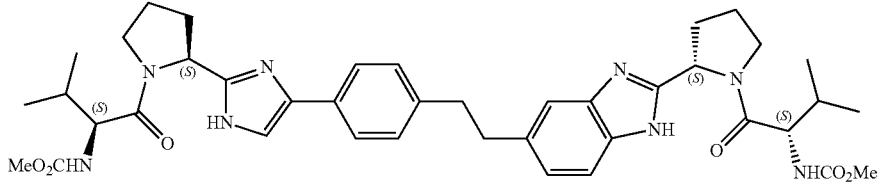

Pd(OH)$_2$ (20% on carbon, 10.8 mg) was added into a solution of the compound from example 492 (10.8 mg, 0.0146 mmol) in EtOH (1.5 mL). The suspension was purged with H$_2$ 3 times and stirred at rt for 6 h under H$_2$ (60 psi) before being filtered through a short pad of Celite. The filtrate was concentrated. The crude was purified by flash column chromatography (silica, CH$_2$Cl$_2$-MeOH) to give the title compound as a white solid (7.2 mg, 59%). ESIMS m/z=741.13 [M+H]$^+$.

mg, 0.0169 mmol) at 0° C. Excess diazomethane (solution in ether) was added with a plastic pipette until the starting material was consumed. The suspension was concentrated. The residue was taken up in dichloromethane and filtered through a short pad of celite. The filtrate was purified by flash column chromatography (silica, hexanes-ethyl acetate) to give the title compounds as a colorless oil (0.106 g, 70%). The regiochemistry of the SEM group and the stereochemistry of the cyclopropyl ring were not determined. ESIMS m/z=899.07 [M+H]$^+$.

Example 495

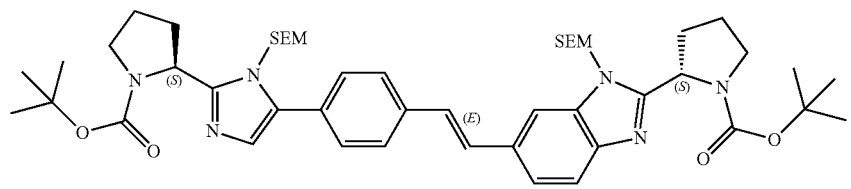

To a solution of the compound from example 491 (0.268 g, 0.430 mmol) in DMF (6 mL) was added NaH (60% in mineral oil, 36.0 mg, 0.902 mmol) at rt. The suspension was stirred at rt for 1 hour. SEMCl (0.154 mL, 0.868 mmol) was added dropwise at rt. After 1.5 hour at rt, the reaction was quenched with saturated NH$_4$Cl solution and extracted with EtOAc. The organic layer was washed with saturated NaHCO$_3$, brine, dried (Na$_2$SO$_4$), filtered and concentrated. The crude was purified by flash column chromatography (silica, hexanes-ethyl acetate) to give the title compound as a yellow foam (0.290 g, 76%). The regiochemistry of the SEM groups was not determined. ESIMS m/z=885.25 [M+H]$^+$.

Example 496

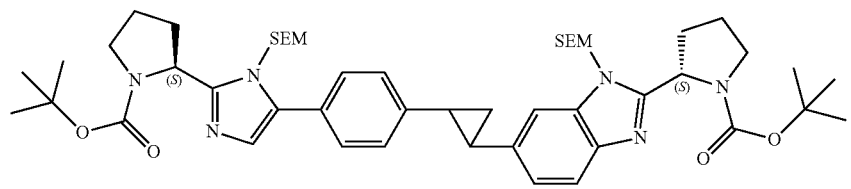

To a solution of the compound from example 495 (0.150 g, 0.169 mmol) in THF (1.5 mL) was added Pd(OAc)$_2$ (3.8

Example 497

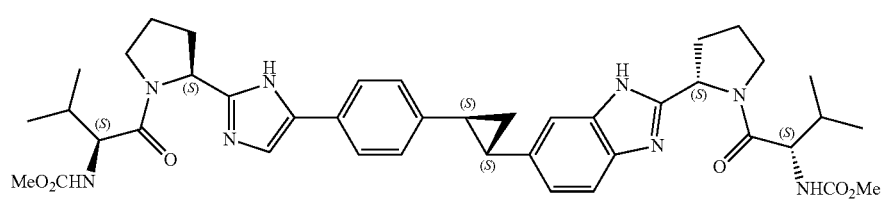

497-a
tentative

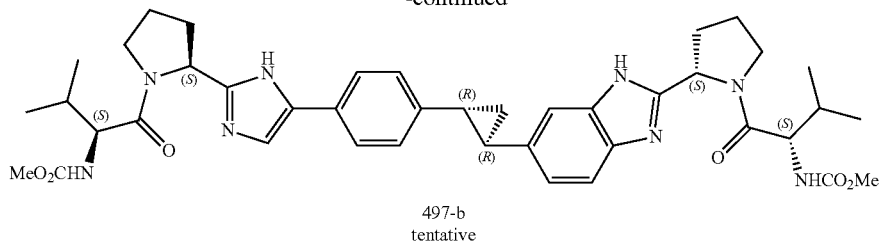

497-b
tentative

Step 497a.

A solution of the compound of example 496 (0.106 g, 0.118 mmol) in 1,4-dioxane (2 mL) was treated with HCl in 1,4-dioxane (4 M, 12 mL) at 50° C. for 4 hour. The volatiles were evaporated off to give the crude desired compounds as a yellow solid which was used directly in the next step.

Step 497b.

A mixture of the crude compound from step 497a (0.118 mmol at most) and (5)-2-(methoxycarbonylamino)-3-methylbutanoic acid (41.3 mg, 0.236 mmol) in DMF (3 mL) was treated with HATU (85.2 mg, 0.224 mmol) in the presence of DIPEA (0.41 mL, 2.360 mmol) for 1 hours at rt and the volatiles were evaporated off to provide a brown syrup. The residue was patitioned (EtOAc—H$_2$O). The organic layer was washed with brine, dried (Na$_2$SO$_4$), filtered and concentrated. The residue was purified by RP-HPLC (NH$_4$HCO$_3$ buffer-MeOH) to give the title compounds: the major diastereomer (497-a, tentative) as a yellow solid (19.4 mg), ESIMS m/z=753.12 [M+H]$^+$; and the minor diastereomer (497-b, tentative) as a yellow solid (3.1 mg), ESIMS m/z=753.12 [M+H]$^+$. The stereochemistry of the cyclopropyl rings was not determined.

Example 498

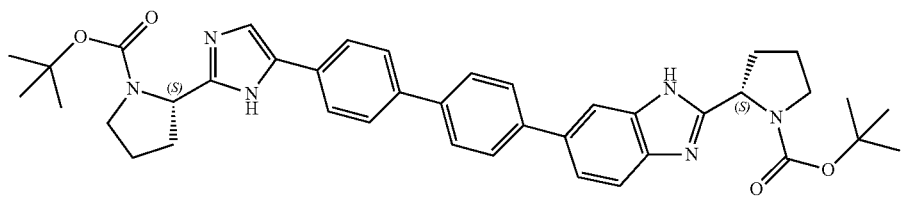

Step 498a.

A mixture of the compound from step 458e (0.250 g, 0.605 mmol), 1-bromo-4-iodobenzene (0.257 g, 0.908 mmol), NaHCO$_3$ (0.203 g, 2.42 mmol) and Pd(PPh$_3$)$_4$ (34.9 mg, 30.2 μmol) in DME (12 mL) and water (4 mL) was degassed and heated to 85° C. under N$_2$ overnight. The volatiles were evaporated and the residue was partitioned (EtOAc-water). The organics were washed with brine, dried (Na$_2$SO$_4$), filtered and evaporated. The residue was purified by flash column chromatography (silica, hexanes-ethyl acetate) to give the desired compound as a very light yellow solid (0.246 g, 92%). ESIMS m/z=442.00, 444.00 [M+H]$^+$.

Step 498b.

A mixture of the compound from step 1e (81.1 mg, 0.185 mmol), the compound from step 498a (85.8 mg, 0.194 mmol), Pd(PPh$_3$)$_4$, (21.4 mg, 18.5 μmol) and NaHCO$_3$ (62.1 mg, 0.739 mmol) in DME (3 mL) and H$_2$O (1 mL) was degassed and heated at 80° C. under N$_2$ for 22 hours. The volatiles were evaporated and the residue was partitioned (EtOAc—H$_2$O). The organics were washed with brine, dried (Na$_2$SO$_4$), filtered and evaporated. The residue was purified by chromatography (silica, hexanes-ethyl acetate with 1% Et$_3$N in ethyl acetate) to give the title compound as a yellow solid (0.100 g, 81%). ESIMS m/z=675.17 [M+H]$^+$.

Example 499

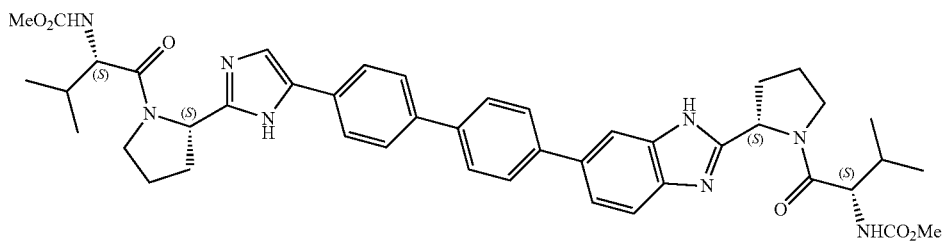

The title compound was prepared from the compound of example 498 using procedures similar to that described in example 448. ESIMS m/z=789.06 [M+H]$^+$.

Example 500

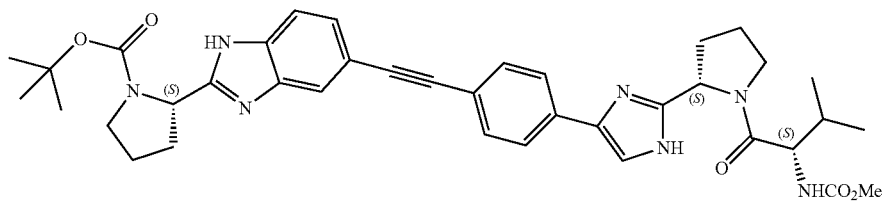

Step 500a.

A solution of the compound from step 515b (2.000 g, 4.553 mmol) in 1,4-dioxane (25 mL) was treated with HCl in 1,4-dioxane (4 M, 50 mL) at rt for 1.5 hours. The volatiles were evaporated off to give the crude desired compound as a yellow solid which was used directly in the next step. ESIMS m/z=339.89 [M+H]$^+$.

Step 500b.

A mixture of the crude compound from step 500a (4.553 mmol at most) and (5)-2-(methoxycarbonylamino)-3-methylbutanoic acid (0.798 g, 4.553 mmol) in DMF (15 mL) was treated with HATU (1.644 g, 4.325 mmol) in the presence of DIPEA (7.93 mL, 45.53 mmol) for 1.5 hours at rt and the volatiles were evaporated off. The residue was partitioned (EtOAc—H$_2$O). The organics were washed with brine, dried (Na$_2$SO$_4$), filtered and evaporated. The residue was purified by chromatography (silica, hexanes-ethyl acetate with 1% Et$_3$N in ethyl acetate) to give the title compound as a yellow foam (2.026 g, 90% over 2 steps). ESIMS m/z=496.90 [M+H]$^+$.

Step 500c.

A mixture of compound from step 500b (0.800 g, 1.612 mmol), the compound from step 515d (0.501 g, 1.612 mmol), Pd(PPh$_3$)$_4$, (5 mol %, 93.1 mg, 80.6 µmol) and CuI (3 mol %, 9.2 mg, 48.3 µmol) in Et$_3$N (4 mL) and THF (12 mL) was degassed and stirred at 40° C. under N$_2$ for 18 hours. The volatiles were evaporated. The residue was purified by chromatography (silica, hexanes-ethyl acetate with 1% Et$_3$N in ethyl acetate) to give the title compound as a yellow solid (0.705 g, 64%). ESIMS m/z=680.09 [M+H]$^+$.

Example 501

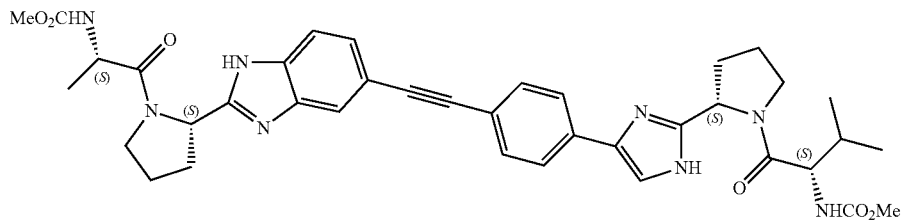

The title compound was prepared from the compound of example 500 and (S)-2-(methoxy-carbonylamino)propanoic acid using procedures similar to that described in steps 500a and 500b. ESIMS m/z=709.05 [M+H]$^+$.

Example 502

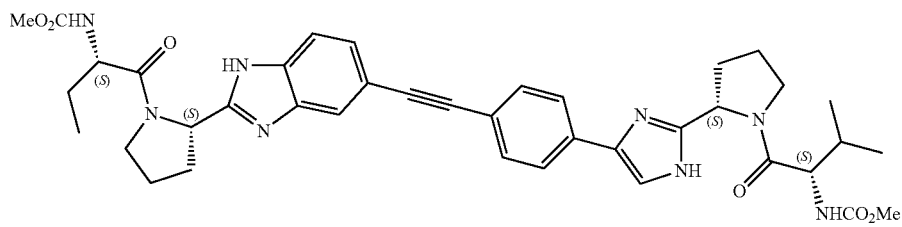

The title compound was prepared from the compound of example 500 and (S)-2-(methoxycarbonylamino)butanoic acid using procedures similar to that described in steps 500a and 500b. ESIMS m/z=723.05 [M+H]$^+$.

Example 503

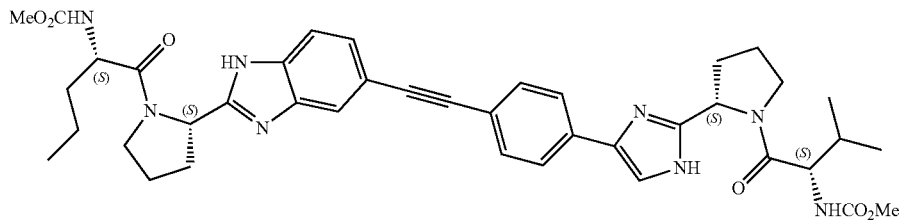

The title compound was prepared from the compound of example 500 and (S)-2-(methoxycarbonylamino)pentanoic acid using procedures similar to that described in steps 500a and 500b. ESIMS m/z=737.09 [M+H]⁺.

Example 504

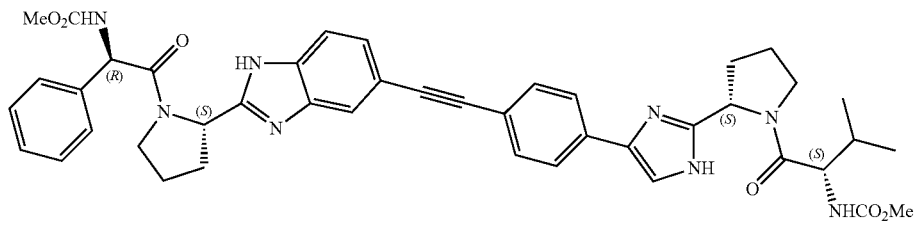

The title compound was prepared from the compound of example 500 and (R)-(methoxycarbonyl)amino phenyl acetic acid using procedures similar to that described in steps 500a and 500b. ESIMS m/z=771.06 [M+H]⁺.

Example 505

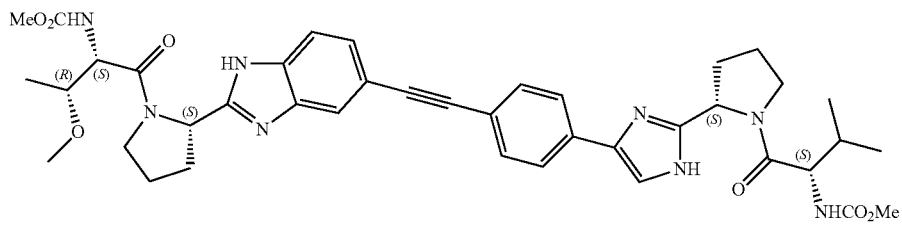

The title compound was prepared from the compound of example 500 and (2S,3R)-3-methoxy-2-(methoxycarbonylamino)butanoic acid using procedures similar to that described in steps 500a and 500b. ESIMS m/z=753.05 [M+H]⁺.

Example 506

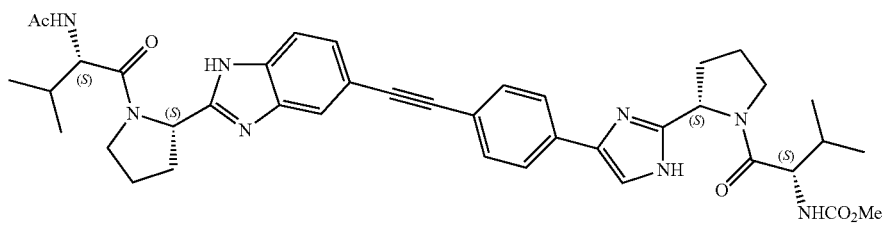

The title compound was prepared from the compound of example 500 and (S)-2-acetamido-3-methylbutanoic acid using procedures similar to that described in steps 500a and 500b. ESIMS m/z=721.48 [M+H]⁺.

Example 507

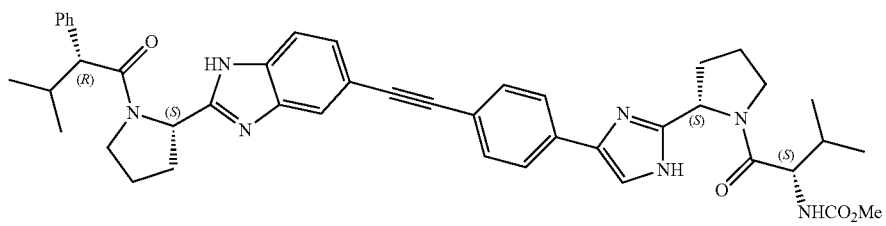

The title compound was prepared from the compound of example 500 and (R)-3-methyl-2-phenylbutanoic acid using procedures similar to that described in steps 500a and 500b. ESIMS m/z=740.50 [M+H]$^+$.

Example 508

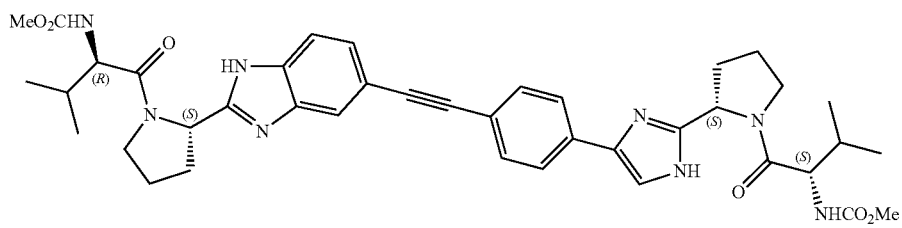

The title compound was prepared from the compound of example 500 and (R)-2-(methoxy-carbonylamino)-3-methylbutanoic acid using procedures similar to that described in steps 500a and 500b. ESIMS m/z=737.49 [M+H]$^+$.

Example 509

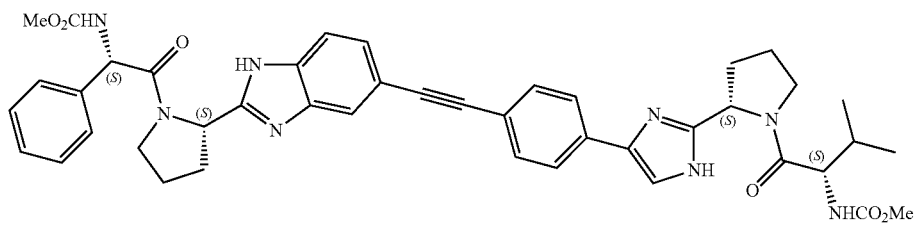

The title compound was prepared from the compound of example 500 and (S)-2-(methoxy-carbonylamino)-2-phenylacetic acid using procedures similar to that described in steps 500a and 500b. ESIMS m/z=771.40 [M+H]$^+$.

Example 510

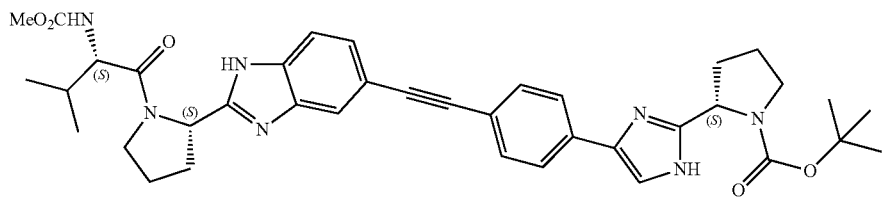

Step 510a.

A solution of the compound from the compound from step 515d (1 g, 3.21 mmol) in dichloromethane (20 mL) was treated with HCl in 1,4-dioxane (4 M, 12 mL) at room temperature for 1 hour. The volatiles were evaporated off to give the crude desired compound as a yellow solid which was used directly in the next step.

Step 510b.

The mixture of compounds from step 510a (3.21 mml at most) and the compound from step 515g (562 mg, 3.21 mmol) in DMF (12 mL) was added diisopropylethylamine (4.56 mL, 32 mmol) and HATU (1.22 g, 3.21 mmol). The resulting solution was stirred at room temperature for 1 hour before all volatiles were removed to provide a brown slurry, which was partitioned between EtOAc and aqueous NaOH (0.5M). The organic phase was separated, dried (Na$_2$SO$_4$) and concentrated to afford a brown oil, which was purified by flash column chromatography (silica, EtOAc-methanol) to give the desired compound.

Step 510c.

The title compound was prepared from the compound from step 510b and 515b using procedures similar to that described in step 500c. ESIMS m/z=680.36 [M+H]$^+$.

Example 511

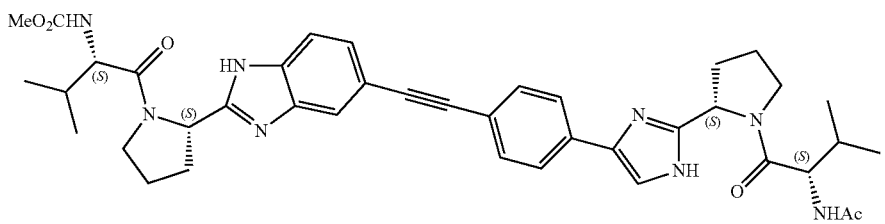

The title compound was prepared from the compound of example 510 and (S)-2-acetamido-3-methylbutanoic acid using procedures similar to that described in steps 500a and 500b. ESIMS m/z=721.49 [M+H]$^+$.

Example 512

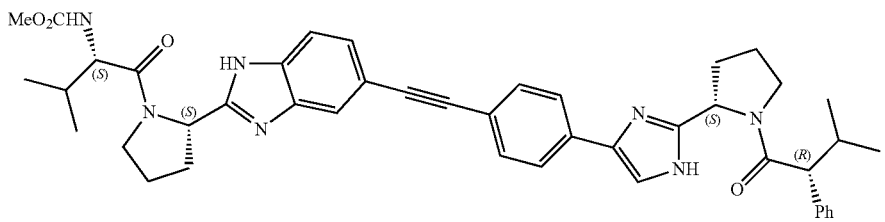

The title compound was prepared from the compound of example 510 and (R)-3-methyl-2-phenylbutanoic acid using procedures similar to that described in steps 500a and 500b. ESIMS m/z=740.51 [M+H]$^+$.

Example 513

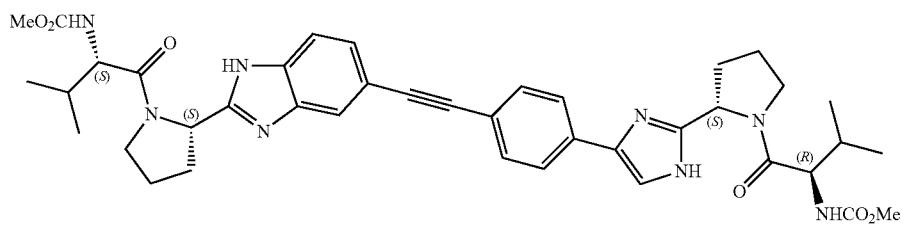

The title compound was prepared from the compound of example 510 and (R)-2-(methoxycarbonylamino)-3-methylbutanoic acid using procedures similar to that described in steps 500a and 500b. ESIMS m/z=737.50 [M+H]⁺.

Example 514

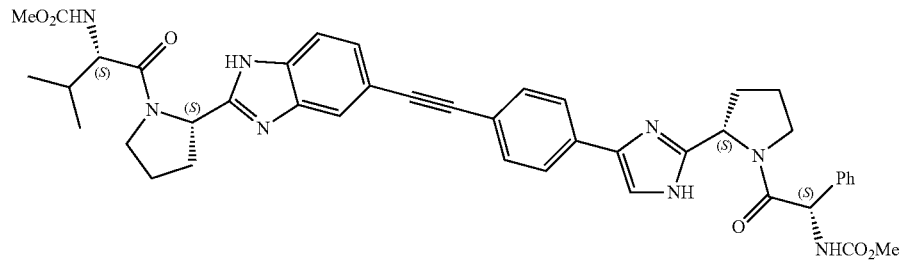

The title compound was prepared from the compound of example 510 and (S)-2-(methoxycarbonylamino)-2-phenylacetic acid using procedures similar to that described in steps 500a and 500b. ESIMS m/z=771.49 [M+H]⁺.

Example 515

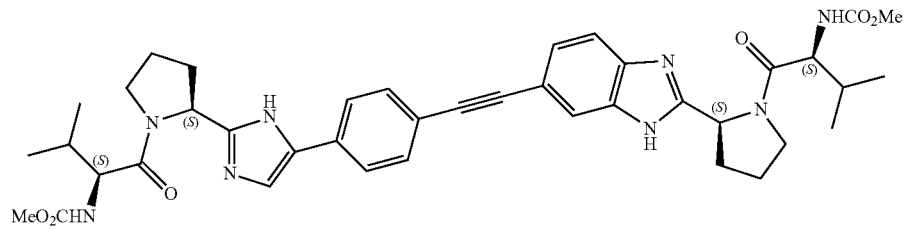

Step 515a.

Into a mixture of 2-bromo-1-(4-iodophenyl)ethanone (5 g, 15.4 mmol) and (S)-1-(tert-butoxycarbonyl)pyrrolidine-2-carboxylic acid (3.48 g, 16.1 mmol) in acetonitrile (40 mL) was added diisopropylethylamine (2.4 mL, 17 mmol). The resulting mixture was stirred at rt for 3 hours before being partitioned between EtOAc and aqueous NaHCO₃. The organic phase was separated, dried (Na₂SO₄) and concentrated to afford a brown oil. It was purified by flash column chromatography (silica, hexane-EtOAc) to give the desired product as light yellow oil (6.0 g, 86%). ESIMS m/z=481.94 [M+Na]⁺.

Step 515b.

The mixture of compound from step 515a (6.0 g, 12.5 mmol) and ammonium acetate (15.1 g, 196 mmol) in toluene (80 mL) was stirred at 80° C. for 3 hours before being partitioned between water and aqueous NaHCO₃. The organic phase was separated, dried (Na₂SO₄) and concentrated to afford a deep red oil. It was purified by flash column chromatography (silica, hexane-EtOAc) to give the desired product as light yellow solid (5.34 g, 93%). ESIMS m/z=439.83 [M+H]⁺.

Step 515c.

A mixture of the compound from step 1b (2.010 g, 5.488 mmol), trimethylsilyl-acetylene (2.33 ml, 16.46 mmol), CuI (0.110 g, 0.576 mmol) and Pd(PPh₃)₂Cl₂ (0.308 g, 0.439 mmol) in Et₃N (50 mL) was degased and then heated at 80° C. under N₂ overnight before being evaporated. The residue was purified by chromatography (silica, hexanes-ethyl acetate with 1% Et₃N in ethyl acetate) to give the desired compound as a yellow foam (1.140 g, 54%). ESIMS m/z=384.22 [M+H]⁺.

Step 515d.

A suspension of the compound from step 515c (1.140 g, 2.972 mmol) and K₂CO₃ (1.027 g, 7.430 mmol) in methanol (30 ml) was stirred at rt for 2 hour. The volatiles were evaporated off. The residue was patitioned (EtOAc—H₂O). The organic layer was washed with brine, dried (Na₂SO₄), filtered and concentrated. The residue was purified by chromatography (silica, hexanes-ethyl acetate with 1% Et₃N in ethyl acetate) to give the desired compound as a yellow foam (0.792 g, 86%). ESIMS m/z=312.18 [M+H]⁺.

Step 515e.

The mixture of compounds from step 515b (9.1 g, 20.7 mmol) and step 515d (6.45 g, 20.7 mmol) in THF (200 mL), triethylamine (60 mL) and acetonitrile (200 mL) was added tetrakis(triphenylphosphine)palladium(0) (1.15 g, 1 mmol) and copper(I) iodide (119 mg, 0.62 mmol). The resulting mixture was purged with nitrogen before being stirred at room temperature for 12 hours, at 50° C. for 2 hours and at 60° C. for 1 hour. After addition of aqueous NaOH (1M, 100 mL), the organic phase was separated, dried (Na₂SO₄) and concentrated to afford a brown slurry, which was absorbed with silica and purified by flash column chromatography (silica, EtOAc-methanol) to give the desired compound as light yellow solid (10.8 g, 84%). ESIMS m/z=623.07 [M+H]⁺.

Step 515f.

A solution of the compound from step 515e (3 g, 4.58 mmol) in dichloromethane (50 mL) and MeOH (5 mL) was treated with HCl in 1,4-dioxane (4 M, 40 mL) at rt for 2 hours. The volatiles were evaporated off to give the crude desired compound as a yellow solid which was used directly in the next step. ESIMS m/z=423.06 [M+H]⁺.

Step 515g.

The mixture of L-valine (50 g, 0.427 mol) in 1,4-dioxane (140 mL) was added water (630 mL), NaOH (54.7 g, 1.4 mol) and methyl chloroformate (65.7 mL, 0.85 mol). The resulting solution was stirred at 60° C. for 22 hours before being added dichloromethane (400 mL). The aqueous phase was separated and extracted with dichloromethane (400 mL) before acidification with hydrochloric acid (37% in water, 90 mL). The cloudy suspension was extracted with EtOAc (500 mL) twice and the combined organic phases were dried (Na$_2$SO$_4$) and concentrated to afford a white solid, which was recrystallized with hexane and EtOAc to afford the desired product as colorless needle like crystals (54 g, 72%). $^1$H NMR (d$^6$-DMSO) 12.52 (s, 1H), 7.33 (d, 1H), 3.85 (dd, 1H), 3.56 (s, 3H), 2.06 (m, 1H), 0.98 (m, 6H).

Step 515h.

The mixture of compounds from step 515f (4.58 mml at most) and step 515g (1.61 g, 9.16 mmol) in acetonitrile (50 mL) was added diisopropylethylamine (5.21 mL, 39 mmol) and HATU (3.31 g, 8.7 mmol). The resulting solution was stirred at room temperature for 35 minutes before being partitioned between EtOAc (500 mL) and aqueous NaOH (0.5M, 50 mL). The organic phase was separated, dried (Na$_2$SO$_4$) and concentrated to afford a brown slurry, which was purified by flash column chromatography (silica, EtOAc-methanol) to give the title compound as light yellow solid (2.31 g, 65% over 2 steps). ESIMS m/z=737.12 [M+H]$^+$.

Example 516

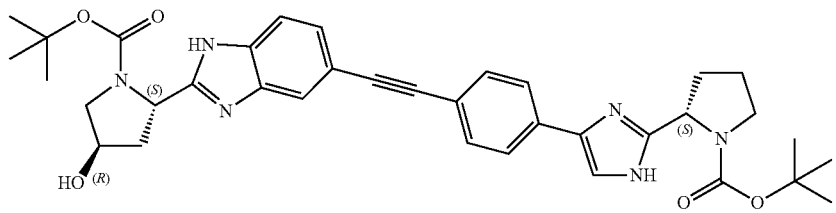

The title compound was prepared from (2S,4R)-1-(tert-butoxycarbonyl)-4-hydroxypyrrolidine-2-carboxylic acid using procedures similar to that described in steps 515a to 515e. ESIMS m/z=639.36 [M+H]$^+$.

Example 517

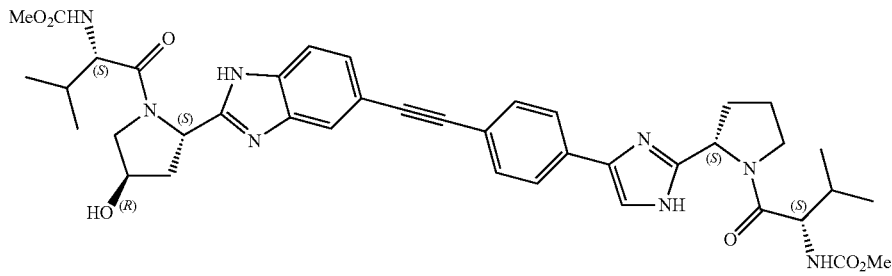

The title compound was prepared from the compound of example 516 using procedures similar to that described in example 448. ESIMS m/z=753.46 [M+H]$^+$.

Example 518

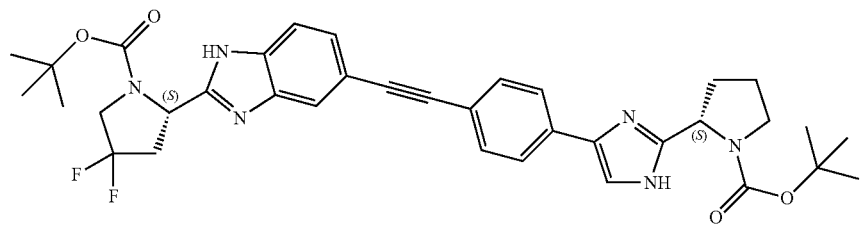

The title compound was prepared from (2S)-1-(tert-butoxycarbonyl)-4,4-difluoropyrrolidine-2-carboxylic acid using procedures similar to that described in steps 515a to 515e. ESIMS m/z=659.35 [M+H]$^+$.

Example 519

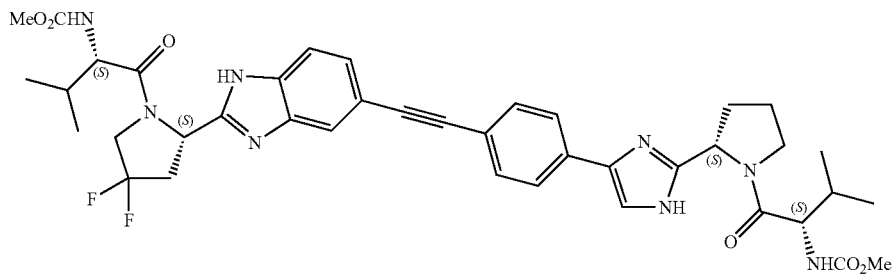

The title compound was prepared from the compound of example 518 using procedures similar to that described in example 448. ESIMS m/z=773.34 [M+H]$^+$.

Example 520

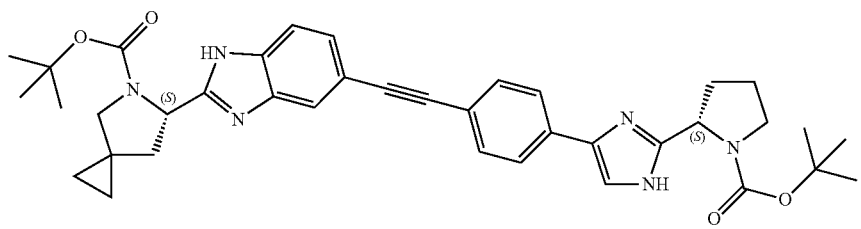

The title compound was prepared from the compound from step 1-ib, 4-bromo-1,2-diaminobenzene and (6S)-5-[(tert-butoxy)carbonyl]-5-azaspiro[2.4]heptane-6-carboxylic acid (prepared according to WO 2009/102325) using procedures similar to that described in examples 1 and 1-1. ESIMS m/z=649.30 [M+H]$^+$.

Example 521

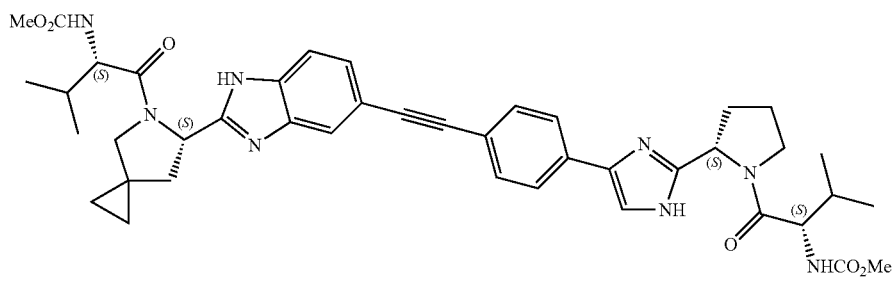

The title compound was prepared from the compound of Example 521 using procedures similar to that described in example 448. ESIMS m/z=763.30 [M+H]$^+$.

Example 522

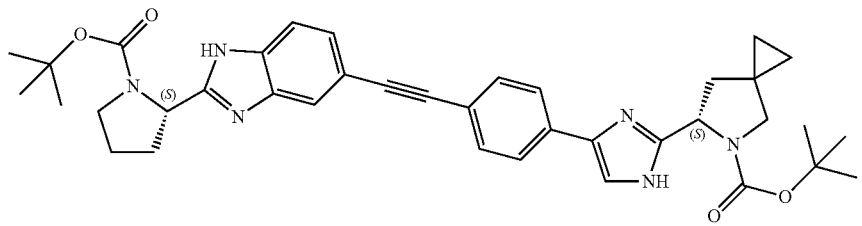

The title compound was prepared from 2,4'-dibromoacetophenone, the compound from step 515d and (6S)-5-[(tert-butoxy)carbonyl]-5-azaspiro[2.4]heptane-6-carboxylic acid (prepared according to WO 2009/102325) using procedures similar to that described in examples 1 and 515. ESIMS m/z=649.35 [M+H]$^+$.

Example 523

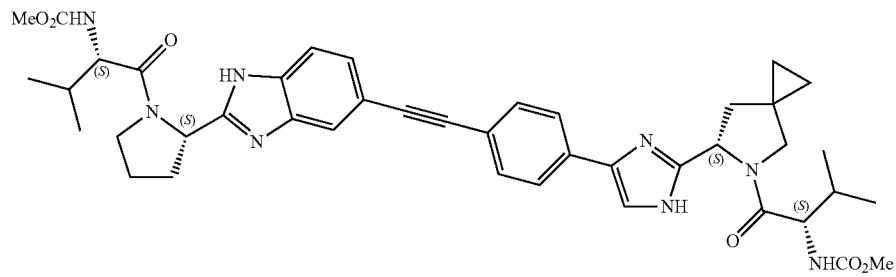

The title compound was prepared from the compound of Example 522 using procedures similar to that described in example 448. ESIMS m/z=763.44 [M+H]$^+$.

Example 524

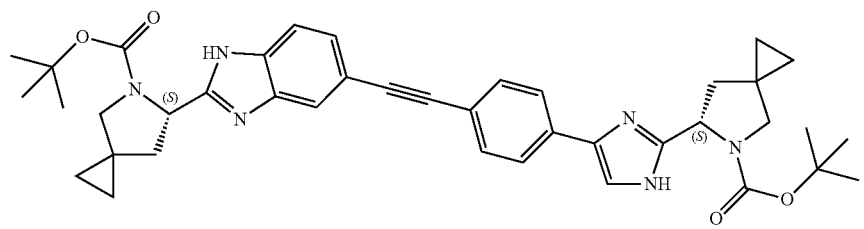

The title compound was prepared from 2,4'-dibromoacetophenone, 4-bromo-1,2-diaminobenzene and (6S)-5-[(tert-butoxy)carbonyl]-5-azaspiro[2.4]heptane-6-carboxylic acid (prepared according to WO 2009/102325) using procedures similar to that described in examples 1 and 515. ESIMS m/z=675.35 [M+H]$^+$.

Example 525

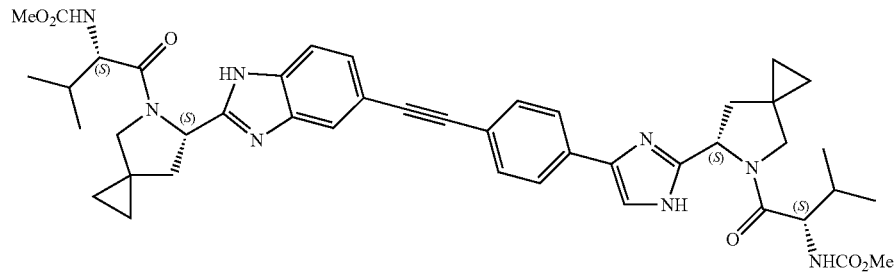

The title compound was prepared from the compound of Example 524 using procedures similar to that described in example 448. ESIMS m/z=789.47 [M+H]$^+$.

Example 526

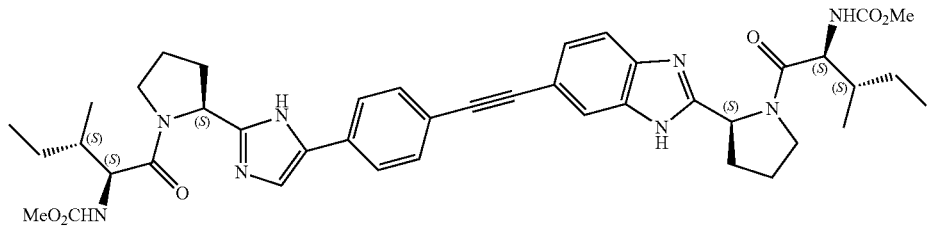

A mixture of the crude compound from step 515f (0.105 mmol at most) and (2S,3S)-2-(methoxycarbonylamino)-3-methylpentanoic acid (prepared by procedure similar to that in step 515g, 35 mg, 0.21 mmol) in acetonitrile (2 mL) was treated with HATU (79 mg, 0.21 mmol) in the presence of DIPEA (0.15 mL, 1.05 mmol) for 2 hours at rt and the volatiles were evaporated off to provide a brown oil. It was purified by flash column chromatography (silica, $CH_2Cl_2$-MeOH) to give the title compound as a yellow solid (60 mg, 2 steps 75%). ESIMS m/z=765.14 $[M+H]^+$.

A mixture of the crude compound from step 480a (0.015 mmol at most) and (S)-2-cyclopropyl-2-(methoxycarbonylamino)acetic acid (prepared by procedure similar to that described in step 515g, 2.6 mg, 0.015 mmol) in acetonitrile (2 mL) was treated with HATU (5.7 mg, 0.015 mmol) in the presence of DIPEA (0.03 mL, 0.15 mmol) for 2 hours at rt and the volatiles were evaporated off to provide a brown oil. It was purified by flash column chromatography (silica, $CH_2Cl_2$-MeOH) to give the title compound as a yellow solid (7.6 mg, 2 steps 69%). ESIMS m/z=735.22 $[M+H]^+$.

Example 527

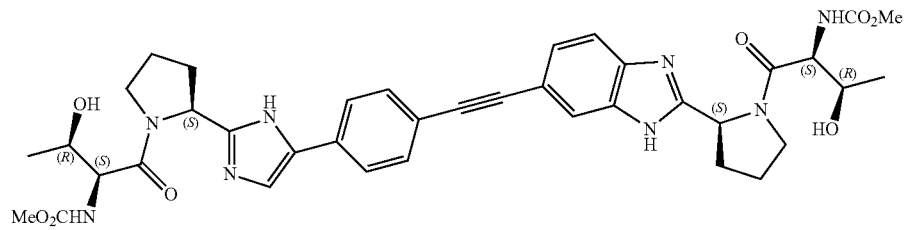

A mixture of the crude compound from step 515f (0.10 mmol at most) and (2S,3R)-3-hydroxy-2-(methoxycarbonylamino)butanoic acid (prepared by procedure similar to that described in step 515g, 35 mg, 0.20 mmol) in DMF (2 mL) was treated with HATU (76 mg, 0.20 mmol) in the presence of DIPEA (0.12 mL, 0.80 mmol) for 2 hours at rt and the volatiles were evaporated off to provide a brown oil. It was purified by flash column chromatography (silica, $CH_2Cl_2$-MeOH) to give the title compound as a yellow solid (64 mg, 2 steps 86%). ESIMS m/z=741.07 $[M+H]^+$.

Example 528

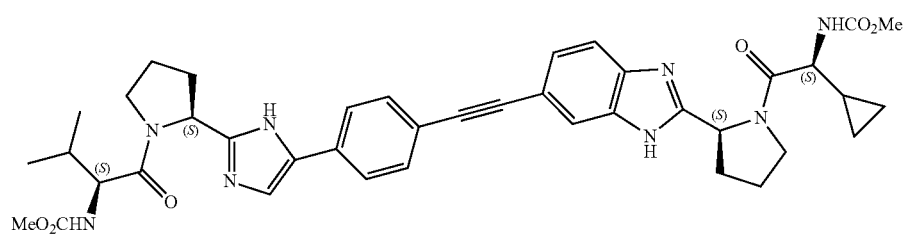

Example 529

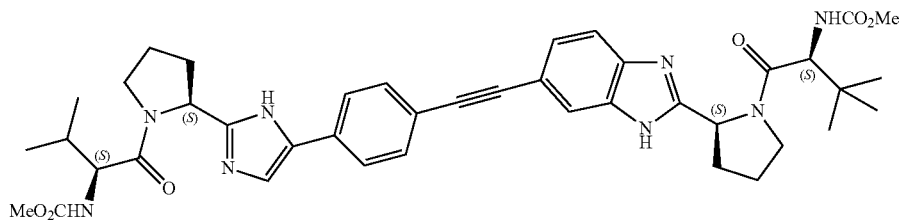

The title compound as a yellow solid (7.9 mg, 2 steps 71%) was prepared from the crude compound from step 480a (0.015 mmol at most) and (S)-2-(methoxycarbonylamino)-3,3-dimethylbutanoic acid (2.8 mg, 0.015 mmol) using the procedures similar to that described in example 528. ESIMS m/z=751.55 [M+H]$^+$.

Example 530

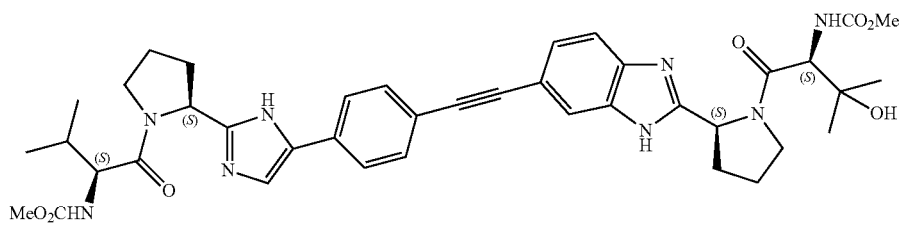

The title compound as a yellow solid (7.3 mg, 2 steps 65%) was prepared from the crude compound from step 480a (0.015 mmol at most) and (S)-3-hydroxy-2-(methoxycarbonyl-amino)-3-methylbutanoic acid (2.8 mg, 0.015 mmol) using the procedures similar to that described in example 528. ESIMS m/z=753.36 [M+H]$^+$.

Example 531

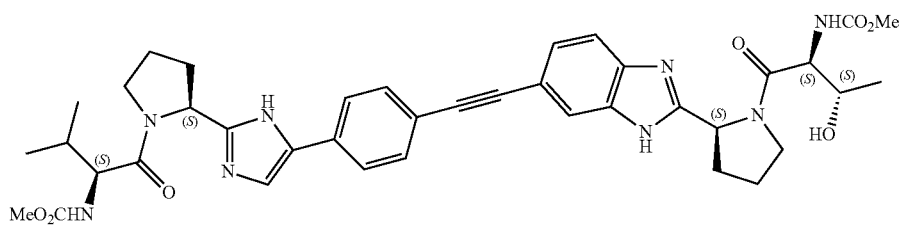

The title compound as a yellow solid (4.0 mg, 2 steps 36%) was prepared from the crude compound from step 480a (0.015 mmol at most) and (2S,3S)-3-hydroxy-2-(methoxycarbonyl-amino)butanoic acid (2.6 mg, 0.015 mmol) using the procedures similar to that described in example 528. ESIMS m/z=739.26 [M+H]$^+$.

Example 532

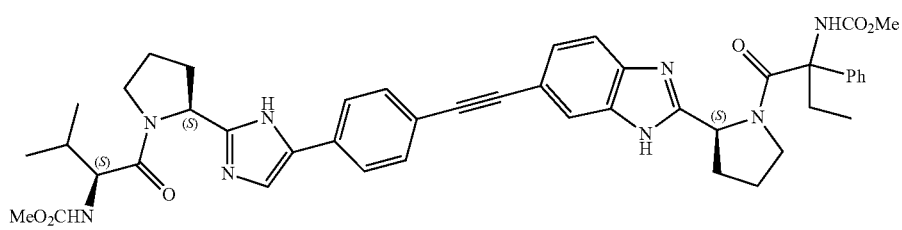

The title compounds as a yellow solid (5.5 mg, 2 steps 46%) was prepared from the crude compound from step 480a (0.015 mmol at most) and 2-(methoxycarbonylamino)-2-phenylbutanoic acid (2.6 mg, 0.015 mmol) using the procedures similar to that described in example 528. ESIMS m/z=799.46 [M+H]⁺.

Example 533

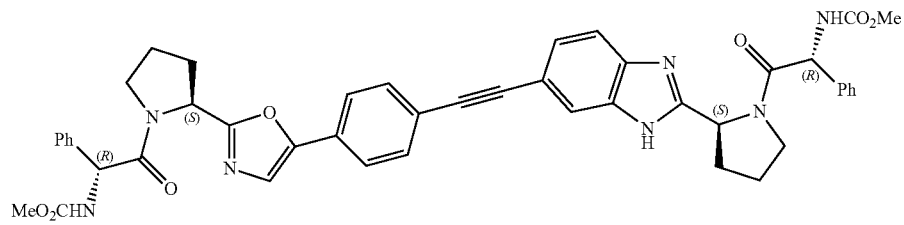

Step 533a.

A mixture of (S)-tert-butyl 2-(5-(4-bromophenyl)oxazol-2-yl)pyrrolidine-1-carboxylate (prepared according to US2008/311075A1, 47.5 mg, 0.12 mmol) and the compound from step 515d (38 mg, 0.12 mg) in triethylamine (10 mL) was added tetrakis(triphenylphosphine)palladium(0) (14 mg, 0.012 mmol) and copper(I) iodide (2 mg, 0.01 mmol). The resulting mixture was purged with nitrogen before being stirred at 100° C. for 12 hours. The mixture was partitioned between water and EtOAc and the organic phase was separated, dried (Na₂SO₄) and concentrated to afford a brown slurry, which was purified by flash column chromatography (silica, hexane-EtOAc) to give the desired product as a light yellow solid (56 mg, 59%). ESIMS m/z=623.95 [M+H]⁺.

Step 533b.

The desired product was prepared from the compound of step 533a using procedures similar to that described in step 2-1a. ESIMS m/z=424.02 [M+H]⁺.

Step 533c.

The title compound was prepared from the compound of step 533b using procedures similar to that described in step 2-1b. ESIMS m/z=805.92 [M+H]⁺.

Example 534

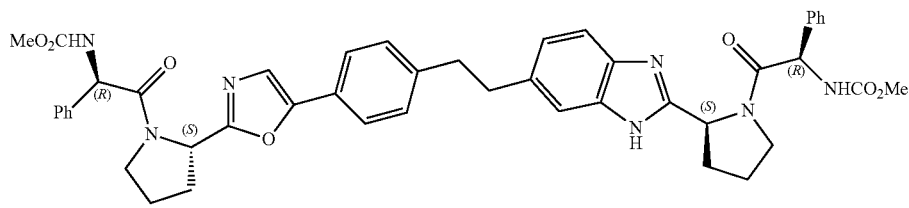

The title compound was prepared from the compound of example 533 using procedures similar to that described in example 2-2. ESIMS m/z=810.10 [M+H]⁺.

Example 535

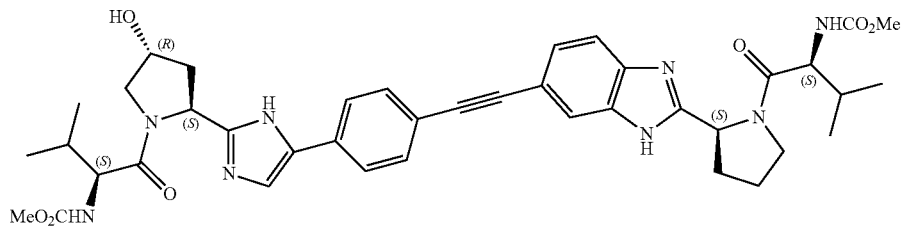

Step 535a.

The desired product was prepared from (2S,4R)-1-(tert-butoxycarbonyl)-4-hydroxypyrrolidine-2-carboxylic acid using procedures similar to that described in step 515a. ESIMS m/z=476.14 [M+H]$^+$.

Step 535b.

The desired product was prepared from the compound of step 535a using procedures similar to that described in step 515b. ESIMS m/z=455.99 [M+H]$^+$.

Step 535c.

The desired product was prepared from the compound of step 535b and the compound of step 515d using procedures similar to that described in step 515e. ESIMS m/z=639.30 [M+H]$^+$.

Step 535d.

The desired product was prepared from the compound of step 535c using procedures similar to that described in step 515f. ESIMS m/z=439.26 [M+H]$^+$.

Step 535e.

The title compound was prepared from the compound of step 535d and the compound of step 515g using procedures similar to that described in step 515h. ESIMS m/z=753.40 [M+H]$^+$.

Example 536

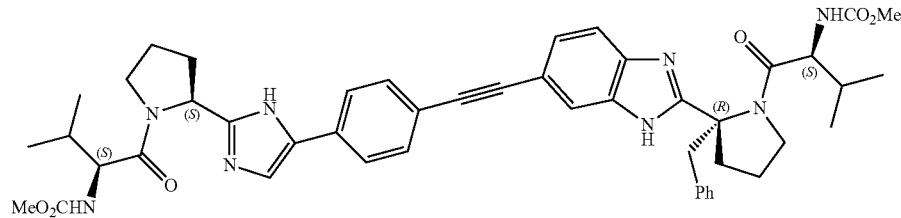

Step 536a.

The mixture of (R)-2-benzyl-1-(tert-butoxycarbonyl)pyrrolidine-2-carboxylic acid (200 mg, 0.66 mmol) and 4-bromo-1,2-diaminobenzene (135 mg, 0.73 mmol) in acetonitrile (2 mL) was added EDC (138 mg, 0.73 mmol) and 4-dimethylaminopyridine (40 mg, 0.2 mmol). The resulting mixture was stirred at room temperature for 1 hour before being partitioned between water and EtOAc. The organic phase was separated, dried (Na$_2$SO$_4$) and concentrated to afford a brown slurry, which was purified by flash column chromatography (silica, hexane-EtOAc) to give the desired product as a light yellow solid (190 mg, 61%). ESIMS m/z=474.18 [M+H]$^+$.

Step 536b.

The desired product was prepared from the compound of step 536a using procedures similar to that described in step 1b. ESIMS m/z=456.17 [M+H]$^+$.

Step 536c.

The desired product was prepared from the compound of step 536b and the compound from step 1-1b using procedures similar to that described in step 1-1c. ESIMS m/z=713.46 [M+H]$^+$.

Step 536d.

The desired product was prepared from the compound of step 536c using procedures similar to that described in step 515f. ESIMS m/z=513.30 [M+H]$^+$.

Step 536e.

The title compound was prepared from the compound of step 536d and the compound from step 515g using procedures similar to that described in step 515h. ESIMS m/z=827.49 [M+H]$^+$.

Example 537

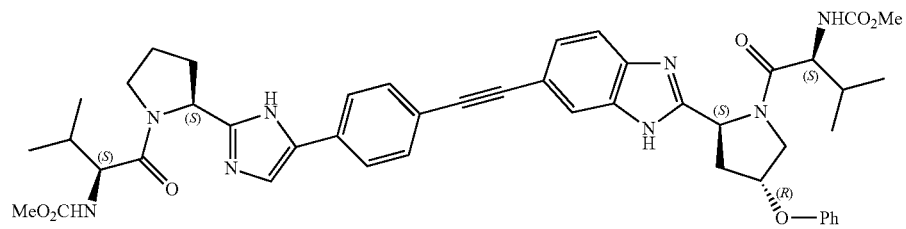

Step 537a.

The desired product was prepared from (2S,4R)-1-(tert-butoxycarbonyl)-4-phenoxypyrrolidine-2-carboxylic acid using procedures similar to that described in step 536a. ESIMS m/z=476.14 [M+H]$^+$.

Step 537b.

The desired product was prepared from the compound of step 537a using procedures similar to that described in step 1b. ESIMS m/z=458.16 [M+H]$^+$.

Step 537c.

The desired product was prepared from the compound of step 537b and the compound of step 1-1b using procedures similar to that described in step 1-1c. ESIMS m/z=715.36 [M+H]$^+$.

Step 537d.

The desired product was prepared from the compound of step 537c using procedures similar to that described in step 515f. ESIMS m/z=515.19 [M+H]⁺.

Step 537e.

The title compound was prepared from the compound from step 537d and the compound from step 515g using procedures similar to that described in step 515h. ESIMS m/z=829.35 [M+H]⁺.

Example 538

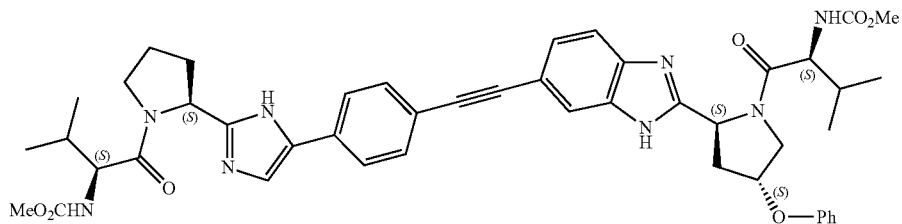

The title compound was prepared from (2S,4S)-1-(tert-butoxycarbonyl)-4-phenoxypyrroli-dine-2-carboxylic acid using procedures similar procedures similar to that described in example 537. ESIMS m/z=829.42 [M+H]⁺.

Example 539

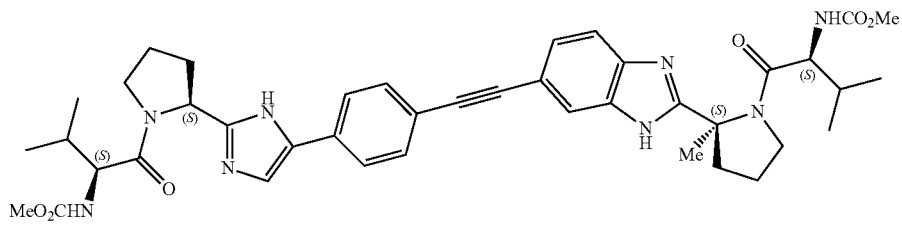

The title compound was prepared from (S)-1-(tert-butoxycarbonyl)-2-methylpyrrolidine-2-carboxylic acid using procedures similar procedures similar to that described in example 536. ESIMS m/z=751.34 [M+H]⁺.

Example 540

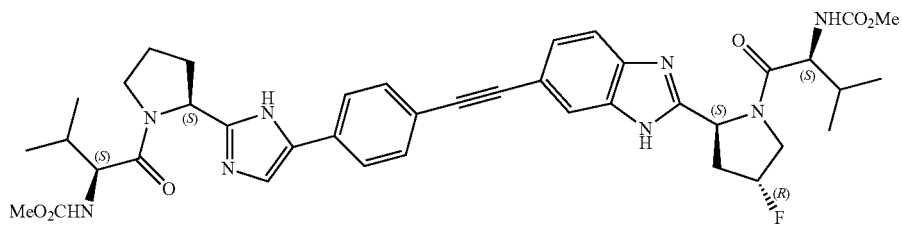

Step 540a.

The desired product was prepared from (2S,4R)-1-(tert-butoxycarbonyl)-4-fluoropyrrolidine-2-carboxylic acid using procedures similar to that described in step 536a. ESIMS m/z=402.07 [M+H]$^+$.

Step 540b.

The desired product was prepared from the compound from step 540a using procedures similar to that described in step 1b. ESIMS m/z=384.09 [M+H]$^+$.

Step 540c.

The desired product was prepared from the compound from step 540b and the compound from step 1-1b using procedures similar to that described in step 1-1c. ESIMS m/z=641.32 [M+H]$^+$.

Step 540d.

The desired product was prepared from the compound from step 540c using procedures similar to that described in step 515f. ESIMS m/z=441.13 [M+H]$^+$.

Step 540e.

The title compound was prepared from the compound from step 540d and the compound from step 515g using procedures similar to that described in step 515h. ESIMS m/z=755.31 [M+H]$^+$.

Example 541

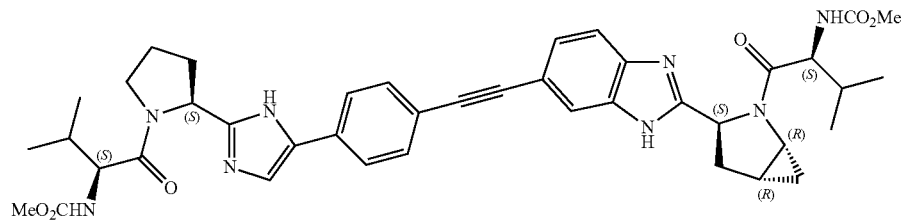

Step 541a.

The desired product was prepared from (1R,3S,5R)-2-(tert-butoxycarbonyl)-2-azabicyclo[3.1.0]hexane-3-carboxylic acid (prepared according to WO2009/102325) using procedures similar to that described in step 536a. ESIMS m/z=396.13 [M+H]$^+$.

Step 541b.

The desired product was prepared from compound 541a using procedures similar to that described in step 1b. ESIMS m/z=378.11 [M+H]$^+$.

Step 541c.

The desired product was prepared from the compound from step 541b and the compound from step 1-1b using procedures similar to that described in step 1-1c. ESIMS m/z=635.43 [M+H]$^+$.

Step 541d.

The desired product was prepared from the compound from step 541c using procedures similar to that described in step 515f. ESIMS m/z=435.31 [M+H]$^+$.

Step 541e.

The title compound was prepared from the compound from step 541d and the compound from step 515g using procedures similar to that described in step 515h. ESIMS m/z=749.45 [M+H]$^+$.

Example 542

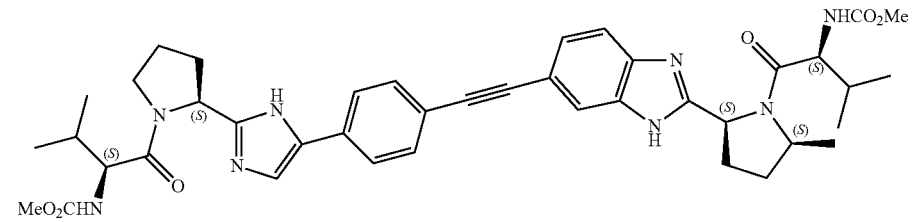

Step 542a.

The desired product was prepared from (2S,5S)-1-(tert-butoxycarbonyl)-5-methylpyrrolidine-2-carboxylic acid (prepared according to *Journal of Medicinal Chemistry* 2009, 49, 3250) using procedures similar to that described in step 536a. ESIMS m/z=398.07 [M+H]$^+$.

Step 542b.

The desired product was prepared from the compound from step 542a using procedures similar to that described in step 1b. ESIMS m/z=380.01 [M+H]$^+$.

Step 542c.

The desired product was prepared from the compound from step 542b and the compound from step 1-1b using procedures similar to that described in step 1-1c. ESIMS m/z=637.39 [M+H]$^+$.

Step 542d.

The desired product was prepared from the compound from step 542c using procedures similar to that described in step 515f. ESIMS m/z=437.26 [M+H]$^+$.

Step 542e.

The title compound was prepared from the compound from step 542d and the compound from step 515g using procedures similar to that described in step 515h. ESIMS m/z=751.44 [M+H]$^+$.

Example 543

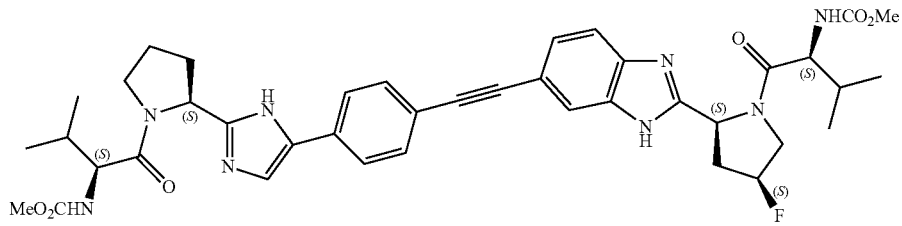

The title compound was prepared from (2S,4S)-1-(tert-butoxycarbonyl)-4-fluoropyrrolidine-2-carboxylic acid using procedures similar procedures similar to that described in example 540. ESIMS m/z=755.42 [M+H]⁺.

Example 544

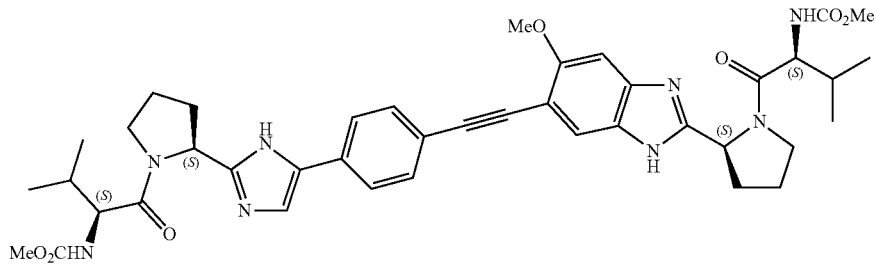

Step 544a.

The desired product was prepared from (S)-1-(tert-butoxycarbonyl)pyrrolidine-2-carboxylic acid and 4-bromo-5-methoxybenzene-1,2-diamine (prepared according to *Journal of Medicinal Chemistry* 1997, 40, 730) using procedures similar procedures similar to that described in step 536a. ESIMS m/z=414.10 [M+H]⁺.

Step 544b.
The desired product was prepared from the compound from step 544a using procedures similar procedures similar to that described in step 1b. ESIMS m/z=396.06 [M+H]⁺.

Step 544c.
The desired product was prepared from the compound from step 544b and the compound from step 1-1b using procedures similar procedures similar to that described in step 1-1c. ESIMS m/z=653.39 [M+H]⁺.

Step 544d.

The desired product was prepared from the compound from step 544c using procedures similar procedures similar to that described in step 515f. ESIMS m/z=453.27 [M+H]⁺.

Step 544e.

The title compound was prepared from the compound from step 544d and the compound from step 515g using procedures similar procedures similar to that described in step 515h. ESIMS m/z=767.47 [M+H]⁺.

Example 545

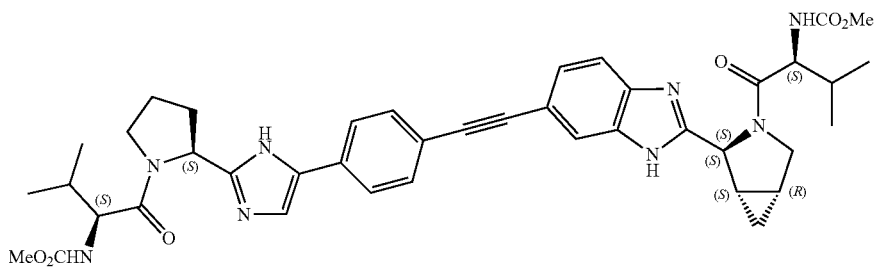

Step 545a.

The desired product was prepared from (1S,2S,5R)-3-(tert-butoxycarbonyl)-3-azabicyclo[3.1.0]hexane-2-carboxylic acid (prepared according to *J. Org. Chem.,* 1999, 64, 547) using procedures similar to that described in step 536a. ESIMS m/z=396.25 [M+H]⁺.

Step 545b.

The desired product was prepared from the compound from step 545a using procedures similar to that described in step 1b. ESIMS m/z=378.21 [M+H]+.

Step 545c.

The desired product was prepared from the compound from step 545b and the compound from step 1-1b using procedures similar to that described in step 1-1c. ESIMS m/z=635.33 [M+H]+.

Step 545d.

The desired product was prepared from the compound from step 545c using procedures similar to that described in step 1f. ESIMS m/z=435.28 [M+H]+.

Step 545e.

The title compound was prepared from the compound from step 545d and the compound from step 515g using procedures similar to that described in step 515h. ESIMS m/z=749.44 [M+H]+.

Example 548

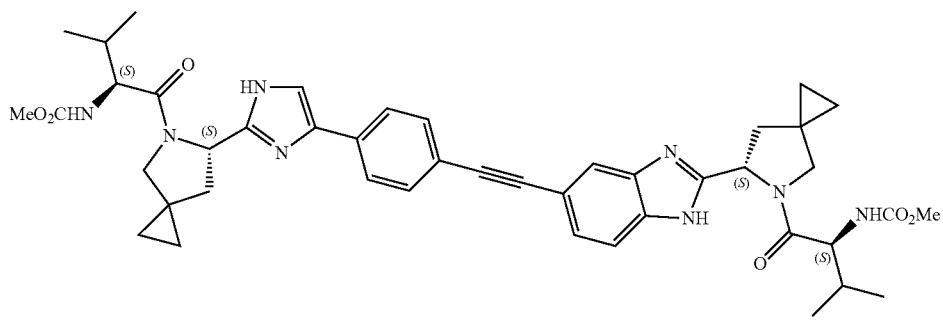

Step 548a.

To a solution of (6S)-5-[(tert-butoxy)carbonyl]-5-azaspiro[2.4]heptane-6-carboxylic acid (prepared according to WO 2009/102325, 3.210 g, 13.30 mmol) and 2-bromo-1-(4-iodophenyl)ethanone (5.044 g, 13.97 mmol) in acetonitrile (100 mL) was added DIPEA (5.79 mL, 33.26 mmol) dropwise. The resulting solution was stirred at rt for 3 hours before being concentrated. The residue was purified by chromatography (silica, hexanes-ethyl acetate) to afford the desired compound as a yellow foam (6.191 g, 96%). ESIMS m/z=486.26 [M+H]+.

Step 548b.

To a solution of the compound from step 548a (6.191 g, 12.76 mmol) in toluene (60 mL) was added ammonium acetate (10.82 g, 0.140 mol). The resulting mixture was heated at 110° C. for 15 hours before being cooled down and concentrated. The residue was partitioned (EtOAc—H$_2$O). The organic phase was washed with brine, dried (Na$_2$SO$_4$), filtered and concentrated. The crude product was purified by chromatography (silica, hexanes-ethyl acetate) to afford the desired compound as a yellow foam (5.730 g, 96%). ESIMS m/z=466.26 [M+H]+.

Step 548c.

To a solution of (6S)-5-[(tert-butoxy)carbonyl]-5-azaspiro[2.4]heptane-6-carboxylic acid (prepared according to WO 2009/102325, 10.00 g, 41.45 mmol) and 1,2-diaminobenzene (8.527 g, 45.59 mmol) in CH$_3$CN (250 mL) at rt was added EDC.HCl (10.33 g, 53.88 mmol), followed by DMAP (0.506 g, 4.145 mmol). The mixture was stirred at rt overnight before being concentrated. The residue was purified by chromatography (silica, EtOAc-hexanes) to give the desired compound as a yellow foam (15.04 g, 88%). ESIMS m/z=410.36, 412.36 [M+H]+.

Step 548d.

A solution of the compound from step 548c (3.270 g, 7.970 mmol) in glacial acetic acid (50 mL) was heated at 50° C. for 8 hours. The volatiles were evaporated off. The residue was purified by chromatography (silica, hexanes-ethyl acetate) to give the desired compound as a yellow foam (3.120 g, 100%). ESIMS m/z=392.12, 394.12 [M+H]+.

Step 548e.

A mixture of the compound from step 548d (3.120 g, 7.953 mmol), trimethylsilylacetylene (16.86 ml, 0.119 mol), CuI (45.4 mg, 0.239 mmol) and Pd(PPh$_3$)$_4$ (0.459 g, 0.398 mmol) in Et$_3$N (100 mL) was degassed and then heated at 90° C. under N$_2$ overnight. More trimethylsilylacetylene (5.62 ml, 39.67 mmol) was added. The mixture was heated at 90° C. for 4 more hours before being evaporated. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a yellow foam (2.820 g, 87%). ESIMS m/z=410.41 [M+H]+.

Step 548f.

A suspension of the compound from step 548e (14.20 g, 34.67 mmol) and K$_2$CO$_3$ (11.98 g, 86.67 mmol) in methanol (200 ml) was stirred at rt for 2.5 hours. The volatiles were evaporated off. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a yellow foam (10.818 g, 92%). ESIMS m/z=338.25 [M+H]+.

Step 548g.

A mixture of the compound from step 548b (3.282 g, 7.054 mmol), the compound from step 548f (2.380 g, 7.054 mmol), Pd(PPh$_3$)$_4$ (0) (0.407 g, 0.353 mmol) and copper(I) iodide (40.3 mg, 0.212 mmol) in triethylamine (40 mL) and acetonitrile (40 mL) was degassed and then heated at 35° C. for 15 hours under N$_2$. The mixture was concentrated. The residue was purified by chromatography (silica, hexanes-EtOAc, with 1% Et$_3$N in EtOAc) to give the desired compound as a yellow solid (4.160 g, 87%). ESIMS m/z=675.58 [M+H]+.

Step 548h.

A solution of the compound from step 548g (4.160 g, 6.165 mmol) in CH$_2$Cl$_2$/MeOH (3/1, 40 mL) was treated with HCl in 1,4-dioxane (4 M, 70 mL) for 2 hours. The volatiles were evaporated off to give the crude desired compound as a yellow solid, which was used directly in the next step.

Step 548i.

A mixture of the crude compound from step 548h (6.165 mmol at most) and the compound from step 515g (2.160 g, 12.33 mmol) in DMF (40 mL) was treated with HATU (4.453 g, 11.71 mmol) in the presence of DIPEA (21.47 mL, 0.1233 mol) for 1 hour at rt. The volatiles were evaporated off. The residue was partitioned (EtOAc/CH$_2$Cl$_2$—H$_2$O). The organics were washed with brine, dried (Na$_2$SO$_4$), filtered and evaporated. The residue was purified by chromatography (silica, EtOAc-MeOH) to give the title compound as a yellow solid (4.000 g, 85% over 2 steps). ESIMS m/z=789.68 [M+H]$^+$.

Example 630

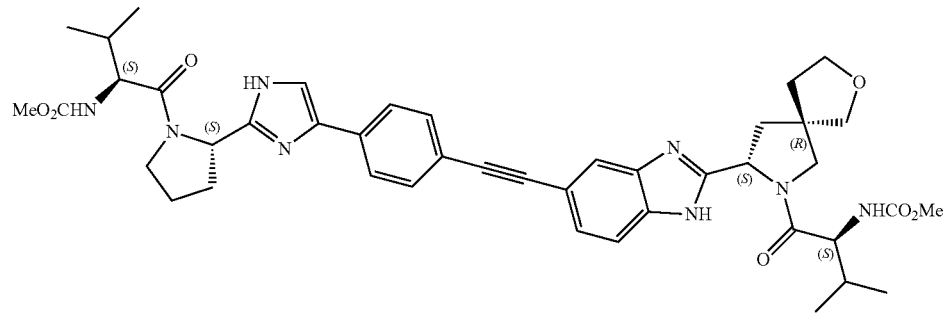

Step 630a.

To a mixture of 2-bromo-1-(4-iodophenyl)ethanone (5.00 g, 15.4 mmol) and N-Boc-L-proline (3.48 g, 16.1 mmol) in acetonitrile (40 mL) was added diisopropylethylamine (2.4 mL, 17 mmol). The resulting mixture was stirred at rt for 3 hours before being partitioned (EtOAc-aqueous NaHCO$_3$). The organic phase was washed with brine, dried (Na$_2$SO$_4$) and concentrated to afford a brown oil. It was purified by chromatography (silica, hexanes-ethyl acetate) to give the desired compound as a light yellow oil (6.00 g, 86%). ESIMS m/z=481.94 [M+Na]$^+$.

Step 630b.

A mixture of the compound from step 630a (6.00 g, 12.5 mmol) and ammonium acetate (15.1 g, 196 mmol) in toluene (80 mL) was stirred at 80° C. for 3 hours before being partitioned (EtOAc-aqueous NaHCO$_3$). The organic phase was washed with brine, dried (Na$_2$SO$_4$) and concentrated to afford a deep red oil. It was purified by chromatography (silica, hexanes-ethyl acetate) to give the desired compound as a light yellow solid (5.34 g, 93%). ESIMS m/z=439.83 [M+H]$^+$.

Step 630c.

To a solution of LiHMDS (1.0 M in THF, 5.17 mL, 5.17 mmol) in THF (20 mL) at −78° C. was added a solution of (+)-(3R,7aS)-tetrahydro-3-phenyl-3H,5H-pyrrolo[1,2-c]oxazol-5-one (0.500 g, 2.460 mmol) in THF (10 mL) under N$_2$. The mixture was stirred at −78° C. for 30 min before ClCO$_2$Me (0.19 mL, 2.460 mmol) was added at −78° C. After 30 minutes at −78° C., the reaction was quenched with saturated NH$_4$Cl solution. The mixture was allowed to warm up to rt and the volatiles were evaporated. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a colorless oil (0.598 g, 93%). ESIMS m/z=262.13 [M+H]$^+$.

Step 630d.

To a solution of the compound from step 630c (0.350 g, 1.340 mmol) in THF (13 mL) at 0° C. was added NaH (60% in mineral oil, 64.3 mg, 1.607 mmol). After addition, the cooling bath was removed. The mixture was stirred at rt for 15 minutes before allyl bromide (0.13 mL, 1.474 mmol) was added. After 1 hour at rt, the reaction was quenched with saturated NH$_4$Cl solution. The mixture was partitioned (EtOAc—H$_2$O). The organics were washed with brine, dried (Na$_2$SO$_4$), filtered and evaporated. The residue was purified by chromatography (silica, hexanes-ethyl acetate) to give the desired compounds as two separated diastereomers: minor diastereomer (less polar, 56.0 mg, 14%), (3R,6R,7aS)-methyl 6-allyl-5-oxo-3-phenylhexahydropyrrolo[1,2-c]oxazole-6-carboxylate, ESIMS m/z=302.19 [M+H]$^+$; $^1$H NMR (CDCl$_3$) 7.44-7.33 (m, 5H), 6.32 (s, 1H), 5.75-5.66 (m, 1H), 5.19-5.18 (m, 1H), 5.16 (s, 1H), 4.28-4.22 (m, 2H), 3.78 (s, 3H), 3.57-3.52 (m, 1H), 2.90 (dd, J=6.7, 13.4 Hz, 1H), 2.85 (dd, J=7.9, 14.1 Hz, 1H), 2.58 (dd, J=6.7, 14.1 Hz, 1H), 1.89 (dd, J=6.6, 13.2 Hz, 1H); major diastereomer (more polar, 0.222 g, 55%), (3R,6S,7aS)-methyl 6-allyl-5-oxo-3-phenylhexahydropyrrolo[1,2-c]oxazole-6-carboxylate, ESIMS m/z=302.19 [M+H]$^+$; $^1$H NMR (CDCl$_3$) 7.46-7.33 (m, 5H), 6.33 (s, 1H), 5.82-5.73 (m, 1H), 5.23-5.18 (m, 2H), 4.28 (dd, J=6.2, 6.5 Hz, 1H), 4.08-4.02 (m, 1H), 3.82 (s, 3H), 3.67 (t, J=8.3 Hz, 1H), 2.80 (dd, J=7.5, 14.0 Hz, 1H), 2.71 (dd, J=7.1, 14.0 Hz, 1H), 2.54 (dd, J=4.9, 12.8 Hz, 1H), 2.38 (dd, J=7.9, 13.8 Hz, 1H).

Step 630e.

To a solution of the major diastereomer from step 630d (0.160 g, 0.585 mmol) in THF/H$_2$O (1/1, 6 mL) at rt was added OsO$_4$ (4 wt % in H$_2$O, 7.5 μL, 0.012 mmol), followed by NaIO$_4$ (0.263 g, 1.229 mmol). The resulting mixture was stirred at rt for 2 hours before being quenched with saturated Na$_2$S$_2$O$_3$ solution. The mixture was partitioned (EtOAc—H$_2$O). The organics were washed with brine, dried (Na$_2$SO$_4$), filtered and evaporated to afford the desired compound as a cololess oil (0.133 g), which was used directly for next step.

Step 630f.

To a solution of the compound from step 630e (0.133 g, 0.438 mmol at most) in EtOH (5 mL) at 0° C. was added NaBH$_4$ (33.2 mg, 0.877 mmol). After 20 minutes at 0° C., the resulting mixture was stirred at rt for 2.5 hours. More NaBH$_4$ (16.6 mg, 0.438 mmol) was added. After 2 hours at rt, the reaction was quenched with saturated NH$_4$Cl solution. The volatiles were evaporated. The residue was taken up in EtOAc (with 5% MeOH) and filtered. The filtrate was evaporated to dryness. The residue was purified by chromatography (silica, EtOAc-MeOH) to give the desired compound as a white foam (67.6 mg, 46% over 2 steps). ESIMS m/z=278.17 [M+H]$^+$.

Step 630g.

To a solution of the compound from step 630f (0.793 g, 2.860 mmol) in pyridine (28 mL) at rt was added tosyl chloride (TsCl, 0.600 g, 3.145 mmol). The resulting solution was stirred at rt for 40 hours. More TsCl (0.600 g, 3.145 mmol) was added. After 24 hours at rt, the reaction was quenched with saturated NaHCO$_3$ solution. The mixture was evaporated to dryness. The residue was taken up in CH$_2$Cl$_2$ and filtered. The filtrate was directly purified by chromatography (silica, hexanes-ethyl acetate) to give the desired compound as a colorless oil (0.511 g, 69%). ESIMS m/z=260.16 [M+H]$^+$.

Step 630h.

To a solution of the compound from step 630g (0.540 g, 2.082 mmol) in THF (20 mL) at rt was added LiAlH$_4$ (1.0 M in Et$_2$O, 4.16 mL, 4.16 mmol). The resulting mixture was heated at 60° C. for 2 hours before being cooled down. The reaction was quenched by carefully adding H$_2$O (0.16 mL), followed by 15% NaOH solution (0.16 mL) and then H$_2$O (0.32 mL). The suspension was filtered through a short pad of Celite. The filtrate was evaporated to give the desired compound as a white semi-solid (0.572 g), which was used directly for the next step. ESIMS m/z=248.20 [M+H]$^+$.

Step 630i.

To a solution of the compound from step 630h (2.082 mmol at most) in MeOH (15 mL) at rt was added HOAc (0.16 mL, 2.71 mmol), followed by Pd/C (10 wt %, 0.100 g). The resulting mixture was stirred at rt under H$_2$ (60 psi) for 2 hours before being filtered throught a short pad of Celite. The filtrate was evaporated to give the desired compound as a colorless oil, which was used directly for the next step. ESIMS m/z=158.11 [M+H]$^+$.

Step 630j.

To a solution of the compound from step 630i (2.082 mmol at most) in 1,4-dioxane/H$_2$O (1/2, 21 mL) at rt was added NaHCO$_3$ (1.399 g, 16.66 mmol), followed by (Boc)$_2$O (0.545 g, 2.498 mmol). The resulting mixture was stirred at rt for 15 hours. The volatiles were evaporated. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a colorless oil (0.252 g, 45% over 3 steps). ESIMS m/z=258.18 [M+H]$^+$.

Step 630k.

To a biphasic mixture of the compound from step 630j (0.252 g, 0.979 mmol) in CCl$_4$/CH$_3$CN/H$_2$O (3/4/5, 12 mL) at rt was added RuCl$_3$.xH$_2$O (4.1 mg, 0.020 mmol), followed by NaIO$_4$ (0.419 g, 1.959 mmol). The resulting mixture was stirred at rt for 2 hours. The volatiles were evaporated. The residue was taken up in EtOAc and filtered. The filtrate was washed with brine, dried (Na$_2$SO$_4$) and filtered. The solid from the filtration was dissolved in diluted brine, acidified to pH ~2 and extracted with EtOAc. The combined organics were washed with brine, dried (Na$_2$SO$_4$), filtered and evaporated. The residue was purified by chromatography (silica, EtOAc-MeOH) to give the desired compound as a colorless oil (0.260 g, 98%). ESIMS m/z=272.24 [M+H]$^+$.

Step 630l.

A mixture of the compound from step 630k (0.260 g, 0.958 mmol) and 4-bromo-1,2-diaminobenzene (0.197 g, 1.054 mmol) in CH$_3$CN (6 mL) was treated with EDC.HCl (0.239 g, 1.246 mmol) and DMAP (11.7 mg, 0.096 mmol) at rt. The mixture was stirred at rt for 3 hours before being evaporated. The residue was purified by chromatography (silica, hexanes-ethyl acetate) to give the desired compound as a yellow foam (0.277 g, 64%). ESIMS m/z=440.29, 442.29 [M+H]$^+$.

Step 630m.

A solution of the compound from step 630l (0.277 g, 0.629 mmol) in glacial acetic acid (7 mL) was heated at 50° C. for 15 hours. The volatiles were evaporated off. Et$_3$N (5 mL) was added and the mixture was evaporated again. The residue was purified by chromatography (silica, hexanes-ethyl acetate, with 1% Et$_3$N in ethyl acetate) to give the desired compound as a yellow foam (0.247 g, 93%). ESIMS m/z=422.15, 424.15 [M+H]$^+$.

Step 630n.

A mixture of the compound from step 630m (0.247 g, 0.585 mmol), trimethylsilyl-acetylene (1.24 mL, 8.772 mmol), CuI (3.3 mg, 0.018 mmol) and Pd(PPh$_3$)$_4$ (33.8 mg, 0.029 mmol) in Et$_3$N (8 mL) was degassed and then heated at 90° C. under N$_2$ overnight. More trimethylsilyl-acetylene (0.41 mL, 2.924 mmol) and CH$_3$CN (3 mL) were added. The mixture was heated at 90° C. for 1.5 hours before being cooled down and evaporated. The residue was purified by chromatography (silica, hexanes-ethyl acetate) to give the desired compound as a yellow oil (0.270 g). ESIMS m/z=440.22 [M+H]$^+$.

Step 630o.

A suspension of the compound from step 630n (0.270 g, 0.585 mmol at most) and K$_2$CO$_3$ (0.202 g, 1.462 mmol) in methanol (6 mL) was stirred at rt for 2 hours. The volatiles were evaporated off. The residue was taken up in CH$_2$Cl$_2$ and filtered through a short pad of Celite. The filtrate was directly purified by chromatography (silica, hexanes-ethyl acetate) to give the desired compound as a yellow foam (0.186 g, 87% over 2 steps). ESIMS m/z=368.21 [M+H]$^+$.

Step 630p.

The title compound was prepared from the compound from step 630b and the compound from step 630o using procedures similar to that described in steps 548g, 548h and 548i. ESIMS m/z=793.46 [M+H]$^+$.

Example 631

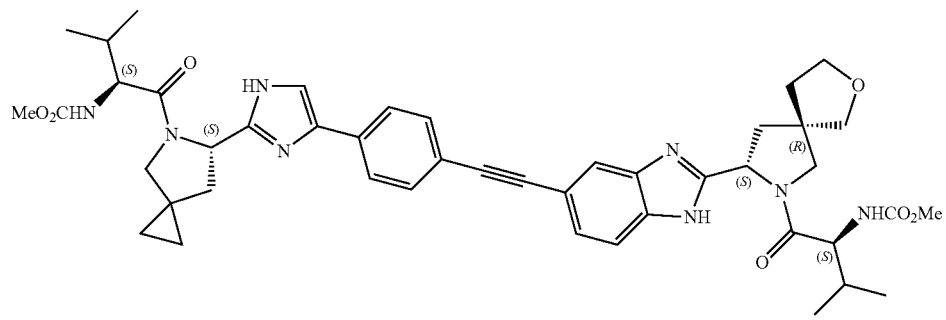

The title compound was prepared from the compound from step 548b and compound from step 630o using procedures similar to that described in steps 548g, 548h and 548i. ESIMS m/z=819.55 [M+H]$^+$.

Example 565

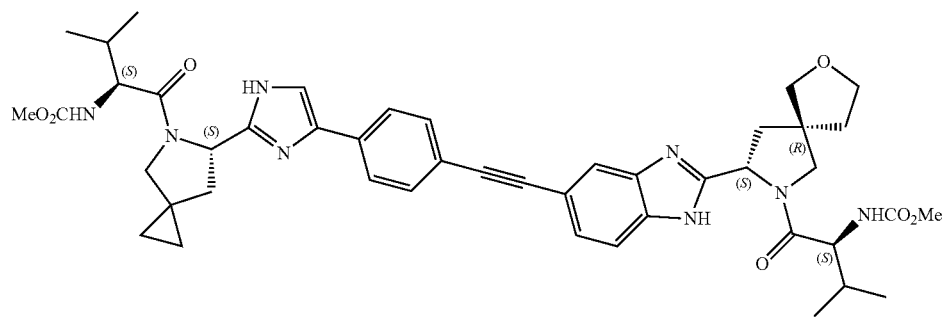

Step 565a.

A mixture of compound from step 548b (1.348 g, 2.897 mmol), trimethylsilylacetylene (0.66 mL, 4.635 mmol), CuI (16.6 mg, 0.0869 mmol) and Pd(PPh$_3$)$_4$ (0.167 g, 0.145 mmol) in Et$_3$N (20 mL) and CH$_3$CN (20 mL) was degassed and then heated at 40° C. under N$_2$ for 15 hours before being cooled down and evaporated. The residue was purified by chromatography (silica, hexanes-ethyl acetate) to give the desired compound as a yellow foam (1.210 g, 96%). ESIMS m/z=436.25 [M+H]$^+$.

Step 565b.

A suspension of the compound from step 565a (1.210 g, 2.778 mmol) and K$_2$CO$_3$ (0.960 g, 6.944 mmol) in methanol (30 mL) was stirred at rt for 2.5 hours. The volatiles were evaporated off. The residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a yellow foam (0.925 g, 92%). ESIMS m/z=364.18 [M+H]$^+$.

Step 565c.

A mixture of (5S,8S)-7-(tert-butoxycarbonyl)-2-oxa-7-azaspiro[4.4]nonane-8-carboxylic acid (prepared from the minor diastereomer from step 630d following the procedures similar to that described from step 630e to step 630k, 0.289 g, 1.115 mmol) and 1,2-diamino-4-iodobenzene (0.287 g, 1.226 mmol) in CH$_3$CN (10 mL) was treated with EDC.HCl (0.278 g, 1.449 mmol) and DMAP (13.6 mg, 0.112 mmol) at rt. The mixture was stirred at rt for 2.5 hours before being evaporated. The residue was purified by chromatography (silica, hexanes-ethyl acetate) to give the desired compound as a yellow solid (0.377 g, 69%). ESIMS m/z=488.16 [M+H]$^+$.

Step 565d.

A solution of the compound from step 565c (0.377 g, 0.774 mmol) in glacial acetic acid (8 mL) was heated at 50° C. for 15 hours. The volatiles were evaporated off. Et$_3$N (5 mL) was added and the mixture was evaporated again. The residue was purified by chromatography (silica, hexanes-ethyl acetate, with 1% Et$_3$N in ethyl acetate) to give the desired compound as a yellow foam (0.324 g, 89%). ESIMS m/z=470.12 [M+H]$^+$.

Step 565e.

The title compound was prepared from the compound from step 565b and the compound from step 565d using procedures similar to that described in steps 548g, 548h and 548i. ESIMS m/z=819.41 [M+H]$^+$.

Example: 564

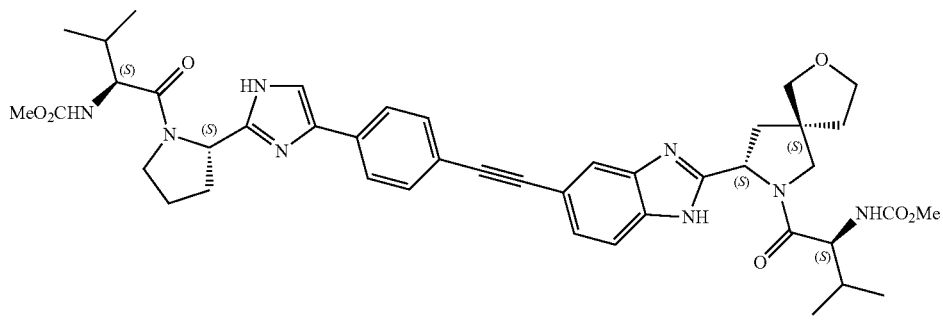

The title compound was prepared from the compound from step 630b and compound from step 565d using procedures similar to that described in example 565. ESIMS m/z=793.48 [M+H]⁺.

Example 571

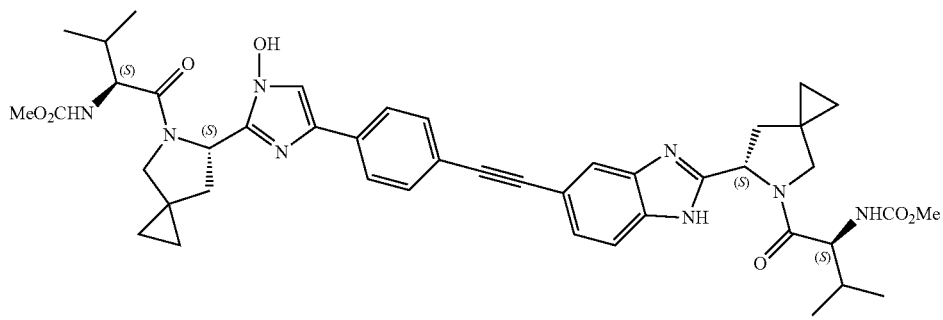

Step 571a.
To a solution of 4'-iodoacetophenone (4.000 g, 16.26 mmol) in THF (65 mL) cooled at 0° C. was added isopentyl nitrile (4.55 mL, 32.51 mmol), followed by HCl in 1,4-dioxane (4 M, 5.28 mL, 21.13 mmol). The resulting red solution was stirred at 0° C. for 30 minutes and then at rt for 6 hours before being concentrated. The residue was partitioned (Et₂O-saturated NaHCO₃). The organics were washed with brine, dried (Na₂SO₄), filtered and evaporated. The residue was purified by chromatography (silica, CH₂Cl₂-ethyl acetate) to give the desired compound 2-(4-iodophenyl)-2-oxoacetaldehyde oxime as a yellow solid (1.530 g, 34%).

Step 571b.
A mixture of the compound from step 571a (0.183 g, 0.666 mmol), (S)-tert-butyl 6-formyl-5-azaspiro[2.4]heptane-5-carboxylate (prepared according to WO 2011/006960, 0.150 g, 0.666 mmol) and ammonium acetate (0.257 g, 3.329 mmol) in glacial acetic acid (4 mL) was stirred at 120° C. for 1.5 hours before being cooled down and concentrated. The residue was purified by chromatography (silica, hexanes-ethyl acetate) to give the desired compound (S)-tert-butyl 6-(1-hydroxy-4-(4-iodophenyl)-1H-imidazol-2-yl)-5-azaspiro[2.4]heptane-5-carboxylate as a yellow sticky oil (0.106 g, 33%). ESIMS m/z=482.09 [M+H]⁺.

Step 571c.
The title compound was prepared from the compound from step 571b and the compound from step 548f using procedures similar to that described in steps 548g, 548h and 548i. ESIMS m/z=805.55 [M+H]⁺.

Example 640

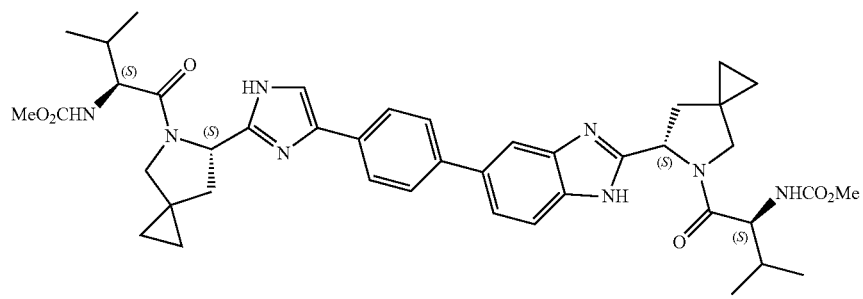

The title compound was prepared from (6S)-5-[(tert-butoxy)carbonyl]-5-azaspiro[2.4]heptane-6-carboxylic acid (prepared according to WO 2009/102325) and the compound from step 515g using procedures similar to that described in examples 1-1 and 1-2. ESIMS m/z=765.49 [M+H]+.

Example 692

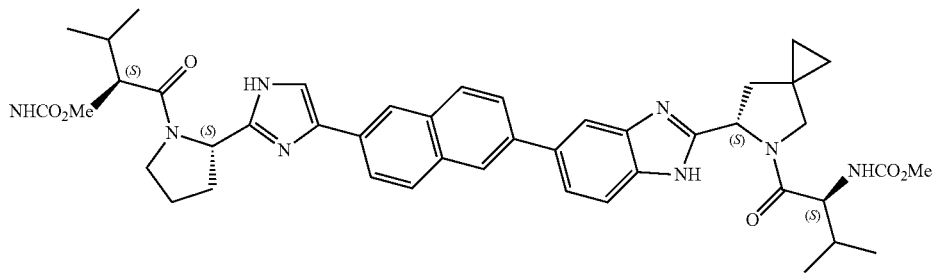

Step 692a.

To a mixture of the compound from step 489a (89.8 mg, 0.184 mmol), the compound from step 548d (60.0 mg, 0.153 mmol) and NaHCO3 (45.0 mg, 0.535 mmol) in DME (3 mL) and H2O (1 mL) was added Pd(PPh3)4 (17.7 mg, 15.3 μmol). The resultant mixture was degassed and then heated at 98° C. under N2 for 3 hours before being cooled down. The volatiles were evaporated off. The residue was taken up in dichloromethane and filtered. The filtrate was directly purified by chromatography (silica, hexanes-ethyl acetate, with 2% MeOH and 1% Et3N in ethyl acetate) to give the desired compound as a yellow solid (84.2 mg, 82%). ESIMS m/z=675.33 [M+H]+.

Step 692b.

The title compound was prepared from the compound from step 592a using procedures similar to that described in steps 548h and 548i. ESIMS m/z=789.40 [M+H]+.

Example 574

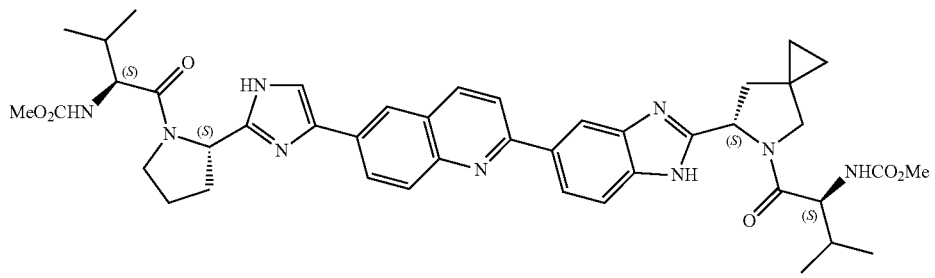

Step 574a.

To a solution of (6S)-5-[(tert-butoxy)carbonyl]-5-azaspiro[2.4]heptane-6-carboxylic acid (91.5 g, 0.379 mol) in dichloromethane (900 mL) was added HOBt.xH2O (66.6 g, 0.493 mol), followed by EDC.HCl (87.2 g, 0.455 mol). The solution was stirred at rt for 5 minutes before being added to a solution of 1,2-diamino-4-iodobenzene (97.6 g, 0.417 mol) in dichloromethane (450 mL) at rt. The mixture was stirred at rt overnight before being quenched with saturated NaHCO3 and partitioned. The organics were washed with H2O, dried (Na2SO4), filtered and evaporated. The residue was purified by chromatography (silica, hexanes-ethyl acetate) to give the desired compound as a light brown foam (159.6 g, 92%). ESIMS m/z=458.05 [M+H]+.

Step 574b.

A solution of the compound from step 574a (159.3 g, 0.348 mol) in glacial acetic acid (1.3 L) was heated at 55° C. for 3 hours. The volatiles were evaporated off. The residue was partitioned (EtOAc-saturated NaHCO3). The organics were washed with brine, dried (Na2SO4), filtered and evaporated. The residue was purified by chromatography (silica, hexanes-ethyl acetate) to give the desired compound as a light orange foam (128.5 g, 84%). ESIMS m/z=440.15 [M+H]+.

Step 574c.

A mixture of the compound from step 574b (3.500 g, 7.967 mmol), bis(pinacolato)diboron (2.529 g, 9.959 mmol), KOAc (1.564 g, 15.93 mmol) and PdCl2(dppf) (0.291 g, 0.398 mmol) in DMSO (40 mL) was degassed and then heated at 60° C. for 4 hours and then at 70° C. for 1.5 hours under N2 before being cooled down. The mixture was partitioned (EtOAc—50% brine). The organics were washed with brine, dried (Na2SO4), filtered and evaporated. The residue was purified by chromatography (silica, hexanes-ethyl acetate) to give the desired compound as a yellow foam (2.370 g, 68%). ESIMS m/z=440.28 [M+H]+.

Step 574d.

A mixture of the compound from step 574c (0.150 g, 0.619 mmol), 6-bromo-2-chloroquinoline (0.272 g, 0.619 mmol), NaHCO3 (0.182 g, 2.165 mmol) and Pd(PPh3)4 (71.5 mg, 61.9 μmol) in DME (4.5 mL) and H2O (1.5 mL) was degassed and then heated at 98° C. under N2 for 3 hours before being cooled down. The volatiles were evaporated. The residue was taken up in dichloromethane and filtered. The filtrate was directly purified by chromatography (silica, hexanes-ethyl acetate) to give the desired compound as a yellow solid (0.307 g, 96%). ESIMS m/z=519.13, 521.12 [M+H]+.

Step 574e.

A mixture of the compound from step 574d (0.200 g, 0.385 mmol), bis(pinacolato)diboron (0.147 g, 0.578 mmol), KOAc (94.5 mg, 0.963 mmol) and Pd(PPh₃)₄ (22.2 mg, 0.0193 mmol) in DMSO (4 mL) was degassed and then heated at 85° C. for 15 hours under N₂ before being cooled down. The mixture was partitioned (EtOAc—H₂O). The organics were washed with brine, dried (Na₂SO₄), filtered and evaporated. The residue was purified by chromatography (silica, hexanes-ethyl acetate) to give the desired compound as a yellow foam (0.131 g, 60%). ESIMS m/z=567.23 [M+H]⁺.

Step 574f.

The title compound was prepared from the compound from step 574e and (5)-tert-butyl 2-(5-bromo-1H-imidazol-2-yl)pyrrolidine-1-carboxylate (prepared according to WO 2008/021927) using procedures similar to that described in example 692. ESIMS m/z=790.44 [M+H]⁺.

Example 644

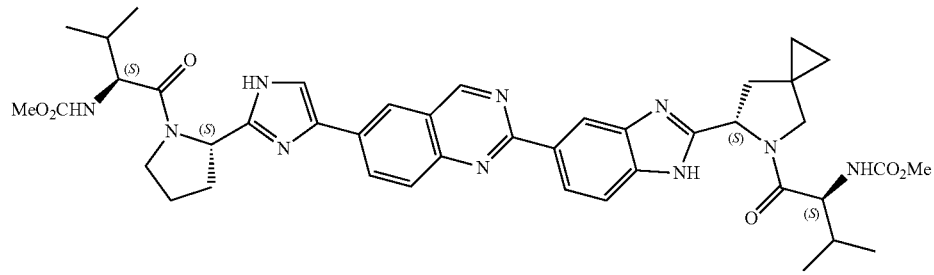

Step 644a.

A mixture of 6-bromo-2-chloroquinazoline (0.300 g, 1.232 mmol), tributyl (1-ethoxyvinyl)tin (0.42 mL, 1.232 mmol) and Pd(PPh₃)₄ (0.142 gg, 0.123 mmol) in toluene (10 mL) was degassed and then heated at 100° C. under N₂ for 24 hours before being cooled down. The mixture was directly purified by chromatography (silica, hexanes-dichloromethane) to give the desired compound as a yellow-green solid (0.160 g, 55%). ESIMS m/z=235.04 [M+H]⁺.

Step 644b.

To a solution of the compound from step 644a (0.160 g, 0.682 mmol) in THF/H₂O (3/1, 4 mL) at 0° C. was added N-bromosuccinimide (0.112 g, 0.627 mmol). The mixture was stirred at 0° C. for 1 hour before being partitioned (EtOAc—H₂O). The organics were washed with satureate NaHCO₃, brine, dried (Na₂SO₄), filtered and evaporated to give the desired compound as a yellow solid, which was used directly for next step.

Step 644c.

To a mixture of the compound from step 644b (0.682 mmol at most) and N-Boc-L-proline (0.145 g, 0.682 mmol) in acetonitrile (6 mL) was added diisopropylethylamine (0.24 mL, 1.364 mmol) at rt. The resulting mixture was stirred at rt for 3 hours before being concentrated. The residue was purified by chromatography (silica, hexanes-ethyl acetate) to give the desired compound as a yellow foam (0.178 g, 62% over 2 steps). ESIMS m/z=420.06 [M+H]⁺.

Step 644d.

A mixture of compound from step 644c (0.178 g, 0.424 mmol) and ammonium acetate (0.359 g, 4.663 mmol) in toluene (5 mL) was stirred at 110° C. for 20 hours. More ammonium acetate (0.359 g, 4.663 mmol) was added. The mixture was stirred at 110° C. for 8 hours before being cooled down and partitioned between EtOAc and aqueous NaHCO₃. The organic phase was washed with brine, dried (Na₂SO₄), filtered and concentrated. The residue was purified by chromatography (silica, hexanes-EtOAc) to give the desired compound as a yellow solid (0.114 g, 67%). ESIMS m/z=400.07 [M+H]⁺.

Step 644e.

The title compound was prepared from the compound from step 644d and the compound from step 574c using procedures similar to that described in example 692. ESIMS m/z=791.42 [M+H]⁺.

Example 575

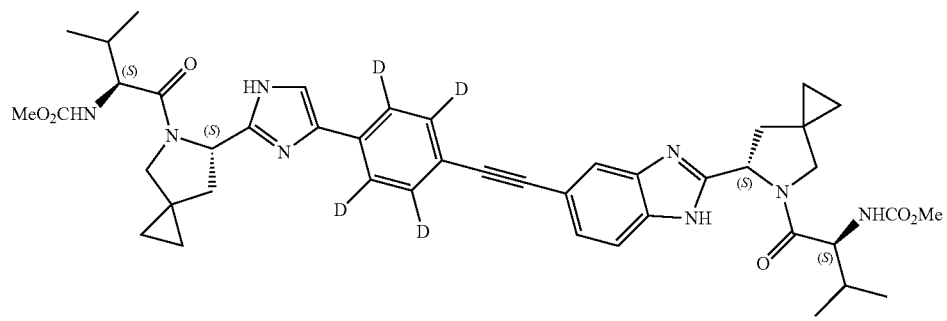

D is deuterium

The title compound was prepared from 4'-bromoacetophenone-d$_7$ and (6S)-5-[(tert-butoxy)carbonyl]-5-azaspiro[2.4]heptane-6-carboxylic acid (prepared according to WO 2009/102325) using procedures similar to that described in Example 488. ESIMS m/z=793.42 [M+H]$^+$.

Example 608

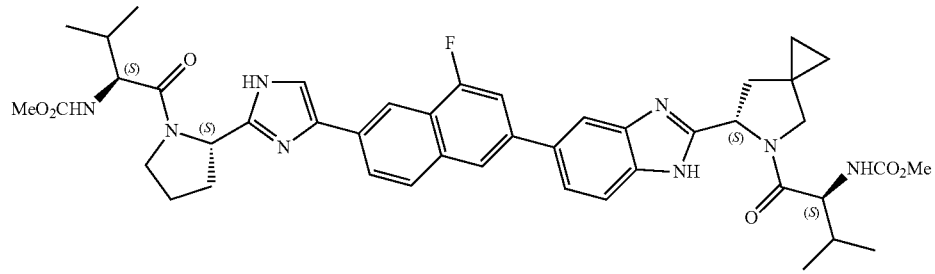

Step 608a.

A mixture of the compound from step 574c (0.248 g, 0.564 mmol), 6-bromo-8-fluoro-2-naphthol (0.136 g, 0.564 mmol), NaHCO$_3$ (0.190 g, 2.257 mmol) and Pd(PPh$_3$)$_4$ (65.2 mg, 56.4 μmol) in DME (4.5 mL) and H$_2$O (1.5 mL) was degassed and then heated at 98° C. under N$_2$ for 3 hours before being cooled down. The volatiles were evaporated off. The residue was taken up in dichloromethane and filtered. The filtrate was directly purified by chromatography (silica, hexanes-ethyl acetate) to give the desired compound as a yellow solid (0.230 g, 86%). ESIMS m/z=474.27 [M+H]$^+$.

Step 608b.

To a suspension of the compound from step 608a (0.352 g, 0.743 mmol) in CH$_2$Cl$_2$ (10 mL) cooled at −78° C. was added Et$_3$N (0.62 mL, 4.460 mmol), followed by trifluoromethanesulfonic anhydride (Tf$_2$O, 1.0 M in CH$_2$Cl$_2$, 2.23 mL, 2.230 mmol). After 15 minutes at −78° C., more Tf$_2$O (1.0 M in CH$_2$Cl$_2$, 0.74 mL, 0.740 mmol) was added. After 10 min at −78° C., the reaction was quenched by saturated NaHCO$_3$ solution. The mixture was partitioned (EtOAc—H$_2$O). The organics were washed with brine, dried (Na$_2$SO$_4$), filtered and evaporated. The residue was purified by chromatography (silica, hexanes-ethyl acetate) to give the desired ditriflate compound as a yellow foam (0.529 g, 97%). ESIMS m/z=738.12 [M+H]$^+$.

Step 608c.

A mixture of the compound from step 608b (0.529 g, 0.717 mmol), bis(pinacolato)diboron (0.364 g, 1.434 mmol), KOAc (0.176 g, 1.793 mmol) and Pd(dppf)Cl$_2$.CH$_2$Cl$_2$ (58.6 mg, 0.0717 mmol) in 1,4-dioxane (7 mL) was degassed and then heated at 100° C. for 2 hours under N$_2$ before being cooled down and concentrated. The residue was taken up in dichloromethane and filtered. The filtrate was directly purified by chromatography (silica, hexanes-ethyl acetate) to give the desired compound as a yellow foam (0.505 g, 98%). ESIMS m/z=716.23 [M+H]$^+$.

Step 608d.

A mixture of the compound from step 608c (0.200 g, 0.280 mmol), (S)-tert-butyl 2-(5-bromo-1H-imidazol-2-yl)pyrrolidine-1-carboxylate (prepared according to WO 2008/021927, 88.4 mg, 0.280 mmol), NaHCO$_3$ (93.9 mg, 1.118 mmol) and Pd(PPh$_3$)$_4$ (32.3 mg, 28.0 μmol) in DME (6 mL) and H$_2$O (2 mL) was degassed and then heated at 98° C. under N$_2$ for 12 hours before being cooled down. The volatiles were evaporated. The residue was taken up in dichloromethane and filtered. The filtrate was directly purified by chromatography (silica, hexanes-ethyl acetate, with 1% MeOH and 1% Et$_3$N in ethyl acetate) to give the desired compound as a yellow solid (0.170 g, 88%). ESIMS m/z=693.29 [M+H]$^+$.

Step 608e.

The title compound was prepared from the compound from step 608d using procedures similar to that described in steps 548h and 548i. ESIMS m/z=807.30 [M+H]$^+$.

Example 616

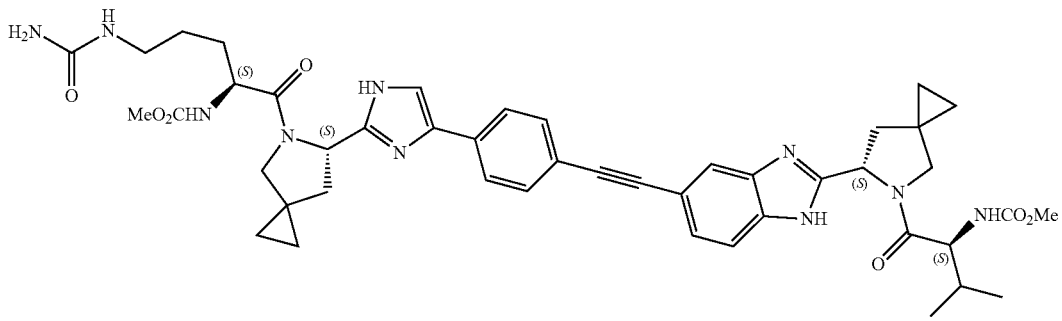

Step 616a.

A solution of the compound from step 548f (0.500 g, 1.482 mmol) in CH$_2$Cl$_2$ (12 mL) was treated with HCl in 1,4-dioxane (4 M, 20 mL) for 1 hour. The volatiles were evaporated off to give the crude desired compound as a yellow solid, which was used directly in the next step.

Step 616b.

A mixture of the crude compound from step 616a (1.482 mmol at most) and the compound from step 515g (0.273 g, 1.556 mmol) in CH$_2$Cl$_2$ (15 mL) was treated with HATU (0.563 g, 1.482 mmol) in the presence of DIPEA (2.58 mL, 14.82 mmol) for 1 hour at rt. The volatiles were evaporated off. The residue was purified by chromatography (silica, hexanes-ethyl acetate) to give the desired compound as a yellow foam (0.580 g, 99% over 2 steps). ESIMS m/z=395.15 [M+H]$^+$.

Step 616c.

A mixture of the compound from step 548b (0.177 g, 0.380 mmol), the compound from step 616b (0.150 g, 0.380 mmol), Pd(PPh$_3$)$_4$ (22.0 mg, 0.0190 mmol) and copper(I) iodide (2.2 mg, 0.0114 mmol) in triethylamine (4 mL) and acetonitrile (4 mL) was degassed and heated at 35° C. for 16 hours under N$_2$. The mixture was concentrated. The residue was purified by chromatography (silica, hexanes-EtOAc, with 1% Et$_3$N &10% MeOH in EtOAc) to give the desired compound as a yellow solid (0.228 g, 82%). ESIMS m/z=732.58 [M+H]$^+$.

Step 616d.

A solution of the compound from step 616c (50.0 mg, 0.0683 mmol) in CH$_2$Cl$_2$/MeOH (3/1, 2 mL) was treated with HCl in 1,4-dioxane (4 M, 3 mL) at rt for 2 hours. The volatiles were evaporated off to give the crude desired compound as a yellow solid, which was used directly in the next step. ESIMS m/z=632.53 [M+H]$^+$.

Step 616e.

A mixture of the crude compound from step 616d (0.0683 mmol at most) and (S)-2-(methoxycarbonylamino)-5-ureidopentanoic acid (prepared from L-citrulline according to WO 2008/021927, 23.9 mg, 0.102 mmol) in DMF (3 mL) was treated with HATU (26.0 mg, 0.0683 mmol) in the presence of DIPEA (0.12 mL, 0.683 mmol) for 1 hour at rt. The volatiles were evaporated off. The residue was purified by HPLC (H$_2$O-MeOH) to give the title compound as a white powder (30.2 mg, 76% over 2 steps). ESIMS m/z=847.45 [M+H]$^+$.

Example 550

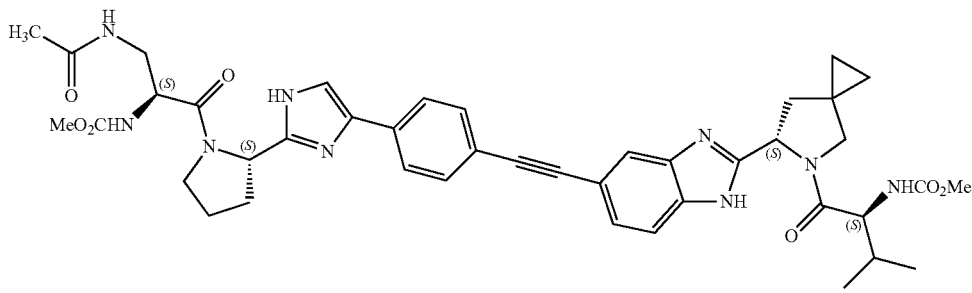

Step 550a.

A mixture of the compound from step 630b (0.635 g, 1.445 mmol), the compound from step 616b (0.570 g, 1.445 mmol), Pd(PPh$_3$)$_4$ (83.5 mg, 72.2 µmol) and copper(I) iodide (8.3 mg, 43.3 µmol) in triethylamine (10 mL) and acetonitrile (10 mL) was degassed and then heated at 35° C. for 16 hours under N$_2$. The mixture was concentrated. The residue was purified by chromatography (silica, hexanes-EtOAc, with 10% MeOH in EtOAc) to give the desired compound (Compound 666) as a yellow solid (0.697 g, 68%). ESIMS m/z=706.34 [M+H]$^+$.

Step 550b.

A solution of the compound from step 550a (0.100 g, 0.142 mmol) in CH$_2$Cl$_2$/MeOH (3/1, 4 mL) was treated with HCl in 1,4-dioxane (4 M, 6 mL) at rt for 1.5 hours. The volatiles were evaporated off to give the crude desired compound as a yellow solid, which was used directly in the next step.

Step 550c.

A mixture of half of the crude compound from step 550b (0.0708 mmol at most) and (S)-2-(methoxycarbonylamino)-3-ureidopropanoic acid (prepared from 3-[(Aminocarbony)amino]-L-alanine according to WO 2008/021927) in DMF (3 mL) was treated with HATU (26.9 mg, 0.0708 mmol) in the presence of DIPEA (0.12 mL, 0.708 mmol) for 1 hour at rt. The volatiles were evaporated off. The residue was purified by HPLC (H$_2$O-MeOH) to give the title compound as an off-white solid (33.0 mg, 59% over 2 steps). ESIMS m/z=793.51 [M+H]$^+$.

Example 620

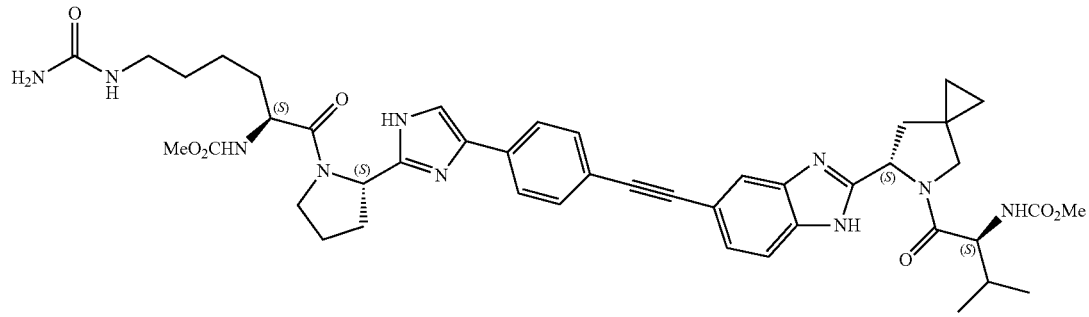

The title compound was prepared from the crude compound from step 550b and (S)-2-(methoxycarbonylamino)-6-ureidohexanoic acid (prepared from L-homocitrulline according to WO 2008/021927) using the procedure similar to that described in step 550c. ESIMS m/z=835.55 [M+H]$^+$.

Example 553

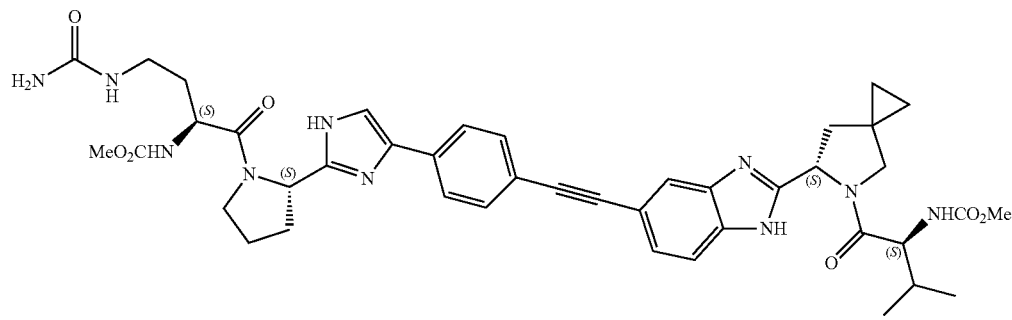

Step 553a.

To a solution of (S)-4-Amino-2-(tert-butoxycarbonylamino)butanoic acid (0.500 g, 2.291 mmol) in H$_2$O (20 mL) was added a small amount of bromocresol purple. The resulting purple solution was heated to 50° C. Potassium cyanate (0.279 g, 3.437 mmol) was added in one portion at 50° C. 2 M HCl solution was added until the solution turned purple with a green tone. The mixture was heated at 50° C. The pH was maintained by dropwise addition of 2 M HCl solution. After 5 hours at 50° C., the mixture was cooled down to 0° C., acidified to pH ~2 with 2 M HCl solution and evaporated off to dryness. The residual yellow solid was taken up in CH$_2$Cl$_2$/MeOH (2/1) and filtered through a short pad of Celite and then a short silica column. The filtrate was concentrated to afford the desired compound as a yellow foam (0.690 g). ESIMS m/z=284.15 [M+Na]$^+$.

Step 553b.

A solution of the compound from step 553a (0.690 g, 2.291 mmol at most) in CH$_2$Cl$_2$/MeOH (3/1, 8 mL) was treated with HCl in 1,4-dioxane (4 M, 8 mL) at rt for 1 hour. The volatiles were evaporated off to give the crude desired compound as a pink solid, which was used directly in the next step.

Step 553c.

To a mixture of the compound from step 553b (2.291 mmol at most) and NaOH solution (1 M in H$_2$O, 4.58 mL, 4.58 mmol) cooled at 0° C. was added Na$_2$CO$_3$ (0.126 g, 1.191 mmol), followed by ClCO$_2$Me (0.19 mL, 2.486 mmol). The resulting solution was stirred at rt overnight. NaHCO$_3$ (0.192 g, 2.291 mmol) was added. After 15 minutes at rt, the mixture was acidified to pH ~2 with 3 M HCl solution and evaporated off to dryness. The residual solid was taken up in CH$_2$Cl$_2$/MeOH (2/1) and filtered through a short pad of Celite and then a short silica column. The filtrate was concentrated to afford the desired compound as a yellow foam (0.587 g).

Step 553d.

The title compound was prepared from the compound from step 550b and the compound from step 553c using the procedure similar to that described in step 550c. ESIMS m/z=807.56 [M+H]⁺.

Example 621

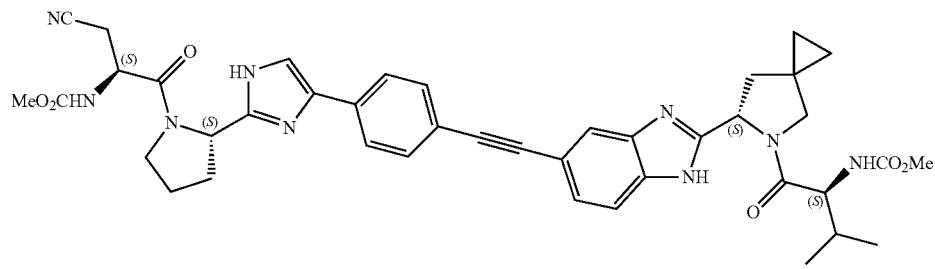

The title compound was prepared from the compound from step 550b and (S)-3-cyano-2-(methoxycarbonylamino) propanoic acid (prepared from β-cyano-L-alanine according to WO 2008/021927) using the procedure similar to that described in step 550c. ESIMS m/z=760.46 [M+H]⁺.

Example 647

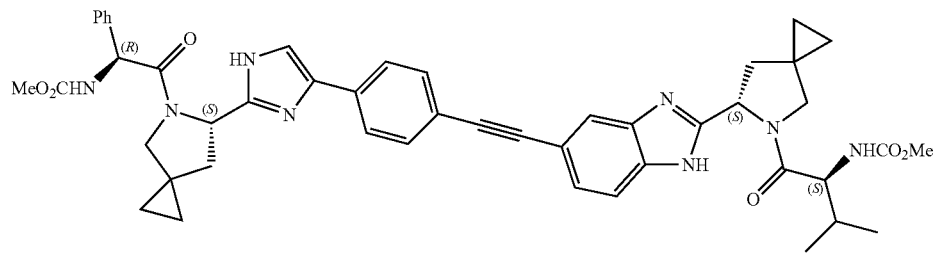

Step 647a.

A solution of the compound from step 548b (1.000 g, 2.149 mmol) in CH₂Cl₂ (12 mL) was treated with HCl in 1,4-dioxane (4 M, 20 mL) for 2 hours. The volatiles were evaporated off to give the crude desired compound as a yellow solid, which was used directly in the next step.

Step 647b.

To a mixture of the crude compound from step 647a (2.149 mmol at most) and (R)-(methoxycarbonyl)amino phenyl acetic acid (prepared according to WO 2008/021927, 0.450 g, 2.149 mmol) in CH₃CN (20 mL) was added DIPEA (3.74 mL, 21.49 mmol), followed by HATU (0.817 g, 2.149 mmol). The solution was stirred at rt for 1 hour. The volatiles were evaporated off. The residue was purified by chromatography (silica, hexanes-ethyl acetate) to give the desired compound as a yellow foam (0.930 g, 78% over 2 steps). ESIMS m/z=557.18 [M+H]⁺.

Step 647c.

A mixture of the compound from step 616b (40.0 mg, 0.101 mmol), the compound from step 647b (56.4 mg, 0.101 mmol), Pd(PPh₃)₄ (5.9 mg, 5.1 μmol) and copper(I) iodide (0.6 mg, 3.0 μmol) in triethylamine (2.5 mL) and acetonitrile (2.5 mL) was degassed and then heated at 40° C. for 15 hours under N₂. The mixture was concentrated. The residue was purified by chromatography (silica, ethyl acetate-methanol) to give the title compound as a yellow solid (67.8 mg, 81%). ESIMS m/z=823.67 [M+H]⁺.

Example 579

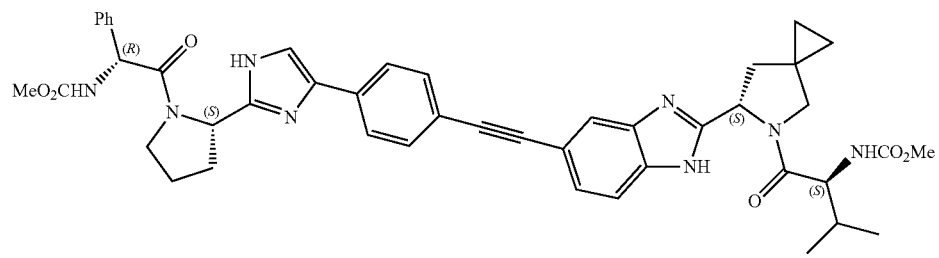

The title compound was prepared from the compound from step 630b, the compound from step 616b and (R)-

(methoxycarbonyl)amino phenyl acetic acid (prepared according to WO 2008/021927) using procedures similar to that described in Example 616. ESIMS m/z=797.55 [M+H]+.

Example 577

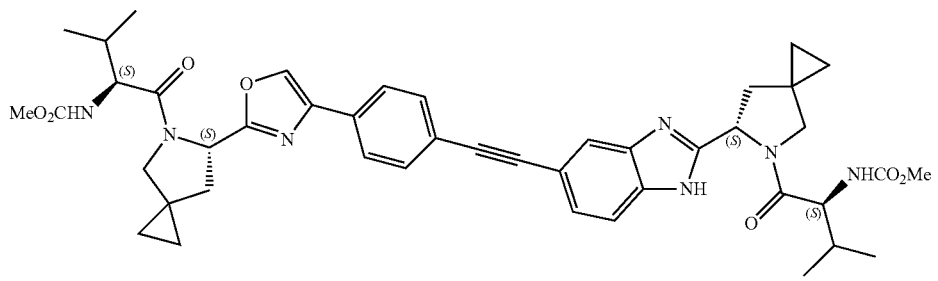

The title compound was prepared from a side product isolated from step 548g using procedures similar to that described in step 548h and 548i. ESIMS m/z=790.50 [M+H]+.

Example XP-21

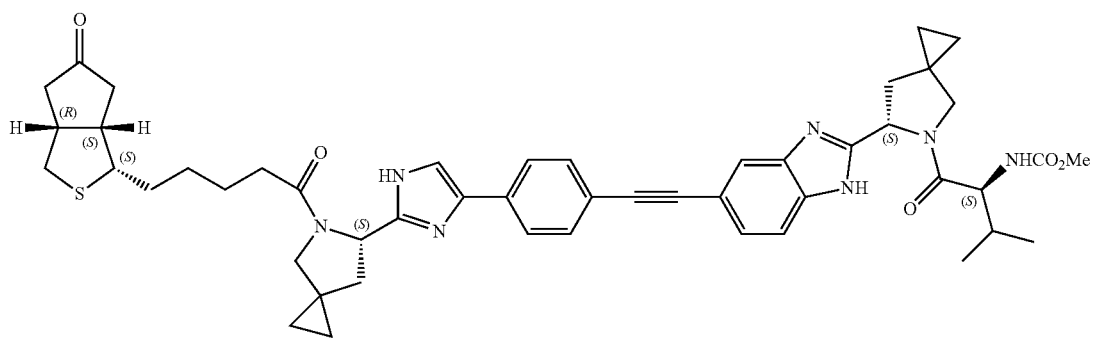

The title compound was prepared from the crude compound from step 616d and biotin using procedure similar to that described in step 616e. ESIMS m/z=858.42 [M+H]+.

Example XP-22

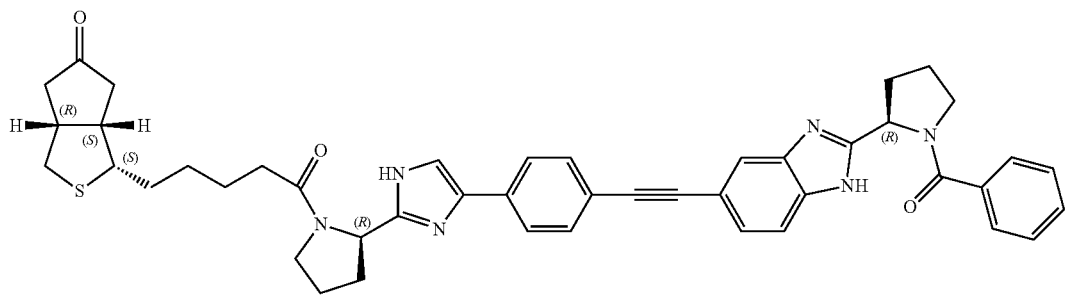

The title compound was prepared from the Boc-D-proline, benzoic acid and biotin using procedures similar to that described in Example 647. ESIMS m/z=753.34 [M+H]+.

Example 555

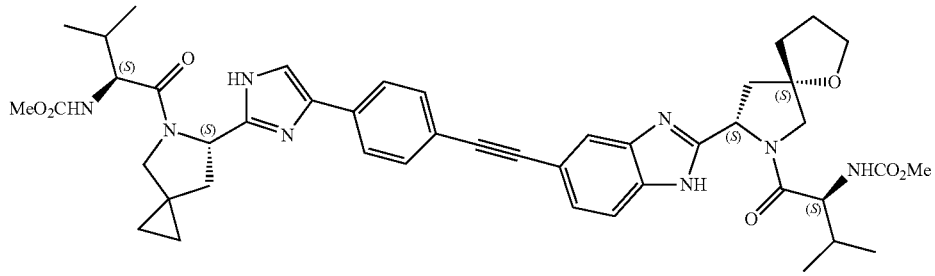

Step 555a.

To a suspension of activated zinc powder (6.37 g, 95.4 mmol) in dry THF (150 mL) was added allyl bromide (8.49 mL, 97.4 mmol) dropwisely. The mixture was cooled to −30° C. before a solution of (S)-1-benzyl 2-methyl 4-oxopyrrolidine-1,2-dicarboxylate (18.0 g, 65.0 mmol) in THF (50 ml) was added dropwisely. The reaction mixture was stirred at <−10° C. for 4 hours before being quenched with HCl (1 N). The mixture was partitioned (EtOAc—$H_2O$). The organics were washed with brine, dried ($Na_2SO_4$), filtered and evaporated. The residue was purified by chromatography (silica, EtOAc-hexanes) to afford the desired compounds as a light yellow oil and disteromeric mixture (13.66 g, 66%). ESIMS m/z=320.15 [M+H]+.

Step 555b.

To a solution of the compound from step 555a (0.200 g, 0.627 mmol) in $CH_3CN$ (4 mL) were added $NaHCO_3$ (0.211 g, 2.51 mmol) and iodine (0.477 g, 1.88 mmol). The resultant mixture were heated up to 50° C. for 4 hours before the second addition of $NaHCO_3$ (0.211 g, 2.51 mmol) and iodine (0.477 g, 1.88 mmol). The reaction was kept at 50° C. for another 3 hours before being cooled down and quenched by aqueous $Na_2S_2O_3$. The volatiles were evaporated and the residue was partitioned (EtOAc—$H_2O$). The organics were washed with brine, dried ($Na_2SO_4$), filtered and evaporated. The residue was purified by chromatography (silica, EtOAc-hexanes) to give the desired compounds as a colorless oil and diastereomeric mixture (79.8 mg, 29%). ESIMS m/z=468.23 [M+Na]+.

Step 555c.

Into a solution of the compound from step 555b (12.72 g, 28.58 mmol) in toluene (250 mL) were added tris(trimethylsilyl)silane (13.2 mL, 42.9 mmol) and 2,2'-azo-bis-isobutyronitrile (235 mg, 1.43 mmol). The mixture were degassed and heated up to 90° C. under $N_2$ for 3 hours before being cooled down and evaporated to dryness. The residue was purified by chromatography (silica, EtOAc-hexanes) to give the desired major compound as a colorless oil (3.75 g, 41%). ESIMS m/z=320.16 [M+H]+; and a minor compound as a colorless oil (162 mg, 2%). ESIMS m/z=320.16 [M+H]+.

Step 555d.

Into a solution of the major compound from step 555c (0.170 g, 0.533 mmol) in MeOH (6 mL) were added palladium hydroxide (20 wt % on carbon, 50.0 mg) and $Boc_2O$ (0.174 g, 0.799 mmol). The resulting mixture was hydrogenated under 60 psi hydrogen gas at rt for 1 day before being filtered through a plug of Celite. The filtrate was concentrated and purified by chromatography (silica, EtOAc-hexanes) to give the desired compound as a colorless oil (0.127 g, 84%). ESIMS m/z=308.14 [M+Na]+.

Step 555e.

Into a solution of the compound from step 555d (0.127 g, 0.447 mmol) in EtOH (4 mL) at 0° C. was added lithium hydroxide monohydrate (22.5 mg, 0.536 mmol) in $H_2O$ (2 mL). The mixture was warmed up to rt and kept at rt for 1 day before being evaporated. The residue was partitioned ($Et_2O$—$H_2O$) and the aqueous phase was acidified to pH ~2 at 0° C. The mixture was then partitioned ($CH_2Cl_2$—$H_2O$) and the organics were washed with brine, dried ($Na_2SO_4$), filtered and evaporated to give the crude desired compound as a colorless oil (0.122 g, 100%). ESIMS m/z=319.14 [M+Li+$CH_3CN$]+.

Step 555f.

Into a mixture of the crude compound from step 555e (60.5 mg, 0.223 mmol at most) and 4-bromo-1,2-diaminobenzene (46.0 mg, 0.246 mmol) in $CH_3CN$ (4 mL) were added EDCBCl (55.7 mg, 0.291 mmol) and DMAP (5.5 mg, 44.7 μmol). The mixture was stirred at rt for 14 hours before being evaporated to dryness. The residue was purified by chromatography (silica, hexanes-ethyl acetate) to give the desired compound as a yellow brown oil (82.0 mg, 83%). ESIMS m/z=440.11, 442.11 [M+H]+.

Step 555g.

A solution of the compound from step 555f (82.0 mg, 0.186 mmol) in AcOH (8 mL) was heated at 50° C. for 16 hours before being evaporated. The residue was partitioned (EtOAc—$H_2O$) and the organics were dried ($Na_2SO_4$), filtered and evaporated. The residue was purified by chromatography (silica, hexanes-ethyl acetate) to give the desired compound as a yellow oil (54.5 mg, 69%). ESIMS m/z=422.11, 424.14 [M+H]+.

Step 555h.

A mixture of the compound from step 555g (1.88 g, 4.47 mmol) and ethynyltrimethylsilane (6.32 mL, 44.7 mmol) in $Et_3N$ (45 mL) were added CuI (25.5 mg, 0.134 mmol) and Pd(PPh$_3$)$_4$ (0.258 g, 0.223 mmol). The resultant mixture were degassed and heated to 95° C. under $N_2$ for 20 hour. The volatiles were evaporated off and the residue was partitioned (EtOAc—$H_2O$). The organics were washed with brine, dried ($Na_2SO_4$), filtered and evaporated. The residue was purified by chromatography (silica, hexanes-ethyl acetate) to give the desired compound as a light yellow brown foam (1.79 g, 91%). ESIMS m/z=440.27 [M+H]+.

Step 555i.

A solution of the compound from step 555h (1.79 g, 4.08 mmol) in MeOH (40 mL) was treated with $K_2CO_3$ (1.41 g, 10.2 mmol) for 2 hours before being evaporated. The residue was partitioned (EtOAc—$H_2O$) and the organics were dried ($Na_2SO_4$), filtered and evaporated. The residue was purified by chromatography (silica, hexanes-ethyl acetate) to give the desired compound as a light yellow solid (1.35 g, 90%). ESIMS m/z=368.23 $[M+H]^+$.

Step 555j.

A mixture of compounds from step 548b (55.3 mg, 0.122 mmol), compounds from step 555i (45.0 mg, 0.122 mmol), $Pd(PPh_3)_4$ (7.1 mg, 6.1 μmol) and copper(I) iodide (0.7 mg, 3.7 μmol) in triethylamine (2 mL) and acetonitrile (2 mL) was degassed and heated at 40° C. for 15 hours under $N_2$. The mixture was evaporated. The residue was purified by chromatography (silica, hexanes-EtOAc, with 1% $Et_3N$ in EtOAc) to give the desired compound as a yellow solid (82.0 mg, 97%). ESIMS m/z=691.45 $[M+H]^+$.

Step 555k.

A solution of the compound from step 555j (0.179 g, 0.254 mmol) in $CH_2Cl_2$ (3 mL) was treated with HCl at rt in 1,4-dioxane (4 M, 6 mL) for 2 hours. The volatiles were evaporated off to give the crude desired compound as a yellow solid which was used directly in the next step. ESIMS m/z=505.30 $[M+H]^+$.

Step 555l.

A mixture of the crude compound from step 555k (0.254 mmol at most) and the compound from step 515g, 93.4 mg, 0.534 mmol) in DMF (5 mL) was treated with HATU (0.193 g, 0.508 mmol) in the presence of DIPEA (0.63 mL, 5.08 mmol) for 1 hour at rt. The volatiles were evaporated off. The residue was purified by chromatography (silica, $CH_2Cl_2$-MeOH) to give the title compound as a light yellow solid (0.168 g, 81% over 2 steps). ESIMS m/z=819.25 $[M+H]^+$.

Example 546

Step 546a.

To a solution of the crude compound from step 555e (60.7 mg, 0.224 mmol) in $CH_3CN$ (4 mL) were added 2-bromo-1-(4'-iodophenyl)ethanone (76.2 mg, 0.235 mmol) and DIPEA (56.0 μL, 0.447 mmol). The resultant mixture were stirred at rt for 1 hour before being evaporated. The residue was partitioned (EtOAc—$H_2O$) and the organics were washed with brine, dried ($Na_2SO_4$), filtered and evaporated. The residue was purified by chromatography (silica, EtOAc-hexanes) to give the desired compound as a colorless oil (98.8 mg, 86%). ESIMS m/z=515.92 $[M+H]^+$.

Step 546b.

To a solution of the compound from step 546a (98.8 mg, 0.192 mmol) in toluene (8 mL) was added $NH_4OAc$ (0.296 g, 3.84 mmol). The resultant mixture were heated up to 100° C. for 12 hours before being cooled down and evaporated to dryness. The residue was partitioned (EtOAc—$H_2O$) and the organics were washed with brine, dried ($Na_2SO_4$), filtered and evaporated. The residue was purified by chromatography (silica, EtOAc-hexanes) to give the desired compound as a light yellow oil (70.8 mg, 75%). ESIMS m/z=495.93 $[M+H]^+$.

Step 546c.

To a mixture of the compound from step 546b (38.5 mg, 77.7 μmol) and the compound from step 548f (28.8 mg, 85.4 μmol) in $CH_3CN$ (4 mL) and $Et_3N$ (4 mL) were added CuI (0.4 mg, 2.3 μmol) and $Pd(PPh_3)_4$ (4.4 mg, 3.8 μmol). The resultant mixture was degassed and heated to 40° C. under $N_2$ for 14 hours. The volatiles were evaporated off and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (43.7 mg, 80%). ESIMS m/z=705.28 $[M+H]^+$.

Step 546d.

A solution of the compound from step 546c (43.7 mg, 62.0 μmol) in $CH_2Cl_2$ (3 mL) was treated with HCl at rt in 1,4-dioxane (4 M, 6 mL) for 1 hour. The volatiles were evaporated off to give the crude desired compound as a yellow solid which was directly used in the next step. ESIMS m/z=505.20 $[M+H]^+$.

Step 546e.

A mixture of the crude compound from step 546d (62.0 μmol at most) and the compound from step 515g, 22.8 mg, 0.130 mmol) in DMF (3 mL) was treated with HATU (47.1 mg, 0.124 mmol) in the presence of DIPEA (0.15 mL, 1.24 mmol) for 1 hour at rt. The volatiles were evaporated off to provide a brown sirup, which was purified by chromatography (silica, $CH_2Cl_2$-MeOH) to give the title compound as a light yellow solid (42.6 mg, 2 steps 84%). ESIMS m/z=819.32 $[M+H]^+$.

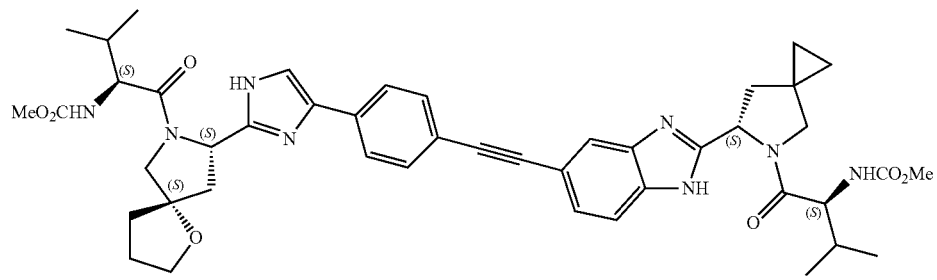

Example 615

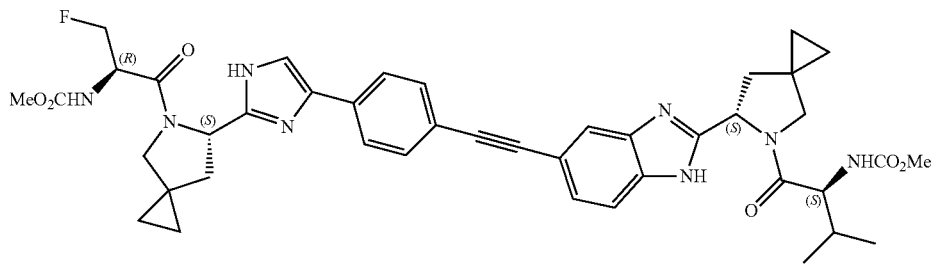

Step 615a.

A solution of L-serine (3.0 g, 28.55 mmol) in acetonitrile (30 mL) was treated with TBSCl (4.518 g, 29.97 mmol) in the presence of DBU (4.12 mL, 29.97 mmol) at rt overnight. The insoluble was filtered off and washed with acetonitrile to afford the desired as white solid (5.74 g, 92%).

Step 615b.

The desired compound (5.1 g, 70%) was prepared from the compound of step 615a (5.74 g, 26.22 mmol) and methyl chloroformate (2.14 mL, 27.79 mmol) in the presence of NaOH (1 M, 26.2 mL) and $Na_2CO_3$ (1.445 g, 13.63 mmol) using procedures similar to that described in WO 2008/021927.

Step 615c.

Into a solution of the compound from step 615b (5.1 g, 18.4 mmol) in toluene (300 mL) were added paraformaldehyde (3.26 g) and p-TsOH (0.175 g, 0.921 mmol). The mixture was slowly heated to reflux with a Dean-Stark trap for 1 hour. The cooled mixture were washed with aqueous $NaHCO_3$, brine, dried ($Na_2SO_4$), filtered and evaporated. The residue was purified by chromatography (silica, hexanes-ethyl acetate) to give the desired compound as a white solid (3.20 g, 60%).

Step 615d.

Into a solution of the compound from step 615c (1.00 g, 3.46 mmol) in $CH_2Cl_2$ (18 mL) at 0° C. were added HF-pyridine (0.69 mL, 27.7 mmol) and Deoxo-Fluor (1.28 mL, 6.92 mmol). The mixture was gradually warmed up to rt and stirred for 20 hour before being quenched slowly with cold aqueous $NaHCO_3$. The mixture was partitioned ($CH_2Cl_2$—$H_2O$) and the organics were washed with $H_2O$, brine, dried ($Na_2SO_4$), filtered and evaporated. The residue was purified by chromatography (silica, hexanes-ethyl acetate) to give the desired compound as a colorless oil (0.387 g, 63%).

Step 615e.

Into a solution of the compound from step 615d (0.387 g, 2.19 mmol) in 1,4-dioxane (11 mL) was added aqueous 2M HCl (10.9 mL, 21.9 mmol). The mixture was heated up to 60° C. for 20 hour before being evaporated to dryness. The residue was partitioned ($CH_2Cl_2$-brine) and the organics were dried ($Na_2SO_4$), filtered and evaporated to give the crude desired compound as a colorless oil (0.310 g, 86%).

Step 615f.

A solution of 548b (0.160 g, 0.344 mmol) in $CH_2Cl_2$ (3 mL) was treated with HCl in 1,4-dioxane (4 M, 6 mL) for 1 hour. The volatiles were evaporated off to give the crude desired compound as a yellow solid which was directly used in the next step. ESIMS m/z=366.03 $[M+H]^+$.

Step 615g.

A mixture of the crude compound from step 615f (0.344 mmol at most) and the compound from step 615e (62.4 mg, 0.378 mmol) in $CH_2Cl_2$ (8 mL) at 0° C. was treated with HATU (0.131 g, 0.344 mmol) in the presence of DIPEA (0.21 mL, 1.72 mmol). The mixture was slowly warmed up to rt and stirred for 12 hours. The volatiles were evaporated and the residue was purified by chromatography (silica, hexanes-ethyl acetate) to give the desired compound as a colorless oil (0.156 g, 2 steps 89%). ESIMS m/z=512.91 $[M+H]^+$.

Step 615h.

The title compound was prepared from the compound from step 615g and the compound from step 616b using procedure similar to that described in step 647c. ESIMS m/z=779.24 $[M+H]^+$.

Example 689

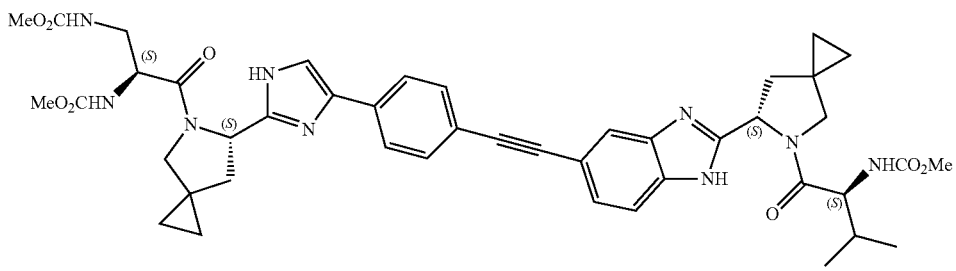

The title compound was prepared from the crude compound from step 616d and (S)-2,3-bis(methoxycarbonylamino)propanoic acid (prepared from L-2,3-diaminopropionic acid hydrochloride using procedures similar to that described in WO 2008/021927) using procedures similar to that described in step 616e. ESIMS m/z=808.53 $[M+H]^+$.

Example 693

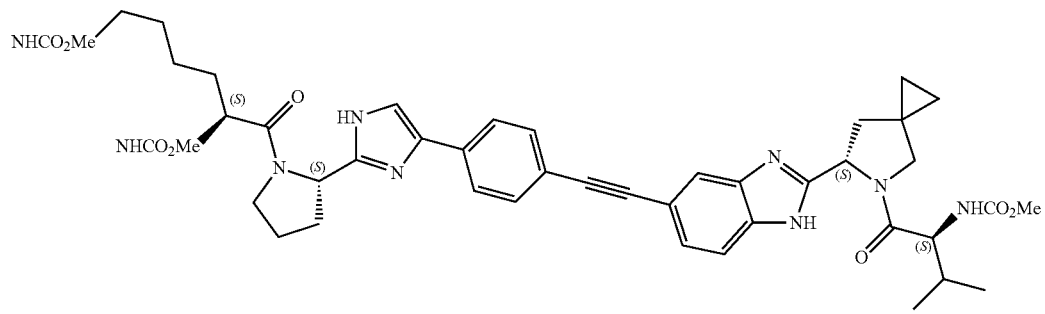

The title compound was prepared from the crude compound from step 550b and (S)-2,6-bis(methoxycarbonylamino)hexanoic acid (prepared from L-lysine, according to WO 2008/021927) using procedures similar to that described in step 616e. ESIMS m/z=850.53 [M+H]$^+$.

Example 551

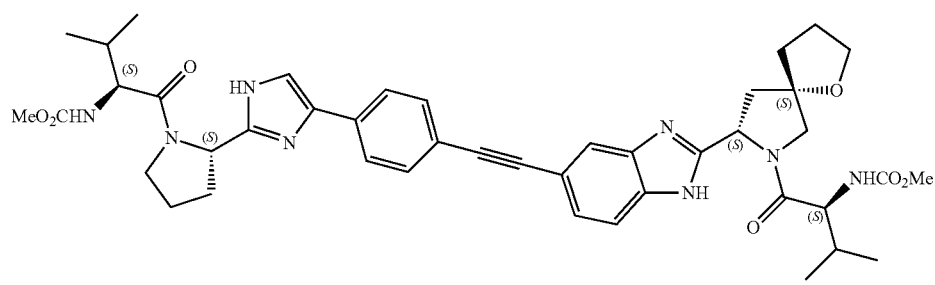

The title compound was prepared from the compound from step 630b and the compound from step 555i using procedures similar to that described in steps 555j, 555k and 555i. ESIMS m/z=793.22 [M+H]$^+$.

Example 558

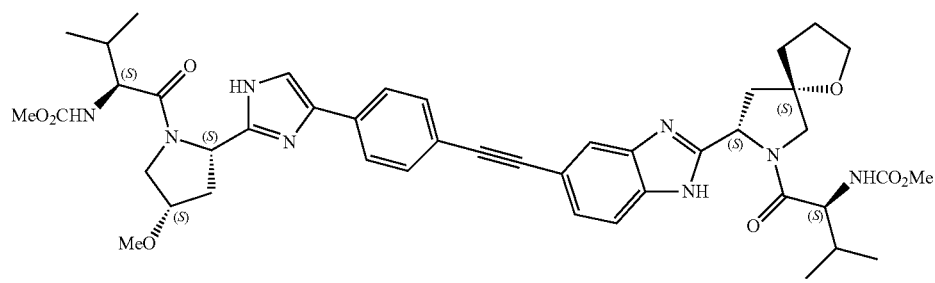

Step 558a.

Into a mixture of L-Boc-cis-Hyp-OMe (0.500 g, 2.04 mmol) and 18-crown-6 (0.323 g, 1.22 mmol) in THF (10 mL) were added MeI (1.27 mL, 20.4 mmol) and NaH (60% in mineral oil, 89.8 mg, 2.25 mmol) in portions. The resultant mixture was stirred at rt for 14 hours before being quenched with aqueous NaHCO$_3$. The volatiles were evaporated and the residue was partitioned (EtOAc—H$_2$O). The organics were washed with brine, dried (Na$_2$SO$_4$), filtered and evaporated. The residue was purified by chromatography (silica, hexanes-ethyl acetate) to give the desired compound as a colorless oil (0.442 g, 84%). ESIMS m/z=282.25 [M+Na]$^+$.

Step 558b.

The title compound was prepared from the compound from step 558a and the compound from step 555i using procedures similar to that described in Example 546. ESIMS m/z=823.47 [M+H]$^+$.

Example 627

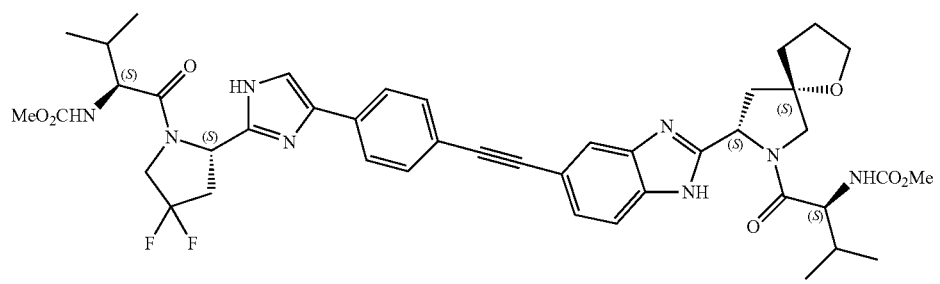

The title compound was prepared from N-Boc-4,4-difluoro-L-proline and the compound from step 555i using procedures similar to that described in Example 546. ESIMS m/z=829.55 [M+H]+.

Example 629

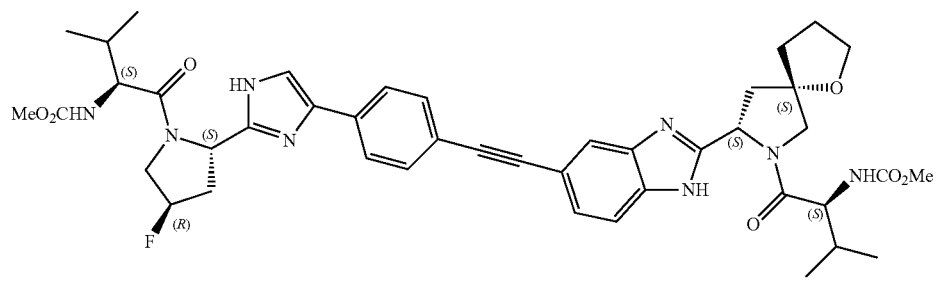

The title compound was prepared from N-Boc-trans-4-fluoro-L-proline and the compound from step 555i using procedures similar to that described in Example 546. ESIMS m/z=811.52 [M+H]+.

Example 561

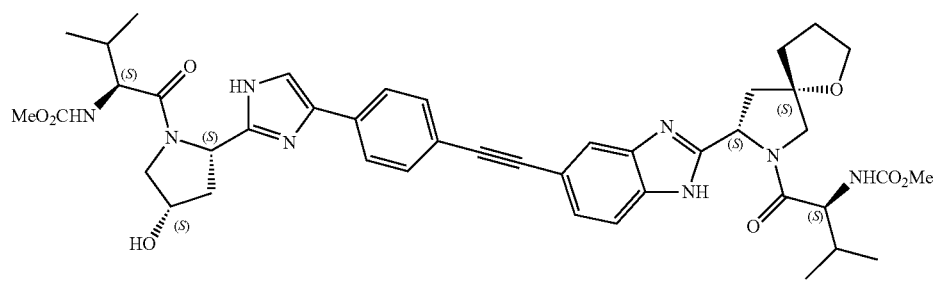

The title compound was prepared from Boc-cis-4-hydroxy-L-proline and the compound from step 555i using procedures similar to that described in Example 546. ESIMS m/z=809.60 [M+H]+.

Example 686

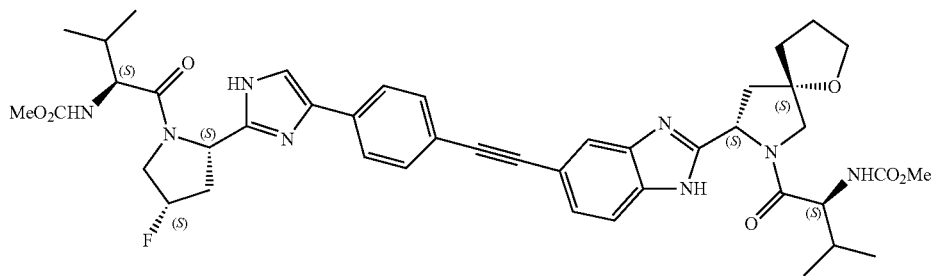

The title compound was prepared from Boc-cis-4-fluoro-L-proline and the compound from step 555i using procedures similar to that described in Example 546. ESIMS m/z=811.56 [M+H]$^+$.

Example 567

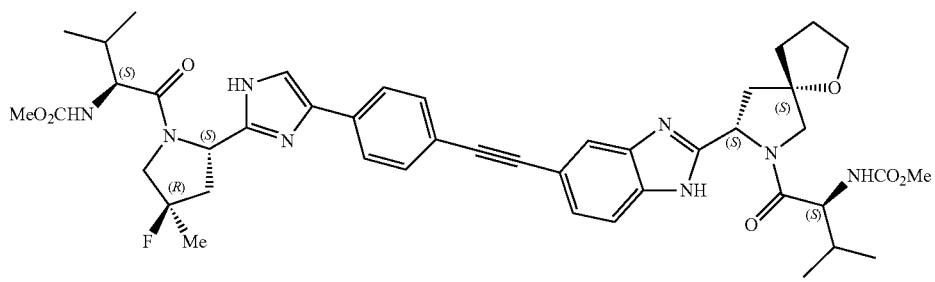

Step 567a.

Into a solution of N-carbobenzoxy-4-oxo-L-proline (1.00 g, 4.37 mmol) in THF (60 mL) at −78° C. was added MeMgBr (3M in Et$_2$O, 3.20 mL, 9.61 mmol). The resultant mixture was kept at −78° C. for 1 hour before being warmed up to rt for 14 hours. The reaction was quenched with 1N aqueous HCl to pH 2, and the volatiles were evaporated off. The residue was partitioned (EtOAc—H$_2$O) and the organics were dried (Na$_2$SO$_4$), filtered and evaporated to give the crude desired compound as a yellow brown oil (0.842 g) which was directly used in the next step. ESIMS m/z=246.20 [M+H]$^+$.

Step 567b.

Into a solution of the crude compound from step 567a (4.37 mmol at most) in MeOH (15 mL) and benzene (15 mL) was added TMSCHN$_2$ (2M in hexane) until the yellow color did not fade. The volatiles were evaporated and the residue was purified by chromatography (silica, hexanes-ethyl acetate) to give the desired compound as a light yellow solid (0.480 g, ~80% purity). ESIMS m/z=260.20 [M+H]$^+$.

Step 567c.

Into a solution of the compound from step 567b (0.480 g, ~80% purity, 1.57 mmol) in CH$_2$Cl$_2$ (30 mL) at 0° C. was added DAST (0.42 mL, 3.15 mmol). The reaction was kept at 0° C. for 1 hour before being quenched with aqueous NaHCO$_3$. The residue was partitioned (CH$_2$Cl$_2$—H$_2$O) and the organics were dried (Na$_2$SO$_4$), filtered and evaporated. The residue was purified by chromatography (silica, hexanes-ethyl acetate) to give the desired compound as a colorless oil (0.259 g, 23% over 3 steps). ESIMS m/z=262.15 [M+H]$^+$.

Step 567d.

The crude acid compound was prepared from the compound from step 567c using procedures similar to that described in step 555e. ESIMS m/z=248.08 [M+H]$^+$.

Step 567e.

The title compound was prepared from the compound from step 567d and the compound from step 555i using procedures similar to that described in Example 546. ESIMS m/z=825.45 [M+H]$^+$.

Example 626

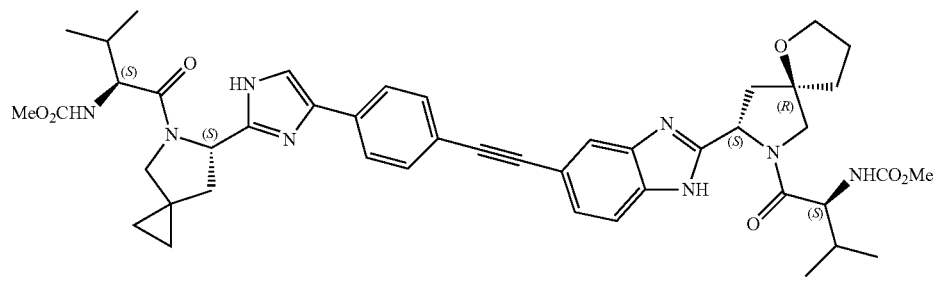

The title compound was prepared from the minor diastereomer isolated from step 555c and the compound from step 548b using procedures similar to that described in Example 555. ESIMS m/z=819.58 [M+H]+.

Example 557

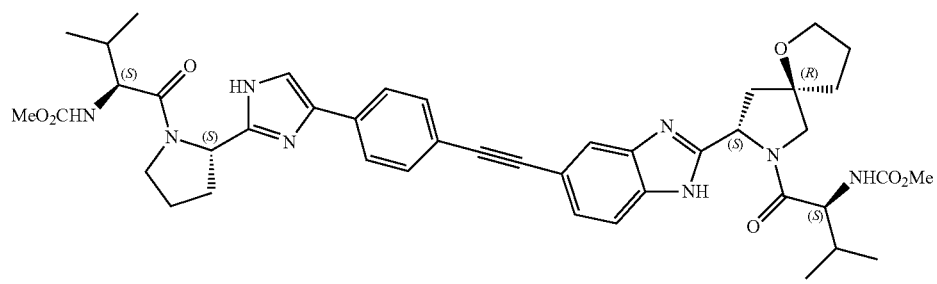

The title compound was prepared from the minor diastereomer isolated from step 555c and the compound from step 630b using procedures similar to that described in Example 555. ESIMS m/z=793.56 [M+H]+.

Example 568

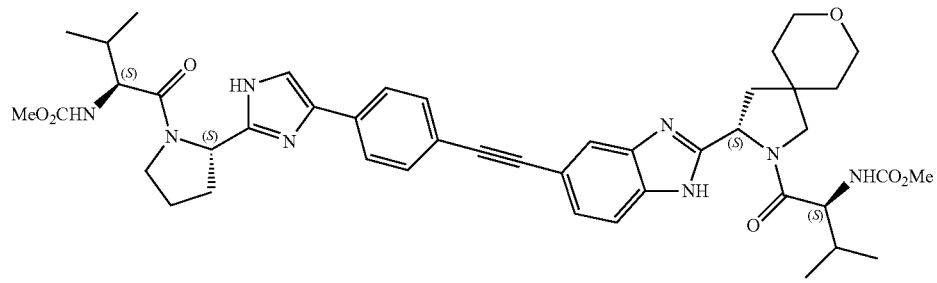

Step 568a.

To a solution of (+)-(3R,7aS)-tetrahydro-3-phenyl-3H,5H-pyrrolo[1,2-c]oxazol-5-one (2.10 g, 9.85 mmol) in THF (60 mL) at −78° C. was added LiHMDS (1 M in THF, 39.4 mL, 39.4 mmol). The resultant mixture was kept at −78° C. for 30 minutes before slow addition of allyl bromide (5.0 mL, 59.1 mmol). The reaction was allowed to gradually warm up to 0° C. and quenched by aqueous NH4Cl solution. The volatiles were evaporated and the residue was parti tioned (EtOAc—H2O). The organics were dried (Na2SO4), filtered and evaporated. The residue was purified by chromatography (silica, hexanes-ethyl acetate) to give the desired diallylation compound as a very light yellow oil (2.30 g, 78%). ESIMS m/z=284.16 [M+H]+.

Step 568b.

Ozone, generated from an ozone generator, was bubbled through a solution of the compound from step 568a (2.30 g, 8.11 mmol) in MeOH (85 mL) at −78° C. until the appearance of blue color. The extra Ozone was removed by the oxygen flow before the addition of NaBH4 (2.46 g, 64.9 mmol) at −78° C. The mixture was gradually warmed up to rt for and kept at rt for 16 hours before being quenched by 2M aqueous HCl to pH 5. The volatiles were evaporated off and the residue was partitioned (EtOAc—H2O). The organics were dried (Na2SO4), filtered and evaporated. The residue was purified by chromatography (silica, hexanes-ethyl acetate) to give the desired compound as a colorless oil (1.61 g, 68%). ESIMS m/z=292.15 [M+H]+.

Step 568c.

Into a mixture of the compound from step 568b (1.52 g, 5.21 mmol), Ag$_2$O (1.81 g, 7.80 mmol) and KI (0.173 g, 1.04 mmol) in CH$_2$Cl$_2$ (40 mL) was added TsCl (1.09 g, 5.73 mmol) in CH$_2$Cl$_2$ (20 mL) slowly. The resultant mixture was stirred at rt for 24 hours before being filtered through Celite. The filtrates were evaporated and the residue was purified by chromatography (silica, hexanes-ethyl acetate) to give the desired compound as a colorless oil (1.38 g, 60%) with the recovery of the compound from step 568b (0.473 g, 31%). ESIMS m/z=446.07 [M+H]$^+$.

Step 568d.

Into a solution of the compound from step 568c (1.38 g, 3.11 mmol) in THF (62 mL) was added NaH (60% in mineral oil, 0.187 g, 4.67 mmol). The resultant mixture was stirred at rt for 24 hours before being quenched by aqueous NH$_4$Cl. The volatiles were evaporated and the residue was partitioned (EtOAc—H$_2$O). The organics were dried (Na$_2$SO$_4$), filtered and evaporated. The residue was purified by chromatography (silica, hexanes-ethyl acetate) to give the desired compound as a colorless oil (0.726 g, 86%). ESIMS m/z=274.10 [M+H]$^+$.

Step 568e.

Into a solution of the compound from step 568d (0.726 g, 2.66 mmol) in THF (50 mL) was added LiAlH$_4$ (1M in THF, 5.3 mL, 5.32 mmol). The resultant mixture was heated to 60° C. for 3 hours before being quenched by sequential addition of H$_2$O (0.20 mL), 15% aqueous NaOH (0.20 mL) and H$_2$O (0.60 mL) at 0° C. The mixture was passed through Celite and the filtrates were evaporated. The residue was partitioned (EtOAc—H$_2$O) and the organics were dried (Na$_2$SO$_4$), filtered and evaporated. The residue was purified by chromatography (silica, hexanes-ethyl acetate) to give the desired compound as a colorless oil (0.718 g). ESIMS m/z=262.21 [M+H]$^+$.

Step 568f.

Into a mixture of compound from step 568e (2.66 mmol at most) and AcOH (0.30 mL, 5.32 mmol) in MeOH (16 mL) was added palladium (10 wt % on carbon, 54.8 mg). The resulting mixture was hydrogenated under 60 psi H$_2$ at rt for 4 hours before being filtered through Celite. The filtrate was concentrated to give the crude desired compound as a colorless oil (0.782 g). ESIMS m/z=172.17 [M+H]$^+$.

Step 568g.

Into a mixture of the crude compound from step 568f (2.66 mmol at most) and NaHCO$_3$ (1.79 g, 21.3 mmol) in 1,4-dioxane (10 mL) and H$_2$O (20 mL) was added Boc$_2$O (0.696 g, 3.19 mmol). The resultant mixture was stirred at rt for 1 day before being evaporated to dryness. The residue was partitioned (EtOAc—H$_2$O) and the organics were dried (Na$_2$SO$_4$), filtered and evaporated. The residue was purified by chromatography (silica, hexanes-ethyl acetate) to give the desired compound as a colorless oil (0.610 g, 3 step 85%). ESIMS m/z=272.26 [M+H]$^+$.

Step 568h.

Into a solution of the compound from step 568g (0.610 g, 2.25 mmol) in carbon tetrachloride (9 mL), CH$_3$CN (12 mL) and H$_2$O (15 mL) were added RuCl$_3$.XH$_2$O (9.3 mg, 45.0 μmol) and NaIO$_4$ (0.963 g, 4.50 mmol). The resultant mixture was stirred at rt for 4 hours before being partitioned (CH$_2$Cl$_2$—H$_2$O). The aqueous phase was acidified to pH 3 and was extracted by CH$_2$Cl$_2$. The combined organics were dried (Na$_2$SO$_4$), filtered and evaporated to give the crude desired compound as a light brown foam (0.640 g). ESIMS m/z=286.24 [M+H]$^+$.

Step 568i.

The title compound was prepared from the compound from step 630b and the compound from step 568h using procedures similar to that described in Example 630. ESIMS m/z=807.71 [M+H]$^+$.

Example 690

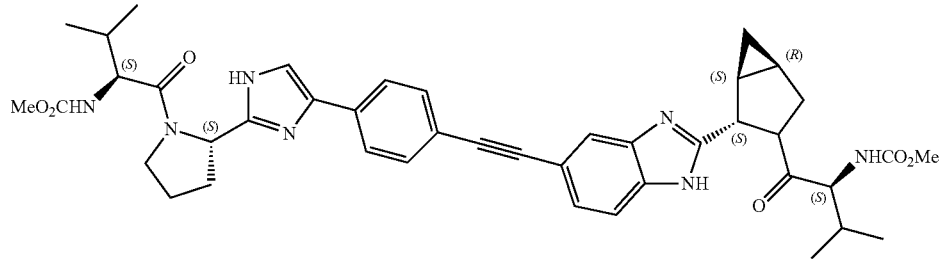

The title compound was prepared from the compound from step 630b and (1S,2S,5R)-3-(tert-butoxycarbonyl)-3-azabicyclo[3.1.0]hexane-2-carboxylic acid (prepared according to WO 2009/102325) using procedures similar to that described in Example 630. ESIMS m/z=749.44 [M+H]$^+$.

Example 588

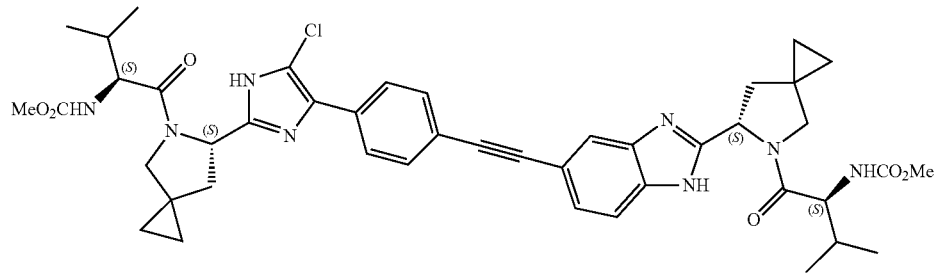

To a solution of the compound of Example 548 (24 mg, 0.030 mmol) in DMF (0.6 mL) was added NCS (4.8 mg, 0.036 mmol). The resulting solution was stirred at 50° C. for 16 h before being partitioned (EtOAc—H$_2$O). The organics were washed with brine, dried (Na$_2$SO$_4$), filtered and concentrated. The residue was purified by preparative thin layer chromatography (EtOAc-hexanes) to afford the title compound as a yellow foam (12 mg, 48%). ESIMS m/z=823.69/825.69 [M+H]$^+$.

Example 657

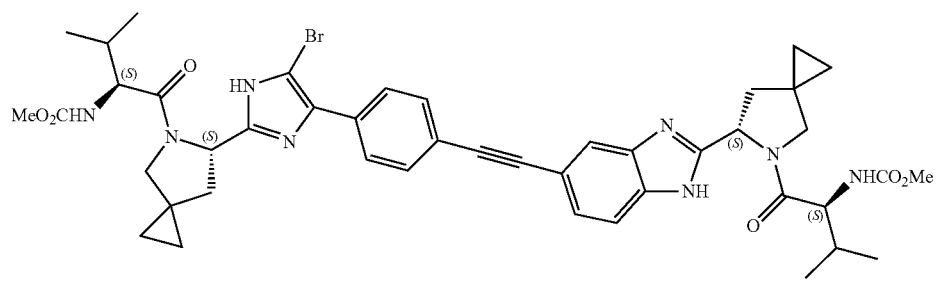

To a solution of the compound of Example 548 (24 mg, 0.030 mmol) in DMF (0.6 mL) was added NBS (6.9 mg, 0.036 mmol). The resulting solution was stirred at rt for 16 hours before being partitioned (EtOAc—H$_2$O). The organics were washed with brine, dried (Na$_2$SO$_4$), filtered and concentrated. The residue was purified by preparative thin layer chromatography (EtOAc-hexanes) to afford the title compound as a yellow foam (13.6 mg, 51%). ESIMS m/z=867.42, 869.42 [M+H]$^+$.

Example 660

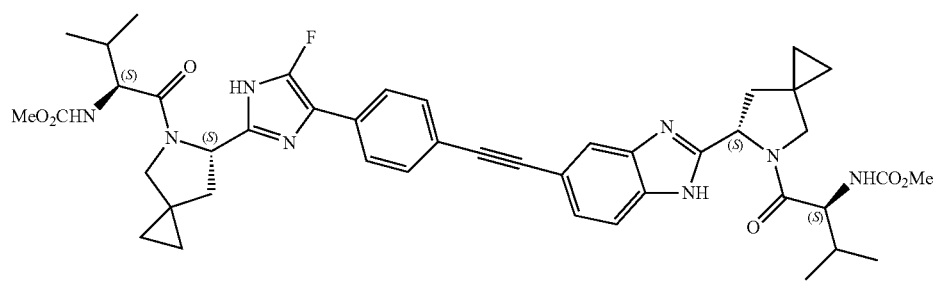

To a solution of the compound of Example 548 (160 mg, 0.20 mmol) in DMF (2 mL) was added Accufluor (45-50% on alumina, 100 mg, 0.33 mmol). The resulting solution was stirred at 60° C. for 4 hours before being cooled to rt and partitioned (EtOAc—H$_2$O). The organics were washed with brine, dried (Na$_2$SO$_4$), filtered and concentrated. The residue was purified by preparative thin layer chromatography (EtOAc-hexanes) to afford the title compound as a yellow foam (10 mg, 6.5%). ESIMS m/z=807.55 [M+H]$^+$.

Example 591

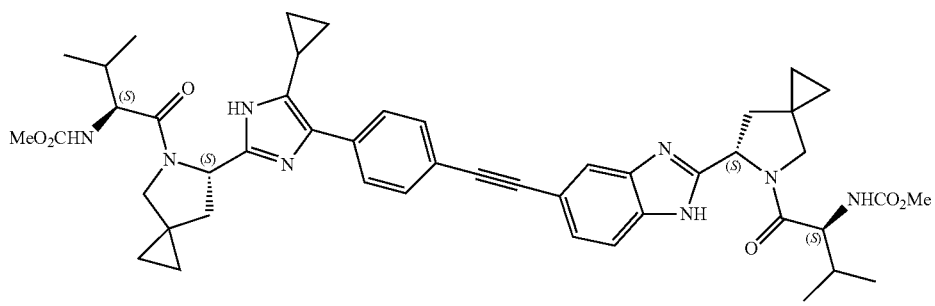

A mixture of the compound from step 657 (45 mg, 0.05 mmol), cyclopropylboronic acid pinacol ester (84 mg, 0.5 mmol), dichloro[1,1'-bis(di-t-butylphosphino)ferrocene]palladium(II) (5.0 mg, 0.0076 mmol) in THF (1 mL) and saturated aqueous NaHCO$_3$ solution (0.2 mL) was degassed and then heated at 100° C. in a sealed tube for 2 hours. The residue was partitioned (EtOAc—H$_2$O). The organics were washed with brine, dried (Na$_2$SO$_4$), filtered and evaporated. The residue was purified by chromatography (silica, hexanes-ethyl acetate) to give the title compound as a yellow foam (17.5 mg, 42%). ESIMS m/z=829.69 [M+H]$^+$.

Example 661

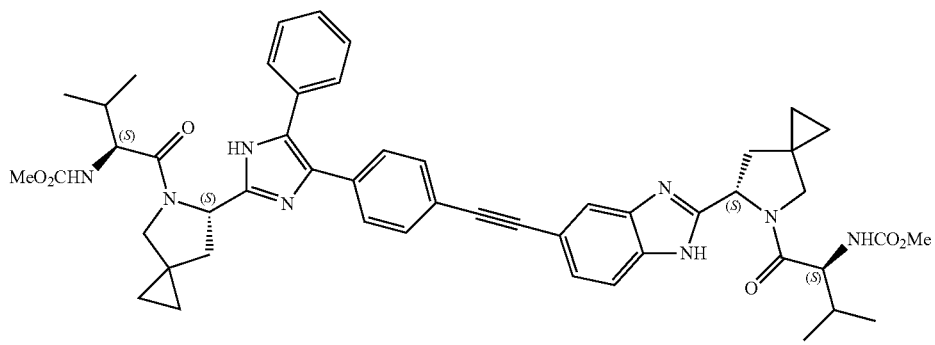

The title compound was prepared from the compound from step 657 and phenylboronic acid pinacol ester using procedures similar to that described in Example 591. ESIMS m/z=865.43 [M+H]$^+$.

Example 593

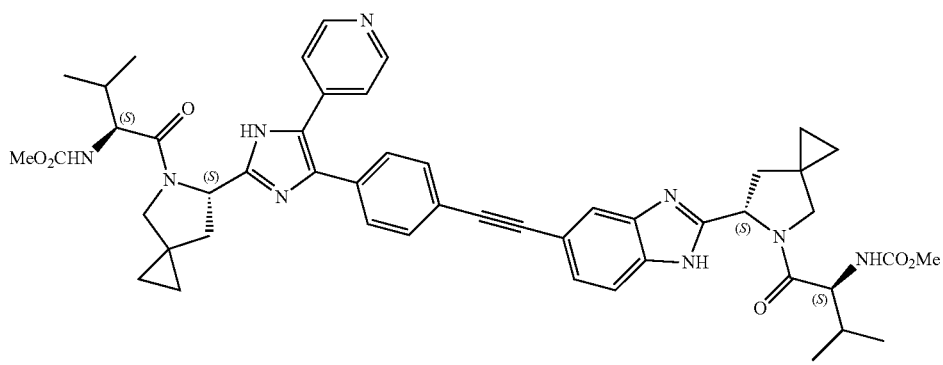

The title compound was prepared from the compound from step 657 and 4-pyridineboronic acid pinacol ester using procedures similar to that described in Example 591. ESIMS m/z=865.43 [M+H]⁺.

Example 662

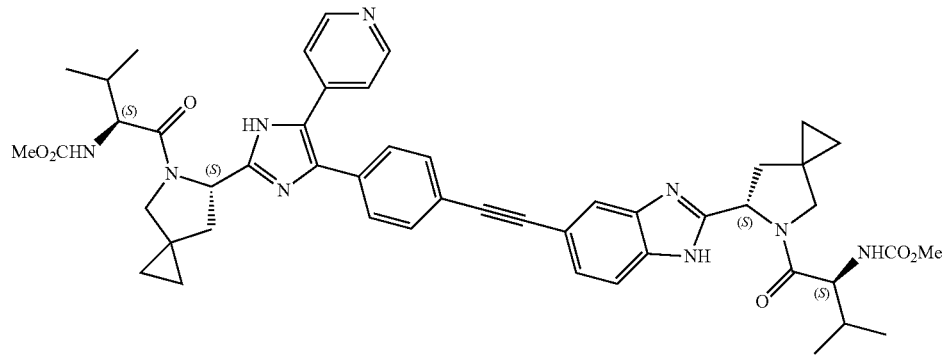

The title compound was prepared from the compound from step 657 and 3-pyridinelboronic acid pinacol ester using procedures similar to that described in Example 591. ESIMS m/z=865.43 [M+H]⁺.

Example 687

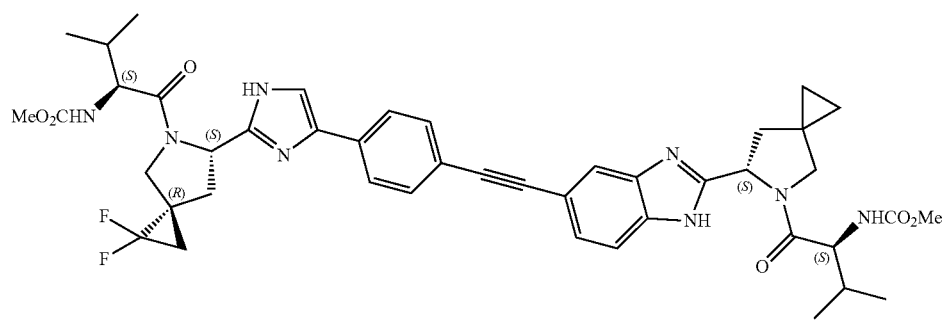

Step 687a.

A solution of (S)-1-benzyl 2-methyl 4-methylenepyrrolidine-1,2-dicarboxylate (1 g, 3.63 mmol) in diglyme (20 mL) was heated to 175° C. A cloudy solution of sodium chlorodifluoroacetate (16.6 g, 108.9 mmol) in diglyme was added via a syring pump over 2.5 hours. The mixture was cooled down and partitioned (EtOAc—H₂O). The organics were washed with brine, dried (Na₂SO₄), filtered and evaporated. The residue was purified by chromatography (silica, hexanes-ethyl acetate) to give two diastereomers, both as colorless oils.

(3S,6S)-5-benzyl 6-methyl 1,1-difluoro-5-azaspiro[2.4]heptane-5,6-dicarboxylate (572 mg, 48%). ¹H NMR (CDCl₃): 7.36 (m, 5H), 5.02-5.21 (m, 2H), 4.45 (dm, 1H) m 3.81 (m, 1H), 3.76, 3.59 (2s, 3H), 3.57 (m, 1H), 2.58 (m, 1H), 1.99 (dd, 1H), 1.37 (m, 2H).

(3R,6S)-5-benzyl 6-methyl 1,1-difluoro-5-azaspiro[2.4]heptane-5,6-dicarboxylate (375 mg, 32%). ¹H NMR (CDCl₃): 7.35 (m, 5H), 5.20 (dd, 1H), 5.10 (dd, 1H), 4.56 (dd, 1H), 3.76, 3.74, 3.63 (2s, 3H), 3.55 (m, 1H), 2.45 (m, 1H), 2.12 (dd, 1H), 1.38 (m, 2H).

Step 687b.

A solution of (3R,6S)-5-benzyl 6-methyl 1,1-difluoro-5-azaspiro[2.4]-heptane-5,6-dicarboxylate from step 687a (350 mg, 1.07 mmol) and di-tert-butyl dicarbonate (281 mg, 1.3 mmol) in MeOH (10 mL) was treated with Pd/C (10 wt %, 50 mg) under hydrogen (60 psi) for 4.5 hours before being filtered through Celite and concentrated. The residue was purified by chromatography (silica, hexanes-ethyl acetate) to give the desired compound as a colorless oil (284 mg, 90%). ¹H NMR (CDCl₃): 4.44 (dd, 1H), 3.76 (s, 3H), 3.71 (dd, 1H), 3.44 (m, 1H), 2.20 (m, 1H), 2.08 (d, 1H), 1.47, 1.42 (2s, 9H), 1.38 (m, 2H).

Step 687c.

To a solution of the compound from step 687b (284 mg, 0.97 mmol) in EtOH (2 mL) and water (1 mL) was added LiOH.H₂O (55 mg, 1.3 mmol). The mixture was stirred at rt overnight before being concentrated. The residue was dissolved in H₂O (5 mL) and acidified to pH ~2 by HCl (1 N). The mixture was extracted with EtOAc and CH₂Cl₂. The organics were dried (Na₂SO₄), filtered and evaporated to give the crude desired compound as a white foam (283 mg). H NMR (CDCl₃): 4.48 (dd, 1H), 3.76 (s, 3H), 3.68 (dd, 1H), 3.45 (m, 1H), 2.38 (m, 1.5H), 2.19 (d, 0.5H), 1.47, 1.42 (2s, 9H), 1.40 (m, 2H).

Step 687d.

To a solution of the crude compound from step 687c (135 mg, 0.487 mmol) and 2-bromo-1-(4-iodophenyl)ethanone (166 mg, 0.51 mmol) in acetonitrile (3 mL) was added DIPEA (0.21 mL, 1.22 mmol). The resulting mixture was stirred at rt for 3 hours before being partitioned between EtOAc and aqueous NaHCO₃. The organic phase was separated, dried (Na₂SO₄) and concentrated to afford a brown oil. The residue was purified by chromatography (silica, hexane- EtOAc) to give the desired product as a light yellow foam (210 mg, 82%). ESIMS m/z=543.92 [M+Na]+.

Step 687e.

A mixture of the compound from step 687d (210 mg, 0.40 mmol) and NH₄OAc (341 mg, 4.43 mmol) in toluene (5 mL) was heated at 105° C. overnight before being partitioned (EtOAc—H₂O). The organic phase was separated, dried (Na₂SO₄) and concentrated. The residue was purified by chromatography (silica, hexane-EtOAc) to give the desired product as a yellow foam (173 mg, 82%). ESIMS m/z=502.50 [M+H]+.

Step 687f.

The title compound was prepared from the compounds from step 687e and 548f using procedures similar to that described in example 548. ESIMS m/z=825.30 [M+H]+.

Example 614

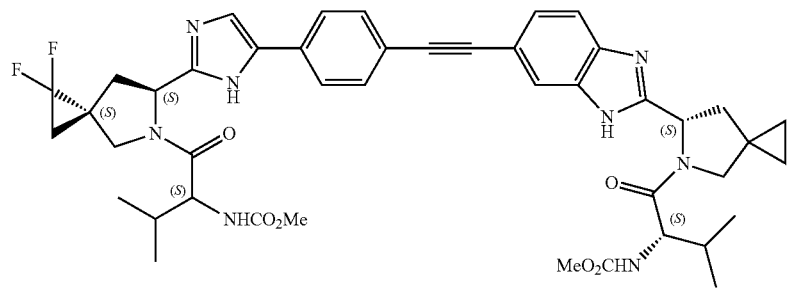

The title compound was prepared from (3S,6S)-5-benzyl 6-methyl 1,1-difluoro-5-azaspiro[2.4]heptane-5,6-dicarboxylate from step 687a using procedures similar to that described in example 687. ESIMS m/z=825.30 [M+H]+.

Example 547

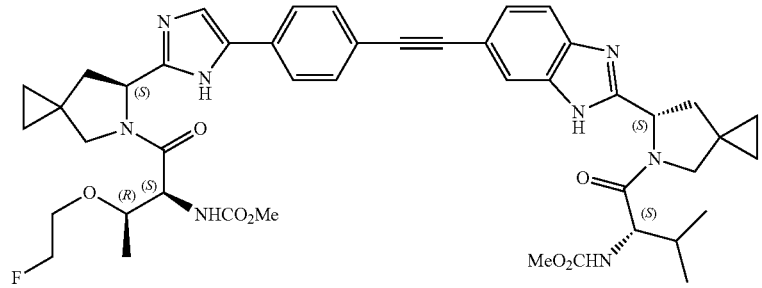

Step 547. A solution of N-Boc-L-threonine (65.8 g, 0.30 mol) in DMF (500 mL) was treated with NaH (26.4 g, 0.66 mmol) portionwisely under −15° C. with mechanical stirring for 2 hours. Allyl bromimde (40 g, 0.33 mol) was added. The mixture was stirred at rt overnight before being quenched with ice-water and extracted with methyl tert-butyl ether (MTBE). The aqueous phase was acidified to pH 4 to 5 by adding aqueous citric acid (10%). This mixture was extracted with EtOAc. The combined organics were washed with brine, dried (Na₂SO₄), filtered and evaporated. The residue was purified by a short silica column (EtOAc) to give the desired compound as a colorless syrup (69.3 g). ESIMS m/z=282.18 [M+Na]+.

Step 547b.

A solution of the compound from step 547547a (22.7 g, 87.5 mmol), benzyl alcohol (10.8 mL, 105 mmol) and HATU (40 g, 105 mmol) in CH₂Cl₂ (250 mL) was treated with DIPEA (36.5 ml, 210 mmol) at 0° C. and stirred at rt for three days. After the mixturte was washed with water and brine, the organics were dried (Na₂SO₄), filtered and evaporated. The residue was purified by chromatography (silica, hexanes-ethyl acetate) to give the desired compound as a colorless oil (19.6 g, 64%). ESIMS m/z=372.09 [M+Na]+.

Step 547c.

A solution of the compound from step 547547b (625 mg, 1.79 mmol) in CH₂Cl₂ (10 mL) and MeOH (10 mL) was treated with a stream of ozone at 0° C. for 15 minutes before being purged with oxygen. NaBH₄ (79 mg, 2.1 mmol) was added. The mixture was stirred for 30 minutes before being quenched with aqueous NH₄Cl and partitioned (CH₂Cl₂-water). The organics were dried (Na₂SO₄), filtered and evaporated. The residue was purified by chromatography (silica, hexanes-ethyl acetate) to give the desired compound as a colorless oil (230 mg, 36%). ESIMS m/z=376.18 [M+Na]+.

Step 547d.

A solution of the compound from step 547c (280 mg, 0.793 mmol) in CH₂Cl₂ (5 mL) was treated with DAST (256 mg, 1.59 mmol) at −78° C. for 1 h before a second portion of diethylaminosulfur trifluoride (DAST, 250 mg, 1.50 mmol) was added. The mixture was stirred for another 1 hour and warmed up to −30° C. before the volatiles were evaporated. The residue was purified by chromatography (silica, hexanes-ethyl acetate) to give the desired compound as a colorless oil (71 mg, 25%). ESIMS m/z=378.16 [M+Na]+.

Step 547e.

A solution of the compound from step 547d (193 mg, 1.79 mmol) in CH₂Cl₂ (3 mL) was treated with HCl (4 M in 1,4-dioxane, 2 mL) at rt for 3 hours. The mixture was concentrated to give a light yellow syrup. This syrup was dissolved in CH₂Cl₂ (3 mL) and DIPEA (0.4 mL). Methyl chloroformate (46 µl, 0.6 mmol) was added. The mixture was stirred at rt for 1 hour before being partitioned (CH₂Cl₂-aq NaHCO₃). The organics were washed with brine, dried (Na₂SO₄), filtered and evaporated. The residue was purified by chromatography (silica, hexanes-ethyl acetate) to give the desired compound as a brown foam (126 mg, 74%). ESIMS m/z=336.16 [M+Na]⁺.

Step 547f.

A solution of the compound from step 547e (38 mg, 0.118 mmol) in MeOH (2 mL) was treated with a hydrogen balloon and Pd/C (10 wt %, 3 mg) at rt for 4 hours before being filtered through Celite. The filtrate was concentrated to give the desired compound as a colorless oil (28 mg, 100%). ESIMS m/z=246.15 [M+Na]⁺.

Step 547g.

The title compound was prepared from the compound from step 547f and the compound from step 616d using the procedure similar to that described in step 616e. ESIMS m/z=837.47 [M+H]⁺.

Example 617 partitioned (EtOAc-water). The organics were washed with water, brine, dried (Na₂SO₄), filtered and evaporated. The residue was purified by chromatography (silica, hexanes-ethyl acetate) to give the desired compound as a colorless oil (481 mg, 79% two steps). ESIMS m/z=201.12 [M-Boc+2H]⁺.

Step 617d.

The desired compound was prepared from the compound from step 617c using procedures similar to that described in step 687c.

Step 617e.

The desired compound was prepared from the compound from step 617d using procedures similar to that described in step 687d. ESIMS m/z=553.03 [M+Na]⁺.

Step 617f.

The desired compounds (2R,4S)-tert-butyl 4-(azidomethyl)-4-hydroxy-2-(5-(4-iodophenyl)-1H-imidazol-2-yl)pyrrolidine-1-carboxylate (minor product, ESIMS m/z=511.05 [M+Na]⁺) and (2R,4R)-tert-butyl 4-(azidomethyl)-4-hydroxy-2-(5-(4-iodophenyl)-1H-imidazol-2-yl)pyrrolidine-1-carboxylate (major product, ESIMS m/z=511.03 [M+Na]⁺) were prepared from the compound

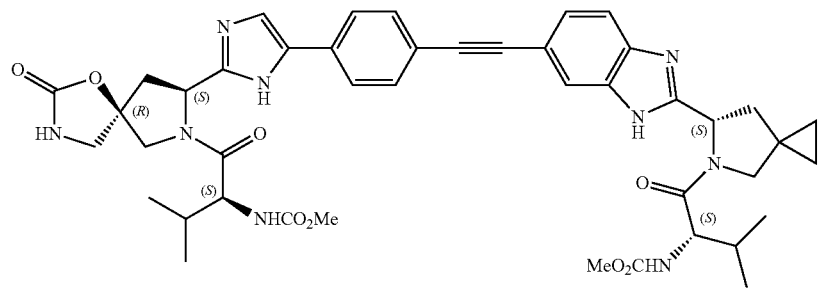

Step 617a.

To a suspension of AD-mix α (2.9 g) in t-BuOH/H₂O (10 mL/10 mL) cooled with ice/water was added a solution of tert-butyl 2-methyl 4-methylenepyrroli-dine-1,2-dicarboxylate (505 mg, 2.1 mmol) in t-BuOH (1 mL). The mixture was gradually warmed up to rt and stirred overnight before Na₂SO₃ (3 g) was added. After another hour, the mixture was partitioned (CH₂Cl₂-water). The aqueous was extracted with CH₂Cl₂. The combined organics were washed with brine, dried (Na₂SO₄), filtered and evaporated. The residue was purified by chromatography (silica, hexanes-ethyl acetate) to give the desired compound as a colorless oil (mixture of diastereomers, 515 mg, 85%). ESIMS m/z=176.17 [M-Boc+2H]⁺.

Step 617b.

A solution of the compound from step 617a (512 mg, 1.86 mmol) in CH₂Cl₂ (5 mL) was treated with DIPEA (0.45 mL, 2.58 mmol) and MsCl (0.16 mL, 2.07 mmol) for 2 hours at 0° C. before being partitioned (CH₂Cl₂-water). The organics were washed with brine, dried (Na₂SO₄), filtered and evaporated to give the crude desired compound as a colorless oil (725 mg), which was used directly in the next step. ESIMS m/z=254.20 [M-Boc+2H]⁺.

Step 617c.

A solution of the compound from step 617b (1.86 mmol at most) in DMF (6 mL) was treated with 15-crown-5 (0.15 mL, 0.75 mmol) and NaN₃ (664 mg, 10.18 mmol) in the presence of K₂CO₃ (1.12 g, 8.12 mmol). The mixture was stirred at 85° C. for 8 hours before being cooled down and from step 617e using procedures similar to that described in step 687e and separated by chromatography (silica, hexanes-ethyl acetate).

Step 617g.

A solution of the major compound from step 617f (113 mg, 0.22 mmol) in THF (1.5 mL) and H₂O (0.2 mL) was treated with trimethylphosphine (PMe₃, 1 M in THF, 1 mL) at 50° C. overnight before being cooled down and concentrated to give the crude desired compound as a yellow syrup, which was used diredctly in the next step. ESIMS m/z=485.1 [M+H]⁺.

Step 617h.

A solution of the crude compound from step 617g (0.22 mmol at most) in THF (2 mL) was treated with CDI (72 mg, 0.42 mmoL) at 50° C. for 4 hours. More CDI (70 mg, 0.41 mmol) was added. The mixture was stirred for 2 more hours before being cooled down and partitioned (CH₂Cl₂-water). The organics were washed with water, brine, dried (Na₂SO₄), filtered and evaporated. The residue was purified by chromatography (silica, hexanes-ethyl acetate) to give the desired compound as a pale yellow oil (55 mg, 50% over two steps). ESIMS m/z=510.98 [M+H]⁺.

Step 617i.

The title compound was prepared from compounds from step 617h and 548f using procedures similar to that described in steps 548g to 548i. ESIMS m/z=834.56 [M+H]⁺.

Example 549

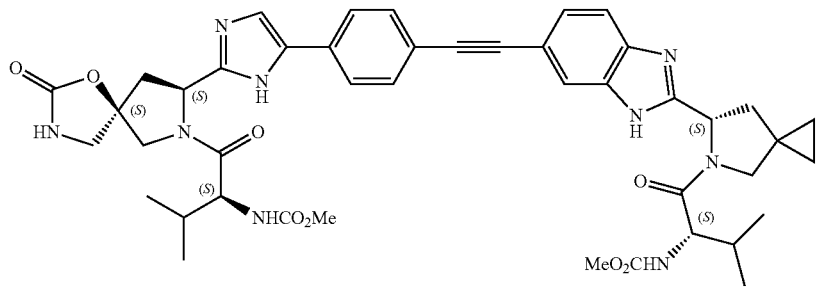

The title compound was prepared from the minor compound from step 617f and 548f using procedures similar to that described in Example 617. ESIMS m/z=834.59 [M+H]+.

Example 619

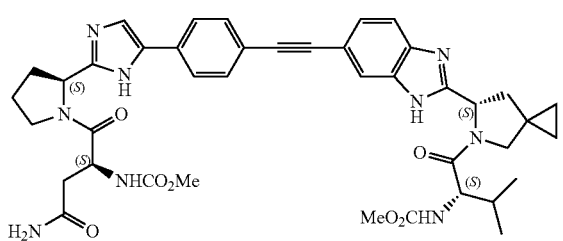

The title compound was prepared from the compound from step 550b and (S)-4-amino-2-(methoxycarbonylamino)-4-oxobutanoic acid (prepared according to WO 2008/021927, 2.160 g, 12.33 mmol) using the procedure similar to that described in step 550c. ESIMS m/z=778.46 [M+H]+.

Example: Compound 552

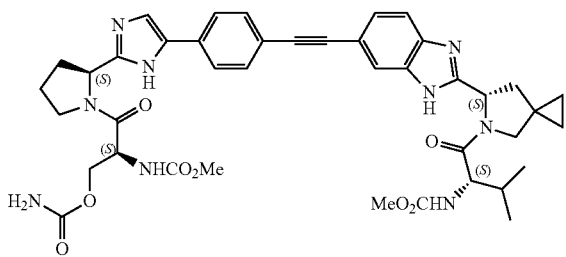

Step 552a.
A solution of L-serine (5.25 g, 50 mmol), Na₂CO₃ (3.07 g, 29 mmol) in water (25 mL) and NaOH (1 M, 52 mL) was treated with methyl chloroformate (4.23 mL, 55 mmoL) at rt overnight. The mixture was extracted with MTBE. The aqueous was acidified to pH ~2 with HCl (4 M), extracted with EtOAc/MeOH. The organics were dried (Na₂SO₄), filtered and evaporated to give the desired compound as a colorless oil (6.12 g, 78%).

Step 552b.
A solution of the crude compound from step 552a (1.5 g, 9.2 mmol) in benzene (24 mL) in a flask equipped with a Dean-Stark trap was treated with benzyl alcohol (1.99 g, 18.42 mmoL) in the presence of TsOH (171 mg, 0.9 mmol). The mixture was refluxed for 6 hours before being cooled down and evaporated. The residue was purified by chromatography (silica, hexanes-ethyl acetate) to give the desired compound as a colorless oil (1.17 g, 50%).

Step 552c.
A solution of the compound from step 552b (450 mg, 1.77 mmol) in toluene (5 mL) was treated with phosgene (1.84 M in toluene, 5.7 mL, 10.6 mmol) at 0° C. for 1 hour before being concentrated. The residual was treated with concentrated NH₄OH (6 mL) for 30 minutes before being partitioned (EtOAc—H₂O). The organics were washed with brine, dried (Na₂SO₄), filtered and evaporated. The residue was purified by crystallization (EtOAc/Hexane) to give the desired compound as a crystal (85 mg, 15%). ¹H NMR (CDCl₃): 7.36 (m, 5H), 5.58 (d, 1H), 1.21 (s, 2H), 4.68-4.35 (m, 5H), 3.72 (s, 3H).

Step 552d.
A solution of the compound from step 552c (83 mg, 0.278 mmol) in MeOH (10 mL) was treated with Pd/C (10 wt %, 5 mg) under hydrogen balloon at rt for 4.5 hours. The mixture was filtered through Celite and concentrated to give the desired compound as a colorless oil (60 mg, 100%). ¹H NMR (D₂O): 4.43 (br, 1H), 4.38-4.25 (m, 2H), 3.67 (s, 3H).

Step 552e.
The title compound was prepared from the compound from step 552d and 550b using procedures similar to that described in step 550c. ESIMS m/z=794.58 [M+H]+.

Example 554

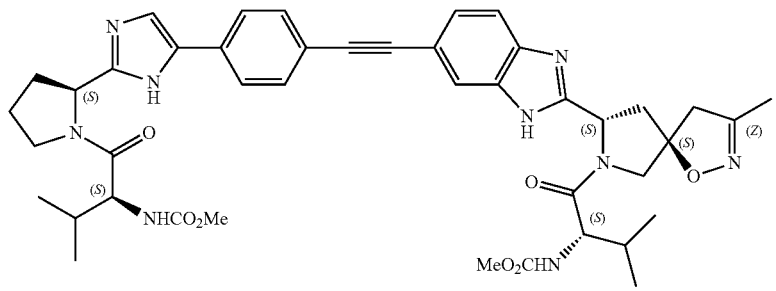

Step 554a.

A solution of (S)-1-(tert-butoxycarbonyl)-4-methyl-enepyrrolidine-2-carboxylic acid (0.98 g, 4.4 mmol) in MeOH (14 mL) and benzene (14 mL) was treated with (trimethylsilyl)diazomethane (TMSCHN$_2$, 2 M in hexanes) dropwisely at rt until the yellow color persisted and no more gas evolved. The solution was concentrated to give the desired compound as a light yellow oil, which was directly used in the next step.

Step 554b.

A solution of the compound from step 554a (4.4 mmol at most) and nitroethane (368 mg, 4.9 mmol) in benzene (20 mL) and TEA (2 drops) was treated with phenyl isocyanate (PhNCO, 1.15 g, 9.7 mmol) at rt overnight before being filtered and partitioned (EtOAc—H$_2$O). The organics were washed with brine, dried (Na$_2$SO$_4$), filtered and evaporated. The residue was purified by chromatography (silica, hexanes-ethyl acetate) to give the desired compounds of ~3:1 inseparable isomeric mixture as a pale yellow oil (0.97 g, 74% over two steps). $^1$H NMR (CDCl$_3$): 4.52-4.25 (m, 1H), 3.82 (dd, 1H), 3.77 (m, 3H), 3.62-3.50 (m, 1H), 2.99 (t, 1H), 2.85 (d, 1H), 2.62, 2.49 (m, m total 1H), 2.30, 2.08 (m, m, total 1H), 2.01 (s, 3H), 1.50-1.40 (m, 9H).

Step 554c.

The two desired compounds (5S,8R)-tert-butyl 8-(5-bromo-1H-benzo[d]imidazol-2-yl)-3-methyl-1-oxa-2,7-diazaspiro[4.4]non-2-ene-7-carboxylate (major isomer, ESIMS m/z=435.10, 437.10 [M+H]$^+$) and (5R,8R)-tert-butyl 8-(5-bromo-1H-benzo[d]imidazol-2-yl)-3-methyl-1-oxa-2,7-diazaspiro[4.4]non-2-ene-7-carboxylate (minor isomer, ESIMS m/z=435.14, 437.14 [M+H]$^+$) were prepared from the compound from step 554b using procedures similar to that described in steps 687c, 548c and 548d and separated by chromatography (silica, hexanes-ethyl acetate).

Step 554d.

The desired compound (5S,8R)-tert-butyl 8-(5-ethynyl-1H-benzo[d]imidazol-2-yl)-3-methyl-1-oxa-2,7-diazaspiro[4.4]non-2-ene-7-carboxylate was prepared from the major isomer from step 554c using procedures similar to that described in 548e and 548f. ESIMS m/z=381.10 [M+H]$^+$.

Step 554e.

The title compound was prepared from the compound from step 554d and the compound from step 630b using procedures similar to that described in steps 548g to 548i. ESIMS m/z=806.43 [M+H]$^+$.

Example 623

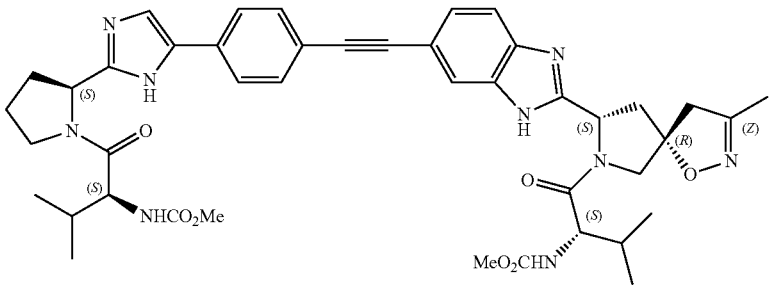

Step 623a.

The desired compound (5R,8R)-tert-butyl 8-(5-ethynyl-1H-benzo[d]imidazol-2-yl)-3-methyl-1-oxa-2,7-diazaspiro[4.4]non-2-ene-7-carboxylate was prepared from the minor isomer from step 554c using procedures similar to that described in 548e and 548f. ESIMS m/z=381.08 [M+H]$^+$.

Step 623b.

The title compound was prepared from the compound from step 623a and the compound from step 630b using procedures similar to that described in steps 548g to 548i. ESIMS m/z=806.57 [M+H]$^+$.

Example 624

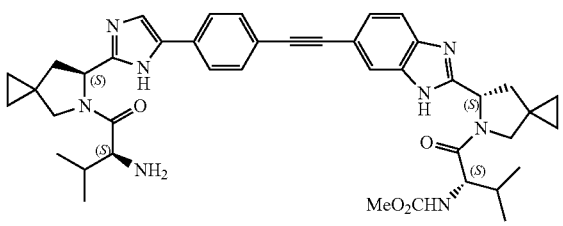

Step 624a.

The desire compound was prepared from the compound from step 548b and (S)-2-(tert-butoxycarbonylamino)-3- methylbutanoic acid using procedure similar to that described in steps 616a and 616b. ESIMS m/z=565.29 [M+H]⁺.

Step 624b.

The title compound was prepared from the compound from step 624a and 616b using procedures similar to that described in steps 616c and 616d and purified by chromatography (silica, MeOH—CH₂Cl₂-ammonia). ESIMS m/z=731.51 [M+H]⁺.

Example 556

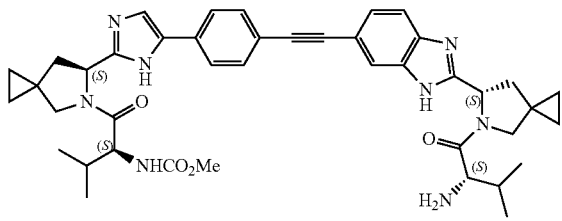

Step 556a.

The desire compound was prepared from the compound from step 548f and (S)-2-(tert-butoxycarbonylamino)-3-methylbutanoic acid using procedure similar to that described in steps 616a and 616b. ESIMS m/z=437.20 [M+H]⁺.

Step 556b.

The title compound was prepared from the compound from step 556a and the compound from step 688a using procedures similar to that described in steps 616c and 616d and purified by chromatography (silica, MeOH—CH₂Cl₂-ammonia). ESIMS m/z=731.66 [M+H]⁺.

Example 625

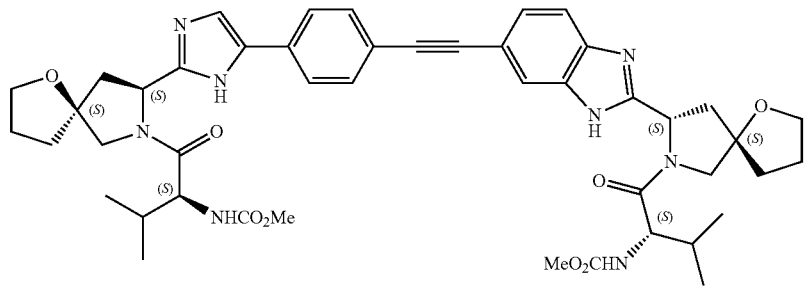

The title compound was prepared from the compound from step 555i and the compound from step 546b using procedures similar to that described in steps 548g to 548i. ESIMS m/z=849.63 [M+H]⁺.

Example 559

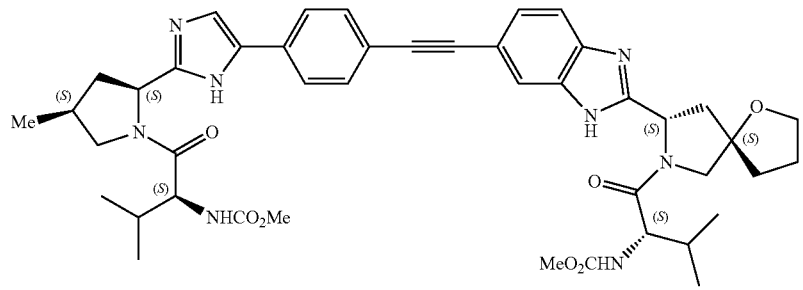

Step 559a.

The desired compounds was prepared from the compound from (S)-1-benzyl 2-methyl 4-methylenepyrrolidine-1,2-dicarboxylate using procedures similar to that described in step 687b. ¹H NMR (CDCl₃): 4.38, 4.25, 4.18 (m, m, m, totally 1H), 3.76, 3.74 (s, s, totally 3H), 3.75, 3.67 (m, m, totally 1H), 2.40 (m, 1H), 2.23, 2.08 (m, m, totally 1H), 1.83, 1.55 (m, m, totally 1H), 1.48, 1.41 (s, s, totally 3H), 1.05 (M, 3H).

Step 559b.

The desired compounds, (2S,4S)-tert-butyl 2-(4-(4-iodophenyl)-1H-imidazol-2-yl)-4-methylpyrrolidine-1-carboxylate (major isomer, ESIMS m/z=454.11 [M+H]⁺) and (2S,4R)-tert-butyl 2-(4-(4-iodophenyl)-1H-imidazol-2-yl)-4-methylpyrrolidine-1-carboxylate (minor isomer, ESIMS m/z=454.16 [M+H]⁺) were prepared from the compound from step 559a using procedures similar to that described in steps 687c to 687e and separated by chromatography (silica, hexanes-ethyl acetate).

Step 559c.

The title compound was prepared from the major isomer from step 559b and the compound from step 555i using procedures similar to that described in steps 548g to 548i. ESIMS m/z=807.61 [M+H]⁺.

Example 628

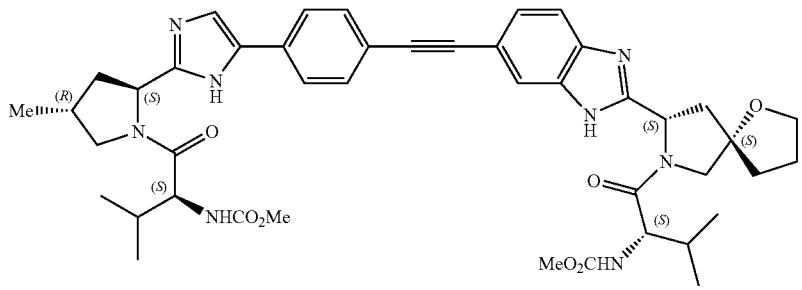

The title compound was prepared from the minor isomer from step 559b and the compound from step 555i using procedures similar to that described in steps 548g to 548i. ESIMS m/z=807.61 [M+H]⁺.

Example 560

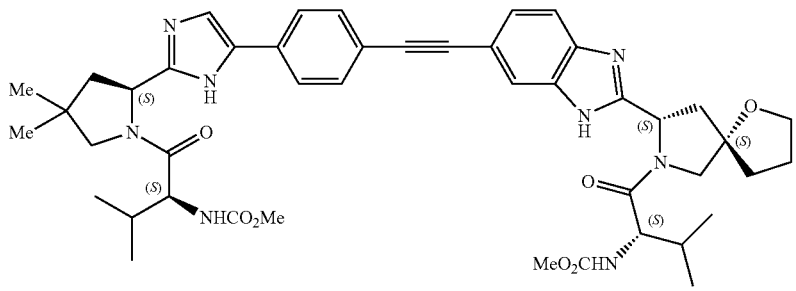

Step 560a.

To a solution of (+)-(3R,7aS)-tetrahydro-3-phenyl-3H,5H-pyrrolo[1,2-c]oxazol-5-one (1.51 g, 7.49 mmol) in THF (15 mL) was added a solution of LiHMDS (1.0 M in THF, 34 mL, 34 mmol) at −78° C. under N₂. The mixture was stirred at −78° C. for 30 minutes before MeI (2.78 mL, 44.4 mmol) was added at −78° C. The mixture was slowly warmed up to ∼−10° C. before being quenched with saturated NH₄Cl solution and evaporated. The residue was partitioned (EtOAc—H₂O). The organics were washed with brine, dried (Na₂SO₄), filtered and evaporated. The residue was purified by chromatography (silica, EtOAc-hexanes) to give the desired compound as a light yellow solid (1.29 g, 75.4%). ESIMS m/z=232.06 [M+H]⁺.

Step 560b.

The desired compound was prepared from the compound from step 560a using procedures similar to that described in steps 630h to 630k and steps 548a to 548b. ESIMS m/z=468.19 [M+H]⁺.

Step 560c.

The title compound was prepared from the compound from step 560b and 555i using procedures similar to that described in steps 548g to 548i. ESIMS m/z=821.53 [M+H]+.

Example 563

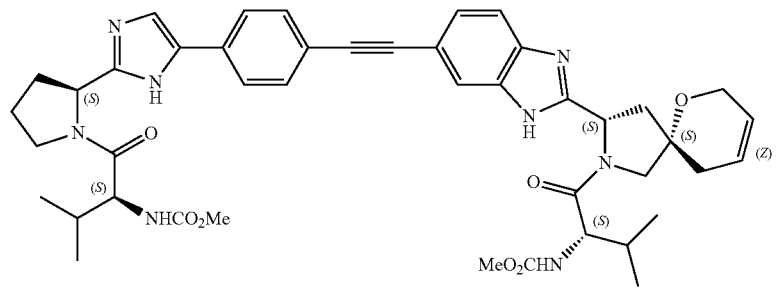

Step 563a.

A mixture of the compound from step 555a (596 mg, 2 mmol, ~8:1 diastereomeric mixture), allyl tert-butyl carbonate (1.26 g, 8 mmol), Pd$_2$(dba)$_3$ (46 mg, 0.05 mmol) and 1,4-bis(diphenylphosphino)butane (dppb, 43 mg, 0.1 mmol) in THF (10 mL) was degassed and then heated at 75° C. under N$_2$ for 1.5 hours. After being cooled down, it was concentrated. The residue was purified by chromatography (silica, hexanes-ethyl acetate) to give the desired compound as a yellow oil containing an isomeric impurity (605 mg, 93%). ESIMS m/z=326.26 [M+H]+.

Step 563b.

A mixture of the compound from step 563a (677 mg, 2.08 mmol) and 1,3-bis(2,4,6-trimethylphenyl)-4,5-dihydroimidazol-2-ylidene[2-(iso-propoxy)-5-(N,N-dimethylaminosulfonyl)phenyl]methylene ruthenium(II)dichloride (Zhan-1B catalyst, 76.4 mg, 0.104 mmol) in toluene (650 mL) was degassed and then heated at 75° C. under N$_2$ for 15 hours. After being cooled down, it was concentrated. The residue was purified by chromatography (silica, hexanes-ethyl acetate) to give the desired compound as a light yellow oil containing an isomeric impurity (585 mg, 94%). ESIMS m/z=298.19 [M+H]+.

Step 563c.

To a solution of the compound from step 563b (160 mg, 0.538 mmol) in EtOH (2 mL) and H$_2$O (2 mL) was added LiOH.H$_2$O (27.1 mg, 0.646 mmol). The resulting mixture was stirred at rt for 3 hours before the volatiles were evaporated off. The residue was dissolved in H$_2$O (10 mL) and acidified to pH ~3 by HCl (4 N). The resulted cloudy mixture was extracted with EtOAc. The organic phase was dried (Na$_2$SO$_4$) and concentrated to afford the desired compound as a colorless oil (142 mg) which was used directly in the next step. ESIMS m/z=284.15 [M+H]+.

Step 563d.

To a solution of the compound from step 563c (142 mg, 0.501 mmol), 4-bromo-1,2-diaminobenzene (93.7 mg 0.501 mmol) and EDC.HCl (115 mg, 0.6 mmol) in acetonitrile (4 mL) was added DMAP (6.1 mg, 0.05 mmol). The resulting solution was stirred at rt overnight (16 h) before being concentrated. The residue was purified by chromatography (silica, EtOAc-hexanes) to afford the desired compounds as a brownish solid (196 mg, 80% over two steps). ESIMS m/z=452.01, 454.09[M+H]+.

Step 563e.

A solution of the compounds from step 563d (0.196 g, 0.434 mmol) in AcOH (4 mL) was heated at 50° C. for 6 hours before being cooled down. The volatiles were evaporated. The crude oil was partitioned (aq. NaHCO$_3$—EtOAc). The organic phase was dried (Na$_2$SO$_4$) and concentrated to afford a brown oil, which was purified by chromatography (silica, EtOAc-hexanes) to afford the desired compound as a yellow foam (116 mg, 62%) as a single isomer. ESIMS m/z=434.13, 436.13[M+H]+.

Step 563f.

To a solution of the compound from step 563e (116 mg, 0.267 mmol), trimethylsilyl acetylene (0.75 mL, 5.34 mmol) in acetonitrile (3 mL) and triethylamine (2 mL) were added Pd(PPh$_3$)$_4$ (31 mg, 0.027 mmol) and CuI (2.5 mg, 0.014 mmol). The resultant mixture was degassed and heated at 90° C. under N$_2$ for 15 hours. After being cooled down, the solution was concentrated. The residue was purified by chromatography (silica, hexanes-ethyl acetate) to give the desired compound as an orange oil (104 mg, 78%). ESIMS m/z=452.27 [M+H]+.

Step 563g.

To a solution of the compound from step 563f (104 mg, 0.230 mmol) in methanol (3 mL) was added potassium carbonate (70 mg 0.5 mmol). The resultant mixture was stirred at rt for 3 hours. The volatiles were evaporated. The residue was partitioned (aq. NaHCO$_3$-EtOAc). The organic phase was dried (Na$_2$SO$_4$) and concentrated to afford a brown oil, which was purified by chromatography (silica, EtOAc-hexanes) to afford the desired compound as a yellow foam (76 mg, 94%). ESIMS m/z=380.20 [M+H]+.

Step 563h.

The title compound was prepared from the compound from step 563g and the compound from step 630b using procedures similar to that described in steps 548g to 548i. ESIMS m/z=805.59 [M+H]+.

Example 632

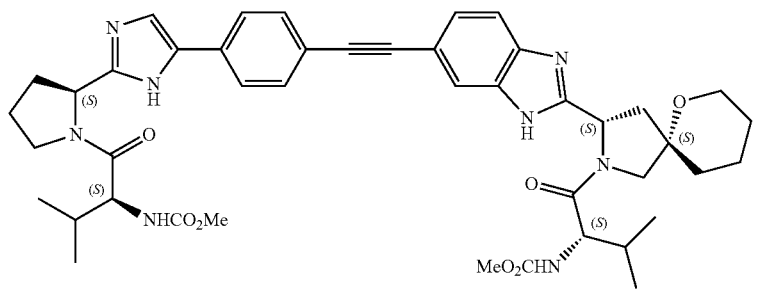

Step 632a.

A solution of the compound from step 563b (152 mg, 0.51 mmol) in MeOH (5 mL) was treated with Pd/C(10 wt %, 10 mg) and hydrogen (60 psi) for 3 hours at rt before being filtered through Celite. The filtrate was concentrated to give the desired compound as a light yellow syrup, which was used directly in the next step. ESIMS m/z=300.17 [M+H]$^+$.

Step 632b.

The desired compound was prepared from the compound from step 632a using procedures similar to that described in steps 563c to 563g. ESIMS m/z=380.22 [M+H]$^+$.

Step 632c.

The title compound was prepared from the compound from step 632b and the compound from step 630b using procedures similar to that described in steps 548g to 548i. ESIMS m/z=807.48 [M+H]$^+$.

Example 633

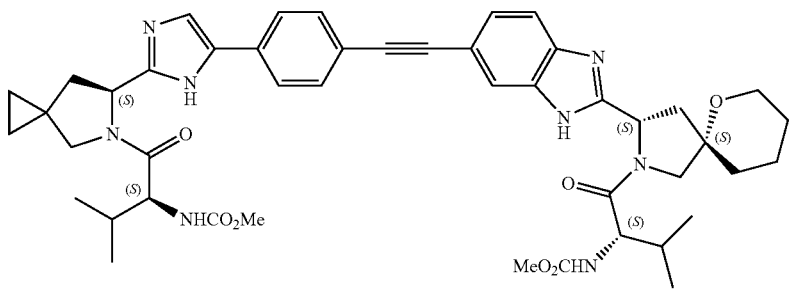

The title compound was prepared from the compound from step 632b and compound 548b using procedures similar to that described in steps 548g to 548i. ESIMS m/z=833.63 [M+H]$^+$.

Example 634

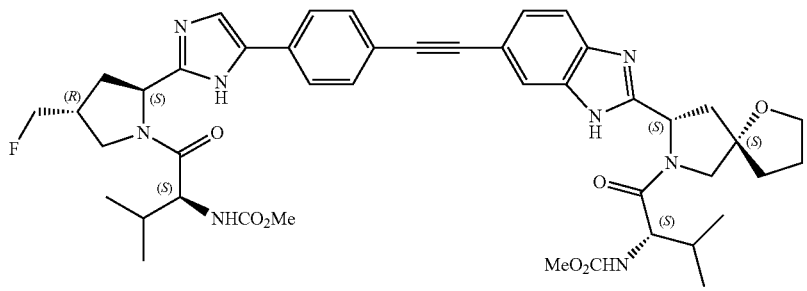

Step 634a.

A solution of (5)-1-benzyl 2-methyl 4-methylenepyrrolidine-1,2-dicarboxylate (666 mg, 2.42 mmol) in THF (8 mL) was treated with 9-borabicyclo-[3,3,1]nonane (9-BBN, 0.5 M in THF, 7 mL, 0.42 mmoL) at rt for 4 hours before NaOH (2.5 N, 2 mL) was added followed by hydrogen peroxide ($H_2O_2$, 30% in water, 1 mL) slowly. The mixture was stirred at rt overnight before being concentrated. The residue was dissolved in water, acidified to pH ~2 by HCl (4 M) and extracted with EtOAc. The organics were dried ($Na_2SO_4$), filtered and evaporated. The residue was dissolved in MeOH (14 mL) and benzene (14 mL) and treated with $TMSCHN_2$ (2 M in hexanes) dropwise until the yellow color persisted. The solution was concentrated. The residue was purified by chromatography (silica, hexanes-ethyl acetate) to give the desired compounds as a colorless oil and isomeric mixture (401 mg, 51%). ESIMS m/z=294.2 [M+H]$^+$.

Step 634b.

A solution of compound from 634a (248 mg, 0.845 mmol) in $CH_2Cl_2$ (3 mL) was treated at rt with Deoxo-Fluor (376 mg, 1.7 mmol) for two hours before a second portion of Deoxo-Fluor (376 mg, 1.7 mmol) was added. The mixture was stirred at rt overnight before being queched dropwisely with aqueous $NaHCO_3$ at 0° C. and partitioned ($CH_2Cl_2$—$H_2O$). The organics were washed with brine, dried ($Na_2SO_4$), filtered and evaporated. The residue was purified by chromatography (silica, hexanes-ethyl acetate) to give the desired compounds as a colorless oil and isomeric mixture (130 mg, 85%). ESIMS m/z=296.11 [M+H]$^+$.

Step 634c.

A solution of the crude compound from step 634b (130 mg, 0.44 mmol) in EtOH (2 mL) and water (2 mL) was treated with LiOH.$H_2O$ (18.5 mg, 0.44 mmol) at rt for 4 hours before being concentrated. The residue was dissolved in $H_2O$ (5 mL) and acidified to pH ~2 by HCl (4 N). The mixture was extracted with EtOAc and $CH_2Cl_2$. The organics were dried ($Na_2SO_4$), filtered and evaporated to give the crude desired compounds as a colorless oil and isomeric mixture (140 mg, 113%). ESIMS m/z=282.10 [M+H]$^+$.

Step 634d.

A solution of compound from step 634c (0.44 mmol at most) and di-tert-butyl dicarbonate (96 mg, 0.44 mmol) in MeOH (10 mL) was treated with Pd/C (10 wt %, 50 mg) under hydrogen (60 psi) overnight at rt before being filtered through Celite. The filtrate was concentrated to give the crude desired compound as a colorless oil and isomeric mixture, which was used directly in the next steps. ESIMS m/z=148.2 [M-Boc+2H]$^+$.

Step 634e.

The desired compounds, (2S,4R)-tert-butyl 4-(fluoromethyl)-2-(5-(4-iodophenyl)-1H-imidazol-2-yl)pyrrolidine-1-carboxylate (major, ESIMS m/z=472.17 [M+H]$^+$) and (2S,4S)-tert-butyl 4-(fluoromethyl)-2-(5-(4-iodophenyl)-1H-imidazol-2-yl)pyrrolidine-1-carboxylate (mior, ESIMS m/z=472.21 [M+H]$^+$) were prepared from the compound from step 634d using procedures similar to that described in step 687d to 687e and separated by chromatography (silica, hexanes-ethyl acetate).

Step 634f.

The title compound was prepared from the major compound from step 634e and the compound from step 555i using procedures similar to that described in steps 548g to 548i. ESIMS m/z=825.49 [M+H]$^+$.

Example 566

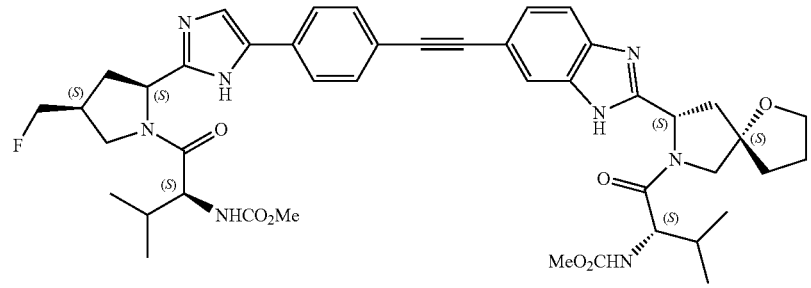

The title compound was prepared from the minor compound from step 634e and the compound from step 555i using procedures similar to that described in steps 548g to 548i. ESIMS m/z=825.38 [M+H]$^+$.

Example 635

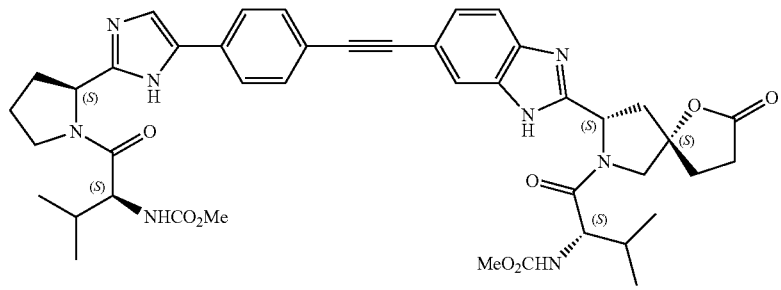

Step 635a.

A solution of (S)-1-(tert-butoxycarbonyl)-4-oxopyrrolidine-2-carboxylic acid (2.0 g, 8.73 mmol) in THF (20 mL) was treated with benzyl bromide (1.14 mL, 9.6 mmol) in the presence of DIPEA (1.67 mL, 9.6 mmol) at rt overnight before being partitioned (EtOAc—H$_2$O). The organic phase was washed with brine, dried (Na$_2$SO$_4$) and concentrated. The residue was purified by chromatography (silica, hexanes-EtOAc) to give the desired product as a colorless oil (1.49 g, 53%). $^1$H NMR (CDCl$_3$): 7.38 (m, 5H), 5.29-5.10 (m, 2H), 4.81 (dd, 1H), 3.90 (m, 2H), 2.92 (m, 1H), 2.58 (m, 1H), 1.45, 1.38 (2s, total 1H).

Step 635b.

To a solution of freshly prepared samarium iodide (SmI$_2$, 10 mmol) in THF (100 mL) was added hexamethylphosphoramide (HMPA, 1.6 mL), followed by a solution of the compound from step 635a (500 mg, 1.56 mmol), methyl acrylate (0.28 mL, 3.13 mmol) and 2-propanol (0.23 mL, 3 mmol) in THF (5 mL) dropwisely. The mixture was stirred at rt for 1.5 hours before being quenched with HCl (1 N) and partitioned (EtOAc—H$_2$O). The organic phase was washed with brine, dried (Na$_2$SO$_4$) and concentrated. The residue was purified by chromatography (silica, hexanes-EtOAc) to give the desired product as a colorless oil (189 mg, 32%). ESIMS m/z=376.18 [M+H]$^+$.

Step 635c.

A solution of the compound from step 635b (189 mg, 0.50 mmol) in MeOH (5 mL) was treated with Pd/C(10 wt %, 15 mg) and H$_2$ (60 psi) at rt for 4 hours before being filtered through a pad of Celite. The filtrate was concentrated to give the desired compound as a colorless syrup, which was used directly in the next step.

Step 635d.

The desired compound was prepared from the compound from step 635c using procedures similar to that described in steps 574a to 574b. ESIMS m/z=483.94 [M+H]$^+$.

Step 635e.

The title compound was prepared from the compound from step 635d and the compound from step 1-1b using procedures similar to that described in steps 548g to 548i. ESIMS m/z=807.64 [M+H]$^+$.

Example 636

Step 636a.

A solution of the compound from step 617b (1.82 mmol at most) in DMF (5 mL) was treated with 15-crown-5 (80 mg, 0.36 mmol) and NaI (1.36 g, 9.1 mmol) in the presence of K$_2$CO$_3$ (1.12 g, 8.12 mmol) at 90° C. overnight before being cooled down and partitioned (EtOAc-water). The organics were washed with water, brine, dried (Na$_2$SO$_4$), filtered and evaporated. The residue was purified by chromatography (silica, hexanes-ethyl acetate) to give the desired compound as a colorless oil (396 mg, 56%) containing an isomeric impurity. ESIMS m/z=386.10 [M+H]$^+$.

Step 636b.

A solution of the compound from step 636a (516 mg, 1.34 mmol) in toluene (10 mL) was treated with totally 4 portions of Bu$_4$SnH (0.36 mL, 1.34 mmol) and AIBN (22 mg, 0.134 mmol) for 12 hours at 110° C. before being cooled down and evaporated. The residue was purified by chromatography (silica, hexanes-ethyl acetate) to give the desired compound as a colorless oil (177 mg, 51%) as a single isomer. ESIMS m/z=260.10 [M+H]$^+$.

Step 636c.

A solution of the compound from step 636b (170 mg, 0.655 mmol) in CH$_2$Cl$_2$ (3 mL) was treated with DAST (0.18 mL, 1.32 mmol) at 0° C. for 1 hours before being quenched with aqueous NaHCO$_3$ dropwisely and partitioned (CH$_2$Cl$_2$-water). The organics were washed with brine, dried (Na$_2$SO$_4$), filtered and evaporated. The residue was purified by chromatography (silica, hexanes-ethyl acetate) to give the desired compound as a colorless oil (177 mg, 51%). ESIMS m/z=260.10 [M+H]$^+$.

Step 636d.

The desired compound was prepared from the compound from step 636c using procedures similar to that described in steps 687c to-687e. ESIMS m/z=472.11 [M+H]$^+$.

Step 636e.

The title compound was prepared from the compound from step 636d and the compound from step 555i using procedures similar to that described in steps 548g to 548i. ESIMS m/z=825.65 [M+H]$^+$.

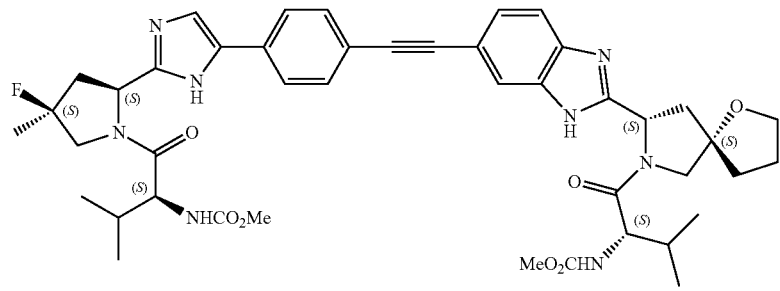

Example 637

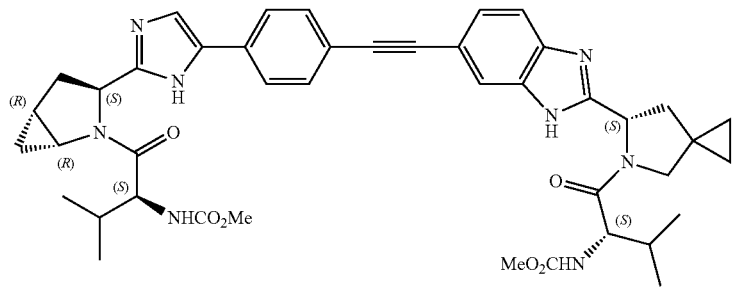

Step 637a.

The desired compound was prepared from (1R,3S,5R)-2-(tert-butoxycarbonyl)-2-azabicyclo[3.1.0]hexane-3-carboxylic acid (prepared according to WO 2009/102325) using procedures similar to that described in steps 548a and 548b. ESIMS m/z=452.04 [M+H]$^+$.

Step 637b.

The title compound was prepared from the compound from step 637a and the compound from step 548f using procedures similar to that described in steps 548g to 548i. ESIMS m/z=775.46 [M+H]$^+$.

Example 569

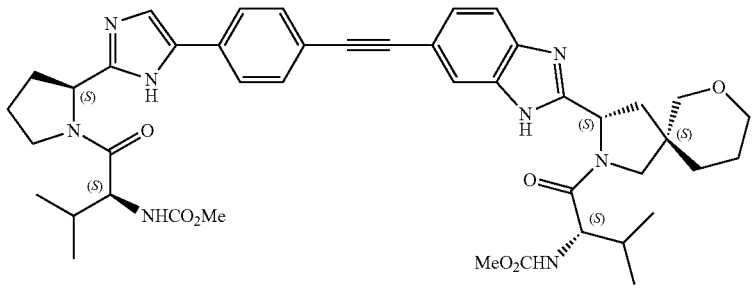

The title compound was prepared from (3S,5S)-tert-butyl 3-(5-iodo-1H-benzo[d]imidazol2-yl)-7-oxa-2-azaspiro[4.5]decane-2-carboxylate (prepared according to WO 2011/081918A1) and the compound from step 1-1b using procedures similar to that described in steps 548g to 548i. ESIMS m/z=807.58 [M+H]$^+$.

Example 638

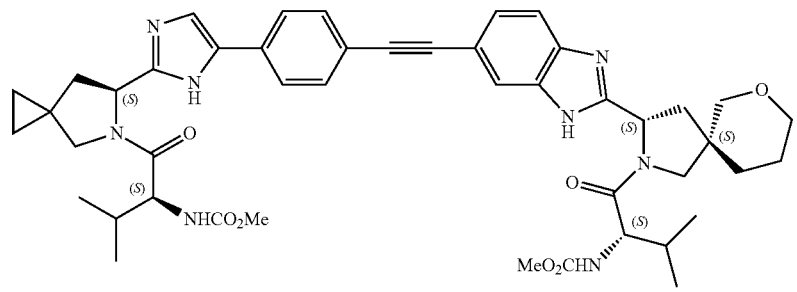

The title compound was prepared from (3S,5S)-tert-butyl 3-(5-iodo-1H-benzo[d]imidazol2-yl)-7-oxa-2-azaspiro[4.5]decane-2-carboxylate (prepared according to WO 2011/081918A1) and the compound from step 565b using procedures similar to that described in steps 548g to 548i. ESIMS m/z=833.50 [M+H]+.

Example 570

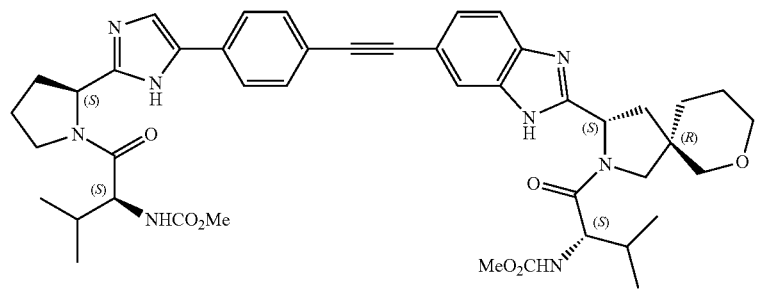

The title compound was prepared from (3S,5R)-tert-butyl 3-(5-iodo-1H-benzo[d]imidazol2-yl)-7-oxa-2-azaspiro[4.5]decane-2-carboxylate ((prepared according to WO 2011/081918A1) and the compound from step 1-1b using procedures similar to that described in steps 548g to 548i. ESIMS m/z=807.58 [M+H]+.

Example 639

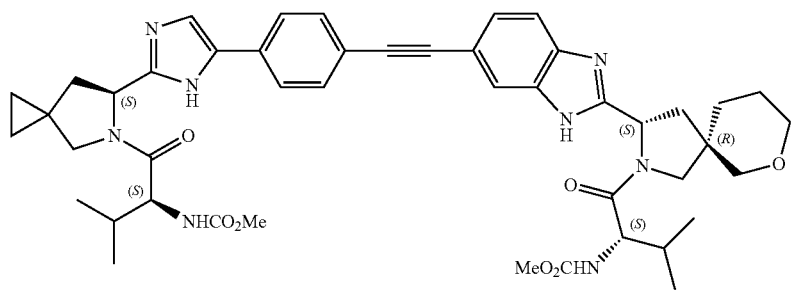

The title compound was prepared from (3S,5R)-tert-butyl 3-(5-iodo-1H-benzo[d]imidazol2-yl)-7-oxa-2-azaspiro[4.5]decane-2-carboxylate (prepared according to WO2011081918A1) and the compound from step 565b using procedures similar to that described in steps 548g to 548i. ESIMS m/z=833.40 [M+H]+.

Example 572

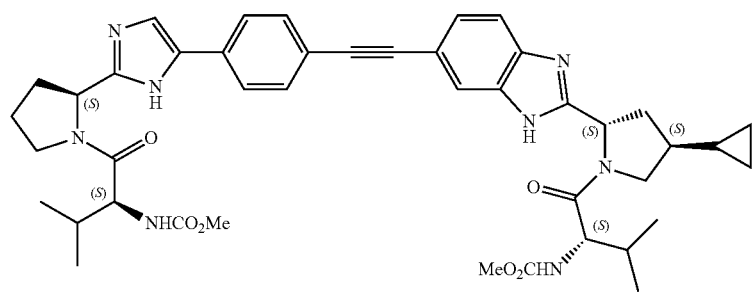

Step 572a.

A solution of (S)-1-tert-butyl 2-methyl 4-methylenepyrrolidine-1,2-dicarboxylate (1.98 mg, 7.2 mmol) in THF (20 mL) was treated with 9-BBN (0.5 M in THF, 21.6 mL, 10.80 mmol) at rt for 6 hours before H$_2$O (20 mL) was added at 0° C. followed by sodium perborate tetrahydrate (NaBO$_3$.4H$_2$O, 3.38 g, 22 mmol). The mixture was stirred at rt overnight before being filtered through Celite. The filtrate was extracted with EtOAc. The organics were dried (Na$_2$SO$_4$), filtered and evaporated. The residue was purified by chromatography (silica, hexanes-ethyl acetate) to give the desired compounds as a colorless oil and isomeric mixture (1.15 g, 61%). ESIMS m/z=260.16 [M+H]$^+$.

Step 572b.

A solution of DMSO (1.11 mL, 15.6 mmol) in CH$_2$Cl$_2$ (20 mL) was treated with oxalyl chloride (1.02 mL, 11.7 mmol) at −78° C. for 0.5 hour before a solution of the compounds from step 572a (1.15 g, 3.9 mmol) in CH$_2$Cl$_2$ (5 mL) was added. After 1 hour at −78° C., the mixture was warmed up to −30° C. before TEA (3 mL) was added. After 1 hour, H$_2$O (20 mL) was added at 0° C. The mixture was partitioned (CH$_2$Cl$_2$—H$_2$O). The organics were washed with brine, dried (Na$_2$SO$_4$), filtered and evaporated. The residue was purified by chromatography (silica, hexanes-ethyl acetate) to give the desired compounds as a colorless oil and isomeric mixture (0.98 g, 85%).

Step 572c.

A solution of the compounds from 572b (840 mg, 3.26 mmol) in THF (5 mL) was added into a suspension of methyltriphenylphosphonium bromide (Ph$_3$PCH$_3$Br, 2.33 g, 6.53 mmol) and potassium t-butoxide (t-BuOK, 660 mg, 5.88 mmol) in THF (10 mL) (pre-mixed for 1 hour) at 0° C. The mixture was stirred at 0° C. for 3 hours before being quenched with H$_2$O (20 mL) and partitioned (EtOAc—H$_2$O). The organics were washed with brine, dried (Na$_2$SO$_4$), filtered and evaporated. The residue was purified by chromatography (silica, hexanes-ethyl acetate) to give the desired compounds as a colorless oil and isomeric mixture (0.55 g, 70%).

Step 572d.

A solution of compounds from 572c (342 mg, 1.34 mmol) in CH$_2$Cl$_2$ (5 mL) was treated with TFA (0.31 mL, 4.02 mmol) at rt for 3 hours before being concentrated. The residue was dissolved in CH$_2$Cl$_2$ (5 mL) and treated with benzyl chloroformate (0.39 mL, 2.7 mol) in the presence of the DIPEA (1 mL) overnight before being partitioned (EtOAc—H$_2$O). The organics were washed with brine, dried (Na$_2$SO$_4$), filtered and evaporated. The residue was purified by chromatography (silica, hexanes-ethyl acetate) to give the desired compounds as a colorless oil and isomeric mixture (410 mg, 105%, contaminated with a small amount of benzyl alcohol). ESIMS m/z=290.12 [M+H]$^+$.

Step 572e.

To a solution of diethylzinc (ZnEt$_2$, 2.75 mL) in CH$_2$Cl$_2$ (30 mL) was added TFA (2.06 mL, 26.8 mmol) very slowly at 0° C. over 30 minutes under N$_2$. After 30 minutes, a solution of diiodomethane (CH$_2$I$_2$, 2.16 mL, 26.8 mmol) in CH$_2$Cl$_2$ (10 mL) was added slowly. The mixture was stirred at 0° C. for 30 minutes before a solution of the compounds from step 572d (1.34 mmol at most) in CH$_2$Cl$_2$ (10 mL) was added. The resulting mixture was stirred for 3 days at rt before being quenched with aqueous NH$_4$Cl and partitioned (CH$_2$Cl$_2$—H$_2$O). The organics were washed with brine, dried (Na$_2$SO$_4$), filtered and evaporated. The residue was purified by chromatography (silica, hexanes-ethyl acetate) to give the desired compounds as a colorless oil and isomeric mixture (289 mg, 70%). ESIMS m/z=304.16 [M+H]$^+$.

Step 572f.

A solution of the compounds from step 572e (286 mg, 0.94 mmol) and di-tert-butyl dicarbonate (281 mg, 1.3 mmol) in MeOH (10 mL) was treated with palladium hydroxide (Pd(OH)$_2$ on carbon, 20 wt %, 25 mg) under hydrogen (60 psi) at rt for 4.5 hours before being filtered through Celite. The filtrate was evaporated to give the desired compounds as a colorless oil and isomeric mixture (350 mg) which was used directly in the next step. ESIMS m/z=270.16 [M+H]$^+$.

Step 572g.

The desired compounds, (2S,4S)-tert-butyl 4-cyclopropyl-2-(6-iodo-1H-benzo[d]imidazol-2-yl)pyrrolidine-1-carboxylate (major, less polar, ESIMS m/z=454.12 [M+H]$^+$) and (2S,4R)-tert-butyl 4-cyclopropyl-2-(6-iodo-1H-benzo[d]imidazol-2-yl)pyrrolidine-1-carboxylate (mior, more polar, ESIMS m/z=454.16 [M+H]$^+$) were prepared from the compound from step 572f using procedures similar to that described in steps 687c, 548c and 548d and separated by chromatography (silica, hexanes-ethyl acetate).

Step 572h.

The title compound was prepared from the major compound from step 572g and the compound from step 1-1b using procedures similar to that described in steps 548g to 548i. ESIMS m/z=777.53 [M+H]$^+$.

Example 641

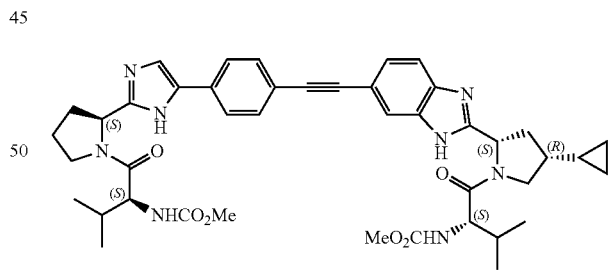

The title compound was prepared from the minor compound from step 572g and the compound from step 1-1b using procedures similar to that described in steps 548g to 548i. ESIMS m/z=777.53 [M+H]$^+$.

Example 612

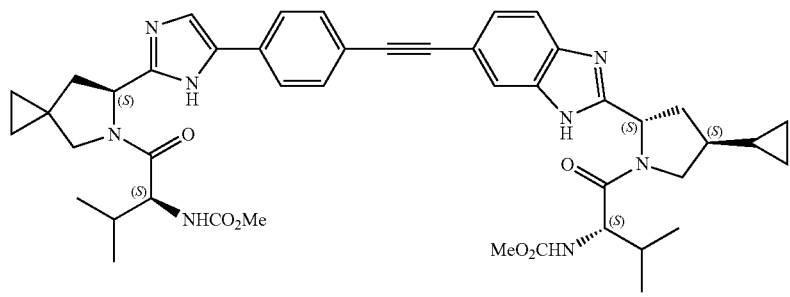

The title compound was prepared from the major compound from step 572g and the compound from step 565b using procedures similar to that described in steps 548g to 548i. ESIMS m/z=803.38 [M+H]$^+$.

Example 691

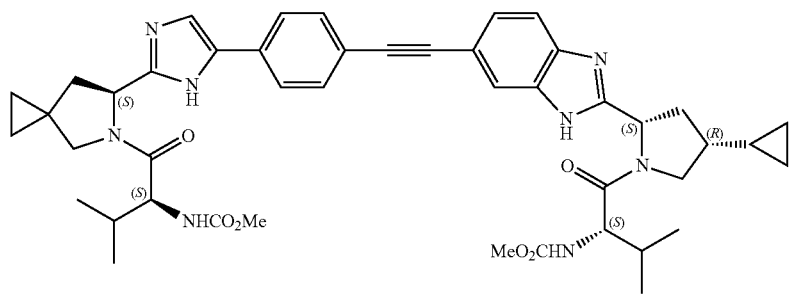

The title compound was prepared from the minor compound from step 572g and the compound from step 565b using procedures similar to that described in steps 548g to 548i. ESIMS m/z=803.31 [M+H]$^+$.

Example 642

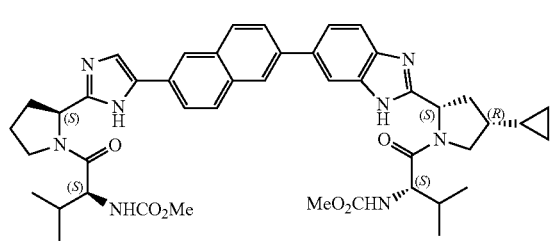

The title compound was prepared from the minor compound from step 572g and the compound from step 489a using procedures similar to that described in Examples 692. ESIMS m/z=803.60 [M+H]$^+$.

Example 643

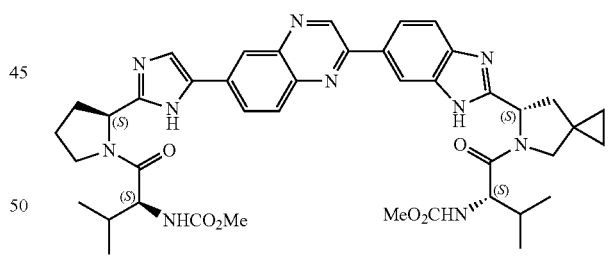

Step 643a.

The desire compound was prepared from 6-bromo-2-chloroquinoxaline (prepared according to WO 2011/004276) and the compound from step 574c using procedures similar to that described in step 574d. ESIMS m/z=520.10 [M+H]$^+$.

Step 643b.

The desire compound was prepared from the compound from step 643a using procedure similar to that described in step 574e. ESIMS m/z=568.27 [M+H]$^+$.

Step 643c.

The title compound was prepared from compound from step 643b (S)-tert-butyl 2-(5-bromo-1H-imidazol-2-yl)pyrrolidine-1-carboxylate (prepared according to WO 2008/

Example 576

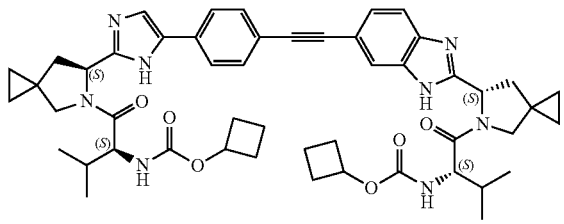

Step 576a.
To a solution of cyclobutyl alcohol (250 mg, 3.47 mmol) and DIPEA (1.21 mL, 6.94 mmol) in CH$_2$Cl$_2$ (8 mL) was added phosgene (20% in toluene, 2.6 mL, 5.2 mmol) very slowly at 0° C. over 30 minutes under N$_2$. The mixture was stirred at 0° C. for 1 hour. A solution of (S)-valine methyl ester hydrochloride (872 mg, 5.2 mmol) in CH$_2$Cl$_2$ (5 mL) and DIPEA (1.8 mL) was added. The mixture was stirred for 4 hours at rt before being quenched with ammonia (2 M in MeOH) and partitioned (CH$_2$Cl$_2$—H$_2$O). The organics were washed with brine, dried (Na$_2$SO$_4$), filtered and evaporated. The residue was purified by chromatography (silica, hexanes-ethyl acetate) to give the desired compound as a colorless oil (360 mg, 52%). $^1$H NMR (CDCl$_3$): 5.21 (d, 1H), 4.87 (m, 1H), 4.20 (m, 1H), 3.68 (s, 3H), 2.25 (m, 2H), 2.09 (m, 1H), 2.00 (m, 2H), 1.71 (m, 1H), 1.53 (m, 1H), 0.91 (d, 3H), 0.85 (d, 3H).

Step 576b.
A solution of the compound from step 576a (355 mg, 1.55 mmol) in EtOH (23 mL) and water (3 mL) was treated with LiOH.H$_2$O (78 mg, 1.86 mmol) and stirred overnight before being concentrated. The residue was dissolved in H$_2$O (5 mL) and acidified to pH ~2 by HCl (1 N). The mixture was extracted with EtOAc and CH$_2$Cl$_2$. The organics were dried (Na$_2$SO$_4$), filtered and evaporated to give the crude desired compound as a white foam (323 mg). $^1$H NMR (CDCl$_3$): 5.14 (m, 1H), 4.97 (m, 1H), 4.31 (m, 1H), 2.36 (m, 1H), 2.22 (m, 1H), 2.05 (m, 1H), 1.78 (m, 1H), 1.60 (m, 1H), 1.01 (d, 3H), 0.95 (d, 3H).

Step 576c.
The title compound was prepared from the compounds from step 576b and the compound from step 548h using the procedure similar to that described in step 548i. ESIMS m/z=869.48 [M+H]$^+$.

Example 645

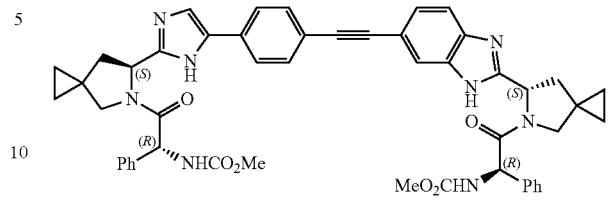

The title compound was prepared from the compounds from step 548h and (R)-(methoxycarbonyl)amino phenyl acetic acid (prepared according to WO 2008/021927) using procedures similar to that described in step 548i. ESIMS m/z=857.65 [M+H]$^+$.

Example 688

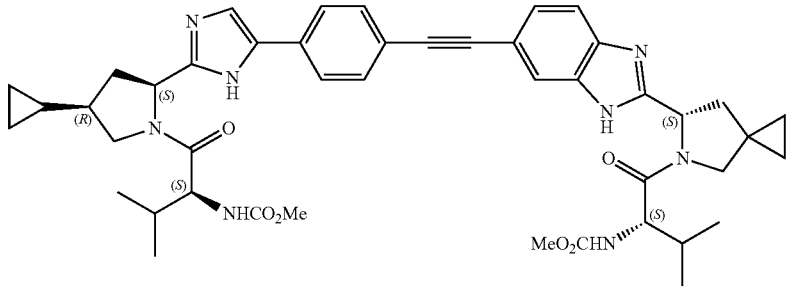

Step 688a.
The desired compound was prepared from the compound from step 572f using procedures similar to that described in steps 687c, 548a and 548b. ESIMS m/z=480.40 [M+H]$^+$.

Step 688b.
The title compound was prepared from the compounds from step 688a and the compound from step 548f using procedure similar to that described in steps 548g to 548i. ESIMS m/z=803.60 [M+H]$^+$.

Example 646

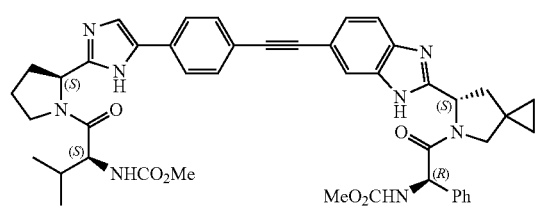

Step 646a.
The desired compound was prepared from the compounds from step 630b and the compound from step 515g using procedures similar to that described in steps 616a and 616b. ESIMS m/z=497.05 [M+H]$^+$.

Step 646b.
The desired compound was prepared from the compound from step 616a and (R)-(methoxycarbonyl)amino phenyl acetic acid (prepared according to WO 2008/021927) using the procedure similar to that described in step 616b. ESIMS m/z=429.26 [M+H]⁺.

Step 646c.

The title compound was prepared from the compounds from step 646a and the compound from step 646b using procedure similar to that described in step 548g. ESIMS m/z=797.71 [M+H]⁺.

Example 578

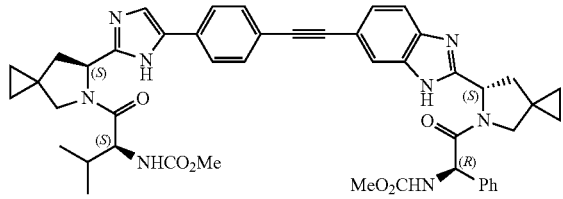

Step 578a.

The desired compound was prepared from the compounds from step 548b and the compound from step 515g using procedure similar to that described in steps 616a and 616b. ESIMS m/z=523.11 [M+H]⁺.

Step 578b.

The title compound was prepared from compounds from step 578a and 646b using procedure similar to that described in step 548g. ESIMS m/z=823.69 [M+H]⁺.

Example 648

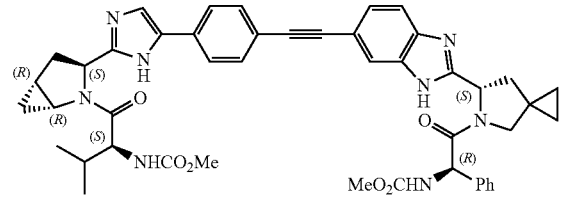

Step 648a.

The desired compound was prepared from the compounds from step 637a and the compound from step 515g using procedure similar to that described in steps 616a and 616b. ESIMS m/z=509.15[M+H]⁺.

Step 648b.

The title compound was prepared from the compounds from step 648a and the compound from step 646b using procedure similar to that described in step 548g. ESIMS m/z=809.08 [M+H]⁺.

Example 583

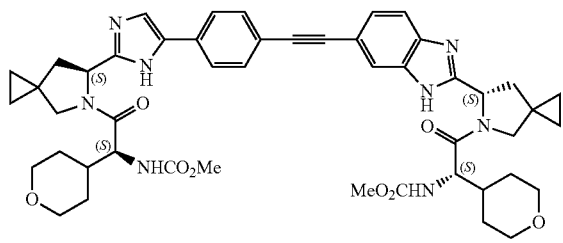

The title compound was prepared from (S)-2-(methoxycarbonylamino)-2-(tetrahydro-2H-pyran-4-yl)acetic acid (prepared according to WO 2011/059887) and the compound from step 548h using procedure similar to that described in step 548i. ESIMS m/z=873.64 [M+H]⁺.

Example 655

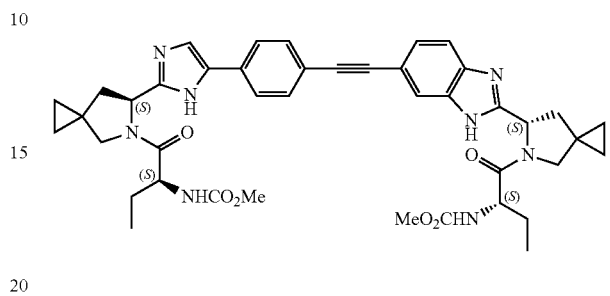

The title compound was prepared from (S)-2-(methoxycarbonylamino)butanoic acid (prepared according to WO 2008/021927) and the compound from step 548h using procedure similar to that described in step 548i. ESIMS m/z=761.54 [M+H]⁺.

Example 586

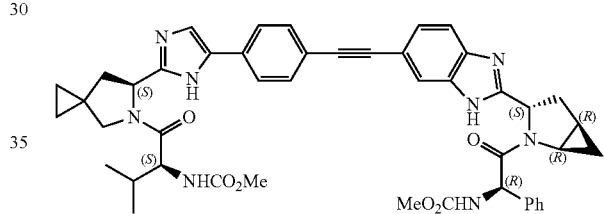

Step 586a.

The desired compound was prepared from (1R,3S,5R)-2-(tert-butoxycarbonyl)-2-azabicyclo[3.1.0]hexane-3-carboxylic acid (prepared according to WO 2009/102325) and (R)-(methoxycarbonyl)amino phenyl acetic acid (prepared according to WO 2008/021927) using procedures similar to that described in steps 548c to 548f, 616a and 616b. ESIMS m/z=415.17[M+H]⁺.

Step 586b.

The title compound was prepared from the compounds from step 586a and step 578a using procedure similar to that described in step 548g. ESIMS m/z=809.39 [M+H]⁺.

Example 658

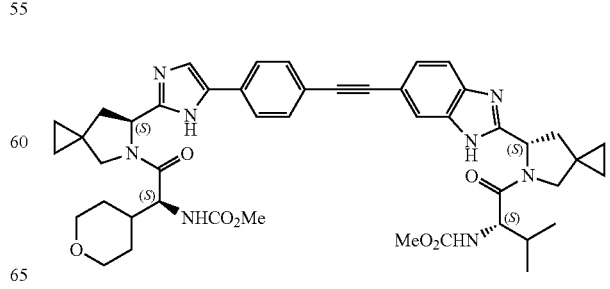

487

Step 658a.

The desired compound was prepared from the compound from step 548b and (5)-2-(methoxycarbonylamino)-2-(tetrahydro-2H-pyran-4-yl)acetic acid (prepared according to WO 2011/059887) using procedures similar to that described in steps 616a and 616b. ESIMS m/z=523.11 [M+H]⁺.

Step 658b.

The title compound was prepared from the compounds from step 658a and step 616b using procedures similar to that described in step 548g. ESIMS m/z=831.51 [M+H]⁺.

Example 590

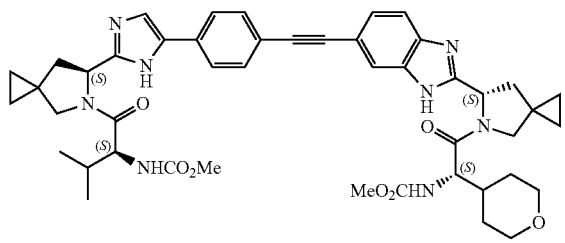

Step 590a.

The desired compound was prepared from the compound from step 548f and (5)-2-(methoxycarbonylamino)-2-(tetrahydro-2H-pyran-4-yl)acetic acid (prepared according to WO 2011/059887) using procedures similar to that described in steps 616a and 616b. ESIMS m/z=437.25 [M+H]⁺.

Step 590b.

The title compound was prepared from the compounds from step 590a and step 578a using the procedure similar to that described in step 548g. ESIMS m/z=831.51 [M+H]⁺.

Example 659

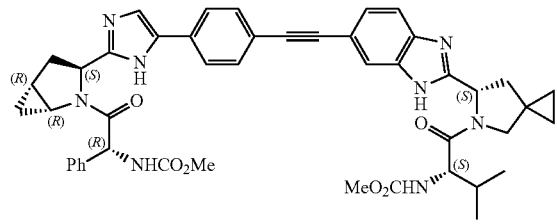

Step 659a.

The desired compound was prepared from the compound from step 637a and (R)-(methoxycarbonyl)amino phenyl acetic acid (prepared according to WO 2008/021927) using procedures similar to that described in steps 616a and 616b. ESIMS m/z=543.03 [M+H]⁺.

Step 659b.

The title compound was prepared from the compounds from step 659a and step 616b using the procedure similar to that described in step 548g. ESIMS m/z=809.26 [M+H]⁺.

488

Example 671

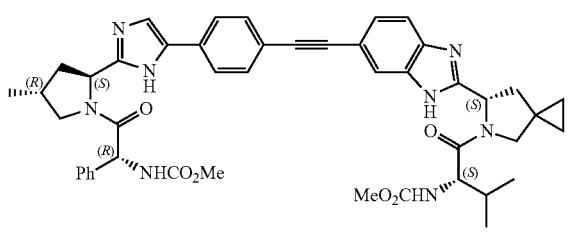

Step 671a.

The desired compound was prepared from the minor compound from step 559b and the compound from step 616b using the procedures similar to that described in step 548g. ESIMS m/z=720.80 [M+H]⁺.

Step 671b.

The title compound was prepared from the compound from step 671a and (R)-(methoxycarbonyl)amino phenyl acetic acid (prepared according to WO 2008/021927) using procedures similar to that described in steps 548h and 548i. ESIMS m/z=811.45 [M+H]⁺.

Example 603

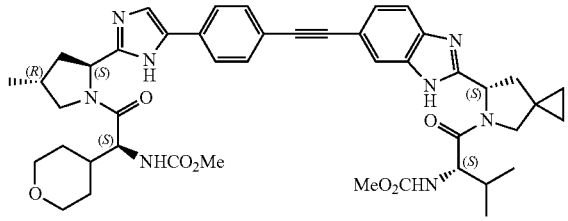

The title compound was prepared from the compound from step 671a and (S)-2-(methoxycarbonylamino)-2-(tetrahydro-2H-pyran-4-yl)acetic acid (prepared according to WO 2011/059887) using procedures similar to that described in steps step 548h and 548i. ESIMS m/z=819.48 [M+H]⁺.

Example 649

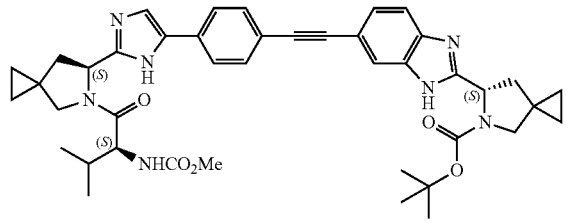

Step 649a.

A solution of the compound from step 548b (10 g, 21.49 mmol) in $CH_2Cl_2$ (119 ml) was treated with HCl (4 M in dioxane, 118 mL, 473 mmol) at rt overnight before being concentrated. The residue was dried under vacuum to afford the desired compound as a yellow solid. ESIMS m/z=366.00 (M+H)⁺.

Step 649b.

DIPEA (35.8 mL, 205 mmol) was added into a mixture of the compound from step 649a (7.85 g, 21.49 mmol), the compound from step 515g (3.59 g, 20.47 mmol), and HATU (8.17 g, 21.49 mmol) in acetonitrile (205 mL). It was stirred at rt for 1 hour before being concentrated. The residue was purified by chromatography (silica, EtOAc—Hexanes) to give the desired product as light brown oil (10.85 g, 100%). ESIMS m/z=523.03 (M+H)⁺.

Step 649c.

A mixture of the compound from step 548f (1.68 g, 4.98 mmol), the compound from step 649b (2.65 g, 5.08 mmol), copper(I) iodide (0.028 g, 0.15 mmol) and Pd(PPh₃)₄ (0.288 g, 0.25 mmol) in acetonitrile (8.30 mL) and TEA (6.30 mL, 44.8 mmol) was degassed and then stirred at 40° C. overnight under N₂ before being concentrated. The residue was purified by chromatography (silica, MeOH—CH₂Cl₂) to give the title compound as a yellow solid (3 g, 82%). ESIMS m/z=732.45 (M+H)⁺.

Example 581

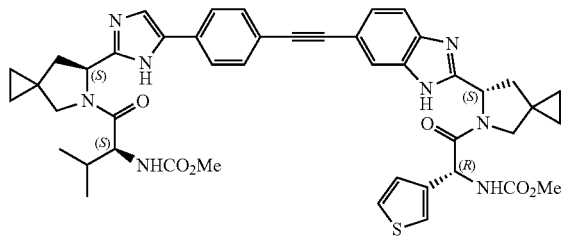

Step 581a.

A solution of the compound of example 649 (0.749 g, 1.02 mmol) in CH₂Cl₂ (19.2 mL) and MeOH (6.40 mL) at rt was treated with HCl (4 M in 1,4-dioxane, 25.6 mL, 102 mmol) at rt for 3 hours before being concentrated and dried under vacuum to afford the crude desired compound (0.856 g) as a yellow solid, which was used directly for next step. ESIMS m/z=632.43 (M+H)⁺.

Step 581b.

To a mixture of the compound from step 581a (0.082 g, 0.11 mmol), (R)-2-(methoxycarbonylamino)-2-(thiophen-3-yl)acetic acid (prepared according to WO2009/102325, 0.029 g, 0.14 mmol) and HATU (0.055 g, 0.14 mmol) in acetonitrile (1.1 mL) was added DIPEA (0.19 mL, 1.11 mmol). It was stirred at rt for 1 hour. After evaporation, the residue was purified by chromatography (silica, hexanes-EtOAc, then MeOH-TEA-EtOAc) to give the title compound as a yellow solid (0.046 g, 50% over 2 steps). ESIMS m/z=829.44 (M+H)⁺.

Example 601

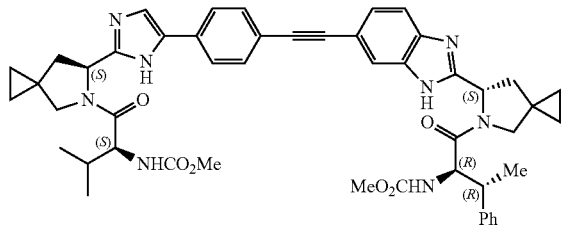

Step 601a.

A solution of N-Boc-erythro-D-β-methylphenylalanine (0.260 g, 0.93 mmol) in CH₂Cl₂ (11.6 mL) at 0° C. was treated with HCl (4 M in 1,4-dioxane, 2.33 mL, 9.31 mmol) at rt for 5 hours before being concentrated and dried under vacuum to afford the crude desired compound as a white solid, which was used directly for next step. ESIMS m/z=180.05 (M+H)⁺.

Step 601b.

Into a solution of the compound from step 601a (0.93 mmol at most) in aqueous NaOH (1 M, 2.79 mL, 2.79 mmol) at rt were added sodium carbonate (0.217 g, 2.05 mmol) and methyl chloroformate (0.16 mL, 2.05 mmol). It was stirred at rt overnight before being diluted with water and extracted with MTBE. The aqueous layer was acidified with concentrated HCl to pH ~1. It was diluted with water and extracted with CH₂Cl₂. The combined extracts were dried (Na₂SO₄), filtered and concentrated. The residue was co-evaporated with toluene, dried under vacuum to afford the desired compound as a crude colorless oil (0.180 g).

Step 601c.

A mixture of the compounds from step 581a (0.072 g, 0.097 mmol) and step 601b (0.030 g, 0.13 mmol) in acetonitrile (1.6 mL) was treated with HATU (0.037 g, 0.097 mmol) and DIPEA (0.170 ml, 0.971 mmol) at rt overnight before evaporation. The residue was purified by chromatography (silica, hexane-EtOAc then MeOH-TEA-EtOAc) to give the title compound as a white solid (0.029 g, 35%). ESIMS m/z=851.34 (M+H)⁺.

Example 669

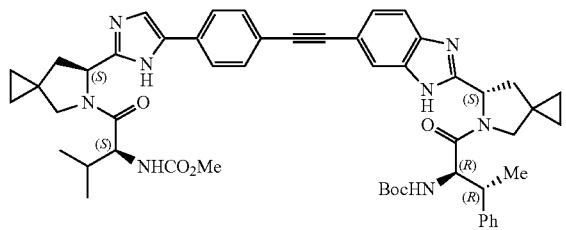

The title compound was isolated as a minor product from step 601c. ESIMS m/z=893.34 (M+H)⁺.

Example 670

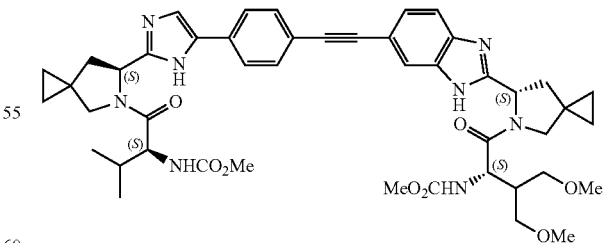

Step 670a.

A solution of methyl 2-(tert-butoxycarbonylamino)-2-(dimethoxyphos-phoryl)acetate (2.52 g, 8.47 mmol) in THF (5 mL) was treated with 1,1,3,3-tetramethyl-guanidine (1.06 ml, 8.47 mmol) at rt for 10 minutes before a solution of 1,3-dimethoxy-propan-2-one (0.5 g, 4.23 mmol) in THF (5 ml) was charged. It was stirred at rt for 48 hours before being concentrated. The residue was dissolved in EtOAc, washed with 1 N HCl, saturated sodium bicarbonate and brine. The organics were dried (Na₂SO₄), filtered and concentrated. The residue was purified by chromatography (silica, EtOAc-hexanes) to give the desired compound (1.04 g, 85%). ESIMS m/z=312.16 [M+Na]⁺.

Step 670b.

A mixture of the compound from step 670a (0.948 g, 3.28 mmol) and (−)-1,2-bis((2S,5S)-2,5-dimethylphos-pholano)ethane(1,5-cyclooctadiene)rhodium(I)tetrafluoroborate (0.018 g, 0.033 mmol) in MeOH (10 mL) was hydrogenated at rt under hydrogen (60 psi) for 60 hours before being filtered through Celite. The filtrate was concentrated to give the crude desired compound (0.95 g), which was used directly in next step. ESIMS m/z=314.18 [M+Na]⁺.

Step 670c.

A solution of the crude compound from step 670b (3.28 mmol at most) in THF (16.4 mL) and MeOH (4.1 ml) at 0° C. was treated with LiOH (1 M, 8.20 mL, 8.20 mmol) at 0° C. for 2 hours and then at rt for 2 hours before being diluted with water, acidified to pH ~2 at 0° C., and extracted with CH₂Cl₂. The organics were washed with water, brine, dried (Na₂SO₄), filtered and concentrated to give the crude desired compound as a yellow oil (0.765 g, 84%). ESIMS m/z=300.10 [M+Na]⁺.

Step 670d.

The title compound was prepared from the compound from step 670c and the compound from step 581a using procedures similar to that described in Example 601. ESIMS m/z=849.40 [M+H]⁺.

Example 610

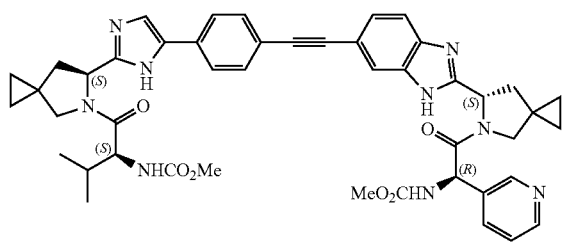

Step 610a.

A solution of (2S)-2-amino-2-(3-pyridyl)acetic acid hydrochloride salt (0.028 g, 0.15 mmol) in NaOH (1 M, 0.45 mL, 0.45 mmol) was treated with methyl chloroformate (0.012 mL, 0.15 mmol) at rt for 1 hour before being acidified with 1 M HCl to pH ~3 and lyophilized to give the crude desired compound. ESIMS m/z=211.06 (M+H)⁺.

Step 610b.

To a mixture of the compound from step 581a (0.082 g, 0.11 mmol), the crude compound from step 610a (0.029 g) and HATU (0.041 g, 0.108 mmol) in DMF (1.1 mL) was added DIPEA (0.19 mL, 1.08 mmol). It was stirred at rt overnight. The volatiles were evaporated off. The residue was purified by chromatography (silica, EtOAc then MeOH-TEA-EtOAc) to give the title compound as a white solid (0.005 g, 5.62% yield). ESIMS m/z=824.35 [M+H]⁺.

The following title compounds were prepared using procedures similar to that described above.

| Example | Structure | ESIMS m/z [M + H]⁺ |
| --- | --- | --- |
| 580 | 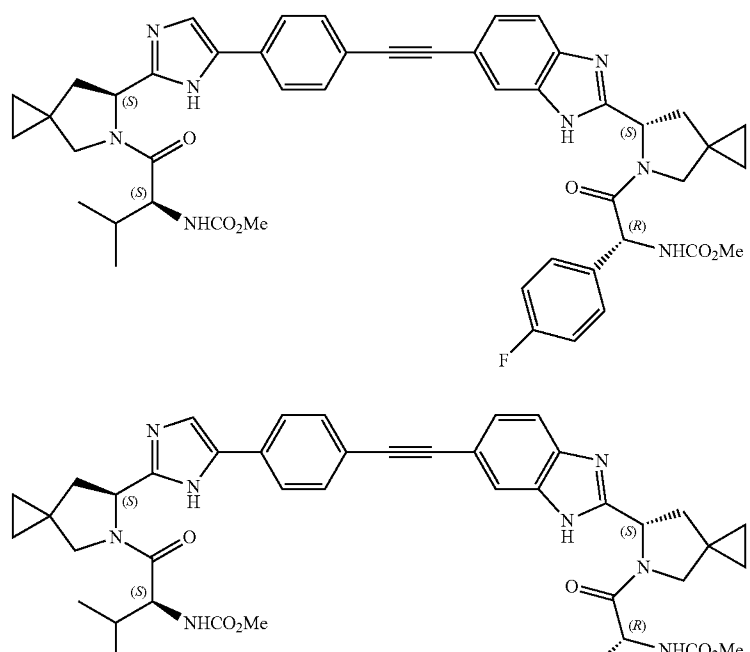 | 841.31 |
| 650 | 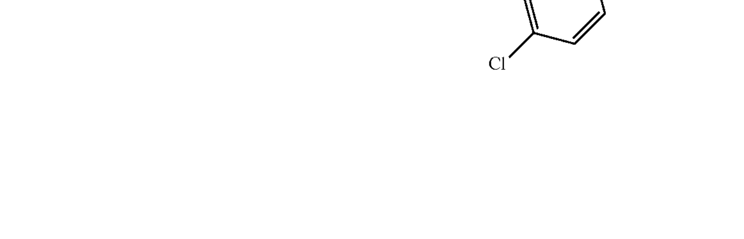 | 857.52 |

| Example | Structure | ESIMS m/z [M + H]+ |
|---|---|---|
| 582 | 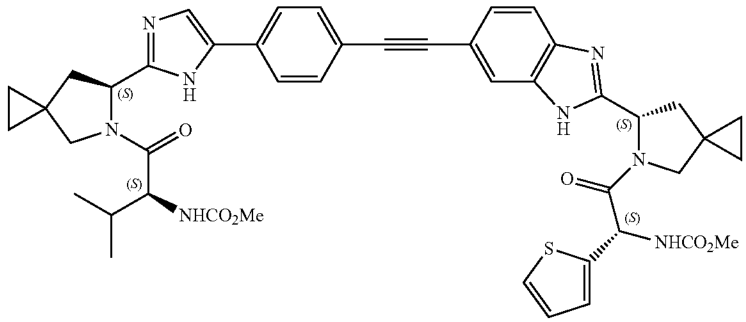 | 829.48 |
| 651 | 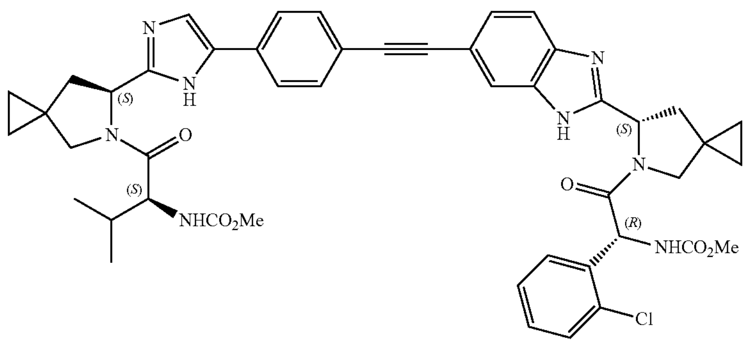 | 857.51 |
| 652 | 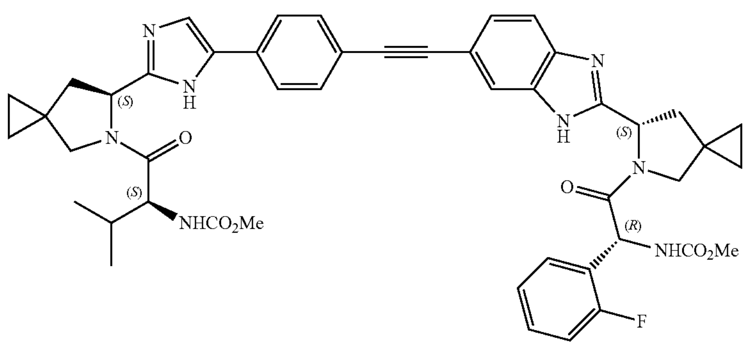 | 841.51 |
| 584 | 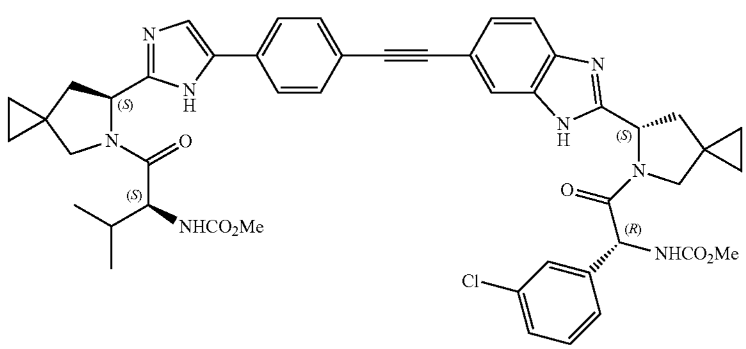 | 857.39 |

-continued

| Example | Structure | ESIMS m/z [M + H]+ |
|---|---|---|
| 653 | 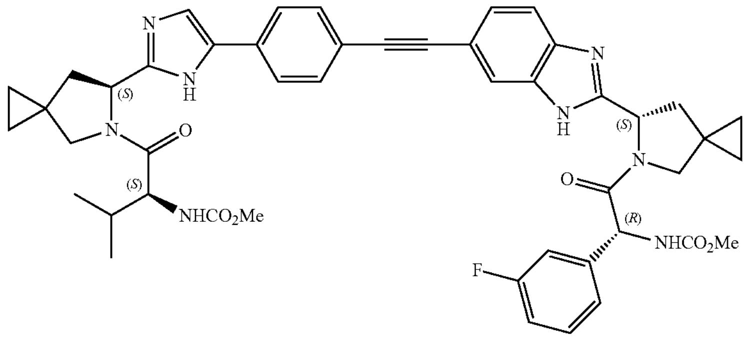 | 841.61 |
| 585 | 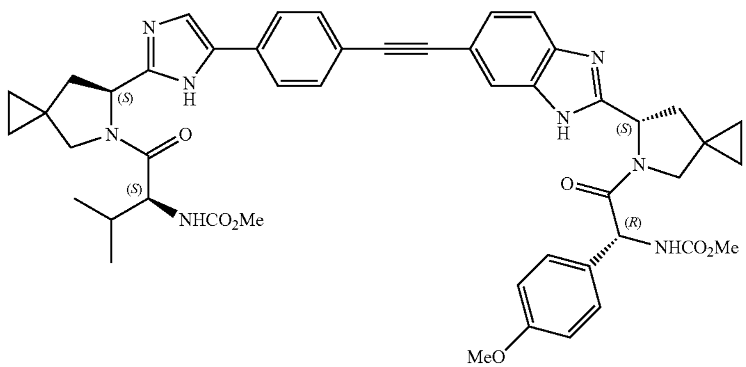 | 853.65 |
| 654 | 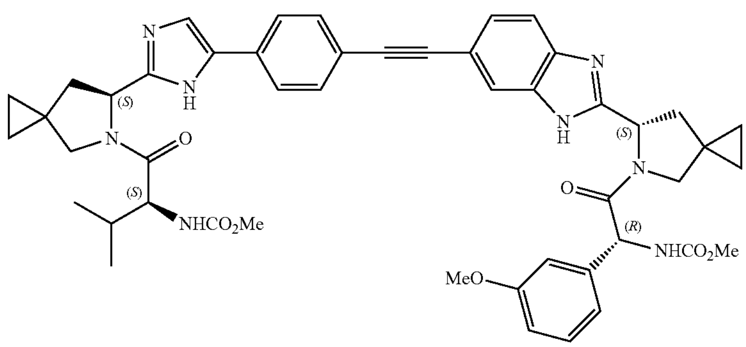 | 853.68 |
| 587 | 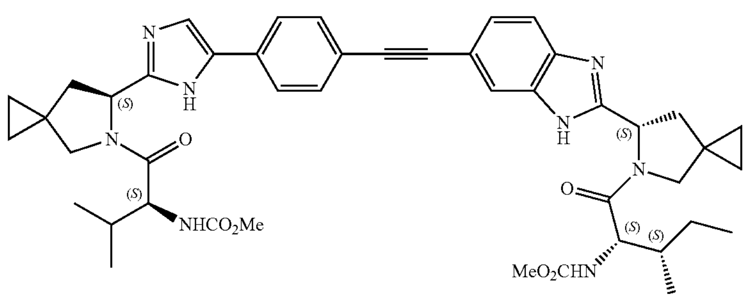 | 803.66 |

| Example | Structure | ESIMS m/z [M + H]+ |
|---|---|---|
| 656 | 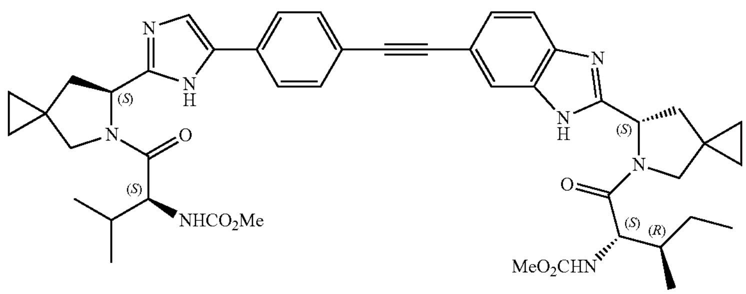 | 803.57 |
| 589 | 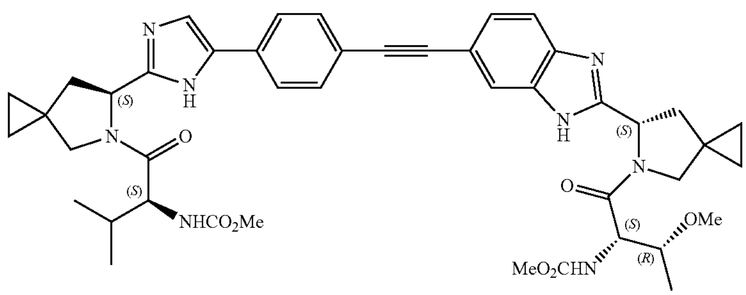 | 805.53 |
| 592 | 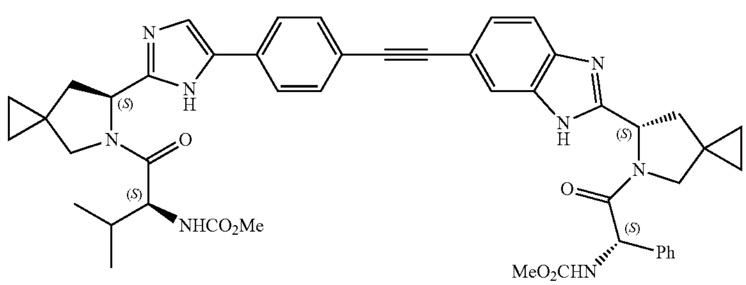 | 823.53 |
| 667 | 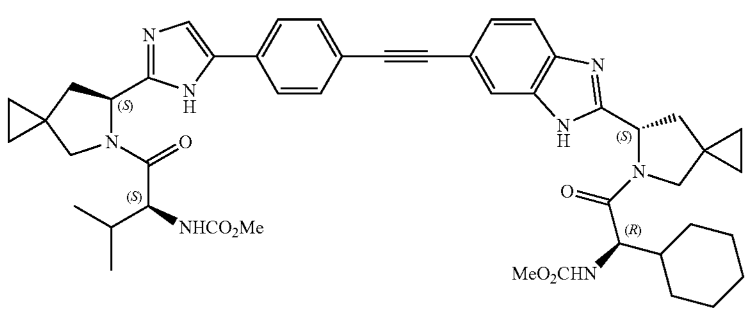 | 829.43 |
| 599 | 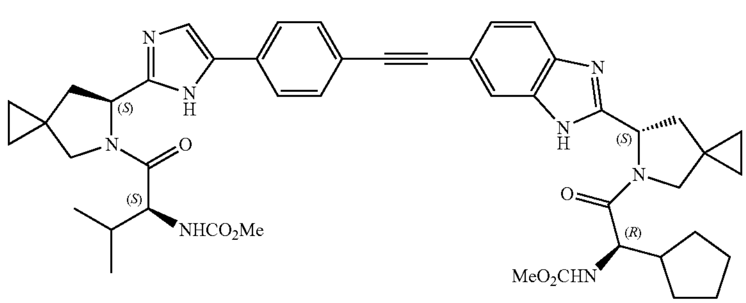 | 815.40 |

| Example | Structure | ESIMS m/z [M + H]+ |
|---|---|---|
| 668 | 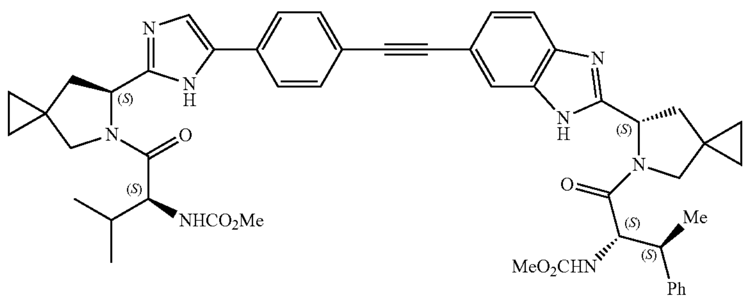 | 851.42 |
| 602 | 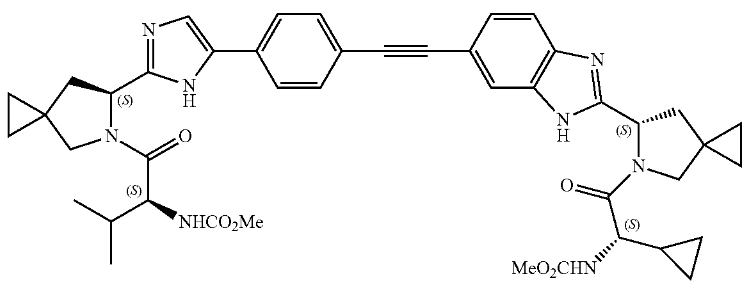 | 787.16 |
| 675 | 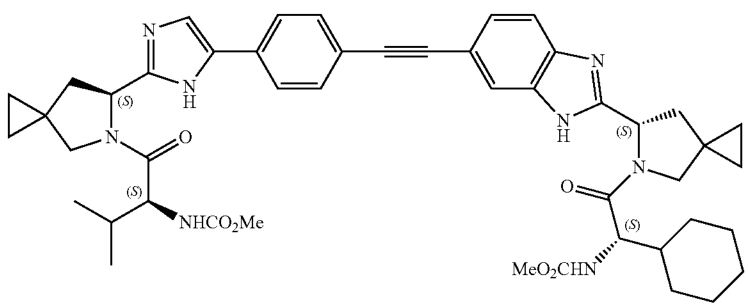 | 829.51 |
| 676 | 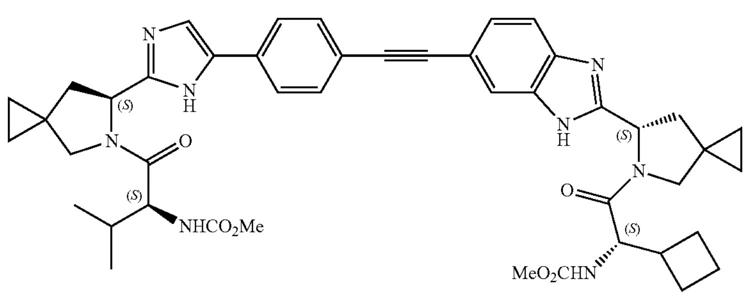 | 801.54 |
| 679 | 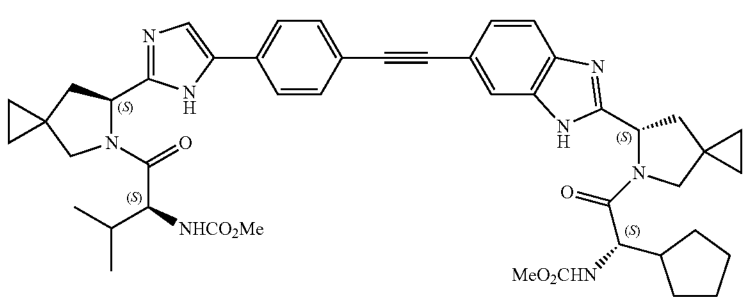 | 815.26 |

| Example | Structure | ESIMS m/z [M + H]+ |
|---|---|---|
| 600 | 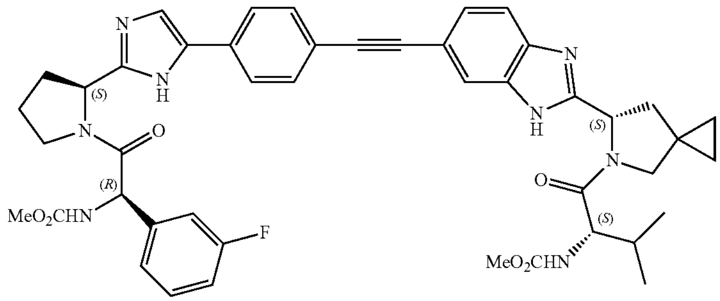 | 815.29 |
| 594 | 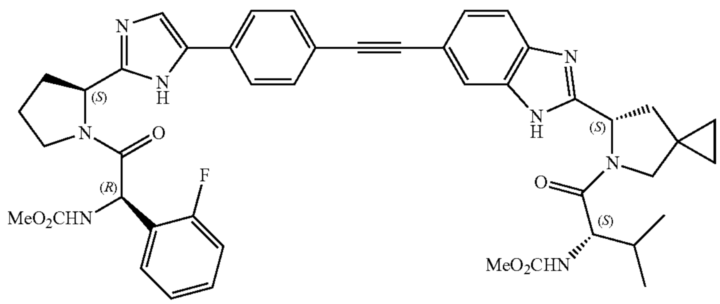 | 815.33 |
| 663 | 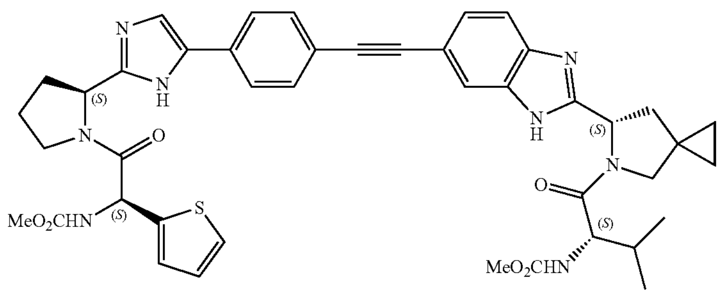 | 803.28 |
| 595 | 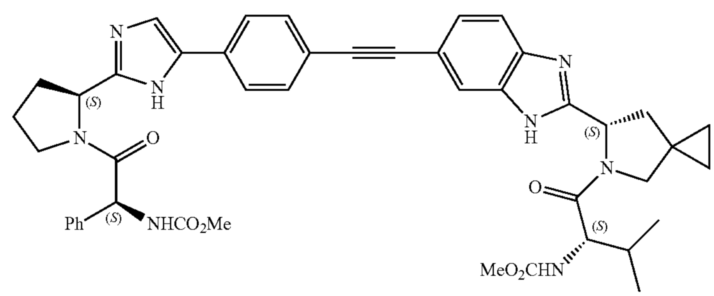 | 797.42 |
| 664 | 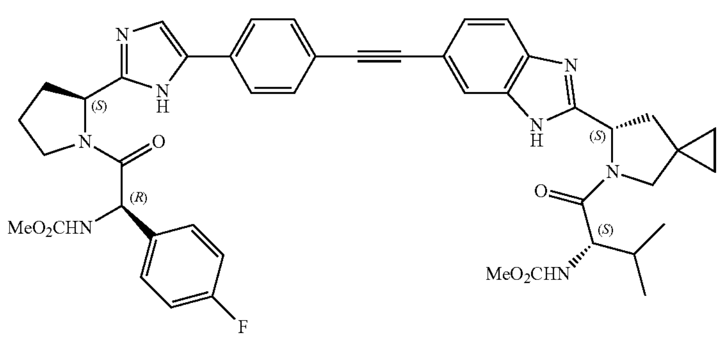 | 815.42 |

-continued

| Example | Structure | ESIMS m/z [M + H]+ |
|---|---|---|
| 596 | 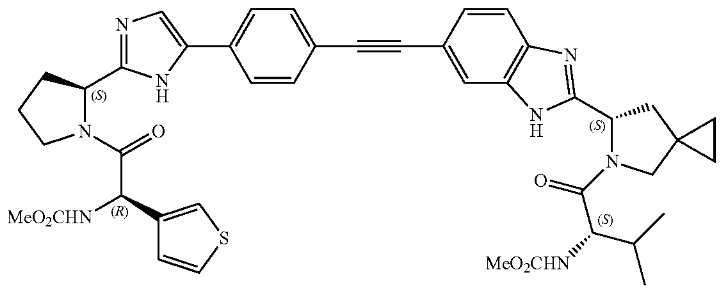 | 803.32 |
| 665 | 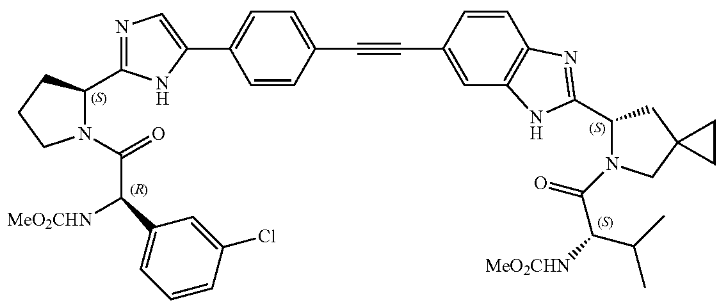 | 831.33 |
| 597 | 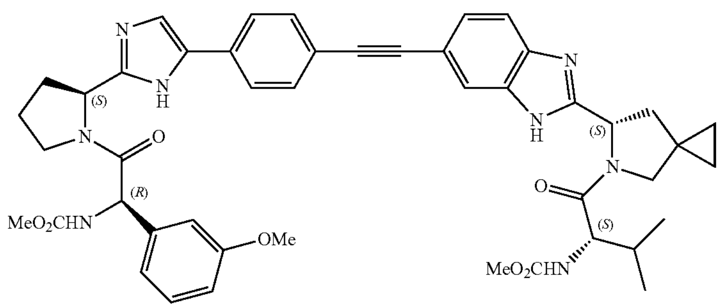 | 827.38 |
| 598 | 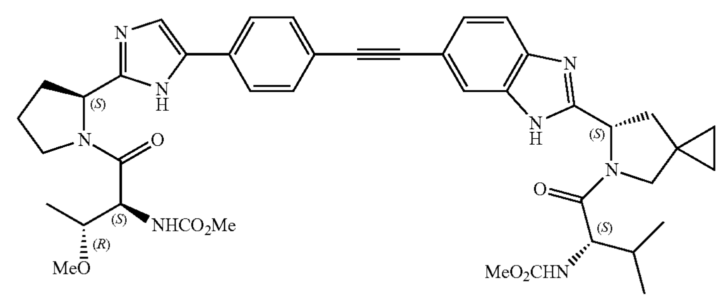 | 779.36 |
| 673 | 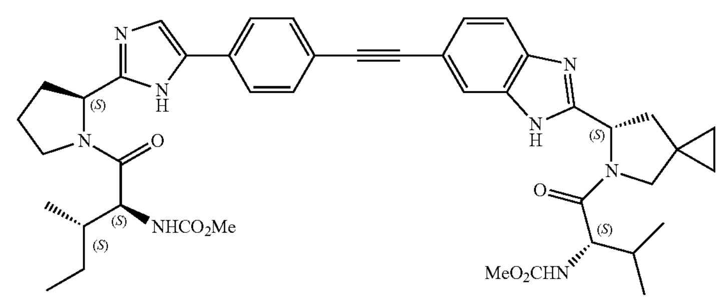 | 777.34 |

| Example | Structure | ESIMS m/z [M + H]+ |
|---|---|---|
| 605 | 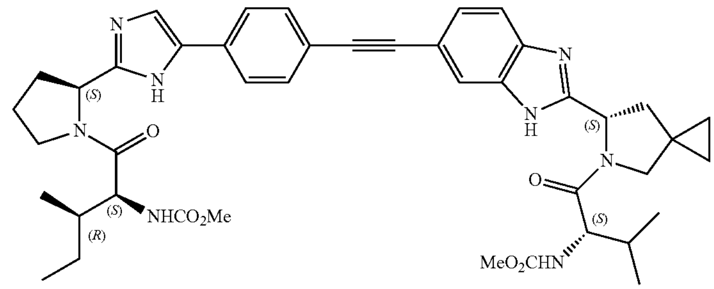 | 777.34 |
| 607 | 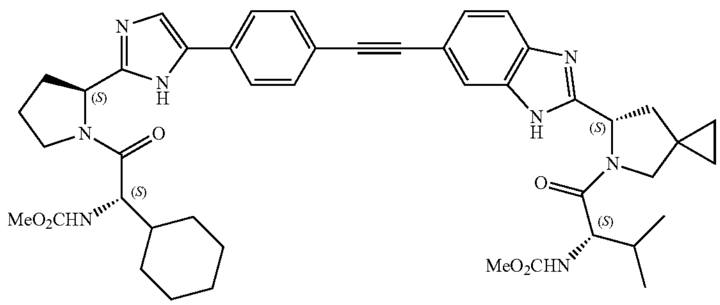 | 803.50 |
| 678 | 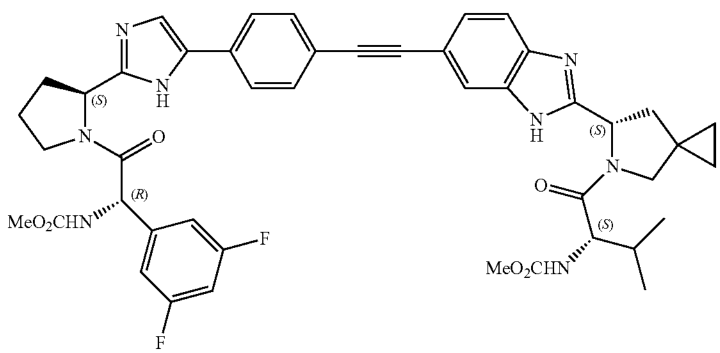 | 833.46 |
| 604 | 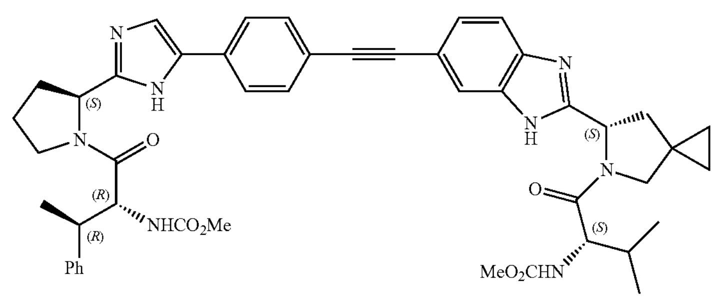 | 825.36 |
| 694 | 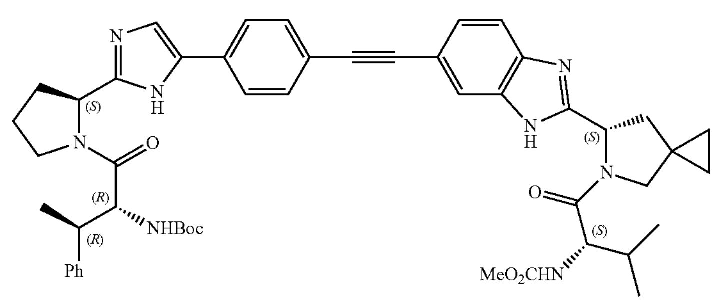 | 867.41 |

| Example | Structure | ESIMS m/z [M + H]⁺ |
|---|---|---|
| 672 | 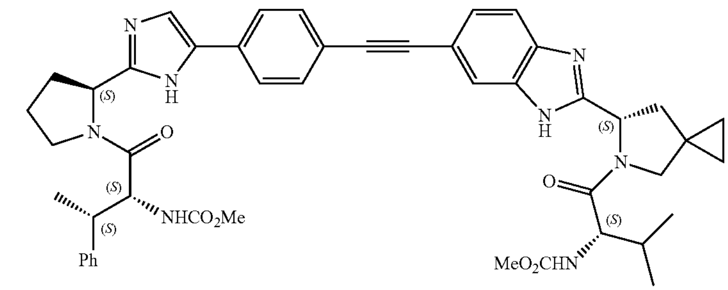 | 825.36 |
| 686 | 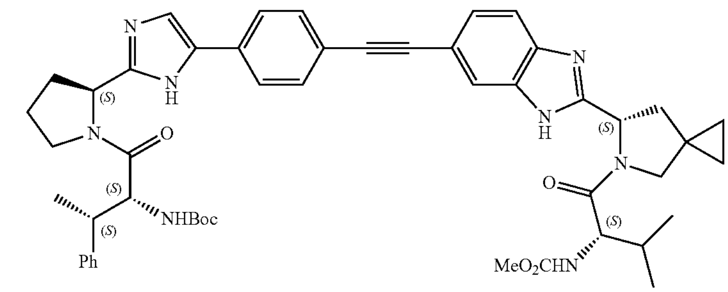 | 867.40 |
| 674 | 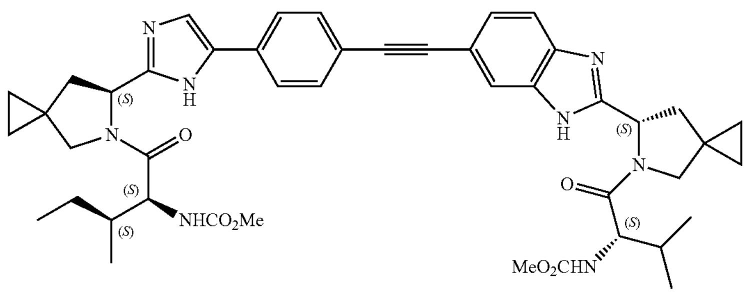 | 803.40 |
| 606 | 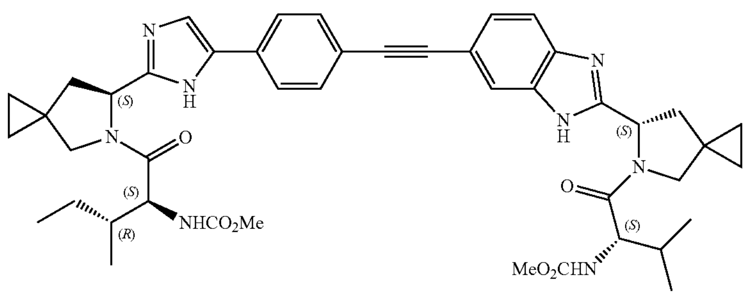 | 803.40 |
| 609 | 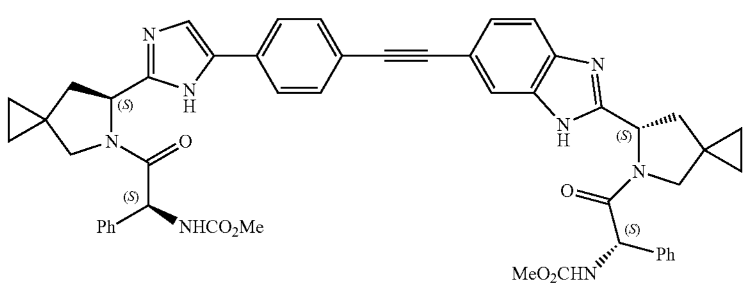 | 857.55 |

| Example | Structure | ESIMS m/z [M + H]+ |
|---|---|---|
| 677 | 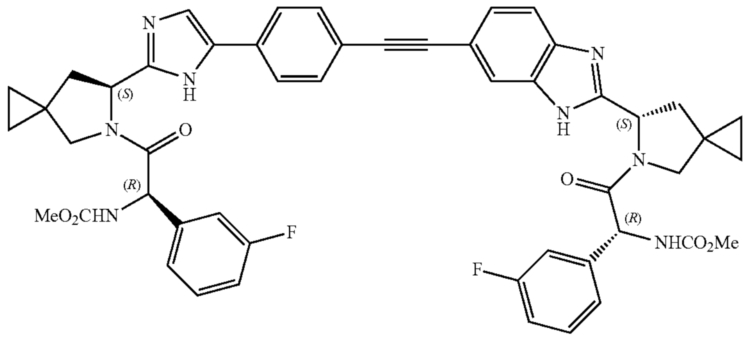 | 893.54 |
| 611 | 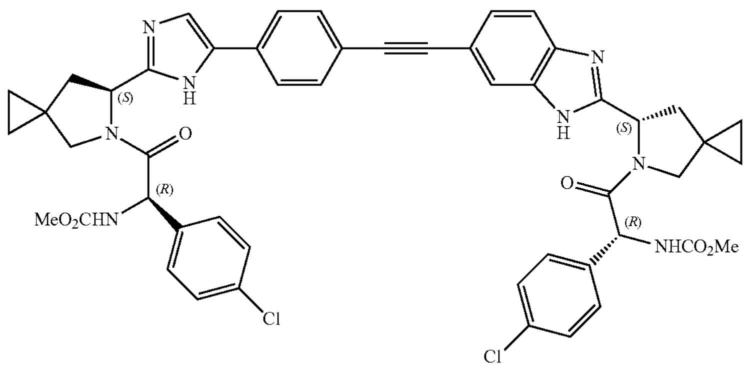 | 925.50 |
| 680 | 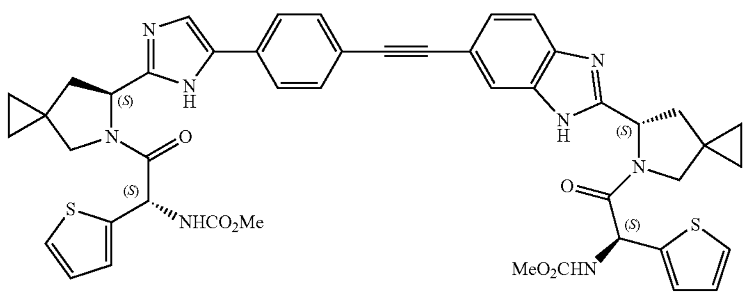 | 869.44 |
| 682 | 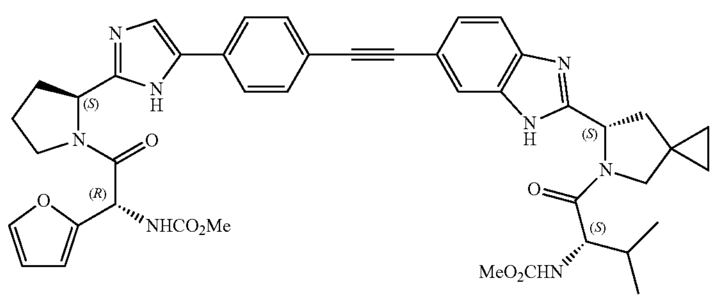 | 787.44 |
| 681 | 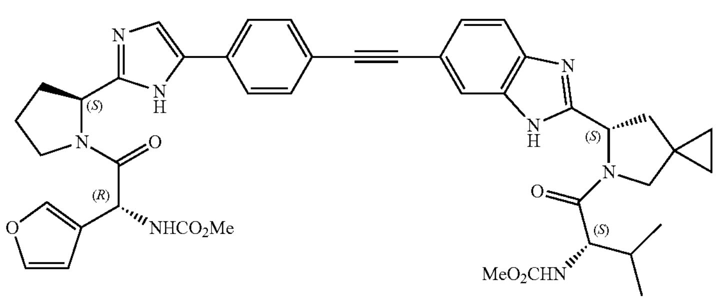 | 787.45 |

| Example | Structure | ESIMS m/z [M + H]+ |
|---|---|---|
| 683 | 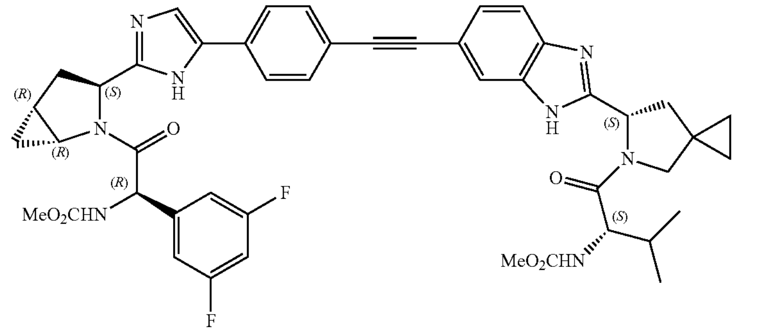 | 845.42 |
| 684 | 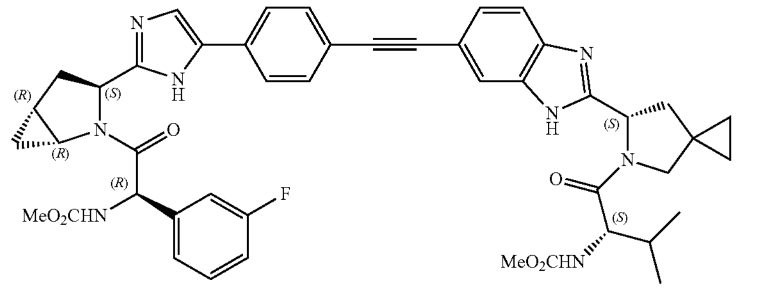 | 827.49 |

Biological Activity

1. HCV Replicon Cell Lines

HCV replicon cell lines (kindly provided by R. Bartenschlager) isolated from colonies as described by Lohman et. al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV), and (vi) HCV NS3 to NS5B genes that harbor cell culture adaptive mutations (E1202G, T1280I, K1846T) and the HCV 3'UTR.

These cell lines were maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/ml or 0.5 mg/ml for 11-7 and Huh-luc/neo-ET cells, respectively.

2. HCV Replicon Assay—qRT-PCR $EC_{50}$ values of single agent compounds and combinations were determined by HCV RNA detection using quantitative RT-PCR, according to the manufacturer's instructions, with a TAQMAN® One-Step RT-PCR Master Mix Reagents Kit (Cat#AB 4309169, Applied Biosystems) on an ABI Model 7500 thermocycler. The TaqMan primers used for detecting and quantifying HCV RNA were obtained from Integrated DNA Technologies. HCV RNA was normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat# AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We used the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat.#31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat.#31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention may inhibit HCV by mechanisms in addition to or other than NS5A inhibition. In one embodiment, the compounds of the present invention inhibit HCV replicon and in another embodiment the compounds of the present invention inhibit NS5A.

The compounds of the present invention can be effective against the HCV 1b genotype. It should also be understood that the compounds of the present invention can inhibit multiple genotypes of HCV. In one embodiment compound of the present invention are active against the 1a, 1b, 2a, 2b, 3a, 4a, and 5a genotypes. Tables 11 and 12 shows the $EC_{50}$ values of representative compounds of the present invention against the HCV 1b and 1a genotype from the above described qRT-PCR or luciferase assay. $EC_{50}$ ranges against HCV 1b and 1a are as follows: A>10 nM; B 1-10 nM; C<1 nM.

TABLE 11

Genotype-1b replicon $EC_{50}$

| Example | Range | Example | Range | Example | Range |
|---|---|---|---|---|---|
| 2 | C | 2-1 | C | 2-2 | C |
| 357 | C | 442 | C | 443 | C |
| 445 | C | 446 | C | 448 | C |
| 449 | C | 451 | C | 453 | C |
| 454 | C | 456 | C | 457 | C |
| 459 | C | 460 | C | 463 | C |
| 464 | C | 465 | C | 466 | C |
| 468 | C | 469 | C | 471 | C |
| 472 | C | 473 | C | 475 | C |
| 477 | C | 479 | C | 480 | C |
| 481 | C | 483 | C | 485 | C |
| 486 | C | 488 | C | 490 | C |
| 492 | C | 493 | C | 494 | C |
| 497-a | C | 497-b | C | 499 | C |
| 500 | B | 501 | C | 502 | C |
| 503 | C | 504 | C | 505 | C |
| 506 | C | 507 | C | 508 | C |
| 509 | C | 510 | C | 511 | C |
| 512 | C | 513 | C | 514 | C |
| 515 | C | 517 | C | 519 | C |
| 521 | C | 523 | C | 525 | C |
| 526 | C | 527 | C | 528 | C |
| 529 | C | 530 | C | 531 | C |
| 532 | C | 533 | C | 534 | C |
| 535 | C | 536 | C | 537 | C |
| 538 | C | 539 | C | 540 | C |
| 541 | C | 542 | C | | |

TABLE 12

Genotype-1b or 1a replicon $EC_{50}$

| Example | 1b $EC_{50}$ Range or (pM) | 1a $EC_{50}$ Range or (pM) | Example | 1b $EC_{50}$ Range or (pM) | 1a $EC_{50}$ Range or (pM) |
|---|---|---|---|---|---|
| 548 | 4 | C | 630 | 11 | C |
| 631 | 8 | C | 565 | 11 | C |
| 564 | 8 | C | 571 | 13 | |
| 640 | 30 | B | 692 | 11 | C |
| 574 | 36 | 127 | 644 | 45 | C |
| 575 | C | C | 608 | | C |
| 616 | 495 | C | 550 | | B |
| 620 | | C | 553 | | B |
| 621 | | 207 | 647 | 8 | C |
| 579 | C | C | 577 | 160 | |
| 555 | 7 | C | 546 | 12 | C |
| 615 | 5 | C | 689 | C | 198 |
| 693 | C | C | 551 | 13 | C |
| 558 | C | C | 627 | 10 | C |
| 629 | 17 | 180 | 561 | 24 | C |
| 686 | C | C | 567 | 15 | C |
| 626 | | 1337 | 557 | | B |
| 568 | 9 | C | 690 | | B |
| 588 | | C | 657 | | C |
| 660 | | C | 591 | | C |
| 661 | | C | 593 | | C |
| 662 | | C | 687 | 10 | C |
| 614 | 4 | C | 547 | 18 | C |
| 617 | | B | 548 | | A |
| 619 | | 699 | 552 | C | C |
| 554 | 28 | | 623 | C | |
| 624 | | A | 556 | | A |
| 625 | C | C | 559 | 14 | |
| 628 | 9 | | 560 | C | |
| 563 | 12 | | 632 | 13 | |
| 633 | C | 35 | 634 | | C |
| 566 | | C | 635 | C | C |
| 636 | 20 | | 637 | 4 | C |
| 569 | 9 | C | 638 | 7 | C |
| 570 | 8 | | 639 | 8 | C |
| 572 | | C | 641 | 7 | C |
| 612 | C | C | 691 | C | C |
| 642 | 7 | | 643 | 54 | C |
| 576 | | A | 645 | 5 | C |
| 88 | C | C | 646 | 5 | C |
| 578 | 6 | | 648 | C | |
| 583 | C | C | 655 | | 34 |
| 586 | | C | 658 | | C |
| 590 | | 17 | 659 | | C |
| 671 | | C | 603 | | C |
| 649 | 304 | | 581 | | C |
| 601 | | A | 669 | | A |
| 670 | | C | 610 | | C |
| 580 | 7 | | 650 | | 79 |
| 582 | | C | 651 | | C |
| 652 | | C | 584 | | C |
| 653 | | C | 585 | | B |
| 654 | | 185 | 587 | | C |
| 656 | | C | 589 | | C |
| 592 | | C | 667 | | B |
| 599 | | B | 668 | | C |
| 602 | | C | 675 | | C |
| 679 | | C | 600 | | C |
| 594 | | C | 663 | | 295 |
| 595 | | C | 664 | | C |
| 596 | | C | 665 | | C |
| 597 | | 227 | 598 | | C |
| 673 | | C | 605 | | C |
| 607 | | C | 678 | | C |
| 604 | | A | 672 | | C |
| 674 | | C | 606 | | C |
| 609 | | B | 677 | | B |
| 611 | | A | 680 | | A |
| 682 | | C | 681 | | 202 |
| 683 | | C | 684 | | C |
| 666 | | A | | | |

While this invention has been particularly shown and described with references to preferred embodiments thereof, it will be understood by those skilled in the art that various changes in form and details may be made therein without departing from the scope of the invention encompassed by the appended claims.
What is claimed is:
1. A compound represented by Formula IIIa:
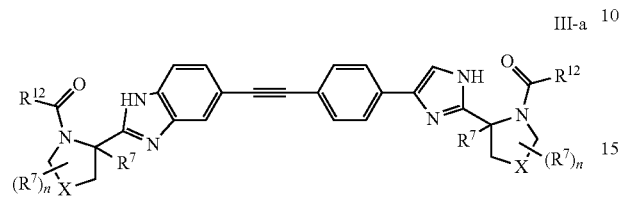
or a pharmaceutically acceptable salt thereof, wherein:
Each
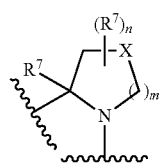
is independently
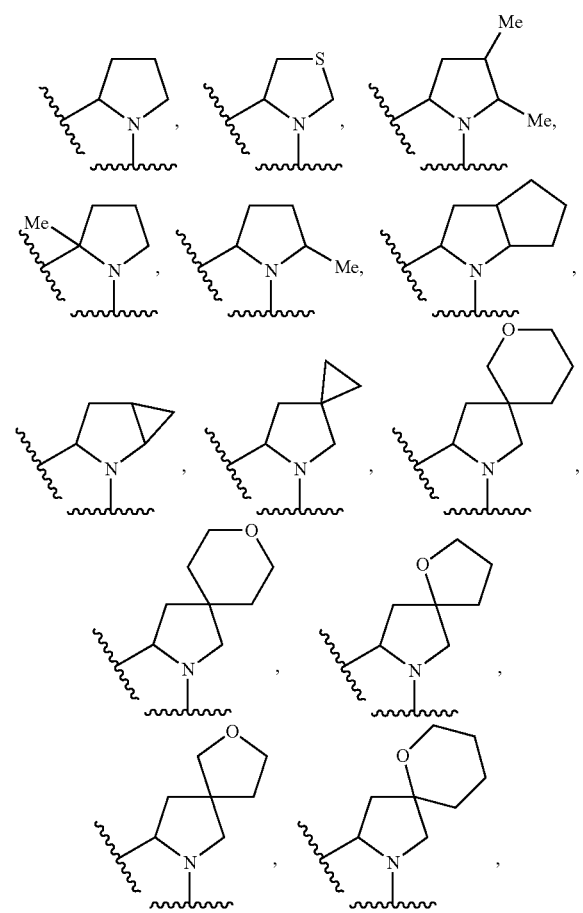
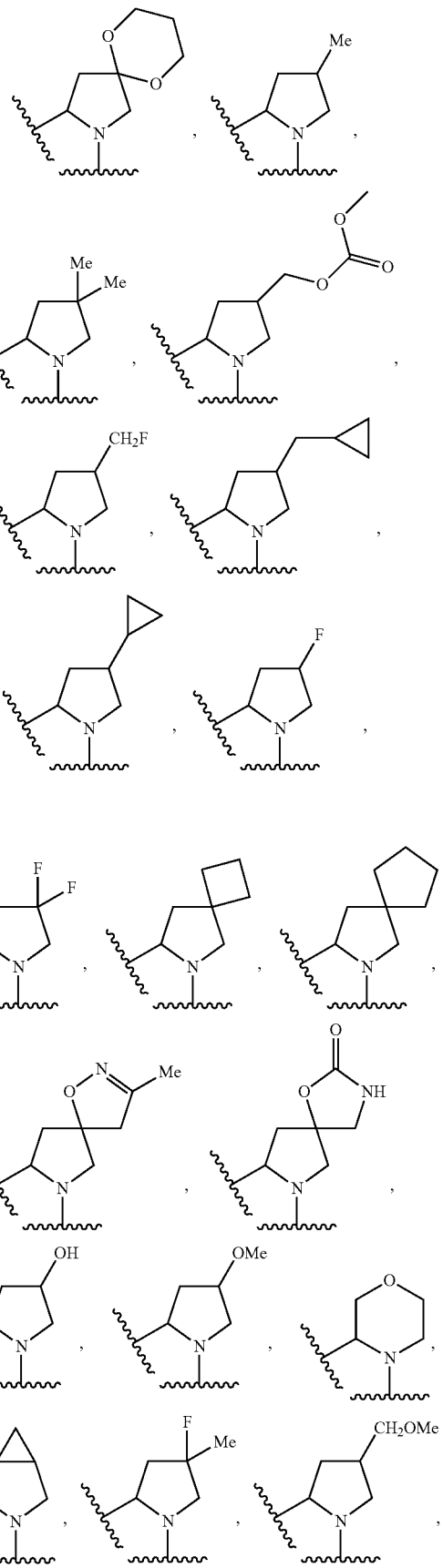

517

-continued

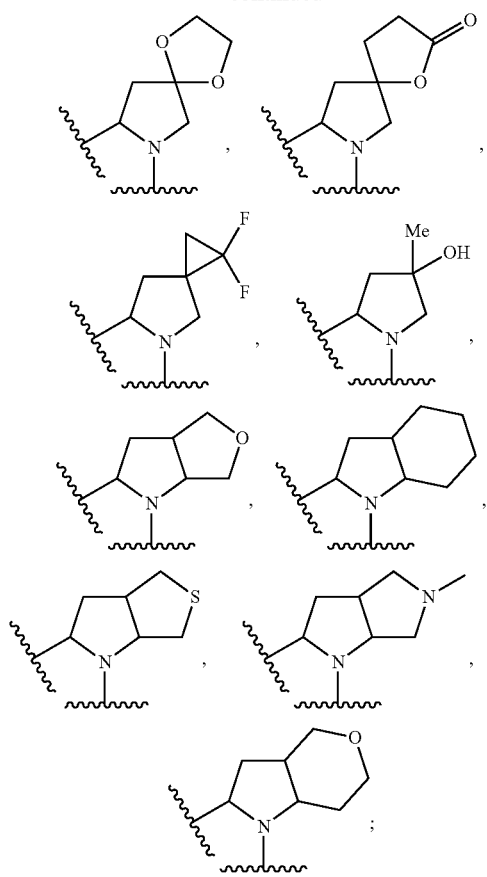

provided that at least one is

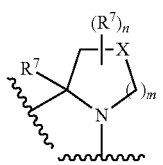

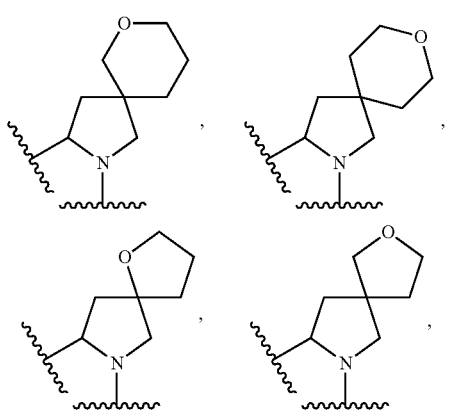

518

-continued

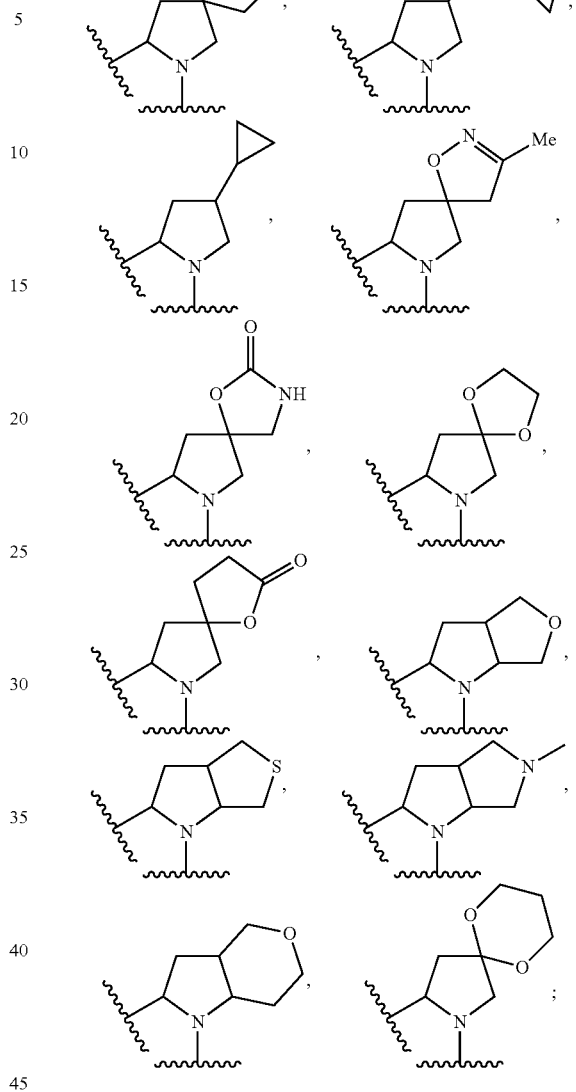

$R^{12}$ at each occurrence is independently selected from the group consisting of —O—$R^{11}$, —$NR^aR^b$, —$R^{13}$, and —$NR^cR^d$;

$R^{11}$ at each occurrence is independently hydrogen or optionally substituted $C_1$-$C_8$ alkyl;

$R^a$ and $R^b$ at each occurrence are independently selected from the group consisting of hydrogen, optionally substituted $C_1$-$C_8$ alkyl, and optionally substituted $C_2$-$C_8$ alkenyl; or $R^a$ and $R^b$ are taken together with the nitrogen atom to which they are attached to form an optionally substituted heterocyclic or optionally substituted heteroaryl group;

$R^{13}$ at each occurrence is independently selected from the group consisting of: hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; and $R^c$ and $R^d$ at each occurrence are independently selected from the group consisting of hydrogen, —$R^{13}$, —C(O)—$R^{13}$, —C(O)—$OR^{13}$, —S(O)$_2$—$R^{13}$, —C(O)N($R^{13}$)$_2$, and —S(O)$_2$N($R^{13}$)$_2$.

2. A compound selected from Table A or a pharmaceutically acceptable salt thereof:

TABLE A
546
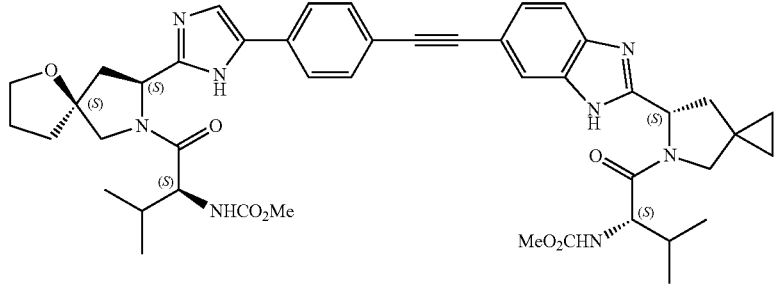
547
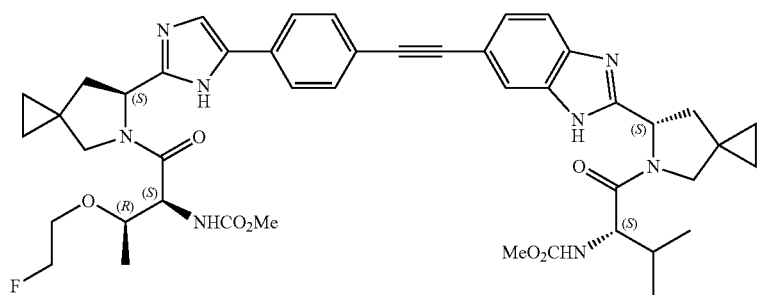
549
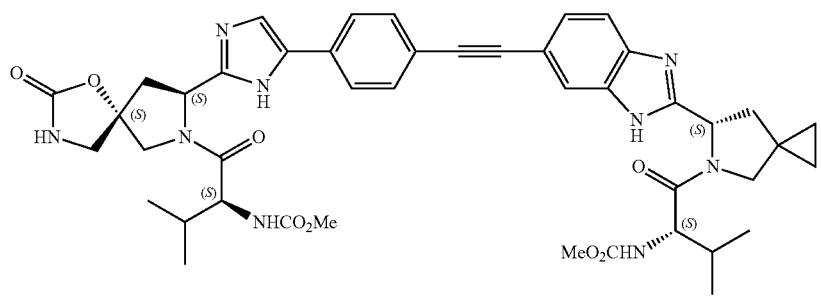
550
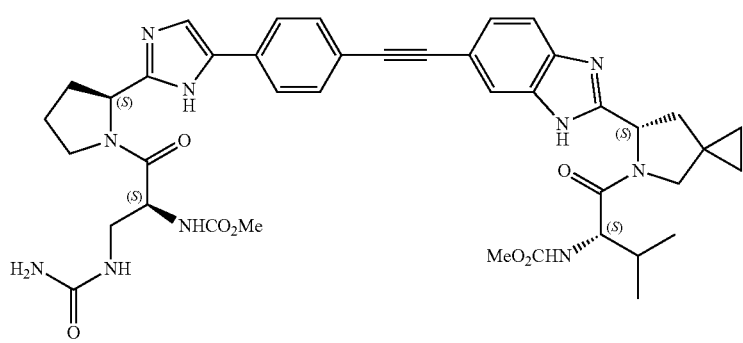
551
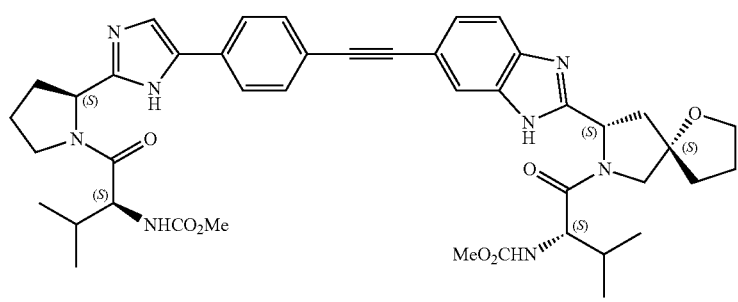

TABLE A-continued
552
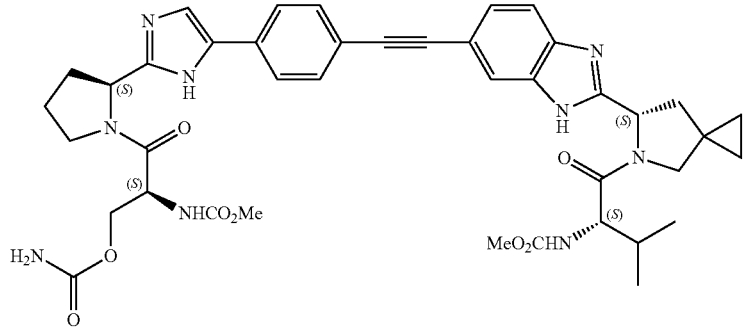
553
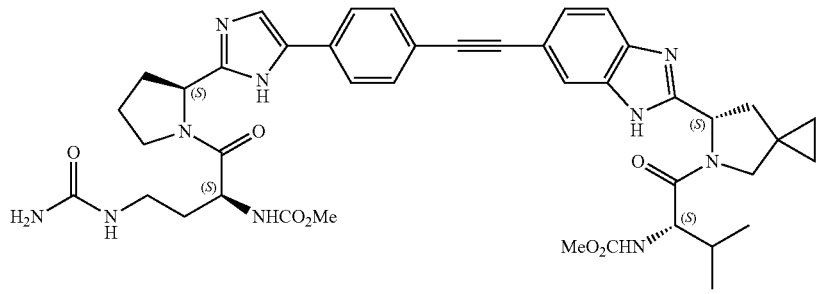
554
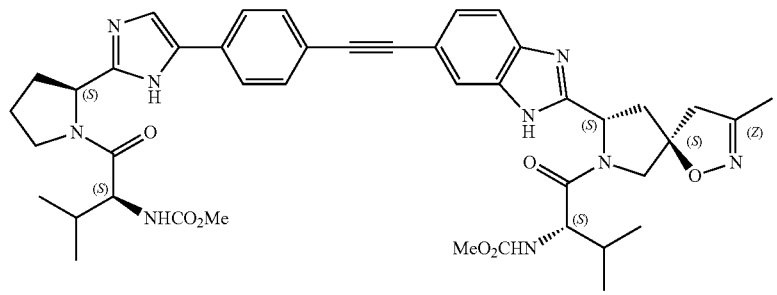
555
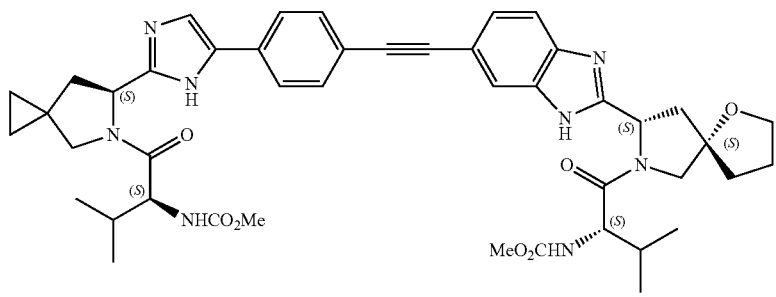
557
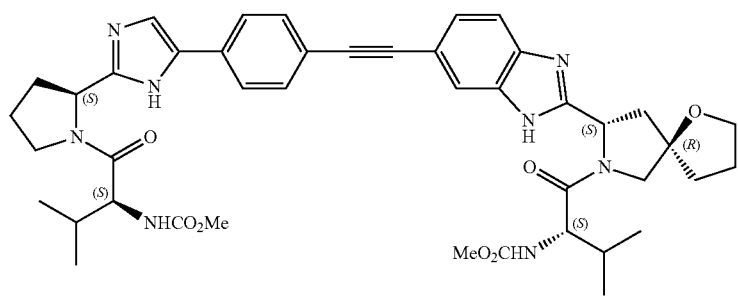

TABLE A-continued
558
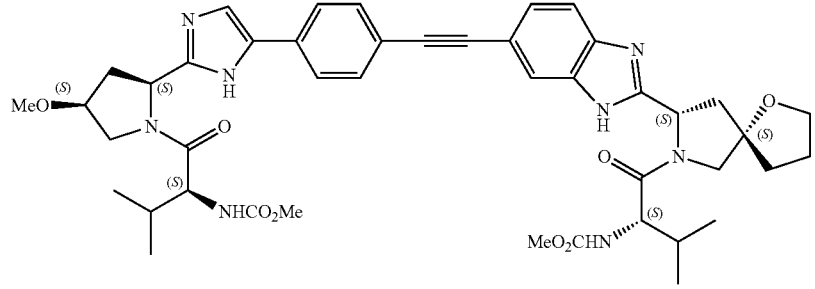
559
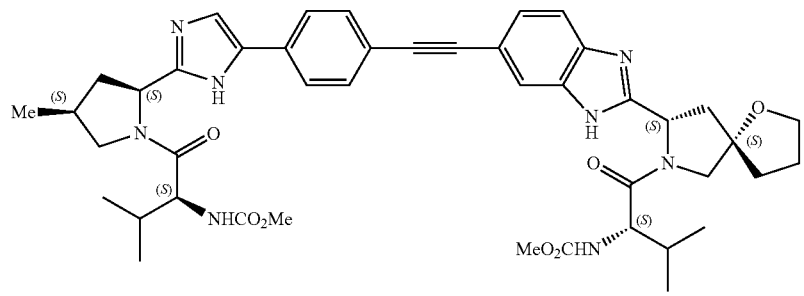
560
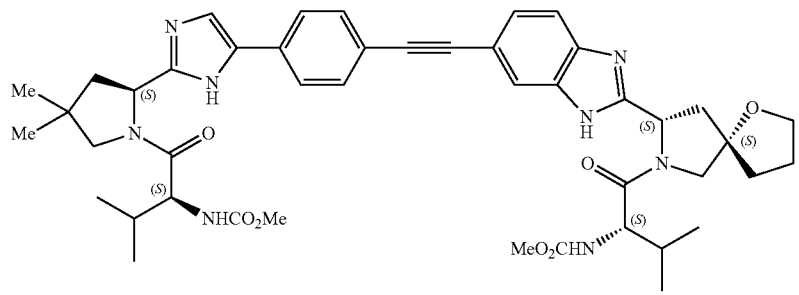
561
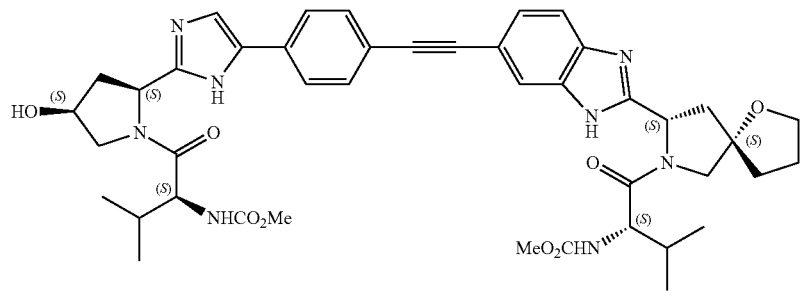
562
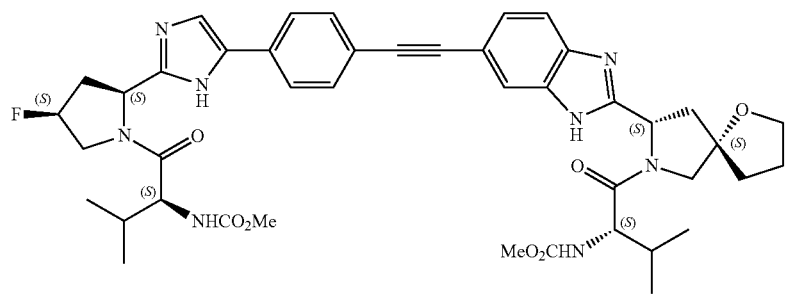

TABLE A-continued
563
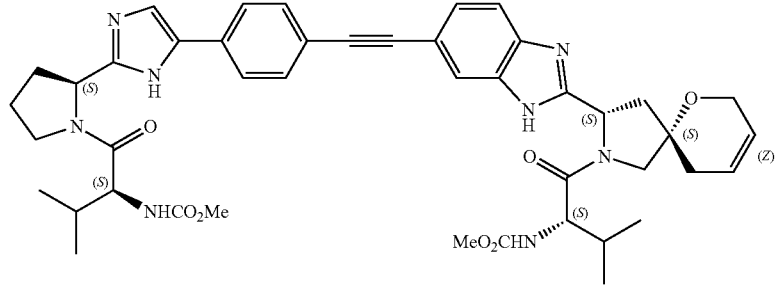
564
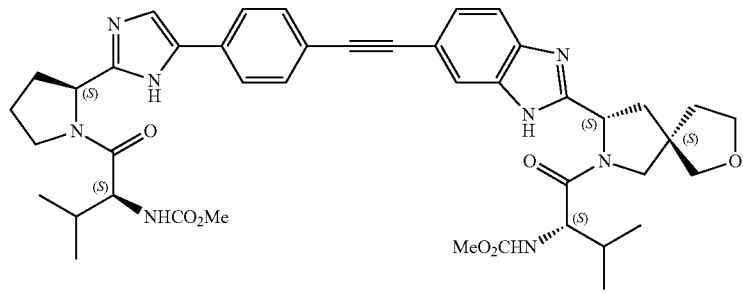
565
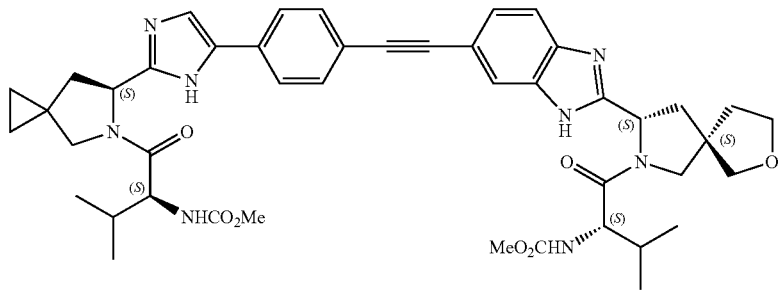
566
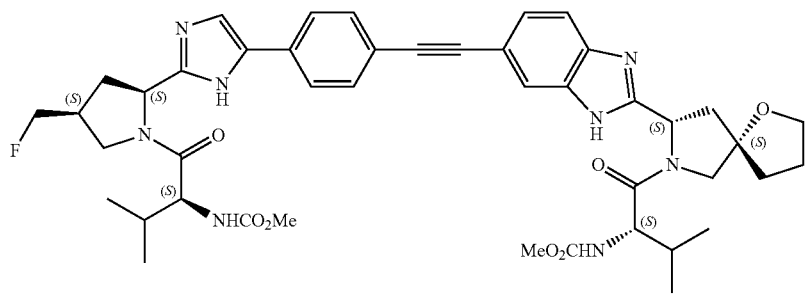
567
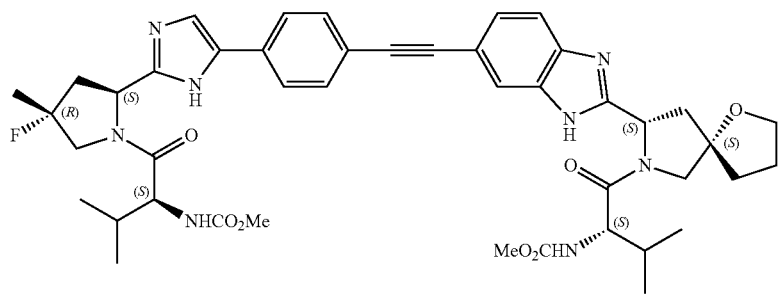

TABLE A-continued
| 568 | 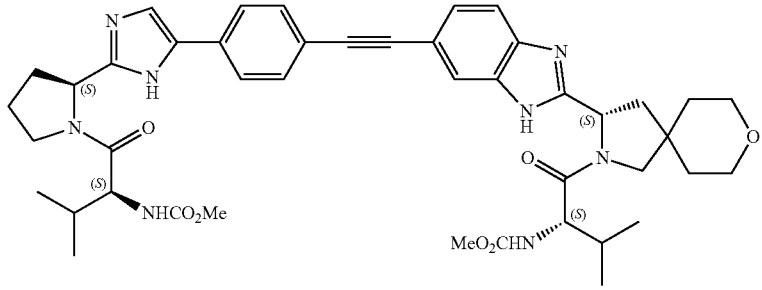 |
| --- | --- |
| 569 | 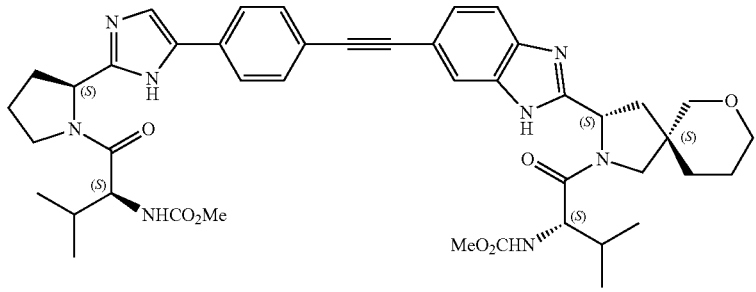 |
| 570 | 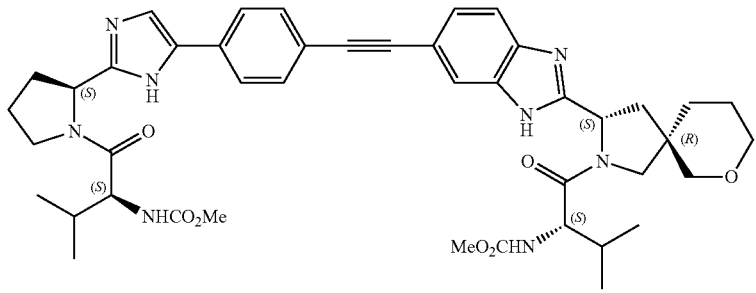 |
| 571 | 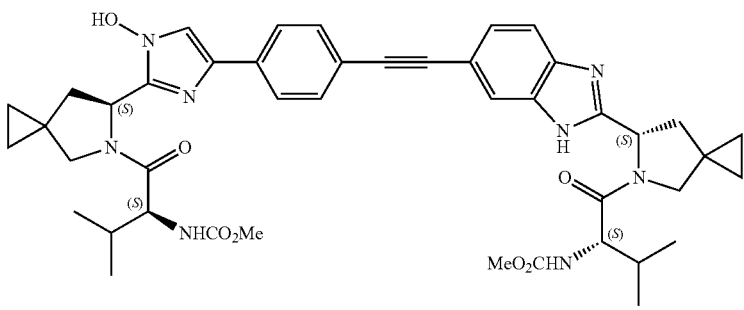 |
| 572 | 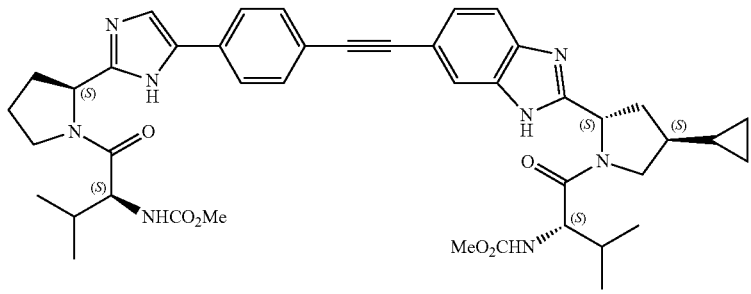 |

TABLE A-continued
573
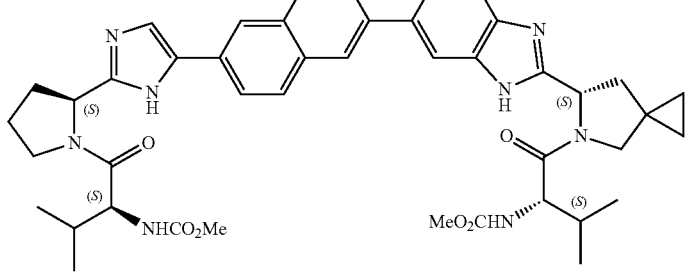
574
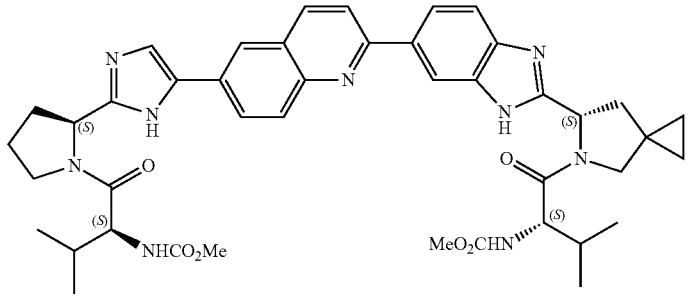
575
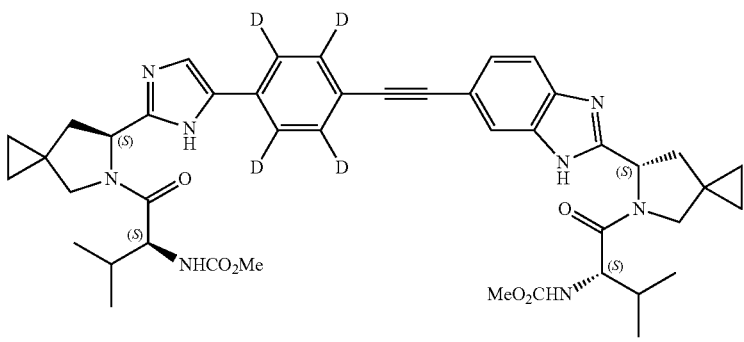
576
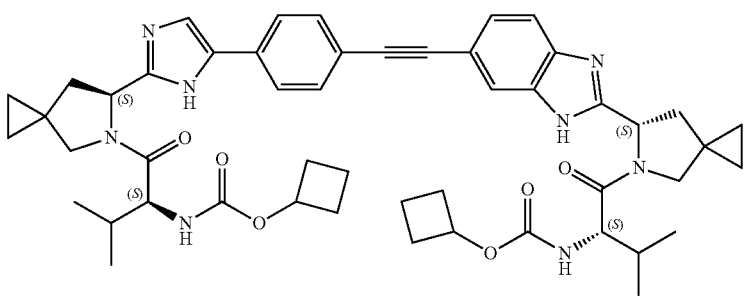
577
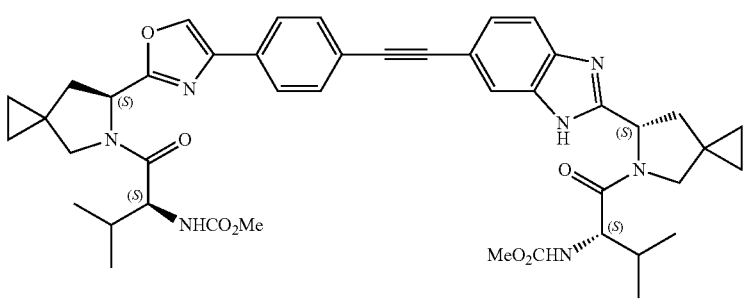

TABLE A-continued
| 580 | 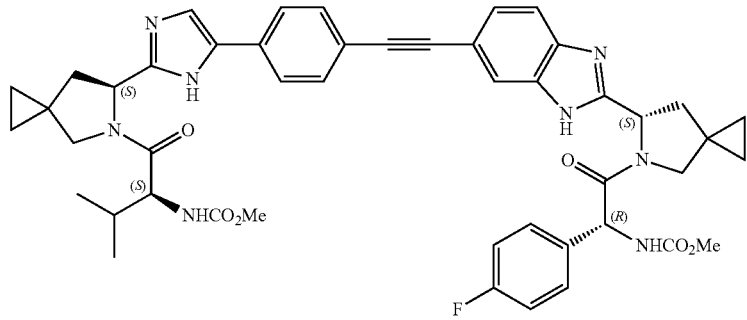 |
| --- | --- |
| 581 | 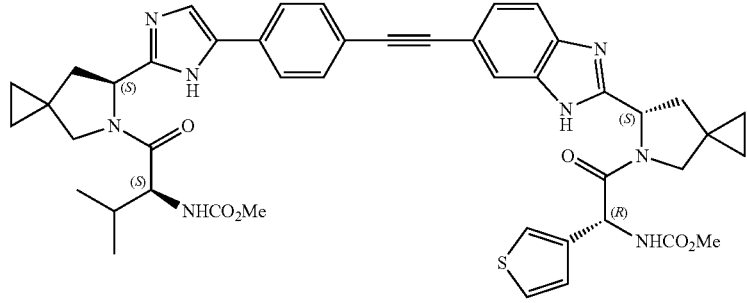 |
| 582 | 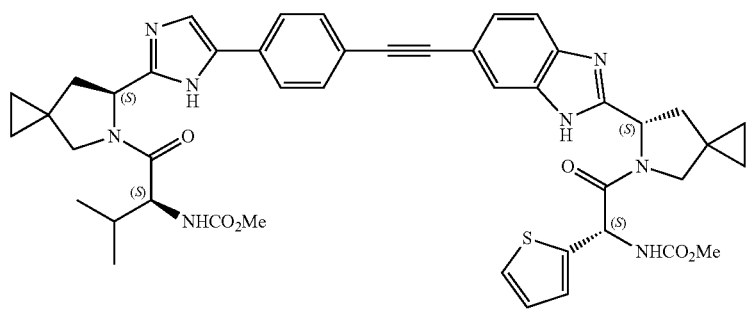 |
| 583 | 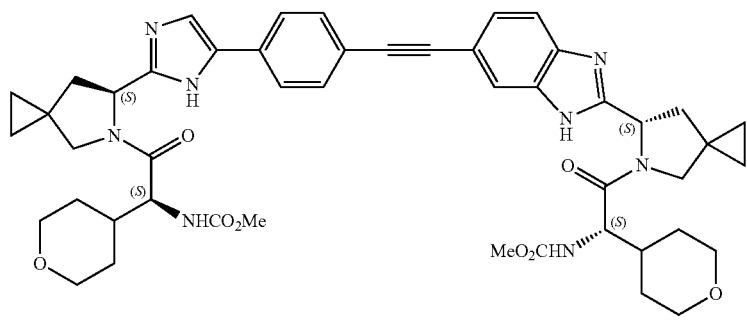 |
| 584 | 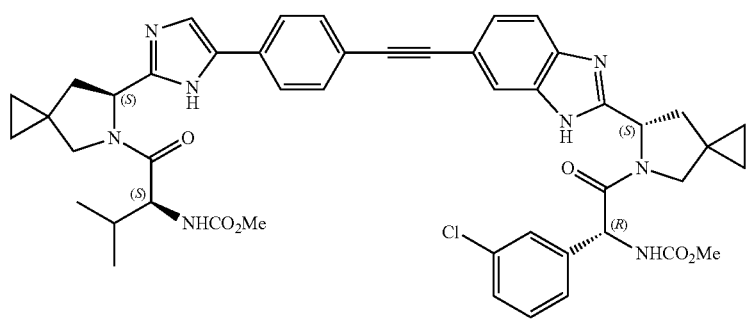 |

585 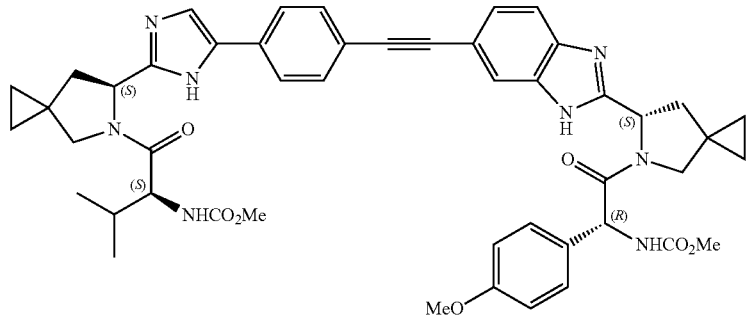
586 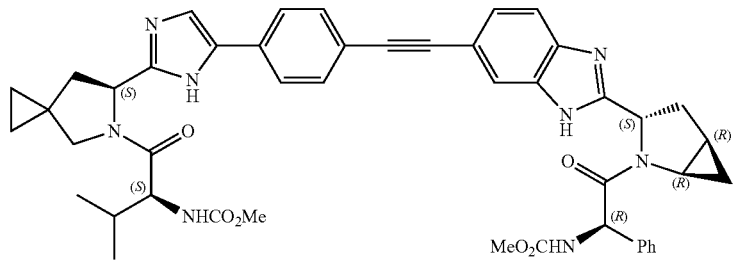
587 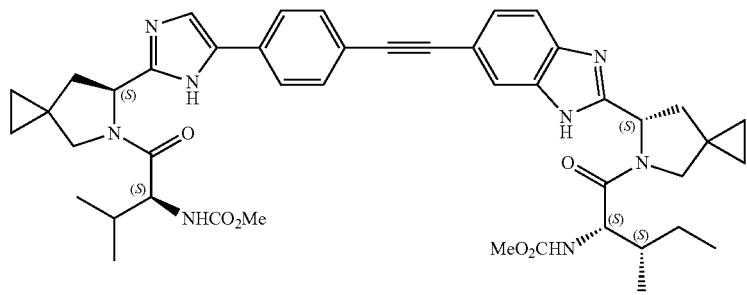
588 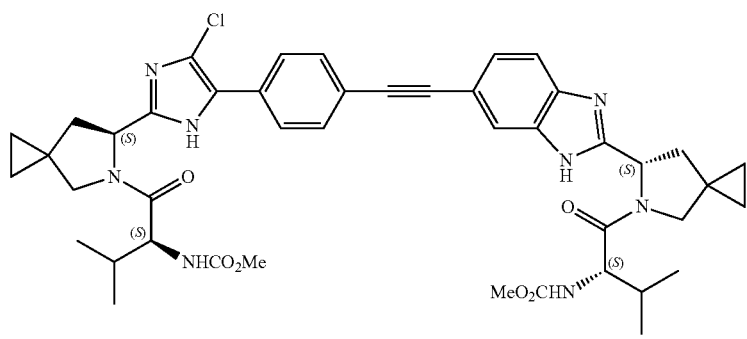
589 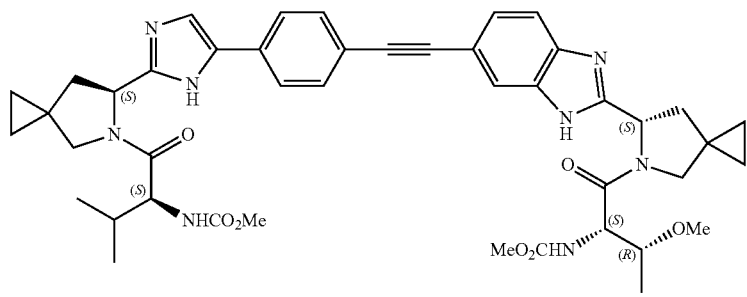

TABLE A-continued
590
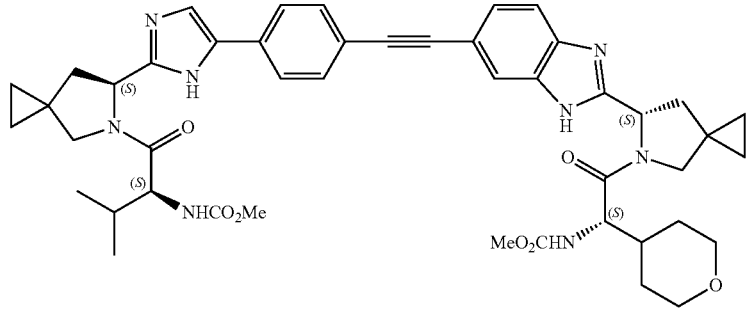
591
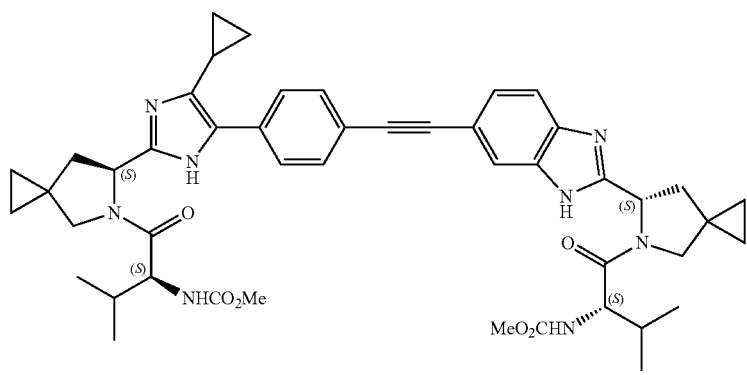
592
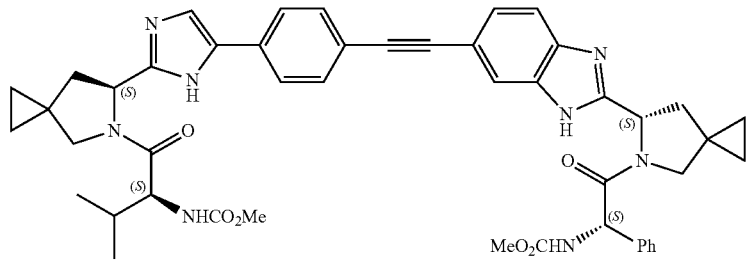
593
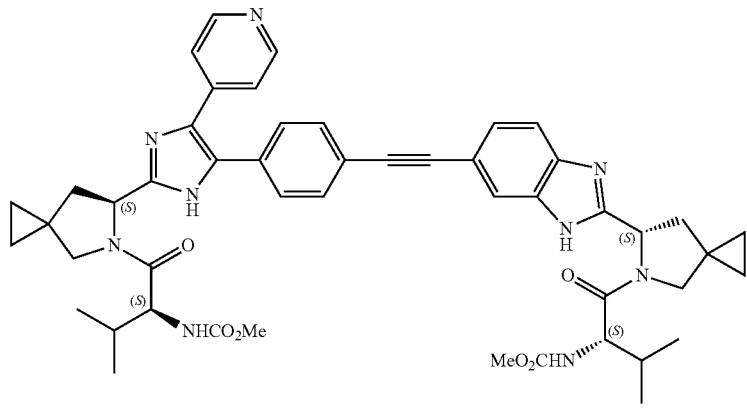

594 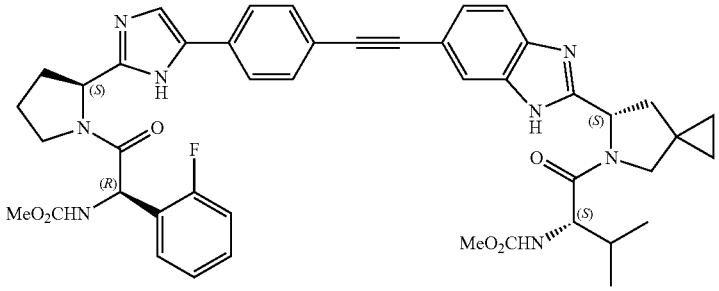
595 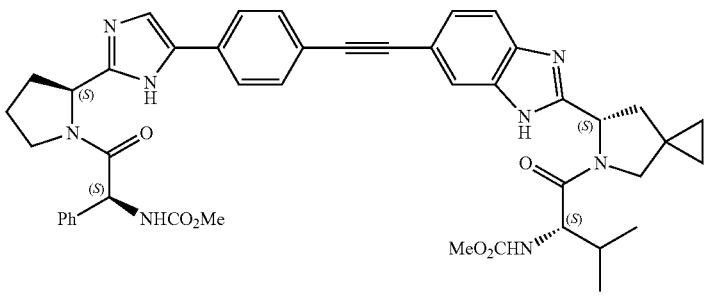
596 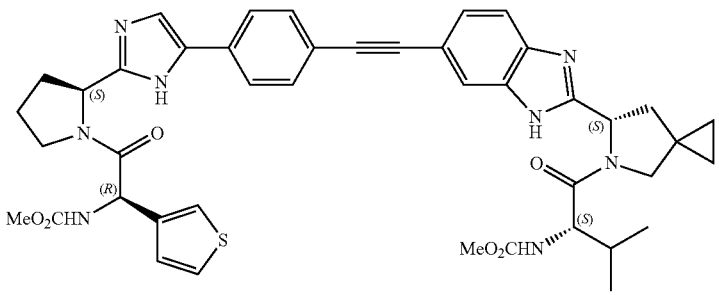
597 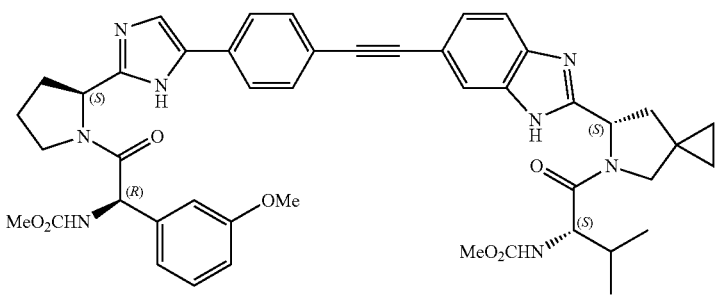
598 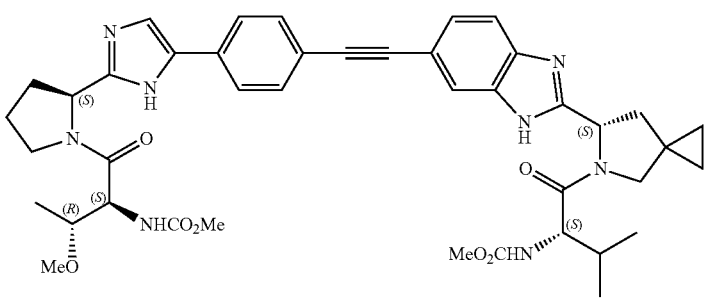

TABLE A-continued
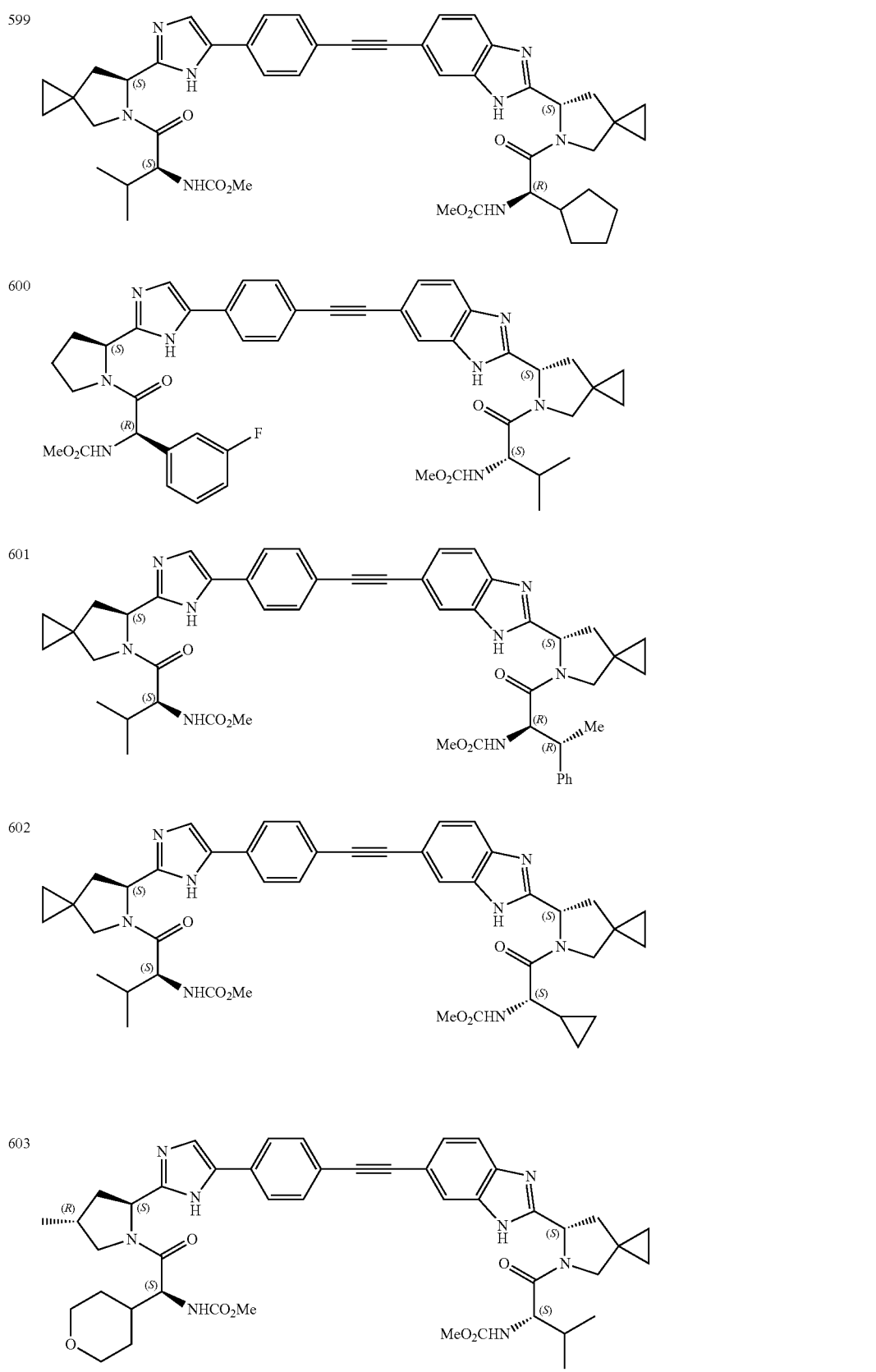

TABLE A-continued
| 604 | 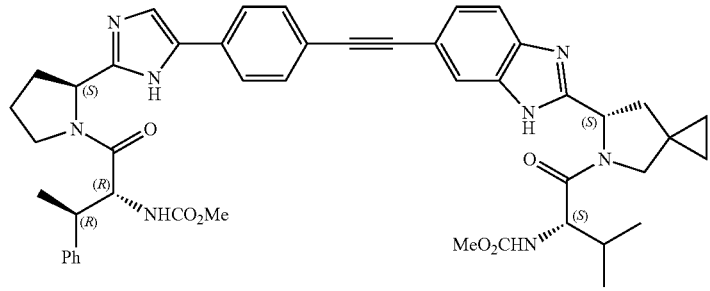 |
| --- | --- |
| 605 | 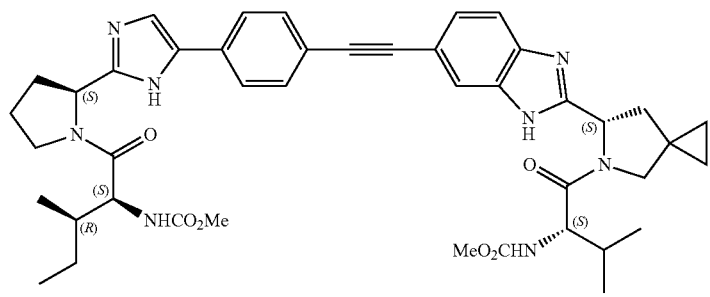 |
| 606 | 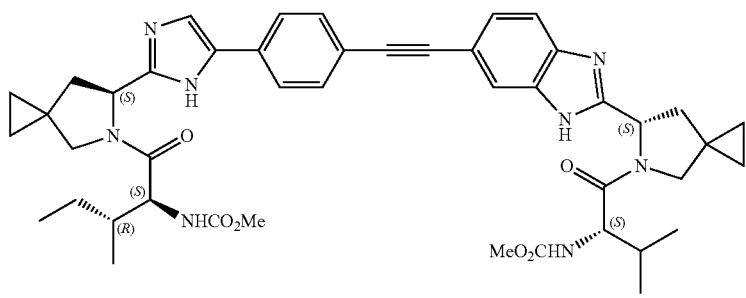 |
| 607 | 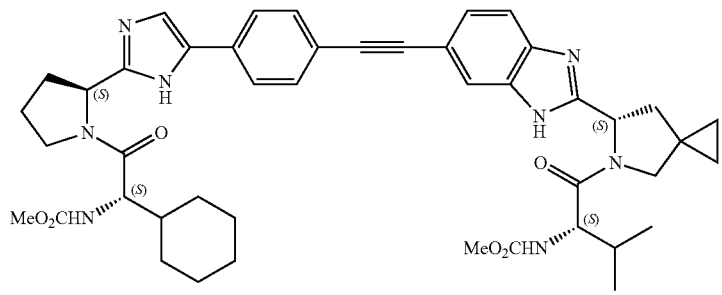 |
| 608 | 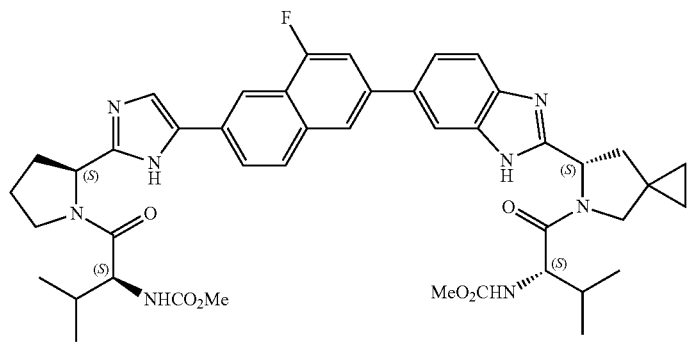 |

TABLE A-continued
609
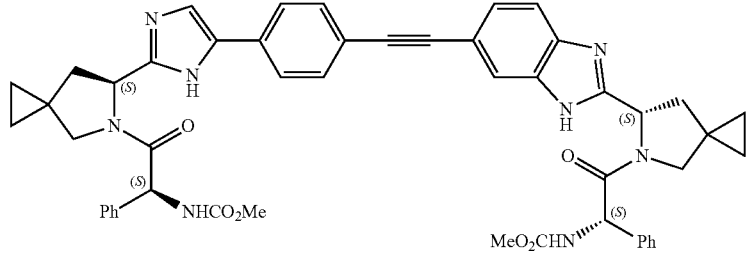
610
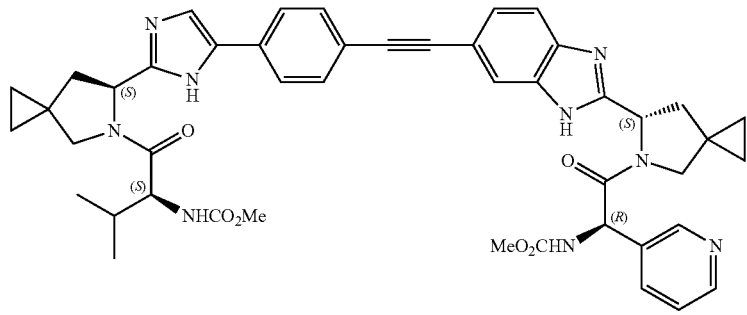
611
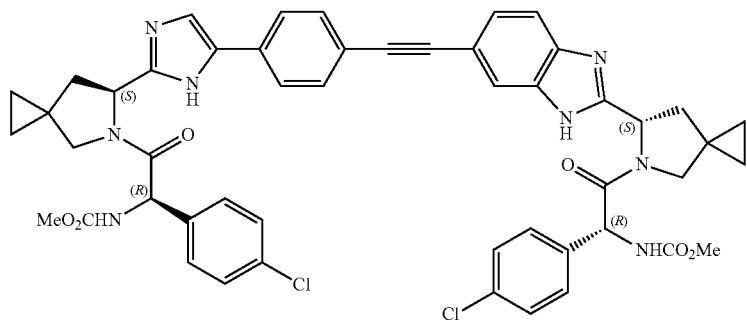
612
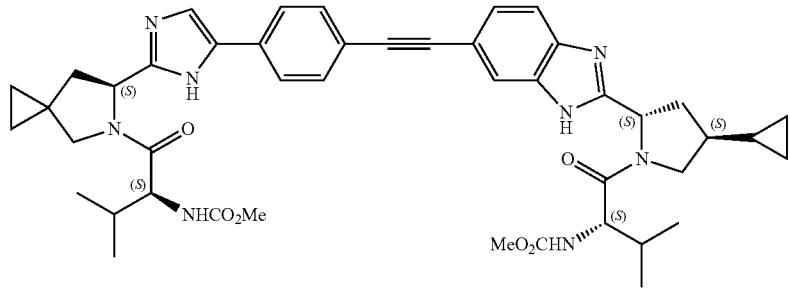
613
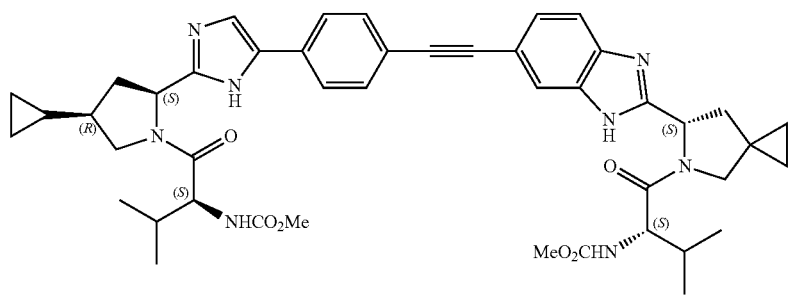

TABLE A-continued
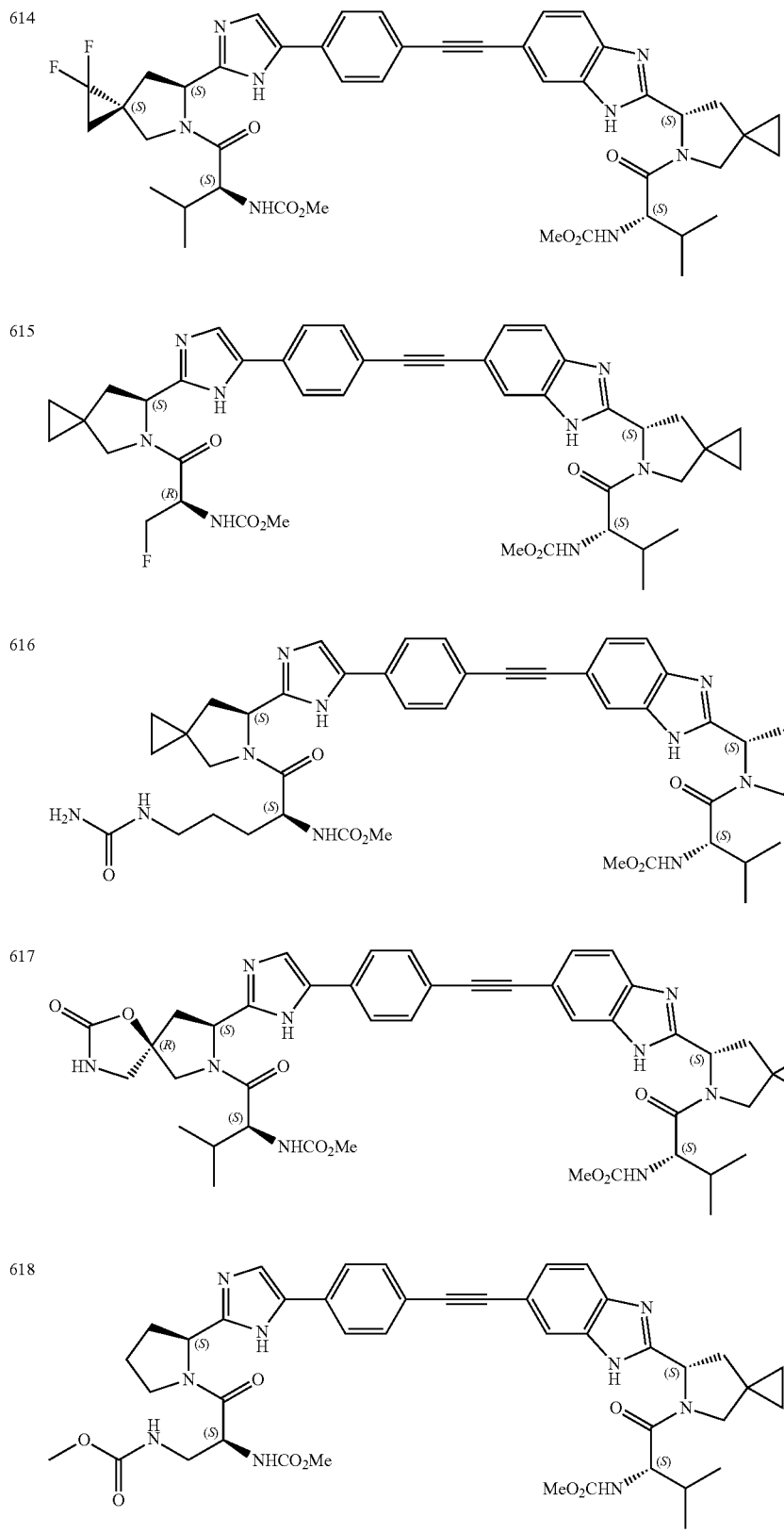

TABLE A-continued
619
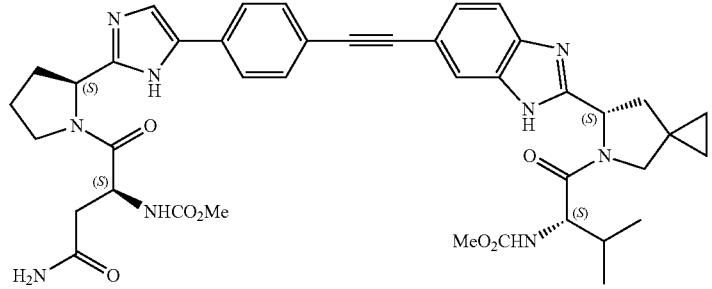
620
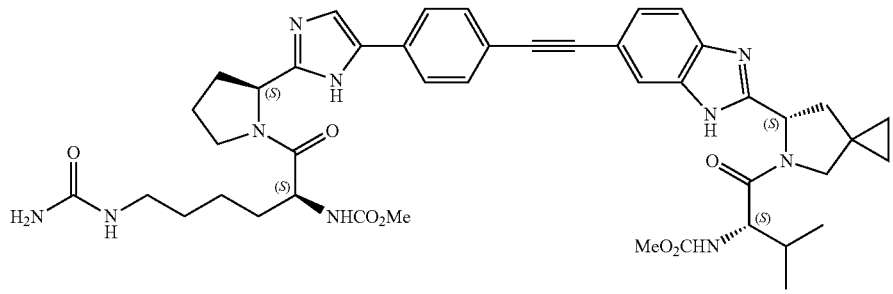
621
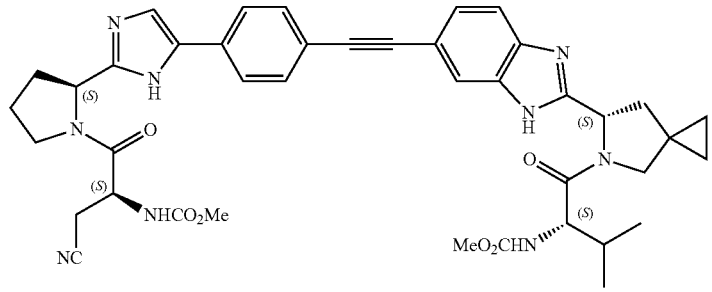
622
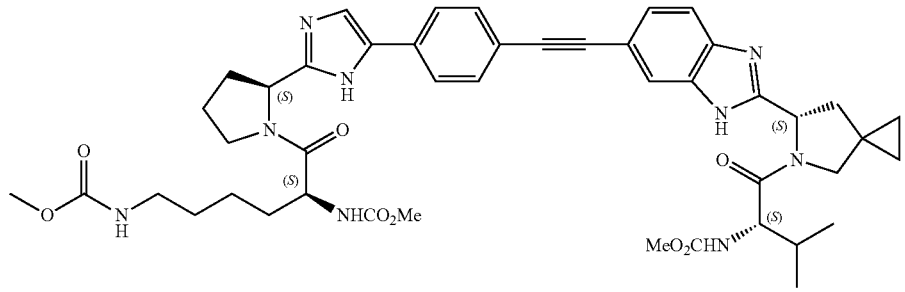
623
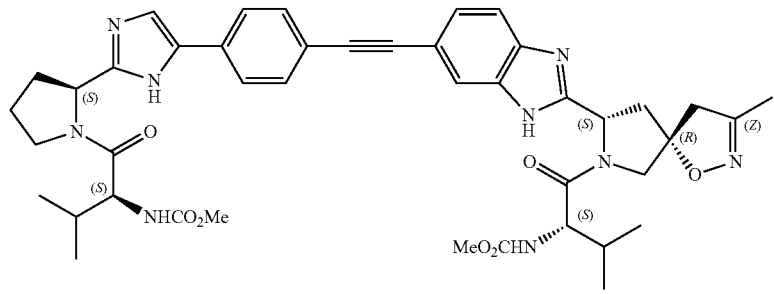

TABLE A-continued
624
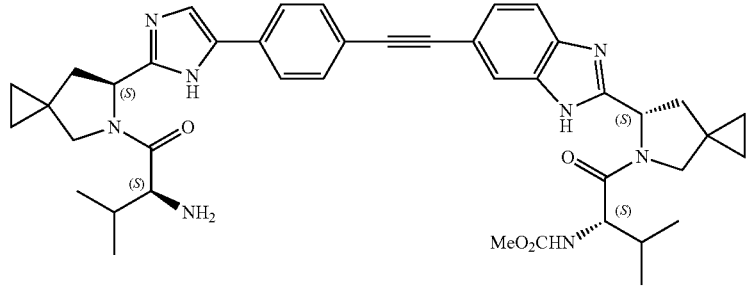
625
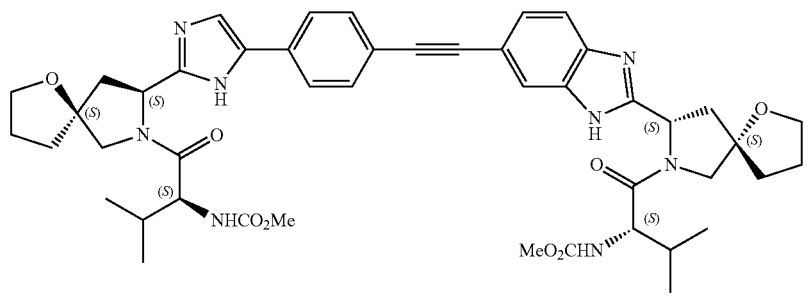
626
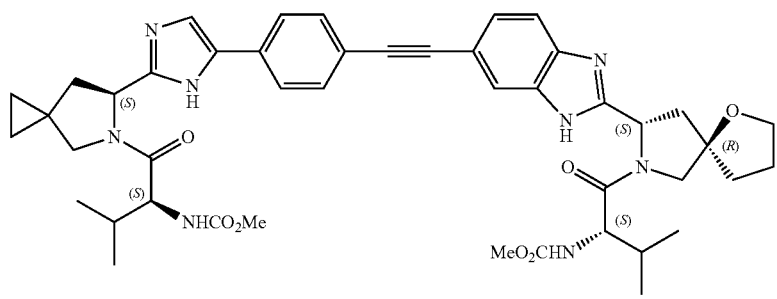
627
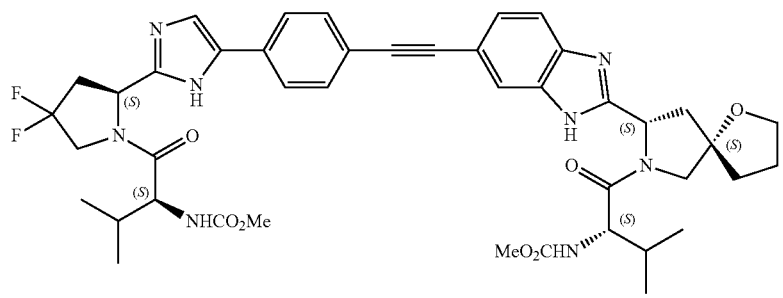
628
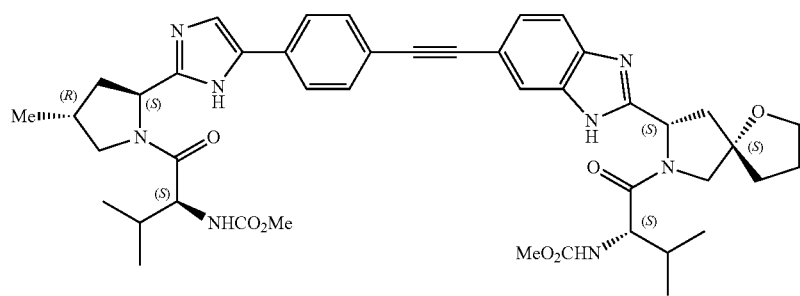

TABLE A-continued
629
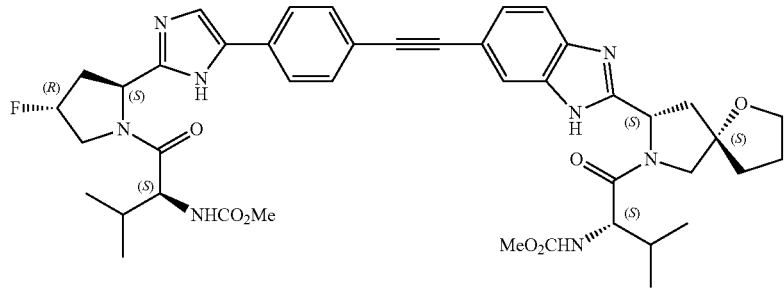
630
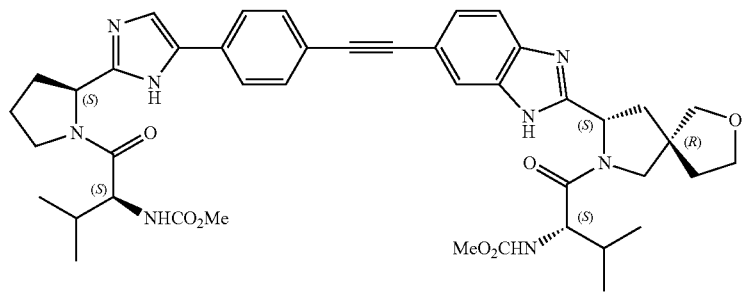
631
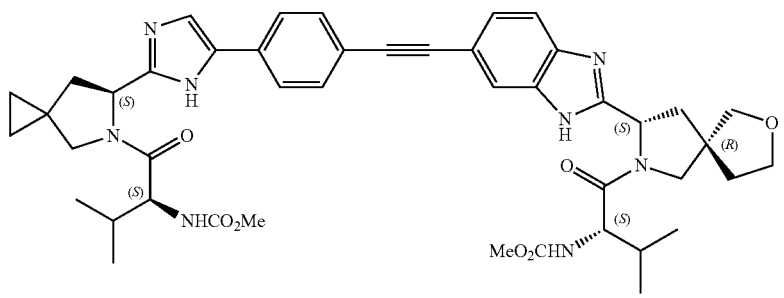
632
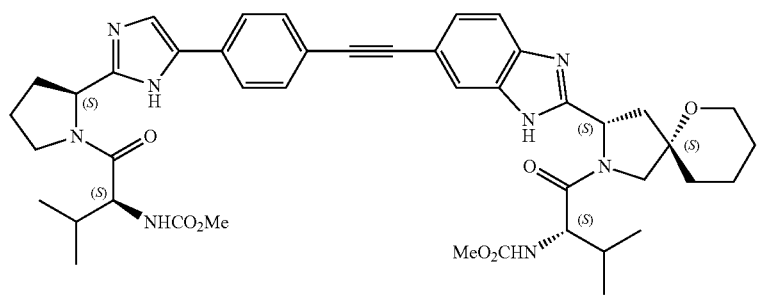
633
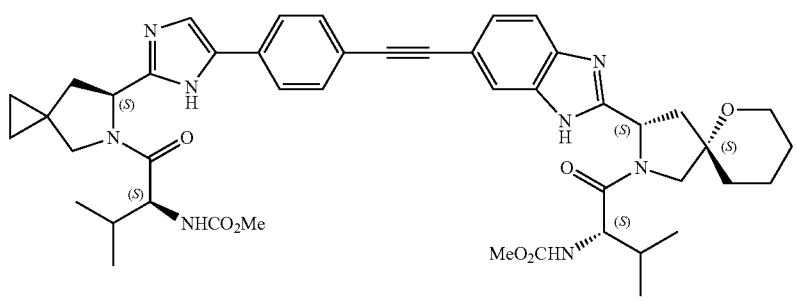

TABLE A-continued
| 634 | 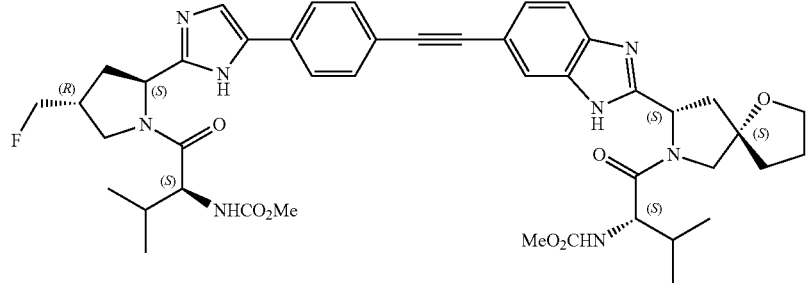 |
| --- | --- |
| 635 | 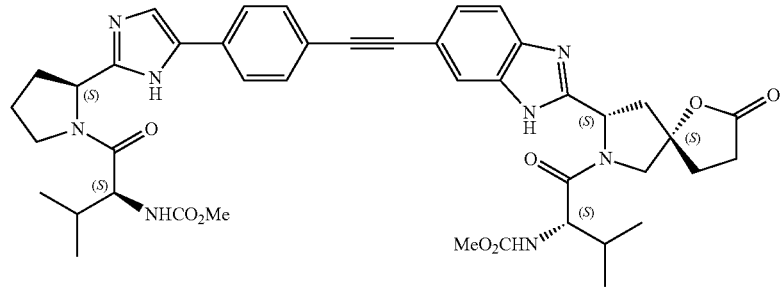 |
| 636 | 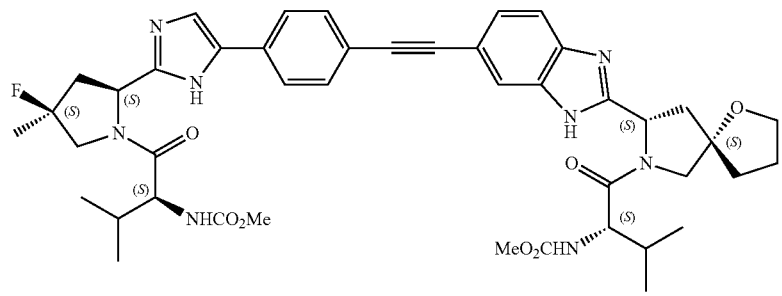 |
| 637 | 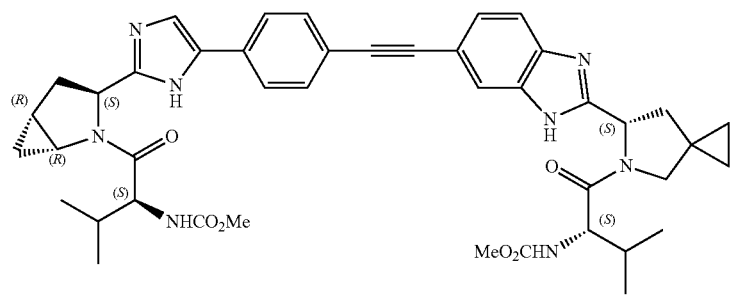 |
| 638 | 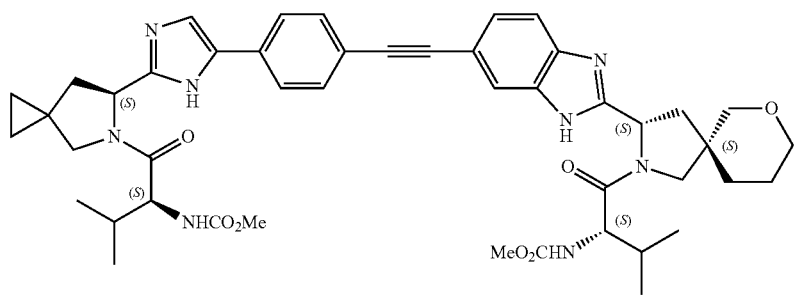 |

TABLE A-continued
639 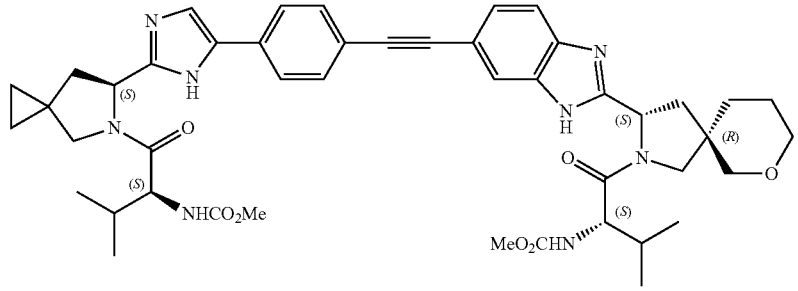
640 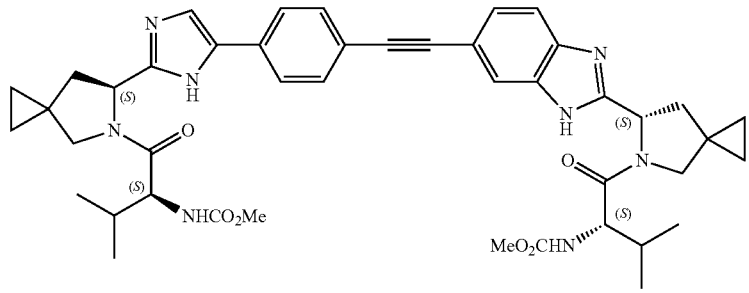
641 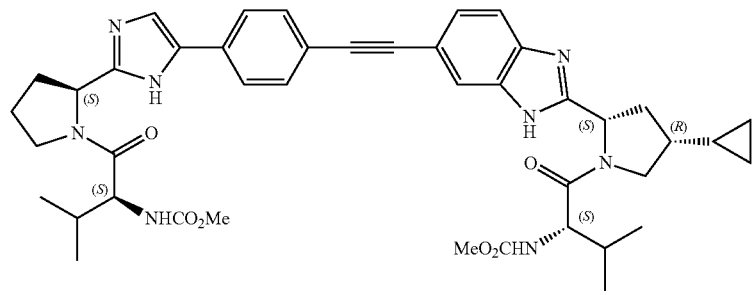
642 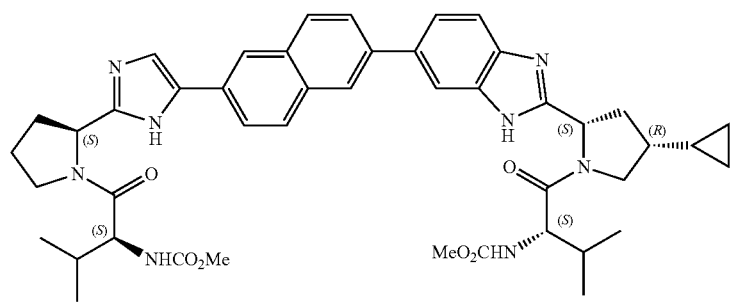
643 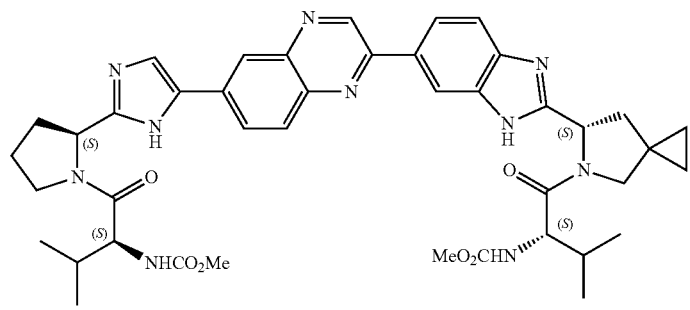

TABLE A-continued
644
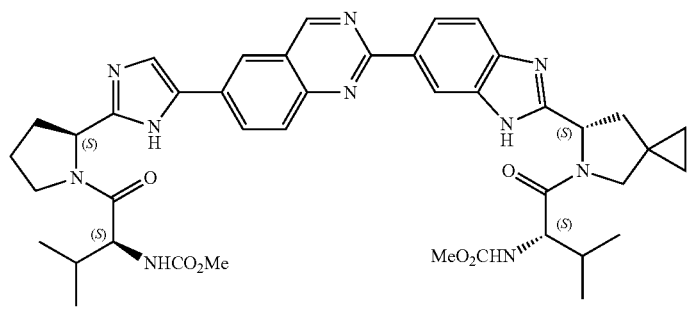
645
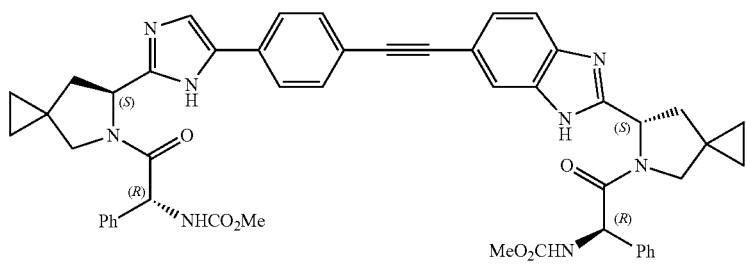
646
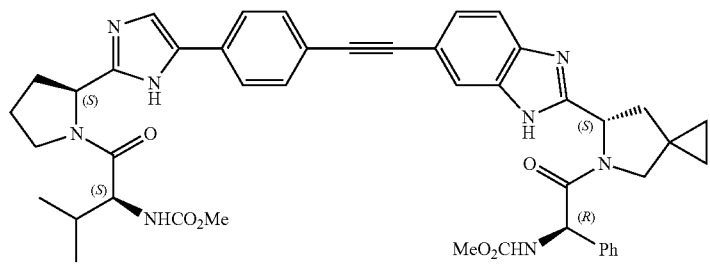
647
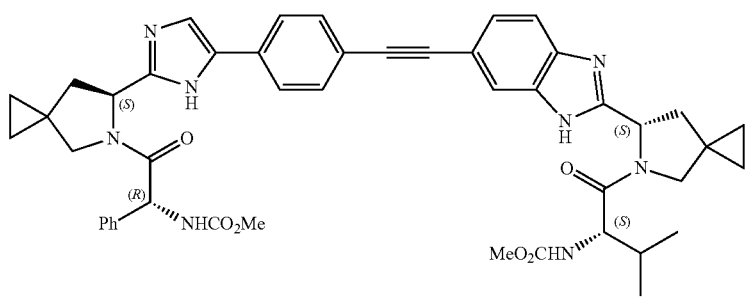
648
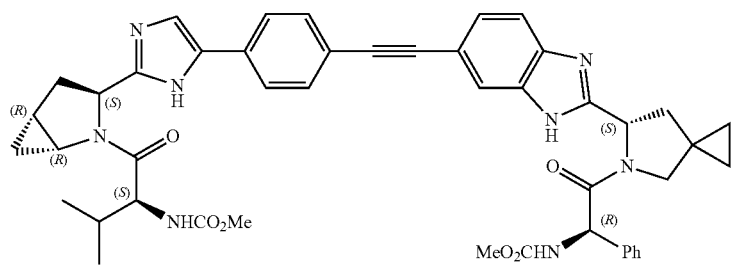

TABLE A-continued
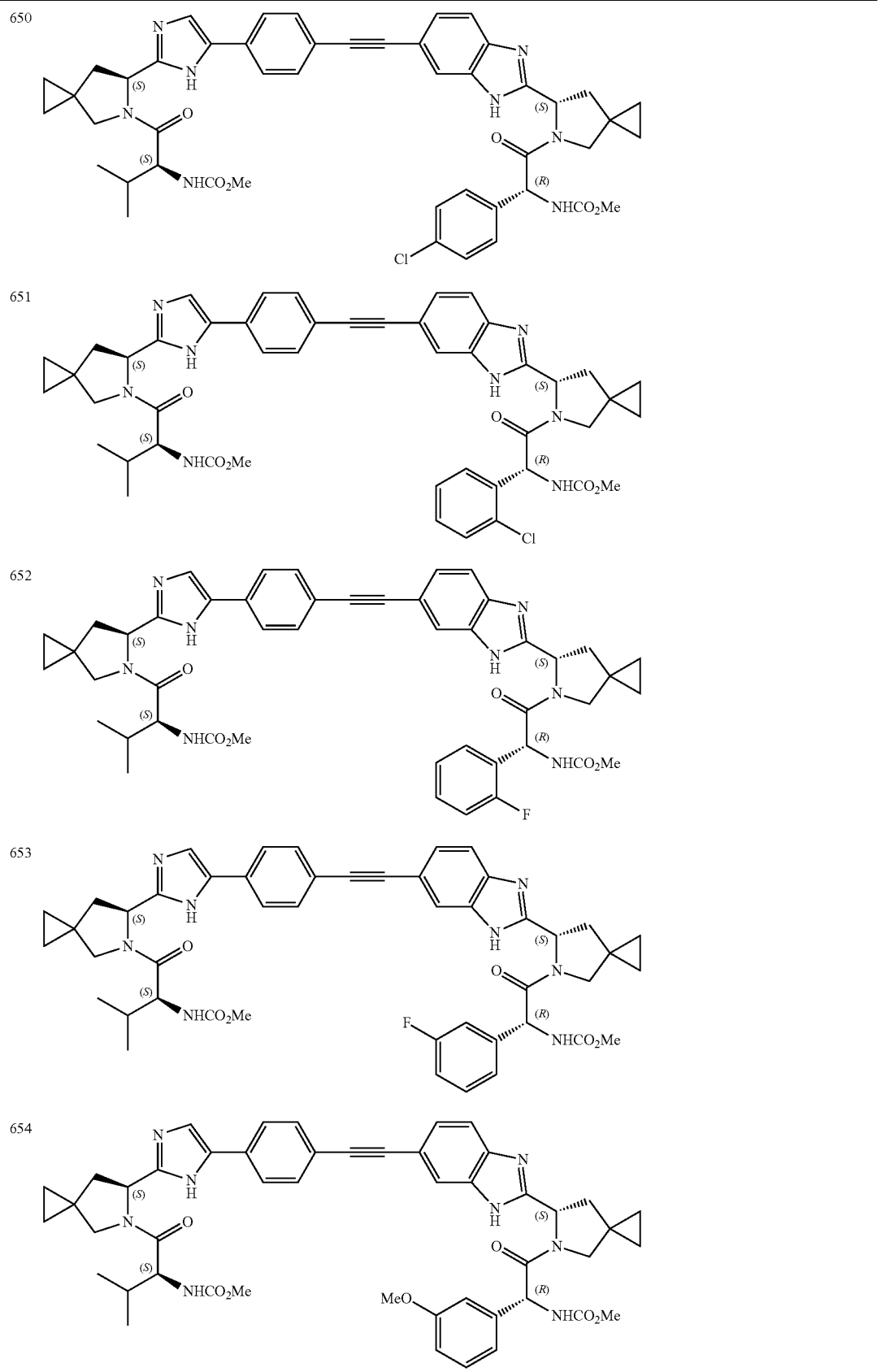

TABLE A-continued
| 655 | 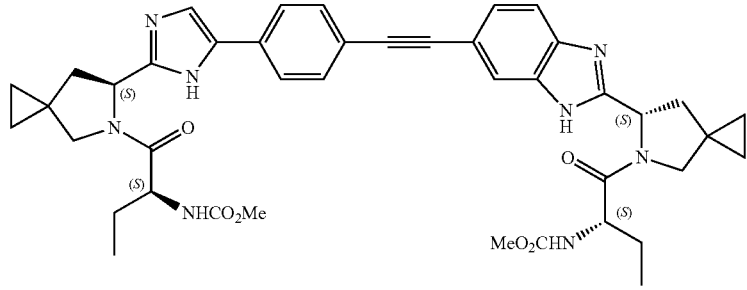 |
| --- | --- |
| 656 | 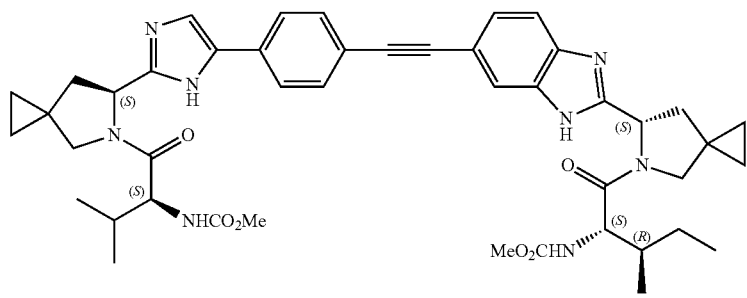 |
| 657 | 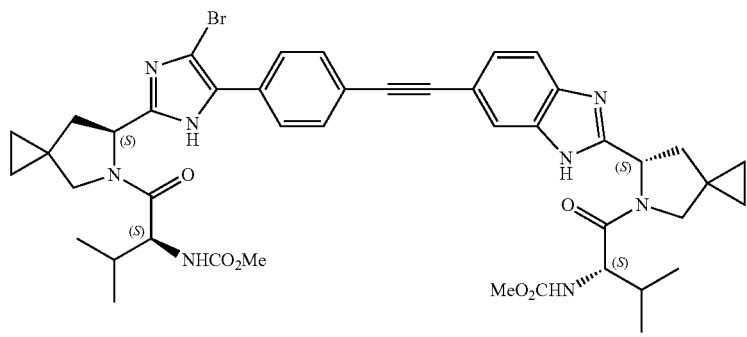 |
| 658 | 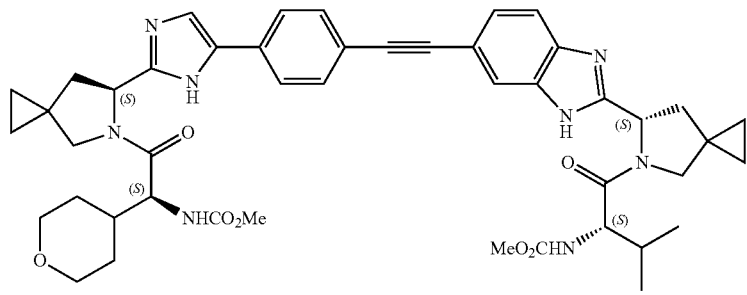 |
| 659 | 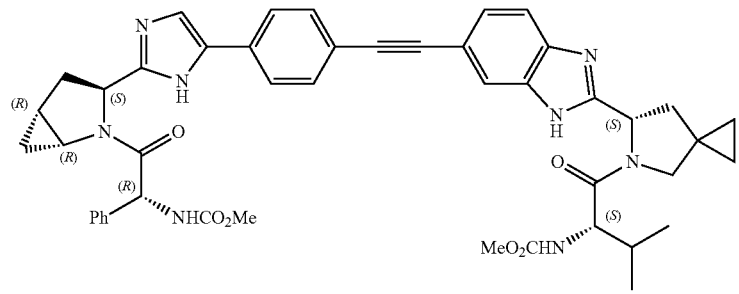 |

TABLE A-continued
660
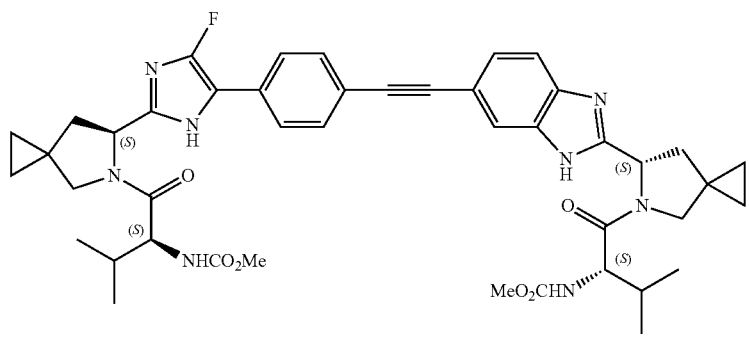
661
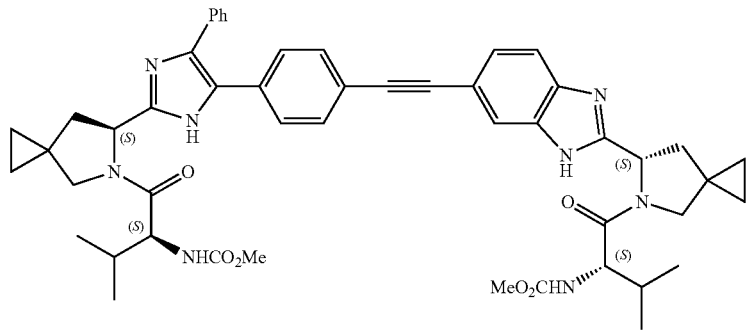
662
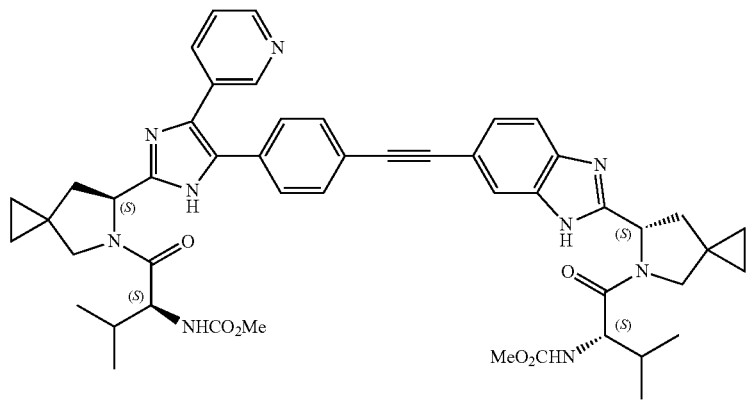
663
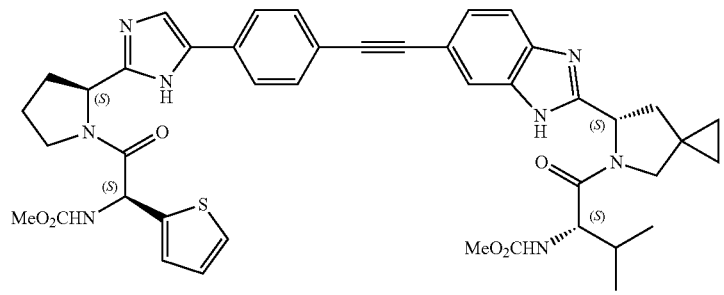

TABLE A-continued
| 664 | 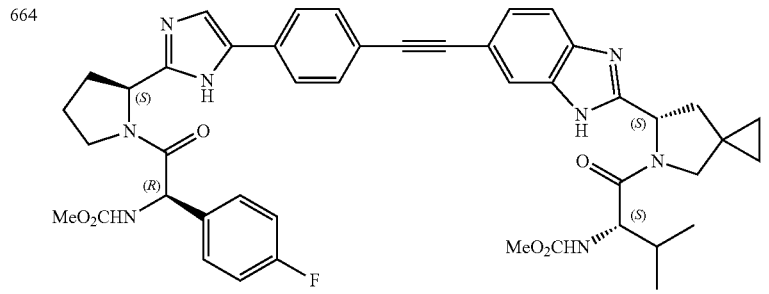 |
| --- | --- |
| 665 | 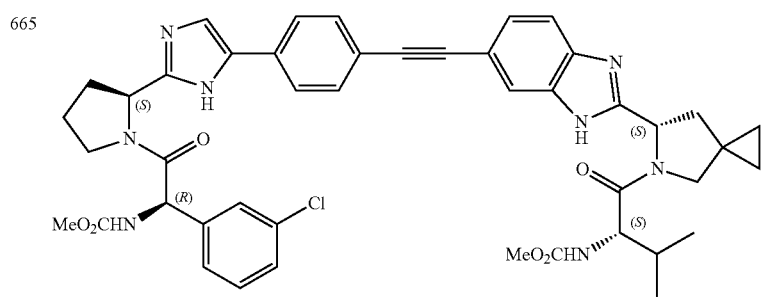 |
| 666 | 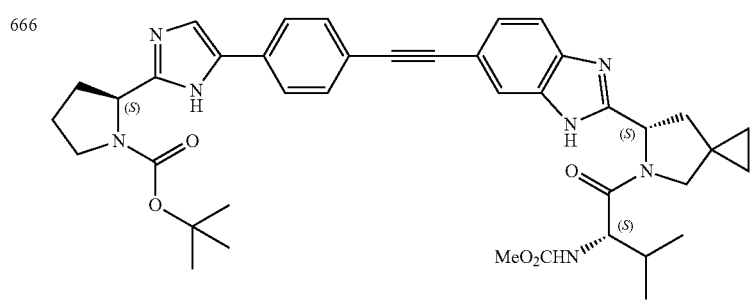 |
| 667 | 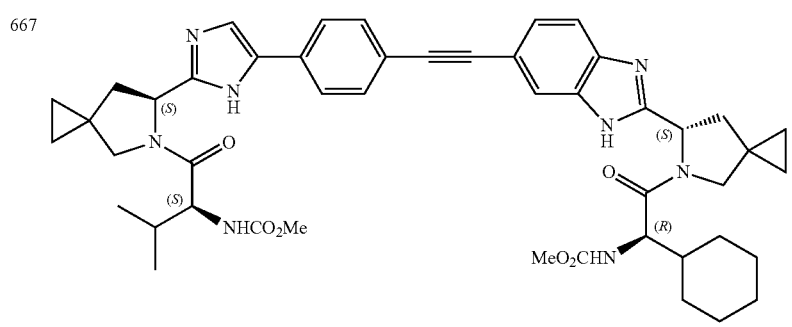 |
| 668 | 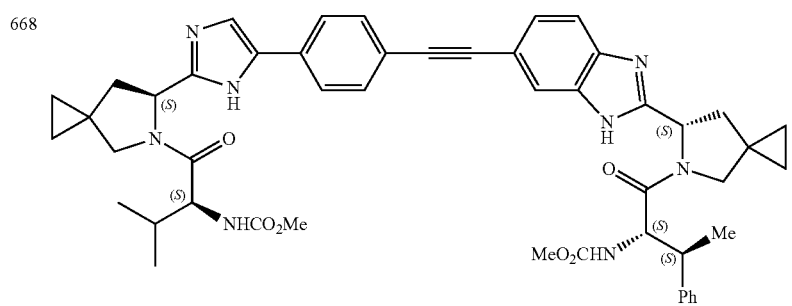 |

TABLE A-continued
| 669 | 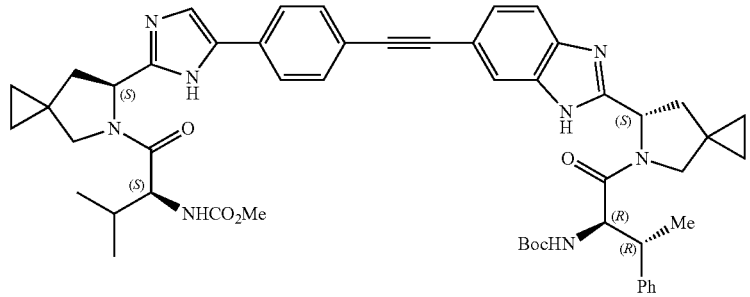 |
| --- | --- |
| 670 | 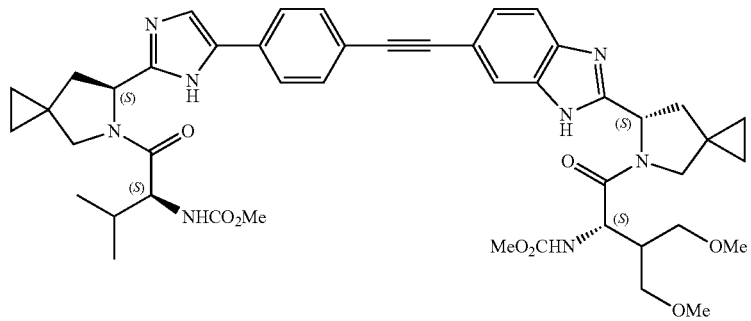 |
| 671 | 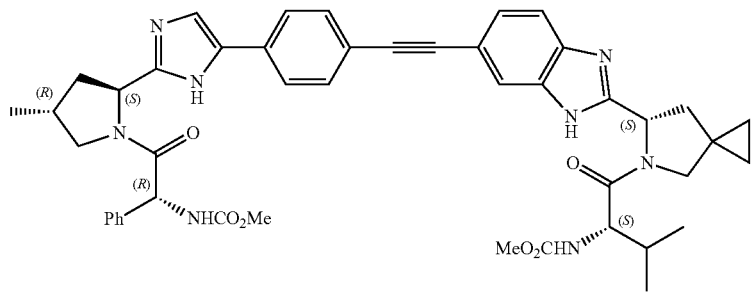 |
| 672 | 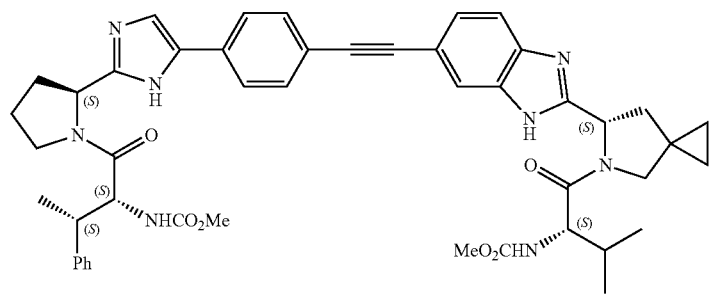 |
| 673 | 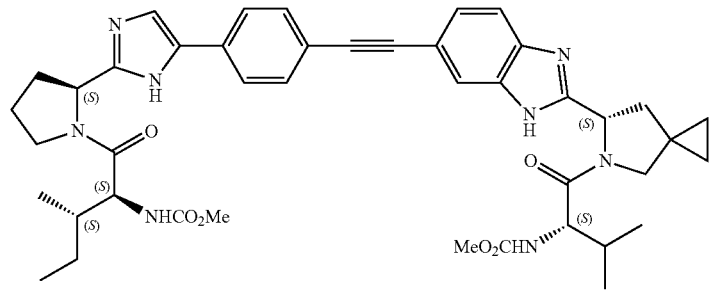 |

TABLE A-continued
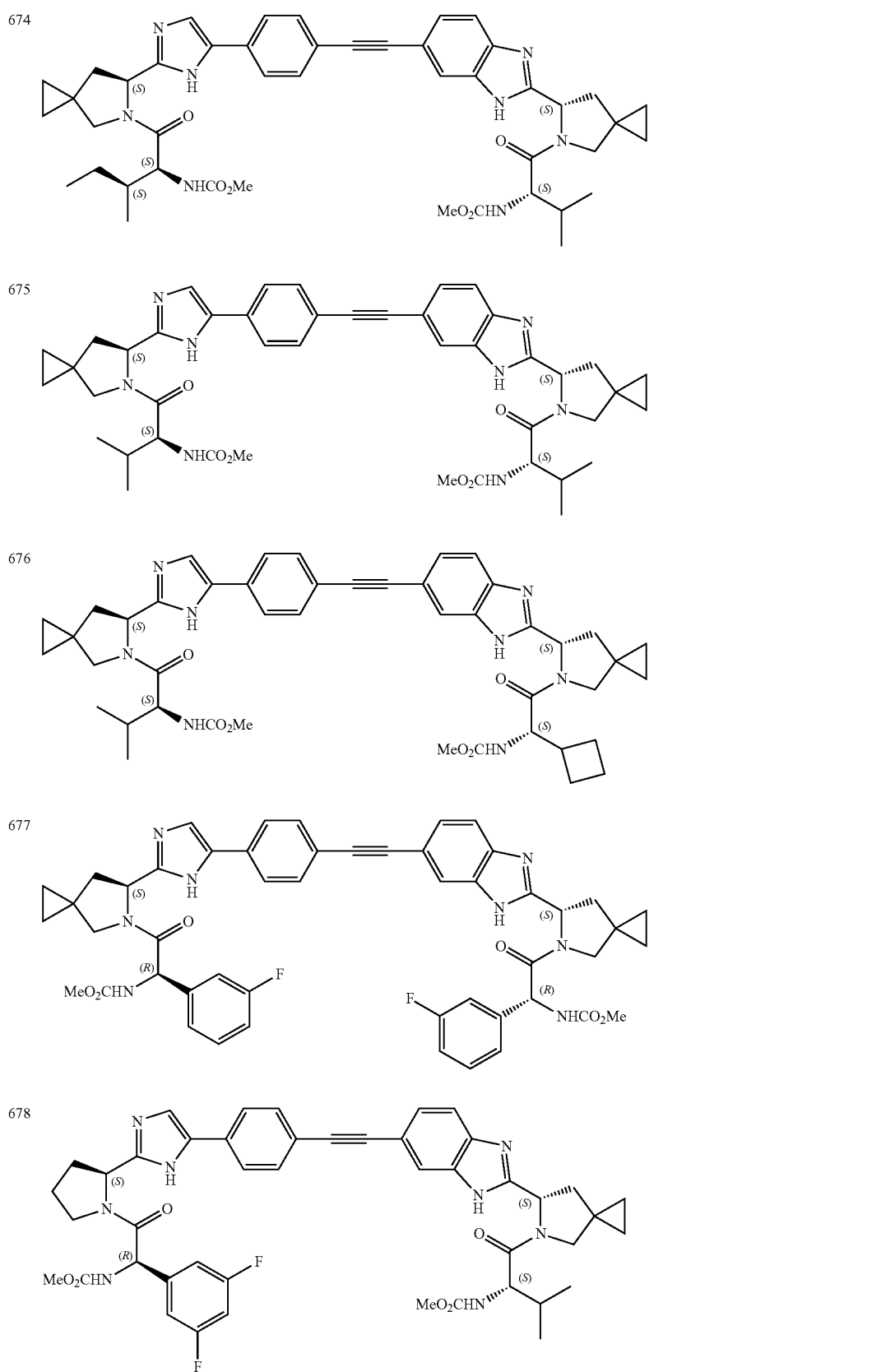

TABLE A-continued
679
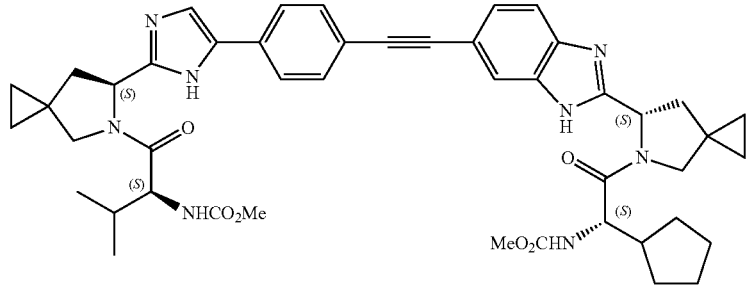
680
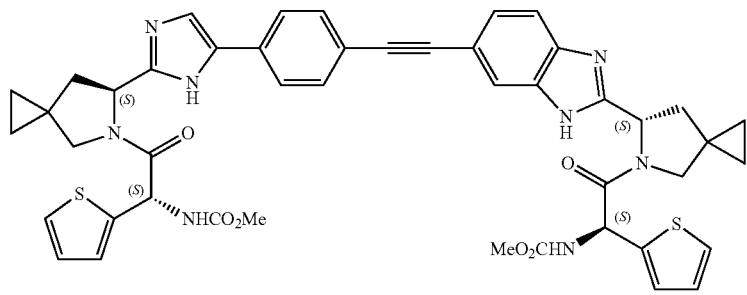
681
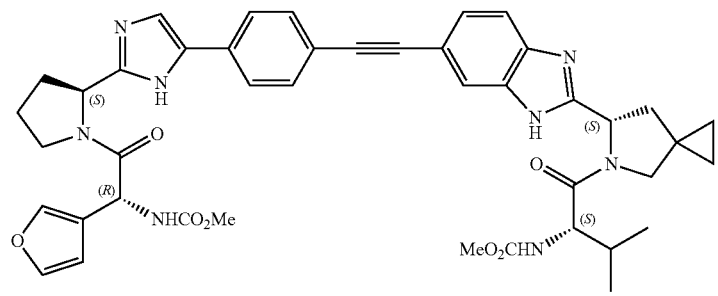
682
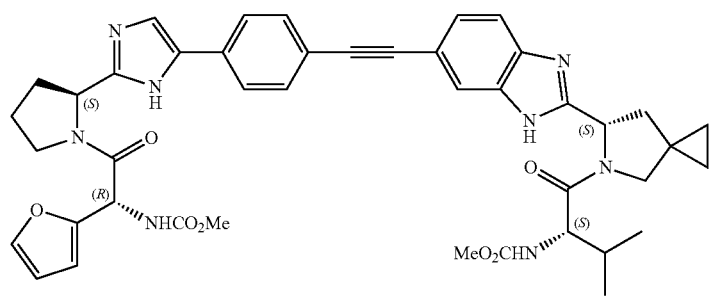
683
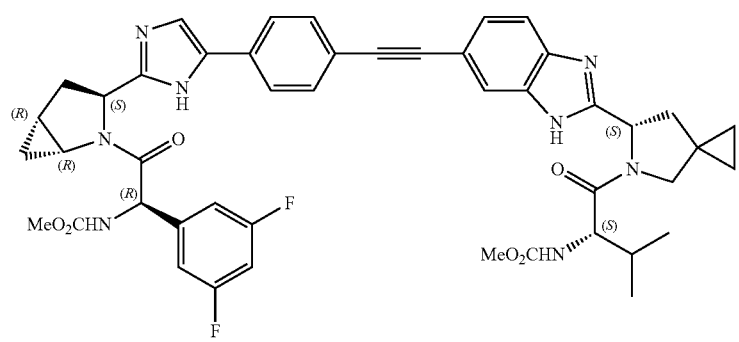

TABLE A-continued
684
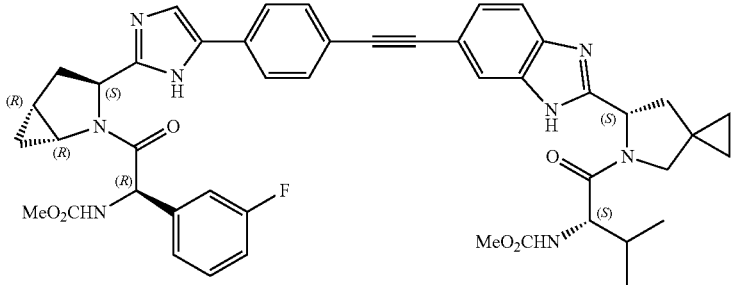
685
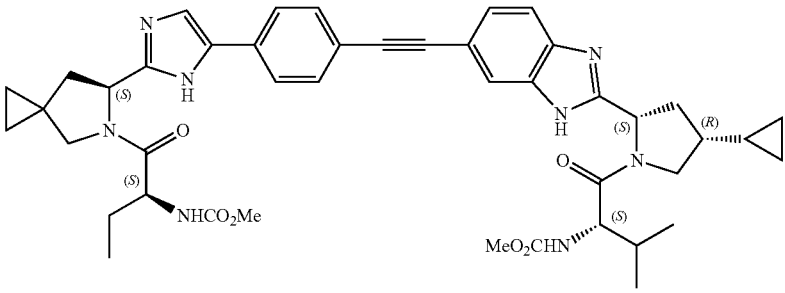
686
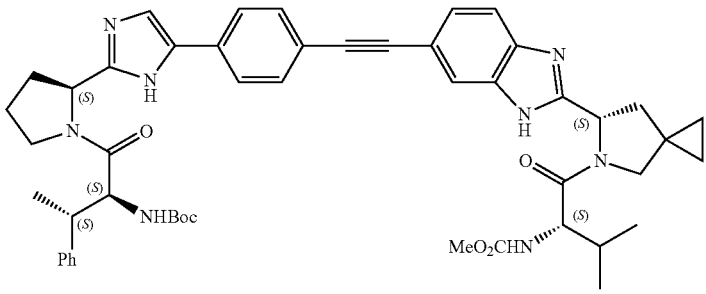
687
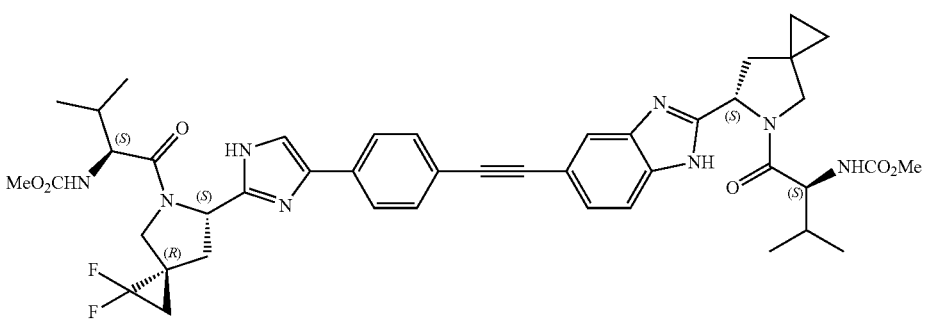
688
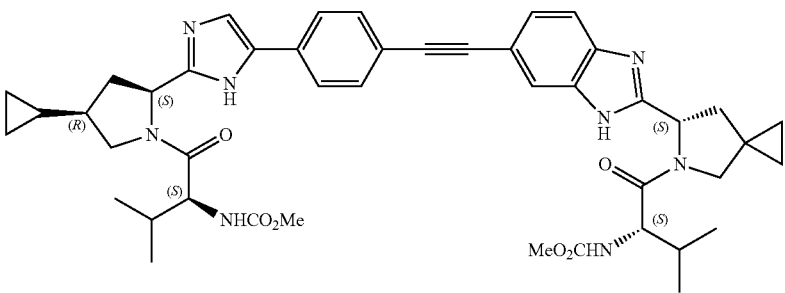

TABLE A-continued
689
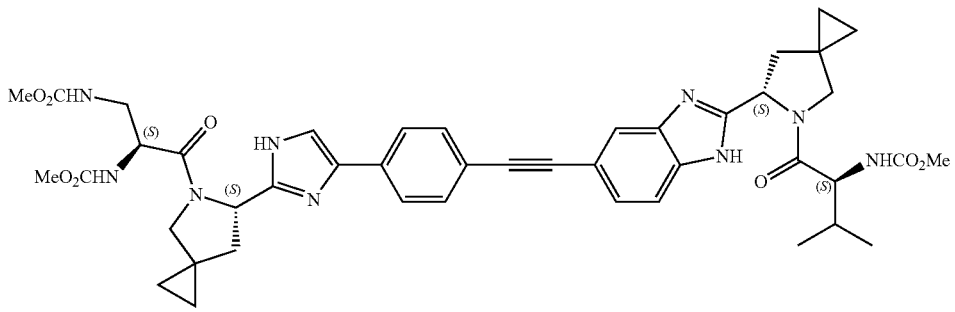
690
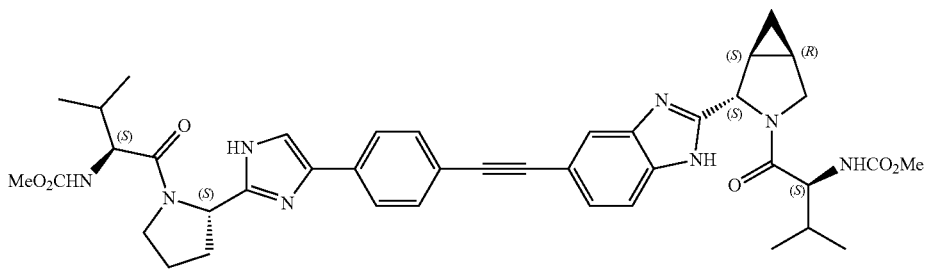
691
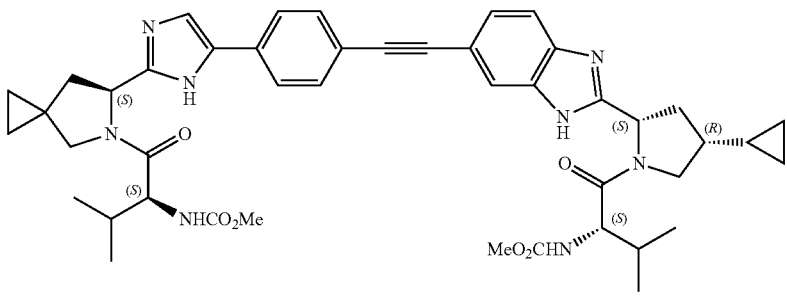
692
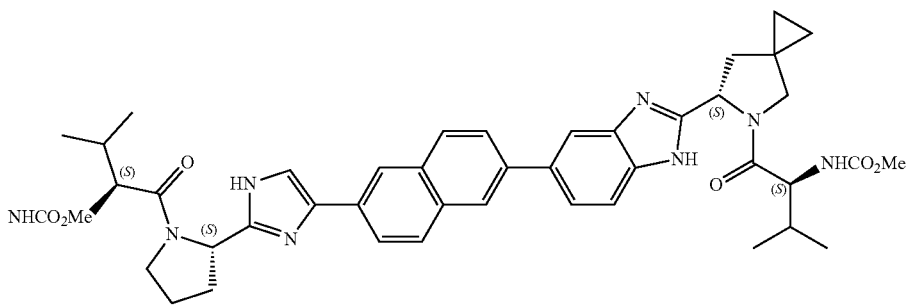
693
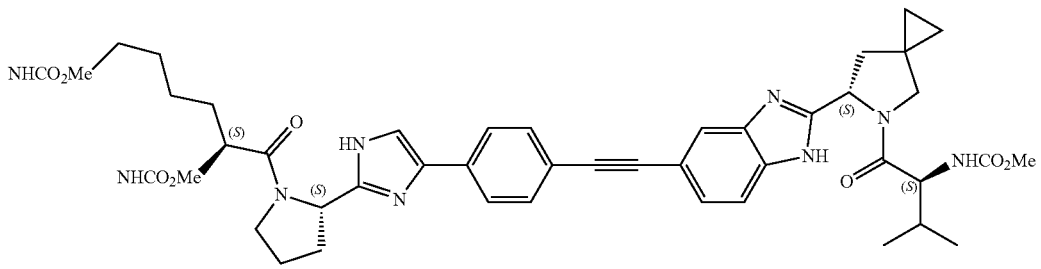

TABLE A-continued

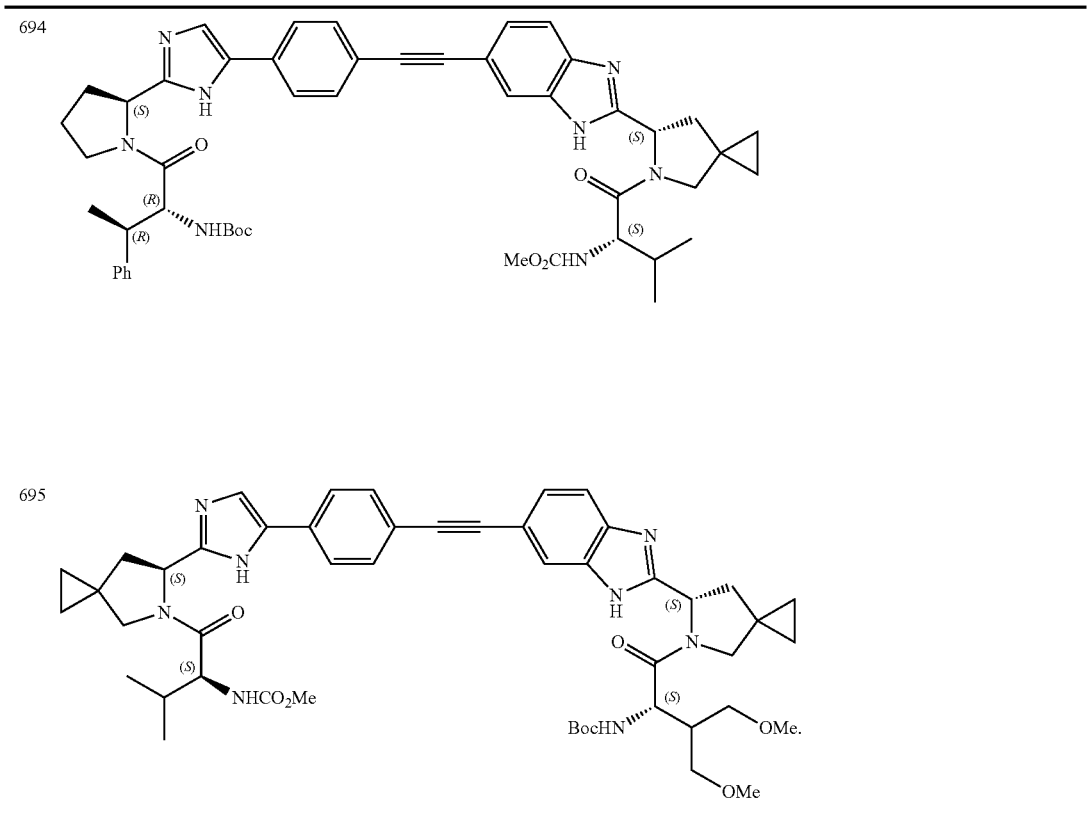

3. A pharmaceutical composition comprising a compound according to claim 1 or a pharmaceutically acceptable salt thereof, in combination with a pharmaceutically acceptable carrier or excipient.

4. A method of inhibiting the replication of hepatitis C virus comprising contacting said virus with a therapeutically effective amount of a compound or combination of compounds of claim 1, or a pharmaceutically acceptable salt thereof.

5. A method of treating a hepatitis C viral infection virus in a subject suffering from said infection, comprising administering to the subject a therapeutically effective amount of a compound or combination of compounds of claim 1, or a pharmaceutically acceptable salt thereof.

6. The method of claim 5, further comprising the step of administering to the subject one or more agents selected from the group consisting of a host immune modulator and an antiviral agent, or a combination thereof.

7. The method of claim 6, wherein the host immune modulator is selected from the group consisting of interferon-alpha, pegylated-interferon-alpha, interferon-beta, interferon-gamma, consensus interferon, a cytokine, and a vaccine.

8. The method of claim 6, wherein the antiviral agents inhibit replication of HCV by inhibiting host cellular functions associated with viral replication.

9. The method of claim 6, wherein the antiviral agent inhibits the replication of HCV by targeting proteins of the viral genome.

10. The method of claim 6, wherein said antiviral agent is an inhibitor of a HCV viral protein, a replication process or a combination thereof, wherein said protein is selected from the group consisting of helicase, protease, polymerase, metalloprotease, NS4A, NS4B, and NS5A, and said replication process is selected from the group consisting assembly, entry, and IRES.

11. The method of claim 5, further comprising the step of administering an agent or combination of agents that treat or alleviate symptoms of HCV infection selected from cirrhosis and inflammation of the liver.

12. The method of claim 5, further comprising the step of administering one or more agents that treat patients for disease caused by hepatitis B (HBV) infection.

13. The method of claim 5, further comprising the step of administering one or more agents that treat patients for disease caused by human immunodeficiency virus (HIV) infection.

14. The pharmaceutical composition of claim 3, further comprising an agent selected from interferon, pegylated interferon, ribavirin, amantadine, an HCV protease inhibitor, an HCV polymerase inhibitor, an HCV helicase inhibitor, or an internal ribosome entry site inhibitor.

15. The pharmaceutical composition of claim 3, further comprising a cytochrome P450 monooxygenase inhibitor or a pharmaceutically acceptable salt thereof.

16. The composition of claim 15, wherein the cytochrome P450 monooxygenase inhibitor is ritonavir.

17. A method of treating hepatitis C infection in a subject suffering from said infection comprising co-administering to said subject a cytochrome P450 monooxygenase inhibitor or a pharmaceutically acceptable salt thereof, and a compound of claim 1 or a pharmaceutically acceptable salt thereof.

18. A compound selected from the compounds set forth below, or a pharmaceutically acceptable salt thereof,

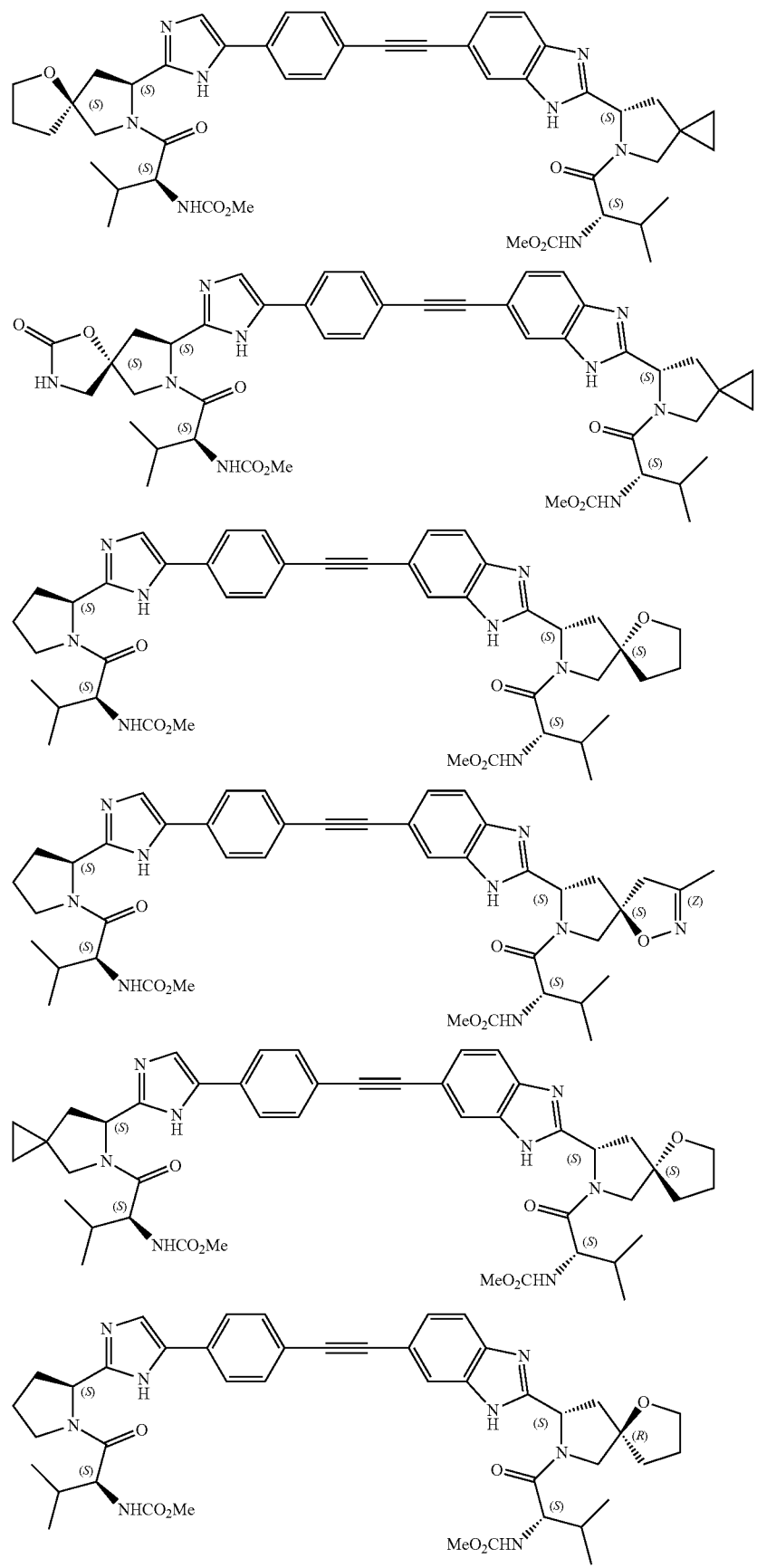

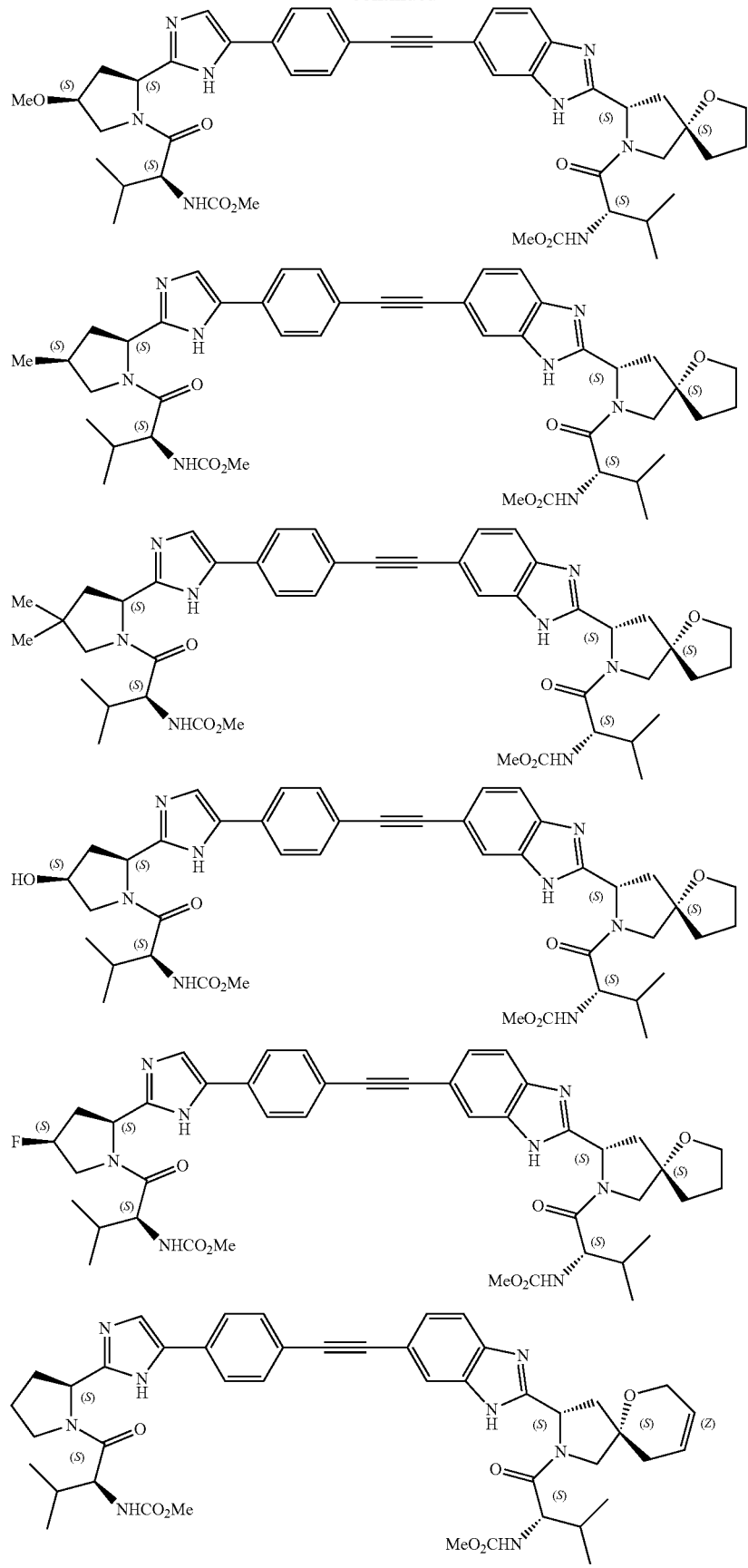

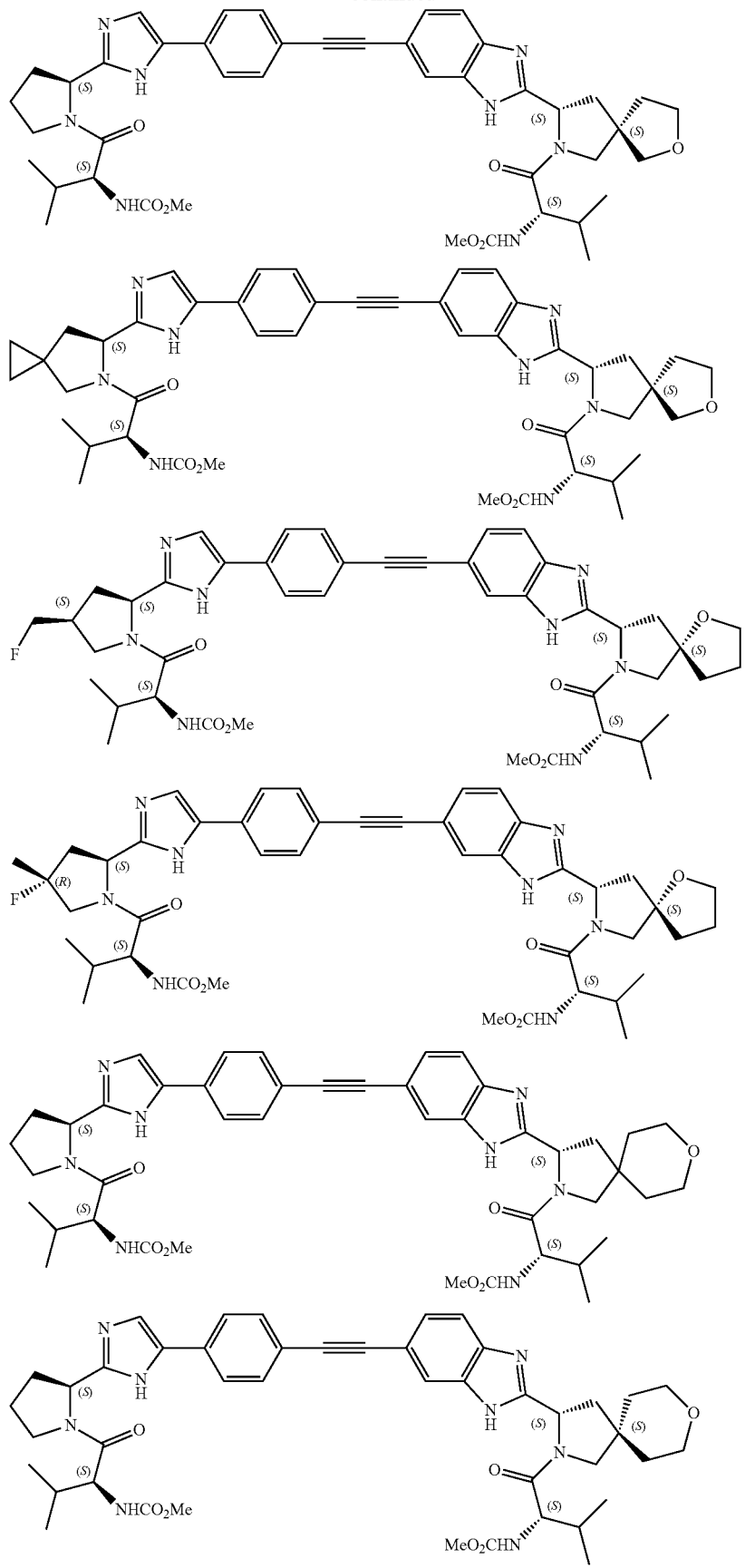

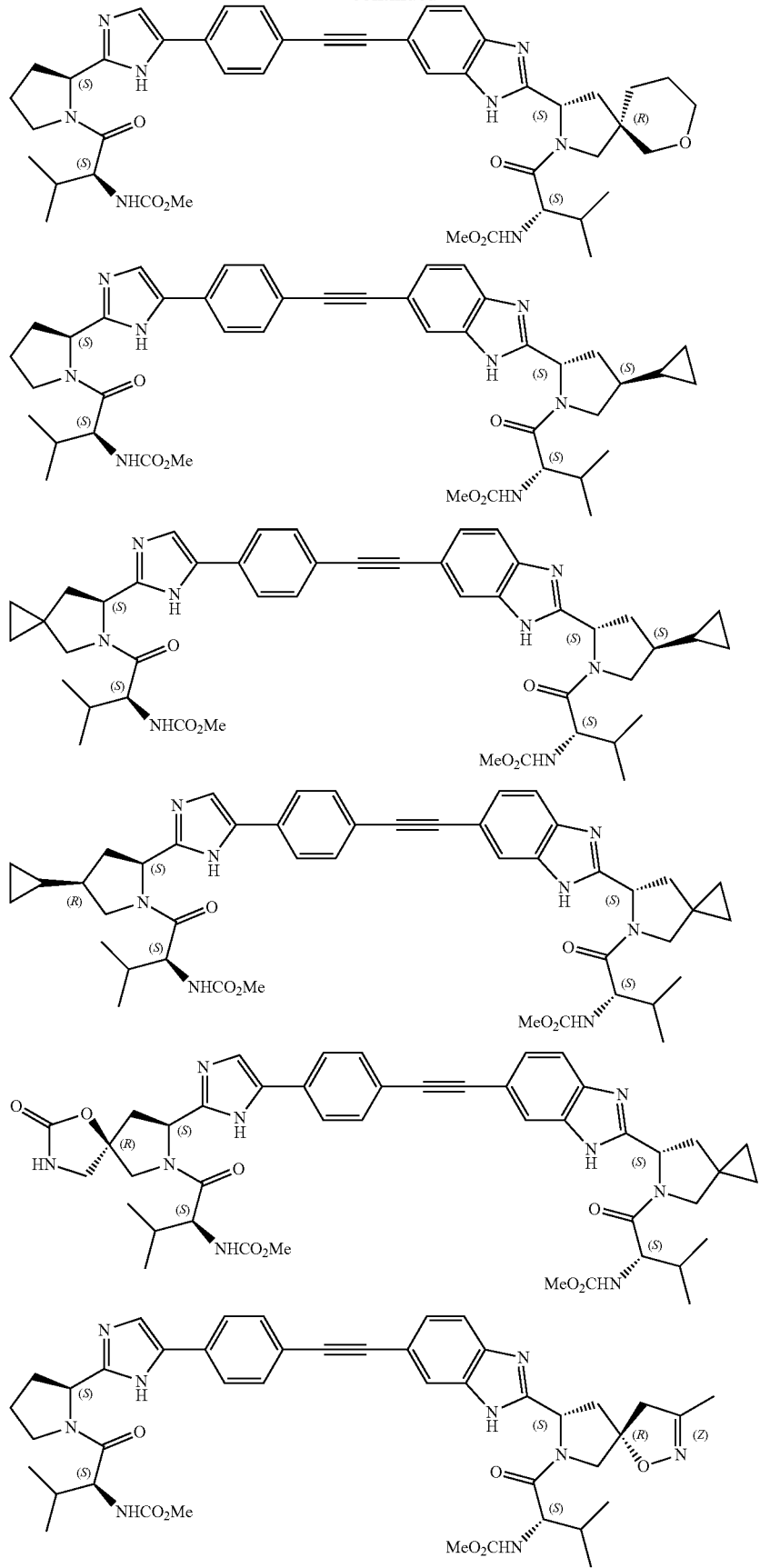

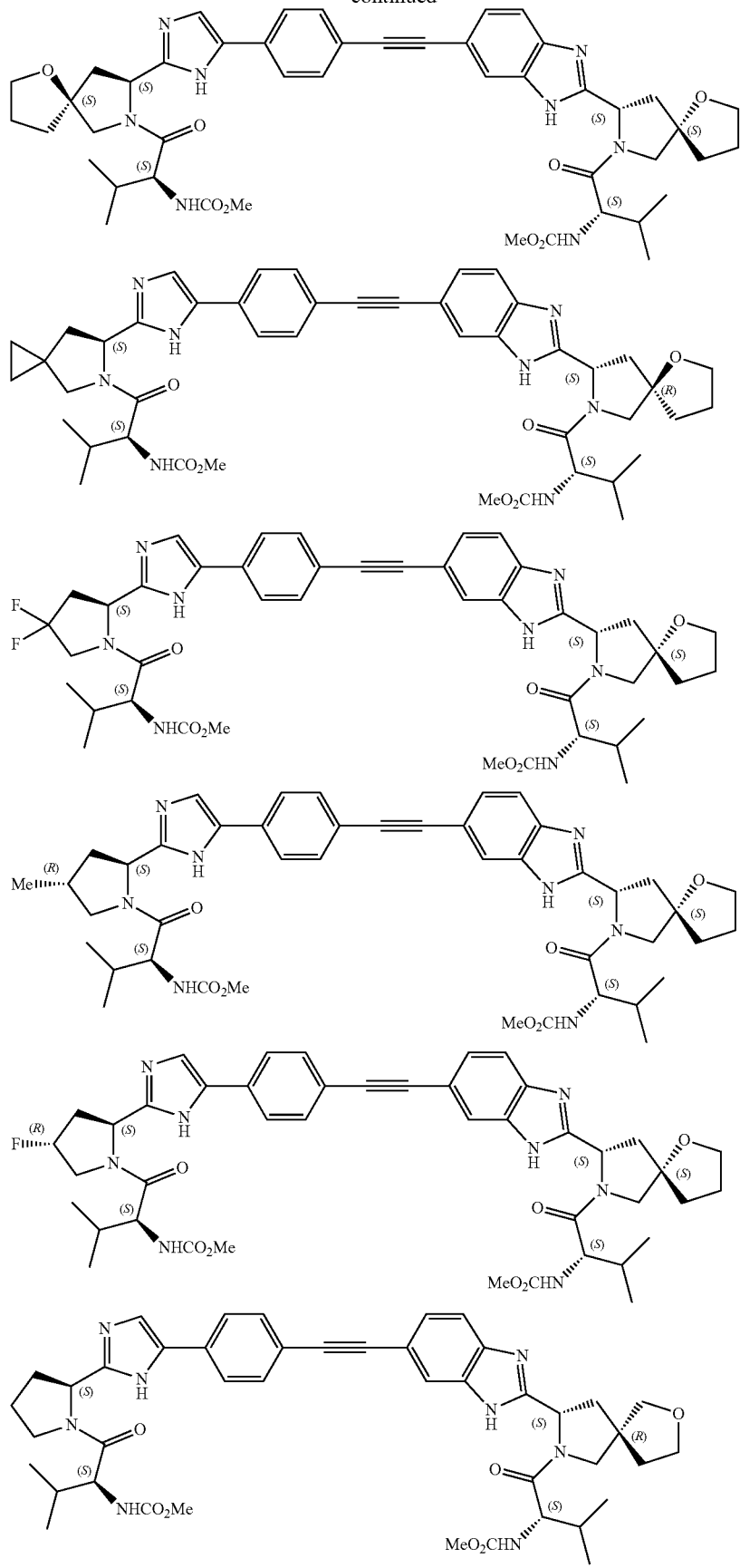

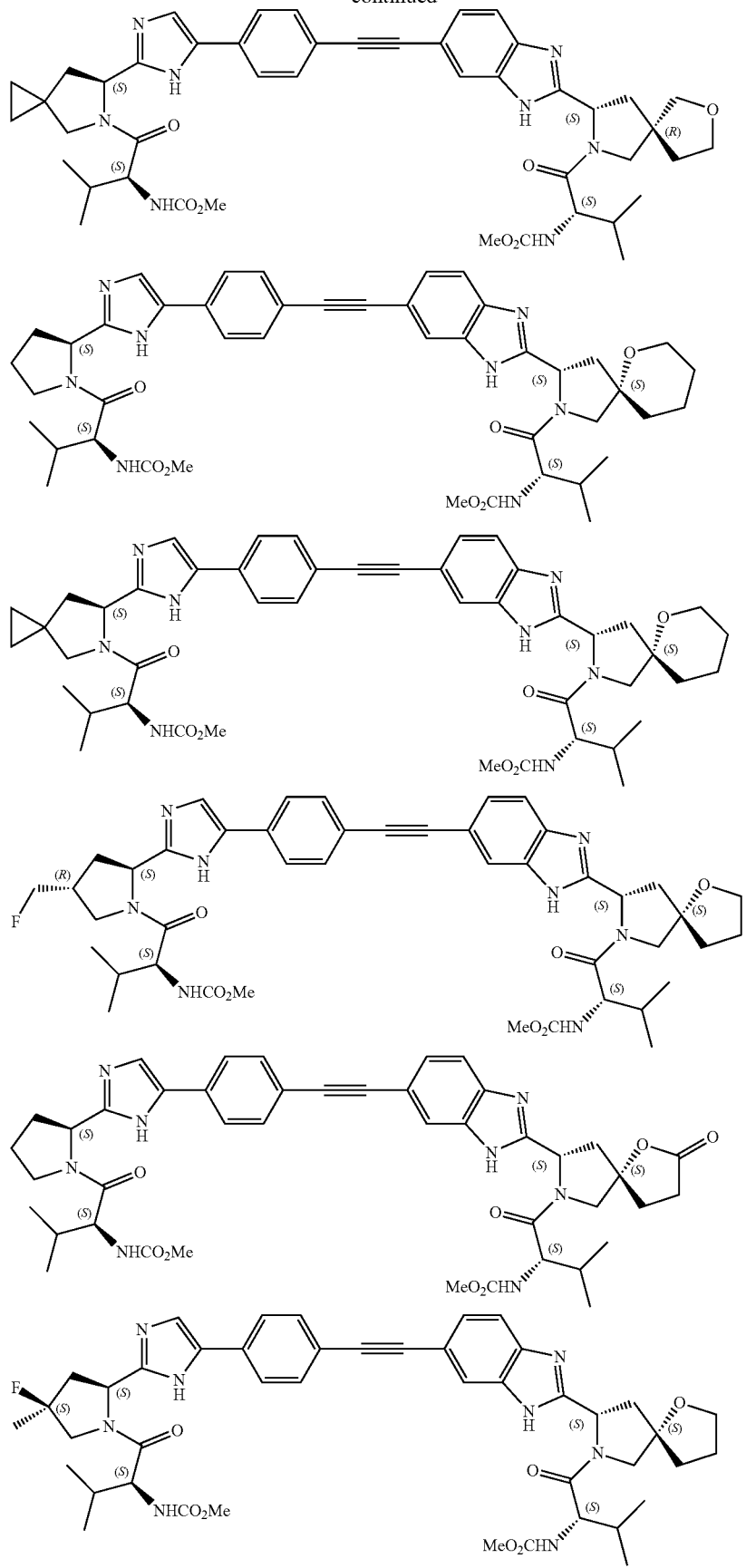

-continued
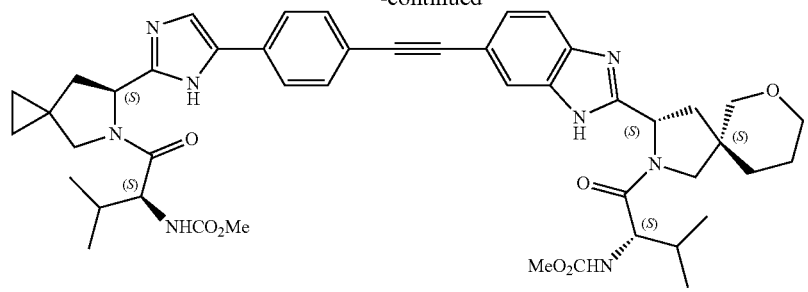
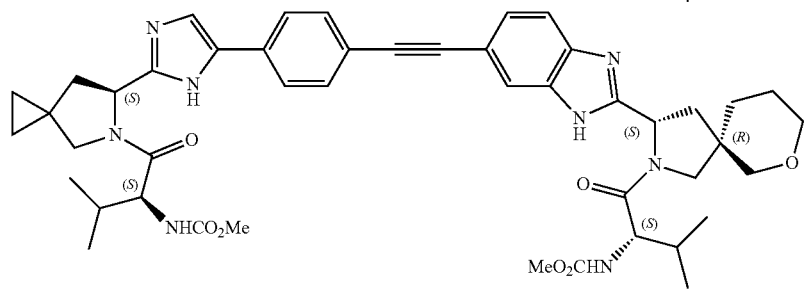
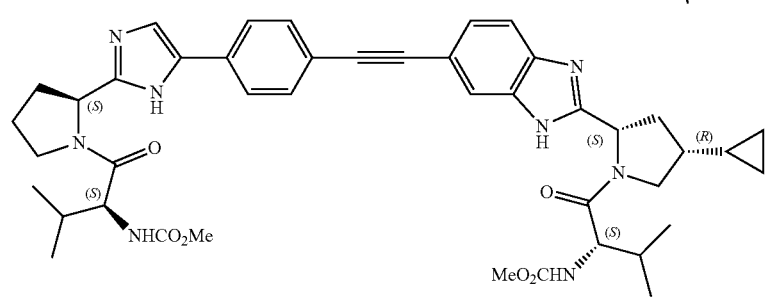
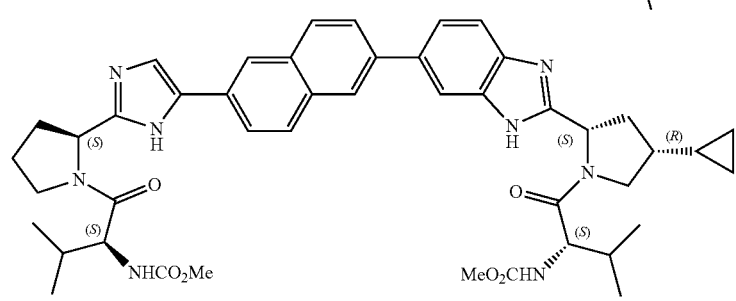
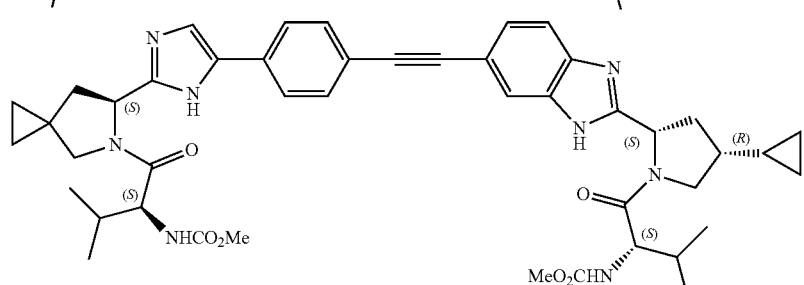
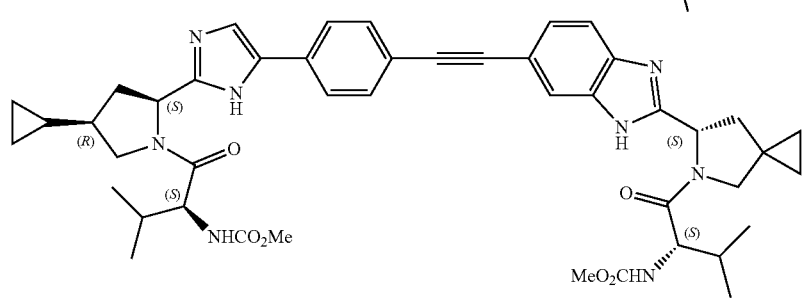

-continued
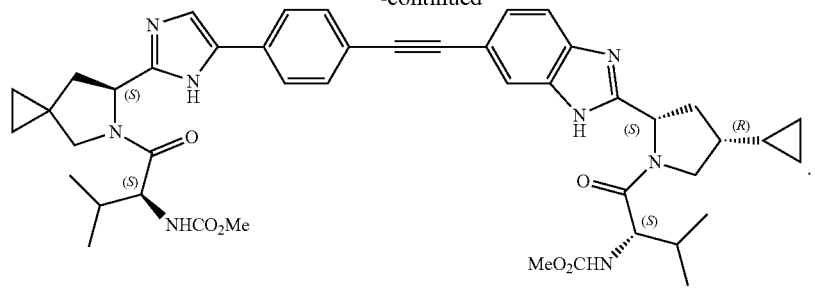
* * * * *

UNITED STATES PATENT AND TRADEMARK OFFICE
CERTIFICATE OF CORRECTION

PATENT NO. : 9,765,087 B2
APPLICATION NO. : 14/245001
DATED : September 19, 2017
INVENTOR(S) : Yao-Ling Qiu et al.

Page 1 of 2

It is certified that error appears in the above-identified patent and that said Letters Patent is hereby corrected as shown below:

In the Claims

At Column 515

In Claim 1, at Line 25, delete " 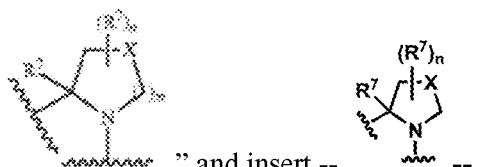 " and insert -- 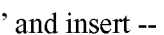 --.

At Column 517

In Claim 1, at Line 40, delete " 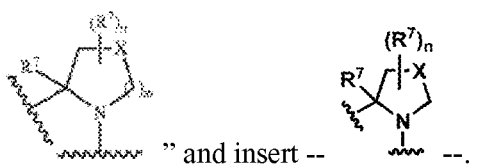 " and insert -- 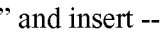 --.

At Columns 569-570

In Claim 2, compound No. 675, delete " 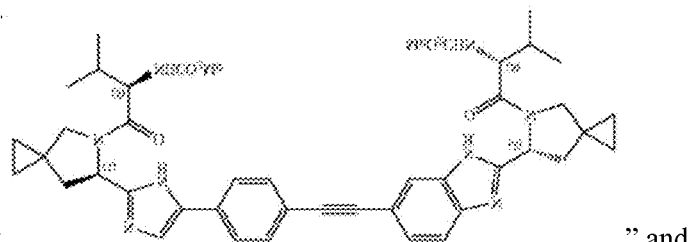 " and

Signed and Sealed this
Twenty-seventh Day of February, 2018

Andrei Iancu
*Director of the United States Patent and Trademark Office*

CERTIFICATE OF CORRECTION (continued)
U.S. Pat. No. 9,765,087 B2

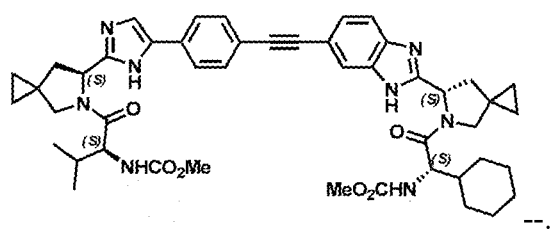

insert -- --.

At Column 577
In Claim 5, at Line 45, after the word infection, delete "virus"; and
In Claim 9, at Line 63, after the word targeting, delete "proteins" and insert -- a protein --.

At Column 578
In Claim 10, at Line 37, after the word consisting, insert -- of --.